United States Patent
Miled et al.

(10) Patent No.: US 9,682,136 B2
(45) Date of Patent: *Jun. 20, 2017

(54) REVERSE GENETICS OF NEGATIVE-STRAND RNA VIRUSES IN YEAST

(71) Applicants: INSTITUT PASTEUR, Paris (FR); CENTRE NATIONAL DE LA RECHERCHE SCIENTIFIQUE, Paris (FR)

(72) Inventors: Chaouki Miled, Antony (FR); Frédéric Tangy, Les Lilas (FR); Yves Jacob, Maintenon (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,459

(22) Filed: Jan. 7, 2015

(65) Prior Publication Data

US 2015/0216962 A1      Aug. 6, 2015

Related U.S. Application Data

(62) Division of application No. 12/865,567, filed as application No. PCT/IB2009/000373 on Jan. 30, 2009, now Pat. No. 8,980,634.

(30) Foreign Application Priority Data

Jan. 31, 2008   (EP) .................................... 08290087

(51) Int. Cl.
*A61K 39/165*     (2006.01)
*C12N 7/00*       (2006.01)
(Continued)

(52) U.S. Cl.
CPC ............ *A61K 39/165* (2013.01); *A61K 39/12* (2013.01); *C07K 14/005* (2013.01); *C12N 7/00* (2013.01);
(Continued)

(58) Field of Classification Search
None
See application file for complete search history.

(56) References Cited

U.S. PATENT DOCUMENTS

| | | |
|---|---|---|
| 8,980,634 B2 * | 3/2015 | Miled .................. A61K 39/165 424/204.1 |
| 2004/0265274 A1 | 12/2004 | Wei et al. |

(Continued)

FOREIGN PATENT DOCUMENTS

| | | |
|---|---|---|
| JP | 2007-135487 A | 6/2007 |
| WO | 0179594 A1 | 4/1986 |

(Continued)

OTHER PUBLICATIONS

European Search Report in International Application No. PCT/IB2009/000373 mailed Jun. 2, 2009.
(Continued)

*Primary Examiner* — Janet L Andres
*Assistant Examiner* — Stuart W Snyder
(74) *Attorney, Agent, or Firm* — Arrigo, Lee & Guttman LLP

(57) ABSTRACT

The present invention relates to a methodology for the generation of infectious ribonucleoparticles (RNPs) of negative-strand RNA viruses, and in particular of non-segmented negative-strand RNA viruses in yeast, especially in budding yeast. Accordingly, the patent application relates to a recombinant yeast strain suitable for the rescue of infectious non-segmented negative-strand RNA virus particles or infectious virus-like particles. The invention also relates to (Continued)

Figure 1:
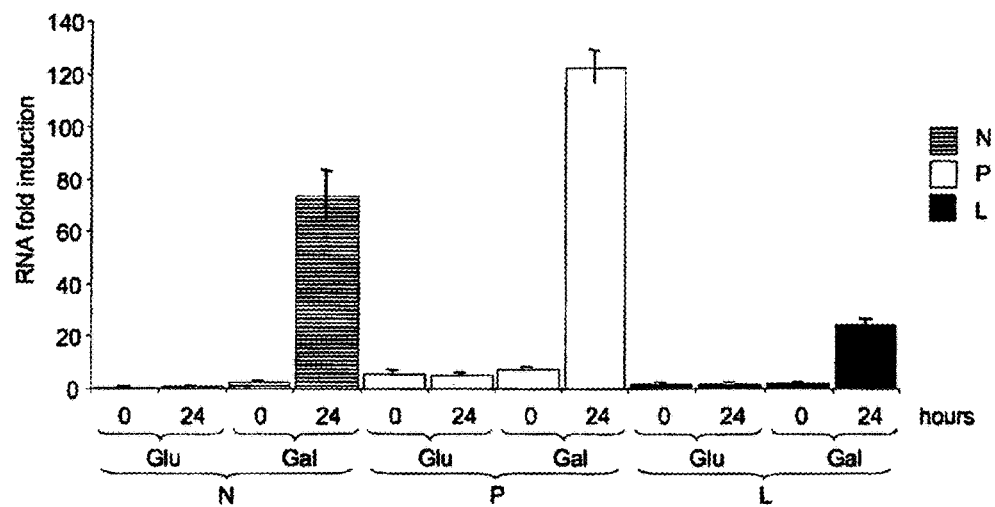

the use of the recombinant yeast to prepare vaccine seed and to the use of the produced RNPs or RNPs-like to prepare vaccine formulations. It also concerns the use of the recombinant yeast for the screening of libraries of DNA.

29 Claims, 153 Drawing Sheets

(51) Int. Cl.
    *C12N 15/81* (2006.01)
    *A61K 39/12* (2006.01)
    *C07K 14/005* (2006.01)
    *A61K 39/00* (2006.01)

(52) U.S. Cl.
    CPC ........ *C12N 15/81* (2013.01); *A61K 2039/525* (2013.01); *A61K 2039/5252* (2013.01); *A61K 2039/5258* (2013.01); *C12N 2760/00051* (2013.01); *C12N 2760/18434* (2013.01); *C12N 2760/18451* (2013.01); *C12N 2770/24134* (2013.01)

(56) References Cited

U.S. PATENT DOCUMENTS

2008/0020371 A1  1/2008  German et al.
2009/0041725 A1  2/2009  Neubert et al.

FOREIGN PATENT DOCUMENTS

| WO | WO 01/20989 A1 | 3/2001 |
| WO | WO 04/000876 | 12/2003 |
| WO | WO 04/000876 A1 | 12/2003 |
| WO | WO 2004/113517 A2 | 12/2004 |
| WO | WO 2006-084746 A1 | 8/2006 |

OTHER PUBLICATIONS

Ito et al., "Transformation of Intact Yeast Cells Treated with Alkali Cations," Journal of Bacteriology, vol. 153, No. 1, Jan. 1983, pp. 163-168.

Janda et al., "RNA-Dependent Replication, Transcription, and Persistence of Brome Mosaic Virus RNA Replicons in *S. cerevisiae*," Cell, vol. 72, Mar. 26, 1993, pp. 961-970.

Naito et al., "An influenza virus replicon system in yeast identified Tat-SF1 as a stimulatory host factor for viral RNA synthesis," PNAS, vol. 104, No. 46, Nov. 13, 2007, www.pnas.org/cgi/doi/10.1073/pnas.0705856104, XP-002487432, pp. 18235-18240.

Tomita et al., "Mutation of Host dnaJ Homolog Inhibits Brome Mosaic Virus Negative-Strand RNA Synthesis," Journal of Virology, vol. 77, No. 5, Mar. 2003, XP-002257964, pp. 2990-2997.

Wolff et al., "A Short Leucine-rich Sequence in the Borna Disease Virus p10 Protein Mediates Association with the Viral Phosphoand Nucleoproteins", Journal of General Virology, vol. 81, No. 4 (2000) pp. 939-947.

Cattaneo, Roberto, et al., "Multiple Viral Mutations Rather Than Host Factors Cause Defective Measles Virus Gene Expression in a Subacute Sclerosing Panencephalitis Cell Line," J. of Virology, vol. 62, No. 4, pp. 1388-1397.

* cited by examiner

W303 NPL MV-eGFP-KANMX4 cells

Cells transfected with yeast RNPs

Vero cells                    HEK293T cells

+UV    -UV
Mice immunization with MV-RNP

FIGURE 15.1

Minigenome α sequence (PCM112)

| | |
|---|---|
| pYES2 vector : | Capital letter |
| Ribozymes Sequence : | Minuscule letter |
| Leader sequence : | Bold capital letter |
| Trailer sequence : | *Bold italic capital letter* |
| KANMX4 sequence : | Bold minuscule letter |
| pYES2 Vector sequence: | Upper Case letter | ccaactttgtttggtctgatgagtccgtgaggacgaaacccggagtcccg
ggtcACCAGACAAAGCTGGGAATAGAAACTTCGTATTTTCAAAGTTTTCT
TTAATATATTGCAAATAATGCCTAACCACCTAGGGCAGGATTAGGGTTCC
GGAGTTCAACCAATTAGTCCTTAATCAGGGCACTGTATCCGACTAACTTA
TACCATatcatcgatgaattcgagctcgtttttcgacactggatggcggcg
ttagtatcgaatcgacagcagtatagcgaccagcattcacatacgattga
cgcatgatattactttctgcgcacttaacttcgcatctgggcagatgatg
tcgaggcgaaaaaaatataaatcacgctaacatttgattaaaatagaac
aactacaatataaaaaaactatacaaatgacaagttcttgaaaacaagaa
tcttttattgtcagtactgattagaaaaactcatcgagcatcaaatgaa
actgcaatttattcatatcaggattatcataccatattttgaaaaagc
cgtttctgtaatgaaggagaaaactcaccgaggcagttccataggatggc
aagatcctggtatcggtctgcgattccgactcgtccaacatcaatacaac
ctattaatttcccctcgtcaaaaataaggttatcaagtgagaaatcacca
tgagtgacgactgaatccggtgagaatggcaaaagcttatgcatttcttt
ccagacttgttcaacaggccagccattacgctcgtcatcaaaatcactcg
catcaaccaaaccgttattcattcgtgattgcgcctgagcgagacgaaat
acgcgatcgctgttaaaaggacaattacaaacaggaatcgaatgcaaccg
gcgcaggaacactgccagcgcatcaacaatatttcacctgaatcaggat
attcttctaatacctggaatgctgttttgccggggatcgcagtggtgagt
aaccatgcatcatcaggagtacggataaaatgcttgatggtcggaagagg
cataaattccgtcagccagtttagtctgaccatctcatctgtaacatcat
tggcaacgctacctttgccatgtttcagaaacaactctggcgcatcgggc

FIGURE 15.2 ttcccatacaatcgatagattgtcgcacctgattgcccgacattatcgcg
agcccatttatacccatataaatcagcatccatgttggaatttaatcgcg
gcctcgaaacgtgagtcttttccttacccatggttgtttatgttcggatg
tgatgtgagaactgtatcctagcaagatttt*CCATCTCGGATATCCCTAA
TCCTGCTCTTGTCCCTGATAATAGGATCTTGAATCCTAAGTGCACTAGAA
GATGATCATTGATTGAACTATCCTTACCCAACTTTGTTTGGT*ggccggca
tggtcccagcctcctcgctggcgccggctgggcaacattccgaggggacc
gtcccctcggtaatggcgaatgggacTCGAGCATGCATCTAGAGGGCCGC
ATCATGTAATTAGTTATGTCAC
GCTTACATTCACGCCCTCCCCCACATCCGCTCTAACCGAAAAGGAAGGA
GTTAGACAACCTGAAGTCTAGGTCCCTATTTATTTTTTATAGTTATGTT
AGTATTAAGAACGTTATTTATATTTCAAATTTTTCTTTTTTTTCTGTACA
GACGCGTGTACGCATGTAACATTATACTGAAAACCTTGCTTGAGAAGGTT
TTGGGACGCTCGAAGGCTTTAATTTGCGGCCCTGCATTAATGAATCGGCC
AACGCGCGGGAGAGGCGGTTTGCGTATTGGGCGCTCTTCCGCTTCCTCG
CTCACTGACTCGCTGCGCTCGGTCGTTCGGCTGCGGCGAGCGGTATCAGC
TCACTCAAAGGCGGTAATACGGTTATCCACAGAATCAGGGGATAACGCAG
GAAAGAACATGTGAGCAAAAGGCCAGCAAAAGCCCAGGAACCGTAAAAAG
GCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGA
CTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTAC
ACTAGAAGGACAGTATTTGGTATCTGCGCTCTGCTGAAGCCAGTTACCTT
CGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAA
CGAAAACTCACGTTAAGGGATTTTGGTCATGAGATTATCAAAAGGATCT
TCACCTAGATCCTTTTAAATTAAAAATGAAGTTTTAAATCAATCTAAAGT
ATATATGAGTAAACTTGGTCTGACAGTTACCAATGCTTAATCAGTGAGGC

FIGURE 15.3

ACCTATCTCAGCGATCTGTCTATTTCGTTCATCCATAGTTGCCTGACTCC
CCGTCGTGTAGATAACTACGATACGGGAGCGCTTACCATCTGGCCCCAGT
GCTGCAATGATACCGCGAGACCCACGCTCACCGGCTCCAGATTTATCAGC
AATAAACCAGCCAGCCGGAAGGGCCGAGCGCAGAAGTGGTCCTGCAACTT
TATCCGCCTCCATTCAGTCTATTAATTGTTGCCGGGAAGCTAGAGTAAGT
AGTTCGCCAGTTAATAGTTTGCGCAACGTTGTTGGCATTGCTACAGGCAT
CGTGGTGTCACTCTCGTCGTTTGGTATGGCTTCATTCAGCTCCGGTTCCC
AACGATCAAGGCGAGTTACATGATCCCCATGTTGTGCAAAAAGCGGTT
AGCTCCTTCGGTCCTCCGATCGTTGTCAGAAGTAAGTTGGCCGCAGTGTT
ATCACTCATGGTTATGGCAGCACTGCATAATTCTCTTACTGTCATGCCAT
CCGTAAGATGCTTTTCTGTGACTGGTGAGTACTCAACCAAGTCATTCTGA
GAATAGTGTATGCGGCGACCGAGTTGCTCTTGCCCGGCGTCAATACGGGA
TAATAGTGTATCACATAGCAGAACTTTAAAAGTGCTCATCATTGGAAAAC
GTTCTTCGGGGCGAAAACTCTCAAGGATCTTACCGCTGTTGAGATCCAGT
TCGATGTAACCCACTCGTGCACCCAACTGATCTTCAGCATCTTTTACTTT
CACCAGCGTTTCTGGGTGAGCAAAAACAGGAAGGCAAAATGCCGCAAAAA
AGGGAATAAGGGCGACACGGAAATGTTGAATACTCATACTCTTCCTTTTT
CAATGGGTAATAACTGATATAATTAAATTGAAGCTCTAATTTGTGAGTTT
AGTATACATGCATTTACTTATAATACAGTTTTTTAGTTTTGCTGGCCGCA
TCTTCTCAAATATGCTTCCCAGCCTGCTTTTCTGTAACGTTCACCCTCTA
CCTTAGCATCCCTTCCCTTTGCAAATAGTCCTCTTCCAACAATAATAATG
TCAGATCCTGTAGAGACCACATCATCCACGGTTCTATACTGTTGACCCAA
TGCGTCTCCCTTGTCATCTAAACCCACACCGGGTGTCATAATCAACCAAT
CGTAACCTTCATCTCTTCCACCCATGTCTCTTTGAGCAATAAAGCCGATA
ACAAAATCTTTGTCGCTCTTCGCAATGTCAACAGTACCCTTAGTATATTC
TCCAGTAGATAGGGAGCCCTTGCATGACAATTCTGCTAACATCAAAAGGC
CTCTAGGTTCCTTTGTTACTTCTTCTGCCGCCTGCTTCAAACCGCTAACA
ATACCTGGGCCCACCACACCGTGTGCATTCGTAATGTCTGCCCATTCTGC
TATTCTGTATACACCCGCAGAGTACTGCAATTTGACTGTATTACCAATGT
CAGCAAATTTTCTGTCTTCGAAGAGTAAAAATTGTACTTGGCGGATAAT
GCCTTTAGCGGCTTAACTGTGCCCTCCATGGAAAATCAGTCAAGATATC
CACATGTGTTTTTAGTAAACAAATTTTGGGACCTAATGCTTCAACTAACT
CCAGTAATTCCTTGGTGGTACGAACATCCAATGAAGCACACAAGTTTGTT
TGCTTTTCGTGCATGATATTAAATAGCTTGGCAGCAACAGGACTAGGATG

FIGURE 15.4

AGTAGCAGCACGTTCCTTATATGTAGCTTTCGACATGATTTATCTTCGTT
TCCTGCAGGTTTTTGTTCTGTGCAGTTGGGTTAAGAATACTGGGCAATTT
CATGTTTCTTCAACACTACATATGCGTATATATACCAATCTAAGTCTGTG
CTCCTTCCTTCGTTCTTCCTTCTGTTCGGAGATTACCGAATCAAAAAAAT
TTCAAAGAAACCGAAATCAAAAAAAGAATAAAAAAAAATGATGAATTG
AATTGAAAAGCTAGCTTATCGATGATAAGCTGTCAAAGATGAGAATTAAT
TCCACGGACTATAGACTATACTAGATACTCCGTCTACTGTACGATACACT
TCCGCTCAGGTCCTTGTCCTTTAACGAGGCCTTACCACTCTTTTGTTACT
CTATTGATCCAGCTCAGCAAAGGCAGTGTGATCTAAGATTCTATCTTCGC
GATGTAGTAAAACTAGCTAGACCGAGAAAGAGACTAGAAATGCAAAAGGC
ACTTCTACAATGGCTGCCATCATTATTATCCGATGTGACGCTGCAGCTTC
TCAATGATATTCGAATACGCTTTGAGGAGATACAGCCTAATATCCGACAA
ACTGTTTTACAGATTTACGATCGTACTTGTTACCCATCATTGAATTTTGA
ACATCCGAACCTGGGAGTTTTCCCTGAAACAGATAGTATATTTGAACCTG
TATAATAATATATAGTCTAGCGCTTTACGGAAGACAATGTATGTATTTCG
GTTCCTGGAGAAACTATTGCATCTATTGCATAGGTAATCTTGCACGTCGC
ATCCCCGGTTCATTTCTGCGTTTCCATCTTGCACTTCAATAGCATATCT
TTGTTAACGAAGCATCTGTGCTTCATTTGTAGAACAAAAATGCAACGCG
AGAGCGCTAATTTTTCAAACAAAGAATCTGAGCTGCATTTTTACAGAACA
GAAATGCAACGCGAAAGCGCTATTTTACCAACGAAGAATCTGTGCTTCAT
TTTTGTAAAACAAAAATGCAACGCGACGAGAGCGCTAATTTTTCAAACAA
AGAATCTGAGCTGCATTTTTACAGAACAGAAATGCAACGCGAGAGCGCTA
TTTTACCAACAAAGAATCTATACTTCTTTTTTGTTCTACAAAAATGCATC
CCGAGAGCGCTATTTTTCTAACAAAGCATCTTAGATTACTTTTTTTCTCC
TTTGTGCGCTCTATAATGCAGTCTCTTGATAACTTTTTGCACTGTAGGTC
CGTTAAGGTTAGAAGAAGGCTACTTTGGTGTCTATTTTCTCTTCCATAAA
AAAAGCCTGACTCCACTTCCCGCGTTTACTGATTACTAGCGAAGCTGCGG
GTGCATTTTTTCAAGATAAAGGCATCCCGATTATATTCTATACCGATGT
GGATTGCGCATACTTTGTAACAGAAAGTGATAGCGTTGATGATTCTTCA
TTGGTCAGAAAATTATGAACGGTTTCTTCTATTTTGTCTCTATATACTAC
GTATAGGAAATGTTTACATTTTCGTATTGTTTTCGATTCACTCTATGAAT
AGTTCTTACTACAATTTTTTTGTCTAAAGAGTAATACTAGAGATAAACAT
AAAAAATGTAGAGGTCGAGTTTAGATGCAAGTTCAAGGAGCGAAAGGTGG
ATGGGTAGGTTATATAGGGATATAGCACAGAGATATATAGCAAAGAGATA

FIGURE 15.5

CTTTTGAGCAATGTTTGTGGAAGCGGTATTCGCAATGGGAAGCTCCACCC
CGGTTGATAATCAGAAAAGCCCCAAAAACAGGAAGATTGTATAAGCAAAT
ATTTAAATTGTAAACGTTAATATTTTGTTAAAATTCGCGTTAAATTTTTG
TTAAATCAGCTCATTTTTTAACGAATAGCCCGAAATCGGCAAAATCCCTT
ATAAATCAAAAGAATAGACCGAGATAGGGTTGAGTGTTGTTCCAGTTTCC
AACAAGAGTCCACTATTAAAGAACGTGGACTCCAACGTCAAAGGGCGAAA
AAGGGTCTATCAGGGCGATGGCCCACTACGTGAACCATCACCCTAATCAA
GTTTTTTGGGGTCGAGGTGCCGTAAAGCAGTAAATCGGAAGGGTAAACGG
ATGCCCCCATTTAGAGCTTGACGGGGAAAGCCGGCGAACGTGGCGAGAAA
GGAAGGGAAGAAAGCGAAAGGAGCGGGGGCTAGGGCGGTGGGAAGTGTAG
GGGTCACGCTGGGCGTAACCACCACACCCGCCGCGCTTAATGGGGCGCTA
CAGGGCGCGTGGGGATGATCCACTAGTACGGATTAGAAGCCGCCGAGCGG
GTGACAGCCCTCCGAAGGAAGACTCTCCTCCGTGCGTCCTCGTCCTCACC
GGTCGCGTTCCTGAAACGCAGATGTGCCTCGCGCCGCACTGCTCCGAACA
ATAAAGATTCTACAATACTAGCTTTTATGGTTATGAAGAGGAAAAATTGG
CAGTAACCTGGCCCCACAAACCTTCAAATGAACGAATCAAATTAACAACC
ATAGGATGATAATGCGATTAGTTTTTTAGCCTTATTTCTGGGGTAATTAA
TCAGCGAAGCGATGATTTTTGATCTATTAACAGATATATAAATGCAAAAA
CTGCATTAACCACTTTAACTAATACTTTCAACATTTTCGGTTTGTATTAC
TTCTTATTCAAATGTAATAAAAGTATCAACAAAAAATTGTTAATATACCT
CTATACTTTAACGTCAAGGAGAAAAAACCCCGGATCGGACTACTAGCAGC
TGTAATACGACTCACTATAGGGAATATTAAGCTTGGTACCGAGCTCGGAT
CCACTAGTAACGGCCGCCAGTGTGCTGGAATTCTGCAGATATCCATCACA
CTGGCGGCCGCATCCGGATATAGTTCCTCCTTTCAGCAAAAAACCCCTCA
AGACCCGTTTAGAGGCCCCAAGGGGTTATGCTAGTTATTGCTCAGCGGTG
GCAGCAGCCAACTCAGCTTCCTTTCGGGCTTTGTTAGCAGCCGGATCGGC
CGC

FIGURE 16.1

Minigenome β sequence (pCM113)

| | |
|---|---|
| pYES2 vector : | Capital letter |
| Ribozymes Sequence : | Minuscule letter |
| Leader sequence : | Bold capital letter |
| Trailer sequence : | Bold italic capital letter |
| KANMX4 sequence : | Bold minuscule letter |
| pYES2 vector sequence: | Upper case letter | ccaactttgtttggtctgatgagtccgtgaggacgaaacccggagtcccg
ggtc**ACCAAACAAAGTTGGGTAAGGATAGTTCAATCAATGATCATCTTCT
AGTGCACTTAGGATTCAAGATCCTATTATCAGGGACAAGAGCAGGATTAG
GGATATCCGAGATGG**aaaatcttgctaggatacagttctcacatcacatc
cgaacataaacaaccatgggtaaggaaaagactcacgtttcgaggccgcg
attaaattccaacatggatgctgatttatatgggtataaatgggctcgcg
ataatgtcgggcaatcaggtgcgacaatctatcgattgtatgggaagccc
gatgcgccagagttgtttctgaaacatggcaaaggtagcgttgccaatga
tgttacagatgagatggtcagactaaactggctgacggaatttatgcctc
ttccgaccatcaagcatttatccgtactcctgatgatgcatggttactc
accactgcgatccccggcaaaacagcattccaggtattagaagaatatcc
tgattcaggtgaaaatattgttgatgcgctggcagtgttcctgcgccggt
tgcattcgattcctgtttgtaattgtccttttaacagcgatcgcgtattt
cgtctcgctcaggcgcaatcacgaatgaataacggtttggttgatgcgag
tgatttgatgacgagcgtaatggctggcctgttgaacaagtctggaaag
aaatgcataagcttttgccattctcaccggattcagtcgtcactcatggt
gatttctcacttgataaccttattttgacgaggggaaattaataggttg
tattgatgttggacgagtcggaatcgcagaccgataccaggatcttgcca
tcctatggaactgcctcggtgagttttctccttcattacagaaacggctt
tttcaaaaatatggtattgataatcctgatatgaataaattgcagtttca
tttgatgctcgatgagttttctaatcagtactgacaataaaaagattct
tgttttcaagaacttgtcatttgtatagttttttatattgtagttgttc
tattttaatcaaatgttagcgtgatttatattttttttcgcctcgacatc
atctgcccagatgcgaagttaagtgcgcagaaagtaatatcatgcgtcaa
tcgtatgtgaatgctggtcgctatactgctgtcgattcgatactaacgcc

FIGURE 16.2 gccatccagtgtcgaaaacgagctcgaattcatcgatgat*ATGGTATAAG*
*TTAGTCGGATACAGTGCCCTGATTAAGGACTAATTGGTTGAACTCCGGAA*
*CCCTAATCCTGCCCTAGGTGGTTAGGCATTATTTGCAATATATTAAAGAA*
*AACTTTGAAAATACGAAGTTTCTATTCCCAGCTTTGTCTGGT*ggccggca
tggtcccagcctcctcgctggcgccggctgggcaacattccgaggggacc
gtcccctcggtaatggcgaatgggacGCGGCCGATCCGGCTGCTAACAAA
GCCCGAAAGGAAGCTGAGTTGGCTGCTGCCACCGCTGAGCAATAACTAGC
ATAACCCCTTGGGGCCTCTAAACGGGTCTTGAGGGGTTTTTTGCTGAAAG
GAGGAACTATATCCGGATGCGGCCGCTCGAGCATGCATCTAGAGGGCCGC
ATCATGTAATTAGTTATGTCACGCTTACATTCACGCCCTCCCCCACATC
CGCTCTAACCGAAAAGGAAGGAGTTAGACAACCTGAAGTCTAGGTCCCTA
TTTATTTTTTTATAGTTATGTTAGTATTAAGAACGTTATTTATATTTCAA
ATTTTTCTTTTTTTTCTGTACAGACGCGTGTACGCATGTAACATTATACT
GAAAACCTTGCTTGAGAAGGTTTTGGGACGCTCGAAGGCTTTAATTTGCG
GCCCTGCATTAATGAATCGGCCAACGCGCGGGGAGAGGCGGTTTGCGTAT
TGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCC
ACAGAATCAGGGGATAACGCAGGAAAGAACATGTGAGCAAAAGGCCAGCA
AAAGCCCAGGAACCGTAAAAAGGCCGCGTTGCTGGCGTTTTTCCATAGGC
TCCGCCCCCCTGACGAGCATCACAAAAATCGACGCTCAAGTCAGAGGTGG
CGAAACCCGACAGGACTATAAAGATACCAGGCGTTTCCCCCTGGAAGCTC
CCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTG
AGTCCAACCCGGTAAGACACGACTTATCGCCACTGGCAGCAGCCACTGGT
AACAGGATTAGCAGAGCGAGGTATGTAGGCGGTGCTACAGAGTTCTTGAA
GTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCA
GATTACGCGCAGAAAAAAGGATCTCAAGAAGATCCTTTGATCTTTTCTA
CGGGGTCTGACGCTCAGTGGAACGAAAACTCACGTTAAGGGATTTTGGTC
ATGAGATTATCAAAAGGATCTTCACCTAGATCCTTTTAAATTAAAAATG
AAGTTTTAAATCAATCTAAAGTATATATGAGTAAACTTGGTCTGACAGTT

FIGURE 16.3

ACCAATGCTTAATCAGTGAGGCACCTATCTCAGCGATCTGTCTATTTCGT
TCATCCATAGTTGCCTGACTCCCCGTCGTGTAGATAACTACGATACGGGA
GCGCTTACCATCTGGCCCCAGTGCTGCAATGATACCGCGAGACCCACGCT
CACCGGCTCCAGATTTATCAGCAATAAACCAGCCAGCCGGAAGGGCCGAG
CGCAGAAGTGGTCCTGCAACTTTATCCGCCTCCATTCAGTCTATTAATTG
TTGCCGGGAAGCTAGAGTAAGTAGTTCGCCAGTTAATAGTTTGCGCAACG
TTGTTGGCATTGCTACAGGCATCGTGGTGTCACTCTCGTCGTTTGGTATG
GCTTCATTCAGCTCCGGTTCCCAACGATCAAGGCGAGTTACATGATCCCC
CATGTTGTGCAAAAAGCGGTTAGCTCCTTCGGTCCTCCGATCGTTGTCA
GAAGTAAGTTGGCCGCAGTGTTATCACTCATGGTTATGGCAGCACTGCAT
AATTCTCTTACTGTCATGCCATCCGTAAGATGCTTTTCTGTGACTGGTGA
GTACTCAACCAAGTCATTCTGAGAATAGTGTATGCGGCGACCGAGTTGCT
CTTGCCCGGCGTCAATACGGGATAATAGTGTATCACATAGCAGAACTTTA
AAAGTGCTCATCATTGGAAAACGTTCTTCGGGGCGAAAACTCTCAAGGAT
CTTACCGCTGTTGAGATCCAGTTCGATGTAACCCACTCGTGCACCCAACT
GATCTTCAGCATCTTTTACTTTCACCAGCGTTTCTGGGTGAGCAAAAACA
GGAAGGCAAAATGCCGCAAAAAGGGAATAAGGGCGACACGGAAATGTTG
AATACTCATACTCTTCCTTTTTCAATGGGTAATAACTGATATAATTAAAT
TGAAGCTCTAATTTGTGAGTTTAGTATACATGCATTTACTTATAATACAG
TTTTTTAGTTTTGCTGGCCGCATCTTCTCAAATATGCTTCCCAGCCTGCT
TTTCTGTAACGTTCACCCTCTACCTTAGCATCCCTTCCCTTTGCAAATAG
TCCTCTTCCAACAATAATAATGTCAGATCCTGTAGAGACCACATCATCCA
CGGTTCTATACTGTTGACCCAATGCGTCTCCCTTGTCATCTAAACCCACA
CCGGGTGTCATAATCAACCAATCGTAACCTTCATCTCTTCCACCCATGTC
TCTTTGAGCAATAAAGCCGATAACAAAATCTTTGTCGCTCTTCGCAATGT
CAACAGTACCCTTAGTATATTCTCCAGTAGATAGGGAGCCCTTGCATGAC
AATTCTGCTAACATCAAAAGGCCTCTAGGTTCCTTTGTTACTTCTTCTGC
CGCCTGCTTCAAACCGCTAACAATACCTGGGCCCACCACACCGTGTGCAT
TCGTAATGTCTGCCCATTCTGCTATTCTGTATACACCCGCAGAGTACTGC
AATTTGACTGTATTACCAATGTCAGCAAATTTTCTGTCTTCGAAGAGTAA
AAAATTGTACTTGGCGGATAATGCCTTTAGCGGCTTAACTGTGCCCTCCA
TGGAAAAATCAGTCAAGATATCCACATGTGTTTTAGTAAACAAATTTTG
GGACCTAATGCTTCAACTAACTCCAGTAATTCCTTGGTGGTACGAACATC
CAATGAAGCACACAAGTTTGTTTGCTTTTCGTGCATGATATTAAATAGCT

FIGURE 16.4

```
TGGCAGCAACAGGACTAGGATGAGTAGCAGCACGTTCCTTATATGTAGCT
TTCGACATGATTTATCTTCGTTTCCTGCAGGTTTTTGTTCTGTGCAGTTG
GGTTAAGAATACTGGGCAATTTCATGTTTCTTCAACACTACATATGCGTA
TATATACCAATCTAAGTCTGTGCTCCTTCCTTCGTTCTTCCTTCTGTTCG
GAGATTACCGAATCAAAAAATTTCAAAGAAACCGAAATCAAAAAAAGA
ATAAAAAAAAATGATGAATTGAATTGAAAAGCTAGCTTATCGATGATAA
GCTGTCAAGATGAGAATTAATTCCACGGACTATAGACTATACTAGATAC
TCCGTCTACTGTACGATACACTTCCGCTCAGGTCCTTGTCCTTTAACGAG
GCCTTACCACTCTTTTGTTACTCTATTGATCCAGCTCAGCAAAGGCAGTG
TGATCTAAGATTCTATCTTCGCGATGTAGTAAAACTAGCTAGACCGAGAA
AGAGACTAGAAATGCAAAGGCACTTCTACAATGGCTGCCATCATTATTA
TCCGATGTGACGCTGCAGCTTCTCAATGATATTCGAATACGCTTTGAGGA
GATACAGCCTAATATCCGACAAACTGTTTTACAGATTTACGATCGTACTT
GTTACCCATCATTGAATTTTGAACATCCGAACCTGGGAGTTTTCCCTGAA
ACAGATAGTATATTTGAACCTGTATAATAATATATAGTCTAGCGCTTTAC
GGAAGACAATGTATGTATTTCGGTTCCTGGAGAAACTATTGCATCTATTG
CATAGGTAATCTTGCACGTCGCATCCCCGGTTCATTTTCTGCGTTTCCAT
CTTGCACTTCAATAGCATATCTTTGTTAACGAAGCATCTGTGCTTCATTT
TGTAGAACAAAATGCAACGCGAGAGCGCTAATTTTTCAAACAAAGAATC
TGAGCTGCATTTTTACAGAACAGAAATGCAACGCGAAAGCGCTATTTTAC
CAACGAAGAATCTGTGCTTCATTTTTGTAAAACAAAAATGCAACGCGACG
AGAGCGCTAATTTTTCAAACAAGAATCTGAGCTGCATTTTTACAGAACA
GAAATGCAACGCGAGAGCGCTATTTTACCAACAAAGAATCTATACTTCTT
TTTTGTTCTACAAAAATGCATCCCGAGAGCGCTATTTTTCTAACAAAGCA
TCTTAGATTACTTTTTTTCTCCTTTGTGCGCTCTATAATGCAGTCTCTTG
ATAACTTTTTGCACTGTAGGTCCGTTAAGGTTAGAAGAAGGCTACTTTGG
TGTCTATTTTCTCTTCCATAAAAAAAGCCTGACTCCACTTCCCGCGTTTA
CTGATTACTAGCGAAGCTGCGGGTGCATTTTTTCAAGATAAAGGCATCCC
CGATTATATTCTATACCGATGTGGATTGCGCATACTTTGTGAACAGAAAG
TGATAGCGTTGATGATTCTTCATTGGTCAGAAAATTATGAACGGTTTCTT
CTATTTTGTCTCTATATACTACGTATAGGAAATGTTTACATTTTCGTATT
GTTTTCGATTCACTCTATGAATAGTTCTTACTACAATTTTTTTGTCTAAA
GAGTAATACTAGAGATAAACATAAAAAATGTAGAGGTCGAGTTTAGATGC
AAGTTCAAGGAGCGAAAGGTGGATGGGTAGGTTATATAGGGATATAGCAC
```

FIGURE 16.5

AGAGATATATAGCAAAGAGATACTTTTGAGCAATGTTTGTGGAAGCGGTA
TTCGCAATGGGAAGCTCCACCCCGGTTGATAATCAGAAAAGCCCCAAAAA
CAGGAAGATTGTATAAGCAAATATTTAAATTGTAAACGTTAATATTTTGT
TAAAATTCGCGTTAAATTTTTGTTAAATCAGCTCATTTTTTAACGAATAG
CCCGAAATCGGCAAAATCCCTTATAAATCAAAAGAATAGACCGAGATAGG
GTTGAGTGTTGTTCCAGTTTCCAACAAGAGTCCACTATTAAAGAACGTGG
ACTCCAACGTCAAAGGGCGAAAAAGGGTCTATCAGGGCGATGGCCCACTA
CGTGAACCATCACCCTAATCAAGTTTTTTGGGGTCGAGGTGCCGTAAAGC
AGTAAATCGGAAGGGTAAACGGATGCCCCCATTTAGAGCTTGACGGGGAA
AGCCGGCGAACGTGGCGAGAAAGGAAGGGAAGAAAGCGAAAGGAGCGGGG
GCTAGGGCGGTGGGAAGTGTAGGGGTCACGCTGGGCGTAACCACCACACC
CGCCGCGCTTAATGGGGCGCTACAGGGCGCGTGGGATGATCCACTAGTA
CGGATTAGAAGCCGCCGAGCGGGTGACAGCCCTCCGAAGGAAGACTCTCC
TCCGTGCGTCCTCGTCCTCACCGGTCGCGTTCCTGAAACGCAGATGTGCC
TCGCGCCGCACTGCTCCGAACAATAAAGATTCTACAATACTAGCTTTTAT
GGTTATGAAGAGGAAAAATTGGCAGTAACCTGGCCCCACAAACCTTCAAA
TGAACGAATCAAATTAACAACCATAGGATGATAATGCGATTAGTTTTTTA
GCCTTATTTCTGGGGTAATTAATCAGCGAAGCGATGATTTTTGATCTATT
AACAGATATATAAATGCAAAAACTGCATTAACCACTTTAACTAATACTTT
CAACATTTTCGGTTTGTATTACTTCTTATTCAAATGTAATAAAAGTATCA
ACAAAAAATTGTTAATATACCTCTATACTTTAACGTCAAGGAGAAAAAAC
CCCGGATCGGACTACTAGCAGCTGTAATACGACTCACTATAGGGAATATT
AAGCTTGGTACCGAGCTCGGATCC

FIGURE 17.1

Minigenome γ sequence (pCM114)

| | |
|---|---|
| pYES2 vector : | Capital letter |
| Ribozymes Sequence : | Minuscule letter |
| Leader sequence : | Bold capital letter |
| Trailer sequence : | Bold italic capital letter |
| KANMX4 sequence : | Bold minuscule letter |
| pYES2 vector sequence: | Upper case letter | ccaactttgtttggtctgatgagtccgtgaggacgaaacccggagtcccg
ggtc**ACCAGACAAAGCTGGGAATAGAAACTTCGTATTTTCAAAGTTTTCT
TTAATATATTGCAAATAATGCCTAACCACCTAGGGCAGGATTAGGGTTCC
GGAGTTCAACCAATTAGTCCTTAATCAGGGCACTGTATCCGACTAACTTA
TACCAT**aaaatcttgctaggatacagttctcacatcacatccgaacataa
acaaccatgggtaaggaaaagactcacgtttcgaggccgcgattaaattc
caacatggatgctgatttatatgggtataaatgggctcgcgataatgtcg
ggcaatcaggtgcgacaatctatcgattgtatgggaagcccgatgcgcca
gagttgtttctgaaacatggcaaaggtagcgttgccaatgatgttacaga
tgagatggtcagactaaactggctgacggaatttatgcctcttccgacca
tcaagcatttatccgtactcctgatgatgcatggttactcaccactgcg
atccccggcaaaacagcattccaggtattagaagaatatcctgattcagg
tgaaaatattgttgatgcgctggcagtgttcctgcgccggttgcattcga
ttcctgtttgtaattgtccttttaacagcgatcgcgtatttcgtctcgct
caggcgcaatcacgaatgaataacggtttggttgatgcgagtgattttga
tgacgagcgtaatggctggcctgttgaacaagtctggaaagaaatgcata
agcttttgccattctcaccggattcagtcgtcactcatggtgatttctca
cttgataaccttatttttgacgaggggaaattaataggttgtattgatgt
tggacgagtcggaatcgcagaccgataccaggatcttgccatcctatgga
actgcctcggtgagttttctccttcattacagaaacggcttttcaaaaa
tatggtattgataatcctgatatgaataaattgcagtttcatttgatgct
cgatgagttttctaatcagtactgacaataaaaagattcttgttttcaa
gaacttgtcatttgtatagttttttatattgtagttgttctattttaat
caaatgttagcgtgatttatatttttttcgcctcgacatcatctgccca
gatgcgaagttaagtgcgcagaaagtaatatcatgcgtcaatcgtatgtg
aatgctggtcgctatactgctgtcgattcgatactaacgccgccatccag

FIGURE 17.2 tgtcgaaaacgagctcgaattcatcgatgat*CCATCTCGGATATCCCTAA*
*TCCTGCTCTTGTCCCTGATAATAGGATCTTGAATCCTAAGTGCACTAGAA*
*GATGATCATTGATTGAACTATCCTTACCCAACTTTGTTTGGT*ggccggca
tggtcccagcctcctcgctggcgccggctgggcaacattccgaggggacc
gtcccctcggtaatggcgaatgggacTCGAGCATGCATCTAGAGGGCCGC
ATCATGTAATTAGTTATGTCAC
GCTTACATTCACGCCCTCCCCCCACATCCGCTCTAACCGAAAAGGAAGGA
GTTAGACAACCTGAAGTCTAGGTCCCTATTTATTTTTTTATAGTTATGTT
AGTATTAAGAACGTTATTTATATTTCAAATTTTTCTTTTTTTTCTGTACA
GACGCGTGTACGCATGTAACATTATACTGAAAACCTTGCTTGAGAAGGTT
TTGGGACGCTCGAAGGCTTTAATTTGCGGCCCTGCATTAATGAATCGGCC
AACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGC
TCACTCAAAGGCGGTAATACGGTTATCCACAGAATCAGGGGATAACGCAG
GAAAGAACATGTGAGCAAAAGGCCAGCAAAAGCCCAGGAACCGTAAAAAG
GCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGA
CTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTAC
ACTAGAAGGACAGTATTTGGTATCTGCGCTCTGCTGAAGCCAGTTACCTT
CGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAA
CGAAAACTCACGTTAAGGGATTTTGGTCATGAGATTATCAAAAAGGATCT
TCACCTAGATCCTTTTAAATTAAAAATGAAGTTTTAAATCAATCTAAAGT
ATATATGAGTAAACTTGGTCTGACAGTTACCAATGCTTAATCAGTGAGGC
ACCTATCTCAGCGATCTGTCTATTTCGTTCATCCATAGTTGCCTGACTCC
CCGTCGTGTAGATAACTACGATACGGGAGCGCTTACCATCTGGCCCCAGT
GCTGCAATGATACCGCGAGACCCACGCTCACCGGCTCCAGATTTATCAGC

FIGURE 17.3

```
AATAAACCAGCCAGCCGGAAGGGCCGAGCGCAGAAGTGGTCCTGCAACTT
TATCCGCCTCCATTCAGTCTATTAATTGTTGCCGGGAAGCTAGAGTAAGT
AGTTCGCCAGTTAATAGTTTGCGCAACGTTGTTGGCATTGCTACAGGCAT
CGTGGTGTCACTCTCGTCGTTTGGTATGGCTTCATTCAGCTCCGGTTCCC
AACGATCAAGGCGAGTTACATGATCCCCATGTTGTGCAAAAAAGCGGTT
AGCTCCTTCGGTCCTCCGATCGTTGTCAGAAGTAAGTTGGCCGCAGTGTT
ATCACTCATGGTTATGGCAGCACTGCATAATTCTCTTACTGTCATGCCAT
CCGTAAGATGCTTTTCTGTGACTGGTGAGTACTCAACCAAGTCATTCTGA
GAATAGTGTATGCGGCGACCGAGTTGCTCTTGCCCGGCGTCAATACGGGA
TAATAGTGTATCACATAGCAGAACTTTAAAAGTGCTCATCATTGGAAAAC
GTTCTTCGGGGCGAAAACTCTCAAGGATCTTACCGCTGTTGAGATCCAGT
TCGATGTAACCCACTCGTGCACCCAACTGATCTTCAGCATCTTTTACTTT
CACCAGCGTTTCTGGGTGAGCAAAAACAGGAAGGCAAAATGCCGCAAAAA
AGGGAATAAGGGCGACACGGAAATGTTGAATACTCATACTCTTCCTTTTT
CAATGGGTAATAACTGATATAATTAAATTGAAGCTCTAATTTGTGAGTTT
AGTATACATGCATTTACTTATAATACAGTTTTTTAGTTTTGCTGGCCGCA
TCTTCTCAAATATGCTTCCCAGCCTGCTTTTCTGTAACGTTCACCCTCTA
CCTTAGCATCCCTTCCCTTTGCAAATAGTCCTCTTCCAACAATAATAATG
TCAGATCCTGTAGAGACCACATCATCCACGGTTCTATACTGTTGACCCAA
TGCGTCTCCCTTGTCATCTAAACCCACACCGGGTGTCATAATCAACCAAT
CGTAACCTTCATCTCTTCCACCCATGTCTCTTTGAGCAATAAAGCCGATA
ACAAAATCTTTGTCGCTCTTCGCAATGTCAACAGTACCCTTAGTATATTC
TCCAGTAGATAGGGAGCCCTTGCATGACAATTCTGCTAACATCAAAAGGC
CTCTAGGTTCCTTTGTTACTTCTTCTGCCGCCTGCTTCAAACCGCTAACA
ATACCTGGGCCCACCACACCGTGTGCATTCGTAATGTCTGCCCATTCTGC
TATTCTGTATACACCCGCAGAGTACTGCAATTTGACTGTATTACCAATGT
CAGCAAATTTTCTGTCTTCGAAGAGTAAAAAATTGTACTTGGCGGATAAT
GCCTTTAGCGGCTTAACTGTGCCCTCCATGGAAAAATCAGTCAAGATATC
CACATGTGTTTTAGTAAACAAATTTTGGGACCTAATGCTTCAACTAACT
CCAGTAATTCCTTGGTGGTACGAACATCCAATGAAGCACACAAGTTTGTT
TGCTTTTCGTGCATGATATTAAATAGCTTGGCAGCAACAGGACTAGGATG
AGTAGCAGCACGTTCCTTATATGTAGCTTTCGACATGATTTATCTTCGTT
TCCTGCAGGTTTTTGTTCTGTGCAGTTGGGTTAAGAATACTGGGCAATTT
CATGTTTCTTCAACACTACATATGCGTATATATACCAATCTAAGTCTGTG
```

FIGURE 17.4

CTCCTTCCTTCGTTCTTCCTTCTGTTCGGAGATTACCGAATCAAAAAAAT
TTCAAAGAAACCGAAATCAAAAAAAGAATAAAAAAAAAATGATGAATTG
AATTGAAAGCTAGCTTATCGATGATAAGCTGTCAAAGATGAGAATTAAT
TCCACGGACTATAGACTATACTAGATACTCCGTCTACTGTACGATACACT
TCCGCTCAGGTCCTTGTCCTTTAACGAGGCCTTACCACTCTTTTGTTACT
CTATTGATCCAGCTCAGCAAAGGCAGTGTGATCTAAGATTCTATCTTCGC
GATGTAGTAAAACTAGCTAGACCGAGAAAGAGACTAGAAATGCAAAGGC
ACTTCTACAATGGCTGCCATCATTATTATCCGATGTGACGCTGCAGCTTC
TCAATGATATTCGAATACGCTTTGAGGAGATACAGCCTAATATCCGACAA
ACTGTTTTACAGATTTACGATCGTACTTGTTACCCATCATTGAATTTTGA
ACATCCGAACCTGGGAGTTTTCCCTGAAACAGATAGTATATTTGAACCTG
TATAATAATATATAGTCTAGCGCTTTACGGAAGACAATGTATGTATTTCG
GTTCCTGGAGAAACTATTGCATCTATTGCATAGGTAATCTTGCACGTCGC
ATCCCCGGTTCATTTTCTGCGTTTCCATCTTGCACTTCAATAGCATATCT
TTGTTAACGAAGCATCTGTGCTTCATTTTGTAGAACAAAAATGCAACGCG
AGAGCGCTAATTTTTCAAACAAAGAATCTGAGCTGCATTTTTACAGAACA
GAAATGCAACGCGAAAGCGCTATTTTACCAACGAAGAATCTGTGCTTCAT
TTTTGTAAAACAAAATGCAACGCGACGAGAGCGCTAATTTTTCAAACAA
AGAATCTGAGCTGCATTTTTACAGAACAGAAATGCAACGCGAGAGCGCTA
TTTTACCAACAAAGAATCTATACTTCTTTTTTGTTCTACAAAAATGCATC
CCGAGAGCGCTATTTTTCTAACAAAGCATCTTAGATTACTTTTTTTCTCC
TTTGTGCGCTCTATAATGCAGTCTCTTGATAACTTTTTGCACTGTAGGTC
CGTTAAGGTTAGAAGAAGGCTACTTTGGTGTCTATTTTCTCTTCCATAAA
AAAAGCCTGACTCCACTTCCCGCGTTTACTGATTACTAGCGAAGCTGCGG
GTGCATTTTTTCAAGATAAAGGCATCCCCGATTATATTCTATACCGATGT
GGATTGCGCATACTTTGTGAACAGAAGTGATAGCGTTGATGATTCTTCA
TTGGTCAGAAAATTATGAACGGTTTCTTCTATTTTGTCTCTATATACTAC
GTATAGGAAATGTTTACATTTTCGTATTGTTTTCGATTCACTCTATGAAT
AGTTCTTACTACAATTTTTTTGTCTAAAGAGTAATACTAGAGATAAACAT
AAAAAATGTAGAGGTCGAGTTTAGATGCAAGTTCAAGGAGCGAAAGGTGG
ATGGGTAGGTTATATAGGGATATAGCACAGAGATATATAGCAAAGAGATA
CTTTTGAGCAATGTTTGTGGAAGCGGTATTCGCAATGGGAAGCTCCACCC
CGGTTGATAATCAGAAAGCCCCAAAAACAGGAAGATTGTATAAGCAAAT
ATTTAAATTGTAAACGTTAATATTTTGTTAAAATTCGCGTTAAATTTTTG

FIGURE 17.5

TTAAATCAGCTCATTTTTTAACGAATAGCCCGAAATCGGCAAAATCCCTT
ATAAATCAAAAGAATAGACCGAGATAGGGTTGAGTGTTGTTCCAGTTTCC
AACAAGAGTCCACTATTAAAGAACGTGGACTCCAACGTCAAAGGGCGAAA
AAGGGTCTATCAGGGCGATGGCCCACTACGTGAACCATCACCCTAATCAA
GTTTTTTGGGGTCGAGGTGCCGTAAAGCAGTAAATCGGAAGGGTAAACGG
ATGCCCCATTTAGAGCTTGACGGGGAAAGCCGGCGAACGTGGCGAGAAA
GGAAGGGAAGAAAGCGAAAGGAGCGGGGGCTAGGGCGGTGGGAAGTGTAG
GGGTCACGCTGGGCGTAACCACCACACCCGCCGCGCTTAATGGGGCGCTA
CAGGGCGCGTGGGGATGATCCACTAGTACGGATTAGAAGCCGCCGAGCGG
GTGACAGCCCTCCGAAGGAAGACTCTCCTCCGTGCGTCCTCGTCCTCACC
GGTCGCGTTCCTGAAACGCAGATGTGCCTCGCCGCACTGCTCCAACA
ATAAAGATTCTACAATACTAGCTTTTATGGTTATGAAGAGGAAAAATTGG
CAGTAACCTGGCCCCACAAACCTTCAAATGAACGAATCAAATTAACAACC
ATAGGATGATAATGCGATTAGTTTTTTAGCCTTATTTCTGGGGTAATTAA
TCAGCGAAGCGATGATTTTTGATCTATTAACAGATATATAAATGCAAAAA
CTGCATTAACCACTTTAACTAATACTTTCAACATTTTCGGTTTGTATTAC
TTCTTATTCAAATGTAATAAAAGTATCAACAAAAAATTGTTAATATACCT
CTATACTTTAACGTCAAGGAGAAAAAACCCCGGATCGGACTACTAGCAGC
TGTAATACGACTCACTATAGGGAATATTAAGCTTGGTACCGAGCTCGGAT
CCACTAGTAACGGCCGCCAGTGTGCTGGAATTCTGCAGATATCCATCACA
CTGGCGGCCGCATCCGGATATAGTTCCTCCTTTCAGCAAAAAACCCCTCA
AGACCCGTTTAGAGGCCCCAAGGGGTTATGCTAGTTATTGCTCAGCGGTG
GCAGCAGCCAACTCAGCTTCCTTTCGGGCTTTGTTAGCAGCCGGATCGGC
CGC

FIGURE 18.1

Minigenome δ sequence (pCM115)

| | |
|---|---|
| pYES2 vector : | Capital letter |
| Ribozymes Sequence : | Minuscule letter |
| Leader sequence : | Bold capital letter |
| Trailer sequence : | Bold italic capital letter |
| KANMX4 sequence : | Bold minuscule letter |
| pYES2 vector sequence: | Upper case letter | ccaactttgtttggtctgatgagtccgtgaggacgaaacccggagtcccg
ggtc**ACCAAACAAAGTTGGGTAAGGATAGTTCAATCAATGATCATCTTCT
AGTGCACTTAGGATTCAAGATCCTATTATCAGGGACAAGAGCAGGATTAG
GGATATCCGAGATGG**atcatcgatgaattcgagctcgttttcgacactgg
atggcggcgttagtatcgaatcgacagcagtatagcgaccagcattcaca
tacgattgacgcatgatattactttctgcgcacttaacttcgcatctggg
cagatgatgtcgaggcgaaaaaaatataaatcacgctaacatttgatta
aaatagaacaactacaatataaaaaactatacaaatgacaagttcttga
aaacaagaatcttttattgtcagtactgattagaaaaactcatcgagca
tcaaatgaaactgcaatttattcatatcaggattatcaataccatatttt
tgaaaaagccgtttctgtaatgaaggagaaaactcaccgaggcagttcca
taggatggcaagatcctggtatcggtctgcgattccgactcgtccaacat
caatacaacctattaatttccctcgtcaaaataaggttatcaagtgag
aaatcaccatgagtgacgactgaatccggtgagaatggcaaaagcttatg
catttctttccagacttgttcaacaggccagccattacgctcgtcatcaa
aatcactcgcatcaaccaaaccgttattcattcgtgattgcgcctgagcg
agacgaaatacgcgatcgctgttaaaaggacaattacaaacaggaatcga
atgcaaccggcgcaggaacactgccagcgcatcaacaatattttcacctg
aatcaggatattcttctaatacctggaatgctgttttgccggggatcgca
gtggtgagtaaccatgcatcatcaggagtacggataaaatgcttgatggt
cggaagaggcataaattccgtcagccagtttagtctgaccatctcatctg
taacatcattggcaacgctacctttgccatgtttcagaaacaactctggc
gcatcgggcttcccatacaatcgatagattgtcgcacctgattgcccgac
attatcgcgagcccatttatacccatataaatcagcatccatgttggaat
ttaatcgcggcctcgaaacgtgagtcttttccttacccatggttgtttat
gttcggatgtgatgtgagaactgtatcctagcaagatttt*ATGGTATAAG*

FIGURE 18.2

*TTAGTCGGATACAGTGCCCTGATTAAGGACTAATTGGTTGAACTCCGGAA*
*CCCTAATCCTGCCCTAGGTGGTTAGGCATTATTTGCAATATATTAAAGAA*
*AACTTTGAAAATACGAAGTTTCTATTCCCAGCTTTGTCTGGT*ggccggca
tggtcccagcctcctcgctggcgccggctgggcaacattccgaggggacc
gtcccctcggtaatggcgaatgggacGCGGCCGATCCGGCTGCTAACAAA
GCCCGAAAGGAAGCTGAGTTGGCTGCTGCCACCGCTGAGCAATAACTAGC
ATAACCCCTTGGGGCCTCTAAACGGGTCTTGAGGGGTTTTTTGCTGAAAG
GAGGAACTATATCCGGATGCGGCCGCTCGAGCATGCATCTAGAGGGCCGC
ATCATGTAATTAGTTATGTCACGCTTACATTCACGCCCTCCCCCCACATC
CGCTCTAACCGAAAAGGAAGGAGTTAGACAACCTGAAGTCTAGGTCCCTA
TTTATTTTTTATAGTTATGTTAGTATTAAGAACGTTATTTATATTTCAA
ATTTTTCTTTTTTTTCTGTACAGACGCGTGTACGCATGTAACATTATACT
GAAAACCTTGCTTGAGAAGGTTTTGGGACGCTCGAAGGCTTTAATTTGCG
GCCCTGCATTAATGAATCGGCCAACGCGCGGGGAGAGGCGGTTTGCGTAT
TGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCC
ACAGAATCAGGGGATAACGCAGGAAAGAACATGTGAGCAAAAGGCCAGCA
AAAGCCCAGGAACCGTAAAAAGGCCGCGTTGCTGGCGTTTTTCCATAGGC
TCCGCCCCCTGACGAGCATCACAAAAATCGACGCTCAAGTCAGAGGTGG
CGAAACCCGACAGGACTATAAAGATACCAGGCGTTTCCCCCTGGAAGCTC
CCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTG
AGTCCAACCCGGTAAGACACGACTTATCGCCACTGGCAGCAGCCACTGGT
AACAGGATTAGCAGAGCGAGGTATGTAGGCGGTGCTACAGAGTTCTTGAA
GTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCA
GATTACGCGCAGAAAAAAGGATCTCAAGAAGATCCTTTGATCTTTTCTA
CGGGGTCTGACGCTCAGTGGAACGAAAACTCACGTTAAGGGATTTTGGTC
ATGAGATTATCAAAAGGATCTTCACCTAGATCCTTTTAAATTAAAAATG
AAGTTTTAAATCAATCTAAAGTATATATGAGTAAACTTGGTCTGACAGTT
ACCAATGCTTAATCAGTGAGGCACCTATCTCAGCGATCTGTCTATTTCGT

FIGURE 18.3

TCATCCATAGTTGCCTGACTCCCCGTCGTGTAGATAACTACGATACGGGA
GCGCTTACCATCTGGCCCCAGTGCTGCAATGATACCGCGAGACCCACGCT
CACCGGCTCCAGATTTATCAGCAATAAACCAGCCAGCCGGAAGGGCCGAG
CGCAGAAGTGGTCCTGCAACTTTATCCGCCTCCATTCAGTCTATTAATTG
TTGCCGGGAAGCTAGAGTAAGTAGTTCGCCAGTTAATAGTTTGCGCAACG
TTGTTGGCATTGCTACAGGCATCGTGGTGTCACTCTCGTCGTTTGGTATG
GCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCAT
AATTCTCTTACTGTCATGCCATCCGTAAGATGCTTTTCTGTGACTGGTGA
GTACTCAACCAAGTCATTCTGAGAATAGTGTATGCGGCGACCGAGTTGCT
CTTGCCCGGCGTCAATACGGGATAATAGTGTATCACATAGCAGAACTTTA
AAAGTGCTCATCATTGGAAAACGTTCTTCGGGGCGAAAACTCTCAAGGAT
CTTACCGCTGTTGAGATCCAGTTCGATGTAACCCACTCGTGCACCCAACT
GATCTTCAGCATCTTTTACTTTCACCAGCGTTTCTGGGTGAGCAAAAACA
GGAAGGCAAAATGCCGCAAAAAGGGAATAAGGGCGACACGGAAATGTTG
AATACTCATACTCTTCCTTTTTCAATGGGTAATAACTGATATAATTAAAT
TGAAGCTCTAATTTGTGAGTTTAGTATACATGCATTTACTTATAATACAG
TTTTTTAGTTTTGCTGGCCGCATCTTCTCAAATATGCTTCCCAGCCTGCT
TTTCTGTAACGTTCACCCTCTACCTTAGCATCCCTTCCCTTTGCAAATAG
TCCTCTTCCAACAATAATAATGTCAGATCCTGTAGAGACCACATCATCCA
CGGTTCTATACTGTTGACCCAATGCGTCTCCCTTGTCATCTAAACCCACA
CCGGGTGTCATAATCAACCAATCGTAACCTTCATCTCTTCCACCCATGTC
TCTTTGAGCAATAAAGCCGATAACAAAATCTTTGTCGCTCTTCGCAATGT
CAACAGTACCCTTAGTATATTCTCCAGTAGATAGGGAGCCCTTGCATGAC
AATTCTGCTAACATCAAAAGGCCTCTAGGTTCCTTTGTTACTTCTTCTGC
CGCCTGCTTCAAACCGCTAACAATACCTGGGCCCACCACACCGTGTGCAT
TCGTAATGTCTGCCCATTCTGCTATTCTGTATACACCCGCAGAGTACTGC
AATTTGACTGTATTACCAATGTCAGCAAATTTTCTGTCTTCGAAGAGTAA
AAAATTGTACTTGGCGGATAATGCCTTTAGCGGCTTAACTGTGCCCTCCA
TGGAAAAATCAGTCAAGATATCCACATGTGTTTTAGTAAACAAATTTTG
GGACCTAATGCTTCAACTAACTCCAGTAATTCCTTGGTGGTACGAACATC
CAATGAAGCACACAAGTTTGTTTGCTTTTCGTGCATGATATTAAATAGCT
TGGCAGCAACAGGACTAGGATGAGTAGCAGCACGTTCCTTATATGTAGCT

FIGURE 18.4

TTCGACATGATTTATCTTCGTTTCCTGCAGGTTTTTGTTCTGTGCAGTTG
GGTTAAGAATACTGGGCAATTTCATGTTTCTTCAACACTACATATGCGTA
TATATACCAATCTAAGTCTGTGCTCCTTCCTTCGTTCTTCCTTCTGTTCG
GAGATTACCGAATCAAAAAAATTTCAAAGAAACCGAAATCAAAAAAAGA
ATAAAAAAAAAATGATGAATTGAATTGAAAAGCTAGCTTATCGATGATAA
GCTGTCAAAGATGAGAATTAATTCCACGGACTATAGACTATACTAGATAC
TCCGTCTACTGTACGATACACTTCCGCTCAGGTCCTTGTCCTTTAACGAG
GCCTTACCACTCTTTTGTTACTCTATTGATCCAGCTCAGCAAAGGCAGTG
TGATCTAAGATTCTATCTTCGCGATGTAGTAAAACTAGCTAGACCGAGAA
AGAGACTAGAAATGCAAAAGGCACTTCTACAATGGCTGCCATCATTATTA
TCCGATGTGACGCTGCAGCTTCTCAATGATATTCGAATACGCTTTGAGGA
GATACAGCCTAATATCCGACAAACTGTTTTACAGATTTACGATCGTACTT
GTTACCCATCATTGAATTTTGAACATCCGAACCTGGGAGTTTTCCCTGAA
ACAGATAGTATATTTGAACCTGTATAATAATATATAGTCTAGCGCTTTAC
GGAAGACAATGTATGTATTTCGGTTCCTGGAGAAACTATTGCATCTATTG
CATAGGTAATCTTGCACGTCGCATCCCCGGTTCATTTCTGCGTTTCCAT
CTTGCACTTCAATAGCATATCTTTGTTAACGAAGCATCTGTGCTTCATTT
TGTAGAACAAAAATGCAACGCGAGAGCGCTAATTTTTCAAACAAAGAATC
TGAGCTGCATTTTTACAGAACAGAAATGCAACGCGAAAGCGCTATTTTAC
CAACGAAGAATCTGTGCTTCATTTTTGTAAAACAAAAATGCAACGCGACG
AGAGCGCTAATTTTTCAAACAAAGAATCTGAGCTGCATTTTTACAGAACA
GAAATGCAACGCGAGAGCGCTATTTTACCAACAAAGAATCTATACTTCTT
TTTTGTTCTACAAAAATGCATCCCGAGAGCGCTATTTTTCTAACAAAGCA
TCTTAGATTACTTTTTTTCTCCTTTGTGCGCTCTATAATGCAGTCTCTTG
ATAACTTTTTGCACTGTAGGTCCGTTAAGGTTAGAAGAAGGCTACTTTGG
TGTCTATTTTCTCTTCCATAAAAAAAGCCTGACTCCACTTCCCGCGTTTA
CTGATTACTAGCGAAGCTGCGGGTGCATTTTTTCAAGATAAAGGCATCCC
CGATTATATTCTATACCGATGTGGATTGCGCATACTTTGTGAACAGAAAG
TGATAGCGTTGATGATTCTTCATTGGTCAGAAAATTATGAACGGTTTCTT
CTATTTTGTCTCTATATACTACGTATAGGAAATGTTTACATTTTCGTATT
GTTTTCGATTCACTCTATGAATAGTTCTTACTACAATTTTTTTGTCTAAA
GAGTAATACTAGAGATAAACATAAAAAATGTAGAGGTCGAGTTTAGATGC
AAGTTCAAGGAGCGAAAGGTGGATGGGTAGGTTATATAGGGATATAGCAC
AGAGATATATAGCAAAGAGATACTTTTGAGCAATGTTTGTGGAAGCGGTA

FIGURE 18.5

TTCGCAATGGGAAGCTCCACCCCGGTTGATAATCAGAAAAGCCCCAAAAA
CAGGAAGATTGTATAAGCAAATATTTAAATTGTAAACGTTAATATTTTGT
TAAAATTCGCGTTAAATTTTTGTTAAATCAGCTCATTTTTTAACGAATAG
CCCGAAATCGGCAAAATCCCTTATAAATCAAAAGAATAGACCGAGATAGG
GTTGAGTGTTGTTCCAGTTTCCAACAAGAGTCCACTATTAAAGAACGTGG
ACTCCAACGTCAAAGGGCGAAAAAGGGTCTATCAGGGCGATGGCCCACTA
CGTGAACCATCACCCTAATCAAGTTTTTGGGGTCGAGGTGCCGTAAAGC
AGTAAATCGGAAGGGTAAACGGATGCCCCATTTAGAGCTTGACGGGGAA
AGCCGGCGAACGTGGCGAGAAAGGAAGGGAAGAAAGCGAAAGGAGCGGGG
GCTAGGGCGGTGGGAAGTGTAGGGGTCACGCTGGGCGTAACCACCACACC
CGCCGCGCTTAATGGGGCGCTACAGGGCGCGTGGGGATGATCCACTAGTA
CGGATTAGAAGCCGCCGAGCGGGTGACAGCCCTCCGAAGGAAGACTCTCC
TCCGTGCGTCCTCGTCCTCACCGGTCGCGTTCCTGAAACGCAGATGTGCC
TCGCGCCGCACTGCTCCGAACAATAAGATTCTACAATACTAGCTTTTAT
GGTTATGAAGAGGAAAAATTGGCAGTAACCTGGCCCCACAAACCTTCAAA
TGAACGAATCAAATTAACAACCATAGGATGATAATGCGATTAGTTTTTA
GCCTTATTTCTGGGGTAATTAATCAGCGAAGCGATGATTTTGATCTATT
AACAGATATATAAATGCAAAACTGCATTAACCACTTTAACTAATACTTT
CAACATTTTCGGTTTGTATTACTTCTTATTCAAATGTAATAAAAGTATCA
ACAAAAATTGTTAATATACCTCTATACTTTAACGTCAAGGAGAAAAAAC
CCCGGATCGGACTACTAGCAGCTGTAATACGACTCACTATAGGGAATATT
AAGCTTGGTACCGAGCTCGGATCC

FIGURE 19.1

**Minigenome based *CAN1* sequence (pCM224)**

| | |
|---|---|
| pYES2 vector : | Capital letter |
| Ribozymes Sequence : | Minuscule letter |
| Leader sequence : | Bold capital letter |
| Trailer sequence : | Bold italic capital letter |
| *CAN1* sequence : | Bold minuscule letter |
| *ADE2* sequence : | Minuscule italic letter | ccaactttgtttggtctgatgagtccgtgaggacgaaacccggagtcccg
ggtcACCAGACAAAGCTGGGAATAGAAACTTCGTATTTTCAAAGTTTTCT
TTAATATATTGCAAATAATGCCTAACCACCTAGGGCAGGATTAGGGTTCC
GGAGTTCAACCAATTAGTCCTTAATCAGGGCACTGTATCCGACTAACTTA
TACCATatcatcgatgaattcgagctcatgacaaattcaaaagaagacgc
cgacatagaggagaagcatatgtacaatgagccggtcacaaccctctttc
acgacgttgaagcttcacaaacacaccacagacgtgggtcaataccattg
aaagatgagaaaagtaaagaattgtatccattgcgctctttcccgacgag
agtaaatggcgaggatacgttctctatggaggatggcataggtgatgaag
atgaaggagaagtacagaacgctgaagtgaagagagagcttaagcaaaga
catattggtatgattgcccttggtggtactattggtacaggtcttttcat
tggtttatccacacctctgaccaacgccggcccagtgggcgctcttatat
catatttatttatgggttctttggcatattctgtcacgcagtccttgggt
gaaatggctacattcatccctgttacatcctctttcacagttttctcaca
aagattcctttctccagcatttggtgcggccaatggttacatgtattggt
tttcttgggcaatcacttttgccctggaacttagtgtagttggccaagtc
attcaattttggacgtacaaagttccactggcggcatggattagtatttt
ttgggtaattatcacaataatgaacttgttccctgtcaaatattacggtg
aattcgagttctgggtcgcttccatcaaagttttagccattatcgggttt
ctaatatactgttttgtatggtttgtggtgctggggttaccggcccagt
tggattccgttattggagaaacccaggtgcctggggtccaggtataatat
ctaaggataaaacgaagggaggttcttaggttgggtttcctctttgatt
aacgctgccttcacatttcaaggtactgaactagttggtatcactgctgg
tgaagctgcaaacccagaaaatccgttccaagagccatcaaaaaagttg
ttttccgtatcttaaccttctacattggctctctattattcattggactt
ttagttccatacaatgaccctaaactaacacaatctacttcctacgtttc

FIGURE 19.2 tacttctccctttattattgctattgagaactctggtacaaaggttttgc
cacatatcttcaacgctgttatcttaacaaccattatttctgccgcaaat
tcaaatatttacgttggttcccgtattttatttggtctatcaaagaacaa
gttggctcctaaattcctgtcaaggaccaccaaaggtggtgttccataca
ttgcagttttcgttactgctgcatttggcgctttggcttacatggagaca
tctactggtggtgacaaagttttcgaatggctattaaatatcactggtgt
tgcaggcttttttgcatggttatttatctcaatctcgcacatcagattta
tgcaagctttgaaataccgtggcatctctcgtgacgagttaccatttaaa
gctaaattaatgcccggcttggcttattatgcggccacatttatgacgat
cattatcattattcaaggtttcacggcttttgcaccaaaattcaatggtg
ttagctttgctgccgcctatatctctatttcctgttcttagctgtttgg
atcttatttcaatgcatattcagatgcagatttatttggaagattggaga
tgtcgacatcgattccgatagaagagacattgaggcaattgtatgggaag
atcatgaaccaaagacttttttgggacaaatttttggaatgttgtagcatag
tccatggttgtttatgttcggatgtgatgtgagaactgtatcctagcaag
atttt*CCATCTCGGATATCCCTAATCCTGCTCTTGTCCCTGATAATAGGA*
*TCTTGAATCCTAAGTGCACTAGAAGATGATCATTGATTGAACTATCCTTA*
*CCCAACTTTGTTTGGT*ggccggcatggtcccagcctcctcgctggcgccg
gctgggcaacattccgaggggaccgtcccctcggtaatggcgaatgggac
TCGAGCATGCATCTAGAGGGCCGCATCATGTAATTAGTTATGTCACGCTT
ACATTCACGCCCTCCCCCCACATCCGCTCTAACCGAAAAGGAAGGAGTTA
GACAACCTGAAGTCTAGGTCCCTATTTATTTTTTTATAGTTATGTTAGTA
TTAAGAACGTTATTTATATTTCAAATTTTTCTTTTTTTTCTGTACAGACG
CGTGTACGCATGTAACATTATACTGAAAACCTTGCTTGAGAAGGTTTTGG
GACGCTCGAAGGCTTTAATTTGCGGCCCTGCATTAATGAATCGGCCAACG
CGCGGGGAGAGGCGGTTTGCGTATTGGGCGCTCTTCCGCTTCCTCGCTCA
CTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAA
GAACATGTGAGCAAAAGGCCAGCAAAAGCCCAGGAACCGTAAAAAGGCCG
CGTTGCTGGCGTTTTTCCATAGGCTCCGCCCCCCTGACGAGCATCACAAA
AATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCG

FIGURE 19.3

CTCCAAGCTGGGCTGTGTGCACGAACCCCCCGTTCAGCCCGACCGCTGCG
CCTTATCCGGTAACTATCGTCTTGAGTCCAACCCGGTAAGACACGACTTA
TCGCCACTGGCAGCAGCCACTGGTAACAGGATTAGCAGAGCGAGGTATGT
AGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAA
AACTCACGTTAAGGGATTTTGGTCATGAGATTATCAAAAAGGATCTTCAC
CTAGATCCTTTTAAATTAAAAATGAAGTTTTAAATCAATCTAAAGTATAT
ATGAGTAAACTTGGTCTGACAGTTACCAATGCTTAATCAGTGAGGCACCT
ATCTCAGCGATCTGTCTATTTCGTTCATCCATAGTTGCCTGACTCCCCGT
CGTGTAGATAACTACGATACGGGAGCGCTTACCATCTGGCCCCAGTGCTG
CAATGATACCGCGAGACCCACGCTCACCGGCTCCAGATTTATCAGCAATA
AACCAGCCAGCCGGAAGGGCCGAGCGCAGAAGTGGTCCTGCAACTTTATC
CGCCTCCATTCAGTCTATTAATTGTTGCCGGGAAGCTAGAGTAAGTAGTT
CGCCAGTTAATAGTTTGCGCAACGTTGTTGGCATTGCTACAGGCATCGTG
GTGTCACTCTCGTCGTTTGGTATGGCTTCATTCAGCTCCGGTTCCCAACG
ATCAAGGCGAGTTACATGATCCCCATGTTGTGCAAAAAGCGGTTAGCT
CCTTCGGTCCTCCGATCGTTGTCAGAAGTAAGTTGGCCGCAGTGTTATCA
CTCATGGTTATGGCAGCACTGCATAATTCTCTTACTGTCATGCCATCCGT
AAGATGCTTTTCTGTGACTGGTGAGTACTCAACCAAGTCATTCTGAGAAT
AGTGTATGCGGCGACCGAGTTGCTCTTGCCCGGCGTCAATACGGGATAAT
AGTGTATCACATAGCAGAACTTTAAAAGTGCTCATCATTGGAAAACGTTC
TTCGGGGCGAAAACTCTCAAGGATCTTACCGCTGTTGAGATCCAGTTCGA
TGTAACCCACTCGTGCACCCAACTGATCTTCAGCATCTTTTACTTTCACC
AGCGTTTCTGGGTGAGCAAAAACAGGAAGGCAAAATGCCGCAAAAAGGG
AATAAGGGCGACACGGAAATGTTGAATACTCATACTCTTCCTTTTTCAAT
GGGTAATAACTGATATAATTAAATTGAAGCTCTAATTTGTGAGTTTAGTA
TACATGCATTTACTTATAATACAGTTTTTTAGTTTTGCTGGCCGCATCTT
CTCAAATATGCTTCCCAGCCTGCTTTTCTGTAACGTTCACCCTCTACCTT
AGCATCCCTTCCCTTTGCAAATAGTCCTCTTCCAACAATAATAATGTCAG
ATCCTGTAGAGACCACATCATCCACGGTTCTATACTGTTGACCCAATGCG
TCTCCCTTGTCATCTAAACCCACACCGGGTGTCATAATCAACCAATCGTA

FIGURE 19.4

ACCTTCATCTCTTCCACCCATGTCTCTTTGAGCAATAAAGCCGATAACAA
AATCTTTGTCGCTCTTCGCAATGTCAACAGTACCCTTAGTATATTCTCCA
GTAGATAGGGAGCCCTTGCATGACAATTCTGCTAACATCAAAAGGCCTCT
AGGTTCCTTTGTTACTTCTTCTGCCGCCTGCTTCAAACCGCTAACAATAC
CTgggcccttgcttcttgttactggatatgtatgtatgtataataagtga
tcttatgtatgaaattcttaaaaaaggacacctgtaagcgttgatttcta
tgtatgaagtccacatttgatgtaatcataacaaagcctaaaaaataggt
atatcattttataattatttgctgtacaagtatatcaataaacttatata
ttacttgttttctagataagcttcgtaaccgacagtttctaacttttgtg
ctttgacaagaacttcttcttcttgctttaataaaaactgttccattttc
gttgtataacttgaatcataagcgccaagcagtctgacagccaacagcgc
agcgttcgtactattattaatagcgacggtagctactggaacacctctag
gcatttgcacaattgaatgtaaagaatctactccatctagacaagaacct
tttacgggcacaccgatgacaggaagtggtgtcattgcagccaccatacc
tggcaagtgagcagccccaccagctccagcgataattgtttttaattccac
gcttgcttgcggaaatagcatatgctgacatcctatgtggagttctatga
gcagagactattgtcacttcaaatggaacgccaaaatcttttaaaaccgc
acatgcggcagacattaccggcaagtcagagtctgatcccatgatgattc
caaccaatggtttgaccattgcttccaagtccaactttgagcgacagag
attttgattggaatatcagttctacctgtaatgtagttcagcctttgttc
acattccgccatactggaggcaataatatttatgtgacctacttttctgt
taggtctagactcttttccatataagtacactgaggaacctggagtcgcc
aatgctctttcgcaagtttctagctctttatctttgtatgtttgtctcc
aagaacatttagcataatggcgttcgttgtaatggtggagaaagatgtga
aattctttggcattggcaaatccaatattgatctcaaatgagcttcaaat
tgagaagtgacgcaagcatcaatggtataatgtccagagttgtgaggcct
tggggcaatttcgttaataagcaattcccctgtttctaaatagaacattt
ccacaccaaatataccacaaccgggaaaagatttgattgcattttctgcc
aacaacttcgccttaagttgaacggagtccggaactctagcaggcgcata
acataagtcacaaatattgtccttgtggatagtctctacaattgggtaag
aaaacactaaaccgttaacagatctcacaatcatgactgctaattcttta
gtaaatggtgcccattttcggcgtacaaggacgatccttcagtacttc
caaagcttccggaatcatttccttattctttacaacgaagttacctcttc
catcgtatgccaaagtcctcgacttcaagacgaatggaaaacccaaatct

FIGURE 19.5 cttccaacattcaatagggacgtctcactggcttgttccacaggaacact
ttgggtaactgctataccattttgattaaatgctcttttgaatatatt
tgtcttgtatcaatctgattgtttctggagaagggtaaattttaatttg
ggatgtttacttgaagattctttagtgtaggaacatcaacatgctcaat
ctcaatcgttagcacatcacattttcagctagtttttcgatatcaagag
gattggaaaaggagccattaacgtggtcattggagttgcttatttgtttg
gcaggagaattttcagcatctagtattaccgtcttaatgttgagcctgtt
tgctgcctcaacaatcatacgtcccaattgtccccctcctaatataccaa
ctgttctagaatccatacttgattgttttgtccgatttcttgttttct
tgattgttatagtaggatgtacttagaagagagatccaacgatttacgc
accaatttatacatgaaatgctccataatattgtccatttagttcttaat
aaaaggtcagcaagagtcaatcacttagtattacccggttcgtagccatg
caacaagagtcatttgtcagcatagctgtaataatcaatcatgacgtaag
aaatgtatcataattaaaagttgttaaagatgtcagtgttatgttggtgt
tacaaaattctcggctagcTTATCGATGATAAGCTGTCAAAGATGAGAAT
TAATTCCACGGACTATAGACTATACTAGATACTCCGTCTACTGTACGATA
CACTTCCGCTCAGGTCCTTGTCCTTTAACGAGGCCTTACCACTCTTTTGT
TACTCTATTGATCCAGCTCAGCAAAGGCAGTGTGATCTAAGATTCTATCT
TCGCGATGTAGTAAAACTAGCTAGACCGAGAAAGAGACTAGAAATGCAAA
AGGCACTTCTACAATGGCTGCCATCATTATTATCCGATGTGACGCTGCAG
CTTCTCAATGATATTCGAATACGCTTTGAGGAGATACAGCCTAATATCCG
ACAAACTGTTTTACAGATTTACGATCGTACTTGTTACCCATCATTGAATT
TTGAACATCCGAACCTGGGAGTTTTCCCTGAAACAGATAGTATATTTGAA
CCTGTATAATAATATATAGTCTAGCGCTTTACGGAAGACAATGTATGTAT
TTCGGTTCCTGGAGAAACTATTGCATCTATTGCATAGGTAATCTTGCACG
TCGCATCCCCGGTTCATTTTCTGCGTTTCCATCTTGCACTTCAATAGCAT
ATCTTTGTTAACGAAGCATCTGTGCTTCATTTTGTAGAACAAAAATGCAA
CGCGAGAGCGCTAATTTTTCAAACAAAGAATCTGAGCTGCATTTTTACAG
AACAGAAATGCAACGCGAAAGCGCTATTTTACCAACGAAGAATCTGTGCT
TCATTTTTGTAAAACAAAAATGCAACGCGACGAGAGCGCTAATTTTTCAA
ACAAAGAATCTGAGCTGCATTTTTACAGAACAGAAATGCAACGCGAGAGC
GCTATTTTACCAACAAAGAATCTATACTTCTTTTTTGTTCTACAAAAATG
CATCCCGAGAGCGCTATTTTTCTAACAAAGCATCTTAGATTACTTTTTTT
CTCCTTTGTGCGCTCTATAATGCAGTCTCTTGATAACTTTTTGCACTGTA

FIGURE 19.6

GGTCCGTTAAGGTTAGAAGAAGGCTACTTTGGTGTCTATTTTCTCTTCCA
TAAAAAAGCCTGACTCCACTTCCCGCGTTTACTGATTACTAGCGAAGCT
GCGGGTGCATTTTTTCAAGATAAAGGCATCCCCGATTATATTCTATACCG
ATGTGGATTGCGCATACTTTGTGAACAGAAAGTGATAGCGTTGATGATTC
TTCATTGGTCAGAAAATTATGAACGGTTTCTTCTATTTTGTCTCTATATA
CTACGTATAGGAAATGTTTACATTTTCGTATTGTTTTCGATTCACTCTAT
GAATAGTTCTTACTACAATTTTTTTGTCTAAAGAGTAATACTAGAGATAA
ACATAAAAAATGTAGAGGTCGAGTTTAGATGCAAGTTCAAGGAGCGAAAG
GTGGATGGGTAGGTTATATAGGGATATAGCACAGAGATATATAGCAAAGA
GATACTTTTGAGCAATGTTTGTGGAAGCGGTATTCGCAATGGGAAGCTCC
ACCCCGGTTGATAATCAGAAAAGCCCCAAAAACAGGAAGATTGTATAAGC
AAATATTTAAATTGTAAACGTTAATATTTTGTTAAAATTCGCGTTAAATT
TTTGTTAAATCAGCTCATTTTTTAACGAATAGCCCGAAATCGGCAAAATC
CCTTATAAATCAAAAGAATAGACCGAGATAGGGTTGAGTGTTGTTCCAGT
TTCCAACAAGAGTCCACTATTAAAGAACGTGGACTCCAACGTCAAAGGGC
GAAAAGGGTCTATCAGGGCGATGGCCCACTACGTGAACCATCACCCTAA
TCAAGTTTTTTGGGGTCGAGGTGCCGTAAAGCAGTAAATCGGAAGGGTAA
ACGGATGCCCCCATTTAGAGCTTGACGGGGAAAGCCGGCGAACGTGGCGA
GAAAGGAAGGGAAGAAAGCGAAGGAGCGGGGGCTAGGGCGGTGGGAAGT
GTAGGGGTCACGCTGGGCGTAACCACCACACCCGCCGCGCTTAATGGGGC
GCTACAGGGCGCGTGGGGATGATCCACTAGTACGGATTAGAAGCCGCCGA
GCGGGTGACAGCCCTCCGAAGGAAGACTCTCCTCCGTGCGTCCTCGTCCT
CACCGGTCGCGTTCCTGAAACGCAGATGTGCCTCGCGCCGCACTGCTCCG
AACAATAAAGATTCTACAATACTAGCTTTTATGGTTATGAAGAGGAAAAA
TTGGCAGTAACCTGGCCCCACAAACCTTCAAATGAACGAATCAAATTAAC
AACCATAGGATGATAATGCGATTAGTTTTTTAGCCTTATTTCTGGGGTAA
TTAATCAGCGAAGCGATGATTTTTGATCTATTAACAGATATATAAATGCA
AAAACTGCATTAACCACTTTAACTAATACTTTCAACATTTTCGGTTTGTA
TTACTTCTTATTCAAATGTAATAAAAGTATCAACAAAAAATTGTTAATAT
ACCTCTATACTTTAACGTCAAGGAGAAAAAACCCCGGATCGGACTACTAG
CAGCTGTAATACGACTCACTATAGGGAATATTAAGCTTGCGGATCC

FIGURE 20.1

**Minigenome based *CAN1* sequence (pCM225)**

| | |
|---|---|
| pYES2 vector : | Capital letter |
| Ribozymes Sequence : | Minuscule letter |
| Leader sequence : | Bold capital letter |
| Trailer sequence : | Bold italic capital letter |
| *CAN1* sequence : | Bold minuscule letter |
| *ADE2* sequence : | Minuscule italic letter | ccaactttgtttggtctgatgagtccgtgaggacgaaacccggagtcccg
ggtcACCAAACAAAGTTGGGTAAGGATAGTTCAATCAATGATCATCTTCT
AGTGCACTTAGGATTCAAGATCCTATTATCAGGGACAAGAGCAGGATTAG
GGATATCCGAGATGGaaaatcttgctaggatacagttctcacatcacatc
cgaacataaacaaccatggactatgctacaacattccaaaatttgtccca
aaaagtctttggttcatgatcttcccatacaattgcctcaatgtctcttc
tatcggaatcgatgtcgacatctccaatcttccaaataaatctgcatctg
aatatgcattgaataagatccaaacagctaagaacaggaaaatagagat
ataggcggcagcaaagctaacaccattgaatttggtgcaaaagccgtga
aaccttgaataatgataatgatcgtcataaatgtggccgcataataagcc
aagccgggcattaatttagctttaaatggtaactcgtcacgagagatgcc
acggtatttcaaagcttgcataaatctgatgtgcgagattgagataaata
accatgcaaaaaagcctgcaacaccagtgatatttaatagccattcgaaa
actttgtcaccaccagtagatgtctccatgtaagccaaagcgccaaatgc
agcagtaacgaaaactgcaatgtatggaacaccacctttggtggtccttg
acaggaatttaggagccaacttgttctttgatagaccaaataaaatacgg
gaaccaacgtaaatatttgaatttgcggcagaaataatggttgttaagat
aacagcgttgaagatatgtggcaaaacctttgtaccagagttctcaatag
caataataagggagaagtagaaacgtaggaagtagattgtgttagttta
gggtcattgtatggaactaaaagtccaatgaataatagagagccaatgta
gaaggttaagatacggaaaacaactttttttgatggctcttggaacggatt
ttctggggtttgcagcttcaccagcagtgataccaactagttcagtacct
tgaaatgtgaaggcagcgttaatcaaagaggaaacccaacctaagaacct
cccttcgttttttatccttagatattatacctggaccccaggcacctgggt
ttctccaataacggaatccaactgggccggtaacccagcaccacaaacc
atacaaaaacagtatattagaaacccgataatggctaaaactttgatgga

FIGURE 20.2 agcgacccagaactcgaattcaccgtaatatttgacagggaacaagttca
ttattgtgataattacccaaaaaatactaatccatgccgccagtggaact
ttgtacgtccaaaattgaatgacttggccaactacactaagttccagggc
aaaagtgattgcccaagaaaaccaatacatgtaaccattggccgcaccaa
atgctggagaaaggaatctttgtgagaaaactgtgaaagaggatgtaaca
gggatgaatgtagccatttcacccaaggactgcgtgacagaatatgccaa
agaacccataaataaatatgatataagagcgcccactgggccggcgttgg
tcagaggtgtggataaaccaatgaaaagacctgtaccaatagtaccacca
agggcaatcataccaatatgtctttgcttaagctctctcttcacttcagc
gttctgtacttctccttcatcttcatcacctatgccatcctccatagaga
acgtatcctcgccatttactctcgtcgggaaagagcgcaatggatacaat
tctttacttttctcatctttcaatggtattgacccacgtctgtggtgtgt
ttgtgaagcttcaacgtcgtgaaagagggttgtgaccggctcattgtaca
tatgcttctcctctatgtcggcgtcttcttttgaatttgtcatgagctcg
aattcatcgatgat*ATGGTATAAGTTAGTCGGATACAGTGCCCTGATTAA*
*GGACTAATTGGTTGAACTCCGGAACCCTAATCCTGCCCTAGGTGGTTAGG*
*CATTATTTGCAATATATTAAAGAAAACTTTGAAAATACGAAGTTTCTATT*
*CCCAGCTTTGTCTGGT*ggccggcatggtcccagcctcctcgctggcgccg
gctgggcaacattccgaggggaccgtccctcggtaatggcgaatgggac
GCGGCCGATCCGGCTGCTAACAAAGCCCGAAAGGAAGCTGAGTTGGCTGC
TGCCACCGCTGAGCAATAACTAGCATAACCCCTTGGGGCCTCTAAACGGG
TCTTGAGGGGTTTTTTGCTGAAAGGAGGAACTATATCCGGATGCGGCCGC
TCGAGCATGCATCTAGAGGGCCGCATCATGTAATTAGTTATGTCACGCTT
ACATTCACGCCCTCCCCCACATCCGCTCTAACCGAAAAGGAAGGAGTTA
GACAACCTGAAGTCTAGGTCCCTATTTATTTTTTATAGTTATGTTAGTA
TTAAGAACGTTATTTATATTTCAAATTTTTCTTTTTTTTCTGTACAGACG
CGTGTACGCATGTAACATTATACTGAAAACCTTGCTTGAGAAGGTTTTGG
GACGCTCGAAGGCTTTAATTTGCGGCCCTGCATTAATGAATCGGCCAACG
CGCGGGGAGAGGCGGTTTGCGTATTGGGCGCTCTTCCGCTTCCTCGCTCA
CTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAA
GAACATGTGAGCAAAAGGCCAGCAAAAGCCCAGGAACCGTAAAAAGGCCG
CGTTGCTGGCGTTTTTCCATAGGCTCCGCCCCCCTGACGAGCATCACAAA
AATCGACGCTCAAGTCAGAGGTGGCGAAACCCGACAGGACTATAAAGATA

FIGURE 20.3

CCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCG
CTCCAAGCTGGGCTGTGTGCACGAACCCCCGTTCAGCCCGACCGCTGCG
CCTTATCCGGTAACTATCGTCTTGAGTCCAACCCGGTAAGACACGACTTA
TCGCCACTGGCAGCAGCCACTGGTAACAGGATTAGCAGAGCGAGGTATGT
AGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTGCAAGCAGCAGATTACGCGCAGAAAAAAGGATCTC
AAGAAGATCCTTTGATCTTTTCTACGGGGTCTGACGCTCAGTGGAACGAA
AACTCACGTTAAGGGATTTTGGTCATGAGATTATCAAAAAGGATCTTCAC
CTAGATCCTTTTAAATTAAAAATGAAGTTTTAAATCAATCTAAAGTATAT
ATGAGTAAACTTGGTCTGACAGTTACCAATGCTTAATCAGTGAGGCACCT
ATCTCAGCGATCTGTCTATTTCGTTCATCCATAGTTGCCTGACTCCCCGT
CGTGTAGATAACTACGATACGGGAGCGCTTACCATCTGGCCCCAGTGCTG
CAATGATACCGCGAGACCCACGCTCACCGGCTCCAGATTTATCAGCAATA
AACCAGCCAGCCGGAAGGGCCGAGCGCAGAAGTGGTCCTGCAACTTTATC
CGCCTCCATTCAGTCTATTAATTGTTGCCGGGAAGCTAGAGTAAGTAGTT
CGCCAGTTAATAGTTTGCGCAACGTTGTTGGCATTGCTACAGGCATCGTG
GTGTCACTCTCGTCGTTTGGTATGGCTTCATTCAGCTCCGGTTCCCAACG
ATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCA
CTCATGGTTATGGCAGCACTGCATAATTCTCTTACTGTCATGCCATCCGT
AAGATGCTTTTCTGTGACTGGTGAGTACTCAACCAAGTCATTCTGAGAAT
AGTGTATGCGGCGACCGAGTTGCTCTTGCCCGGCGTCAATACGGGATAAT
AGTGTATCACATAGCAGAACTTTAAAAGTGCTCATCATTGGAAAACGTTC
TTCGGGGCGAAAACTCTCAAGGATCTTACCGCTGTTGAGATCCAGTTCGA
TGTAACCCACTCGTGCACCCAACTGATCTTCAGCATCTTTTACTTTCACC
AGCGTTTCTGGGTGAGCAAAAACAGGAAGGCAAAATGCCGCAAAAAGGG
AATAAGGGCGACACGGAAATGTTGAATACTCATACTCTTCCTTTTTCAAT
GGGTAATAACTGATATAATTAAATTGAAGCTCTAATTTGTGAGTTTAGTA
TACATGCATTTACTTATAATACAGTTTTTTAGTTTTGCTGGCCGCATCTT
CTCAAATATGCTTCCCAGCCTGCTTTTCTGTAACGTTCACCCTCTACCTT

FIGURE 20.4

AGCATCCCTTCCCTTTGCAAATAGTCCTCTTCCAACAATAATAATGTCAG
ATCCTGTAGAGACCACATCATCCACGGTTCTATACTGTTGACCCAATGCG
TCTCCCTTGTCATCTAAACCCACACCGGGTGTCATAATCAACCAATCGTA
ACCTTCATCTCTTCCACCCATGTCTCTTTGAGCAATAAAGCCGATAACAA
AATCTTTGTCGCTCTTCGCAATGTCAACAGTACCCTTAGTATATTCTCCA
GTAGATAGGGAGCCCTTGCATGACAATTCTGCTAACATCAAAAGGCCTCT
AGGTTCCTTTGTTACTTCTTCTGCCGCCTGCTTCAAACCGCTAACAATAC
CTgggcccttgcttcttgttactggatatgtatgtatgtataataagtga
tcttatgtatgaaattcttaaaaaaggacacctgtaagcgttgatttcta
tgtatgaagtccacatttgatgtaatcataacaaagcctaaaaaataggt
atatcattttataattatttgctgtacaagtatatcaataaacttatata
ttacttgttttctagataagcttcgtaaccgacagtttctaactttgtg
ctttgacaagaacttcttcttcttgctttaataaaaactgttccattttc
gttgtataacttgaatcataagcgccaagcagtctgacagccaacagcgc
agcgttcgtactattattaatagcgacggtagctactggaacacctctag
gcatttgcacaattgaatgtaaagaatctactccatctagacaagaacct
tttacgggcacaccgatgacaggaagtggtgtcattgcagccaccatacc
tggcaagtgagcagccccaccagctccagcgataattgttttaattccac
gcttgcttgcggaaatagcatatgctgacatcctatgtggagttctatga
gcagagactattgtcacttcaaatggaacgccaaaatcttttaaaaccgc
acatgcggcagacattaccggcaagtcagagtctgatcccatgatgattc
caaccaatggtttgaccattgcttccaagtccaacttttgagcgacagag
attttgattggaatatcagttctacctgtaatgtagttcagcctttgttc
acattccgccatactggaggcaataatatttatgtgacctactttctgt
taggtctagactcttttccatataagtacactgaggaacctggagtcgcc
aatgctctttcgcaagtttctagctctttatctttgtatgtttgtctcc
aagaacatttagcataatggcgttcgttgtaatggtggagaaagatgtga
aattctttggcattggcaaatccaatattgatctcaaatgagcttcaaat
tgagaagtgacgcaagcatcaatggtataatgtccagagttgtgaggcct
tggggcaatttcgttaataagcaattcccctgtttctaaatagaacattt
ccacaccaaatataccacaaccgggaaaagatttgattgcattttctgcc
aacaacttcgccttaagttgaacggagtccggaactctagcaggcgcata
acataagtcacaaatattgtccttgtggatagtctctacaattgggtaag
aaaacactaaaccgttaacagatctcacaatcatgactgctaattcttta

FIGURE 20.5 gtaaatggtgcccattttcggcgtacaaaggacgatccttcagtacttc
caaagcttccggaatcatttccttattctttacaacgaagttacctcttc
catcgtatgccaaagtcctcgacttcaagacgaatggaaaacccaaatct
cttccaacattcaatagggacgtctcactggcttgttccacaggaacact
ttgggtaactgctataccattttgattaaatgctcttttgaatatatt
tgtcttgtatcaatctgattgtttctggagaagggtaaattttaatttg
ggatgttttacttgaagattctttagtgtaggaacatcaacatgctcaat
ctcaatcgttagcacatcacattttcagctagttttcgatatcaagag
gattggaaaaggagccattaacgtggtcattggagttgcttatttgtttg
gcaggagaattttcagcatctagtattaccgtcttaatgttgagcctgtt
tgctgcctcaacaatcatacgtcccaattgtcccctcctaatataccaa
ctgttctagaatccatacttgattgttttgtccgatttcttgttttct
tgattgttatagtaggatgtacttagaagagagatccaacgatttacgc
accaattatacatgaaatgctccataatattgtccatttagttcttaat
aaaaggtcagcaagagtcaatcacttagtattacccggttcgtagccatg
caacaagagtcatttgtcagcatagctgtaataatcatcatgacgtaag
aaatgtatcataattaaaagttgttaaagatgtcagtgttatgttggtgt
tacaaaattctcggctagcTTATCGATGATAAGCTGTCAAAGATGAGAAT
TAATTCCACGGACTATAGACTATACTAGATACTCCGTCTACTGTACGATA
CACTTCCGCTCAGGTCCTTGTCCTTTAACGAGGCCTTACCACTCTTTTGT
TACTCTATTGATCCAGCTCAGCAAAGGCAGTGTGATCTAAGATTCTATCT
TCGCGATGTAGTAAAACTAGCTAGACCGAGAAAGAGACTAGAAATGCAAA
AGGCACTTCTACAATGGCTGCCATCATTATTATCCGATGTGACGCTGCAG
CTTCTCAATGATATTCGAATACGCTTTGAGGAGATACAGCCTAATATCCG
ACAAACTGTTTTACAGATTTACGATCGTACTTGTTACCCATCATTGAATT
TTGAACATCCGAACCTGGGAGTTTTCCCTGAAACAGATAGTATATTTGAA
CCTGTATAATAATATATAGTCTAGCGCTTTACGGAAGACAATGTATGTAT
TTCGGTTCCTGGAGAAACTATTGCATCTATTGCATAGGTAATCTTGCACG
TCGCATCCCCGGTTCATTTTCTGCGTTTCCATCTTGCACTTCAATAGCAT
ATCTTTGTTAACGAAGCATCTGTGCTTCATTTTGTAGAACAAAAATGCAA
CGCGAGAGCGCTAATTTTTCAAACAAGAATCTGAGCTGCATTTTTACAG
AACAGAAATGCAACGCGAAAGCGCTATTTTACCAACGAAGAATCTGTGCT
TCATTTTTGTAAAACAAAAATGCAACGCGACGAGAGCGCTAATTTTTCAA
ACAAAGAATCTGAGCTGCATTTTTACAGAACAGAAATGCAACGCGAGAGC

FIGURE 20.6

```
GCTATTTTACCAACAAAGAATCTATACTTCTTTTTTGTTCTACAAAAATG
CATCCCGAGAGCGCTATTTTTCTAACAAAGCATCTTAGATTACTTTTTTT
CTCCTTTGTGCGCTCTATAATGCAGTCTCTTGATAACTTTTTGCACTGTA
GGTCCGTTAAGGTTAGAAGAAGGCTACTTTGGTGTCTATTTTCTCTTCCA
TAAAAAAAGCCTGACTCCACTTCCCGCGTTTACTGATTACTAGCGAAGCT
GCGGGTGCATTTTTTCAAGATAAAGGCATCCCCGATTATATTCTATACCG
ATGTGGATTGCGCATACTTTGTGAACAGAAGTGATAGCGTTGATGATTC
TTCATTGGTCAGAAAATTATGAACGGTTTCTTCTATTTTGTCTCTATATA
CTACGTATAGGAAATGTTTACATTTTCGTATTGTTTTCGATTCACTCTAT
GAATAGTTCTTACTACAATTTTTTTGTCTAAAGAGTAATACTAGAGATAA
ACATAAAAAATGTAGAGGTCGAGTTTAGATGCAAGTTCAAGGAGCGAAAG
GTGGATGGGTAGGTTATATAGGGATATAGCACAGAGATATATAGCAAAGA
GATACTTTTGAGCAATGTTTGTGGAAGCGGTATTCGCAATGGGAAGCTCC
ACCCCGGTTGATAATCAGAAAAGCCCCAAAAACAGGAAGATTGTATAAGC
AAATATTTAAATTGTAAACGTTAATATTTTGTTAAAATTCGCGTTAAATT
TTTGTTAAATCAGCTCATTTTTTAACGAATAGCCCGAAATCGGCAAAATC
CCTTATAAATCAAAAGAATAGACCGAGATAGGGTTGAGTGTTGTTCCAGT
TTCCAACAAGAGTCCACTATTAAAGAACGTGGACTCCAACGTCAAAGGGC
GAAAAAGGGTCTATCAGGGCGATGGCCCACTACGTGAACCATCACCCTAA
TCAAGTTTTTTGGGGTCGAGGTGCCGTAAAGCAGTAAATCGGAAGGGTAA
ACGGATGCCCCCATTTAGAGCTTGACGGGGAAAGCCGGCGAACGTGGCGA
GAAAGGAAGGGAAGAAAGCGAAAGGAGCGGGGGCTAGGGCGGTGGGAAGT
GTAGGGGTCACGCTGGGCGTAACCACCACACCCGCCGCGCTTAATGGGGC
GCTACAGGGCGCGTGGGGATGATCCACTAGTACGGATTAGAAGCCGCCGA
GCGGGTGACAGCCCTCCGAAGGAAGACTCTCCTCCGTGCGTCCTCGTCCT
CACCGGTCGCGTTCCTGAAACGCAGATGTGCCTCGCGCCGCACTGCTCCG
AACAATAAAGATTCTACAATACTAGCTTTTATGGTTATGAAGAGGAAAAA
TTGGCAGTAACCTGGCCCCACAAACCTTCAAATGAACGAATCAAATTAAC
AACCATAGGATGATAATGCGATTAGTTTTTTAGCCTTATTTCTGGGGTAA
TTAATCAGCGAAGCGATGATTTTTGATCTATTAACAGATATATAAATGCA
AAAACTGCATTAACCACTTTAACTAATACTTTCAACATTTTCGGTTTGTA
TTACTTCTTATTCAAATGTAATAAAAGTATCAACAAAAAATTGTTAATAT
ACCTCTATACTTTAACGTCAAGGAGAAAAAACCCCGGATCGGACTACTAG
CAGCTGTAATACGACTCACTATAGGGAATATTAAGCTTGCACTAGTAACG
```

FIGURE 20.7

GCCGCCAGTGTGCTGGCTGCAGATATCCATCACACTGGCGGCCGCTAATA
CGACTCACTATAGGG

FIGURE 21.1

ADE2 plasmid containing minigenome KANMX4 based sequence (pCM226)

| pYES2 vector : | Capital letter |
|---|---|
| Ribozymes Sequence : | Minuscule letter |
| Leader sequence : | Bold capital letter |
| Trailer sequence : | Bold italic capital letter |
| KANMX4 sequence : | Bold minuscule letter |
| *ADE2* sequence : | Minuscule italic letter | ccaactttgtttggtctgatgagtccgtgaggacgaaacccggagtcccg
ggtcACCAGACAAAGCTGGGAATAGAAACTTCGTATTTTCAAAGTTTTCT
TTAATATATTGCAAATAATGCCTAACCACCTAGGGCAGGATTAGGGTTCC
GGAGTTCAACCAATTAGTCCTTAATCAGGGCACTGTATCCGACTAACTTA
TACCATatcatcgatgaattcgagctcgttttcgacactggatggcggcg
ttagtatcgaatcgacagcagtatagcgaccagcattcacatacgattga
cgcatgatattactttctgcgcacttaacttcgcatctgggcagatgatg
tcgaggcgaaaaaaatataaatcacgctaacatttgattaaaatagaac
aactacaatataaaaaactatacaaatgacaagttcttgaaaacaagaa
tcttttattgtcagtactgattagaaaaactcatcgagcatcaaatgaa
actgcaatttattcatatcaggattatcaataccatattttgaaaaagc
cgtttctgtaatgaaggagaaaactcaccgaggcagttccataggatggc
aagatcctggtatcggtctgcgattccgactcgtccaacatcaatacaac
ctattaatttcccctcgtcaaaaataaggttatcaagtgagaaatcacca
tgagtgacgactgaatccggtgagaatggcaaaagcttatgcatttcttt
ccagacttgttcaacaggccagccattacgctcgtcatcaaaatcactcg
catcaaccaaaccgttattcattcgtgattgcgcctgagcgagacgaaat
acgcgatcgctgttaaaaggacaattacaaacaggaatcgaatgcaaccg
gcgcaggaacactgccagcgcatcaacaatatttcacctgaatcaggat
attcttctaatacctggaatgctgttttgccggggatcgcagtggtgagt
aaccatgcatcatcaggagtacggataaaatgcttgatggtcggaagagg
cataaattccgtcagccagtttagtctgaccatctcatctgtaacatcat
tggcaacgctacctttgccatgtttcagaaacaactctggcgcatcgggc
ttcccatacaatcgatagattgtcgcacctgattgcccgacattatcgcg
agcccatttatacccatataaatcagcatccatgttggaatttaatcgcg
gcctcgaaacgtgagtcttttccttacccatggttgtttatgttcggatg

FIGURE 21.2 tgatgtgagaactgtatcctagcaagattttCCATCTCGGATATCCCTAA
TCCTGCTCTTGTCCCTGATAATAGGATCTTGAATCCTAAGTGCACTAGAA
GATGATCATTGATTGAACTATCCTTACCCAACTTTGTTTGGTggccggca
tggtcccagcctcctcgctggcgccggctgggcaacattccgagggacc
gtccctcggtaatggcgaatgggac
TCGAGCATGCATCTAGAGGGCCGCATCATGTAATTAGTTATGTCACGCTT
ACATTCACGCCCTCCCCCACATCCGCTCTAACCGAAAGGAAGGAGTTA
GACAACCTGAAGTCTAGGTCCCTATTTATTTTTTATAGTTATGTTAGTA
TTAAGAACGTTATTTATATTTCAAATTTTTCTTTTTTTTCTGTACAGACG
CGTGTACGCATGTAACATTATACTGAAAACCTTGCTTGAGAAGGTTTTGG
GACGCTCGAAGGCTTTAATTTGCGGCCCTGCATTAATGAATCGGCCAACG
CGCGGGGAGAGGCGGTTTGCGTATTGGGCGCTCTTCCGCTTCCTCGCTCA
CTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAA
GAACATGTGAGCAAAAGGCCAGCAAAAGCCCAGGAACCGTAAAAAGGCCG
CGTTGCTGGCGTTTTTCCATAGGCTCCGCCCCCCTGACGAGCATCACAAA
AATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCG
CCTTATCCGGTAACTATCGTCTTGAGTCCAACCCGGTAAGACACGACTTA
TCGCCACTGGCAGCAGCCACTGGTAACAGGATTAGCAGAGCGAGGTATGT
AGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAA
AACTCACGTTAAGGGATTTTGGTCATGAGATTATCAAAAAGGATCTTCAC
CTAGATCCTTTTAAATTAAAAATGAAGTTTTAAATCAATCTAAAGTATAT
ATGAGTAAACTTGGTCTGACAGTTACCAATGCTTAATCAGTGAGGCACCT
ATCTCAGCGATCTGTCTATTTCGTTCATCCATAGTTGCCTGACTCCCCGT
CGTGTAGATAACTACGATACGGGAGCGCTTACCATCTGGCCCCAGTGCTG
CAATGATACCGCGAGACCCACGCTCACCGGCTCCAGATTTATCAGCAATA

FIGURE 21.3

AACCAGCCAGCCGGAAGGGCCGAGCGCAGAAGTGGTCCTGCAACTTTATC
CGCCTCCATTCAGTCTATTAATTGTTGCCGGGAAGCTAGAGTAAGTAGTT
CGCCAGTTAATAGTTTGCGCAACGTTGTTGGCATTGCTACAGGCATCGTG
GTGTCACTCTCGTCGTTTGGTATGGCTTCATTCAGCTCCGGTTCCCAACG
ATCAAGGCGAGTTACATGATCCCCATGTTGTGCAAAAAAGCGGTTAGCT
CCTTCGGTCCTCCGATCGTTGTCAGAAGTAAGTTGGCCGCAGTGTTATCA
CTCATGGTTATGGCAGCACTGCATAATTCTCTTACTGTCATGCCATCCGT
AAGATGCTTTTCTGTGACTGGTGAGTACTCAACCAAGTCATTCTGAGAAT
AGTGTATGCGGCGACCGAGTTGCTCTTGCCCGGCGTCAATACGGGATAAT
AGTGTATCACATAGCAGAACTTTAAAAGTGCTCATCATTGGAAAACGTTC
TTCGGGGCGAAAACTCTCAAGGATCTTACCGCTGTTGAGATCCAGTTCGA
TGTAACCCACTCGTGCACCCAACTGATCTTCAGCATCTTTTACTTTCACC
AGCGTTTCTGGGTGAGCAAAAACAGGAAGGCAAAATGCCGCAAAAAGGG
AATAAGGGCGACACGGAAATGTTGAATACTCATACTCTTCCTTTTTCAAT
GGGTAATAACTGATATAATTAAATTGAAGCTCTAATTTGTGAGTTTAGTA
TACATGCATTTACTTATAATACAGTTTTTAGTTTTGCTGGCCGCATCTT
CTCAAATATGCTTCCCAGCCTGCTTTTCTGTAACGTTCACCCTCTACCTT
AGCATCCCTTCCCTTTGCAAATAGTCCTCTTCCAACAATAATAATGTCAG
ATCCTGTAGAGACCACATCATCCACGGTTCTATACTGTTGACCCAATGCG
TCTCCCTTGTCATCTAAACCCACACCGGGTGTCATAATCAACCAATCGTA
ACCTTCATCTCTTCCACCCATGTCTCTTTGAGCAATAAAGCCGATAACAA
AATCTTTGTCGCTCTTCGCAATGTCAACAGTACCCTTAGTATATTCTCCA
GTAGATAGGGAGCCCTTGCATGACAATTCTGCTAACATCAAAAGGCCTCT
AGGTTCCTTTGTTACTTCTTCTGCCGCCTGCTTCAAACCGCTAACAATAC
CTgggcccttgcttcttgttactggatatgtatgtatgtataataagtga
tcttatgtatgaaattcttaaaaaaggacacctgtaagcgttgatttcta
tgtatgaagtccacatttgatgtaatcataacaaagcctaaaaataggt
atatcattttataattatttgctgtacaagtatatcaataaacttatata
ttacttgttttctagataagcttcgtaaccgacagtttctaactttgtg
ctttgacaagaacttcttcttcttgctttaataaaaactgttccattttc
gttgtataacttgaatcataagcgccaagcagtctgacagccaacagcgc
agcgttcgtactattattaatagcgacggtagctactggaacacctctag
gcatttgcacaattgaatgtaaagaatctactccatctagacaagaacct
tttacgggcacaccgatgacaggaagtggtgtcattgcagccaccatacc

FIGURE 21.4 tggcaagtgagcagccccaccagctccagcgataattgttttaattccac
gcttgcttgcggaaatagcatatgctgacatcctatgtggagttctatga
gcagagactattgtcacttcaaatggaacgccaaaatcttttaaaaccgc
acatgcggcagacattaccggcaagtcagagtctgatcccatgatgattc
caaccaatggtttgaccattgcttccaagtccaacttttgagcgacagag
attttgattggaatatcagttctacctgtaatgtagttcagcctttgttc
acattccgccatactggaggcaataatatttatgtgacctacttttctgt
taggtctagactcttttccatataagtacactgaggaacctggagtcgcc
aatgctctttcgcaagtttctagctctttatcttttgtatgtttgtctcc
aagaacatttagcataatggcgttcgttgtaatggtggagaaagatgtga
aattctttggcattggcaaatccaatattgatctcaaatgagcttcaaat
tgagaagtgacgcaagcatcaatggtataatgtccagagttgtgaggcct
tggggcaatttcgttaataagcaattccctgtttctaaatagaacattt
ccacaccaaatataccacaaccgggaaaagatttgattgcattttctgcc
aacaacttcgccttaagttgaacggagtccggaactctagcaggcgcata
acataagtcacaaatattgtccttgtggatagtctctacaattgggtaag
aaaacactaaaccgttaacagatctcacaatcatgactgctaattcttta
gtaaatggtgcccattttcggcgtacaaaggacgatccttcagtacttc
caaagcttccggaatcatttccttattctttacaacgaagttacctcttc
catcgtatgccaaagtcctcgacttcaagacgaatggaaaacccaaatct
cttccaacattcatagggacgtctcactggcttgttccacaggaacact
ttgggtaactgctataccattttgattaaatgctctttttgaatatatt
tgtcttgtatcaatctgattgtttctggagaagggtaaattttaatttg
ggatgttttacttgaagattctttagtgtaggaacatcaacatgctcaat
ctcaatcgttagcacatcacattttcagctagttttcgatatcaagag
gattggaaaaggagccattaacgtggtcattggagttgcttatttgtttg
gcaggagaattttcagcatctagtattaccgtcttaatgttgagcctgtt
tgctgcctcaacaatcatacgtcccaattgtcccctcctaatataccaa
ctgttctagaatccatacttgattgttttgtccgatttcttgtttttct
tgattgttatagtaggatgtacttagaagagagatccaacgattttacgc
accaatttatacatgaaatgctccataatattgtccatttagttcttaat
aaaaggtcagcaagagtcaatcacttagtattacccggttcgtagccatg
caacaagagtcatttgtcagcatagctgtaataatcaatcatgacgtaag
aaatgtatcataattaaaagttgttaaagatgtcagtgttatgttggtgt

FIGURE 21.5 tacaaaattctcggctagcTTATCGATGATAAGCTGTCAAAGATGAGAAT
TAATTCCACGGACTATAGACTATACTAGATACTCCGTCTACTGTACGATA
CACTTCCGCTCAGGTCCTTGTCCTTTAACGAGGCCTTACCACTCTTTTGT
TACTCTATTGATCCAGCTCAGCAAAGGCAGTGTGATCTAAGATTCTATCT
TCGCGATGTAGTAAAACTAGCTAGACCGAGAAAGAGACTAGAAATGCAAA
AGGCACTTCTACAATGGCTGCCATCATTATTATCCGATGTGACGCTGCAG
CTTCTCAATGATATTCGAATACGCTTTGAGGAGATACAGCCTAATATCCG
ACAAACTGTTTTACAGATTTACGATCGTACTTGTTACCCATCATTGAATT
TTGAACATCCGAACCTGGGAGTTTTCCCTGAAACAGATAGTATATTTGAA
CCTGTATAATAATATATAGTCTAGCGCTTTACGGAAGACAATGTATGTAT
TTCGGTTCCTGGAGAAACTATTGCATCTATTGCATAGGTAATCTTGCACG
TCGCATCCCCGGTTCATTTTCTGCGTTTCCATCTTGCACTTCAATAGCAT
ATCTTTGTTAACGAAGCATCTGTGCTTCATTTTGTAGAACAAAAATGCAA
CGCGAGAGCGCTAATTTTTCAAACAAAGAATCTGAGCTGCATTTTTACAG
AACAGAAATGCAACGCGAAAGCGCTATTTTACCAACGAAGAATCTGTGCT
TCATTTTTGTAAAACAAAAATGCAACGCGACGAGAGCGCTAATTTTTCAA
ACAAAGAATCTGAGCTGCATTTTTACAGAACAGAAATGCAACGCGAGAGC
GCTATTTTACCAACAAAGAATCTATACTTCTTTTTTGTTCTACAAAAATG
CATCCCGAGAGCGCTATTTTTCTAACAAAGCATCTTAGATTACTTTTTTT
CTCCTTTGTGCGCTCTATAATGCAGTCTCTTGATAACTTTTTGCACTGTA
GGTCCGTTAAGGTTAGAAGAAGGCTACTTTGGTGTCTATTTTCTCTTCCA
TAAAAAAAGCCTGACTCCACTTCCCGCGTTTACTGATTACTAGCGAAGCT
GCGGGTGCATTTTTTCAAGATAAAGGCATCCCCGATTATATTCTATACCG
ATGTGGATTGCGCATACTTTGTGAACAGAAAGTGATAGCGTTGATGATTC
TTCATTGGTCAGAAAATTATGAACGGTTTCTTCTATTTTGTCTCTATATA
CTACGTATAGGAAATGTTTACATTTTCGTATTGTTTTCGATTCACTCTAT
GAATAGTTCTTACTACAATTTTTTTGTCTAAAGAGTAATACTAGAGATAA
ACATAAAAAATGTAGAGGTCGAGTTTAGATGCAAGTTCAAGGAGCGAAAG
GTGGATGGGTAGGTTATATAGGGATATAGCACAGAGATATATAGCAAAGA
GATACTTTTGAGCAATGTTTGTGGAAGCGGTATTCGCAATGGGAAGCTCC
ACCCCGGTTGATAATCAGAAAAGCCCCAAAAACAGGAAGATTGTATAAGC
AAATATTTAAATTGTAAACGTTAATATTTTGTTAAAATTCGCGTTAAATT
TTTGTTAAATCAGCTCATTTTTTAACGAATAGCCCGAAATCGGCAAAATC
CCTTATAAATCAAAAGAATAGACCGAGATAGGGTTGAGTGTTGTTCCAGT

FIGURE 21.6

TTCCAACAAGAGTCCACTATTAAAGAACGTGGACTCCAACGTCAAAGGGC
GAAAAAGGGTCTATCAGGGCGATGGCCCACTACGTGAACCATCACCCTAA
TCAAGTTTTTTGGGGTCGAGGTGCCGTAAAGCAGTAAATCGGAAGGGTAA
ACGGATGCCCCCATTTAGAGCTTGACGGGGAAAGCCGGCGAACGTGGCGA
GAAAGGAAGGGAAGAAAGCGAAAGGAGCGGGGGCTAGGGCGGTGGGAAGT
GTAGGGGTCACGCTGGGCGTAACCACCACACCCGCCGCGCTTAATGGGGC
GCTACAGGGCGCGTGGGGATGATCCACTAGTACGGATTAGAAGCCGCCGA
GCGGGTGACAGCCCTCCGAAGGAAGACTCTCCTCCGTGCGTCCTCGTCCT
CACCGGTCGCGTTCCTGAAACGCAGATGTGCCTCGCGCCGCACTGCTCCG
AACAATAAGATTCTACAATACTAGCTTTTATGGTTATGAAGAGGAAAAA
TTGGCAGTAACCTGGCCCCACAAACCTTCAAATGAACGAATCAAATTAAC
AACCATAGGATGATAATGCGATTAGTTTTTTAGCCTTATTTCTGGGGTAA
TTAATCAGCGAAGCGATGATTTTTGATCTATTAACAGATATATAAATGCA
AAAACTGCATTAACCACTTTAACTAATACTTTCAACATTTTCGGTTTGTA
TTACTTCTTATTCAAATGTAATAAAAGTATCAACAAAAAATTGTTAATAT
ACCTCTATACTTTAACGTCAAGGAGAAAAAACCCCGGATCGGACTACTAG
CAGCTGTAATACGACTCACTATAGGGAATATTAAGCTTGCGGATCC

FIGURE 22.1

*ADE2* plasmid containing minigenome KANMX4 based sequence (pCM227)

| | |
|---|---|
| pYES2 vector : | Capital letter |
| Ribozymes Sequence : | Minuscule letter |
| Leader sequence : | Bold capital letter |
| Trailer sequence : | Bold italic capital letter |
| KANMX4 sequence : | Bold minuscule letter |
| *ADE2* sequence : | Minuscule italic letter | ccaactttgtttggtctgatgagtccgtgaggacgaaacccggagtcccg
ggtc**ACCAAACAAAGTTGGGTAAGGATAGTTCAATCAATGATCATCTTCT
AGTGCACTTAGGATTCAAGATCCTATTATCAGGGACAAGAGCAGGATTAG
GGATATCCGAGATGG**aaaatcttgctaggatacagttctcacatcacatc
cgaacataaacaaccatgggtaaggaaaagactcacgtttcgaggccgcg
attaaattccaacatggatgctgatttatatgggtataaatgggctcgcg
ataatgtcgggcaatcaggtgcgacaatctatcgattgtatgggaagccc
gatgcgccagagttgtttctgaaacatggcaaaggtagcgttgccaatga
tgttacagatgagatggtcagactaaactggctgacggaatttatgcctc
ttccgaccatcaagcattttatccgtactcctgatgatgcatggttactc
accactgcgatccccggcaaaacagcattccaggtattagaagaatatcc
tgattcaggtgaaaatattgttgatgcgctggcagtgttcctgcgccggt
tgcattcgattcctgtttgtaattgtccttttaacagcgatcgcgtattt
cgtctcgctcaggcgcaatcacgaatgaataacggtttggttgatgcgag
tgattttgatgacgagcgtaatggctggcctgttgaacaagtctggaaag
aaatgcataagcttttgccattctcaccggattcagtcgtcactcatggt
gatttctcacttgataaccttattttgacgaggggaaattaataggttg
tattgatgttggacgagtcggaatcgcagaccgataccaggatcttgcca
tcctatggaactgcctcggtgagttttctccttcattacagaaacggctt
tttcaaaaatatggtattgataatcctgatatgaataaattgcagtttca
tttgatgctcgatgagttttctaatcagtactgacaataaaaagattct
tgttttcaagaacttgtcatttgtatagtttttttatattgtagttgttc
tattttaatcaaatgttagcgtgatttatattttttttcgcctcgacatc
atctgcccagatgcgaagttaagtgcgcagaaagtaatatcatgcgtcaa
tcgtatgtgaatgctggtcgctatactgctgtcgattcgatactaacgcc

FIGURE 22.2 gccatccagtgtcgaaaacgagctcgaattcatcgatgat*ATGGTATAAG*
*TTAGTCGGATACAGTGCCCTGATTAAGGACTAATTGGTTGAACTCCGGAA*
*CCCTAATCCTGCCCTAGGTGGTTAGGCATTATTTGCAATATATTAAAGAA*
*AACTTTGAAAATACGAAGTTTCTATTCCCAGCTTTGTCTGGT*ggccggca
tggtcccagcctcctcgctggcgccg
gctgggcaacattccgaggggaccgtcccctcggtaatggcgaatgggac
GCGGCCGATCCGGCTGCTAACAAAGCCCGAAAGGAAGCTGAGTTGGCTGC
TGCCACCGCTGAGCAATAACTAGCATAACCCCTTGGGGCCTCTAAACGGG
TCTTGAGGGGTTTTTTGCTGAAAGGAGGAACTATATCCGGATGCGGCCGC
TCGAGCATGCATCTAGAGGGCCGCATCATGTAATTAGTTATGTCACGCTT
ACATTCACGCCCTCCCCCACATCCGCTCTAACCGAAAAGGAAGGAGTTA
GACAACCTGAAGTCTAGGTCCCTATTTATTTTTTATAGTTATGTTAGTA
TTAAGAACGTTATTTATATTTCAAATTTTTCTTTTTTTTCTGTACAGACG
CGTGTACGCATGTAACATTATACTGAAAACCTTGCTTGAGAAGGTTTTGG
GACGCTCGAAGGCTTTAATTTGCGGCCCTGCATTAATGAATCGGCCAACG
CGCGGGAGAGGCGGTTTGCGTATTGGGCGCTCTTCCGCTTCCTCGCTCA
CTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAA
GAACATGTGAGCAAAAGGCCAGCAAAAGCCCAGGAACCGTAAAAAGGCCG
CGTTGCTGGCGTTTTTCCATAGGCTCCGCCCCCCTGACGAGCATCACAAA
AATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCG
CCTTATCCGGTAACTATCGTCTTGAGTCCAACCCGGTAAGACACGACTTA
TCGCCACTGGCAGCAGCCACTGGTAACAGGATTAGCAGAGCGAGGTATGT
AGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAA
AACTCACGTTAAGGGATTTTGGTCATGAGATTATCAAAAGGATCTTCAC
CTAGATCCTTTTAAATTAAAAATGAAGTTTTAAATCAATCTAAAGTATAT

FIGURE 22.3

ATGAGTAAACTTGGTCTGACAGTTACCAATGCTTAATCAGTGAGGCACCT
ATCTCAGCGATCTGTCTATTTCGTTCATCCATAGTTGCCTGACTCCCCGT
CGTGTAGATAACTACGATACGGGAGCGCTTACCATCTGGCCCCAGTGCTG
CAATGATACCGCGAGACCCACGCTCACCGGCTCCAGATTTATCAGCAATA
AACCAGCCAGCCGGAAGGGCCGAGCGCAGAAGTGGTCCTGCAACTTTATC
CGCCTCCATTCAGTCTATTAATTGTTGCCGGGAAGCTAGAGTAAGTAGTT
CGCCAGTTAATAGTTTGCGCAACGTTGTTGGCATTGCTACAGGCATCGTG
GTGTCACTCTCGTCGTTTGGTATGGCTTCATTCAGCTCCGGTTCCCAACG
ATCAAGGCGAGTTACATGATCCCCATGTTGTGCAAAAAAGCGGTTAGCT
CCTTCGGTCCTCCGATCGTTGTCAGAAGTAAGTTGGCCGCAGTGTTATCA
CTCATGGTTATGGCAGCACTGCATAATTCTCTTACTGTCATGCCATCCGT
AAGATGCTTTTCTGTGACTGGTGAGTACTCAACCAAGTCATTCTGAGAAT
AGTGTATGCGGCGACCGAGTTGCTCTTGCCCGGCGTCAATACGGGATAAT
AGTGTATCACATAGCAGAACTTTAAAAGTGCTCATCATTGGAAAACGTTC
TTCGGGGCGAAAACTCTCAAGGATCTTACCGCTGTTGAGATCCAGTTCGA
TGTAACCCACTCGTGCACCCAACTGATCTTCAGCATCTTTTACTTTCACC
AGCGTTTCTGGGTGAGCAAAAACAGGAAGGCAAAATGCCGCAAAAAAGGG
AATAAGGGCGACACGGAAATGTTGAATACTCATACTCTTCCTTTTTCAAT
GGGTAATAACTGATATAATTAAATTGAAGCTCTAATTTGTGAGTTTAGTA
TACATGCATTTACTTATAATACAGTTTTTTAGTTTTGCTGGCCGCATCTT
CTCAAATATGCTTCCCAGCCTGCTTTTCTGTAACGTTCACCCTCTACCTT
AGCATCCCTTCCCTTTGCAAATAGTCCTCTTCCAACAATAATAATGTCAG
ATCCTGTAGAGACCACATCATCCACGGTTCTATACTGTTGACCCAATGCG
TCTCCCTTGTCATCTAAACCCACACCGGGTGTCATAATCAACCAATCGTA
ACCTTCATCTCTTCCACCCATGTCTCTTTGAGCAATAAAGCCGATAACAA
AATCTTTGTCGCTCTTCGCAATGTCAACAGTACCCTTAGTATATTCTCCA
GTAGATAGGGAGCCCTTGCATGACAATTCTGCTAACATCAAAAGGCCTCT
AGGTTCCTTTGTTACTTCTTCTGCCGCCTGCTTCAAACCGCTAACAATAC
CT*gggcccttgcttcttgttactggatatgtatgtatgtataataagtga*
*tcttatgtatgaaattcttaaaaaaggacacctgtaagcgttgatttcta*
*tgtatgaagtccacatttgatgtaatcataacaaagcctaaaaaataggt*
*atatcattttataattatttgctgtacaagtatatcaataaacttatata*
*ttacttgttttctagataagcttcgtaaccgacagtttctaactttgtg*
*ctttgacaagaacttcttcttcttgctttaataaaaactgttccattttc*

FIGURE 22.4 gttgtataacttgaatcataagcgccaagcagtctgacagccaacagcgc
agcgttcgtactattattaatagcgacggtagctactggaacacctctag
gcatttgcacaattgaatgtaaagaatctactccatctagacaagaacct
tttacgggcacaccgatgacaggaagtggtgtcattgcagccaccatacc
tggcaagtgagcagcccaccagctccagcgataattgttttaattccac
gcttgcttgcggaaatagcatatgctgacatcctatgtggagttctatga
gcagagactattgtcacttcaaatggaacgccaaaatcttttaaaaccgc
acatgcggcagacattaccggcaagtcagagtctgatcccatgatgattc
caaccaatggtttgaccattgcttccaagtccaacttttgagcgacagag
atttgattggaatatcagttctacctgtaatgtagttcagcctttgttc
acattccgccatactggaggcaataatatttatgtgacctacttttctgt
taggtctagactcttttccatataagtacactgaggaacctggagtcgcc
aatgctctttcgcaagtttctagctctttatcttttgtatgtttgtctcc
aagaacatttagcataatggcgttcgttgtaatggtggagaaagatgtga
aattctttggcattggcaaatccaatattgatctcaaatgagcttcaaat
tgagaagtgacgcaagcatcaatggtataatgtccagagttgtgaggcct
tggggcaatttcgttaataagcaattcccctgtttctaaatagaacattt
ccacaccaaatataccacaaccgggaaaagatttgattgcattttctgcc
aacaacttcgccttaagttgaacggagtccggaactctagcaggcgcata
acataagtcacaaatattgtccttgtggatagtctctacaattgggtaag
aaaacactaaaccgttaacagatctcacaatcatgactgctaattcttta
gtaaatggtgcccattttcggcgtacaaaggacgatccttcagtacttc
caaagcttccggaatcatttccttattctttacaacgaagttacctcttc
catcgtatgccaaagtcctcgacttcaagacgaatggaaaacccaaatct
cttccaacattcaatagggacgtctcactggcttgttccacaggaacact
ttgggtaactgctataccatttttgattaaatgctcttttgaatatatt
tgtcttgtatcaatctgattgtttctggagaagggtaaatttttaatttg
ggatgttttacttgaagattctttagtgtaggaacatcaacatgctcaat
ctcaatcgttagcacatcacattttcagctagttttcgatatcaagag
gattggaaaaggagccattaacgtggtcattggagttgcttatttgtttg
gcaggagaattttcagcatctagtattaccgtcttaatgttgagcctgtt
tgctgcctcaacaatcatacgtcccaattgtccccctcctaatataccaa
ctgttctagaatccatacttgattgttttgtccgatttcttgttttct
tgattgttatagtaggatgtacttagaagagagatccaacgattttacgc

FIGURE 22.5 accaatttatacatgaaatgctccataatattgtccatttagttcttaat
aaaaggtcagcaagagtcaatcacttagtattacccggttcgtagccatg
caacaagagtcatttgtcagcatagctgtaataatcaatcatgacgtaag
aaatgtatcataattaaaagttgttaaagatgtcagtgttatgttggtgt
tacaaaattctcggctagcTTATCGATGATAAGCTGTCAAAGATGAGAAT
TAATTCCACGGACTATAGACTATACTAGATACTCCGTCTACTGTACGATA
CACTTCCGCTCAGGTCCTTGTCCTTTAACGAGGCCTTACCACTCTTTTGT
TACTCTATTGATCCAGCTCAGCAAAGGCAGTGTGATCTAAGATTCTATCT
TCGCGATGTAGTAAAACTAGCTAGACCGAGAAAGAGACTAGAAATGCAAA
AGGCACTTCTACAATGGCTGCCATCATTATTATCCGATGTGACGCTGCAG
CTTCTCAATGATATTCGAATACGCTTGAGGAGATACAGCCTAATATCCG
ACAAACTGTTTTACAGATTTACGATCGTACTTGTTACCCATCATTGAATT
TTGAACATCCGAACCTGGGAGTTTTCCCTGAAACAGATAGTATATTTGAA
CCTGTATAATAATATATAGTCTAGCGCTTTACGGAAGACAATGTATGTAT
TTCGGTTCCTGGAGAAACTATTGCATCTATTGCATAGGTAATCTTGCACG
TCGCATCCCCGGTTCATTTTCTGCGTTTCCATCTTGCACTTCAATAGCAT
ATCTTTGTTAACGAAGCATCTGTGCTTCATTTTGTAGAACAAAAATGCAA
CGCGAGAGCGCTAATTTTTCAAACAAAGAATCTGAGCTGCATTTTTACAG
AACAGAAATGCAACGCGAAAGCGCTATTTTACCAACGAAGAATCTGTGCT
TCATTTTTGTAAAACAAAAATGCAACGCGACGAGAGCGCTAATTTTTCAA
ACAAAGAATCTGAGCTGCATTTTTACAGAACAGAAATGCAACGCGAGAGC
GCTATTTTACCAACAAAGAATCTATACTTCTTTTTTGTTCTACAAAAATG
CATCCCGAGAGCGCTATTTTTCTAACAAAGCATCTTAGATTACTTTTTTT
CTCCTTTGTGCGCTCTATAATGCAGTCTCTTGATAACTTTTTGCACTGTA
GGTCCGTTAAGGTTAGAAGAAGGCTACTTTGGTGTCTATTTTCTCTTCCA
TAAAAAAGCCTGACTCCACTTCCCGCGTTTACTGATTACTAGCGAAGCT
GCGGGTGCATTTTTTCAAGATAAAGGCATCCCCGATTATATTCTATACCG
ATGTGGATTGCGCATACTTTGTGAACAGAAAGTGATAGCGTTGATGATTC
TTCATTGGTCAGAAAATTATGAACGGTTTCTTCTATTTTGTCTCTATATA
CTACGTATAGGAAATGTTTACATTTTCGTATTGTTTTCGATTCACTCTAT
GAATAGTTCTTACTACAATTTTTTTGTCTAAAGAGTAATACTAGAGATAA
ACATAAAAAATGTAGAGGTCGAGTTTAGATGCAAGTTCAAGGAGCGAAAG
GTGGATGGGTAGGTTATATAGGGATATAGCACAGAGATATATAGCAAAGA
GATACTTTTGAGCAATGTTTGTGGAAGCGGTATTCGCAATGGGAAGCTCC

FIGURE 22.6

```
ACCCCGGTTGATAATCAGAAAAGCCCCAAAAACAGGAAGATTGTATAAGC
AAATATTTAAATTGTAAACGTTAATATTTTGTTAAAATTCGCGTTAAATT
TTTGTTAAATCAGCTCATTTTTTAACGAATAGCCCGAAATCGGCAAAATC
CCTTATAAATCAAAAGAATAGACCGAGATAGGGTTGAGTGTTGTTCCAGT
TTCCAACAAGAGTCCACTATTAAAGAACGTGGACTCCAACGTCAAAGGGC
GAAAAAGGGTCTATCAGGGCGATGGCCCACTACGTGAACCATCACCCTAA
TCAAGTTTTTTGGGGTCGAGGTGCCGTAAAGCAGTAAATCGGAAGGGTAA
ACGGATGCCCCCATTTAGAGCTTGACGGGGAAAGCCGGCGAACGTGGCGA
GAAAGGAAGGGAAGAAAGCGAAAGGAGCGGGGGCTAGGGCGGTGGGAAGT
GTAGGGGTCACGCTGGGCGTAACCACCACACCCGCCGCGCTTAATGGGGC
GCTACAGGGCGCGTGGGGATGATCCACTAGTACGGATTAGAAGCCGCCGA
GCGGGTGACAGCCCTCCGAAGGAAGACTCTCCTCCGTGCGTCCTCGTCCT
CACCGGTCGCGTTCCTGAAACGCAGATGTGCCTCGCGCCGCACTGCTCCG
AACAATAAAGATTCTACAATACTAGCTTTTATGGTTATGAAGAGGAAAAA
TTGGCAGTAACCTGGCCCCACAAACCTTCAAATGAACGAATCAAATTAAC
AACCATAGGATGATAATGCGATTAGTTTTTTAGCCTTATTTCTGGGGTAA
TTAATCAGCGAAGCGATGATTTTTGATCTATTAACAGATATATAAATGCA
AAAACTGCATTAACCACTTTAACTAATACTTTCAACATTTTCGGTTTGTA
TTACTTCTTATTCAAATGTAATAAAAGTATCAACAAAAATTGTTAATAT
ACCTCTATACTTTAACGTCAAGGAGAAAAAACCCCGGATCGGACTACTAG
CAGCTGTAATACGACTCACTATAGGGAATATTAAGCTTGCACTAGTAACG
GCCGCCAGTGTGCTGGCTGCAGATATCCATCACACTGGCGGCCGCTAATA
CGACTCACTATAGGG
```

FIGURE 23.1 pESC-LEU-N (pCM103)

| | |
|---|---|
| Viral N sequence: | Minuscule letter |
| pESC-LEU vector sequence: | Upper case letter |

TCGCGCGTTTCGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTTGGCGGGTGTC
GGGGCTGGCTTAACTATGCGGCATCAGAGCAGATTGTACTGAGAGTGCACCATATCGACTACGTCG
TAAGGCCGTTTCTGACAGAGTAAAATTCTTGAGGGAACTTTCACCATTATGGGAAATGCTTCAAGA
AGGTATTGACTTAAACTCCATCAAATGGTCAGGTCATTGAGTGTTTTTATTTGTTGTATTTTTT
TTTTTTAGAGAAAATCCTCCAATATCAAATTAGGAATCGTAGTTTCATGATTTTCTGTTACACCTA
ACTTTTTGTGTGGTGCCCTCCTCCTTGTCAATATTAATGTTAAAGTGCAATTCTTTTTCCTTATCA
CGTTGAGCCATTAGTATCAATTTGCTTACCTGTATTCCTTTACTATCCTCCTTTTTCTCCTTCTTG
ATAAATGTATGTAGATTGCGTATATAGTTTCGTCTACCCTATGAACATATTCCATTTTGTAATTTC
GTGTCGTTTCTATTATGAATTTCATTTATAAAGTTTATGTACAAATATCATAAAAAAGAGAATCT
TTTTAAGCAAGGATTTTCTTAACTTCTTCGGCGACAGCATCACCGACTTCGGTGGTACTGTTGGAA
CCACCTAAATCACCAGTTCTGATACCTGCATCCAAAACCTTTTTAACTGCATCTTCAATGGCCTTA
CCTTCTTCAGGCAAGTTCAATGACAATTTCAACATCATTGCAGCAGACAAGATAGTGGCGATAGGG
TCAACCTTATTCTTTGGCAAATCTGGAGCAGAACCGTGGCATGGTTCGTACAAACCAAATGCGGTG
TTCTTGTCTGGCAAAGAGGCCAAGGACGCAGATGGCAACAAACCCAAGGAACCTGGGATAACGGAG
GCTTCATCGGAGATGATATCACCAAACATGTTGCTGGTGATTATAATACCATTTAGGTGGGTTGGG
TTCTTAACTAGGATCATGGCGGCAGAATCAATCAATTGATGTTGAACCTTCAATGTAGGGAATTCG
TTCTTGATGGTTTCCTCCACAGTTTTTCTCCATAATCTTGAAGAGGCCAAAAGATTAGCTTTATCC
AAGGACCAAATAGGCAATGGTGGCTCATGTTGTAGGGCCATGAAAGCGGCCATTCTTGTGATTCTT
TGCACTTCTGGAACGGTGTATTGTTCACTATCCCAAGCGACACCATCACCATCGTCTTCCTTTCTC
TTACCAAAGTAAATACCTCCCACTAATTCTCTGACAACAACGAAGTCAGTACCTTTAGCAAATTGT
GGCTTGATTGGAGATAAGTCTAAAAGAGAGTCGGATGCAAAGTTACATGGTCTTAAGTTGGCGTAC
AATTGAAGTTCTTTACGGATTTTTAGTAAACCTTGTTCAGGTCTAACACTACCGGTACCCCATTTA
GGACCACCCACAGCACCTAACAAAACGGCATCAGCCTTCTTGGAGGCTTCCAGCGCCTCATCTGGA
AGTGGAACACCTGTAGCATCGATAGCAGCACCACCAATTAAATGATTTTCGAAATCGAACTTGACA
TTGGAACGAACATCAGAAATAGCTTTAAGAACCTTAATGGCTTCGGCTGTGATTTCTTGACCAACG
TGGTCACCTGGCAAAACGACGATCTTCTTAGGGGCAGACATTAGAATGGTATATCCTTGAAATATA
TATATATATATTGCTGAAATGTAAAAGGTAAGAAAAGTTAGAAAGTAAGACGATTGCTAACCACCT
ATTGGAAAAACAATAGGTCCTTAAATAATATTGTCAACTTCAAGTATTGTGATGCAAGCATTTAG
TCATGAACGCTTCTCTATTCTATATGAAAAGCCGGTTCCGGCGCTCTCACCTTTCCTTTTTCTCCC

FIGURE 23.2

AATTTTTCAGTTGAAAAAGGTATATGCGTCAGGCGACCTCTGAAATTAACAAAAAATTTCCAGTCA
TCGAATTTGATTCTGTGCGATAGCGCCCCTGTGTGTTCTCGTTATGTTGAGGAAAAAAATAATGGT
TGCTAAGAGATTCGAACTCTTGCATCTTACGATACCTGAGTATTCCCACAGTTAACTGCGGTCAAG
ATATTTCTTGAATCAGGCGCCTTAGACCGCTCGGCCAAACAACCAATTACTTGTTGAGAAATAGAG
TATAATTATCCTATAAATATAACGTTTTTGAACACACATGAACAAGGAAGTACAGGACAATTGATT
TTGAAGAGAATGTGGATTTTGATGTAATTGTTGGGATTCCATTTTTAATAAGGCAATAATATTAGG
TATGTAGATATACTAGAAGTTCTCCTCGACCGTCGATATGCGGTGTGAAATACCGCACAGATGCGT
AAGGAGAAAATACCGCATCAGGAAATTGTAAACGTTAATATTTGTTAAAATTCGCGTTAAATTTT
TGTTAAATCAGCTCATTTTTTAACCAATAGGCCGAAATCGGCAAAATCCCTTATAAATCAAAAGAA
TAGACCGAGATAGGGTTGAGTGTTGTTCCAGTTTGGAACAAGAGTCCACTATTAAAGAACGTGGAC
TCCAACGTCAAAGGGCGAAAAACCGTCTATCAGGGCGATGGCCCACTACGTGAACCATCACCCTAA
TCAAGTTTTTTGGGGTCGAGGTGCCGTAAAGCACTAAATCGGAACCCTAAAGGGAGCCCCCGATTT
AGAGCTTGACGGGGAAAGCCGGCGAACGTGGCGAGAAAGGAAGGGAAGAAAGCGAAAGGAGCGGGC
GCTAGGGCGCTGGCAAGTGTAGCGGTCACGCTGCGCGTAACCACCACACCCGCCGCGCTTAATGCG
CCGCTACAGGGCGCGTCCATTCGCCATTCAGGCTGCGCAACTGTTGGGAAGGGCGATCGGTGCGGG
CCTCTTCGCTATTACGCCAGCTGAATTGGAGCGACCTCATGCTATACCTGAGAAAGCAACCTGACC
TACAGGAAAGAGTTACTCAAGAATAAGAATTTTCGTTTTAAAACCTAAGAGTCACTTTAAAATTTG
TATACACTTATTTTTTTTATAACTTATTTAATAATAAAAATCATAAATCATAAGAAATTCGCTTAT
TTAGAAGTGTCAACAACGTATCTACCAACGATTTGACCCTTTTCCATCTTTTCGTAAATTTCTGGC
AAGGTAGACAAGCCGACAACCTTGATTGGAGACTTGACCAAACCTCTGGCGAAGAATTGTTAATTA
AGAGCTCAGATCTTATCGTCGTCATCCTTGTAATCCATCGATACTAGTGCGGCCGCCCTTTAGTGA
GGGTTGAATTCGAATTTTCAAAAATTCTTACTTTTTTTTTGGATGGACGCAAAGAAGTTTAATAAT
CATATTACATGGCATTACCACCATATACATATCCATATACATATCCATATCTAATCTTACTTATAT
GTTGTGGAAATGTAAAGAGCCCCATTATCTTAGCCTAAAAAAACCTTCTCTTTGGAACTTTCAGTA
ATACGCTTAACTGCTCATTGCTATATTGAAGTACGGATTAGAAGCCGCCGAGCGGGTGACAGCCCT
CCGAAGGAAGACTCTCCTCCGTGCGTCCTCGTCTTCACCGGTCGCGTTCCTGAAACGCAGATGTGC
CTCGCGCCGCACTGCTCCGAACAATAAAGATTCTACAATACTAGCTTTTATGGTTATGAAGAGGAA
AAATTGGCAGTAACCTGGCCCCACAAACCTTCAAATGAACGAATCAAATTAACAACCATAGGATGA
TAATGCGATTAGTTTTTTAGCCTTATTTCTGGGGTAATTAATCAGCGAAGCGATGATTTTTGATCT
ATTAACAGATATATAAATGCAAAAACTGCATAACCACTTTAACTAATACTTTCAACATTTTCGGTT
TGTATTACTTCTTATTCAAATGTAATAAAAGTATCAACAAAAAATTGTTAATATACCTCTATACTT
TAACGTCAAGGAGAAAAAACCCCGGATCCGTAATACGACTCACTATAGGGCCCGGCgtcgacaag
agcaggattagggatatccgagatggccacactttaaggagcttagcattgttcaaaagaaacaa
ggacaaaccacccattacatcaggatccggtggagccatcagaggaatcaaacacattattatagt

FIGURE 23.3 accaatccctggagattcctcaattaccactcgatccagacttctggaccggttggtgaggttaat
tggaaacccggatgtgagcgggcccaaactaacaggggcactaataggtatattatccttatttgt
ggagtctccaggtcaattgattcagaggatcaccgatgaccctgacgttagcataaggctgttaga
ggttgtccagagtgaccagtcacaatctggccttaccttcgcatcaagaggtaccaacatggagga
tgaggcggaccaatacttttcacatgatgatccaattagtagtgatcaatccaggttcggatggtt
cgggaacaaggaaatctcagatattgaagtgcaagacctgagggattcaacatgattctgggtac
catcctagcccaaatttgggtcttgctcgcaaaggcggttacggccccagacacggcagctgattc
ggagctaagaaggtggataaagtacacccaacaaagaagggtagttggtgaatttagattggagag
aaaatggttggatgtggtgaggaacaggattgccgaggacctctccttacgccgattcatggtcgc
tctaatcctggatatcaagagaacacccggaaacaaaccaggattgctgaaatgatatgtgacat
tgatacatatcgtagaggcaggattagccagttttatcctgactattaagtttgggatagaaac
tatgtatcctgctcttggactgcatgaatttgctggtgagttatccacacttgagtccttgatgaa
cctttaccagcaaatgggggaaactgcaccctacatggtaatcctggagaactcaattcagaacaa
gttcagtgcaggatcataccctctgctctggagctatgccatgggagtaggagtggaacttgaaaa
ctccatgggagggtttgaactttggccgatcttactttgatccagcatatttttagattagggcaaga
gatggtaaggaggtcagctggaaaggtcagttccacattggcatctgaactcggtatcactgccga
ggatgcaaggcttgtttcagagattgcaatgcatactactgaggacaagatcagtagagcggttgg
acccagacaagcccaagtatcatttctacacggtgatcaaagtgagaatgagctaccgagattggg
gggcaaggaagataggagggtcaaacagagtcgaggagaagccagggagagctacagagaaaccgg
gcccagcagagcaagtgatgcgagagctgcccatcttccaaccggcacacccctagacattgacac
tgcaacggagtccagccaagatccgcaggacagtcgaaggtcagctgacgccctgcttaggctgca
agccatggcaggaatctcggaagaacaaggctcagacacggacaccctatagtgtacaatgacag
aaatcttctagactaggtgcgagaggccgagggccagaacaacatccgcctaccatccatcattgt
tataaaaacttaggaaccaggtccacacagccgccagcccatcaaccatccactcgagTAAGCTT
GGTACCGCGGCTAGCTAAGATCCGCTCTAACCGAAAAGGAAGGAGTTAGACAACCTGAAGTCTAGG
TCCCTATTTATTTTTTTATAGTTATGTTAGTATTAAGAACGTTATTTATATTTCAAATTTTTCTTT
TTTTTCTGTACAGACGCGTGTACGCATGTAACATTATACTGAAAACCTTGCTTGAGAAGGTTTTGG
GACGCTCGAAGATCCAGCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAAGAACATGT
GAGCAAAAGGCCAGCAAAAGGCCAGGAACCGTAAAAAGGCCGCGTTGCTGGCGTTTTTCCATAGGC
TCCGCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGCTCACGCTGTA

FIGURE 23.4

```
GGTATCTCAGTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACGACTTATCGC
CACTGGCAGCAGCCACTGGTAACAGGATTAGCAGAGCGAGGTATGTAGGCGGTGCTACAGAGTTCT
TGAAGTGGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAGGATCTCAAGAAGATCCTTTGATCT
TTTCTACGGGGTCTGACGCTCAGTGGAACGAAAACTCACGTTAAGGGATTTTGGTCATGAGATTAT
CAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTC
TATTTCGTTCATCCATAGTTGCCTGACTCCCCGTCGTGTAGATAACTACGATACGGGAGGGCTTAC
CATCTGGCCCCAGTGCTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTATCCGCCTCCATCCAGT
CTATTAATTGTTGCCGGGAAGCTAGAGTAAGTAGTTCGCCAGTTAATAGTTTGCGCAACGTTGTTG
CCATTGCTACAGGCATCGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATGGCAGCACTGCATAATT
CTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAAGGG
CGACACGGAAATGTTGAATACTCATACTCTTCCTTTTTCAATATTATTGAAGCATTTATCAGGGTT
ATTGTCTCATGAGCGGATACATATTTGAATGTATTTAGAAAAATAAACAAATAGGGGTTCCGCGCA
CATTTCCCCGAAAAGTGCCACCTGAACGAAGCATCTGTGCTTCATTTTGTAGAACAAAAATGCAAC
GCGAGAGCGCTAATTTTTCAAACAAAGAATCTGAGCTGCATTTTTACAGAACAGAAATGCAACGCG
AAAGCGCTATTTTACCAACGAAGAATCTGTGCTTCATTTTTGTAAAACAAAAATGCAACGCGAGAG
CGCTAATTTTTCAAACAAAGAATCTGAGCTGCATTTTTACAGAACAGAAATGCAACGCGAGAGCGC
TATTTTACCAACAAAGAATCTATACTTCTTTTTTGTTCTACAAAAATGCATCCCGAGAGCGCTATT
TTTCTAACAAAGCATCTTAGATTACTTTTTTTCTCCTTTGTGCGCTCTATAATGCAGTCTCTTGAT
AACTTTTTGCACTGTAGGTCCGTTAAGGTTAGAAGAAGGCTACTTTGGTGTCTATTTTCTCTTCCA
TAAAAAAGCCTGACTCCACTTCCCGCGTTTACTGATTACTAGCGAAGCTGCGGGTGCATTTTTTC
AAGATAAAGGCATCCCCGATTATATTCTATACCGATGTGGATTGCGCATACTTTGTGAACAGAAAG
TGATAGCGTTGATGATTCTTCATTGGTCAGAAAATTATGAACGGTTTCTTCTATTTTGTCTCTATA
TACTACGTATAGGAAATGTTTACATTTTCGTATTGTTTTCGATTCACTCTATGAATAGTTCTTACT
```

FIGURE 23.5

```
ACAATTTTTTTGTCTAAAGAGTAATACTAGAGATAAACATAAAAAATGTAGAGGTCGAGTTTAGAT
GCAAGTTCAAGGAGCGAAAGGTGGATGGGTAGGTTATATAGGGATATAGCACAGAGATATATAGCA
AAGAGATACTTTTGAGCAATGTTTGTGGAAGCGGTATTCGCAATATTTAGTAGCTCGTTACAGTC
CGGTGCGTTTTTGGTTTTTTGAAAGTGCGTCTTCAGAGCGCTTTTGGTTTTCAAAAGCGCTCTGAA
GTTCCTATACTTTCTAGAGAATAGGAACTTCGGAATAGGAACTTCAAAGCGTTTCCGAAAACGAGC
GCTTCCGAAAATGCAACGCGAGCTGCGCACATACAGCTCACTGTTCACGTCGCACCTATATCTGCG
TGTTGCCTGTATATATATACATGAGAAGAACGGCATAGTGCGTGTTTATGCTTAAATGCGTACT
TATATGCGTCTATTTATGTAGGATGAAAGGTAGTCTAGTACCTCCTGTGATATTATCCCATTCCAT
GCGGGTATCGTATGCTTCCTTCAGCACTACCCTTTAGCTGTTCTATATGCTGCCACTCCTCAATT
GGATTAGTCTCATCCTTCAATGCTATCATTTCCTTTGATATTGGATCATACTAAGAAACCATTATT
ATCATGACATTAACCTATAAAAATAGGCGTATCACGAGGCCCTTTCGTC
```

FIGURE 24.1 pESC-TRP-P (pCM104)

Viral P sequence:         Minuscule letter
pESC-TRP vector sequence: Upper case letter TCGCGCGTTTCGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTTGGCGGGTGTC
GGGGCTGGCTTAACTATGCGGCATCAGAGCAGATTGTACTGAGAGTGCACCATAAACGACATTACT
ATATATATAATATAGGAAGCATTTAATAGAACAGCATCGTAATATATGTGTACTTTGCAGTTATGA
CGCCAGATGGCAGTAGTGGAAGATATTCTTTATTGAAAAATAGCTTGTCACCTTACGTACAATCTT
GATCCGGAGCTTTTCTTTTTTTGCCGATTAAGAATTAATTCGGTCGAAAAAAGAAAAGGAGAGGGC
CAAGAGGGAGGGCATTGGTGACTATTGAGCACGTGAGTATACGTGATTAAGCACACAAAGGCAGCT
TGGAGTATGTCTGTTATTAATTTCACAGGTAGTTCTGGTCCATTGGTGAAAGTTTGCGGCTTGCAG
AGCACAGAGGCCGCAGAATGTGCTCTAGATTCCGATGCTGACTTGCTGGGTATTATATGTGTGCCC
AATAGAAAGAGAACAATTGACCCGGTTATTGCAAGGAAAATTTCAAGTCTTGTAAAAGCATATAAA
AATAGTTCAGGCACTCCGAAATACTTGGTTGGCGTGTTTCGTAATCAACCTAAGGAGGATGTTTTG
GCTCTGGTCAATGATTACGGCATTGATATCGTCCAACTGCATGGAGATGAGTCGTGGCAAGAATAC
CAAGAGTTCCTCGGTTTGCCAGTTATTAAAAGACTCGTATTTCCAAAAGACTGCAACATACTACTC
AGTGCAGCTTCACAGAAACCTCATTCGTTTATTCCCTTGTTTGATTCAGAAGCAGGTGGGACAGGT
GAACTTTTGGATTGGAACTCGATTTCTGACTGGGTTGGAAGGCAAGAGAGCCCCGAAAGCTTACAT
TTTATGTTAGCTGGTGGACTGACGCCAGAAAATGTTGGTGATGCGCTTAGATTAAATGGCGTTATT
GGTGTTGATGTAAGCGGAGGTGTGGAGACAAATGGTGTAAAAGACTCTAACAAAATAGCAAATTTC
GTCAAAAATGCTAAGAAATAGGTTATTACTGAGTAGTATTTATTTAAGTATTGTTTGTGCACTTGC
CTATGCGGTGTGAAATACCGCACAGATGCGTAAGGAGAAAATACCGCATCAGGAAATTGTAAACGT
TAATATTTTGTTAAAATTCGCGTTAAATTTTTGTTAAATCAGCTCATTTTTTAACCAATAGGCCGA
AATCGGCAAAATCCCTTATAAATCAAAAGAATAGACCGAGATAGGGTTGAGTGTTGTTCCAGTTTG
GAACAAGAGTCCACTATTAAAGAACGTGGACTCCAACGTCAAAGGGCGAAAAACCGTCTATCAGGG
CGATGGCCCACTACGTGAACCATCACCCTAATCAAGTTTTTTGGGGTCGAGGTGCCGTAAAGCACT
AAATCGGAACCCTAAAGGGAGCCCCCGATTTAGAGCTTGACGGGGAAAGCCGGCGAACGTGGCGAG
AAAGGAAGGGAAGAAAGCGAAAGGAGCGGGCGCTAGGGCGCTGGCAAGTGTAGCGGTCACGCTGCG
CGTAACCACCACACCCGCCGCGCTTAATGCGCCGCTACAGGGCGCGTCCATTCGCCATTCAGGCTG
CGCAACTGTTGGGAAGGGCGATCGGTGCGGGCCTCTTCGCTATTACGCCAGCTGAATTGGAGCGAC
CTCATGCTATACCTGAGAAAGCAACCTGACCTACAGGAAAGAGTTACTCAAGAATAAGAATTTTCG
TTTTAAAACCTAAGAGTCACTTTAAAATTTGTATACACTTATTTTTTTTATAACTTATTTAATAAT

FIGURE 24.2

AAAAATCATAAATCATAAGAAATTCGCTTATTTAGAAGTGTCAACAACGTATCTACCAACGATTTG
ACCCTTTTCCATCTTTTCGTAAATTTCTGGCAAGGTAGACAAGCCGACAACCTTGATTGGAGACTT
GACCAAACCTCTGGCGAAGAATTGTTAATTAAGAGCTCAGATCTTATCGTCGTCATCCTTGTAATC
CATCGATACTAGTGCGGCCGCCCTTTAGTGAGGGTTGAATTCGAATTTTCAAAAATTCTTACTTTT
TTTTTGGATGGACGCAAAGAAGTTTAATAATCATATTACATGGCATTACCACCATATACATATCCA
TATACATATCCATATCTAATCTTACTTATATGTTGTGGAAATGTAAAGAGCCCCATTATCTTAGCC
TAAAAAAACCTTCTCTTTGGAACTTTCAGTAATACGCTTAACTGCTCATTGCTATATTGAAGTACG
GATTAGAAGCCGCCGAGCGGGTGACAGCCCTCCGAAGGAAGACTCTCCTCCGTGCGTCCTCGTCTT
CACCGGTCGCGTTCCTGAAACGCAGATGTGCCTCGCGCCGCACTGCTCCGAACAATAAAGATTCTA
CAATACTAGCTTTTATGGTTATGAAGAGGAAAAATTGGCAGTAACCTGGCCCCACAAACCTTCAAA
TGAACGAATCAAATTAACAACCATAGGATGATAATGCGATTAGTTTTTTAGCCTTATTTCTGGGGT
AATTAATCAGCGAAGCGATGATTTTTGATCTATTAACAGATATATAAATGCAAAAACTGCATAACC
ACTTTAACTAATACTTTCAACATTTTCGGTTTGTATTACTTCTTATTCAAATGTAATAAAAGTATC
AACAAAAAATTGTTAATATACCTCTATACTTTAACGTCAAGGAGAAAAAACCCCGGATCCGTAATA
CGACTCACTATAGGGCCCGGGCgtcgactaggtgcgagaggccgagggccagaacaacatccgcct
accatccatcattgttataaaaacttaggaaccaggtccacacagccgccagccatcaaccatc
cactcccacgattggagccaatggcagaagagcaggcacgccatgtcaaaaacggactggaatgca
tccgggctctcaaggccgagcccatcggctcactggccatcgaggaagctatggcagcatggtcag
aaatatcagacaacccaggacaggagcgagccacctgcagggaagagaaggcaggcagttcgggtc
tcagcaaaccatgcctctcagcaattggatcaactgaaggcggtgcacctcgcatccgcggtcagg
gacctggagagagcgatgacgacgctgaaactttgggaatcccccaagaaatctccaggcatcaa
gcactgggttacagtgttattacgtttatgatcacagcggtgaagcggttaagggaatccaagatg
ctgactctatcatggttcaatcaggccttgatggtgatagcaccctctcaggaggagacaatgaat
ctgaaaacagcgatgtggatattggcgaacctgataccgagggatatgctatcactgaccgggat
ctgctcccatctctatggggttcagggcttctgatgttgaaactgcagaaggaggggagatccacg
agctcctgagactccaatccagaggcaacaactttccgaagcttgggaaaactctcaatgttcctc
cgcccccggaccccggtagggccagcacttccgggacacccattaaaaagggcacagacgcgagat
tagcctcatttggaacggagatcgcgtctttattgacaggtggtgcaacccaatgtgctcgaaagt
caccctcggaaccatcagggccaggtgcacctgcggggaatgtccccgagtgtgtgagcaatgccg
cactgatacaggagtggacacccgaatctggtaccacaatctccccgagatcccagaataatgaag
aagggggagactattatgatgatgagctgttctctgatgtccaagatattaaaacagccttggcca
aaatacacgaggataatcagaagataatctccaagctagaatcactgctgttattgaagggagaag
ttgagtcaattaagaagcagatcaacaggcaaaatatcagcatatccaccctggaaggacacctct
caagcatcatgatcgccattcctggacttgggaaggatcccaacgaccccactgcagatgtcgaaa

FIGURE 24.3 tcaatcccgacttgaaacccatcataggcagagattcaggccgagcactggccgaagttctcaaga
aacccgttgccagccgacaactccaaggaatgacaaatggacggaccagttccagaggacagctgc
tgaaggaatttcagctaaagccgatcgggaaaaagatgagctcagccgtcgggtttgttcctgaca
ccggccctgcatcacgcagtgtaatccgctccattataaaatccagccggctagaggaggatcgga
agcgttacctgatgactctccttgatgatatcaaaggagccaatgatcttgccaagttccaccaga
tgctgatgaagataataatgaagtagctacagctcgagTAAGCTTGGTACCGCGGCTAGCTAAGAT
CCGCTCTAACCGAAAAGGAAGGAGTTAGACAACCTGAAGTCTAGGTCCCTATTTATTTTTTATAG
TTATGTTAGTATTAAGAACGTTATTTATATTTCAAATTTTTCTTTTTTTTCTGTACAGACGCGTGT
ACGCATGTAACATTATACTGAAAACCTTGCTTGAGAAGGTTTTGGGACGCTCGAAGATCCAGCTGC
ATTAATGAATCGGCCAACGCGCGGGAGAGGCGGTTTGCGTATTGGGCGCTCTTCCGCTTCCTCGC
TCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCAGC
AGATTACGCGCAGAAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTGCTGCAA
TGATACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAAAAGTGC

FIGURE 24.4

```
TCATCATTGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTGCCAC
CTGAACGAAGCATCTGTGCTTCATTTTGTAGAACAAAAATGCAACGCGAGAGCGCTAATTTTTCAA
ACAAAGAATCTGAGCTGCATTTTTACAGAACAGAAATGCAACGCGAAAGCGCTATTTTACCAACGA
AGAATCTGTGCTTCATTTTTGTAAAACAAAAATGCAACGCGAGAGCGCTAATTTTTCAAACAAAGA
ATCTGAGCTGCATTTTTACAGAACAGAAATGCAACGCGAGAGCGCTATTTTACCAACAAAGAATCT
ATACTTCTTTTTTGTTCTACAAAAATGCATCCCGAGAGCGCTATTTTTCTAACAAAGCATCTTAGA
TTACTTTTTTTCTCCTTTGTGCGCTCTATAATGCAGTCTCTTGATAACTTTTTGCACTGTAGGTCC
GTTAAGGTTAGAAGAAGGCTACTTTGGTGTCTATTTTCTCTTCCATAAAAAAAGCCTGACTCCACT
TCCCGCGTTTACTGATTACTAGCGAAGCTGCGGGTGCATTTTTTCAAGATAAAGGCATCCCCGATT
ATATTCTATACCGATGTGGATTGCGCATACTTTGTGAACAGAAAGTGATAGCGTTGATGATTCTTC
ATTGGTCAGAAAATTATGAACGGTTTCTTCTATTTTGTCTCTATATACTACGTATAGGAAATGTTT
ACATTTTCGTATTGTTTTCGATTCACTCTATGAATAGTTCTTACTACAATTTTTTGTCTAAAGAG
TAATACTAGAGATAAACATAAAAAATGTAGAGGTCGAGTTTAGATGCAAGTTCAAGGAGCGAAAGG
TGGATGGGTAGGTTATATAGGGATATAGCACAGAGATATATAGCAAAGAGATACTTTTGAGCAATG
TTTGTGGAAGCGGTATTCGCAATATTTTAGTAGCTCGTTACAGTCCGGTGCGTTTTGGTTTTTTG
AAAGTGCGTCTTCAGAGCGCTTTTGGTTTTCAAAAGCGCTCTGAAGTTCCTATACTTTCTAGAGAA
TAGGAACTTCGGAATAGGAACTTCAAAGCGTTTCCGAAAACGAGCGCTTCCGAAAATGCAACGCGA
GCTGCGCACATACAGCTCACTGTTCACGTCGCACCTATATCTGCGTGTTGCCTGTATATATATATA
CATGAGAAGAACGGCATAGTGCGTGTTTATGCTTAAATGCGTACTTATATGCGTCTATTTATGTAG
GATGAAAGGTAGTCTAGTACCTCCTGTGATATTATCCCATTCCATGCGGGTATCGTATGCTTCCT
TCAGCACTACCCTTTAGCTGTTCTATATGCTGCCACTCCTCAATTGGATTAGTCTCATCCTTCAAT
GCTATCATTTCCTTTGATATTGGATCATATTAAGAAACCATTATTATCATGACATTAACCTATAAA
AATAGGCGTATCACGAGGCCCTTTCGTC
```

FIGURE 25.1 pESC-LEU-NP (pCM106)

| | |
|---|---|
| Viral N sequence: | Bold minuscule letter |
| Viral P sequence: | Minuscule letter |
| pESC-LEU vector sequence: | Upper case letter |

TCGCGCGTTTCGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTTGGCGGGTGTC
GGGGCTGGCTTAACTATGCGGCATCAGAGCAGATTGTACTGAGAGTGCACCATATCGACTACGTCG
TAAGGCCGTTTCTGACAGAGTAAAATTCTTGAGGGAACTTTCACCATTATGGGAAATGCTTCAAGA
AGGTATTGACTTAAACTCCATCAAATGGTCAGGTCATTGAGTGTTTTTATTTGTTGTATTTTTT
TTTTTAGAGAAAATCCTCCAATATCAAATTAGGAATCGTAGTTTCATGATTTTCTGTTACACCTA
ACTTTTTGTGTGGTGCCCTCCTCCTTGTCAATATTAATGTTAAAGTGCAATTCTTTTTCCTTATCA
CGTTGAGCCATTAGTATCAATTTGCTTACCTGTATTCCTTTACTATCCTCCTTTTTCTCCTTCTTG
ATAAATGTATGTAGATTGCGTATATAGTTTCGTCTACCCTATGAACATATTCCATTTTGTAATTTC
GTGTCGTTTCTATTATGAATTTCATTTATAAAGTTTATGTACAAATATCATAAAAAAGAGAATCT
TTTTAAGCAAGGATTTTCTTAACTTCTTCGGCGACAGCATCACCGACTTCGGTGGTACTGTTGGAA
CCACCTAAATCACCAGTTCTGATACCTGCATCCAAAACCTTTTTAACTGCATCTTCAATGGCCTTA
CCTTCTTCAGGCAAGTTCAATGACAATTTCAACATCATTGCAGCAGACAAGATAGTGGCGATAGGG
TCAACCTTATTCTTTGGCAAATCTGGAGCAGAACCGTGGCATGGTTCGTACAAACCAAATGCGGTG
TTCTTGTCTGGCAAAGAGGCCAAGGACGCAGATGGCAACAAACCCAAGGAACCTGGGATAACGGAG
GCTTCATCGGAGATGATATCACCAAACATGTTGCTGGTGATTATAATACCATTTAGGTGGGTTGGG
TTCTTAACTAGGATCATGGCGGCAGAATCAATCAATTGATGTTGAACCTTCAATGTAGGGAATTCG
TTCTTGATGGTTTCCTCCACAGTTTTTCTCCATAATCTTGAAGAGGCCAAAAGATTAGCTTTATCC
AAGGACCAAATAGGCAATGGTGGCTCATGTTGTAGGGCCATGAAAGCGGCCATTCTTGTGATTCTT
TGCACTTCTGGAACGGTGTATTGTTCACTATCCCAAGCGACACCATCACCATCGTCTTCCTTTCTC
TTACCAAAGTAAATACCTCCCACTAATTCTCTGACAACAACGAAGTCAGTACCTTTAGCAAATTGT
GGCTTGATTGGAGATAAGTCTAAAAGAGAGTCGGATGCAAAGTTACATGGTCTTAAGTTGGCGTAC
AATTGAAGTTCTTTACGGATTTTTAGTAAACCTTGTTCAGGTCTAACACTACCGGTACCCCATTTA
GGACCACCCACAGCACCTAACAAAACGGCATCAGCCTTCTTGGAGGCTTCCAGCGCCTCATCTGGA
AGTGGAACACCTGTAGCATCGATAGCAGCACCACCAATTAAATGATTTTCGAAATCGAACTTGACA
TTGAACGAACATCAGAAATAGCTTTAAGAACCTTAATGGCTTCGGCTGTGATTTCTTGACCAACG
TGGTCACCTGGCAAAACGACGATCTTCTTAGGGGCAGACATTAGAATGGTATATCCTTGAAATATA
TATATATATATTGCTGAAATGTAAAGGTAAGAAAAGTTAGAAAGTAAGACGATTGCTAACCACCT
ATTGGAAAAAACAATAGGTCCTTAAATAATATTGTCAACTTCAAGTATTGTGATGCAAGCATTTAG

FIGURE 25.2

```
TCATGAACGCTTCTCTATTCTATATGAAAAGCCGGTTCCGGCGCTCTCACCTTTCCTTTTTCTCCC
AATTTTTCAGTTGAAAAAGGTATATGCGTCAGGCGACCTCTGAAATTAACAAAAAATTTCCAGTCA
TCGAATTTGATTCTGTGCGATAGCGCCCTGTGTGTTCTCGTTATGTTGAGGAAAAAAATAATGGT
TGCTAAGAGATTCGAACTCTTGCATCTTACGATACCTGAGTATTCCCACAGTTAACTGCGGTCAAG
ATATTTCTTGAATCAGGCGCCTTAGACCGCTCGGCCAAACAACCAATTACTTGTTGAGAAATAGAG
TATAATTATCCTATAAATATAACGTTTTTGAACACACATGAACAAGGAAGTACAGGACAATTGATT
TTGAAGAGAATGTGGATTTTGATGTAATTGTTGGGATTCCATTTTTAATAAGGCAATAATATTAGG
TATGTAGATATACTAGAAGTTCTCCTCGACCGTCGATATGCGGTGTGAAATACCGCACAGATGCGT
AAGGAGAAAATACCGCATCAGGAAATTGTAAACGTTAATATTTTGTTAAAATTCGCGTTAAATTTT
TGTTAAATCAGCTCATTTTTTAACCAATAGGCCGAAATCGGCAAATCCCTTATAAATCAAAAGAA
TAGACCGAGATAGGGTTGAGTGTTGTTCCAGTTTGGAACAAGAGTCCACTATTAAAGAACGTGGAC
TCCAACGTCAAAGGGCGAAAACCGTCTATCAGGGCGATGGCCCACTACGTGAACCATCACCCTAA
TCAAGTTTTTTGGGGTCGAGGTGCCGTAAAGCACTAAATCGGAACCCTAAAGGGAGCCCCCGATTT
AGAGCTTGACGGGGAAAGCCGGCGAACGTGGCGAGAAAGGAAGGGAAGAAAGCGAAAGGAGCGGGC
GCTAGGGCGCTGGCAAGTGTAGCGGTCACGCTGCGCGTAACCACCACACCCGCCGCGCTTAATGCG
CCGCTACAGGGCGCGTCCATTCGCCATTCAGGCTGCGCAACTGTTGGGAAGGGCGATCGGTGCGGG
CCTCTTCGCTATTACGCCAGCTGAATTGGAGCGACCTCATGCTATACCTGAGAAAGCAACCTGACC
TACAGGAAAGAGTTACTCAAGAATAAGAATTTTCGTTTTAAAACCTAAGAGTCACTTTAAAATTTG
TATACACTTATTTTTTTTATAACTTATTTAATAATAAAAATCATAAATCATAAGAAATTCGCTTAT
TTAGAAGTGTCAACAACGTATCTACCAACGATTTGACCCTTTTCCATCTTTTCGTAAATTTCTGGC
AAGGTAGACAAGCCGACAACCTTGATTGGAGACTTGACCAAACCTCTGGCGAAGAATTGTTAATTA
AGAGCTgctgtagctacttcattattatcttcatcagcatctggtggaacttggcaagatcattgg
ctcctttgatatcatcaaggagagtcatcaggtaacgcttccgatcctcctctagccggctggatt
ttataatggagcggattacactgcgtgatgcagggccggtgtcaggaacaaacccgacggctgagc
tcatcttttcccgatcggctttagctgaaattccttcagcagctgtcctctggaactggtccgtc
catttgtcattccttggagttgtcggctggcaacgggtttcttgagaacttcggccagtgctcggc
ctgaatctctgcctatgatgggtttcaagtcgggattgatttcgacatctgcagtggggtcgttgg
gatccttcccaagtccaggaatggcgatcatgatgcttgagaggtgtccttccagggtggatatgc
tgatattttgcctgttgatctgcttcttaattgactcaacttctcccttcaataacagcagtgatt
ctagcttggagattatcttctgattatcctcgtgtattttggccaaggctgttttaatatcttgga
catcagagaacagctcatcatcataatagtctcccccttcttcattattctgggatctcggggaga
ttgtggtaccagattcgggtgtccactcctgtatcagtgcggcattgctcacacactcggggacat
tccccgcaggtgcacctggccctgatggttccgagggtgactttcgagcacattggttgcaccac
ctgtcaataaagacgcgatctccgttccaaatgaggctaatctcgcgtctgtgcccttttaatgg
```

FIGURE 25.3

```
gtgtcccggaagtgctggccctaccggggtccggggcggaggaacattgagagttttcccaagct
tcggaaagttgttgcctctggattggagtctcaggagctcgtggatctcccctcttctgcagttt
caacatcagaagccctgaacccatagagatgggagcagatccccggtcagtgatagcatatccct
cggtatcaggttcgccaatatccacatcgctgttttcagattcattgtctcctcctgagagggtgc
tatcaccatcaaggcctgattgaaccatgatagagtcagcatcttggattcccttaaccgcttcac
cgctgtgatcataaacgtaataacactgtaacccagtgcttgatgcctggagatttcttgggggga
ttcccaaagtttcagcgtcgtcatcgctctctccaggtccctgaccgcggatgcgaggtgcaccgc
cttcagttgatccaattgctgagaggcatggtttgctgagacccgaactgcctgccttctcttccc
tgcaggtggctcgctcctgtcctgggttgtctgatatttctgaccatgctgccatagcttcctcga
tggccagtgagccgatgggctcggccttgagagcccggatgcattccagtccgttttttgacatggc
gtgcctgctcttctgccattggctccaatcgtgggagtggatggttgatgggctggcggctgtgtg
gacctggttcctaagttttttataacaatgatggatggtaggcggatgttgttctggccctcggcc
tctcgcacctagGCCCTTTAGTGAGGGTTGAATTCGAATTTTCAAAAATTCTTACTTTTTTTTGG
ATGGACGCAAAGAAGTTTAATAATCATATTACATGGCATTACCACCATATACATATCCATATACAT
ATCCATATCTAATCTTACTTATATGTTGTGGAAATGTAAAGAGCCCCATTATCTTAGCCTAAAAAA
ACCTTCTCTTTGGAACTTTCAGTAATACGCTTAACTGCTCATTGCTATATTGAAGTACGGATTAGA
AGCCGCCGAGCGGGTGACAGCCCTCCGAAGGAAGACTCTCCTCCGTGCGTCCTCGTCTTCACCGGT
CGCGTTCCTGAAACGCAGATGTGCCTCGCGCCGCACTGCTCCGAACAATAAAGATTCTACAATACT
AGCTTTTATGGTTATGAAGAGGAAAAATTGGCAGTAACCTGGCCCCACAAACCTTCAAATGAACGA
ATCAAATTAACAACCATAGGATGATAATGCGATTAGTTTTTTAGCCTTATTTCTGGGGTAATTAAT
CAGCGAAGCGATGATTTTTGATCTATTAACAGATATATAAATGCAAAAACTGCATAACCACTTTAA
CTAATACTTTCAACATTTTCGGTTTGTATTACTTCTTATTCAAATGTAATAAAAGTATCAACAAAA
AATTGTTAATATACCTCTATACTTTAACGTCAAGGAGAAAAAACCCCGGATCCGTAATACGACTCA
CTATAGGGCCCGGGCgtcgacaagagcaggattagggatatccgagatggccacacttttaaggag
cttagcattgttcaaaagaaacaaggacaaaccacccattacatcaggatccggtggagccatcag
aggaatcaaacacattattatagtaccaatccctggagattcctcaattaccactcgatccagact
tctggaccggttggtgaggttaattggaaacccggatgtgagcgggcccaaactaacaggggcact
aataggtatattatccttatttgtggagtctccaggtcaattgattcagaggatcaccgatgaccc
tgacgttagcataaggctgttagaggttgtccagagtgaccagtcacaatctggccttaccttcgc
atcaagaggtaccaacatggaggatgaggcggaccaatactttcacatgatgatccaattagtag
tgatcaatccaggttcggatggttcgggaacaaggaaatctcagatattgaagtgcaagaccctga
gggattcaacatgattctgggtaccatcctagcccaaatttgggtcttgctcgcaaaggcggttac
ggccccagacacggcagctgattcggagctaagaaggtggataaagtacacccaacaaagaagggt
agttggtgaatttagattggagagaaaatggttggatgtggtgaggaacaggattgccgaggacct
```

FIGURE 25.4 ctccttacgccgattcatggtcgctctaatcctggatatcaagagaacacccggaaacaaacccag
gattgctgaaatgatatgtgacattgatacatatatcgtagaggcaggattagccagttttatcct
gactattaagtttgggatagaaactatgtatcctgctcttggactgcatgaatttgctggtgagtt
atccacacttgagtccttgatgaacctttaccagcaaatgggggaaactgcacccctacatggtaat
cctggagaactcaattcagaacaagttcagtgcaggatcataccctctgctctggagctatgccat
gggagtaggagtggaacttgaaaactccatgggaggtttgaactttggccgatcttactttgatcc
agcatattttagattagggcaagagatggtaaggaggtcagctggaaaggtcagttccacattggc
atctgaactcggtatcactgccgaggatgcaaggcttgtttcagagattgcaatgcatactactga
ggacaagatcagtagagcggttggacccagacaagcccaagtatcatttctacacggtgatcaaag
tgagaatgagctaccgagattgggggggcaaggaagataggagggtcaaacagagtcgaggagaagc
cagggagagctacagagaaaccgggcccagcagagcaagtgatgcgagagctgccatcttccaac
cggcacaccctagacattgacactgcaacggagtccagccaagatccgcaggacagtcgaaggtc
agctgacgccctgcttaggctgcaagccatggcaggaatctcggaagaacaaggctcagacacgga
caccctatagtgtacaatgacagaaatcttctagactaggtgcgagaggccgagggccagaacaa
catccgcctaccatccatcattgttataaaaaacttaggaaccaggtccacacagccgccagccca
tcaaccatccactcgagTAAGCTTGGTACCGCGGCTAGCTAAGATCCGCTCTAACCGAAAAGGAAG
GAGTTAGACAACCTGAAGTCTAGGTCCCTATTTATTTTTTTATAGTTATGTTAGTATTAAGAACGT
TATTTATATTTCAAATTTTTCTTTTTTTTCTGTACAGACGCGTGTACGCATGTAACATTATACTGA
AAACCTTGCTTGAGAAGGTTTTGGGACGCTCGAAGATCCAGCTGCATTAATGAATCGGCCAACGCG
CGGGGAGAGGCGGTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAACTCACGTT
AAGGGATTTTGGTCATGAGATTATCAAAAGGATCTTCACCTAGATCCTTTTAAATTAAAAATGAA
GTTTTAAATCAATCTAAAGTATATATGAGTAAACTTGGTCTGACAGTTACCAATGCTTAATCAGTG

FIGURE 25.5

```
AGGCACCTATCTCAGCGATCTGTCTATTTCGTTCATCCATAGTTGCCTGACTCCCCGTCGTGTAGA
TAACTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAG
TTAATAGTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCATGTTGTGCAAAA
AAGCGGTTAGCTCCTTCGGTCCTCCGATCGTTGTCAGAAGTAAGTTGGCCGCAGTGTTATCACTCA
TGGTTATGGCAGCACTGCATAATTCTCTTACTGTCATGCCATCCGTAAGATGCTTTTCTGTGACTG
GTGAGTACTCAACCAAGTCATTCTGAGAATAGTGTATGCGGCGACCGAGTTGCTCTTGCCCGGCGT
CAATACGGGATAATACCGCGCCACATAGCAGAACTTTAAAAGTGCTCATCATTGGAAAACGTTCTT
CGGGGCGAAAACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAAT
ATTATTGAAGCATTTATCAGGGTTATTGTCTCATGAGCGGATACATATTTGAATGTATTTAGAAAA
ATAAACAAATAGGGGTTCCGCGCACATTTCCCCGAAAAGTGCCACCTGAACGAAGCATCTGTGCTT
CATTTTGTAGAACAAAAATGCAACGCGAGAGCGCTAATTTTTCAAACAAAGAATCTGAGCTGCATT
TTTACAGAACAGAAATGCAACGCGAAAGCGCTATTTTACCAACGAAGAATCTGTGCTTCATTTTTG
TAAAACAAAAATGCAACGCGAGAGCGCTAATTTTTCAAACAAAGAATCTGAGCTGCATTTTTACAG
AACAGAAATGCAACGCGAGAGCGCTATTTTACCAACAAAGAATCTATACTTCTTTTTTGTTCTACA
AAAATGCATCCCGAGAGCGCTATTTTTCTAACAAAGCATCTTAGATTACTTTTTTTCTCCTTTGTG
CGCTCTATAATGCAGTCTCTTGATAACTTTTTGCACTGTAGGTCCGTTAAGGTTAGAAGAAGGCTA
CTTTGGTGTCTATTTTCTCTTCCATAAAAAAAGCCTGACTCCACTTCCCGCGTTTACTGATTACTA
GCGAAGCTGCGGGTGCATTTTTTCAAGATAAAGGCATCCCCGATTATATTCTATACCGATGTGGAT
TGCGCATACTTTGTGAACAGAAAGTGATAGCGTTGATGATTCTTCATTGGTCAGAAAATTATGAAC
GGTTTCTTCTATTTTGTCTCTATATACTACGTATAGGAAATGTTTACATTTTCGTATTGTTTTCGA
TTCACTCTATGAATAGTTCTTACTACAATTTTTTTGTCTAAAGAGTAATACTAGAGATAAACATAA
AAAATGTAGAGGTCGAGTTTAGATGCAAGTTCAAGGAGCGAAAGGTGGATGGGTAGGTTATATAGG
GATATAGCACAGAGATATATAGCAAAGAGATACTTTTGAGCAATGTTTGTGGAAGCGGTATTCGCA
ATATTTTAGTAGCTCGTTACAGTCCGGTGCGTTTTTGGTTTTTTGAAAGTGCGTCTTCAGAGCGCT
TTTGGTTTTCAAAAGCGCTCTGAAGTTCCTATACTTTCTAGAGAATAGGAACTTCGGAATAGGAAC
TTCAAAGCGTTTCCGAAAACGAGCGCTTCCGAAAATGCAACGCGAGCTGCGCACATACAGCTCACT
GTTCACGTCGCACCTATATCTGCGTGTTGCCTGTATATATATATACATGAGAAGAACGGCATAGTG
CGTGTTTATGCTTAAATGCGTACTTATATGCGTCTATTTATGTAGGATGAAAGGTAGTCTAGTACC
TCCTGTGATATTATCCCATTCCATGCGGGGTATCGTATGCTTCCTTCAGCACTACCCTTTAGCTGT
```

FIGURE 25.6

TCTATATGCTGCCACTCCTCAATTGGATTAGTCTCATCCTTCAATGCTATCATTTCCTTTGATATT
GGATCATACTAAGAAACCATTATTATCATGACATTAACCTATAAAAATAGGCGTATCACGAGGCCC
TTTCGTC

FIGURE 26.1 pESC-HIS-L (pCM105)

Viral L sequence: Minuscule letter
pESC-HIS vector sequence: Upper case letter

TCGCGCGTTTCGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTTGGCGGGTGTC
GGGGCTGGCTTAACTATGCGGCATCAGAGCAGATTGTACTGAGAGTGCACCATAAATTCCCGTTTT
AAGAGCTTGGTGAGCGCTAGGAGTCACTGCCAGGTATCGTTTGAACACGGCATTAGTCAGGGAAGT
CATAACACAGTCCTTTCCCGCAATTTTCTTTTTCTATTACTCTTGGCCTCCTCTAGTACACTCTAT
ATTTTTTATGCCTCGGTAATGATTTTCATTTTTTTTTTCCCCTAGCGGATGACTCTTTTTTTTT
CTTAGCGATTGGCATTATCACATAATGAATTATACATTATATAAAGTAATGTGATTTCTTCGAAGA
ATATACTAAAAAATGAGCAGGCAAGATAAACGAAGGCAAAGATGACAGAGCAGAAAGCCCTAGTAA
AGCGTATTACAAATGAAACCAAGATTCAGATTGCGATCTCTTTAAAGGGTGGTCCCCTAGCGATAG
AGCACTCGATCTTCCCAGAAAAAGAGGCAGAAGCAGTAGCAGAACAGGCCACACAATCGCAAGTGA
TTAACGTCCACACAGGTATAGGGTTTCTGGACCATATGATACATGCTCTGGCCAAGCATTCCGGCT
GGTCGCTAATCGTTGAGTGCATTGGTGACTTACACATAGACGACCATCACACCACTGAAGACTGCG
GGATTGCTCTCGGTCAAGCTTTTAAAGAGGCCCTAGGGGCCGTGCGTGGAGTAAAAAGGTTTGGAT
CAGGATTTGCGCCTTTGGATGAGGCACTTTCCAGAGCGGTGGTAGATCTTTCGAACAGGCCGTACG
CAGTTGTCGAACTTGGTTTGCAAAGGGAGAAAGTAGGAGATCTCTCTTGCGAGATGATCCCGCATT
TTCTTGAAAGCTTTGCAGAGGCTAGCAGAATTACCCTCCACGTTGATTGTCTGCGAGGCAAGAATG
ATCATCACCGTAGTGAGAGTGCGTTCAAGGCTCTTGCGGTTGCCATAAGAGAAGCCACCTCGCCCA
ATGGTACCAACGATGTTCCCTCCACCAAAGGTGTTCTTATGTAGTGACACCGATTATTTAAAGCTG
CAGCATACGATATATATACATGTGTATATATGTATACCTATGAATGTCAGTAAGTATGTATACGAA
CAGTATGATACTGAAGATGACAAGGTAATGCATCATTCTATACGTGTCATTCTGAACGAGGCGCGC
TTTCCTTTTTCTTTTTGCTTTTTCTTTTTTTTCTCTTGAACTCGACGGATCTATGCGGTGTGAA
ATACCGCACAGATGCGTAAGGAGAAAATACCGCATCAGGAAATTGTAAACGTTAATATTTTGTTAA
AATTCGCGTTAAATTTTTGTTAAATCAGCTCATTTTTTAACCAATAGGCCGAAATCGGCAAAATCC
CTTATAAATCAAAAGAATAGACCGAGATAGGGTTGAGTGTTGTTCCAGTTTGGAACAAGAGTCCAC
TATTAAAGAACGTGGACTCCAACGTCAAAGGGCGAAAAACCGTCTATCAGGGCGATGGCCCACTAC
GTGAACCATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGGAAGGGAAGA
AAGCGAAAGGAGCGGGCGCTAGGGCGCTGGCAAGTGTAGCGGTCACGCTGCGCGTAACCACCACAC
CCGCCGCGCTTAATGCGCCGCTACAGGGCGCGTCCATTCGCCATTCAGGCTGCGCAACTGTTGGGA
AGGGCGATCGGTGCGGGCCTCTTCGCTATTACGCCAGCTGAATTGGAGCGACCTCATGCTATACCT

FIGURE 26.2

GAGAAAGCAACCTGACCTACAGGAAAGAGTTACTCAAGAATAAGAATTTTCGTTTTAAAACCTAAG
AGTCACTTTAAAATTTGTATACACTTATTTTTTTATAACTTATTTAATAATAAAAATCATAAATC
ATAAGAAATTCGCTTATTTAGAAGTGTCAACAACGTATCTACCAACGATTTGACCCTTTTCCATCT
TTTCGTAAATTTCTGGCAAGGTAGACAAGCCGACAACCTTGATTGGAGACTTGACCAAACCTCTGG
CGAAGAATTGTTAATTAAGAGCTCAGATCTTATCGTCGTCATCCTTGTAATCCATCGATACTAGTG
CGGCCGCCCTTTAGTGAGGGTTGAATTCGAATTTTCAAAAATTCTTACTTTTTTTTGGATGGACG
CAAAGAAGTTTAATAATCATATTACATGGCATTACCACCATATACATATCCATATACATATCCATA
TCTAATCTTACTTATATGTTGTGGAAATGTAAAGAGCCCCATTATCTTAGCCTAAAAAAACCTTCT
CTTTGGAACTTTCAGTAATACGCTTAACTGCTCATTGCTATATTGAAGTACGGATTAGAAGCCGCC
GAGCGGGTGACAGCCCTCCGAAGGAAGACTCTCCTCCGTGCGTCCTCGTCTTCACCGGTCGCGTTC
CTGAAACGCAGATGTGCCTCGCGCCGCACTGCTCCGAACAATAAAGATTTTACAATACTAGCTTTT
ATGGTTATGAAGAGGAAAAATTGGCAGTAACCTGGCCCCACAAACCTTCAAATGAACGAATCAAAT
TAACAACCATAGGATGATAATGCGATTAGTTTTTTAGCCTTATTTCTGGGGTAATTAATCAGCGAA
GCGATGATTTTTGATCTATTAACAGATATATAAATGCAAAAAATGCATAACCACTTTAACTAATAC
TTTCAACATTTTCGGTTTGTATTACTTTTTATTCAAATGTAATAAAAGTATCAACAAAAAATTGTT
AATATACCTCTATACTTTAACGTCAAGGAGAAAAAACCCCGGATCCGTAATACGACTCACTATAGG
GCCCGGGCGtgtgaaatagacatcagaattaagaaaaacgtagggtccaagtggttccccgttatg
gactcgctatctgtcaaccagatcttataccctgaagttcacctagatagcccgatagttaccaat
aagatagtagccatcctggagtatgctcgagtccctcacgcttacagcctggaggaccctacactg
tgtcagaacatcaagcaccgcctaaaaaacggatttccaaccaaatgattataaacaatgtggaa
gttgggaatgtcatcaagtccaagcttaggagttatccggcccactctcatattccatatccaaat
tgtaatcaggatttatttaacatagaagacaaagagtcaacgaggaagatccgtgaactcctcaaa
aaggggaattcgctgtactccaaagtcagtgataaggttttccaatgcttaagggacactaactca
cggcttggcctaggctccgaattgagggaggacatcaaggagaaagttattaacttgggagtttac
atgcacagctcccagtggtttgagccctttctgttttggtttacagtcaagactgagatgaggtca
gtgattaaatcacaaacccatacttgccataggaggagacacacacctgtattcttcactggtagt
tcagttgagttgctaatctctcgtgaccttgttgctataatcagtaaagagtctcaacatgtatat
tacctgacatttgaactggttttgatgtattgtgatgtcatagaggggaggttaatgacagagacc
gctatgactattgatgctaggtatacagagcttctaggaagagtcagatacatgtggaaactgata
gatggtttcttccctgcactcgggaatccaacttatcaaattgtagccatgctggagcctctttca
cttgcttacctgcagctgagggatataacagtagaactcagaggtgctttccttaaccactgcttt
actgaaatacatgatgttcttgaccaaaacgggttttctgatgaaggtacttatcatgagttaact
gaagctctagattacatttcataactgatgacatacatctgacaggggagattttctcattttc
agaagtttcggccaccccagacttgaagcagtaacggctgctgaaaatgttaggaaatacatgaat

FIGURE 26.3 cagcctaaagtcattgtgtatgagactctgatgaaaggtcatgccatatttgtggaatcataatc
aacggctatcgtgacaggcacggaggcagttggccaccgctgaccctcccctgcatgctgcagac
acaatccggaatgctcaagcttcaggtgaagggttaacacatgagcagtgcgttgataactggaa
tcttttgctggagtgaaatttggctgctttatgcctcttagcctggatagtgatctgacaatgtac
ctaaaggacaaggcacttgctgctctccaaagggaatgggattcagtttacccgaaagagttcctg
cgttacgaccctcccaagggaaccgggtcacggaggcttgtagatgttttccttaatgattcgagc
tttgacccatatgatgtgataatgtatgttgtaagtggagcttacctccatgaccctgagttcaac
ctgtcttacagcctgaaagaaaaggagatcaaggaaacaggtagacttttttgctaaaatgacttac
aaaatgagggcatgccaagtgattgctgaaaatctaatctcaaacgggattggcaaatatttaag
gacaatgggatggccaaggatgagcacgatttgactaaggcactccacactctagctgtctcagga
gtccccaaagatctcaaagaaagtcacaggggggggccagtcttaaaaacctactcccgaagccca
gtccacacaagtaccaggaacgtgagagcagcaaaagggtttatagggttccctcaagtaattcgg
caggaccaagacactgatcatccggagaatatggaagcttacgagacagtcagtgcatttatcacg
actgatctcaagaagtactgccttaattggagatatgagaccatcagcttgtttgcacagaggcta
aatgagatttacggattgccctcattttccagtggctgcataagaggcttgagacctctgtcctg
tatgtaagtgaccctcattgccccccgaccttgacgcccatatccgttatataaagtccccaat
gatcaaatcttcattaagtacccatgggaggtatagaagggtattgtcagaagctgtggaccatc
agcaccattccctatctatacctggctgcttatgagagcggagtaaggattgcttcgttagtgcaa
ggggacaatcagaccatagccgtaacaaaaagggtacccagcacatggccctacaaccttaagaaa
cgggaagctgctagagtaactagagattactttgtaattcttaggcaaaggctacatgatattggc
catcacctcaaggcaaatgagacaattgtttcatcacatttttttgtctattcaaaaggaatatat
tatgatgggctacttgtgtcccaatcactcaagagcatcgcaagatgtgtattctggtcagagact
atagttgatgaaacaagggcagcatgcagtaatattgctacaacaatggctaaaagcatcgagaga
ggttatgaccgttaccttgcatattccctgaacgtcctaaaagtgatacagcaaattctgatctct
cttggcttcacaatcaattcaaccatgacccgggatgtagtcatacccctcctcacaaacaacgac
ctcttaataaggatggcactgttgcccgctcctattgggggggatgaattatctgaatatgagcagg
ctgtttgtcagaaacatcggtgatccagtaacatcatcaattgctgatctcaagagaatgattctc
gcctcactaatgcctgaagagaccctccatcaagtaatgacacaacaaccgggggactcttcattc
ctagactgggctagcgacccttactcagcaaatcttgtatgtgtccagagcatcactagactcctc
aagaacataactgcaaggtttgtcctgatccatagtccaaacccaatgttaaaaggattattccat
gatgacagtaaagaagaggacgagggactggcggcattcctcatggacaggcatattatagtacct
agggcagctcatgaaatcctggatcatagtgtcacaggggcaagagagtctattgcaggcatgctg
gataccacaaaaggcttgattcgagccagcatgaggaagggggggttaacctctcgagtgataacc
agattgtccaattatgactatgaacaattcagagcagggatggtgctattgacaggaagaaagaga

FIGURE 26.4 aatgtcctcattgacaaagagtcatgttcagtgcagctggcgagagctctaagaagccatatgtgg
gcgaggctagctcgaggacggcctatttacggccttgaggtccctgatgtactagaatctatgcga
ggccaccttattcggcgtcatgagacatgtgtcatctgcgagtgtggatcagtcaactacggatgg
tttttgtccctcgggttgccaactggatgatattgacaaggaaacatcatccttgagagtccca
tatattggttctaccactgatgagagaacagacatgaagcttgccttcgtaagagcccaagtcga
tccttgcgatctgctgttagaatagcaacagtgtactcatgggcttacggtgatgatgatagctct
tggaacgaagcctggttgttggctaggcaaagggccaatgtgagcctggaggagctaagggtgatc
actcccatctcaacttcgactaatttagcgcataggttgagggatcgtagcactcaagtgaaatac
tcaggtacatccttgtccgagtggcgaggtataccacaatctccaacgacaatctctcatttgtc
atatcagataagaaggttgatactaactttatataccaacaaggaatgcttctagggttgggtgtt
ttagaaacattgtttcgactcgagaaagataccggatcatctaacacggtattacatcttcacgtc
gaaacagattgttgcgtgatcccgatgatagatcatcccaggatacccagctcccgcaagctagag
ctgagggcagagctatgtaccaacccattgatatatgataatgcacctttaattgacagagatgca
acaaggctatacacccagagccataggaggcaccttgtggaatttgttacatggtccacaccccaa
ctatatcacattttagctaagtccacagcactatctatgattgacctggtaacaaaatttgagaag
gaccatatgaatgaaatttcagctctcataggggatgacgatatcaatagtttcataactgagttt
ctgctcatagagccaagattattcactatctacttgggccagtgtgcggccatcaattgggcattt
gatgtacattatcatagaccatcagggaaatatcagatgggtgagctgttgtcatcgttcctttct
agaatgagcaaaggagtgtttaaggtgcttgtcaatgctctaagccacccaaagatctacaagaaa
ttctggcattgtggtattatagagcctatccatggtccttcacttgatgctcaaaacttgcacaca
actgtgtgcaacatggtttacacatgctatatgacctacctcgacctgttgttgaatgaagagtta
gaagagttcacatttctcttgtgtgaaagcgacgaggatgtagtaccggacagattcgacaacatc
caggcaaaacacttatgtgttctggcagatttgtactgtcaaccagggacctgcccaccaattcga
ggtctaagaccggtagagaaatgtgcagttctaaccgaccatatcaaggcagaggctatgttatct
ccagcaggatcttcgtggaacataaatccaattattgtagaccattactcatgctctctgacttat
ctccggcgaggatcgatcaaacagataagattgagagttgatccaggattcatttcgacgccctc
gctgaggtaaatgtcagtcagccaaagatcggcagcaacaacatctcaaatatgagcatcaaggct
ttcagacccccacacgatgatgttgcaaaattgctcaaagatatcaacacaagcaagcacaatctt
cccatttcagggggcaatctcgccaattatgaaatccatgctttccgcagaatcgggttgaactca
tctgcttgctacaaagctgttgagatatcaacattaattaggagatgccttgagccaggggaggac
ggcttgttcttgggtgagggatcggttctatgttgatcacttataaagagatacttaaactaaac
aagtgcttctataatagtggggtttccgccaattctagatctggtcaaagggaattagcaccctat
ccctccgaagttggccttgtcgaacacagaatgggagtaggtaatattgtcaaagtgctctttaac
gggaggcccgaagtcacgtgggtaggcagtgtagattgcttcaatttcatagttagtaatatccct

FIGURE 26.5

```
acctctagtgtggggtttatccattcagatatagagaccttgcctgacaaagatactatagagaag
ctagaggaattggcagccatcttatcgatggctctgctcctgggcaaaataggatcaatactggtg
attaagcttatgcctttcagcggggatttttgttcagggatttataagttatgtagggtctcattat
agagaagtgaaccttgtatacccctagatacagcaacttcatctctactgaatcttatttggttatg
acagatctcaaggctaaccggctaatgaatcctgaaaagattaagcagcagataattgaatcatct
gtgaggacttcacctggacttataggtcacatcctatccattaagcaactaagctgcatacaagca
attgtgggagacgcagttagtagaggtgatatcaatcctactctgaaaaacttacacctatagag
caggtgctgatcaattgcgggttggcaattaacggacctaagctgtgcaaagaattgatccaccat
gatgttgcctcagggcaagatggattgcttaattctatactcatcctctacagggagttggcaaga
ttcaaagacaaccaaagaagtcaacaagggatgttccacgcttacccgtattggtaagtagcagg
caacgagaacttatatctaggatcacccgcaaattctggggcacattcttcttactccgggaac
aaaaagttgataaataagtttatccagaatctcaagtccggctatctgatactagacttacaccag
aatatcttcgttaagaatctatccaagtcagagaaacagattattatgacgggggtttgaaacgt
gagtgggtttttaaggtaacagtcaaggagaccaaagaatggtataagttagtcggatacagtgcc
ctgattaaggactaattggttgaactccggaaccctaatcctgccctaggtggttaggcattattt
gcaatatattaaagaaaactttgaaaatacgaagtttctattcccagctttgtctggtggccggca
tggtcccagcctTCGAGTAAGCTTGGTACCGCGGCTAGCTAAGATCCGCTCTAACCGAAAAGGAAG
GAGTTAGACAACCTGAAGTCTAGGTCCCTATTTATTTTTTTATAGTTATGTTAGTATTAAGAACGT
TATTTATATTTCAAATTTTTCTTTTTTTTCTGTACAGACGCGTGTACGCATGTAACATTATACTGA
AAACCTTGCTTGAGAAGGTTTTGGGACGCTCGAAGATCCAGCTGCATTAATGAATCGGCCAACGCG
CGGGGAGAGGCGGTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACCGTAAAAAGGCCG
CGTTGCTGGCGTTTTTCCATAGGCTCCGCCCCCTGACGAGCATCACAAAAATCGACGCTCAAGTC
AGAGGTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAACTCACGTT
AAGGGATTTTGGTCATGAGATTATCAAAAGGATCTTCACCTAGATCCTTTTAAATTAAAAATGAA
```

FIGURE 26.6

```
GTTTTAAATCAATCTAAAGTATATATGAGTAAACTTGGTCTGACAGTTACCAATGCTTAATCAGTG
AGGCACCTATCTCAGCGATCTGTCTATTTCGTTCATCCATAGTTGCCTGACTCCCCGTCGTGTAGA
TAACTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAG
TTAATAGTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCCGCAGTGTTATCACTCA
TGGTTATGGCAGCACTGCATAATTCTCTTACTGTCATGCCATCCGTAAGATGCTTTTCTGTGACTG
GTGAGTACTCAACCAAGTCATTCTGAGAATAGTGTATGCGGCGACCGAGTTGCTCTTGCCCGGCGT
CAATACGGGATAATACCGCGCCACATAGCAGAACTTTAAAAGTGCTCATCATTGGAAAACGTTCTT
CGGGGCGAAAACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAAT
ATTATTGAAGCATTTATCAGGGTTATTGTCTCATGAGCGGATACATATTTGAATGTATTTAGAAAA
ATAAACAAATAGGGGTTCCGCGCACATTTCCCCGAAAAGTGCCACCTGAACGAAGCATCTGTGCTT
CATTTTGTAGAACAAAAATGCAACGCGAGAGCGCTAATTTTTCAAACAAAGAATCTGAGCTGCATT
TTTACAGAACAGAAATGCAACGCGAAAGCGCTATTTTACCAACGAAGAATCTGTGCTTCATTTTTG
TAAAACAAAAATGCAACGCGAGAGCGCTAATTTTTCAAACAAAGAATCTGAGCTGCATTTTTACAG
AACAGAAATGCAACGCGAGAGCGCTATTTTACCAACAAAGAATCTATACTTCTTTTTTGTTCTACA
AAAATGCATCCCGAGAGCGCTATTTTTCTAACAAAGCATCTTAGATTACTTTTTTTCTCCTTTGTG
CGCTCTATAATGCAGTCTCTTGATAACTTTTTGCACTGTAGGTCCGTTAAGGTTAGAAGAAGGCTA
CTTTGGTGTCTATTTTCTCTTCCATAAAAAAAGCCTGACTCCACTTCCCGCGTTTACTGATTACTA
GCGAAGCTGCGGGTGCATTTTTTCAAGATAAAGGCATCCCCGATTATATTCTATACCGATGTGGAT
TGCGCATACTTTGTGAACAGAAAGTGATAGCGTTGATGATTCTTCATTGGTCAGAAAATTATGAAC
GGTTTCTTCTATTTTGTCTCTATATACTACGTATAGGAAATGTTTACATTTTCGTATTGTTTTCGA
TTCACTCTATGAATAGTTCTTACTACAATTTTTTGTCTAAAGAGTAATACTAGAGATAAACATAA
AAAATGTAGAGGTCGAGTTTAGATGCAAGTTCAAGGAGCGAAAGGTGGATGGGTAGGTTATATAGG
GATATAGCACAGAGATATATAGCAAAGAGATACTTTTGAGCAATGTTTGTGGAAGCGGTATTCGCA
ATATTTTAGTAGCTCGTTACAGTCCGGTGCGTTTTGGTTTTTTGAAAGTGCGTCTTCAGAGCGCT
TTTGGTTTTCAAAAGCGCTCTGAAGTTCCTATACTTTCTAGAGAATAGGAACTTCGGAATAGGAAC
TTCAAAGCGTTTCCGAAAACGAGCGCTTCCGAAAATGCAACGCGAGCTGCGCACATACAGCTCACT
GTTCACGTCGCACCTATATCTGCGTGTTGCCTGTATATATATACATGAGAAGAACGGCATAGTG
CGTGTTTATGCTTAAATGCGTACTTATATGCGTCTATTTATGTAGGATGAAAGGTAGTCTAGTACC
```

FIGURE 26.7

```
TCCTGTGATATTATCCCATTCCATGCGGGGTATCGTATGCTTCCTTCAGCACTACCCTTTAGCTGT
TCTATATGCTGCCACTCCTCAATTGGATTAGTCTCATCCTTCAATGCTATCATTTCCTTTGATATT
GGATCATCTAAGAAACCATTATTATCATGACATTAACCTATAAAAATAGGCGTATCACGAGGCCCT
TTCGTC
```

FIGURE 27.1 pCM105-CAN1 (pCM201)

| | |
|---|---|
| Viral L sequence: | Minuscule letter |
| pESC-HIS vector sequence: | Upper case letter |
| Yeast *CAN1* sequence: | Bold minuscule letter |

TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATAAATTCCCGTTTTAA
GAGCTTGGTGAGCGCTAGGAGTCACTGCCAGGTATCGTTTGAACACGGCA
TTAGTCAGGGAAGTCATAACACAGTCCTTTCCCGCAATTTTCTTTTTCTA
TTACTCTTGGCCTCCTCTAGTACACTCTATATTTTTTATGCCTCGGTAA
TGATTTTCATTTTTTTTTTCCCCTAGCGGATGACTCTTTTTTTTTCTTA
GCGATTGGCATTATCACATAATGAATTATACATTATATAAAGTAATGTGA
TTTCTTCGAAGAATATACTAAAAAATGAGCAGGCAAGATAAACGAAGGCA
AAGATGACAGAGCAGAAAGCCCTAGTAAAGCGTATTACAAATGAAACCAA
GATTCAGATTGCGATCTCTTTAAAGGGTGGTCCCCTAGCGATAGAGCACT
CGATCTTCCCAGAAAAGAGGCAGAAGCAGTAGCAGAACAGGCCACACAA
TCGCAAGTGATTAACGTCCACACAGGTATAGGGTTTCTGGACCATATGAT
ACATGCTCTGGCCAAGCATTCCGGCTGGTCGCTAATCGTTGAGTGCATTG
GTGACTTACACATAGACGACCATCACACCACTGAAGACTGCGGGATTGCT
CTCGGTCAAGCTTTTAAAGAGGCCCTAGGGGCCGTGCGTGGAGTAAAAAG
GTTTGGATCAGGATTTGCGCCTTTGGATGAGGCACTTTCCAGAGCGGTGG
TAGATCTTTCGAACAGGCCGTACGCAGTTGTCGAACTTGGTTTGCAAAGG
GAGAAAGTAGGAGATCTCTCTTGCGAGATGATCCCGCATTTTCTTGAAAG
CTTTGCAGAGGCTAGCAGAATTACCCTCCACGTTGATTGTCTGCGAGGCA
AGAATGATCATCACCGTAGTGAGAGTGCGTTCAAGGCTCTTGCGGTTGCC
ATAAGAGAAGCCACCTCGCCCAATGGTACCAACGATGTTCCCTCCACCAA
AGGTGTTCTTATGTAGTGACACCGATTATTTAAAGCTGCAGCATACGATA
TATATACATGTGTATATATGTATACCTATGAATGTCAGTAAGTATGTATA
CGAACAGTATGATACTGAAGATGACAAGGTAATGCATCATTCTATACGTG
TCATTCTGAACGAGGCGCGCTTTCCTTTTTTCTTTTTGCTTTTTCTTTTT
TTTTCTCTTGAACTCGACGGATCTATGCGGTGTGAAATACCGCACAGATG
CGTAAGGAGAAAATACCGCATCAGGAAATTGTAAACGTTAATATTTTGTT

FIGURE 27.2

AAAATTCGCGTTAAATTTTTGTTAAATCAGCTCATTTTTTAACCAATAGG
CCGAAATCGGCAAAATCCCTTATAAATCAAAAGAATAGACCGAGATAGGG
TTGAGTGTTGTTCCAGTTTGGAACAAGAGTCCACTATTAAAGAACGTGGA
CTCCAACGTCAAAGGGCGAAAAACCGTCTATCAGGGCGATGGCCCACTAC
GTGAACCATCACCCTAATCAAGTTTTTTGGGGTCGAGGTGCCGTAAAGCA
CTAAATCGGAACCCTAAAGGGAGCCCCCGATTTAGAGCTTGACGGGGAAA
GCCGGCGAACGTGGCGAGAAAGGAAGGGAAGAAAGCGAAGGAGCGGGCG
CTAGGGCGCTGGCAAGTGTAGCGGTCACGCTGCGCGTAACCACCACACCC
GCCGCGCTTAATGCGCCGCTACAGGGCGCGTCCATTCGCCATTCAGGCTG
CGCAACTGTTGGGAAGGGCGATCGGTGCGGCCTCTTCGCTATTACGCCA
GCTGAATTGGAGCGACCTCATGCTATACCTGAGAAAGCAACCTGACCTAC
AGGAAAGAGTTACTCAAGAATAAGAATTTTCGTTTTAAAACCTAAGAGTC
ACTTTAAAATTTGTATACACTTATTTTTTTATAACTTATTTAATAATAA
AAATCATAAATCATAAGAAATTCGCTTATTTAGAAGTGTCAACAACGTAT
CTACCAACGATTTGACCCTTTTCCATCTTTTCGTAAATTTCTGGCAAGGT
AGACAAGCCGACAACCTTGATTGGAGACTTGACCAAACCTCTGGCGAAGA
ATTGTTAATTAAGAGCTCAGATCTTATCGTCGTCATCCTTGTAATCCATC
GATactagcactatgctacaacattccaaaatttgtcccaaaaagtcttt
ggttcatgatcttcccatacaattgcctcaatgtctcttctatcggaatc
gatgtcgacatctccaatcttccaaataaatctgcatctgaatatgcatt
gaaataagatccaaacagctaagaacaggaaaatagagatataggcggca
gcaaagctaacaccattgaattttggtgcaaaagccgtgaaaccttgaat
aatgataatgatcgtcataaatgtggccgcataataagccaagccgggca
ttaatttagctttaaatggtaactcgtcacgagagatgccacggtatttc
aaagcttgcataaatctgatgtgcgagattgagataaataaccatgcaaa
aaagcctgcaacaccagtgatatttaatagccattcgaaaactttgtcac
caccagtagatgtctccatgtaagccaaagcgccaaatgcagcagtaacg
aaaactgcaatgtatggaacaccacctttggtggtccttgacaggaattt
aggagccaacttgttctttgatagaccaaataaaatacgggaaccaacgt
aaatatttgaatttgcggcagaaataatggttgttaagataacagcgttg
aagatatgtggcaaaacctttgtaccagagttctcaatagcaataataaa
gggagaagtagaaacgtaggaagtagattgtgttagtttagggtcattgt
atggaactaaaagtccaatgaataatagagagccaatgtagaaggttaag
atacggaaaacaacttttttgatggctcttggaacggatttttctggggtt

FIGURE 27.3 tgcagcttcaccagcagtgataccaactagttcagtaccttgaaatgtga
aggcagcgttaatcaaagaggaaacccaacctaagaacctcccttcgttt
ttatccttagatattatacctggacccccaggcacctgggtttctccaata
acggaatccaactgggccggtaaccccagcaccacaaaccatacaaaaac
agtatattagaaacccgataatggctaaaactttgatggaagcgacccag
aactcgaattcaccgtaatatttgacagggaacaagttcattattgtgat
aattacccaaaaaatactaatccatgccgccagtggaactttgtacgtcc
aaaattgaatgacttggccaactacactaagttccagggcaaaagtgatt
gcccaagaaaaccaatacatgtaaccattggccgcaccaaatgctggaga
aaggaatctttgtgagaaaactgtgaaagaggatgtaacagggatgaatg
tagccatttcacccaaggactgcgtgacagaatatgccaaagaacccata
aataaatatgatataagagcgcccactgggccggcgttggtcagaggtgt
ggataaaccaatgaaaagacctgtaccaatagtaccaccaagggcaatca
taccaatatgtctttgcttaagctctctcttcacttcagcgttctgtact
tctccttcatcttcatcacctatgccatcctccatagagaacgtatcctc
gccattactctcgtcgggaaagagcgcaatggatacaattctttacttt
tctcatctttcaatggtattgacccacgtctgtggtgtgtttgtgaagct
tcaacgtcgtgaaagagggttgtgaccggctcattgtacatatgcttctc
ctctatgtcggcgtcttcttttgaatttgtcatgcggccgcCCTTTAGTG
AGGGTTGAATTCGAATTTTCAAAAATTCTTACTTTTTTTTGGATGGACG
CAAAGAAGTTTAATAATCATATTACATGGCATTACCACCATATACATATC
CATATACATATCCATATCTAATCTTACTTATATGTTGTGGAAATGTAAAG
AGCCCCATTATCTTAGCCTAAAAAAACCTTCTCTTTGGAACTTTCAGTAA
TACGCTTAACTGCTCATTGCTATATTGAAGTACGGATTAGAAGCCGCCGA
GCGGGTGACAGCCCTCCGAAGGAAGACTCTCCTCCGTGCGTCCTCGTCTT
CACCGGTCGCGTTCCTGAAACGCAGATGTGCCTCGCGCCGCACTGCTCCG
AACAATAAGATTTTACAATACTAGCTTTTATGGTTATGAAGAGGAAAAA
TTGGCAGTAACCTGGCCCCACAAACCTTCAAATGAACGAATCAAATTAAC
AACCATAGGATGATAATGCGATTAGTTTTTTAGCCTTATTTCTGGGGTAA
TTAATCAGCGAAGCGATGATTTTTGATCTATTAACAGATATATAAATGCA
AAAAATGCATAACCACTTTAACTAATACTTTCAACATTTTCGGTTTGTAT
TACTTTTTATTCAAATGTAATAAAAGTATCAACAAAAAATTGTTAATATA
CCTCTATACTTTAACGTCAAGGAGAAAAAACCCCGGATCCGTAATACGAC
TCACTATAGGGCCCGGGCGtgtgaaatagacatcagaattaagaaaaacg

FIGURE 27.4 tagggtccaagtggttccccgttatggactcgctatctgtcaaccagatc
ttatacccctgaagttcacctagatagcccgatagttaccaataagatagt
agccatcctggagtatgctcgagtccctcacgcttacagcctggaggacc
ctacactgtgtcagaacatcaagcaccgcctaaaaaacggatttccaac
caaatgattataaacaatgtggaagttgggaatgtcatcaagtccaagct
taggagttatccggcccactctcatattccatatccaaattgtaatcagg
atttatttaacatagaagacaaagagtcaacgaggaagatccgtgaactc
ctcaaaaaggggaattcgctgtactccaaagtcagtgataaggttttcca
atgcttaagggacactaactcacggcttggcctaggctccgaattgaggg
aggacatcaaggagaaagttattaacttgggagtttacatgcacagctcc
cagtggtttgagccctttctgttttggtttacagtcaagactgagatgag
gtcagtgattaaatcacaaacccatacttgccataggaggagacacacac
ctgtattcttcactggtagttcagttgagttgctaatctctcgtgacctt
gttgctataatcagtaaagagtctcaacatgtatattacctgacatttga
actggttttgatgtattgtgatgtcatagaggggaggttaatgacagaga
ccgctatgactattgatgctaggtatacagagcttctaggaagagtcaga
tacatgtggaaactgatagatggtttcttccctgcactcgggaatccaac
ttatcaaattgtagccatgctggagcctctttcacttgcttacctgcagc
tgagggatataacagtagaactcagaggtgctttccttaaccactgcttt
actgaaatacatgatgttcttgaccaaaacgggttttctgatgaaggtac
ttatcatgagttaactgaagctctagattacattttcataactgatgaca
tacatctgacaggggagattttctcattttcagaagtttcggccacccc
agacttgaagcagtaacggctgctgaaaatgttaggaaatacatgaatca
gcctaaagtcattgtgtatgagactctgatgaaaggtcatgccatatttt
gtggaatcataatcaacggctatcgtgacaggcacggaggcagttggcca
ccgctgaccctcccctgcatgctgcagacacaatccggaatgctcaagc
ttcaggtgaagggttaacacatgagcagtgcgttgataactggaaatctt
ttgctggagtgaaatttggctgctttatgcctcttagcctggatagtgat
ctgacaatgtacctaaaggacaaggcacttgctgctctccaaagggaatg
ggattcagtttacccgaaagagttcctgcgttacgaccctcccaagggaa
ccgggtcacggaggcttgtagatgttttccttaatgattcgagctttgac
ccatatgatgtgataatgtatgttgtaagtggagcttacctccatgaccc
tgagttcaacctgtcttacagcctgaaagaaaggagatcaaggaaacag
gtagacttttgctaaaatgacttacaaaatgagggcatgccaagtgatt

FIGURE 27.5

```
gctgaaaatctaatctcaaacgggattggcaaatattttaaggacaatgg
gatggccaaggatgagcacgatttgactaaggcactccacactctagctg
tctcaggagtccccaaagatctcaaagaaagtcacaggggggggccagtc
ttaaaaacctactcccgaagcccagtccacacaagtaccaggaacgtgag
agcagcaaaagggtttatagggttccctcaagtaattcggcaggaccaag
acactgatcatccggagaatatggaagcttacgagacagtcagtgcattt
atcacgactgatctcaagaagtactgccttaattggagatatgagaccat
cagcttgtttgcacagaggctaaatgagatttacggattgccctcatttt
tccagtggctgcataagaggcttgagacctctgtcctgtatgtaagtgac
cctcattgccccccgaccttgacgcccatatcccgttatataaagtccc
caatgatcaaatcttcattaagtaccctatgggaggtatagaagggtatt
gtcagaagctgtggaccatcagcaccattccctatctatacctggctgct
tatgagagcggagtaaggattgcttcgttagtgcaaggggacaatcagac
catagccgtaacaaaaagggtacccagcacatggccctacaaccttaaga
aacgggaagctgctagagtaactagagattactttgtaattcttaggcaa
aggctacatgatattggccatcacctcaaggcaaatgagacaattgtttc
atcacatttttttgtctattcaaaaggaatatattatgatgggctacttg
tgtcccaatcactcaagagcatcgcaagatgtgtattctggtcagagact
atagttgatgaaacaagggcagcatgcagtaatattgctacaacaatggc
taaaagcatcgagagaggttatgaccgttaccttgcatattccctgaacg
tcctaaaagtgatacagcaaattctgatctctcttggcttcacaatcaat
tcaaccatgacccgggatgtagtcataccctcctcacaaacaacgacct
cttaataaggatggcactgttgcccgctcctattgggggatgaattatc
tgaatatgagcaggctgtttgtcagaaacatcggtgatccagtaacatca
tcaattgctgatctcaagagaatgattctcgcctcactaatgcctgaaga
gaccctccatcaagtaatgacacaacaaccgggggactcttcattcctag
actgggctagcgacccttactcagcaaatcttgtatgtgtccagagcatc
actagactcctcaagaacataactgcaaggtttgtcctgatccatagtcc
aaacccaatgttaaaaggattattccatgatgacagtaaagaagaggacg
agggactggcggcattcctcatggacaggcatattatagtacctagggca
gctcatgaaatcctggatcatagtgtcacaggggcaagagagtctattgc
aggcatgctggataccacaaaaggcttgattcgagccagcatgaggaagg
gggggttaacctctcgagtgataaccagattgtccaattatgactatgaa
caattcagagcagggatggtgctattgacaggaagaaagagaaatgtcct
```

FIGURE 27.6 cattgacaaagagtcatgttcagtgcagctggcgagagctctaagaagcc
atatgtgggcgaggctagctcgaggacggcctatttacggccttgaggtc
cctgatgtactagaatctatgcgaggccaccttattcggcgtcatgagac
atgtgtcatctgcgagtgtggatcagtcaactacggatggttttttgtcc
cctcggggttgccaactggatgatattgacaaggaaacatcatccttgaga
gtcccatatattggttctaccactgatgagagaacagacatgaagcttgc
cttcgtaagagccccaagtcgatccttgcgatctgctgttagaatagcaa
cagtgtactcatgggcttacggtgatgatgatagctcttggaacgaagcc
tggttgttggctaggcaaagggccaatgtgagcctggaggagctaagggt
gatcactcccatctcaacttcgactaatttagcgcataggttgagggatc
gtagcactcaagtgaaatactcaggtacatccttgtccgagtggcgagg
tataccacaatctccaacgacaatctctcatttgtcatatcagataagaa
ggttgatactaactttatataccaacaaggaatgcttctagggttgggtg
ttttagaaacattgtttcgactcgagaaagataccggatcatctaacacg
gtattacatcttcacgtcgaaacagattgttgcgtgatcccgatgataga
tcatcccaggatacccagctcccgcaagctagagctgagggcagagctat
gtaccaacccattgatatatgataatgcacctttaattgacagagatgca
acaaggctatacacccagagccataggaggcaccttgtggaatttgttac
atggtccacaccccaactatatcacattttagctaagtccacagcactat
ctatgattgacctggtaacaaaatttgagaaggaccatatgaatgaaatt
tcagctctcataggggatgacgatatcaatagtttcataactgagtttct
gctcatagagccaagattattcactatctacttgggccagtgtgcggcca
tcaattgggcatttgatgtacattatcatagaccatcagggaaatatcag
atgggtgagctgttgtcatcgttcctttctagaatgagcaaaggagtgtt
taaggtgcttgtcaatgctctaagccacccaaagatctacaagaaattct
ggcattgtggtattatagagcctatccatggtccttcacttgatgctcaa
aacttgcacacaactgtgtgcaacatggtttacacatgctatatgaccta
cctcgacctgttgttgaatgaagagttagaagagttcacatttctcttgt
gtgaaagcgacgaggatgtagtaccggacagattcgacaacatccaggca
aaacacttatgtgttctggcagatttgtactgtcaaccagggacctgccc
accaattcgaggtctaagaccggtagagaaatgtgcagttctaaccgacc
atatcaaggcagaggctatgttatctccagcaggatcttcgtggaacata
aatccaattattgtagaccattactcatgctctctgacttatctccggcg
aggatcgatcaaacagataagattgagagttgatccaggattcattttcg

FIGURE 27.7 acgccctcgctgaggtaaatgtcagtcagccaaagatcggcagcaacaac
atctcaaatatgagcatcaaggctttcagaccccacacgatgatgttgc
aaaattgctcaaagatatcaacacaagcaagcacaatcttcccatttcag
ggggcaatctcgccaattatgaaatccatgctttccgcagaatcgggttg
aactcatctgcttgctacaaagctgttgagatatcaacattaattaggag
atgccttgagccaggggaggacggcttgttcttgggtgagggatcgggtt
ctatgttgatcacttataaagagatacttaaactaaacaagtgcttctat
aatagtggggtttccgccaattctagatctggtcaaagggaattagcacc
ctatccctccgaagttggccttgtcgaacacagaatgggagtaggtaata
ttgtcaaagtgctctttaacgggaggcccgaagtcacgtgggtaggcagt
gtagattgcttcaatttcatagttagtaatatccctacctctagtgtggg
gtttatccattcagatatagagaccttgcctgacaaagatactatagaga
agctagaggaattggcagccatcttatcgatggctctgctcctgggcaaa
ataggatcaatactggtgattaagcttatgcctttcagcggggatttgt
tcagggatttataagttatgtagggtctcattatagagaagtgaaccttg
tataccctagatacagcaacttcatctctactgaatcttatttggttatg
acagatctcaaggctaaccggctaatgaatcctgaaaagattaagcagca
gataattgaatcatctgtgaggacttcacctggacttataggtcacatcc
tatccattaagcaactaagctgcatacaagcaattgtgggagacgcagtt
agtagaggtgatatcaatcctactctgaaaaaacttacacctatagagca
ggtgctgatcaattgcggggttggcaattaacggacctaagctgtgcaaag
aattgatccaccatgatgttgcctcagggcaagatggattgcttaattct
atactcatcctctacagggagttggcaagattcaaagacaaccaaagaag
tcaacaagggatgttccacgcttaccccgtattggtaagtagcaggcaac
gagaacttatatctaggatcacccgcaaattctgggggcacattcttctt
tactccgggaacaaaaagttgataaataagtttatccagaatctcaagtc
cggctatctgatactagacttacaccagaatatcttcgttaagaatctat
ccaagtcagagaaacagattattatgacggggggtttgaaacgtgagtgg
gtttttaaggtaacagtcaaggagaccaaagaatggtataagttagtcgg
atacagtgccctgattaaggactaattggttgaactccggaaccctaatc
ctgccctaggtggttaggcattatttgcaatatattaaagaaaactttga
aaatacgaagtttctattcccagctttgtctggtggccggcatggtccca
gcctcctCGCTGGCGGTAAGCTTGGTACCGCGGCTAGCTAAGATCCGCTC
TAACCGAAAAGGAAGGAGTTAGACAACCTGAAGTCTAGGTCCCTATTTAT

FIGURE 27.8

TTTTTTATAGTTATGTTAGTATTAAGAACGTTATTTATATTTCAAATTTT
TCTTTTTTTTCTGTACAGACGCGTGTACGCATGTAACATTATACTGAAAA
CCTTGCTTGAGAAGGTTTTGGGACGCTCGAAGATCCAGCTGCATTAATGA
ATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGG
TATCAGCTCACTCAAAGGCGGTAATACGGTTATCCACAGAATCAGGGGAT
AACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAA
GACACGACTTATCGCCACTGGCAGCAGCCACTGGTAACAGGATTAGCAGA
GCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAG
TTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTC
AGTGGAACGAAAACTCACGTTAAGGGATTTTGGTCATGAGATTATCAAAA
AGGATCTTCACCTAGATCCTTTTAAATTAAAAATGAAGTTTTAAATCAAT
CTAAAGTATATATGAGTAAACTTGGTCTGACAGTTACCAATGCTTAATCA
GTGAGGCACCTATCTCAGCGATCTGTCTATTTCGTTCATCCATAGTTGCC
TGACTCCCCGTCGTGTAGATAACTACGATACGGGAGGGCTTACCATCTGG
CCCCAGTGCTGCAATGATACCGCGAGACCCACGCTCACCGGCTCCAGATT
TATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCC
GGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTC
ATGCCATCCGTAAGATGCTTTTCTGTGACTGGTGAGTACTCAACCAAGTC

FIGURE 27.9

ATTCTGAGAATAGTGTATGCGGCGACCGAGTTGCTCTTGCCCGGCGTCAA
TACGGGATAATACCGCGCCACATAGCAGAACTTTAAAAGTGCTCATCATT
GGAAAACGTTCTTCGGGGCGAAAACTCTCAAGGATCTTACCGCTGTTGAG
ATCCAGTTCGATGTAACCCACTCGTGCACCCAACTGATCTTCAGCATCTT
TTACTTTCACCAGCGTTTCTGGGTGAGCAAAACAGGAAGGCAAAATGCC
GCAAAAAGGGAATAAGGGCGACACGGAAATGTTGAATACTCATACTCTT
CCTTTTTCAATATTATTGAAGCATTTATCAGGGTTATTGTCTCATGAGCG
GATACATATTTGAATGTATTTAGAAAAATAAACAAATAGGGGTTCCGCGC
ACATTTCCCCGAAAAGTGCCACCTGAACGAAGCATCTGTGCTTCATTTTG
TAGAACAAAAATGCAACGCGAGAGCGCTAATTTTTCAAACAAAGAATCTG
AGCTGCATTTTTACAGAACAGAAATGCAACGCGAAAGCGCTATTTTACCA
ACGAAGAATCTGTGCTTCATTTTTGTAAAACAAAAATGCAACGCGAGAGC
GCTAATTTTTCAAACAAAGAATCTGAGCTGCATTTTTACAGAACAGAAAT
GCAACGCGAGAGCGCTATTTTACCAACAAAGAATCTATACTTCTTTTTTG
TTCTACAAAAATGCATCCCGAGAGCGCTATTTTTCTAACAAAGCATCTTA
GATTACTTTTTTTCTCCTTTGTGCGCTCTATAATGCAGTCTCTTGATAAC
TTTTTGCACTGTAGGTCCGTTAAGGTTAGAAGAAGGCTACTTTGGTGTCT
ATTTTCTCTTCCATAAAAAAGCCTGACTCCACTTCCCGCGTTTACTGAT
TACTAGCGAAGCTGCGGGTGCATTTTTTCAAGATAAAGGCATCCCCGATT
ATATTCTATACCGATGTGGATTGCGCATACTTTGTGAACAGAAAGTGATA
GCGTTGATGATTCTTCATTGGTCAGAAAATTATGAACGGTTTCTTCTATT
TTGTCTCTATATACTACGTATAGGAAATGTTTACATTTTCGTATTGTTTT
CGATTCACTCTATGAATAGTTCTTACTACAATTTTTTTGTCTAAAGAGTA
ATACTAGAGATAAACATAAAAAATGTAGAGGTCGAGTTTAGATGCAAGTT
CAAGGAGCGAAAGGTGGATGGGTAGGTTATATAGGGATATAGCACAGAGA
TATATAGCAAAGAGATACTTTTGAGCAATGTTTGTGGAAGCGGTATTCGC
AATATTTTAGTAGCTCGTTACAGTCCGGTGCGTTTTGGTTTTTTGAAAG
TGCGTCTTCAGAGCGCTTTTGGTTTTCAAAAGCGCTCTGAAGTTCCTATA
CTTTCTAGAGAATAGGAACTTCGGAATAGGAACTTCAAAGCGTTTCCGAA
AACGAGCGCTTCCGAAAATGCAACGCGAGCTGCGCACATACAGCTCACTG
TTCACGTCGCACCTATATCTGCGTGTTGCCTGTATATATATACATGAG
AAGAACGGCATAGTGCGTGTTTATGCTTAAATGCGTACTTATATGCGTCT
ATTTATGTAGGATGAAAGGTAGTCTAGTACCTCCTGTGATATTATCCCAT
TCCATGCGGGGTATCGTATGCTTCCTTCAGCACTACCCTTTAGCTGTTCT

FIGURE 27.10

ATATGCTGCCACTCCTCAATTGGATTAGTCTCATCCTTCAATGCTATCAT
TTCCTTTGATATTGGATCATCTAAGAAACCATTATTATCATGACATTAAC
CTATAAAAATAGGCGTATCACGAGGCCCTTTCGTC

FIGURE 28.1 pESC-URA-MV (pCM101)

pESC-URA vector :   Capital letter
Ribozymes Sequence :   Bold minuscule letter
Viral genome sequence:   Bold capital letter ccaactttgtttggtctgatgagtccgtgaggacgaaacccggagtcccg
ggtcACCAAACAAAGTTGGGTAAGGATAGTTCAATCAATGATCATCTTCT
AGTGCACTTAGGATTCAAGATCCTATTATCAGGGACAAGAGCAGGATTAG
GGATATCCGAGATGGCCACACTTTTAAGGAGCTTAGCATTGTTCAAAAGA
AACAAGGACAAACCACCCATTACATCAGGATCCGGTGGAGCCATCAGAGG
AATCAAACACATTATTATAGTACCAATCCCTGGAGATTCCTCAATTACCA
CTCGATCCAGACTTCTGGACCGGTTGGTGAGGTTAATTGGAAACCCGGAT
GTGAGCGGGCCCAAACTAACAGGGGCACTAATAGGTATATTATCCTTATT
TGTGGAGTCTCCAGGTCAATTGATTCAGAGGATCACCGATGACCCTGACG
TTAGCATAAGGCTGTTAGAGGTTGTCCAGAGTGACCAGTCACAATCTGGC
CTTACCTTCGCATCAAGAGGTACCAACATGGAGGATGAGGCGGACCAATA
CTTTTCACATGATGATCCAATTAGTAGTGATCAATCCAGGTTCGGATGGT
TCGGGAACAAGGAAATCTCAGATATTGAAGTGCAAGACCCTGAGGGATTC
AACATGATTCTGGGTACCATCCTAGCCCAAATTTGGGTCTTGCTCGCAAA
GGCGGTTACGGCCCCAGACACGGCAGCTGATTCGGAGCTAAGAAGGTGGA
TAAAGTACACCCAACAAAGAAGGGTAGTTGGTGAATTTAGATTGGAGAGA
AAATGGTTGGATGTGGTGAGGAACAGGATTGCCGAGGACCTCTCCTTACG
CCGATTCATGGTCGCTCTAATCCTGGATATCAAGAGAACACCCGGAAACA
AACCCAGGATTGCTGAAATGATATGTGACATTGATACATATATCGTAGAG
GCAGGATTAGCCAGTTTTATCCTGACTATTAAGTTTGGGATAGAAACTAT
GTATCCTGCTCTTGGACTGCATGAATTTGCTGGTGAGTTATCCACACTTG
AGTCCTTGATGAACCTTTACCAGCAAATGGGGGAAACTGCACCCTACATG
GTAATCCTGGAGAACTCAATTCAGAACAAGTTCAGTGCAGGATCATACCC
TCTGCTCTGGAGCTATGCCATGGGAGTAGGAGTGGAACTTGAAAACTCCA
TGGGAGGTTTGAACTTTGGCCGATCTTACTTTGATCCAGCATATTTTAGA
TTAGGGCAAGAGATGGTAAGGAGGTCAGCTGGAAAGGTCAGTTCCACATT

FIGURE 28.2

GGCATCTGAACTCGGTATCACTGCCGAGGATGCAAGGCTTGTTTCAGAGA
TTGCAATGCATACTACTGAGGACAAGATCAGTAGAGCGGTTGGACCCAGA
CAAGCCCAAGTATCATTTCTACACGGTGATCAAAGTGAGAATGAGCTACC
GAGATTGGGGGGCAAGGAAGATAGGAGGGTCAAACAGAGTCGAGGAGAAG
CCAGGGAGAGCTACAGAGAAACCGGGCCCAGCAGAGCAAGTGATGCGAGA
GCTGCCCATCTTCCAACCGGCACACCCTAGACATTGACACTGCAACGGA
GTCCAGCCAAGATCCGCAGGACAGTCGAAGGTCAGCTGACGCCCTGCTTA
GGCTGCAAGCCATGGCAGGAATCTCGGAAGAACAAGGCTCAGACACGGAC
ACCCCTATAGTGTACAATGACAGAAATCTTCTAGACTAGGTGCGAGAGGC
CGAGGGCCAGAACAACATCCGCCTACCATCCATCATTGTTATAAAAACT
TAGGAACCAGGTCCACACAGCCGCCAGCCCATCAACCATCCACTCCCACG
ATTGGAGCCAATGGCAGAAGAGCAGGCACGCCATGTCAAAAACGGACTGG
AATGCATCCGGGCTCTCAAGGCCGAGCCCATCGGCTCACTGGCCATCGAG
GAAGCTATGGCAGCATGGTCAGAAATATCAGACAACCCAGGACAGGAGCG
AGCCACCTGCAGGGAAGAGAAGGCAGGCAGTTCGGGTCTCAGCAAACCAT
GCCTCTCAGCAATTGGATCAACTGAAGGCGGTGCACCTCGCATCCGCGGT
CAGGGACCTGGAGAGAGCGATGACGACGCTGAAACTTTGGGAATCCCCCC
AAGAAATCTCCAGGCATCAAGCACTGGGTTACAGTGTTATTACGTTTATG
ATCACAGCGGTGAAGCGGTTAAGGGAATCCAAGATGCTGACTCTATCATG
GTTCAATCAGGCCTTGATGGTGATAGCACCCTCTCAGGAGGAGACAATGA
ATCTGAAAACAGCGATGTGGATATTGGCGAACCTGATACCGAGGGATATG
CTATCACTGACCGGGGATCTGCTCCCATCTCTATGGGGTTCAGGGCTTCT
GATGTTGAAACTGCAGAAGGAGGGGAGATCCACGAGCTCCTGAGACTCCA
ATCCAGAGGCAACAACTTTCCGAAGCTTGGGAAAACTCTCAATGTTCCTC
CGCCCCCGGACCCCGGTAGGGCCAGCACTTCCGGGACACCCATTAAAAAG
GGCACAGACGCGAGATTAGCCTCATTTGGAACGGAGATCGCGTCTTTATT
GACAGGTGGTGCAACCCAATGTGCTCGAAAGTCACCCTCGGAACCATCAG
GGCCAGGTGCACCTGCGGGGAATGTCCCCGAGTGTGTGAGCAATGCCGCA
CTGATACAGGAGTGGACACCCGAATCTGGTACCACAATCTCCCCGAGATC
CCAGAATAATGAAGAAGGGGGAGACTATTATGATGATGAGCTGTTCTCTG
ATGTCCAAGATATTAAAACAGCCTTGGCCAAAATACACGAGGATAATCAG
AAGATAATCTCCAAGCTAGAATCACTGCTGTTATTGAAGGGAGAAGTTGA
GTCAATTAAGAAGCAGATCAACAGGCAAAATATCAGCATATCCACCCTGG
AAGGACACCTCTCAAGCATCATGATCGCCATTCCTGGACTTGGGAAGGAT

FIGURE 28.3

```
CCCAACGACCCCACTGCAGATGTCGAAATCAATCCCGACTTGAAACCCAT
CATAGGCAGAGATTCAGGCCGAGCACTGGCCGAAGTTCTCAAGAAACCCG
TTGCCAGCCGACAACTCCAAGGAATGACAAATGGACGGACCAGTTCCAGA
GGACAGCTGCTGAAGGAATTTCAGCTAAAGCCGATCGGGAAAAGATGAG
CTCAGCCGTCGGGTTTGTTCCTGACACCGGCCCTGCATCACGCAGTGTAA
TCCGCTCCATTATAAAATCCAGCCGGCTAGAGGAGGATCGGAAGCGTTAC
CTGATGACTCTCCTTGATGATATCAAAGGAGCCAATGATCTTGCCAAGTT
CCACCAGATGCTGATGAAGATAATAATGAAGTAGCTACAGCTCAACTTAC
CTGCCAACCCCATGCCAGTCGACCCAACTAGTACAACCTAAATCCATTAT
AAAAAACTTAGGAGCAAAGTGATTGCCTCCCAAGGTCCACAATGACAGAG
ACCTACGACTTCGACAAGTCGGCATGGGACATCAAAGGGTCGATCGCTCC
GATACAACCCACCACCTACAGTGATGGCAGGCTGGTGCCCCAGGTCAGAG
TCATAGATCCTGGTCTAGGCGACAGGAAGGATGAATGCTTTATGTACATG
TTTCTGCTGGGGGTTGTTGAGGACAGCGATTCCCTAGGGCCTCCAATCGG
GCGAGCATTTGGGTTCCTGCCCTTAGGTGTTGGCAGATCCACAGCAAAGC
CCGAAAAACTCCTCAAAGAGGCCACTGAGCTTGACATAGTTGTTAGACGT
ACAGCAGGGCTCAATGAAAAACTGGTGTTCTACAACAACACCCCACTAAC
TCTCCTCACACCTTGGAGAAAGGTCCTAACAACAGGGAGTGTCTTCAACG
CAAACCAAGTGTGCAATGCGGTTAATCTGATACCGCTCGATACCCCGCAG
AGGTTCCGTGTTGTTTATATGAGCATCACCCGTCTTTCGGATAACGGGTA
TTACACCGTTCCTAGAAGAATGCTGGAATTCAGATCGGTCAATGCAGTGG
CCTTCAACCTGCTGGTGACCCTTAGGATTGACAAGGCGATAGGCCCTGGG
AAGATCATCGACAATACAGAGCAACTTCCTGAGGCAACATTTATGGTCCA
CATCGGGAACTTCAGGAGAAAGAAGAGTGAAGTCTACTCTGCCGATTATT
GCAAAATGAAAATCGAAAAGATGGGCCTGGTTTTTGCACTTGGTGGGATA
GGGGGCACCAGTCTTCACATTAGAAGCACAGGCAAAATGAGCAAGACTCT
CCATGCACAACTCGGGTTCAAGAAGACCTTATGTTACCCGCTGATGGATA
TCAATGAAGACCTTAATCGATTACTCTGGAGGAGCAGATGCAAGATAGTA
AGAATCCAGGCAGTTTTGCAGCCATCAGTTCCTCAAGAATTCCGCATTTA
CGACGACGTGATCATAAATGATGACCAAGGACTATTCAAAGTTCTGTAGA
CCGTAGTGCCCAGCAATGCCCGAAAACGACCCCCCTCACAATGACAGCCA
GAAGGCCCGGACAAAAAAGCCCCCTCCGAAAGACTCCACGGACCAAGCGA
GAGGCCAGCCAGCAGCCGACGGCAAGCGCGAACACCAGGCGGCCCCAGCA
CAGAACAGCCCTGACACAAGGCCACCACCAGCCACCCCAATCTGCATCCT
```

FIGURE 28.4

CCTCGTGGGACCCCCGAGGACCAACCCCCAAGGCTGCCCCCGATCCAAAC
CACCAACCGCATCCCCACCACCCCGGGAAAGAAACCCCCAGCAATTGGA
AGGCCCCTCCCCCTCTTCCTCAACACAAGAACTCCACAACCGAACCGCAC
AAGCGACCGAGGTGACCCAACCGCAGGCATCCGACTCCCTAGACAGATCC
TCTCTCCCCGGCAAACTAAACAAAACTTAGGGCCAAGGAACATACACACC
CAACAGAACCCAGACCCCGGCCCACGGCGCCGCGCCCCAACCCCCGACA
ACCAGAGGGAGCCCCCAACCAATCCCGCCGGCTCCCCGGTGCCCACAGG
CAGGGACACCAACCCCCGAACAGACCCAGCACCCAACCATCGACAATCCA
AGACGGGGGGGCCCCCCCAAAAAAAGGCCCCCAGGGGCCGACAGCCAGCA
CCGCGAGGAAGCCCACCCACCCCACACACGACCACGGCAACCAAACCAGA
ACCCAGACCACCCTGGGCCACCAGCTCCCAGACTCGGCCATCACCCCGCA
GAAAGGAAAGGCCACAACCCGCGCACCCCAGCCCCGATCCGGCGGGGAGC
CACCCAACCCGAACCAGCACCCAAGAGCGATCCCCGAAGGACCCCCGAAC
CGCAAAGGACATCAGTATCCCACAGCCTCTCCAAGTCCCCCGGTCTCCTC
CTCTTCTCGAAGGGACCAAAAGATCAATCCACCACACCCGACGACACTCA
ACTCCCCACCCCTAAAGGAGACACCGGGAATCCCAGAATCAAGACTCATC
CAATGTCCATCATGGGTCTCAAGGTGAACGTCTCTGCCATATTCATGGCA
GTACTGTTAACTCTCCAAACACCCACCGGTCAAATCCATTGGGGCAATCT
CTCTAAGATAGGGGTGGTAGGAATAGGAAGTGCAAGCTACAAAGTTATGA
CTCGTTCCAGCCATCAATCATTAGTCATAAAATTAATGCCCAATATAACT
CTCCTCAATAACTGCACGAGGGTAGAGATTGCAGAATACAGGAGACTACT
GAGAACAGTTTTGGAACCAATTAGAGATGCACTTAATGCAATGACCCAGA
ATATAAGACCGGTTCAGAGTGTAGCTTCAAGTAGGAGACACAAGAGATTT
GCGGGAGTAGTCCTGGCAGGTGCGGCCCTAGGCGTTGCCACAGCTGCTCA
GATAACAGCCGGCATTGCACTTCACCAGTCCATGCTGAACTCTCAAGCCA
TCGACAATCTGAGAGCGAGCCTGGAAACTACTAATCAGGCAATTGAGACA
ATCAGACAAGCAGGGCAGGAGATGATATTGGCTGTTCAGGGTGTCCAAGA
CTACATCAATAATGAGCTGATACCGTCTATGAACCAACTATCTTGTGATT
TAATCGGCCAGAAGCTCGGGCTCAAATTGCTCAGATACTATACAGAAATC
CTGTCATTATTTGGCCCCAGTTTACGGGACCCCATATCTGCGGAGATATC
TATCCAGGCTTTGAGCTATGCGCTTGGAGGAGACATCAATAAGGTGTTAG
AAAAGCTCGGATACAGTGGAGGTGATTTACTGGGCATCTTAGAGAGCGGA
GGAATAAAGGCCCGGATAACTCACGTCGACACAGAGTCCTACTTCATTGT
CCTCAGTATAGCCTATCCGACGCTGTCCGAGATTAAGGGGGTGATTGTCC

FIGURE 28.5

```
ACCGGCTAGAGGGGGTCTCGTACAACATAGGCTCTCAAGAGTGGTATACC
ACTGTGCCCAAGTATGTTGCAACCCAAGGGTACCTTATCTCGAATTTTGA
TGAGTCATCGTGTACTTTCATGCCAGAGGGGACTGTGTGCAGCCAAAATG
CCTTGTACCCGATGAGTCCTCTGCTCCAAGAATGCCTCCGGGGGTACACC
AAGTCCTGTGCTCGTACACTCGTATCCGGGTCTTTTGGGAACCGGTTCAT
TTTATCACAAGGGAACCTAATAGCCAATTGTGCATCAATCCTTTGCAAGT
GTTACACAACAGGAACGATCATTAATCAAGACCCTGACAAGATCCTAACA
TACATTGCTGCCGATCACTGCCCGGTAGTCGAGGTGAACGGCGTGACCAT
CCAAGTCGGGAGCAGGAGGTATCCAGACGCTGTGTACTTGCACAGAATTG
ACCTCGGTCCTCCCATATCATTGGAGAGGTTGGACGTAGGGACAAATCTG
GGGAATGCAATTGCTAAGTTGGAGGATGCCAAGGAATTGTTGGAGTCATC
GGACCAGATATTGAGGAGTATGAAAGGTTTATCGAGCACTAGCATAGTCT
ACATCCTGATTGCAGTGTGTCTTGGAGGGTTGATAGGGATCCCCGCTTTA
ATATGTTGCTGCAGGGGCGTTGTAACAAAAAGGGAGAACAAGTTGGTAT
GTCAAGACCAGGCCTAAAGCCTGATCTTACGGGAACATCAAAATCCTATG
TAAGGTCGCTCTGATCCTCTACAACTCTTGAAACACAAATGTCCCACAAG
TCTCCTCTTCGTCATCAAGCAACCACCGCACCCAGCATCAAGCCCACCTG
AAATTATCTCCGGCTTCCCTCTGGCCGAACAATATCGGTAGTTAATCAAA
ACTTAGGGTGCAAGATCATCCACAATGTCACCACAACGAGACCGGATAAA
TGCCTTCTACAAAGATAACCCCCATCCCAAGGGAAGTAGGATAGTCATTA
ACAGAGAACATCTTATGATTGATAGACCTTATGTTTTGCTGGCTGTTCTG
TTTGTCATGTTTCTGAGCTTGATCGGGTTGCTAGCCATTGCAGGCATTAG
ACTTCATCGGGCAGCCATCTACACCGCAGAGATCCATAAAAGCCTCAGCA
CCAATCTAGATGTAACTAACTCAATCGAGCATCAGGTCAAGGACGTGCTG
ACACCACTCTTCAAAATCATCGGTGATGAAGTGGGCCTGAGGACACCTCA
GAGATTCACTGACCTAGTGAAATTAATCTCTGACAAGATTAAATTCCTTA
ATCCGGATAGGGAGTACGACTTCAGAGATCTCACTTGGTGTATCAACCCG
CCAGAGAGAATCAAATTGGATTATGATCAATACTGTGCAGATGTGGCTGC
TGAAGAGCTCATGAATGCATTGGTGAACTCAACTCTACTGGAGACCAGAA
CAACCAATCAGTTCCTAGCTGTCTCAAAGGGAAACTGCTCAGGGCCCACT
ACAATCAGAGGTCAATTCTCAAACATGTCGCTGTCCCTGTTAGACTTGTA
TTTAGGTCGAGGTTACAATGTGTCATCTATAGTCACTATGACATCCCAGG
GAATGTATGGGGGAACTTACCTAGTGGAAAAGCCTAATCTGAGCAGCAAA
AGGTCAGAGTTGTCACAACTGAGCATGTACCGAGTGTTTGAAGTAGGTGT
```

FIGURE 28.6

TATCAGAAATCCGGGTTTGGGGGCTCCGGTGTTCCATATGACAAACTATC
TTGAGCAACCAGTCAGTAATGATCTCAGCAACTGTATGGTGGCTTTGGGG
GAGCTCAAACTCGCAGCCCTTTGTCACGGGGAAGATTCTATCACAATTCC
CTATCAGGGATCAGGGAAAGGTGTCAGCTTCCAGCTCGTCAAGCTAGGTG
TCTGGAAATCCCCAACCGACATGCAATCCTGGGTCCCCTTATCAACGGAT
GATCCAGTGATAGACAGGCTTTACCTCTCATCTCACAGAGGTGTTATCGC
TGACAATCAAGCAAAATGGGCTGTCCCGACAACACGAACAGATGACAAGT
TGCGAATGGAGACATGCTTCCAACAGGCGTGTAAGGGTAAAATCCAAGCA
CTCTGCGAGAATCCCGAGTGGGCACCATTGAAGGATAACAGGATTCCTTC
ATACGGGGTCTTGTCTGTTGATCTGAGTCTGACAGTTGAGCTTAAAATCA
AAATTGCTTCGGGATTCGGGCCATTGATCACACACGGTTCAGGGATGGAC
CTATACAAATCCAACCACAACAATGTGTATTGGCTGACTATCCCGCCAAT
GAAGAACCTAGCCTTAGGTGTAATCAACACATTGGAGTGGATACCGAGAT
TCAAGGTTAGTCCCTACCTCTTCACTGTCCCAATTAAGGAAGCAGGCGAA
GACTGCCATGCCCCAACATACCTACCTGCGGAGGTGGATGGTGATGTCAA
ACTCAGTTCCAATCTGGTGATTCTACCTGGTCAAGATCTCCAATATGTTT
TGGCAACCTACGATACTTCCAGGGTTGAACATGCTGTGGTTTATTACGTT
TACAGCCCAAGCCGCTCATTTTCTTACTTTTATCCTTTTAGGTTGCCTAT
AAAGGGGGTCCCCATCGAATTACAAGTGGAATGCTTCACATGGGACCAAA
AACTCTGGTGCCGTCACTTCTGTGTGCTTGCGGACTCAGAATCTGGTGGA
CATATCACTCACTCTGGGATGGTGGGCATGGAGTCAGCTGCACAGTCAC
CCGGGAAGATGGAACCAATCGCAGATAGGGCTGCTAGTGAACCAATCACA
TGATGTCACCCAGACATCAGGCATACCCACTAGTGTGAAATAGACATCAG
AATTAAGAAAAACGTAGGGTCCAAGTGGTTCCCCGTTATGGACTCGCTAT
CTGTCAACCAGATCTTATACCCTGAAGTTCACCTAGATAGCCCGATAGTT
ACCAATAAGATAGTAGCCATCCTGGAGTATGCTCGAGTCCCTCACGCTTA
CAGCCTGGAGGACCCTACACTGTGTCAGAACATCAAGCACCGCCTAAAAA
ACGGATTTTCCAACCAAATGATTATAAACAATGTGGAAGTTGGGAATGTC
ATCAAGTCCAAGCTTAGGAGTTATCCGGCCCACTCTCATATTCCATATCC
AAATTGTAATCAGGATTTATTTAACATAGAAGACAAAGAGTCAACGAGGA
AGATCCGTGAACTCCTCAAAAAGGGGAATTCGCTGTACTCCAAAGTCAGT
GATAAGGTTTTCCAATGCTTAAGGGACACTAACTCACGGCTTGGCCTAGG
CTCCGAATTGAGGGAGGACATCAAGGAGAAAGTTATTAACTTGGGAGTTT
ACATGCACAGCTCCCAGTGGTTTGAGCCCTTTCTGTTTTGGTTTACAGTC

FIGURE 28.7

```
AAGACTGAGATGAGGTCAGTGATTAAATCACAAACCCATACTTGCCATAG
GAGGAGACACACACCTGTATTCTTCACTGGTAGTTCAGTTGAGTTGCTAA
TCTCTCGTGACCTTGTTGCTATAATCAGTAAAGAGTCTCAACATGTATAT
TACCTGACATTTGAACTGGTTTTGATGTATTGTGATGTCATAGAGGGGAG
GTTAATGACAGAGACCGCTATGACTATTGATGCTAGGTATACAGAGCTTC
TAGGAAGAGTCAGATACATGTGGAAACTGATAGATGGTTTCTTCCCTGCA
CTCGGGAATCCAACTTATCAAATTGTAGCCATGCTGGAGCCTCTTTCACT
TGCTTACCTGCAGCTGAGGGATATAACAGTAGAACTCAGAGGTGCTTTCC
TTAACCACTGCTTTACTGAAATACATGATGTTCTTGACCAAAACGGGTTT
TCTGATGAAGGTACTTATCATGAGTTAACTGAAGCTCTAGATTACATTTT
CATAACTGATGACATACATCTGACAGGGGAGATTTTCTCATTTTTCAGAA
GTTTCGGCCACCCCAGACTTGAAGCAGTAACGGCTGCTGAAAATGTTAGG
AAATACATGAATCAGCCTAAAGTCATTGTGTATGAGACTCTGATGAAAGG
TCATGCCATATTTTGTGGAATCATAATCAACGGCTATCGTGACAGGCACG
GAGGCAGTTGGCCACCGCTGACCCTCCCCCTGCATGCTGCAGACACAATC
CGGAATGCTCAAGCTTCAGGTGAAGGGTTAACACATGAGCAGTGCGTTGA
TAACTGGAAATCTTTTGCTGGAGTGAAATTTGGCTGCTTTATGCCTCTTA
GCCTGGATAGTGATCTGACAATGTACCTAAAGGACAAGGCACTTGCTGCT
CTCCAAAGGGAATGGGATTCAGTTTACCCGAAAGAGTTCCTGCGTTACGA
CCCTCCCAAGGGAACCGGGTCACGGAGGCTTGTAGATGTTTTCCTTAATG
ATTCGAGCTTTGACCCATATGATGTGATAATGTATGTTGTAAGTGGAGCT
TACCTCCATGACCCTGAGTTCAACCTGTCTTACAGCCTGAAAGAAAAGGA
GATCAAGGAAACAGGTAGACTTTTTGCTAAAATGACTTACAAAATGAGGG
CATGCCAAGTGATTGCTGAAAATCTAATCTCAAACGGGATTGGCAAATAT
TTTAAGGACAATGGGATGGCCAAGGATGAGCACGATTTGACTAAGGCACT
CCACACTCTAGCTGTCTCAGGAGTCCCCAAAGATCTCAAAGAAAGTCACA
GGGGGGGGCCAGTCTTAAAAACCTACTCCCGAAGCCCAGTCCACACAAGT
ACCAGGAACGTGAGAGCAGCAAAAGGGTTTATAGGGTTCCCTCAAGTAAT
TCGGCAGGACCAAGACACTGATCATCCGGAGAATATGGAAGCTTACGAGA
CAGTCAGTGCATTTATCACGACTGATCTCAAGAAGTACTGCCTTAATTGG
AGATATGAGACCATCAGCTTGTTTGCACAGAGGCTAAATGAGATTTACGG
ATTGCCCTCATTTTTCCAGTGGCTGCATAAGAGGCTTGAGACCTCTGTCC
TGTATGTAAGTGACCCTCATTGCCCCCCCGACCTTGACGCCCATATCCCG
TTATATAAAGTCCCCAATGATCAAATCTTCATTAAGTACCCTATGGGAGG
```

FIGURE 28.8

```
TATAGAAGGGTATTGTCAGAAGCTGTGGACCATCAGCACCATTCCCTATC
TATACCTGGCTGCTTATGAGAGCGGAGTAAGGATTGCTTCGTTAGTGCAA
GGGGACAATCAGACCATAGCCGTAACAAAAAGGGTACCCAGCACATGGCC
CTACAACCTTAAGAAACGGGAAGCTGCTAGAGTAACTAGAGATTACTTTG
TAATTCTTAGGCAAAGGCTACATGATATTGGCCATCACCTCAAGGCAAAT
GAGACAATTGTTTCATCACATTTTTTTGTCTATTCAAAAGGAATATATTA
TGATGGGCTACTTGTGTCCCAATCACTCAAGAGCATCGCAAGATGTGTAT
TCTGGTCAGAGACTATAGTTGATGAAACAAGGGCAGCATGCAGTAATATT
GCTACAACAATGGCTAAAAGCATCGAGAGAGGTTATGACCGTTACCTTGC
ATATTCCCTGAACGTCCTAAAAGTGATACAGCAAATTCTGATCTCTCTTG
GCTTCACAATCAATTCAACCATGACCCGGGATGTAGTCATACCCCTCCTC
ACAAACAACGACCTCTTAATAAGGATGGCACTGTTGCCCGCTCCTATTGG
GGGGATGAATTATCTGAATATGAGCAGGCTGTTTGTCAGAAACATCGGTG
ATCCAGTAACATCATCAATTGCTGATCTCAAGAGAATGATTCTCGCCTCA
CTAATGCCTGAAGAGACCCTCCATCAAGTAATGACACAACAACCGGGGGA
CTCTTCATTCCTAGACTGGGCTAGCGACCCTTACTCAGCAAATCTTGTAT
GTGTCCAGAGCATCACTAGACTCCTCAAGAACATAACTGCAAGGTTTGTC
CTGATCCATAGTCCAAACCCAATGTTAAAAGGATTATTCCATGATGACAG
TAAAGAAGAGGACGAGGGACTGGCGGCATTCCTCATGGACAGGCATATTA
TAGTACCTAGGGCAGCTCATGAAATCCTGGATCATAGTGTCACAGGGGCA
AGAGAGTCTATTGCAGGCATGCTGGATACCACAAAAGGCTTGATTCGAGC
CAGCATGAGGAAGGGGGGGTTAACCTCTCGAGTGATAACCAGATTGTCCA
ATTATGACTATGAACAATTCAGAGCAGGGATGGTGCTATTGACAGGAAGA
AAGAGAAATGTCCTCATTGACAAAGAGTCATGTTCAGTGCAGCTGGCGAG
AGCTCTAAGAAGCCATATGTGGGCGAGGCTAGCTCGAGGACGGCCTATTT
ACGGCCTTGAGGTCCCTGATGTACTAGAATCTATGCGAGGCCACCTTATT
CGGCGTCATGAGACATGTGTCATCTGCGAGTGTGGATCAGTCAACTACGG
ATGGTTTTTTGTCCCCTCGGGTTGCCAACTGGATGATATTGACAAGGAAA
CATCATCCTTGAGAGTCCCATATATTGGTTCTACCACTGATGAGAGAACA
GACATGAAGCTTGCCTTCGTAAGAGCCCCAAGTCGATCCTTGCGATCTGC
TGTTAGAATAGCAACAGTGTACTCATGGGCTTACGGTGATGATGATAGCT
CTTGGAACGAAGCCTGGTTGTTGGCTAGGCAAAGGGCCAATGTGAGCCTG
GAGGAGCTAAGGGTGATCACTCCCATCTCAACTTCGACTAATTTAGCGCA
TAGGTTGAGGGATCGTAGCACTCAAGTGAAATACTCAGGTACATCCCTTG
```

FIGURE 28.9

```
TCCGAGTGGCGAGGTATACCACAATCTCCAACGACAATCTCTCATTTGTC
ATATCAGATAAGAAGGTTGATACTAACTTTATATACCAACAAGGAATGCT
TCTAGGGTTGGGTGTTTTAGAAACATTGTTTCGACTCGAGAAAGATACCG
GATCATCTAACACGGTATTACATCTTCACGTCGAAACAGATTGTTGCGTG
ATCCCGATGATAGATCATCCAGGATACCCAGCTCCCGCAAGCTAGAGCT
GAGGGCAGAGCTATGTACCAACCCATTGATATATGATAATGCACCTTTAA
TTGACAGAGATGCAACAAGGCTATACACCCAGAGCCATAGGAGGCACCTT
GTGGAATTTGTTACATGGTCCACACCCCAACTATATCACATTTTAGCTAA
GTCCACAGCACTATCTATGATTGACCTGGTAACAAAATTTGAGAAGGACC
ATATGAATGAAATTTCAGCTCTCATAGGGGATGACGATATCAATAGTTTC
ATAACTGAGTTTCTGCTCATAGAGCCAAGATTATTCACTATCTACTTGGG
CCAGTGTGCGGCCATCAATTGGGCATTTGATGTACATTATCATAGACCAT
CAGGGAAATATCAGATGGGTGAGCTGTTGTCATCGTTCCTTTCTAGAATG
AGCAAAGGAGTGTTTAAGGTGCTTGTCAATGCTCTAAGCCACCCAAAGAT
CTACAAGAAATTCTGGCATTGTGGTATTATAGAGCCTATCCATGGTCCTT
CACTTGATGCTCAAAACTTGCACACAACTGTGTGCAACATGGTTTACACA
TGCTATATGACCTACCTCGACCTGTTGTTGAATGAAGAGTTAGAAGAGTT
CACATTTCTCTTGTGTGAAAGCGACGAGGATGTAGTACCGGACAGATTCG
ACAACATCCAGGCAAAACACTTATGTGTTCTGGCAGATTTGTACTGTCAA
CCAGGGACCTGCCCACCAATTCGAGGTCTAAGACCGGTAGAGAAATGTGC
AGTTCTAACCGACCATATCAAGGCAGAGGCTATGTTATCTCCAGCAGGAT
CTTCGTGGAACATAAATCCAATTATTGTAGACCATTACTCATGCTCTCTG
ACTTATCTCCGGCGAGGATCGATCAAACAGATAAGATTGAGAGTTGATCC
AGGATTCATTTTCGACGCCCTCGCTGAGGTAAATGTCAGTCAGCCAAAGA
TCGGCAGCAACAACATCTCAAATATGAGCATCAAGGCTTTCAGACCCCCA
CACGATGATGTTGCAAAATTGCTCAAAGATATCAACACAAGCAAGCACAA
TCTTCCCATTTCAGGGGGCAATCTCGCCAATTATGAAATCCATGCTTTCC
GCAGAATCGGGTTGAACTCATCTGCTTGCTACAAAGCTGTTGAGATATCA
ACATTAATTAGGAGATGCCTTGAGCCAGGGGAGGACGGCTTGTTCTTGGG
TGAGGGATCGGGTTCTATGTTGATCACTTATAAAGAGATACTTAAACTAA
ACAAGTGCTTCTATAATAGTGGGGTTTCCGCCAATTCTAGATCTGGTCAA
AGGGAATTAGCACCCTATCCCTCCGAAGTTGGCCTTGTCGAACACAGAAT
GGGAGTAGGTAATATTGTCAAAGTGCTCTTTAACGGGAGGCCCGAAGTCA
CGTGGGTAGGCAGTGTAGATTGCTTCAATTTCATAGTTAGTAATATCCCT
```

FIGURE 28.10

ACCTCTAGTGTGGGGTTTATCCATTCAGATATAGAGACCTTGCCTGACAA
AGATACTATAGAGAAGCTAGAGGAATTGGCAGCCATCTTATCGATGGCTC
TGCTCCTGGGCAAAATAGGATCAATACTGGTGATTAAGCTTATGCCTTTC
AGCGGGATTTTGTTCAGGGATTTATAAGTTATGTAGGGTCTCATTATAG
AGAAGTGAACCTTGTATACCCTAGATACAGCAACTTCATCTCTACTGAAT
CTTATTTGGTTATGACAGATCTCAAGGCTAACCGGCTAATGAATCCTGAA
AAGATTAAGCAGCAGATAATTGAATCATCTGTGAGGACTTCACCTGGACT
TATAGGTCACATCCTATCCATTAAGCAACTAAGCTGCATACAAGCAATTG
TGGGAGACGCAGTTAGTAGAGGTGATATCAATCCTACTCTGAAAAAACTT
ACACCTATAGAGCAGGTGCTGATCAATTGCGGGTTGGCAATTAACGGACC
TAAGCTGTGCAAAGAATTGATCCACCATGATGTTGCCTCAGGGCAAGATG
GATTGCTTAATTCTATACTCATCCTCTACAGGGAGTTGGCAAGATTCAAA
GACAACCAAAGAAGTCAACAAGGGATGTTCCACGCTTACCCCGTATTGGT
AAGTAGCAGGCAACGAGAACTTATATCTAGGATCACCCGCAAATTCTGGG
GGCACATTCTTCTTTACTCCGGGAACAAAAAGTTGATAAATAAGTTTATC
CAGAATCTCAAGTCCGGCTATCTGATACTAGACTTACACCAGAATATCTT
CGTTAAGAATCTATCCAAGTCAGAGAAACAGATTATTATGACGGGGGGTT
TGAAACGTGAGTGGGTTTTTAAGGTAACAGTCAAGGAGACCAAAGAATGG
TATAAGTTAGTCGGATACAGTGCCCTGATTAAGGACTAATTGGTTGAACT
CCGGAACCCTAATCCTGCCCTAGGTGGTTAGGCATTATTTGCAATATATT
AAAGAAAACTTTGAAAATACGAAGTTTCTATTCCCAGCTTTGTCTGGTgg
ccggcatggtccagcctcctcgctggcgccggctgggcaacattccgag
gggaccgtccctcggtaatggcgaatgggacGCGGCCGATCCGGCTGCT
AACAAAGCCCGAAAGGAAGCTGAGTTGGCTGCTGCCACCGCTGAGCAATA
ACTAGCATAACCCCTTGGGGCCTCTAAACGGGTCTTGAGGGGTTTTTTGC
TGAAAGGAGGAACTATATCCGGATGCGGCCGCACTAGTATCGATGGATTA
CAAGGATGACGACGATAAGATCTGAGCTCTTAATTAACAATTCTTCGCCA
GAGGTTTGGTCAAGTCTCCAATCAAGGTTGTCGGCTTGTCTACCTTGCCA
GAAATTTACGAAAGATGGAAAAGGGTCAAATCGTTGGTAGATACGTTGT
TGACACTTCTAAATAAGCGAATTTCTTATGATTTATGATTTTTATTATTA
AATAAGTTATAAAAAAATAAGTGTATACAAATTTTAAAGTGACTCTTAG
GTTTTAAAACGAAAATTCTTATTCTTGAGTAACTCTTTCCTGTAGGTCAG
GTTGCTTTCTCAGGTATAGCATGAGGTCGCTCCAATTCAGCTGGCGTAAT
AGCGAAGAGGCCCGCACCGATCGCCCTTCCCAACAGTTGCGCAGCCTGAA

FIGURE 28.11

TGGCGAATGGACGCGCCCTGTAGCGGCGCATTAAGCGCGGCGGGTGTGGT
GGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGT
CAAGCTCTAAATCGGGGCTCCCTTTAGGGTTCCGATTTAGTGCTTTACG
GCACCTCGACCCCAAAAAACTTGATTAGGGTGATGGTTCACGTAGTGGGC
CATCGCCCTGATAGACGGTTTTTCGCCCTTTGACGTTGGAGTCCACGTTC
TTTAATAGTGGACTCTTGTTCCAAACTGGAACAACACTCAACCCTATCTC
GGTCTATTCTTTTGATTTATAAGGGATTTTGCCGATTTCGGCCTATTGGT
TAAAAAATGAGCTGATTTAACAAAAATTTAACGCGAATTTTAACAAAATA
TTAACGTTTACAATTTCCTGATGCGGTATTTTCTCCTTACGCATCTGTGC
GGTATTTCACACCGCATAGGGTAATAACTGATATAATTAAATTGAAGCTC
TAATTTGTGAGTTTAGTATACATGCATTTACTTATAATACAGTTTTTTAG
TTTTGCTGGCCGCATCTTCTCAAATATGCTTCCCAGCCTGCTTTTCTGTA
ACGTTCACCCTCTACCTTAGCATCCCTTCCCTTTGCAAATAGTCCTCTTC
CAACAATAATAATGTCAGATCCTGTAGAGACCACATCATCCACGGTTCTA
TACTGTTGACCCAATGCGTCTCCCTTGTCATCTAAACCCACACCGGGTGT
CATAATCAACCAATCGTAACCTTCATCTCTTCCACCCATGTCTCTTTGAG
CAATAAAGCCGATAACAAAATCTTTGTCGCTCTTCGCAATGTCAACAGTA
CCCTTAGTATATTCTCCAGTAGATAGGGAGCCCTTGCATGACAATTCTGC
TAACATCAAAAGGCCTCTAGGTTCCTTTGTTACTTCTTCTGCCGCCTGCT
TCAAACCGCTAACAATACCTGGGCCCACCACACCGTGTGCATTCGTAATG
TCTGCCCATTCTGCTATTCTGTATACACCCGCAGAGTACTGCAATTTGAC
TGTATTACCAATGTCAGCAAATTTTCTGTCTTCGAAGAGTAAAAAATTGT
ACTTGGCGGATAATGCCTTTAGCGGCTTAACTGTGCCCTCCATGGAAAAA
TCAGTCAAGATATCCACATGTGTTTTTAGTAAACAAATTTTGGGACCTAA
TGCTTCAACTAACTCCAGTAATTCCTTGGTGGTACGAACATCCAATGAAG
CACACAAGTTTGTTTGCTTTTCGTGCATGATATTAAATAGCTTGGCAGCA
ACAGGACTAGGATGAGTAGCAGCACGTTCCTTATATGTAGCTTTCGACAT
GATTTATCTTCGTTTCCTGCAGGTTTTTGTTCTGTGCAGTTGGGTTAAGA
ATACTGGGCAATTTCATGTTTCTTCAACACTACATATGCGTATATATACC
AATCTAAGTCTGTGCTCCTTCCTTCGTTCTTCCTTCTGTTCGGAGATTAC
CGAATCAAAAAAATTTCAAAGAAACCGAAATCAAAAAAAGAATAAAAAA
AAAATGATGAATTGAATTGAAAGCTGTGGTATGGTGCACTCTCAGTACA
ATCTGCTCTGATGCCGCATAGTTAAGCCAGCCCCGACACCCGCCAACACC

FIGURE 28.12

```
CGCTGACGCGCCCTGACGGGCTTGTCTGCTCCCGGCATCCGCTTACAGAC
AAGCTGTGACCGTCTCCGGGAGCTGCATGTGTCAGAGGTTTTCACCGTCA
TCACCGAAACGCGCGAGACGAAAGGGCCTCGTGATACGCCTATTTTTATA
GGTTAATGTCATGATAATAATGGTTTCTTAGTATGATCCAATATCAAAGG
AAATGATAGCATTGAAGGATGAGACTAATCCAATTGAGGAGTGGCAGCAT
ATAGAACAGCTAAAGGGTAGTGCTGAAGGAAGCATACGATACCCCGCATG
GAATGGGATAATATCACAGGAGGTACTAGACTACCTTTCATCCTACATAA
ATAGACGCATATAAGTACGCATTTAAGCATAAACACGCACTATGCCGTTC
TTCTCATGTATATATATACAGGCAACACGCAGATATAGGTGCGACGTG
AACAGTGAGCTGTATGTGCGCAGCTCGCGTTGCATTTTCGGAAGCGCTCG
TTTTCGGAAACGCTTTGAAGTTCCTATTCCGAAGTTCCTATTCTCTAGAA
AGTATAGGAACTTCAGAGCGCTTTTGAAAACCAAAAGCGCTCTGAAGACG
CACTTTCAAAAAACCAAAAACGCACCGGACTGTAACGAGCTACTAAAATA
TTGCGAATACCGCTTCCACAAACATTGCTCAAAAGTATCTCTTTGCTATA
TATCTCTGTGCTATATCCCTATATAACCTACCCATCCACCTTTCGCTCCT
TGAACTTGCATCTAAACTCGACCTCTACATTTTTTATGTTTATCTCTAGT
ATTACTCTTTAGACAAAAAAATTGTAGTAAGAACTATTCATAGAGTGAAT
CGAAAACAATACGAAAATGTAAACATTTCCTATACGTAGTATATAGAGAC
AAAATAGAAGAAACCGTTCATAATTTTCTGACCAATGAAGAATCATCAAC
GCTATCACTTTCTGTTCACAAAGTATGCGCAATCCACATCGGTATAGAAT
ATAATCGGGGATGCCTTTATCTTGAAAAAATGCACCCGCAGCTTCGCTAG
TAATCAGTAAACGCGGGAAGTGGAGTCAGGCTTTTTTATGGAAGAGAAA
ATAGACACCAAAGTAGCCTTCTTCTAACCTTAACGGACCTACAGTGCAAA
AAGTTATCAAGAGACTGCATTATAGAGCGCACAAGGAGAAAAAAGTAA
TCTAAGATGCTTTGTTAGAAAAATAGCGCTCTCGGGATGCATTTTGTAG
AACAAAAAGAAGTATAGATTCTTTGTTGGTAAAATAGCGCTCTCGCGTT
GCATTTCTGTTCTGTAAAAATGCAGCTCAGATTCTTTGTTTGAAAAATTA
GCGCTCTCGCGTTGCATTTTTGTTTACAAAAATGAAGCACAGATTCTTC
GTTGGTAAAATAGCGCTTTCGCGTTGCATTTCTGTTCTGTAAAAATGCAG
CTCAGATTCTTTGTTTGAAAAATTAGCGCTCTCGCGTTGCATTTTGTTC
TACAAAATGAAGCACAGATGCTTCGTTCAGGTGGCACTTTTCGGGGAAAT
GTGCGCGGAACCCCTATTTGTTTATTTTTCTAAATACATTCAAATATGTA
TCCGCTCATGAGACAATAACCCTGATAAATGCTTCAATAATATTGAAAAA
GGAAGAGTATGAGTATTCAACATTTCCGTGTCGCCCTTATTCCCTTTTTT
```

FIGURE 28.13

GCGGCATTTTGCCTTCCTGTTTTTGCTCACCCAGAAACGCTGGTGAAAGT
AAAAGATGCTGAAGATCAGTTGGGTGCACGAGTGGGTTACATCGAACTGG
ATCTCAACAGCGGTAAGATCCTTGAGAGTTTTCGCCCCGAAGAACGTTTT
CCAATGATGAGCACTTTTAAAGTTCTGCTATGTGGCGCGGTATTATCCCG
TATTGACGCCGGGCAAGAGCAACTCGGTCGCCGCATACACTATTCTCAGA
ATGACTTGGTTGAGTACTCACCAGTCACAGAAAGCATCTTACGGATGGC
ATGACAGTAAGAGAATTATGCAGTGCTGCCATAACCATGAGTGATAACAC
TGCGGCCAACTTACTTCTGACAACGATCGGAGGACCGAAGGAGCTAACCG
CTTTTTTGCACAACATGGGGGATCATGTAACTCGCCTTGATCGTTGGGAA
CCGGAGCTGAATGAAGCCATACCAAACGACGAGCGTGACACCACGATGCC
TGTAGCAATGGCAACAACGTTGCGCAAACTATTAACTGGCGAACTACTTA
CTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGA
TAAATCTGGAGCCGGTGAGCGTGGGTCTCGCGGTATCATTGCAGCACTGG
GGCCAGATGGTAAGCCCTCCCGTATCGTAGTTATCTACACGACGGGGAGT
CAGGCAACTATGGATGAACGAAATAGACAGATCGCTGAGATAGGTGCCTC
ACTGATTAAGCATTGGTAACTGTCAGACCAAGTTTACTCATATATACTTT
AGATTGATTTAAAACTTCATTTTTAATTTAAAAGGATCTAGGTGAAGATC
CTTTTTGATAATCTCATGACCAAAATCCCTTAACGTGAGTTTTCGTTCCA
CTGAGCGTCAGACCCCGTAGAAAAGATCAAAGGATCTTCTTGAGATCCTT
TTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGT
AACTGGCTTCAGCAGAGCGCAGATACCAAATACTGTCCTTCTAGTGTAGC
CGTAGTTAGGCCACCACTTCAAGAACTCTGTAGCACCGCCTACATACCTC
GCTCTGCTAATCCTGTTACCAGTGGCTGCTGCCAGTGGCGATAAGTCGTG
TCTTACCGGGTTGGACTCAAGACGATAGTTACCGGATAAGGCGCAGCGGT
CGGGCTGAACGGGGGGTTCGTGCACACAGCCCAGCTTGGAGCGAACGACC
TACACCGAACTGAGATACCTACAGCGTGAGCTATGAGAAAGCGCCACGCT
TCCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATG
CTCGTCAGGGGGCGGAGCCTATGGAAAAACGCCAGCAACGCGGCCTTTT
TACGGTTCCTGGCCTTTTGCTGGCCTTTTGCTCACATGTTCTTTCCTGCG
TTATCCCCTGATTCTGTGGATAACCGTATTACCGCCTTTGAGTGAGCTGA

FIGURE 28.14

TACCGCTCGCCGCAGCCGAACGACCGAGCGCAGCGAGTCAGTGAGCGAGG
AAGCGGAAGAGCGCCCAATACGCAAACCGCCTCTCCCCGCGCGTTGGCCG
ATTCATTAATGCAGCTGGATCTTCGAGCGTCCCAAAACCTTCTCAAGCAA
GGTTTTCAGTATAATGTTACATGCGTACACGCGTCTGTACAGAAAAAAAA
GAAAAATTTGAAATATAAATAACGTTCTTAATACTAACATAACTATAAAA
AAATAAATAGGGACCTAGACTTCAGGTTGTCTAACTCCTTCCTTTTCGGT
TAGAGCGGATCTTAGCTAGCCGCGGTACCAAGCTTACTCGAGGTCTTCTT
CGGAAATCAACTTCTGTTCCATGTCGACGCCCGGGCCCTATAGTGAGTCG
TATTACGGATCCGGGTTTTTTCTCCTTGACGTTAAAGTATAGAGGTATA
TTAACAATTTTTGTTGATACTTTATTACATTTGAATAAGAAGTAATAC
AAACCGAAAATGTTGAAAGTATTAGTTAAAGTGGTTATGCAGTTTTTGCA
TTTATATATCTGTTAATAGATCAAAAATCATCGCTTCGCTGATTAATTAC
CCCAGAAATAAGGCTAAAAAACTAATCGCATTATCATCCTATGGTTGTTA
ATTTGATTCGTTCATTTGAAGGTTTGTGGGCCAGGTTACTGCCAATTTT
TCCTCTTCATAACCATAAAAGCTAGTATTGTAGAATCTTTATTGTTCGGA
GCAGTGCGGCGCGAGGCACATCTGCGTTTCAGGAACGCGACCGGTGAAGA
CGAGGACGCACGGAGGAGAGTCTTCCTTCGGAGGGCTGTCACCCGCTCGG
CGGCTTCTAATCCGTACTTCAATATAGCAATGAGCAGTTAAGCGTATTAC
TGAAAGTTCCAAAGAGAAGGTTTTTTTAGGCTAAGATAATGGGCTCTTT
ACATTTCCACAACATATAAGTAAGATTAGATATGGATATGTATATGGATA
TGTATATGGTGGTAATGCCATGTAATATGATTATTAAACTTCTTTGCGTC
CATCCAAAAAAAAGTAAGAATTTTTGAAAATTCGAATTCAACCCTCACT
AAAGGGCGGCCGCTAATACGACTCACTATAGGG

FIGURE 29.1

Gap repair plasmid based sequence (pCM476)

| | |
|---|---|
| pYES2 vector : | Capital letter |
| Ribozymes Sequence : | Minuscule letter |
| Leader sequence : | Bold capital letter |
| Trailer sequence : | *Bold italic capital letter* |
| *MCS* sequence : | *Minuscule italic letter* |

GTACGGATTAGAAGCCGCCGAGCGGGTGACAGCCCTCCGAAGGAAGACTC
TCCTCCGTGCGTCCTCGTCCTCACCGGTCGCGTTCCTGAAACGCAGATGT
GCCTCGCGCCGCACTGCTCCGAACAATAAAGATTCTACAATACTAGCTTT
TATGGTTATGAAGAGGAAAAATTGGCAGTAACCTGGCCCCACAAACCTTC
AAATGAACGAATCAAATTAACAACCATAGGATGATAATGCGATTAGTTTT
TTAGCCTTATTTCTGGGGTAATTAATCAGCGAAGCGATGATTTTTGATCT
ATTAACAGATATATAAATGCAAAAACTGCATTAACCACTTTAACTAATAC
TTTCAACATTTTCGGTTTGTATTACTTCTTATTCAAATGTAATAAAAGTA
TCAACAAAAATTGTTAATATACCTCTATACTTTAACGTCAAGGAGAAAA
AACCCCGGATCGGACTACTAGCAGCTGTAATACGACTCACTATAGGGAAT
ATTAAGCTTGGTACCGAGCTCGGATCCACTAGTAACGGCCGCCAGTGTGC
TGgaattcgagctcggtacctcgcgaatgcatctagatatcggatcccgcggccgccaactttgtttg
gtctgatgagtccgtgaggacgaaacccggagtcccgggtc
ACCAGACAAAGCTGGGAATAGAAACTTCGTATTTTCAAAGT
TTTCTTTAATATATTGCAAATAATGCCTAACCACCTAGGGCAGGATTAGG
GTTCCGGAGTTCAACCAATTAGTCCTTAATCAGGGCACTGTATCCGACTA
ACTTATACCAT *tctttggactagtgacgtccgcggtcgacacgtgagatc*tga
*TGGCCATCTCGGATATCCCTAATCCTGCTCTTGTCCCTGATAATAGG*
*ATCTTGAATCCTAAGTGCACTAGAAGATGATCATTGATTGAACTATCCTT*
*ACCCAACTTTGTTTGGT* ggccggcatggtcccagcctcctcgctggcgccggctgggcaacat
tccgagggggaccgtcccctcggtaatggcgaatgggacGGGcccgtcgactgcagaggcctg
CATGCATCTAGAGGGCCGCATCATG
TAATTAGTTATGTCACGCTTACATTCACGCCCTCCCCCACATCCGCTCT
AACCGAAAAGGAAGGAGTTAGACAACCTGAAGTCTAGGTCCCTATTTATT
TTTTTATAGTTATGTTAGTATTAAGAACGTTATTTATATTTCAAATTTTT
CTTTTTTTTCTGTACAGACGCGTGTACGCATGTAACATTATACTGAAAAC
CTTGCTTGAGAAGGTTTTGGGACGCTCGAAGGCTTTAATTTGCGGCCCTG
CATTAATGAATCGGCCAACGCGCGGGGAGAGGCGGTTTGCGTATTGGGCG
CTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAA
TCAGGGGATAACGCAGGAAAGAACATGTGAGCAAAAGGCCAGCAAAAGCC
CAGGAACCGTAAAAAGGCCGCGTTGCTGGCGTTTTTCCATAGGCTCCGCC
CCCTGACGAGCATCACAAAAATCGACGCTCAAGTCAGAGGTGGCGAAAC
CCGACAGGACTATAAAGATACCAGGCGTTTCCCCCTGGAAGCTCCCTCGT
GCGCTCTCCTGTTCCGACCCTGCCGCTTACCGGATACCTGTCCGCCTTTC

FIGURE 29.2

```
TCCCTTCGGGAAGCGTGGCGCTTTCTCATAGCTCACGCTGTAGGTATCTC
AGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCA
ACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGC
TGAAGCCAGTTACCTTCGGAAAAAGAGTTGGTAGCTCTTGATCCGGCAAA
CAAACCACCGCTGGTAGCGGTGGTTTTTTTGTTTGCAAGCAGCAGATTAC
GCGCAGAAAAAAGGATCTCAAGAAGATCCTTTGATCTTTTCTACGGGGT
CTGACGCTCAGTGGAACGAAAACTCACGTTAAGGGATTTTGGTCATGAGA
TTATCAAAAAGGATCTTCACCTAGATCCTTTTAAATTAAAAATGAAGTTT
TAAATCAATCTAAAGTATATATGAGTAAACTTGGTCTGACAGTTACCAAT
GCTTAATCAGTGAGGCACCTATCTCAGCGATCTGTCTATTTCGTTCATCC
ATAGTTGCCTGACTCCCCGTCGTGTAGATAACTACGATACGGGAGCGCTT
ACCATCTGGCCCCAGTGCTGCAATGATACCGCGAGACCCACGCTCACCGG
CTCCAGATTTATCAGCAATAAACCAGCCAGCCGGAAGGGCCGAGCGCAGA
AGTGGTCCTGCAACTTTATCCGCCTCCATTCAGTCTATTAATTGTTGCCG
GGAAGCTAGAGTAAGTAGTTCGCCAGTTAATAGTTTGCGCAACGTTGTTG
GCATTGCTACAGGCATCGTGGTGTCACTCTCGTCGTTTGGTATGGCTTCA
TTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCT
CTTACTGTCATGCCATCCGTAAGATGCTTTTCTGTGACTGGTGAGTACTC
AACCAAGTCATTCTGAGAATAGTGTATGCGGCGACCGAGTTGCTCTTGCC
CGGCGTCAATACGGGATAATAGTGTATCACATAGCAGAACTTTAAAAGTG
CTCATCATTGGAAAACGTTCTTCGGGGCGAAAACTCTCAAGGATCTTACC
GCTGTTGAGATCCAGTTCGATGTAACCCACTCGTGCACCCAACTGATCTT
CAGCATCTTTTACTTTCACCAGCGTTTCTGGGTGAGCAAAAACAGGAAGG
CAAAATGCCGCAAAAAAGGGAATAAGGGCGACACGGAAATGTTGAATACT
CATACTCTTCCTTTTTCAATGGGTAATAACTGATATAATTAAATTGAAGC
TCTAATTTGTGAGTTTAGTATACATGCATTTACTTATAATACAGTTTTTT
AGTTTTGCTGGCCGCATCTTCTCAAATATGCTTCCCAGCCTGCTTTTCTG
TAACGTTCACCCTCTACCTTAGCATCCCTTCCCTTTGCAAATAGTCCTCT
TCCAACAATAATAATGTCAGATCCTGTAGAGACCACATCATCCACGGTTC
TATACTGTTGACCCAATGCGTCTCCCTTGTCATCTAAACCCACACCGGGT
GTCATAATCAACCAATCGTAACCTTCATCTCTTCCACCCATGTCTCTTTG
AGCAATAAAGCCGATAACAAAATCTTTGTCGCTCTTCGCAATGTCAACAG
TACCCTTAGTATATTCTCCAGTAGATAGGGAGCCCTTGCATGACAATTCT
GCTAACATCAAAAGGCCTCTAGGTTCCTTTGTTACTTCTTCTGCCGCCTG
CTTCAAACCGCTAACAATACCTGGGCCCACCACACCGTGTGCATTCGTAA
TGTCTGCCCATTCTGCTATTCTGTATACACCCGCAGAGTACTGCAATTTG
ACTGTATTACCAATGTCAGCAAATTTTCTGTCTTCGAAGAGTAAAAAATT
GTACTTGGCGGATAATGCCTTTAGCGGCTTAACTGTGCCCTCCATGGAAA
AATCAGTCAAGATATCCACATGTGTTTTTAGTAAACAAATTTTGGGACCT
AATGCTTCAACTAACTCCAGTAATTCCTTGGTGGTACGAACATCCAATGA
AGCACACAAGTTTGTTTGCTTTTCGTGCATGATATTAAATAGCTTGGCAG
CAACAGGACTAGGATGAGTAGCAGCACGTTCCTTATATGTAGCTTTCGAC
ATGATTTATCTTCGTTTCCTGCAGGTTTTTGTTCTGTGCAGTTGGGTTAA
```

FIGURE 29.3

```
GAATACTGGGCAATTTCATGTTTCTTCAACACTACATATGCGTATATATA
CCAATCTAAGTCTGTGCTCCTTCCTTCGTTCTTCCTTCTGTTCGGAGATT
ACCGAATCAAAAAAATTTCAAAGAAACCGAAATCAAAAAAAAGAATAAAA
AAAAAATGATGAATTGAATTGAAAAGCTAGCTTATCGATGATAAGCTGTC
AAAGATGAGAATTAATTCCACGGACTATAGACTATACTAGATACTCCGTC
TACTGTACGATACACTTCCGCTCAGGTCCTTGTCCTTTAACGAGGCCTTA
CCACTCTTTTGTTACTCTATTGATCCAGCTCAGCAAAGGCAGTGTGATCT
AAGATTCTATCTTCGCGATGTAGTAAAACTAGCTAGACCGAGAAAGAGAC
TAGAAATGCAAAAGGCACTTCTACAATGGCTGCCATCATTATTATCGAT
GTGACGCTGCAGCTTCTCAATGATATTCGAATACGCTTTGAGGAGATACA
GCCTAATATCCGACAAACTGTTTTACAGATTTACGATCGTACTTGTTACC
CATCATTGAATTTTGAACATCCGAACCTGGGAGTTTTCCCTGAAACAGAT
AGTATATTTGAACCTGTATAATAATATATAGTCTAGCGCTTTACGGAAGA
CAATGTATGTATTTCGGTTCCTGGAGAAACTATTGCATCTATTGCATAGG
TAATCTTGCACGTCGCATCCCCGGTTCATTTTCTGCGTTTCCATCTTGCA
CTTCAATAGCATATCTTTGTTAACGAAGCATCTGTGCTTCATTTTGTAGA
ACAAAAATGCAACGCGAGAGCGCTAATTTTTCAAACAAAGAATCTGAGCT
GCATTTTTACAGAACAGAAATGCAACGCGAAAGCGCTATTTTACCAACGA
AGAATCTGTGCTTCATTTTTGTAAAACAAAAATGCAACGCGACGAGAGCG
CTAATTTTTCAAACAAAGAATCTGAGCTGCATTTTTACAGAACAGAAATG
CAACGCGAGAGCGCTATTTTACCAACAAAGAATCTATACTTCTTTTTTGT
TCTACAAAAATGCATCCCGAGAGCGCTATTTTTCTAACAAAGCATCTTAG
ATTACTTTTTTTCTCCTTTGTGCGCTCTATAATGCAGTCTCTTGATAACT
TTTTGCACTGTAGGTCCGTTAAGGTTAGAAGAAGGCTACTTTGGTGTCTA
TTTTCTCTTCCATAAAAAAGCCTGACTCCACTTCCCGCGTTTACTGATT
ACTAGCGAAGCTGCGGGTGCATTTTTTCAAGATAAAGGCATCCCCGATTA
TATTCTATACCGATGTGGATTGCGCATACTTTGTGAACAGAAAGTGATAG
CGTTGATGATTCTTCATTGGTCAGAAAATTATGAACGGTTTCTTCTATTT
TGTCTCTATATACTACGTATAGGAAATGTTTACATTTTCGTATTGTTTTC
GATTCACTCTATGAATAGTTCTTACTACAATTTTTTGTCTAAAGAGTAA
TACTAGAGATAAACATAAAAAATGTAGAGGTCGAGTTTAGATGCAAGTTC
AAGGAGCGAAAGGTGGATGGGTAGGTTATATAGGGATATAGCACAGAGAT
ATATAGCAAAGAGATACTTTTGAGCAATGTTTGTGGAAGCGGTATTCGCA
ATGGGAAGCTCCACCCCGGTTGATAATCAGAAAAGCCCCAAAAACAGGAA
GATTGTATAAGCAAATATTTAAATTGTAAACGTTAATATTTTGTTAAAAT
TCGCGTTAAATTTTTGTTAAATCAGCTCATTTTTTAACGAATAGCCCGAA
ATCGGCAAAATCCCTTATAAATCAAAAGAATAGACCGAGATAGGGTTGAG
TGTTGTTCCAGTTTCCAACAAGAGTCCACTATTAAAGAACGTGGACTCCA
ACGTCAAAGGGCGAAAAAGGGTCTATCAGGGCGATGGCCCACTACGTGAA
CCATCACCCTAATCAAGTTTTTTGGGGTCGAGGTGCCGTAAAGCAGTAAA
TCGGAAGGGTAAACGGATGCCCCATTTAGAGCTTGACGGGGAAAGCCGG
CGAACGTGGCGAGAAAGGAAGGGAAGAAAGCGAAAGGAGCGGGGGCTAGG
GCGGTGGGAAGTGTAGGGGTCACGCTGGGCGTAACCACCACACCCGCCGC
GCTTAATGGGGCGCTACAGGGCGCGTGGGGATGATCCACTA
```

FIGURE 30.1

Recombinant measles genome sequence: 2nd Gap repair plasmid (pCM402)

| | |
|---|---|
| pTM vector : | Capital letter |
| Measles genome sequence: | Capital letter |
| Ribozymes Sequence : | Minuscule letter |
| Leader sequence : | Bold capital letter |
| Trailer sequence : | Bold italic capital letter |
| *eGFP* sequence : | Bold minuscule letter |
| *KANMX4* sequence : | Minuscule italic letter |

GCGGCCGCTAATACGACTCACTATAGGG ccaactttgtttggtctgatga
gtccgtgaggacgaaacccggagtcccgggtc ACCAAACAAAGTTGGGTA
AGGATAGTTCAATCAATGATCATCTTCTAGTGCACTTAGGATTCAAGATC
CTATTATCAGGGACAAGAGCAGGATTAGGGATAT CCGAG
atggccacactttaaggagcttagcattgttcaaaagaaacaaggacaa
accacccattacatcaggatccggtggagccatcagaggaatcaaacaca
ttattatagtaccaatccctggagattcctcaattaccactcgatccaga
cttctggaccggttggtgaggttaattggaaacccggatgtgagcgggcc
caaactaacaggggcactaataggtatattatccttatttgtggagtctc
caggtcaattgattcagaggatcaccgatgaccctgacgttagcataagg
ctgttagaggttgtccagagtgaccagtcacaatctggccttaccttcgc
atcaagaggtaccaacatggaggatgaggcggaccaatacttttcacatg
atgatccaattagtagtgatcaatccaggttcggatggttcgggaacaag
gaaatctcagatattgaagtgcaagaccctgagggattcaacatgattct
gggtaccatcctagcccaaatttgggtcttgctcgcaaaggcggttacgg
ccccagacacggcagctgattcggagctaagaaggtggataaagtacacc
caacaaagaagggtagttggtgaatttagattggagagaaaatggttgga
tgtggtgaggaacaggattgccgaggacctctccttacgccgattcatgg
tcgctctaatcctggatatcaagagaacacccggaaacaaacccaggatt
gctgaaatgatatgtgacattgatacatatatcgtagaggcaggattagc
cagttttatcctgactattaagtttgggatagaaactatgtatcctgctc
ttggactgcatgaatttgctggtgagttatccacacttgagtccttgatg
aacctttaccagcaaatgggggaaactgcaccctacatggtaatcctgga
gaactcaattcagaacaagttcagtgcaggatcataccctctgctctgga
gctatgccatgggagtaggagtggaacttgaaaactccatgggaggtttg
aactttggccgatcttactttgatccagcatattttagattagggcaaga
gatggtaaggaggtcagctggaaaggtcagttccacattggcatctgaac
tcggtatcactgccgaggatgcaaggcttgtttcagagattgcaatgcat
actactgaggacaagatcagtagagcggttggacccagacaagcccaagt
atcatttctacacggtgatcaaagtgagaatgagctaccgagattgggggg
gcaaggaagataggagggtcaaacagagtcgaggagaagccagggagagc
tacagagaaaccgggcccagcagagcaagtgatgcgagagctgcccatct
tccaaccggcacacccctagacattgacactgcaacggagtccagccaag
atccgcaggacagtcgaaggtcagctgacgccctgcttaggctgcaagcc
atggcaggaatctcggaagaacaaggctcagacacggacacccctatagt

FIGURE 30.2 gtacaatgacagaaatcttctagactag
GTGCGAGAGGCCGAGGGCCAGAACAACATCCGC
CTACCATCCATCATTGTTATAAAAAACTTAGGAACCAGGTCCACACAGCC
GCCAGCCCATCAACCATCCACTCCCACGATTGGAGCCAATGGCAGAAGAG
CAGGCACGCCATGTCAAAAACGGACTGGAATGCATCCGGGCTCTCAAGGC
CGAGCCCATCGGCTCACTGGCCATCGAGGAAGCTATGGCAGCATGGTCAG
AAATATCAGACAACCCAGGACAGGAGCGAGCCACCTGCAGGGAAGAGAAG
GCAGGCAGTTCGGGTCTCAGCAAACCATGCCTCTCAGCAATTGGATCAAC
TGAAGGCGGTGCACCTCGCATCCGCGGTCAGGGACCTGGAGAGAGCGATG
ACGACGCTGAAACTTTGGGAATCCCCCAAGAAATCTCCAGGCATCAAGC
ACTGGGTTACAGTGTTATTACGTTTATGATCACAGCGGTGAAGCGGTTAA
GGGAATCCAAGATGCTGACTCTATCATGGTTCAATCAGGCCTTGATGGTG
ATAGCACCCTCTCAGGAGGAGACAATGAATCTGAAAACAGCGATGTGGAT
ATTGGCGAACCTGATACCGAGGGATATGCTATCACTGACCGGGGATCTGC
TCCCATCTCTATGGGGTTCAGGGCTTCTGATGTTGAAACTGCAGAAGGAG
GGGAGATCCACGAGCTCCTGAGACTCCAATCCAGAGGCAACAACTTTCCG
AAGCTTGGGAAAACTCTCAATGTTCCTCCGCCCCGGACCCCGGTAGGGC
CAGCACTTCCGGGACACCCATTAAAAAGGGCACAGACGCGAGATTAGCCT
CATTTGGAACGGAGATCGCGTCTTTATTGACAGGTGGTGCAACCCAATGT
GCTCGAAAGTCACCCTCGGAACCATCAGGGCCAGGTGCACCTGCGGGGAA
TGTCCCCGAGTGTGTGAGCAATGCCGCACTGATACAGGAGTGGACACCCG
AATCTGGTACCACAATCTCCCCGAGATCCCAGAATAATGAAGAAGGGGGA
GACTATTATGATGATGAGCTGTTCTCTGATGTCCAAGATATTAAAACAGC
CTTGGCCAAAATACACGAGGATAATCAGAAGATAATCTCCAAGCTAGAAT
CACTGCTGTTATTGAAGGGAGAAGTTGAGTCAATTAAGAAGCAGATCAAC
AGGCAAAATATCAGCATATCCACCCTGGAAGGACACCTCTCAAGCATCAT
GATCGCCATTCCTGGACTTGGGAAGGATCCCAACGACCCCACTGCAGATG
TCGAAATCAATCCCGACTTGAAACCCATCATAGGCAGAGATTCAGGCCGA
GCACTGGCCGAAGTTCTCAAGAAACCCGTTGCCAGCCGACAACTCCAAGG
AATGACAAATGGACGGACCAGTTCCAGAGGACAGCTGCTGAAGGAATTTC
AGCTAAAGCCGATCGGGAAAAAGATGAGCTCAGCCGTCGGGTTTGTTCCT
GACACCGGCCCTGCATCACGCAGTGTAATCCGCTCCATTATAAAATCCAG
CCGGCTAGAGGAGGATCGGAAGCGTTACCTGATGACTCTCCTTGATGATA
TCAAAGGAGCCAATGATCTTGCCAAGTTCCACCAGATGCTGATGAAGATA
ATAATGAAGTAGCTACAGCTCAACTTACCTGCCAACCCCATGCCAGTCGA
CCCAA CTAGCCTACCCTCCATCATTGTTATAAAAAACTTAGGAACCAGGTCCACA
CAGCCGCCAGCCCATCAACGCGTACG ATGGTGAGCAAGGGCGAGG
AGCTGTTCACCGGGGTGGTGCCCATCCTGGTCGAGCTGGACGGCGACGTA
AACGGCCACAAGTTCAGCGTGTCCGGCGAGGGCGAGGGCGATGCCACCTA
CGGCAAGCTGACCCTGAAGTTCATCTGCACCACCGGCAAGCTGCCCGTGC
CCTGGCCCACCCTCGTGACCACCCTGACCTACGGCGTGCAGTGCTTCAGC
CGCTACCCCGACCACATGAAGCAGCACGACTTCTTCAAGTCCGCCATGCC
CGAAGGCTACGTCCAGGAGCGCACCATCTTCTTCAAGGACGACGGCAACT
ACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCA
CAAGCTGGAGTACAACTACAACAGCCACAACGTCTATATCATGGCCGACA
AGCAGAAGAACGGCATCAAGGTGAACTTCAAGATCCGCCACAACATCGAG
GACGGCAGCGTGCAGCTCGCCGACCACTACCAGCAGAACACCCCCATCGG

FIGURE 30.3

CGACGGCCCCGTGCTGCTGCCCGACAACCACTACCTGAGCACCCAGTCCG
CCCTGAGCAAAGACCCCAACGAGAAGCGCGATCACATGGTCCTGCTGGAG
TTCGTGACCGCCGCCGGGATCACTCTCGGCATGGACGAGCTGTACAAGTA
GGCGCGCAGCGCTTAGACGTCTCGCGATCGATACTAGTACAACCTAAATC
CATTATAAAAAACTTAGGAGCAAAGTGATTGCCTCCCAAGGTCCACAATG
ACAGAGACCTACGACTTCGACAAGTCGGCATGGGACATCAAAGGGTCGAT
CGCTCCGATACAACCCACCACCTACAGTGATGGCAGGCTGGTGCCCCAGG
TCAGAGTCATAGATCCTGGTCTAGGCGACAGGAAGGATGAATGCTTTATG
TACATGTTTCTGCTGGGGGTTGTTGAGGACAGCGATTCCCTAGGGCCTCC
AATCGGGCGAGCATTTGGGTTCCTGCCCTTAGGTGTTGGCAGATCCACAG
CAAAGCCCGAAAAACTCCTCAAAGAGGCCACTGAGCTTGACATAGTTGTT
AGACGTACAGCAGGGCTCAATGAAAAACTGGTGTTCTACAACAACACCCC
ACTAACTCTCCTCACACCTTGGAGAAAGGTCCTAACAACAGGGAGTGTCT
TCAACGCAAACCAAGTGTGCAATGCGGTTAATCTGATACCGCTCGATACC
CCGCAGAGGTTCCGTGTTGTTTATATGAGCATCACCCGTCTTTCGGATAA
CGGGTATTACACCGTTCCTAGAAGAATGCTGGAATTCAGATCGGTCAATG
CAGTGGCCTTCAACCTGCTGGTGACCCTTAGGATTGACAAGGCGATAGGC
CCTGGGAAGATCATCGACAATACAGAGCAACTTCCTGAGGCAACATTTAT
GGTCCACATCGGGAACTTCAGGAGAAAGAAGAGTGAAGTCTACTCTGCCG
ATTATTGCAAAATGAAAATCGAAAAGATGGGCCTGGTTTTTGCACTTGGT
GGGATAGGGGGCACCAGTCTTCACATTAGAAGCACAGGCAAAATGAGCAA
GACTCTCCATGCACAACTCGGGTTCAAGAAGACCTTATGTTACCCGCTGA
TGGATATCAATGAAGACCTTAATCGATTACTCTGGAGGAGCAGATGCAAG
ATAGTAAGAATCCAGGCAGTTTTGCAGCCATCAGTTCCTCAAGAATTCCG
CATTTACGACGACGTGATCATAAATGATGACCAAGGACTATTCAAAGTTC
TGTAGACCGTAGTGCCCAGCAATGCCCGAAAACGACCCCCCTCACAATGA
CAGCCAGAAGGCCCGGACAAAAAAGCCCCCTCCGAAAGACTCCACGGACC
AAGCGAGAGGCCAGCCAGCAGCCGACGGCAAGCGCGAACACCAGGCGGCC
CCAGCACAGAACAGCCCTGACACAAGGCCACCACCAGCCACCCCAATCTG
CATCCTCCTCGTGGGACCCCGAGGACCAACCCCCAAGGCTGCCCCCGAT
CCAAACCACCAACCGCATCCCCACCACCCCGGGAAAGAAACCCCCAGCA
ATTGGAAGGCCCCTCCCCCTCTTCCTCAACACAAGAACTCCACAACCGAA
CCGCACAAGCGACCGAGGTGACCCAACCGCAGGCATCCGACTCCCTAGAC
AGATCCTCTCTCCCCGGCAAACTAAACAAAACTTAGGGCCAAGGAACATA
CACACCCAACAGAACCCAGACCCCGGCCCACGGCGCCGCGCCCCCAACCC
CCGACAACCAGAGGGAGCCCCCAACCAATCCCGCCGGCTCCCCGGTGCC
CACAGGCAGGGACACCAACCCCGAACAGACCCAGCACCCAACCATCGAC
AATCCAAGACGGGGGGGCCCCCCAAAAAAAGGCCCCCAGGGGCCGACAG
CCAGCACCGCGAGGAAGCCCACCCACCCCACACACGACCACGGCAACCAA
ACCAGAACCCAGACCACCCTGGGCCACCAGCTCCCAGACTCGGCCATCAC
CCCGCAGAAAGGAAAGGCCACAACCCGCGCACCCCAGCCCCGATCCGGCG
GGGAGCCACCCAACCCGAACCAGCACCCAAGAGCGATCCCCGAAGGACCC
CCGAACCGCAAAGGACATCAGTATCCCACAGCCTCTCCAAGTCCCCGGT
CTCCTCCTCTTCTCGAAGGGACCAAAAGATCAATCCACCACACCCGACGA
CACTCAACTCCCCACCCCTAAAGGAGACACCGGGAATCCCAGAATCAAGA
CTCATCCAATGTCCATCATGGGTCTCAAGGTGAACGTCTCTGCCATATTC
ATGGCAGTACTGTTAACTCTCCAAACACCCACCGGTCAAATCCATTGGGG
CAATCTCTCTAAGATAGGGGTGGTAGGAATAGGAAGTGCAAGCTACAAAG

FIGURE 30.4

```
TTATGACTCGTTCCAGCCATCAATCATTAGTCATAAAATTAATGCCCAAT
ATAACTCTCCTCAATAACTGCACGAGGGTAGAGATTGCAGAATACAGGAG
ACTACTGAGAACAGTTTTGGAACCAATTAGAGATGCACTTAATGCAATGA
CCCAGAATATAAGACCGGTTCAGAGTGTAGCTTCAAGTAGGAGACACAAG
AGATTTGCGGGAGTAGTCCTGGCAGGTGCGGCCCTAGGCGTTGCCACAGC
TGCTCAGATAACAGCCGGCATTGCACTTCACCAGTCCATGCTGAACTCTC
AAGCCATCGACAATCTGAGAGCGAGCCTGGAAACTACTAATCAGGCAATT
GAGACAATCAGACAAGCAGGGCAGGAGATGATATTGGCTGTTCAGGGTGT
CCAAGACTACATCAATAATGAGCTGATACCGTCTATGAACCAACTATCTT
GTGATTTAATCGGCCAGAAGCTCGGGCTCAAATTGCTCAGATACTATACA
GAAATCCTGTCATTATTTGGCCCCAGTTTACGGGACCCCATATCTGCGGA
GATATCTATCCAGGCTTTGAGCTATGCGCTTGGAGGAGACATCAATAAGG
TGTTAGAAAAGCTCGGATACAGTGGAGGTGATTTACTGGGCATCTTAGAG
AGCGGAGGAATAAAGGCCCGGATAACTCACGTCGACACAGAGTCCTACTT
CATTGTCCTCAGTATAGCCTATCCGACGCTGTCCGAGATTAAGGGGGTGA
TTGTCCACCGGCTAGAGGGGGTCTCGTACAACATAGGCTCTCAAGAGTGG
TATACCACTGTGCCCAAGTATGTTGCAACCCAAGGGTACCTTATCTCGAA
TTTTGATGAGTCATCGTGTACTTTCATGCCAGAGGGGACTGTGTGCAGCC
AAAATGCCTTGTACCCGATGAGTCCTCTGCTCCAAGAATGCCTCCGGGGG
TACACCAAGTCCTGTGCTCGTACACTCGTATCCGGGTCTTTTGGGAACCG
GTTCATTTTATCACAAGGGAACCTAATAGCCAATTGTGCATCAATCCTTT
GCAAGTGTTACACAACAGGAACGATCATTAATCAAGACCCTGACAAGATC
CTAACATACATTGCTGCCGATCACTGCCCGGTAGTCGAGGTGAACGGCGT
GACCATCCAAGTCGGGAGCAGGAGGTATCCAGACGCTGTGTACTTGCACA
GAATTGACCTCGGTCCTCCCATATCATTGGAGAGGTTGGACGTAGGGACA
AATCTGGGGAATGCAATTGCTAAGTTGGAGGATGCCAAGGAATTGTTGGA
GTCATCGGACCAGATATTGAGGAGTATGAAAGGTTTATCGAGCACTAGCA
TAGTCTACATCCTGATTGCAGTGTGTCTTGGAGGGTTGATAGGGATCCCC
GCTTTAATATGTTGCTGCAGGGGGCGTTGTAACAAAAAGGGAGAACAAGT
TGGTATGTCAAGACCAGGCCTAAAGCCTGATCTTACGGGAACATCAAAAT
CCTATGTAAGGTCGCTCTGATCCTCTACAACTCTTGAAACACAAATGTCC
CACAAGTCTCCTCTTCGTCATCAAGCAACCACCGCACCCAGCATCAAGCC
CACCTGAAATTATCTCCGGCTTCCCTCTGGCCGAACAATATCGGTAGTTA
ATCAAAACTTAGGGTGCAAGATCATCCACAATGTCACCACAACGAGACCG
GATAAATGCCTTCTACAAAGATAACCCCATCCCAAGGGAAGTAGGATAG
TCATTAACAGAGAACATCTTATGATTGATAGACCTTATGTTTTGCTGGCT
GTTCTGTTTGTCATGTTTCTGAGCTTGATCGGGTTGCTAGCCATTGCAGG
CATTAGACTTCATCGGGCAGCCATCTACACCGCAGAGATCCATAAAAGCC
TCAGCACCAATCTAGATGTAACTAACTCAATCGAGCATCAGGTCAAGGAC
GTGCTGACACCACTCTTCAAAATCATCGGTGATGAAGTGGGCCTGAGGAC
ACCTCAGAGATTCACTGACCTAGTGAAATTAATCTCTGACAAGATTAAAT
TCCTTAATCCGGATAGGGAGTACGACTTCAGAGATCTCACTTGGTGTATC
AACCCGCCAGAGAGAATCAAATTGGATTATGATCAATACTGTGCAGATGT
GGCTGCTGAAGAGCTCATGAATGCATTGGTGAACTCAACTCTACTGGAGA
CCAGAACAACCAATCAGTTCCTAGCTGTCTCAAAGGGAAACTGCTCAGGG
CCCACTACAATCAGAGGTCAATTCTCAAACATGTCGCTGTCCCTGTTAGA
CTTGTATTTAGGTCGAGGTTACAATGTGTCATCTATAGTCACTATGACAT
CCCAGGGAATGTATGGGGGAACTTACCTAGTGGAAAAGCCTAATCTGAGC
```

FIGURE 30.5

AGCAAAAGGTCAGAGTTGTCACAACTGAGCATGTACCGAGTGTTTGAAGT
AGGTGTTATCAGAAATCCGGGTTTGGGGGCTCCGGTGTTCCATATGACAA
ACTATCTTGAGCAACCAGTCAGTAATGATCTCAGCAACTGTATGGTGGCT
TTGGGGGAGCTCAAACTCGCAGCCCTTTGTCACGGGGAAGATTCTATCAC
AATTCCCTATCAGGGATCAGGGAAAGGTGTCAGCTTCCAGCTCGTCAAGC
TAGGTGTCTGGAAATCCCCAACCGACATGCAATCCTGGGTCCCCTTATCA
ACGGATGATCCAGTGATAGACAGGCTTTACCTCTCATCTCACAGAGGTGT
TATCGCTGACAATCAAGCAAATGGGCTGTCCCGACAACACGAACAGATG
ACAAGTTGCGAATGGAGACATGCTTCCAACAGGCGTGTAAGGGTAAAATC
CAAGCACTCTGCGAGAATCCCGAGTGGGCACCATTGAAGGATAACAGGAT
TCCTTCATACGGGGTCTTGTCTGTTGATCTGAGTCTGACAGTTGAGCTTA
AAATCAAAATTGCTTCGGGATTCGGGCCATTGATCACACGGTTCAGGG
ATGGACCTATACAAATCCAACCACAACAATGTGTATTGGCTGACTATCCC
GCCAATGAAGAACCTAGCCTTAGGTGTAATCAACACATTGGAGTGGATAC
CGAGATTCAAGGTTAGTCCCTACCTCTTCACTGTCCCAATTAAGGAAGCA
GGCGAAGACTGCCATGCCCCAACATACCTACCTGCGGAGGTGGATGGTGA
TGTCAAACTCAGTTCCAATCTGGTGATTCTACCTGGTCAAGATCTCCAAT
ATGTTTTGGCAACCTACGATACTTCCAGGGTTGAACATGCTGTGGTTTAT
TACGTTTACAGCCCAAGCCGCTCATTTTCTTACTTTTATCCTTTTAGGTT
GCCTATAAAGGGGGTCCCCATCGAATTACAAGTGGAATGCTTCACATGGG
ACCAAAAACTCTGGTGCCGTCACTTCTGTGTGCTTGCGGACTCAGAATCT
GGTGGACATATCACTCACTCTGGGATGGTGGGCATGGGAGTCAGCTGCAC
AGTCACCCGGGAAGATGGAACCAATCGCAGATAGGGCTGCTAGTGAACCA
ATCACATGATGTCACCCAGACATCAGGCATACCC
ACTAGTCTACCCTCCATCATTGTTATAAAAAACTTAGGAACCAGGTCCAC
ACAGCCGCCAGCCCATCAACGCGTACG
*atgggtaaggaaaagactcacgtttcgaggccgcgattaaattccaacat*
*ggatgctgatttatatgggtataaatgggctcgcgataatgtcgggcaat*
*caggtgcgacaatctatcgattgtatgggaagcccgatgcgccagagttg*
*tttctgaaacatggcaaaggtagcgttgccaatgatgttacagatgagat*
*ggtcagactaaactggctgacggaatttatgcctcttccgaccatcaagc*
*attttatccgtactcctgatgatgcatggttactcaccactgcgatcccc*
*ggcaaaacagcattccaggtattagaagaatatcctgattcaggtgaaaa*
*tattgttgatgcgctggcagtgttcctgcgccggttgcattcgattcctg*
*tttgtaattgtccttttaacagcgatcgcgtatttcgtctcgctcaggcg*
*caatcacgaatgaataacggtttggttgatgcgagtgattttgatgacga*
*gcgtaatggctggcctgttgaacaagtctggaaagaaatgcataagcttt*
*tgccattctcaccggattcagtcgtcactcatggtgatttctcacttgat*
*aaccttatttttgacgaggggaaattaataggttgtattgatgttggacg*
*agtcggaatcgcagaccgataccaggatcttgccatcctatggaactgcc*
*tcggtgagttttctccttcattacagaaacggcttttcaaaaatatggt*
*attgataatcctgatatgaataaattgcagtttcatttgatgctcgatga*
*gtttttctaa* GCGCGCAGCGCTTAGACGTCTCGCGATCGATGCTAGTGTG
AAATAGACATCAGAATTAAGAAAAACGTAGGGTCCAAGT
GGTTCCCCGTTATGGACTCGCTATCTGTCAACCAGATCTTATACCCTGAA
GTTCACCTAGATAGCCCGATAGTTACCAATAAGATAGTAGCCATCCTGGA
GTATGCTCGAGTCCCTCACGCTTACAGCCTGGAGGACCCTACACTGTGTC
AGAACATCAAGCACCGCCTAAAAAACGGATTTTCCAACCAAATGATTATA

FIGURE 30.6

```
AACAATGTGGAAGTTGGGAATGTCATCAAGTCCAAGCTTAGGAGTTATCC
GGCCCACTCTCATATTCCATATCCAAATTGTAATCAGGATTTATTTAACA
TAGAAGACAAAGAGTCAACGAGGAAGATCCGTGAACTCCTCAAAAAGGGG
AATTCGCTGTACTCCAAAGTCAGTGATAAGGTTTTCCAATGCTTAAGGGA
CACTAACTCACGGCTTGGCCTAGGCTCCGAATTGAGGGAGGACATCAAGG
AGAAAGTTATTAACTTGGGAGTTTACATGCACAGCTCCCAGTGGTTTGAG
CCCTTTCTGTTTTGGTTTACAGTCAAGACTGAGATGAGGTCAGTGATTAA
ATCACAAACCCATACTTGCCATAGGAGGAGACACACCTGTATTCTTCA
CTGGTAGTTCAGTTGAGTTGCTAATCTCTCGTGACCTTGTTGCTATAATC
AGTAAAGAGTCTCAACATGTATATTACCTGACATTTGAACTGGTTTTGAT
GTATTGTGATGTCATAGAGGGGAGGTTAATGACAGAGACCGCTATGACTA
TTGATGCTAGGTATACAGAGCTTCTAGGAAGAGTCAGATACATGTGGAAA
CTGATAGATGGTTTCTTCCCTGCACTCGGGAATCCAACTTATCAAATTGT
AGCCATGCTGGAGCCTCTTTCACTTGCTTACCTGCAGCTGAGGGATATAA
CAGTAGAACTCAGAGGTGCTTTCCTTAACCACTGCTTTACTGAAATACAT
GATGTTCTTGACCAAAACGGGTTTTCTGATGAAGGTACTTATCATGAGTT
AACTGAAGCTCTAGATTACATTTTCATAACTGATGACATACATCTGACAG
GGGAGATTTTCTCATTTTTCAGAAGTTTCGGCCACCCCAGACTTGAAGCA
GTAACGGCTGCTGAAAATGTTAGGAAATACATGAATCAGCCTAAAGTCAT
TGTGTATGAGACTCTGATGAAAGGTCATGCCATATTTTGTGGAATCATAA
TCAACGGCTATCGTGACAGGCACGGAGGCAGTTGGCCACCGCTGACCCTC
CCCCTGCATGCTGCAGACACAATCCGGAATGCTCAAGCTTCAGGTGAAGG
GTTAACACATGAGCAGTGCGTTGATAACTGGAAATCTTTTGCTGGAGTGA
AATTTGGCTGCTTTATGCCTCTTAGCCTGGATAGTGATCTGACAATGTAC
CTAAAGGACAAGGCACTTGCTGCTCTCCAAAGGGAATGGGATTCAGTTTA
CCCGAAAGAGTTCCTGCGTTACGACCCTCCCAAGGGAACCGGGTCACGGA
GGCTTGTAGATGTTTTCCTTAATGATTCGAGCTTTGACCCATATGATGTG
ATAATGTATGTTGTAAGTGGAGCTTACCTCCATGACCCTGAGTTCAACCT
GTCTTACAGCCTGAAAGAAAAGGAGATCAAGGAAACAGGTAGACTTTTTG
CTAAAATGACTTACAAAATGAGGGCATGCCAAGTGATTGCTGAAAATCTA
ATCTCAAACGGGATTGGCAAATATTTTAAGGACAATGGGATGGCCAAGGA
TGAGCACGATTTGACTAAGGCACTCCACACTCTAGCTGTCTCAGGAGTCC
CCAAAGATCTCAAAGAAAGTCACAGGGGGGGGCCAGTCTTAAAAACCTAC
TCCCGAAGCCCAGTCCACACAAGTACCAGGAACGTGAGAGCAGCAAAAGG
GTTTATAGGGTTCCCTCAAGTAATTCGGCAGGACCAAGACACTGATCATC
CGGAGAATATGGAAGCTTACGAGACAGTCAGTGCATTTATCACGACTGAT
CTCAAGAAGTACTGCCTTAATTGGAGATATGAGACCATCAGCTTGTTTGC
ACAGAGGCTAAATGAGATTTACGGATTGCCCTCATTTTTCCAGTGGCTGC
ATAAGAGGCTTGAGACCTCTGTCCTGTATGTAAGTGACCCTCATTGCCCC
CCCGACCTTGACGCCCATATCCCGTTATATAAAGTCCCAATGATCAAAT
CTTCATTAAGTACCCTATGGGAGGTATAGAAGGGTATTGTCAGAAGCTGT
GGACCATCAGCACCATTCCCTATCTATACCTGGCTGCTTATGAGAGCGGA
GTAAGGATTGCTTCGTTAGTGCAAGGGGACAATCAGACCATAGCCGTAAC
AAAAAGGGTACCCAGCACATGGCCCTACAACCTTAAGAAACGGGAAGCTG
CTAGAGTAACTAGAGATTACTTTGTAATTCTTAGGCAAAGGCTACATGAT
ATTGGCCATCACCTCAAGGCAAATGAGACAATTGTTTCATCACATTTTTT
TGTCTATTCAAAAGGAATATATTATGATGGGCTACTTGTGTCCCAATCAC
TCAAGAGCATCGCAAGATGTGTATTCTGGTCAGAGACTATAGTTGATGAA
```

FIGURE 30.7

```
ACAAGGGCAGCATGCAGTAATATTGCTACAACAATGGCTAAAAGCATCGA
GAGAGGTTATGACCGTTACCTTGCATATTCCCTGAACGTCCTAAAAGTGA
TACAGCAAATTCTGATCTCTCTTGGCTTCACAATCAATTCAACCATGACC
CGGGATGTAGTCATACCCCTCCTCACAAACAACGACCTCTTAATAAGGAT
GGCACTGTTGCCCGCTCCTATTGGGGGGATGAATTATCTGAATATGAGCA
GGCTGTTTGTCAGAAACATCGGTGATCCAGTAACATCATCAATTGCTGAT
CTCAAGAGAATGATTCTCGCCTCACTAATGCCTGAAGAGACCCTCCATCA
AGTAATGACACAACAACCGGGGGACTCTTCATTCCTAGACTGGGCTAGCG
ACCCTTACTCAGCAAATCTTGTATGTGTCCAGAGCATCACTAGACTCCTC
AAGAACATAACTGCAAGGTTTGTCCTGATCCATAGTCCAAACCCAATGTT
AAAAGGATTATTCCATGATGACAGTAAAGAAGAGGACGAGGGACTGGCGG
CATTCCTCATGGACAGGCATATTATAGTACCTAGGGCAGCTCATGAAATC
CTGGATCATAGTGTCACAGGGGCAAGAGAGTCTATTGCAGGCATGCTGGA
TACCACAAAAGGCTTGATTCGAGCCAGCATGAGGAAGGGGGGGTTAACCT
CTCGAGTGATAACCAGATTGTCCAATTATGACTATGAACAATTCAGAGCA
GGGATGGTGCTATTGACAGGAAGAAAGAGAAATGTCCTCATTGACAAAGA
GTCATGTTCAGTGCAGCTGGCGAGAGCTCTAAGAAGCCATATGTGGGCGA
GGCTAGCTCGAGGACGGCCTATTTACGGCCTTGAGGTCCCTGATGTACTA
GAATCTATGCGAGGCCACCTTATTCGGCGTCATGAGACATGTGTCATCTG
CGAGTGTGGATCAGTCAACTACGGATGGTTTTTTGTCCCCTCGGGTTGCC
AACTGGATGATATTGACAAGGAAACATCATCCTTGAGAGTCCCATATATT
GGTTCTACCACTGATGAGAGAACAGACATGAAGCTTGCCTTCGTAAGAGC
CCCAAGTCGATCCTTGCGATCTGCTGTTAGAATAGCAACAGTGTACTCAT
GGGCTTACGGTGATGATGATAGCTCTTGGAACGAAGCCTGGTTGTTGGCT
AGGCAAAGGGCCAATGTGAGCCTGGAGGAGCTAAGGGTGATCACTCCCAT
CTCAACTTCGACTAATTTAGCGCATAGGTTGAGGGATCGTAGCACTCAAG
TGAAATACTCAGGTACATCCCTTGTCCGAGTGGCGAGGTATACCACAATC
TCCAACGACAATCTCTCATTTGTCATATCAGATAAGAAGGTTGATACTAA
CTTTATATACCAACAAGGAATGCTTCTAGGGTTGGGTGTTTTAGAAACAT
TGTTTCGACTCGAGAAAGATACCGGATCATCTAACACGGTATTACATCTT
CACGTCGAAACAGATTGTTGCGTGATCCCGATGATAGATCATCCCAGGAT
ACCCAGCTCCCGCAAGCTAGAGCTGAGGGCAGAGCTATGTACCAACCCAT
TGATATATGATAATGCACCTTTAATTGACAGAGATGCAACAAGGCTATAC
ACCCAGAGCCATAGGAGGCACCTTGTGGAATTTGTTACATGGTCCACACC
CCAACTATATCACATTTTAGCTAAGTCCACAGCACTATCTATGATTGACC
TGGTAACAAAATTTGAGAAGGACCATATGAATGAAATTTCAGCTCTCATA
GGGGATGACGATATCAATAGTTTCATAACTGAGTTTCTGCTCATAGAGCC
AAGATTATTCACTATCTACTTGGGCCAGTGTGCGGCCATCAATTGGGCAT
TTGATGTACATTATCATAGACCATCAGGGAAATATCAGATGGGTGAGCTG
TTGTCATCGTTCCTTTCTAGAATGAGCAAAGGAGTGTTTAAGGTGCTTGT
CAATGCTCTAAGCCACCCAAAGATCTACAAGAAATTCTGGCATTGTGGTA
TTATAGAGCCTATCCATGGTCCTTCACTTGATGCTCAAAACTTGCACACA
ACTGTGTGCAACATGGTTTACACATGCTATATGACCTACCTCGACCTGTT
GTTGAATGAAGAGTTAGAAGAGTTCACATTTCTCTTGTGTGAAAGCGACG
AGGATGTAGTACCGGACAGATTCGACAACATCCAGGCAAAACACTTATGT
GTTCTGGCAGATTTGTACTGTCAACCAGGGACCTGCCCACCAATTCGAGG
TCTAAGACCGGTAGAGAAATGTGCAGTTCTAACCGACCATATCAAGGCAG
AGGCTATGTTATCTCCAGCAGGATCTTCGTGGAACATAAATCCAATTATT
```

FIGURE 30.8

GTAGACCATTACTCATGCTCTCTGACTTATCTCCGGCGAGGATCGATCAA
ACAGATAAGATTGAGAGTTGATCCAGGATTCATTTTCGACGCCCTCGCTG
AGGTAAATGTCAGTCAGCCAAAGATCGGCAGCAACAACATCTCAAATATG
AGCATCAAGGCTTTCAGACCCCCACACGATGATGTTGCAAAATTGCTCAA
AGATATCAACACAAGCAAGCACAATCTTCCCATTTCAGGGGGCAATCTCG
CCAATTATGAAATCCATGCTTTCCGCAGAATCGGGTTGAACTCATCTGCT
TGCTACAAAGCTGTTGAGATATCAACATTAATTAGGAGATGCCTTGAGCC
AGGGGAGGACGGCTTGTTCTTGGGTGAGGGATCGGGTTCTATGTTGATCA
CTTATAAAGAGATACTTAAACTAAACAAGTGCTTCTATAATAGTGGGGTT
TCCGCCAATTCTAGATCTGGTCAAAGGGAATTAGCACCCTATCCCTCCGA
AGTTGGCCTTGTCGAACACAGAATGGGAGTAGGTAATATTGTCAAAGTGC
TCTTTAACGGGAGGCCCGAAGTCACGTGGGTAGGCAGTGTAGATTGCTTC
AATTTCATAGTTAGTAATATCCCTACCTCTAGTGTGGGGTTTATCCATTC
AGATATAGAGACCTTGCCTGACAAAGATACTATAGAGAAGCTAGAGGAAT
TGGCAGCCATCTTATCGATGGCTCTGCTCCTGGGCAAAATAGGATCAATA
CTGGTGATTAAGCTTATGCCTTTCAGCGGGGATTTTGTTCAGGGATTTAT
AAGTTATGTAGGGTCTCATTATAGAGAAGTGAACCTTGTATACCCTAGAT
ACAGCAACTTCATCTCTACTGAATCTTATTTGGTTATGACAGATCTCAAG
GCTAACCGGCTAATGAATCCTGAAAAGATTAAGCAGCAGATAATTGAATC
ATCTGTGAGGACTTCACCTGGACTTATAGGTCACATCCTATCCATTAAGC
AACTAAGCTGCATACAAGCAATTGTGGGAGACGCAGTTAGTAGAGGTGAT
ATCAATCCTACTCTGAAAAAACTTACACCTATAGAGCAGGTGCTGATCAA
TTGCGGGTTGGCAATTAACGGACCTAAGCTGTGCAAAGAATTGATCCACC
ATGATGTTGCCTCAGGGCAAGATGGATTGCTTAATTCTATACTCATCCTC
TACAGGGAGTTGGCAAGATTCAAAGACAACCAAAGAAGTCAACAAGGGAT
GTTCCACGCTTACCCCGTATTGGTAAGTAGCAGGCAACGAGAACTTATAT
CTAGGATCACCCGCAAATTCTGGGGGCACATTCTTCTTTACTCCGGGAAC
AAAAAGTTGATAAATAAGTTTATCCAGAATCTCAAGTCCGGCTATCTGAT
ACTAGACTTACACCAGAATATCTTCGTTAAGAATCTATCCAAGTCAGAGA
AACAGATTATTATGACGGGGGGTTTGAAACGTGAGTGGGTTTTTAAGGTA
ACAGTCAAGGAGACCAAAGA *ATGGTATAAGTTAGTCGGATACAGTGCCCT*
*GATTAAGGACTAA TTGGTTGAACTCCGGAACCCTAATCCTGCCCTAGGTG*
*GTTAGGCATTATTTGCAATATATTAAAGAAAACTTTGAAAATACGAAGTT*
*TCTATTCCCAGCTTTGTCTGGT*
ggccggcatggtcccagcctcctcgctggcgccggctgggcaacattccgaggggaccgt
cccctcggtaatggcgaatgggac
GCGGCCGATCCGGCTGCTAACAAAGCCCGAAAGGAAGCTGAGTTGGCTGC
TGCCACCGCTGAGCAATAACTAGCATAACCCCTTGGGGCCTCTAAACGGG
TCTTGAGGGGTTTTTTGCTGAAAGGAGGAACTATATCCGGATGCGGCCGC
GGGCCCTATGGTACCCAGCTTTTGTTCCCTTTAGTGAGGGTTAATT
CCGAGCTTGGCGTAATCATGGTCATAGCTGTTTCCTGTGTGAAATTGT
TATCCGCTCACAATTCCACACAACATAGGAGCCGGAAGCATAAAGTGTAA
AGCCTGGGGTGCCTAATGAGTGAGGTAACTCACATTAATTGCGTTGCGCT
CACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGG
TATCAGCTCACTCAAAGGCGGTAATACGGTTATCCACAGAATCAGGGGAT
AACGCAGGAAAGAACATGTGAGCAAAAGGCCAGCAAAAGGCCAGGAACCG

FIGURE 30.9

```
TAAAAAGGCCGCGTTGCTGGCGTTTTTCCATAGGCTCGGCCCCCCTGACG
AGCATCACAAAAATCGACGCTCAAGTCAGAGGTGGCGAAACCCGACAGGA
CTATAAAGATACCAGGCGTTCCCCCCTGGAAGCTCCCTCGTGCGCTCTCC
TGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTG
TAGGTCGTTCGCTCCAAGCTGGGCTGTGTGCACGAACCCCCGTTCAGCC
CGACCGCTGCGCCTTATCCGGTAACTATCGTCTTGAGTCCAACCCGGTAA
GACACGACTTATCGCCACTGGCAGCAGCCACTGGTAACAGGATTAGCAGA
GCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAG
TTACCTTCGGAAAAGAGTTGGTAGCTCTTGATCCGGCAAACAAACCACC
GCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTC
AGTGGAACGAAAACTCACGTTAAGGGATTTTGGTCATGAGATTATCAAAA
AGGATCTTCACCTAGATCCTTTTAAATTAAAAATGAAGTTTTAAATCAAT
CTAAAGTATATATGAGTAAACTTGGTCTGACAGTTACCAATGCTTAATCA
GTGAGGCACCTATCTCAGCGATCTGTCTATTTCGTTCATCCATAGTTGCC
TGACTGCCCGTCGTGTAGATAACTACGATACGGGAGGGCTTACCATCTGG
CCCCAGTGCTGCAATGATACCGCGAGACCCACGCTCACCGGCTCCAGATT
TATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCC
GGTTCCCAACGATCAAGGCGAGTTACATGATCCCCCATGTTGTGAAAAAA
AGCGGTTAGCTCCTTCGGTCCTCCGATCGTTGTCAGAAGTAAGTTGGCCG
CAGTGTTATCACTCATGCTTATGGCAGCACTGCATAATTCTCTTACTGTC
ATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAA
TACGGGATAATACCGCGCCACATAGCAGAACTTTAAAAGTGCTCATCATT
GGAAAACGTTCTTCGGGGCGAAAACTCTCAAGGATCTTACCGCTGTTGAG
ATCCAGTTCGATGTAACCCACTCGTGCACCCAACTGATCTTCAGCATCTT
TTACTTTCACCAGCGTTTCTGGGTGAGCAAAAACAGGAAGGCAAAATGCC
GCAAAAAGGGAATAAGGGCGACACGGAAATGTTGAATACTCATACTCTT
CCTTTTTCAATATTATTGAAGCATTTATCAGGGTTATTGTCTCATGAGCG
GATACATATTTGAATGTATTTAGAAAAATAAACAAATAGGGGTTCCGCGC
ACATTTCCCCGAAAAGTGCCACCTGAAATTGTAAACGTTAATATTTTGTT
AAAATTCGCGTTAAATTTTTGTTAAATCAGCTCATTTTTTAACCAATAGG
CCGAAATCGGCAAAATCCCTTATAAATCAAAAGAATAGACCGAGATAGGG
TTGAGTGTTGTTCCAGTTTGGAACAAGAGTCCACTATTAAAGAACGTGGA
CTCCAACGTCAAAGGGCGAAAAACCGTCTATCAGGGCGATGGCCCACTAC
GTGAACCATCACCCTAATCAAGTTTTTTGGGGTCGAGGTGCCGTAAAGCA
CTAAATCGGAACCCTAAAGGGAGCCCCGATTTAGAGCTTGACGGGGAAA
GCCGGCGAACGTGGCGAGAAAGGAAGGGAAGAAAGCGAAAGGAGCGGGCG
CTAGGGCGCTGGCAAGTGTAGCGGTCACGCTGCGCGTAACCACCACACCC
GCCGCGCTTAATGCGCCGCTACAGGGCGCGTCCCATTCGCCATTCAGGCT
gCGCAACTGTTGGGAAGGGCGATCGGTGCGGGCCTCTTCGCTATTACGCC
AGCCACCGCGGTG
```

FIGURE 31.1

Recombinant measles genome sequence of the resulting plasmid after the Gap repair (pCM403)

| | |
|---|---|
| pYES2 vector : | Capital letter |
| Measles genome sequence: | Capital letter |
| Ribozymes Sequence : | Minuscule letter |
| Leader sequence : | Bold capital letter |
| Trailer sequence : | Bold italic capital letter |
| *eGFP* sequence : | Bold minuscule letter |
| *KANMX4* sequence : | Minuscule italic letter |

```
TAGTGGATCATCCCCACGCGCCCTGTAGCGCCCCATTAAGCGCGGCGGGT
GTGGTGGTTACGCCCAGCGTGACCCCTACACTTCCCACCGCCCTAGCCCC
CGCTCCTTTCGCTTTCTTCCCTTCCTTTCTCGCCACGTTCGCCGGCTTTC
CCCGTCAAGCTCTAAATGGGGGCATCCGTTTACCCTTCCGATTTACTGCT
TTACGGCACCTCGACCCCAAAAAACTTGATTAGGGTGATGGTTCACGTAG
TGGGCCATCGCCCTGATAGACCCTTTTTCGCCCTTTGACGTTGGAGTCCA
CGTTCTTTAATAGTGGACTCTTGTTGGAAACTGGAACAACACTCAACCCT
ATCTCGGTCTATTCTTTTGATTTATAAGGGATTTTGCCGATTTCGGGCTA
TTCGTTAAAAAATGAGCTGATTTAACAAAAATTTAACGCGAATTTTAACA
AAATATTAACGTTTACAATTTAAATATTTGCTTATACAATCTTCCTGTTT
TTGGGGCTTTTCTGATTATCAACCGGGGTGGAGCTTCCCATTGCAATAC
CGCTTCCACAAACATTGCTCAAAAGTATCTCTTTGCTATATATCTCTGTG
CTATATCCCTATATAACCTACCCATCCACCTTTCGCTCCTTGAACTTGCA
TCTAAACTCGACCTCTACATTTTTTATGTTTATCTCTAGTATTACTCTTT
AGACAAAAAAATTGTAGTAAGAACTATTCATAGAGTGAATCGAAAACAAT
ACGAAAATGTAAACATTTCCTATACGTAGTATATAGAGACAAAATAGAAG
AAACCGTTCATAATTTTCTGACCAATGAAGAATCATCAACGCTATCACTT
TCTGTTCACAAAGTATGCGCAATCCACATCGGTATAGAATATAATCGGGG
ATGCCTTTATCTTGAAAAAATGCACCCGCAGCTTCGCTAGTAATCAGTAA
ACGCGGGAAGTGGAGTCAGGCTTTTTTTATGGAAGAGAAAATAGACACCA
AAGTAGCCTTCTTCTAACCTTAACGGACCTACAGTGCAAAAAGTTATCAA
GAGACTGCATTATAGAGCGCACAAAGGAGAAAAAAAGTAATCTAAGATGC
TTTGTTAGAAAAATAGCGCTCTCGGGATGCATTTTTGTAGAACAAAAAAG
AAGTATAGATTCTTTGTTGGTAAAATAGCGCTCTCGCGTTGCATTTCTGT
TCTGTAAAAATGCAGCTCAGATTCTTTGTTTGAAAAATTAGCGCTCTCGT
CGCGTTGCATTTTTGTTTTACAAAAATGAAGCACAGATTCTTCGTTGGTA
AAATAGCGCTTTCGCGTTGCATTTCTGTTCTGTAAAAATGCAGCTCAGAT
TCTTTGTTTGAAAAATTAGCGCTCTCGCGTTGCATTTTTGTTCTACAAAA
TGAAGCACAGATGCTTCGTTAACAAAGATATGCTATTGAAGTGCAAGATG
GAAACGCAGAAATGAACCGGGGATGCGACGTGCAAGATTACCTATGCAA
TAGATGCAATAGTTTCTCCAGGAACCGAAATACATACATTGTCTTCCGTA
AAGCGCTAGACTATATATTATTATACAGGTTCAAATATACTATCTGTTTC
AGGGAAAACTCCCAGGTTCGGATGTTCAAAATTCAATGATGGGTAACAAG
```

FIGURE 31.2

```
TACGATCGTAAATCTGTAAAACAGTTTGTCGGATATTAGGCTGTATCTCC
TCAAAGCGTATTCGAATATCATTGAGAAGCTGCAGCGTCACATCGGATAA
TAATGATGGCAGCCATTGTAGAAGTGCCTTTTGCATTTCTAGTCTCTTTC
TCGGTCTAGCTAGTTTTACTACATCGCGAAGATAGAATCTTAGATCACAC
TGCCTTTGCTGAGCTGGATCAATAGAGTAACAAAAGAGTGGTAAGGCCTC
GTTAAAGGACAAGGACCTGAGCGGAAGTGTATCGTACAGTAGACGGAGTA
TCTAGTATAGTCTATAGTCCGTGGAATTAATTCTCATCTTTGACAGCTTA
TCATCGATAAGCTAGCTTTTCAATTCAATTCATCATTTTTTTTTATTCT
TTTTTTTGATTTCGGTTTCTTTGAAATTTTTTTGATTCGGTAATCTCCGA
ACAGAAGGAAGAACGAAGGAAGGAGCACAGACTTAGATTGGTATATATAC
GCATATGTAGTGTTGAAGAAACATGAAATTGCCCAGTATTCTTAACCCAA
CTGCACAGAACAAAAACCTGCAGGAAACGAAGATAAATCATGTCGAAAGC
TACATATAAGGAACGTGCTGCTACTCATCCTAGTCCTGTTGCTGCCAAGC
TATTTAATATCATGCACGAAAAGCAAACAAACTTGTGTGCTTCATTGGAT
GTTCGTACCACCAAGGAATTACTGGAGTTAGTTGAAGCATTAGGTCCCAA
AATTTGTTTACTAAAAACACATGTGGATATCTTGACTGATTTTTCCATGG
AGGGCACAGTTAAGCCGCTAAAGGCATTATCCGCCAAGTACAATTTTTTA
CTCTTCGAAGACAGAAAATTTGCTGACATTGGTAATACAGTCAAATTGCA
GTACTCTGCGGGTGTATACAGAATAGCAGAATGGGCAGACATTACGAATG
CACACGGTGTGGTGGGCCCAGGTATTGTTAGCGGTTTGAAGCAGGCGGCA
GAAGAAGTAACAAAGGAACCTAGAGGCCTTTTGATGTTAGCAGAATTGTC
ATGCAAGGGCTCCCTATCTACTGGAGAATATACTAAGGGTACTGTTGACA
TTGCGAAGAGCGACAAAGATTTTGTTATCGGCTTTATTGCTCAAAGAGAC
ATGGGTGGAAGAGATGAAGGTTACGATTGGTTGATTATGACACCCGGTGT
GGGTTTAGATGACAAGGGAGACGCATTGGGTCAACAGTATAGAACCGTGG
ATGATGTGGTCTCTACAGGATCTGACATTATTATTGTTGGAAGAGGACTA
TTTGCAAAGGGAAGGGATGCTAAGGTAGAGGGTGAACGTTACAGAAAAGC
AGGCTGGGAAGCATATTTGAGAAGATGCGGCCAGCAAAACTAAAAAACTG
TATTATAAGTAAATGCATGTATACTAAACTCACAAATTAGAGCTTCAATT
TAATTATATCAGTTATTACCCATTGAAAAAGGAAGAGTATGAGTATTCAA
CATTTCCGTGTCGCCCTTATTCCCTTTTTGCGGCATTTTGCCTTCCTGT
TTTTGCTCACCCAGAAACGCTGGTGAAAGTAAAAGATGCTGAAGATCAGT
TGGGTGCACGAGTGGGTTACATCGAACTGGATCTCAACAGCGGTAAGATC
CTTGAGAGTTTTCGCCCCGAAGAACGTTTTCCAATGATGAGCACTTTTAA
AGTTCTGCTATGTGATACACTATTATCCCGTATTGACGCCGGGCAAGAGC
AACTCGGTCGCCGCATACACTATTCTCAGAATGACTTGGTTGAGTACTCA
CCAGTCACAGAAAAGCATCTTACGGATGGCATGACAGTAAGAGAATTATG
CAGTGCTGCCATAACCATGAGTGATAACACTGCGGCCAACTTACTTCTGA
CAACGATCGGAGGACCGAAGGAGCTAACCGCTTTTTTGCACAACATGGGG
GATCATGTAACTCGCCTTGATCGTTGGGAACCGGAGCTGAATGAAGCCAT
ACCAAACGACGAGAGTGACACCACGATGCCTGTAGCAATGCCAACAACGT
TGCGCAAACTATTAACTGGCGAACTACTTACTCTAGCTTCCCGGCAACAA
TTAATAGACTGAATGGAGGCGGATAAAGTTGCAGGACCACTTCTGCGCTC
GGCCCTTCCGGCTGGCTGGTTTATTGCTGATAAATCTGGAGCCGGTGAGC
GTGGGTCTCGCGGTATCATTGCAGCACTGGGGCCAGATGGTAAGCGCTCC
CGTATCGTAGTTATCTACACGACGGGGAGTCAGGCAACTATGGATGAACG
AAATAGACAGATCGCTGAGATAGGTGCCTCACTGATTAAGCATTGGTAAC
TGTCAGACCAAGTTTACTCATATATACTTTAGATTGATTTAAAACTTCAT
```

FIGURE 31.3

TTTTAATTTAAAAGGATCTAGGTGAAGATCCTTTTTGATAATCTCATGAC
CAAAATCCCTTAACGTGAGTTTTCGTTCCACTGAGCGTCAGACCCCGTAG
AAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGA
TCAAGAGCTACCAACTCTTTTTCCGAAGGTAACTGGCTTCAGCAGAGCGC
AGATACCAAATACTGTCCTTCTAGTGTAGCCGTAGTTAGGCCACCACTTC
AAGAACTCTGTAGCACCGCCTACATACCTCGCTCTGCTAATCCTGTTACC
AGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCG
TGCACACAGCCCAGCTTGGAGCGAACGACCTACACCGAACTGAGATACCT
ACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAG
CTTCCAGGGGGAAACGCCTGGTATCTTTATAGTCCTGTCGGGTTTCGCCA
CCTCTGACTTGAGCGTCGATTTTTGTGATGCTCGTCAGGGGGCGGAGCC
TATGGAAAAACGCCAGCAACGCGGCCTTTTTACGGTTCCTGGGCTTTTGC
TGGCCTTTTGCTCACATGTTCTTTCCTGCGTTATCCCCTGATTCTGTGGA
TAACCGTATTACCGCCTTTGAGTGAGCTGATACCGCTCGCCGCAGCCGAA
CGACCGAGCGCAGCGAGTCAGTGAGCGAGGAAGCGGAAGAGCGCCCAATA
CGCAAACCGCCTCTCCCCGCGCGTTGGCCGATTCATTAATGCAGGGCCGC
AAATTAAAGCCTTCGAGCGTCCCAAAACCTTCTCAAGCAAGGTTTTCAGT
ATAATGTTACATGCGTACACGCGTCTGTACAGAAAAAAAAGAAAAATTTG
AAATATAAATAACGTTCTTAATACTAACATAACTATAAAAAAATAAATAG
GGACCTAGACTTCAGGTTGTCTAACTCCTTCCTTTTCGGTTAGAGCGGAT
GTGGGGGGAGGGCGTGAATGTAAGCGTGACATAACTAATTACATGATGCG
GCCCTCTAGATGCATG CAGGCCTCTGCAGTCGACGGGCCC gtcccattcg
ccattaccgaggggacggtcccctcggaatgttgcccagccggcgccagc
gaggaggctgggaccatgccggcc ACCAAACAAAGTTGGGTAAGGATAGT
TCAATCAATGATCATCTTCTAGTGCACTTAGGATTCAAGATCCTATTATC
AGGGACAAGAGCAGGATTAGGGATATCCGAGATGG CCACACTTTTAAGGA
GCTTAGCATTGTTCAAAAGAAACAAGGACAAACCACCCATTACATCAGGA
TCCGGTGGAGCCATCAGAGGAATCAAACACATTATTATAGTACCAATCCC
TGGAGATTCCTCAATTACCACTCGATCCAGACTTCTGGACCGGTTGGTGA
GGTTAATTGGAAACCCGGATGTGAGCGGGCCCAAACTAACAGGGGCACTA
ATAGGTATATTATCCTTATTTGTGGAGTCTCCAGGTCAATTGATTCAGAG
GATCACCGATGACCCTGACGTTAGCATAAGGCTGTTAGAGGTTGTCCAGA
GTGACCAGTCACAATCTGGCCTTACCTTCGCATCAAGAGGTACCAACATG
GAGGATGAGGCGGACCAATACTTTTCACATGATGATCCAATTAGTAGTGA
TCAATCCAGGTTCGGATGGTTCGGGAACAAGGAAATCTCAGATATTGAAG
TGCAAGACCCTGAGGGATTCAACATGATTCTGGGTACCATCCTAGCCCAA
ATTTGGGTCTTGCTCGCAAAGGCGGTTACGGCCCAGACACGGCAGCTGA
TTCGGAGCTAAGAAGGTGGATAAAGTACACCCAACAAGAAGGGTAGTTG
GTGAATTTAGATTGGAGAGAAATGGTTGGATGTGGTGAGGAACAGGATT
GCCGAGGACCTCTCCTTACGCCGATTCATGGTCGCTCTAATCCTGGATAT
CAAGAGAACACCCGGAAACAAACCCAGGATTGCTGAAATGATATGTGACA
TTGATACATATCGTAGAGGCAGGATTAGCCAGTTTTATCCTGACTATT
AAGTTTGGGATAGAAACTATGTATCCTGCTCTTGGACTGCATGAATTTGC
TGGTGAGTTATCCACACTTGAGTCCTTGATGAACCTTTACCAGCAAATGG
GGGAAACTGCACCCTACATGGTAATCCTGGAGAACTCAATTCAGAACAAG

FIGURE 31.4

TTCAGTGCAGGATCATACCCTCTGCTCTGGAGCTATGCCATGGGAGTAGG
AGTGGAACTTGAAAACTCCATGGGAGGTTTGAACTTTGGCCGATCTTACT
TTGATCCAGCATATTTTAGATTAGGGCAAGAGATGGTAAGGAGGTCAGCT
GGAAAGGTCAGTTCCACATTGGCATCTGAACTCGGTATCACTGCCGAGGA
TGCAAGGCTTGTTTCAGAGATTGCAATGCATACTACTGAGGACAAGATCA
GTAGAGCGGTTGGACCCAGACAAGCCCAAGTATCATTTCTACACGGTGAT
CAAAGTGAGAATGAGCTACCGAGATTGGGGGGCAAGGAAGATAGGAGGGT
CAAACAGAGTCGAGGAGAAGCCAGGGAGAGCTACAGAGAAACCGGGCCCA
GCAGAGCAAGTGATGCGAGAGCTGCCCATCTTCCAACCGGCACACCCCTA
GACATTGACACTGCAACGGAGTCCAGCCAAGATCCGCAGGACAGTCGAAG
GTCAGCTGACGCCCTGCTTAGGCTGCAAGCCATGGCAGGAATCTCGGAAG
AACAAGGCTCAGACACGGACACCCCTATAGTGTACAATGACAGAAATCTT
CTAGACTAGGTGCGAGAGGCCGAGGGCCAGAACAACATCCGCCTACCATC
CATCATTGTTATAAAAAACTTAGGAACCAGGTCCACACAGCCGCCAGCCC
ATCAACCATCCACTCCCACGATTGGAGCCAATGGCAGAAGAGCAGGCACG
CCATGTCAAAAACGGACTGGAATGCATCCGGGCTCTCAAGGCCGAGCCCA
TCGGCTCACTGGCCATCGAGGAAGCTATGGCAGCATGGTCAGAAATATCA
GACAACCCAGGACAGGAGCGAGCCACCTGCAGGGAAGAGAAGGCAGGCAG
TTCGGGTCTCAGCAAACCATGCCTCTCAGCAATTGGATCAACTGAAGGCG
GTGCACCTCGCATCCGCGGTCAGGGACCTGGAGAGAGCGATGACGACGCT
GAAACTTTGGGAATCCCCCAAGAAATCTCCAGGCATCAAGCACTGGGTT
ACAGTGTTATTACGTTTATGATCACAGCGGTGAAGCGGTTAAGGGAATCC
AAGATGCTGACTCTATCATGGTTCAATCAGGCCTTGATGGTGATAGCACC
CTCTCAGGAGGAGACAATGAATCTGAAAACAGCGATGTGGATATTGGCGA
ACCTGATACCGAGGGATATGCTATCACTGACCGGGGATCTGCTCCCATCT
CTATGGGGTTCAGGGCTTCTGATGTTGAAACTGCAGAAGGAGGGGAGATC
CACGAGCTCCTGAGACTCCAATCCAGAGGCAACAACTTTCCGAAGCTTGG
GAAAACTCTCAATGTTCCTCCGCCCCGGACCCCGGTAGGGCCAGCACTT
CCGGGACACCCATTAAAAAGGGCACAGACGCGAGATTAGCCTCATTTGGA
ACGGAGATCGCGTCTTTATTGACAGGTGGTGCAACCCAATGTGCTCGAAA
GTCACCCTCGGAACCATCAGGGCCAGGTGCACCTGCGGGGAATGTCCCCG
AGTGTGTGAGCAATGCCGCACTGATACAGGAGTGGACACCCGAATCTGGT
ACCACAATCTCCCCGAGATCCCAGAATAATGAAGAAGGGGGAGACTATTA
TGATGATGAGCTGTTCTCTGATGTCCAAGATATTAAAACAGCCTTGGCCA
AAATACACGAGGATAATCAGAAGATAATCTCCAAGCTAGAATCACTGCTG
TTATTGAAGGGAGAAGTTGAGTCAATTAAGAAGCAGATCAACAGGCAAAA
TATCAGCATATCCACCCTGGAAGGACACCTCTCAAGCATCATGATCGCCA
TTCCTGGACTTGGGAAGGATCCCAACGACCCCACTGCAGATGTCGAAATC
AATCCCGACTTGAAACCCATCATAGGCAGAGATTCAGGCCGAGCACTGGC
CGAAGTTCTCAAGAAACCCGTTGCCAGCCGACAACTCCAAGGAATGACAA
ATGGACGGACCAGTTCCAGAGGACAGCTGCTGAAGGAATTTCAGCTAAAG
CCGATCGGGAAAAGATGAGCTCAGCCGTCGGGTTTGTTCCTGACACCGG
CCCTGCATCACGCAGTGTAATCCGCTCCATTATAAAATCCAGCCGGCTAG
AGGAGGATCGGAAGCGTTACCTGATGACTCTCCTTGATGATATCAAAGGA
GCCAATGATCTTGCCAAGTTCCACCAGATGCTGATGAAGATAATAATGAA
GTAGCTACAGCTCAACTTACCTGCCAACCCCATGCCAGTCGACCCAACTA
GCCTACCCTCCATCATTGTTATAAAAAACTTAGGAACCAGGTCCACACAG
CCGCCAGCCCATCAACGCGTACG atggtgagcaagggcgaggagctgttc

FIGURE 31.5 accggggtggtgcccatcctggtcgagctggacggcgacgtaaacggcca
caagttcagcgtgtccggcgagggcgagggcgatgccacctacggcaagc
tgaccctgaagttcatctgcaccaccggcaagctgcccgtgccctggccc
accctcgtgaccaccctgacctacggcgtgcagtgcttcagccgctaccc
cgaccacatgaagcagcacgacttcttcaagtccgccatgcccgaaggct
acgtccaggagcgcaccatcttcttcaaggacgacggcaactacaagacc
cgcgccgaggtgaagttcgagggcgacaccctggtgaaccgcatcgagct
gaagggcatcgacttcaaggaggacggcaacatcctggggcacaagctgg
agtacaactacaacagccacaacgtctatatcatggccgacaagcagaag
aacggcatcaaggtgaacttcaagatccgccacaacatcgaggacggcag
cgtgcagctcgccgaccactaccagcagaacacccccatcggcgacggcc
ccgtgctgctgcccgacaaccactacctgagcacccagtccgccctgagc
aaagaccccaacgagaagcgcgatcacatggtcctgctggagttcgtgac
cgccgccgggatcactctcggcatggacgagctgtacaagtag GCGCGCA
GCGCTTAGACGTCTCGCGATCGATACTAGTACAACCTAAATCCATTATAA
AAAACTTAGGAGCAAAGTGATTGCCTCCCAAGGTCCACAATGACAGAGAC
CTACGACTTCGACAAGTCGGCATGGGACATCAAAGGGTCGATCGCTCCGA
TACAACCCACCACCTACAGTGATGGCAGGCTGGTGCCCCAGGTCAGAGTC
ATAGATCCTGGTCTAGGCGACAGGAAGGATGAATGCTTTATGTACATGTT
TCTGCTGGGGGTTGTTGAGGACAGCGATTCCCTAGGGCCTCCAATCGGGC
GAGCATTTGGGTTCCTGCCCTTAGGTGTTGGCAGATCCACAGCAAAGCCC
GAAAAACTCCTCAAAGAGGCCACTGAGCTTGACATAGTTGTTAGACGTAC
AGCAGGGCTCAATGAAAACTGGTGTTCTACAACAACACCCCACTAACTC
TCCTCACACCTTGGAGAAAGGTCCTAACAACAGGGAGTGTCTTCAACGCA
AACCAAGTGTGCAATGCGGTTAATCTGATACCGCTCGATACCCCGCAGAG
GTTCCGTGTTGTTTATATGAGCATCACCCGTCTTTCGGATAACGGGTATT
ACACCGTTCCTAGAAGAATGCTGGAATTCAGATCGGTCAATGCAGTGGCC
TTCAACCTGCTGGTGACCCTTAGGATTGACAAGGCGATAGGCCCTGGGAA
GATCATCGACAATACAGAGCAACTTCCTGAGGCAACATTTATGGTCCACA
TCGGGAACTTCAGGAGAAAGAAGAGTGAAGTCTACTCTGCCGATTATTGC
AAAATGAAAATCGAAAAGATGGGCCTGGTTTTTGCACTTGGTGGGATAGG
GGGCACCAGTCTTCACATTAGAAGCACAGGCAAAATGAGCAAGACTCTCC
ATGCACAACTCGGGTTCAAGAAGACCTTATGTTACCCGCTGATGGATATC
AATGAAGACCTTAATCGATTACTCTGGAGGAGCAGATGCAAGATAGTAAG
AATCCAGGCAGTTTTGCAGCCATCAGTTCCTCAAGAATTCCGCATTTACG
ACGACGTGATCATAAATGATGACCAAGGACTATTCAAAGTTCTGTAGACC
GTAGTGCCCAGCAATGCCCGAAAACGACCCCCCTCACAATGACAGCCAGA
AGGCCCGGACAAAAAGCCCCTCCGAAAGACTCCACGGACCAAGCGAGA
GGCCAGCCAGCAGCCGACGGCAAGCGCGAACACCAGGCGGCCCCAGCACA
GAACAGCCCTGACACAAGGCCACCACCAGCCACCCCAATCTGCATCCTCC
TCGTGGGACCCCGAGGACCAACCCCCAAGGCTGCCCCGATCCAAACCA
CCAACCGCATCCCCACCACCCCGGGAAAGAAACCCCAGCAATTGGAAG
GCCCCTCCCCCTCTTCCTCAACACAAGAACTCCACAACCGAACCGCACAA
GCGACCGAGGTGACCCAACCGCAGGCATCCGACTCCCTAGACAGATCCTC
TCTCCCCGGCAAACTAAACAAAACTTAGGGCCAAGGAACATACACACCCA
ACAGAACCCAGACCCCGGCCCACGGCGCCGCGCCCCAACCCCCGACAAC
CAGAGGGAGCCCCCAACCAATCCCGCCGGCTCCCCGGTGCCCACAGGCA
GGGACACCAACCCCCGAACAGACCCAGCACCCAACCATCGACAATCCAAG

FIGURE 31.6

ACGGGGGGGCCCCCCCAAAAAAAGGCCCCCAGGGGCCGACAGCCAGCACC
GCGAGGAAGCCCACCCACCCCACACACGACCACGGCAACCAAACCAGAAC
CCAGACCACCCTGGGCCACCAGCTCCCAGACTCGGCCATCACCCCGCAGA
AAGGAAAGGCCACAACCCGCGCACCCCAGCCCCGATCCGGCGGGGAGCCA
CCCAACCCGAACCAGCACCCAAGAGCGATCCCCGAAGGACCCCCGAACCG
CAAAGGACATCAGTATCCCACAGCCTCTCCAAGTCCCCGGTCTCCTCCT
CTTCTCGAAGGGACCAAAAGATCAATCCACCACACCCGACGACACTCAAC
TCCCCACCCCTAAAGGAGACACCGGGAATCCCAGAATCAAGACTCATCCA
ATGTCCATCATGGGTCTCAAGGTGAACGTCTCTGCCATATTCATGGCAGT
ACTGTTAACTCTCCAAACACCCACCGGTCAAATCCATTGGGGCAATCTCT
CTAAGATAGGGGTGGTAGGAATAGGAAGTGCAAGCTACAAAGTTATGACT
CGTTCCAGCCATCAATCATTAGTCATAAAATTAATGCCCAATATAACTCT
CCTCAATAACTGCACGAGGGTAGAGATTGCAGAATACAGGAGACTACTGA
GAACAGTTTTGGAACCAATTAGAGATGCACTTAATGCAATGACCCAGAAT
ATAAGACCGGTTCAGAGTGTAGCTTCAAGTAGGAGACACAAGAGATTTGC
GGGAGTAGTCCTGGCAGGTGCGGCCCTAGGCGTTGCCACAGCTGCTCAGA
TAACAGCCGGCATTGCACTTCACCAGTCCATGCTGAACTCTCAAGCCATC
GACAATCTGAGAGCGAGCCTGGAAACTACTAATCAGGCAATTGAGACAAT
CAGACAAGCAGGGCAGGAGATGATATTGGCTGTTCAGGGTGTCCAAGACT
ACATCAATAATGAGCTGATACCGTCTATGAACCAACTATCTTGTGATTTA
ATCGGCCAGAAGCTCGGGCTCAAATTGCTCAGATACTATACAGAAATCCT
GTCATTATTTGGCCCCAGTTTACGGGACCCCATATCTGCGGAGATATCTA
TCCAGGCTTTGAGCTATGCGCTTGGAGGAGACATCAATAAGGTGTTAGAA
AAGCTCGGATACAGTGGAGGTGATTTACTGGGCATCTTAGAGAGCGGAGG
AATAAAGGCCCGGATAACTCACGTCGACACAGAGTCCTACTTCATTGTCC
TCAGTATAGCCTATCCGACGCTGTCCGAGATTAAGGGGGTGATTGTCCAC
CGGCTAGAGGGGGTCTCGTACAACATAGGCTCTCAAGAGTGGTATACCAC
TGTGCCCAAGTATGTTGCAACCCAAGGGTACCTTATCTCGAATTTTGATG
AGTCATCGTGTACTTTCATGCCAGAGGGGACTGTGTGCAGCCAAAATGCC
TTGTACCCGATGAGTCCTCTGCTCCAAGAATGCCTCCGGGGGTACACCAA
GTCCTGTGCTCGTACACTCGTATCCGGGTCTTTTGGGAACCGGTTCATTT
TATCACAAGGGAACCTAATAGCCAATTGTGCATCAATCCTTTGCAAGTGT
TACACAACAGGAACGATCATTAATCAAGACCCTGACAAGATCCTAACATA
CATTGCTGCCGATCACTGCCCGGTAGTCGAGGTGAACGGCGTGACCATCC
AAGTCGGGAGCAGGAGGTATCCAGACGCTGTGTACTTGCACAGAATTGAC
CTCGGTCCTCCCATATCATTGGAGAGGTTGGACGTAGGGACAAATCTGGG
GAATGCAATTGCTAAGTTGGAGGATGCCAAGGAATTGTTGGAGTCATCGG
ACCAGATATTGAGGAGTATGAAAGGTTTATCGAGCACTAGCATAGTCTAC
ATCCTGATTGCAGTGTGTCTTGGAGGGTTGATAGGGATCCCCGCTTTAAT
ATGTTGCTGCAGGGGGCGTTGTAACAAAAAGGGAGAACAAGTTGGTATGT
CAAGACCAGGCCTAAAGCCTGATCTTACGGGAACATCAAAATCCTATGTA
AGGTCGCTCTGATCCTCTACAACTCTTGAAACACAAATGTCCCACAAGTC
TCCTCTTCGTCATCAAGCAACCACCGCACCCAGCATCAAGCCCACCTGAA
ATTATCTCCGGCTTCCCTCTGGCCGAACAATATCGGTAGTTAATCAAAAC
TTAGGGTGCAAGATCATCCACAATGTCACCACAACGAGACCGGATAAATG
CCTTCTACAAAGATAACCCCCATCCCAAGGGAAGTAGGATAGTCATTAAC
AGAGAACATCTTATGATTGATAGACCTTATGTTTTGCTGGCTGTTCTGTT
TGTCATGTTTCTGAGCTTGATCGGGTTGCTAGCCATTGCAGGCATTAGAC

FIGURE 31.7

TTCATCGGGCAGCCATCTACACCGCAGAGATCCATAAAAGCCTCAGCACC
AATCTAGATGTAACTAACTCAATCGAGCATCAGGTCAAGGACGTGCTGAC
ACCACTCTTCAAAATCATCGGTGATGAAGTGGGCCTGAGGACACCTCAGA
GATTCACTGACCTAGTGAAATTAATCTCTGACAAGATTAAATTCCTTAAT
CCGGATAGGGAGTACGACTTCAGAGATCTCACTTGGTGTATCAACCCGCC
AGAGAGAATCAAATTGGATTATGATCAATACTGTGCAGATGTGGCTGCTG
AAGAGCTCATGAATGCATTGGTGAACTCAACTCTACTGGAGACCAGAACA
ACCAATCAGTTCCTAGCTGTCTCAAAGGGAAACTGCTCAGGGCCCACTAC
AATCAGAGGTCAATTCTCAAACATGTCGCTGTCCCTGTTAGACTTGTATT
TAGGTCGAGGTTACAATGTGTCATCTATAGTCACTATGACATCCCAGGGA
ATGTATGGGGGAACTTACCTAGTGGAAAAGCCTAATCTGAGCAGCAAAAG
GTCAGAGTTGTCACAACTGAGCATGTACCGAGTGTTTGAAGTAGGTGTTA
TCAGAAATCCGGGTTTGGGGGCTCCGGTGTTCCATATGACAAACTATCTT
GAGCAACCAGTCAGTAATGATCTCAGCAACTGTATGGTGGCTTTGGGGGA
GCTCAAACTCGCAGCCCTTTGTCACGGGGAAGATTCTATCACAATTCCCT
ATCAGGGATCAGGGAAAGGTGTCAGCTTCCAGCTCGTCAAGCTAGGTGTC
TGGAAATCCCCAACCGACATGCAATCCTGGGTCCCCTTATCAACGGATGA
TCCAGTGATAGACAGGCTTTACCTCTCATCTCACAGAGGTGTTATCGCTG
ACAATCAAGCAAAATGGGCTGTCCCGACAACACGAACAGATGACAAGTTG
CGAATGGAGACATGCTTCCAACAGGCGTGTAAGGGTAAAATCCAAGCACT
CTGCGAGAATCCCGAGTGGGCACCATTGAAGGATAACAGGATTCCTTCAT
ACGGGGTCTTGTCTGTTGATCTGAGTCTGACAGTTGAGCTTAAAATCAAA
ATTGCTTCGGGATTCGGGCCATTGATCACACACGGTTCAGGGATGGACCT
ATACAAATCCAACCACAACAATGTGTATTGGCTGACTATCCCGCCAATGA
AGAACCTAGCCTTAGGTGTAATCAACACATTGGAGTGGATACCGAGATTC
AAGGTTAGTCCCTACCTCTTCACTGTCCCAATTAAGGAAGCAGGCGAAGA
CTGCCATGCCCCAACATACCTACCTGCGGAGGTGGATGGTGATGTCAAAC
TCAGTTCCAATCTGGTGATTCTACCTGGTCAAGATCTCCAATATGTTTTG
GCAACCTACGATACTTCCAGGGTTGAACATGCTGTGGTTTATTACGTTTA
CAGCCCAAGCCGCTCATTTTCTTACTTTTATCCTTTTAGGTTGCCTATAA
AGGGGGTCCCCATCGAATTACAAGTGGAATGCTTCACATGGGACCAAAAA
CTCTGGTGCCGTCACTTCTGTGTGCTTGCGGACTCAGAATCTGGTGGACA
TATCACTCACTCTGGGATGGTGGGCATGGGAGTCAGCTGCACAGTCACCC
GGGAAGATGGAACCAATCGCAGATAGGGCTGCTAGTGAACCAATCACATG
ATGTCACCCAGACATCAGGCATACCCACTAGTCTACCCTCCATCATTGTT
ATAAAAACTTAGGAACCAGGTCCACACAGCCGCCAGCCCATCAACGCGT
ACG *atgggtaaggaaaagactcacgtttcgaggccgcgattaaattccaa*
*catggatgctgatttatatgggtataaatgggctcgcgataatgtcgggc*
*aatcaggtgcgacaatctatcgattgtatgggaagcccgatgcgccagag*
*ttgtttctgaaacatggcaaaggtagcgttgccaatgatgttacagatga*
*gatggtcagactaaactggctgacggaatttatgcctcttccgaccatca*
*agcattttatccgtactcctgatgatgcatggttactcaccactgcgatc*
*cccggcaaaacagcattccaggtattagaagaatatcctgattcaggtga*
*aaatattgttgatgcgctggcagtgttcctgcgccggttgcattcgattc*
*ctgtttgtaattgtccttttaacagcgatcgcgtatttcgtctcgctcag*
*gcgcaatcacgaatgaataacggtttggttgatgcgagtgattttgatga*
*cgagcgtaatggctggcctgttgaacaagtctggaaagaaatgcataagc*
*ttttgccattctcaccggattcagtcgtcactcatggtgatttctcactt*

FIGURE 31.8

*gataaccttattttttgacgaggggaaattaataggttgtattgatgttgg*
*acgagtcggaatcgcagaccgataccaggatcttgccatcctatggaact*
*gcctcggtgagttttctccttcattacagaaacggcttttttcaaaaatat*
*ggtattgataatcctgatatgaataaattgcagtttcatttgatgctcga*
*tgagttttctaa* GCGCGCAGCGCTTAGACGTCTCGCGATCGATGCTAGT
GTGAAATAGACATCAGAATTAAGAAAAACGTAGGGTCCAAGTGGTTCCCC
GTTATGGACTCGCTATCTGTCAACCAGATCTTATACCCTGAAGTTCACCT
AGATAGCCCGATAGTTACCAATAAGATAGTAGCCATCCTGGAGTATGCTC
GAGTCCCTCACGCTTACAGCCTGGAGGACCCTACACTGTGTCAGAACATC
AAGCACCGCCTAAAAAACGGATTTTCCAACCAAATGATTATAAACAATGT
GGAAGTTGGGAATGTCATCAAGTCCAAGCTTAGGAGTTATCCGGCCCACT
CTCATATTCCATATCCAAATTGTAATCAGGATTTATTTAACATAGAAGAC
AAAGAGTCAACGAGGAAGATCCGTGAACTCCTCAAAAAGGGGAATTCGCT
GTACTCCAAAGTCAGTGATAAGGTTTTCCAATGCTTAAGGGACACTAACT
CACGGCTTGGCCTAGGCTCCGAATTGAGGGAGGACATCAAGGAGAAAGTT
ATTAACTTGGGAGTTTACATGCACAGCTCCCAGTGGTTTGAGCCCTTTCT
GTTTTGGTTTACAGTCAAGACTGAGATGAGGTCAGTGATTAAATCACAAA
CCCATACTTGCCATAGGAGGAGACACACACCTGTATTCTTCACTGGTAGT
TCAGTTGAGTTGCTAATCTCTCGTGACCTTGTTGCTATAATCAGTAAAGA
GTCTCAACATGTATATTACCTGACATTTGAACTGGTTTTGATGTATTGTG
ATGTCATAGAGGGGAGGTTAATGACAGAGACCGCTATGACTATTGATGCT
AGGTATACAGAGCTTCTAGGAAGAGTCAGATACATGTGGAAACTGATAGA
TGGTTTCTTCCCTGCACTCGGGAATCCAACTTATCAAATTGTAGCCATGC
TGGAGCCTCTTTCACTTGCTTACCTGCAGCTGAGGGATATAACAGTAGAA
CTCAGAGGTGCTTTCCTTAACCACTGCTTTACTGAAATACATGATGTTCT
TGACCAAAACGGGTTTTCTGATGAAGGTACTTATCATGAGTTAACTGAAG
CTCTAGATTACATTTTCATAACTGATGACATACATCTGACAGGGGAGATT
TTCTCATTTTTCAGAAGTTTCGGCCACCCCAGACTTGAAGCAGTAACGGC
TGCTGAAAATGTTAGGAAATACATGAATCAGCCTAAAGTCATTGTGTATG
AGACTCTGATGAAAGGTCATGCCATATTTTGTGGAATCATAATCAACGGC
TATCGTGACAGGCACGGAGGCAGTTGGCCACCGCTGACCCTCCCCCTGCA
TGCTGCAGACACAATCCGGAATGCTCAAGCTTCAGGTGAAGGGTTAACAC
ATGAGCAGTGCGTTGATAACTGGAAATCTTTTGCTGGAGTGAAATTTGGC
TGCTTTATGCCTCTTAGCCTGGATAGTGATCTGACAATGTACCTAAAGGA
CAAGGCACTTGCTGCTCTCCAAAGGGAATGGGATTCAGTTTACCCGAAAG
AGTTCCTGCGTTACGACCCTCCCAAGGGAACCGGGTCACGGAGGCTTGTA
GATGTTTTCCTTAATGATTCGAGCTTTGACCCATATGATGTGATAATGTA
TGTTGTAAGTGGAGCTTACCTCCATGACCCTGAGTTCAACCTGTCTTACA
GCCTGAAAGAAAAGGAGATCAAGGAAACAGGTAGACTTTTTGCTAAAATG
ACTTACAAAATGAGGGCATGCCAAGTGATTGCTGAAAATCTAATCTCAAA
CGGGATTGGCAAATATTTTAAGGACAATGGGATGGCCAAGGATGAGCACG
ATTTGACTAAGGCACTCCACACTCTAGCTGTCTCAGGAGTCCCCAAAGAT
CTCAAAGAAAGTCACAGGGGGGGGCCAGTCTTAAAAACCTACTCCCGAAG
CCCAGTCCACACAAGTACCAGGAACGTGAGAGCAGCAAAAGGGTTTATAG
GGTTCCCTCAAGTAATTCGGCAGGACCAAGACACTGATCATCCGGAGAAT
ATGGAAGCTTACGAGACAGTCAGTGCATTTATCACGACTGATCTCAAGAA
GTACTGCCTTAATTGGAGATATGAGACCATCAGCTTGTTTGCACAGAGGC
TAAATGAGATTTACGGATTGCCCTCATTTTTCCAGTGGCTGCATAAGAGG

FIGURE 31.9

```
CTTGAGACCTCTGTCCTGTATGTAAGTGACCCTCATTGCCCCCCGACCT
TGACGCCCATATCCCGTTATATAAAGTCCCCAATGATCAAATCTTCATTA
AGTACCCTATGGGAGGTATAGAAGGGTATTGTCAGAAGCTGTGGACCATC
AGCACCATTCCCTATCTATACCTGGCTGCTTATGAGAGCGGAGTAAGGAT
TGCTTCGTTAGTGCAAGGGGACAATCAGACCATAGCCGTAACAAAAGGG
TACCCAGCACATGGCCCTACAACCTTAAGAAACGGGAAGCTGCTAGAGTA
ACTAGAGATTACTTTGTAATTCTTAGGCAAAGGCTACATGATATTGGCCA
TCACCTCAAGGCAAATGAGACAATTGTTTCATCACATTTTTTGTCTATT
CAAAAGGAATATATTATGATGGGCTACTTGTGTCCCAATCACTCAAGAGC
ATCGCAAGATGTGTATTCTGGTCAGAGACTATAGTTGATGAAACAAGGGC
AGCATGCAGTAATATTGCTACAACAATGGCTAAAAGCATCGAGAGAGGTT
ATGACCGTTACCTTGCATATTCCCTGAACGTCCTAAAAGTGATACAGCAA
ATTCTGATCTCTCTTGGCTTCACAATCAATTCAACCATGACCCGGGATGT
AGTCATACCCCTCCTCACAAACAACGACCTCTTAATAAGGATGGCACTGT
TGCCCGCTCCTATTGGGGGGATGAATTATCTGAATATGAGCAGGCTGTTT
GTCAGAAACATCGGTGATCCAGTAACATCATCAATTGCTGATCTCAAGAG
AATGATTCTCGCCTCACTAATGCCTGAAGAGACCCTCCATCAAGTAATGA
CACAACAACCGGGGGACTCTTCATTCCTAGACTGGGCTAGCGACCCTTAC
TCAGCAAATCTTGTATGTGTCCAGAGCATCACTAGACTCCTCAAGAACAT
AACTGCAAGGTTTGTCCTGATCCATAGTCCAAACCCAATGTTAAAAGGAT
TATTCCATGATGACAGTAAAGAAGAGGACGAGGGACTGGCGGCATTCCTC
ATGGACAGGCATATTATAGTACCTAGGGCAGCTCATGAAATCCTGGATCA
TAGTGTCACAGGGGCAAGAGAGTCTATTGCAGGCATGCTGGATACCACAA
AAGGCTTGATTCGAGCCAGCATGAGGAAGGGGGGGTTAACCTCTCGAGTG
ATAACCAGATTGTCCAATTATGACTATGAACAATTCAGAGCAGGGATGGT
GCTATTGACAGGAAGAAAGAGAAATGTCCTCATTGACAAAGAGTCATGTT
CAGTGCAGCTGGCGAGAGCTCTAAGAAGCCATATGTGGGCGAGGCTAGCT
CGAGGACGGCCTATTTACGGCCTTGAGGTCCCTGATGTACTAGAATCTAT
GCGAGGCCACCTTATTCGGCGTCATGAGACATGTGTCATCTGCGAGTGTG
GATCAGTCAACTACGGATGGTTTTTTGTCCCCTCGGGTTGCCAACTGGAT
GATATTGACAAGGAAACATCATCCTTGAGAGTCCCATATATTGGTTCTAC
CACTGATGAGAGAACAGACATGAAGCTTGCCTTCGTAAGAGCCCCAAGTC
GATCCTTGCGATCTGCTGTTAGAATAGCAACAGTGTACTCATGGGCTTAC
GGTGATGATGATAGCTCTTGGAACGAAGCCTGGTTGTTGGCTAGGCAAAG
GGCCAATGTGAGCCTGGAGGAGCTAAGGGTGATCACTCCCATCTCAACTT
CGACTAATTTAGCGCATAGGTTGAGGGATCGTAGCACTCAAGTGAAATAC
TCAGGTACATCCCTTGTCCGAGTGGCGAGGTATACCACAATCTCCAACGA
CAATCTCTCATTTGTCATATCAGATAAGAAGGTTGATACTAACTTTATAT
ACCAACAAGGAATGCTTCTAGGGTTGGGTGTTTTAGAAACATTGTTTCGA
CTCGAGAAAGATACCGGATCATCTAACACGGTATTACATCTTCACGTCGA
AACAGATTGTTGCGTGATCCCGATGATAGATCATCCCAGGATACCCAGCT
CCCGCAAGCTAGAGCTGAGGGCAGAGCTATGTACCAACCCATTGATATAT
GATAATGCACCTTTAATTGACAGAGATGCAACAAGGCTATACACCCAGAG
CCATAGGAGGCACCTTGTGGAATTTGTTACATGGTCCACACCCCAACTAT
ATCACATTTTAGCTAAGTCCACAGCACTATCTATGATTGACCTGGTAACA
AAATTTGAGAAGGACCATATGAATGAAATTTCAGCTCTCATAGGGGATGA
CGATATCAATAGTTTCATAACTGAGTTTCTGCTCATAGAGCCAAGATTAT
TCACTATCTACTTGGGCCAGTGTGCGGCCATCAATTGGGCATTTGATGTA
```

FIGURE 31.10

```
CATTATCATAGACCATCAGGGAAATATCAGATGGGTGAGCTGTTGTCATC
GTTCCTTTCTAGAATGAGCAAAGGAGTGTTTAAGGTGCTTGTCAATGCTC
TAAGCCACCCAAAGATCTACAAGAAATTCTGGCATTGTGGTATTATAGAG
CCTATCCATGGTCCTTCACTTGATGCTCAAAACTTGCACACAACTGTGTG
CAACATGGTTTACACATGCTATATGACCTACCTCGACCTGTTGTTGAATG
AAGAGTTAGAAGAGTTCACATTTCTCTTGTGTGAAAGCGACGAGGATGTA
GTACCGGACAGATTCGACAACATCCAGGCAAAACACTTATGTGTTCTGGC
AGATTTGTACTGTCAACCAGGGACCTGCCCACCAATTCGAGGTCTAAGAC
CGGTAGAGAAATGTGCAGTTCTAACCGACCATATCAAGGCAGAGGCTATG
TTATCTCCAGCAGGATCTTCGTGGAACATAAATCCAATTATTGTAGACCA
TTACTCATGCTCTCTGACTTATCTCCGGCGAGGATCGATCAAACAGATAA
GATTGAGAGTTGATCCAGGATTCATTTTCGACGCCTCGCTGAGGTAAAT
GTCAGTCAGCCAAAGATCGGCAGCAACAACATCTCAAATATGAGCATCAA
GGCTTTCAGACCCCCACACGATGATGTTGCAAAATTGCTCAAAGATATCA
ACACAAGCAAGCACAATCTTCCCATTTCAGGGGGCAATCTCGCCAATTAT
GAAATCCATGCTTTCCGCAGAATCGGGTTGAACTCATCTGCTTGCTACAA
AGCTGTTGAGATATCAACATTAATTAGGAGATGCCTTGAGCCAGGGGAGG
ACGGCTTGTTCTTGGGTGAGGGATCGGGTTCTATGTTGATCACTTATAAA
GAGATACTTAAACTAAACAAGTGCTTCTATAATAGTGGGGTTTCCGCCAA
TTCTAGATCTGGTCAAAGGGAATTAGCACCCTATCCCTCCGAAGTTGGCC
TTGTCGAACACAGAATGGGAGTAGGTAATATTGTCAAAGTGCTCTTTAAC
GGGAGGCCCGAAGTCACGTGGGTAGGCAGTGTAGATTGCTTCAATTTCAT
AGTTAGTAATATCCCTACCTCTAGTGTGGGGTTTATCCATTCAGATATAG
AGACCTTGCCTGACAAAGATACTATAGAGAAGCTAGAGGAATTGGCAGCC
ATCTTATCGATGGCTCTGCTCCTGGGCAAAATAGGATCAATACTGGTGAT
TAAGCTTATGCCTTTCAGCGGGGATTTTGTTCAGGGATTTATAAGTTATG
TAGGGTCTCATTATAGAGAAGTGAACCTTGTATACCCTAGATACAGCAAC
TTCATCTCTACTGAATCTTATTTGGTTATGACAGATCTCAAGGCTAACCG
GCTAATGAATCCTGAAAAGATTAAGCAGCAGATAATTGAATCATCTGTGA
GGACTTCACCTGGACTTATAGGTCACATCCTATCCATTAAGCAACTAAGC
TGCATACAAGCAATTGTGGGAGACGCAGTTAGTAGAGGTGATATCAATCC
TACTCTGAAAAAACTTACACCTATAGAGCAGGTGCTGATCAATTGCGGGT
TGGCAATTAACGGACCTAAGCTGTGCAAAGAATTGATCCACCATGATGTT
GCCTCAGGGCAAGATGGATTGCTTAATTCTATACTCATCCTCTACAGGGA
GTTGGCAAGATTCAAAGACAACCAAAGAAGTCAACAAGGGATGTTCCACG
CTTACCCCGTATTGGTAAGTAGCAGGCAACGAGAACTTATATCTAGGATC
ACCCGCAAATTCTGGGGGCACATTCTTCTTTACTCCGGGAACAAAAAGTT
GATAAATAAGTTTATCCAGAATCTCAAGTCCGGCTATCTGATACTAGACT
TACACCAGAATATCTTCGTTAAGAATCTATCCAAGTCAGAGAAACAGATT
ATTATGACGGGGGGTTTGAAACGTGAGTGGGTTTTTAAGGTAACAGTCAA
GGAGACCAAAGA *ATGGTATAAGTTAGTCGGATACAGTGCCCTGATTAAGG*
*ACTAATTGGTTGAACTCCGGAACCCTAATCCTGCCCTAGGTGGTTAGGCA*
*TTATTTGCAATATATTAAAGAAAACTTTGAAAATACGAAGTTTCTATTCC*
*CAGCTTTGTCTGGT* gacccgggactccgggtttcgtcctcacggactcat
cagaccaaacaaagttgg CGGCCGCGGGATCCGATATCTAGATGCATTCGCGAGGTA
CCGAGCTCGAATTCCAGCACACTGGCGGCCGTTACTAGTGGAT
CCGAGCTCGGTACCAAGCTTAATATTCCCTATAGTGAGTCGTATTACAGC
TGCTAGTAGTCCGATCCGGGGTTTTTTCTCCTTGACGTTAAAGTATAGAG
```

FIGURE 31.11

```
GTATATTAACAATTTTTTGTTGATACTTTTATTACATTTGAATAAGAAGT
AATACAAACCGAAAATGTTGAAAGTATTAGTTAAAGTGGTTAATGCAGTT
TTTGCATTTATATATCTGTTAATAGATCAAAAATCATCGCTTCGCTGATT
AATTACCCCAGAAATAAGGCTAAAAAACTAATCGCATTATCATCCTATGG
TTGTTAATTTGATTCGTTCATTTGAAGGTTTGTGGGGCCAGGTTACTGCC
AATTTTTCCTCTTCATAACCATAAAAGCTAGTATTGTAGAATCTTTATTG
TTCGGAGCAGTGCGGCGCGAGGCACATCTGCGTTTCAGGAACGCGACCGG
TGAGGACGAGGACGCACGGAGGAGAGTCTTCCTTCGGAGGGCTGTCACCC
GCTCGGCGGCTTCTAATCCGTAC
```

FIGURE 32.1

Recombinant measles genome sequence (pCM503)

| | |
|---|---|
| pYES2 vector : | Capital letter |
| Measles genome sequence: | Capital letter |
| Ribozymes Sequence : | Minuscule letter |
| Leader sequence : | Bold capital letter |
| Trailer sequence : | Bold italic capital letter |
| eGFP sequence : | Bold minuscule letter |
| KANMX4 sequence : | Minuscule italic letter |

```
CTGCATTAATGAATCGGCCAACGCGCGGGGAGAGGCGGTTTGCGTATTGG
GCGCTCTTCCGCTTCCTCGCTCACTGACTCGCTGCGCTCGGTCGTTCGGC
TGCGGCGAGCGGTATCAGCTCACTCAAAGGCGGTAATACGGTTATCCACA
GAATCAGGGGATAACGCAGGAAAGAACATGTGAGCAAAAGGCCAGCAAAA
GCCCAGGAACCGTAAAAAGGCCGCGTTGCTGGCGTTTTTCCATAGGCTCC
GCCCCCTGACGAGCATCACAAAAATCGACGCTCAAGTCAGAGGTGGCGA
AACCCGACAGGACTATAAAGATACCAGGCGTTTCCCCCTGGAAGCTCCCT
CGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACC
CCCCGTTCAGCCCGACCGCTGCGCCTTATCCGGTAACTATCGTCTTGAGT
CCAACCCGGTAAGACACGACTTATCGCCACTGGCAGCAGCCACTGGTAAC
AGGATTAGCAGAGCGAGGTATGTAGGCGGTGCTACAGAGTTCTTGAAGTG
GTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGG
GGTCTGACGCTCAGTGGAACGAAAACTCACGTTAAGGGATTTTGGTCATG
AGATTATCAAAAAGGATCTTCACCTAGATCCTTTTAAATTAAAAATGAAG
TTTTAAATCAATCTAAAGTATATATGAGTAAACTTGGTCTGACAGTTACC
AATGCTTAATCAGTGAGGCACCTATCTCAGCGATCTGTCTATTTCGTTCA
TCCATAGTTGCCTGACTCCCCGTCGTGTAGATAACTACGATACGGGAGCG
CTTACCATCTGGCCCCAGTGCTGCAATGATACCGCGAGACCCACGCTCAC
CGGCTCCAGATTTATCAGCAATAAACCAGCCAGCCGGAAGGGCCGAGCGC
AGAAGTGGTCCTGCAACTTTATCCGCCTCCATTCAGTCTATTAATTGTTG
CCGGGAAGCTAGAGTAAGTAGTTCGCCAGTTAATAGTTTGCGCAACGTTG
TTGGCATTGCTACAGGCATCGTGGTGTCACTCTCGTCGTTTGGTATGGCT
TCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAAT
TCTCTTACTGTCATGCCATCCGTAAGATGCTTTTCTGTGACTGGTGAGTA
CTCAACCAAGTCATTCTGAGAATAGTGTATGCGGCGACCGAGTTGCTCTT
GCCCGGCGTCAATACGGGATAATAGTGTATCACATAGCAGAACTTTAAAA
GTGCTCATCATTGGAAAACGTTCTTCGGGGCGAAAACTCTCAAGGATCTT
ACCGCTGTTGAGATCCAGTTCGATGTAACCCACTCGTGCACCCAACTGAT
CTTCAGCATCTTTTACTTTCACCAGCGTTTCTGGGTGAGCAAAAACAGGA
```

FIGURE 32.2

AGGCAAAATGCCGCAAAAAGGGAATAAGGGCGACACGGAAATGTTGAAT
ACTCATACTCTTCCTTTTTCAATGGGTAATAACTGATATAATTAAATTGA
AGCTCTAATTTGTGAGTTTAGTATACATGCATTTACTTATAATACAGTTT
TTTAGTTTTGCTGGCCGCATCTTCTCAAATATGCTTCCCAGCCTGCTTTT
CTGTAACGTTCACCCTCTACCTTAGCATCCCTTCCCTTTGCAAATAGTCC
TCTTCCAACAATAATAATGTCAGATCCTGTAGAGACCACATCATCCACGG
TTCTATACTGTTGACCCAATGCGTCTCCCTTGTCATCTAAACCCACACCG
GGTGTCATAATCAACCAATCGTAACCTTCATCTCTTCCACCCATGTCTCT
TTGAGCAATAAAGCCGATAACAAAATCTTTGTCGCTCTTCGCAATGTCAA
CAGTACCCTTAGTATATTCTCCAGTAGATAGGGAGCCCTTGCATGACAAT
TCTGCTAACATCAAAAGGCCTCTAGGTTCCTTTGTTACTTCTTCTGCCGC
CTGCTTCAAACCGCTAACAATACCTGGGCCCACCACACCGTGTGCATTCG
TAATGTCTGCCCATTCTGCTATTCTGTATACACCCGCAGAGTACTGCAAT
TTGACTGTATTACCAATGTCAGCAAATTTTCTGTCTTCGAAGAGTAAAAA
ATTGTACTTGGCGGATAATGCCTTTAGCGGCTTAACTGTGCCCTCCATGG
AAAAATCAGTCAAGATATCCACATGTGTTTTAGTAAACAAATTTTGGGA
CCTAATGCTTCAACTAACTCCAGTAATTCCTTGGTGGTACGAACATCCAA
TGAAGCACACAAGTTTGTTTGCTTTTCGTGCATGATATTAAATAGCTTGG
CAGCAACAGGACTAGGATGAGTAGCAGCACGTTCCTTATATGTAGCTTTC
GACATGATTTATCTTCGTTTCCTGCAGGTTTTTGTTCTGTGCAGTTGGGT
TAAGAATACTGGGCAATTTCATGTTTCTTCAACACTACATATGCGTATAT
ATACCAATCTAAGTCTGTGCTCCTTCCTTCGTTCTTCCTTCTGTTCGGAG
ATTACCGAATCAAAAAAATTTCAAAGAAACCGAAATCAAAAAAAAGAATA
AAAAAAAAATGATGAATTGAATTGAAAAGCTAGCTTATCGATGATAAGCT
GTCAAAGATGAGAATTAATTCCACGGACTATAGACTATACTAGATACTCC
GTCTACTGTACGATACACTTCCGCTCAGGTCCTTGTCCTTTAACGAGGCC
TTACCACTCTTTTGTTACTCTATTGATCCAGCTCAGCAAAGGCAGTGTGA
TCTAAGATTCTATCTTCGCGATGTAGTAAAACTAGCTAGACCGAGAAAGA
GACTAGAAATGCAAAAGGCACTTCTACAATGGCTGCCATCATTATTATCC
GATGTGACGCTGCAGCTTCTCAATGATATTCGAATACGCTTTGAGGAGAT
ACAGCCTAATATCCGACAAACTGTTTTACAGATTTACGATCGTACTTGTT
ACCCATCATTGAATTTTGAACATCCGAACCTGGGAGTTTTCCCTGAAACA
GATAGTATATTTGAACCTGTATAATAATATATAGTCTAGCGCTTTACGGA
AGACAATGTATGTATTTCGGTTCCTGGAGAAACTATTGCATCTATTGCAT
AGGTAATCTTGCACGTCGCATCCCCGGTTCATTTTCTGCGTTTCCATCTT
GCACTTCAATAGCATATCTTTGTTAACGAAGCATCTGTGCTTCATTTTGT
AGAACAAAAATGCAACGCGAGAGCGCTAATTTTTCAAACAAGAATCTGA
GCTGCATTTTTACAGAACAGAAATGCAACGCGAAAGCGCTATTTTACCAA
CGAAGAATCTGTGCTTCATTTTTGTAAAACAAAAATGCAACGCGACGAGA
GCGCTAATTTTTCAAACAAAGAATCTGAGCTGCATTTTTACAGAACAGAA
ATGCAACGCGAGAGCGCTATTTTACCAACAAAGAATCTATACTTCTTTTT
TGTTCTACAAAAATGCATCCCGAGAGCGCTATTTTTCTAACAAAGCATCT
TAGATTACTTTTTTTCTCCTTTGTGCGCTCTATAATGCAGTCTCTTGATA
ACTTTTTGCACTGTAGGTCCGTTAAGGTTAGAAGAAGGCTACTTTGGTGT
CTATTTTCTCTTCCATAAAAAAAGCCTGACTCCACTTCCCGCGTTTACTG
ATTACTAGCGAAGCTGCGGGTGCATTTTTTCAAGATAAAGGCATCCCCGA
TTATATTCTATACCGATGTGGATTGCGCATACTTTGTGAACAGAAAGTGA
TAGCGTTGATGATTCTTCATTGGTCAGAAAATTATGAACGGTTTCTTCTA

FIGURE 32.3

TTTTGTCTCTATATACTACGTATAGGAAATGTTTACATTTTCGTATTGTT
TTCGATTCACTCTATGAATAGTTCTTACTACAATTTTTTTGTCTAAAGAG
TAATACTAGAGATAAACATAAAAAATGTAGAGGTCGAGTTTAGATGCAAG
TTCAAGGAGCGAAAGGTGGATGGGTAGGTTATATAGGGATATAGCACAGA
GATATATAGCAAAGAGATACTTTTGAGCAATGTTTGTGGAAGCGGTATTC
GCAATGGGAAGCTCCACCCCGGTTGATAATCAGAAAAGCCCCAAAAACAG
GAAGATTGTATAAGCAAATATTTAAATTGTAAACGTTAATATTTTGTTAA
AATTCGCGTTAAATTTTTGTTAAATCAGCTCATTTTTAACGAATAGCCC
GAAATCGGCAAAATCCCTTATAAATCAAAAGAATAGACCGAGATAGGGTT
GAGTGTTGTTCCAGTTTCCAACAAGAGTCCACTATTAAAGAACGTGGACT
CCAACGTCAAAGGGCGAAAAAGGGTCTATCAGGGCGATGGCCCACTACGT
GAACCATCACCCTAATCAAGTTTTTTGGGGTCGAGGTGCCGTAAAGCAGT
AAATCGGAAGGGTAAACGGATGCCCCATTTAGAGCTTGACGGGGAAAGC
CGGCGAACGTGGCGAGAAAGGAAGGGAAGAAAGCGAAGGAGCGGGGGCT
AGGGCGGTGGGAAGTGTAGGGGTCACGCTGGGCGTAACCACCACACCCGC
CGCGCTTAATGGGGCGCTACAGGGCGCGTGGGGATGATCCACTAGTACGG
ATTAGAAGCCGCCGAGCGGGTGACAGCCCTCCGAAGGAAGACTCTCCTCC
GTGCGTCCTCGTCCTCACCGGTCGCGTTCCTGAAACGCAGATGTGCCTCG
CGCCGCACTGCTCCGAACAATAAAGATTCTACAATACTAGCTTTTATGGT
TATGAAGAGGAAAAATTGGCAGTAACCTGGCCCCACAAACCTTCAAATGA
ACGAATCAAATTAACAACCATAGGATGATAATGCGATTAGTTTTTTAGCC
TTATTTCTGGGGTAATTAATCAGCGAAGCGATGATTTTTGATCTATTAAC
AGATATATAAATGCAAAAACTGCATTAACCACTTTAACTAATACTTTCAA
CATTTTCGGTTTGTATTACTTCTTATTCAAATGTAATAAAAGTATCAACA
AAAAATTGTTAATATACCTCTATACTTTAACGTCAAGGAGAAAAAACCCC
GGATCGGACTACTAGCAGCTGTAATACGACTCACTATAGGGAATATTAAG
CTTGGTACCGAGCTCGGATCCACTAGTAACGGCCGCCAGTGTGCTGGAAT
TCTGCAGATATCCATCACACTGGCGGCCGCTAATACGACTCACTATAGGG
ccaactttgtttggtctgatgagtccgtgaggacgaaacccggagtcccg
ggtc ACCAAACAAAGTTGGGTAAGGATAGTTCAATCAATGATCATCTTCT
AGTGCACTTAGGATTCAAGATCCTATTATCAGGGACAAGAGCAGGATTAG
GGATATCCGAGATGG CCACACTTTTAAGGAGCTTAGCATTGTTCAAAAGA
AACAAGGACAAACCACCCATTACATCAGGATCCGGTGGAGCCATCAGAGG
AATCAAACACATTATTATAGTACCAATCCCTGGAGATTCCTCAATTACCA
CTCGATCCAGACTTCTGGACCGGTTGGTGAGGTTAATTGGAAACCCGGAT
GTGAGCGGGCCCAAACTAACAGGGGCACTAATAGGTATATTATCCTTATT
TGTGGAGTCTCCAGGTCAATTGATTCAGAGGATCACCGATGACCCTGACG
TTAGCATAAGGCTGTTAGAGGTTGTCCAGAGTGACCAGTCACAATCTGGC
CTTACCTTCGCATCAAGAGGTACCAACATGGAGGATGAGGCGGACCAATA
CTTTTCACATGATGATCCAATTAGTAGTGATCAATCCAGGTTCGGATGGT
TCGGGAACAAGGAAATCTCAGATATTGAAGTGCAAGACCCTGAGGGATTC
AACATGATTCTGGGTACCATCCTAGCCCAAATTTGGGTCTTGCTCGCAAA
GGCGGTTACGGCCCCAGACACGGCAGCTGATTCGGAGCTAAGAAGGTGGA
TAAAGTACACCCAACAAAGAAGGGTAGTTGGTGAATTTAGATTGGAGAGA
AAATGGTTGGATGTGGTGAGGAACAGGATTGCCGAGGACCTCTCCTTACG
CCGATTCATGGTCGCTCTAATCCTGGATATCAAGAGAACACCCGGAAACA
AACCCAGGATTGCTGAAATGATATGTGACATTGATACATATATCGTAGAG
GCAGGATTAGCCAGTTTTATCCTGACTATTAAGTTTGGGATAGAAACTAT

FIGURE 32.4

```
GTATCCTGCTCTTGGACTGCATGAATTTGCTGGTGAGTTATCCACACTTG
AGTCCTTGATGAACCTTTACCAGCAAATGGGGGAAACTGCACCCTACATG
GTAATCCTGGAGAACTCAATTCAGAACAAGTTCAGTGCAGGATCATACCC
TCTGCTCTGGAGCTATGCCATGGGAGTAGGAGTGGAACTTGAAAACTCCA
TGGGAGGTTTGAACTTTGGCCGATCTTACTTTGATCCAGCATATTTTAGA
TTAGGGCAAGAGATGGTAAGGAGGTCAGCTGGAAAGGTCAGTTCCACATT
GGCATCTGAACTCGGTATCACTGCCGAGGATGCAAGGCTTGTTTCAGAGA
TTGCAATGCATACTACTGAGGACAAGATCAGTAGAGCGGTTGGACCCAGA
CAAGCCCAAGTATCATTTCTACACGGTGATCAAAGTGAGAATGAGCTACC
GAGATTGGGGGGCAAGGAAGATAGGAGGGTCAAACAGAGTCGAGGAGAAG
CCAGGGAGAGCTACAGAGAAACCGGGCCCAGCAGAGCAAGTGATGCGAGA
GCTGCCCATCTTCCAACCGGCACACCCTAGACATTGACACTGCAACGGA
GTCCAGCCAAGATCCGCAGGACAGTCGAAGGTCAGCTGACGCCCTGCTTA
GGCTGCAAGCCATGGCAGGAATCTCGGAAGAACAAGGCTCAGACACGGAC
ACCCCTATAGTGTACAATGACAGAAATCTTCTAGACTAGGTGCGAGAGGC
CGAGGGCCAGAACAACATCCGCCTACCATCCATCATTGTTATAAAAAACT
TAGGAACCAGGTCCACACAGCCGCCAGCCCATCAACCATCCACTCCCACG
ATTGGAGCCAATGGCAGAAGAGCAGGCACGCCATGTCAAAAACGGACTGG
AATGCATCCGGGCTCTCAAGGCCGAGCCCATCGGCTCACTGGCCATCGAG
GAAGCTATGGCAGCATGGTCAGAAATATCAGACAACCCAGGACAGGAGCG
AGCCACCTGCAGGGAAGAGAAGGCAGGCAGTTCGGGTCTCAGCAAACCAT
GCCTCTCAGCAATTGGATCAACTGAAGGCGGTGCACCTCGCATCCGCGGT
CAGGGACCTGGAGAGAGCGATGACGACGCTGAAACTTTGGGAATCCCCCC
AAGAAATCTCCAGGCATCAAGCACTGGGTTACAGTGTTATTACGTTTATG
ATCACAGCGGTGAAGCGGTTAAGGGAATCCAAGATGCTGACTCTATCATG
GTTCAATCAGGCCTTGATGGTGATAGCACCCTCTCAGGAGGAGACAATGA
ATCTGAAAACAGCGATGTGGATATTGGCGAACCTGATACCGAGGGATATG
CTATCACTGACCGGGGATCTGCTCCCATCTCTATGGGGTTCAGGGCTTCT
GATGTTGAAACTGCAGAAGGAGGGGAGATCCACGAGCTCCTGAGACTCCA
ATCCAGAGGCAACAACTTTCCGAAGCTTGGGAAAACTCTCAATGTTCCTC
CGCCCCGGACCCCGGTAGGGCCAGCACTTCCGGGACACCCATTAAAAAG
GGCACAGACGCGAGATTAGCCTCATTTGGAACGGAGATCGCGTCTTTATT
GACAGGTGGTGCAACCCAATGTGCTCGAAAGTCACCCTCGGAACCATCAG
GGCCAGGTGCACCTGCGGGGAATGTCCCCGAGTGTGTGAGCAATGCCGCA
CTGATACAGGAGTGGACACCCGAATCTGGTACCACAATCTCCCCGAGATC
CCAGAATAATGAAGAAGGGGAGACTATTATGATGATGAGCTGTTCTCTG
ATGTCCAAGATATTAAAACAGCCTTGGCCAAAATACACGAGGATAATCAG
AAGATAATCTCCAAGCTAGAATCACTGCTGTTATTGAAGGGAGAAGTTGA
GTCAATTAAGAAGCAGATCAACAGGCAAAATATCAGCATATCCACCCTGG
AAGGACACCTCTCAAGCATCATGATCGCCATTCCTGGACTTGGGAAGGAT
CCCAACGACCCCACTGCAGATGTCGAAATCAATCCCGACTTGAAACCCAT
CATAGGCAGAGATTCAGGCCGAGCACTGGCCGAAGTTCTCAAGAAACCCG
TTGCCAGCCGACAACTCCAAGGAATGACAAATGGACGGACCAGTTCCAGA
GGACAGCTGCTGAAGGAATTTCAGCTAAAGCCGATCGGGAAAAAGATGAG
CTCAGCCGTCGGGTTTGTTCCTGACACCGGCCCTGCATCACGCAGTGTAA
TCCGCTCCATTATAAAATCCAGCCGGCTAGAGGAGGATCGGAAGCGTTAC
CTGATGACTCTCCTTGATGATATCAAAGGAGCCAATGATCTTGCCAAGTT
CCACCAGATGCTGATGAAGATAATAATGAAGTAGCTACAGCTCAACTTAC
```

FIGURE 32.5

```
CTGCCAACCCCATGCCAGTCGACCCAACTAGTACAACCTAAATCCATTAT
AAAAAACTTAGGAGCAAAGTGATTGCCTCCCAAGGTCCACAATGACAGAG
ACCTACGACTTCGACAAGTCGGCATGGGACATCAAAGGGTCGATCGCTCC
GATACAACCCACCACCTACAGTGATGGCAGGCTGGTGCCCCAGGTCAGAG
TCATAGATCCTGGTCTAGGCGACAGGAAGGATGAATGCTTTATGTACATG
TTTCTGCTGGGGGTTGTTGAGGACAGCGATTCCCTAGGGCCTCCAATCGG
GCGAGCATTTGGGTTCCTGCCCTTAGGTGTTGGCAGATCCACAGCAAAGC
CCGAAAAACTCCTCAAAGAGGCCACTGAGCTTGACATAGTTGTTAGACGT
ACAGCAGGGCTCAATGAAAAACTGGTGTTCTACAACAACACCCACTAAC
TCTCCTCACACCTTGGAGAAAGGTCCTAACAACAGGGAGTGTCTTCAACG
CAAACCAAGTGTGCAATGCGGTTAATCTGATACCGCTCGATACCCCGCAG
AGGTTCCGTGTTGTTTATATGAGCATCACCCGTCTTTCGGATAACGGGTA
TTACACCGTTCCTAGAAGAATGCTGGAATTCAGATCGGTCAATGCAGTGG
CCTTCAACCTGCTGGTGACCCTTAGGATTGACAAGGCGATAGGCCCTGGG
AAGATCATCGACAATACAGAGCAACTTCCTGAGGCAACATTTATGGTCCA
CATCGGGAACTTCAGGAGAAAGAAGAGTGAAGTCTACTCTGCCGATTATT
GCAAAATGAAAATCGAAAAGATGGGCCTGGTTTTTGCACTTGGTGGGATA
GGGGGCACCAGTCTTCACATTAGAAGCACAGGCAAAATGAGCAAGACTCT
CCATGCACAACTCGGGTTCAAGAAGACCTTATGTTACCCGCTGATGGATA
TCAATGAAGACCTTAATCGATTACTCTGGAGGAGCAGATGCAAGATAGTA
AGAATCCAGGCAGTTTTGCAGCCATCAGTTCCTCAAGAATTCCGCATTTA
CGACGACGTGATCATAAATGATGACCAAGGACTATTCAAAGTTCTGTAGA
CCGTAGTGCCCAGCAATGCCCGAAAACGACCCCCCTCACAATGACAGCCA
GAAGGCCCGGACAAAAAAGCCCCCTCCGAAAGACTCCACGGACCAAGCGA
GAGGCCAGCCAGCAGCCGACGGCAAGCGCGAACACCAGGCGGCCCCAGCA
CAGAACAGCCCTGACACAAGGCCACCACCAGCCACCCCAATCTGCATCCT
CCTCGTGGGACCCCCGAGGACCAACCCCCAAGGCTGCCCCGATCCAAAC
CACCAACCGCATCCCCACCACCCCGGGAAAGAAACCCCAGCAATTGGA
AGGCCCCTCCCCCTCTTCCTCAACACAAGAACTCCACAACCGAACCGCAC
AAGCGACCGAGGTGACCCAACCGCAGGCATCCGACTCCCTAGACAGATCC
TCTCTCCCCGGCAAACTAAACAAAACTTAGGGCCAAGGAACATACACACC
CAACAGAACCCAGACCCCGGCCCACGGCGCCGCGCCCCAACCCCCGACA
ACCAGAGGGAGCCCCCAACCAATCCCGCCGGCTCCCCCGGTGCCCACAGG
CAGGGACACCAACCCCCGAACAGACCCAGCACCCAACCATCGACAATCCA
AGACGGGGGGGCCCCCCAAAAAAAGGCCCCCAGGGGCCGACAGCCAGCA
CCGCGAGGAAGCCCACCCACCCCACACACGACCACGGCAACCAAACCAGA
ACCCAGACCACCCTGGGCCACCAGCTCCCAGACTCGGCCATCACCCCGCA
GAAAGGAAAGGCCACAACCCGCGCACCCCAGCCCCGATCCGGCGGGGAGC
CACCCAACCCGAACCAGCACCCAAGAGCGATCCCCGAAGGACCCCCGAAC
CGCAAAGGACATCAGTATCCCACAGCCTCTCCAAGTCCCCCGGTCTCCTC
CTCTTCTCGAAGGGACCAAAAGATCAATCCACCACACCCGACGACACTCA
ACTCCCCACCCCTAAAGGAGACACCGGGAATCCCAGAATCAAGACTCATC
CAATGTCCATCATGGGTCTCAAGGTGAACGTCTCTGCCATATTCATGGCA
GTACTGTTAACTCTCCAAACACCCACCGGTCAAATCCATTGGGGCAATCT
CTCTAAGATAGGGGTGGTAGGAATAGGAAGTGCAAGCTACAAAGTTATGA
CTCGTTCCAGCCATCAATCATTAGTCATAAAATTAATGCCCAATATAACT
CTCCTCAATAACTGCACGAGGGTAGAGATTGCAGAATACAGGAGACTACT
GAGAACAGTTTTGGAACCAATTAGAGATGCACTTAATGCAATGACCCAGA
```

FIGURE 32.6

ATATAAGACCGGTTCAGAGTGTAGCTTCAAGTAGGAGACACAAGAGATTT
GCGGGAGTAGTCCTGGCAGGTGCGGCCCTAGGCGTTGCCACAGCTGCTCA
GATAACAGCCGGCATTGCACTTCACCAGTCCATGCTGAACTCTCAAGCCA
TCGACAATCTGAGAGCGAGCCTGGAAACTACTAATCAGGCAATTGAGACA
ATCAGACAAGCAGGGCAGGAGATGATATTGGCTGTTCAGGGTGTCCAAGA
CTACATCAATAATGAGCTGATACCGTCTATGAACCAACTATCTTGTGATT
TAATCGGCCAGAAGCTCGGGCTCAAATTGCTCAGATACTATACAGAAATC
CTGTCATTATTTGGCCCCAGTTTACGGGACCCCATATCTGCGGAGATATC
TATCCAGGCTTTGAGCTATGCGCTTGGAGGAGACATCAATAAGGTGTTAG
AAAAGCTCGGATACAGTGGAGGTGATTTACTGGGCATCTTAGAGAGCGGA
GGAATAAAGGCCCGGATAACTCACGTCGACACAGAGTCCTACTTCATTGT
CCTCAGTATAGCCTATCCGACGCTGTCCGAGATTAAGGGGGTGATTGTCC
ACCGGCTAGAGGGGGTCTCGTACAACATAGGCTCTCAAGAGTGGTATACC
ACTGTGCCCAAGTATGTTGCAACCCAAGGGTACCTTATCTCGAATTTTGA
TGAGTCATCGTGTACTTTCATGCCAGAGGGGACTGTGTGCAGCCAAAATG
CCTTGTACCCGATGAGTCCTCTGCTCCAAGAATGCCTCCGGGGGTACACC
AAGTCCTGTGCTCGTACACTCGTATCCGGGTCTTTTGGGAACCGGTTCAT
TTTATCACAAGGGAACCTAATAGCCAATTGTGCATCAATCCTTTGCAAGT
GTTACACAACAGGAACGATCATTAATCAAGACCCTGACAAGATCCTAACA
TACATTGCTGCCGATCACTGCCCGGTAGTCGAGGTGAACGGCGTGACCAT
CCAAGTCGGGAGCAGGAGGTATCCAGACGCTGTGTACTTGCACAGAATTG
ACCTCGGTCCTCCCATATCATTGGAGAGGTTGGACGTAGGGACAAATCTG
GGGAATGCAATTGCTAAGTTGGAGGATGCCAAGGAATTGTTGGAGTCATC
GGACCAGATATTGAGGAGTATGAAAGGTTTATCGAGCACTAGCATAGTCT
ACATCCTGATTGCAGTGTGTCTTGGAGGGTTGATAGGGATCCCCGCTTTA
ATATGTTGCTGCAGGGGCGTTGTAACAAAAGGGAGAACAAGTTGGTAT
GTCAAGACCAGGCCTAAAGCCTGATCTTACGGGAACATCAAAATCCTATG
TAAGGTCGCTCTGATCCTCTACAACTCTTGAAACACAAATGTCCCACAAG
TCTCCTCTTCGTCATCAAGCAACCACCGCACCCAGCATCAAGCCCACCTG
AAATTATCTCCGGCTTCCCTCTGGCCGAACAATATCGGTAGTTAATCAAA
ACTTAGGGTGCAAGATCATCCACAATGTCACCACAACGAGACCGGATAAA
TGCCTTCTACAAAGATAACCCCCATCCCAAGGGAAGTAGGATAGTCATTA
ACAGAGAACATCTTATGATTGATAGACCTTATGTTTTGCTGGCTGTTCTG
TTTGTCATGTTTCTGAGCTTGATCGGGTTGCTAGCCATTGCAGGCATTAG
ACTTCATCGGGCAGCCATCTACACCGCAGAGATCCATAAAAGCCTCAGCA
CCAATCTAGATGTAACTAACTCAATCGAGCATCAGGTCAAGGACGTGCTG
ACACCACTCTTCAAAATCATCGGTGATGAAGTGGGCCTGAGGACACCTCA
GAGATTCACTGACCTAGTGAAATTAATCTCTGACAAGATTAAATTCCTTA
ATCCGGATAGGGAGTACGACTTCAGAGATCTCACTTGGTGTATCAACCCG
CCAGAGAGAATCAAATTGGATTATGATCAATACTGTGCAGATGTGGCTGC
TGAAGAGCTCATGAATGCATTGGTGAACTCAACTCTACTGGAGACCAGAA
CAACCAATCAGTTCCTAGCTGTCTCAAAGGGAAACTGCTCAGGGCCCACT
ACAATCAGAGGTCAATTCTCAAACATGTCGCTGTCCCTGTTAGACTTGTA
TTTAGGTCGAGGTTACAATGTGTCATCTATAGTCACTATGACATCCCAGG
GAATGTATGGGGAACTTACCTAGTGGAAAAGCCTAATCTGAGCAGCAAA
AGGTCAGAGTTGTCACAACTGAGCATGTACCGAGTGTTTGAAGTAGGTGT
TATCAGAAATCCGGGTTTGGGGGCTCCGGTGTTCCATATGACAAACTATC
TTGAGCAACCAGTCAGTAATGATCTCAGCAACTGTATGGTGGCTTTGGGG

FIGURE 32.7

GAGCTCAAACTCGCAGCCCTTTGTCACGGGGAAGATTCTATCACAATTCC
CTATCAGGGATCAGGGAAAGGTGTCAGCTTCCAGCTCGTCAAGCTAGGTG
TCTGGAAATCCCCAACCGACATGCAATCCTGGGTCCCCTTATCAACGGAT
GATCCAGTGATAGACAGGCTTTACCTCTCATCTCACAGAGGTGTTATCGC
TGACAATCAAGCAAATGGGCTGTCCCGACAACACGAACAGATGACAAGT
TGCGAATGGAGACATGCTTCCAACAGGCGTGTAAGGGTAAAATCCAAGCA
CTCTGCGAGAATCCCGAGTGGGCACCATTGAAGGATAACAGGATTCCTTC
ATACGGGGTCTTGTCTGTTGATCTGAGTCTGACAGTTGAGCTTAAAATCA
AAATTGCTTCGGGATTCGGGCCATTGATCACACACGGTTCAGGGATGGAC
CTATACAAATCCAACCACAACAATGTGTATTGGCTGACTATCCCGCCAAT
GAAGAACCTAGCCTTAGGTGTAATCAACACATTGGAGTGGATACCGAGAT
TCAAGGTTAGTCCCTACCTCTTCACTGTCCCAATTAAGGAAGCAGGCGAA
GACTGCCATGCCCAACATACCTACCTGCGGAGGTGGATGGTGATGTCAA
ACTCAGTTCCAATCTGGTGATTCTACCTGGTCAAGATCTCCAATATGTTT
TGGCAACCTACGATACTTCCAGGGTTGAACATGCTGTGGTTTATTACGTT
TACAGCCCAAGCCGCTCATTTTCTTACTTTTATCCTTTTAGGTTGCCTAT
AAAGGGGGTCCCCATCGAATTACAAGTGGAATGCTTCACATGGGACCAAA
AACTCTGGTGCCGTCACTTCTGTGTGCTTGCGGACTCAGAATCTGGTGGA
CATATCACTCACTCTGGGATGGTGGGCATGGGAGTCAGCTGCACAGTCAC
CCGGGAAGATGGAACCAATCGCAGATAGGGCTGCTAGTGAACCAATCACA
TGATGTCACCCAGACATCAGGCATACCCACTAGTCTACCCTCCATCATTG
TTATAAAAAACTTAGGAACCAGGTCCACACAGCCGCCAGCCCATCAACGC
GTACG atgagtaaaggagaagaacttttcactggagttgtcccaattctt
gttgaattagatggtgatgttaatgggcacaaattttctgtcagtggaga
gggtgaaggtgatgcaacatacggaaaacttaccttaaatttatttgca
ctactggaaaactacctgttccatggccaacacttgtcactactttcacc
tatggtgttcaatgcttttcaagatacccagatcatatgaaacggcatga
cttttcaagagtgccatgcccgaaggttatgtacaggaaagaactatat
ttttcaaagatgacgggaactacaagacacgtgctgaagtcaagtttgaa
ggtgatacccttgttaatagaatcgagttaaaaggtattgatttaaaga
agatggaaacattcttggacacaaattggaatacaactataactcacaca
atgtatacatcatggcagacaaacaaaagaatggaatcaaagttaacttc
aaaattagacacaacattgaagatggaagcgttcaactagcagaccatta
tcaacaaaatactccaattggcgatggccctgtccttttaccagacaacc
attacctgtccacacaatctgccctttcgaaagatcccaacgaaaagaga
gaccacatggtccttcttgagtttgtaacagctgctgggattacacatgg
catggatgaactatacaaatag TGAGCGCGCAGCGCTTAGACGTCTCGCG
ATCGATGCTAGTGTGAAATAGACATCAGAATTAAGAAAAACGTAGGGTCC
AAGTGGTTCCCCGTTATGGACTCGCTATCTGTCAACCAGATCTTATACCC
TGAAGTTCACCTAGATAGCCCGATAGTTACCAATAAGATAGTAGCCATCC
TGGAGTATGCTCGAGTCCCTCACGCTTACAGCCTGGAGGACCCTACACTG
TGTCAGAACATCAAGCACCGCCTAAAAAACGGATTTTCCAACCAAATGAT
TATAAACAATGTGGAAGTTGGGAATGTCATCAAGTCCAAGCTTAGGAGTT
ATCCGGCCCACTCTCATATTCCATATCCAAATTGTAATCAGGATTTATTT
AACATAGAAGACAAAGAGTCAACGAGGAAGATCCGTGAACTCCTCAAAAA
GGGGAATTCGCTGTACTCCAAAGTCAGTGATAAGGTTTTCCAATGCTTAA
GGGACACTAACTCACGGCTTGGCCTAGGCTCCGAATTGAGGGAGGACATC
AAGGAGAAAGTTATTAACTTGGGAGTTTACATGCACAGCTCCCAGTGGTT

FIGURE 32.8

```
TGAGCCCTTTCTGTTTTGGTTTACAGTCAAGACTGAGATGAGGTCAGTGA
TTAAATCACAAACCCATACTTGCCATAGGAGGAGACACACACCTGTATTC
TTCACTGGTAGTTCAGTTGAGTTGCTAATCTCTCGTGACCTTGTTGCTAT
AATCAGTAAAGAGTCTCAACATGTATATTACCTGACATTTGAACTGGTTT
TGATGTATTGTGATGTCATAGAGGGGAGGTTAATGACAGAGACCGCTATG
ACTATTGATGCTAGGTATACAGAGCTTCTAGGAAGAGTCAGATACATGTG
GAAACTGATAGATGGTTTCTTCCCTGCACTCGGGAATCCAACTTATCAAA
TTGTAGCCATGCTGGAGCCTCTTTCACTTGCTTACCTGCAGCTGAGGGAT
ATAACAGTAGAACTCAGAGGTGCTTTCCTTAACCACTGCTTTACTGAAAT
ACATGATGTTCTTGACCAAAACGGGTTTTCTGATGAAGGTACTTATCATG
AGTTAACTGAAGCTCTAGATTACATTTTCATAACTGATGACATACATCTG
ACAGGGGAGATTTTCTCATTTTTCAGAAGTTTCGGCCACCCCAGACTTGA
AGCAGTAACGGCTGCTGAAAATGTTAGGAAATACATGAATCAGCCTAAAG
TCATTGTGTATGAGACTCTGATGAAAGGTCATGCCATATTTTGTGGAATC
ATAATCAACGGCTATCGTGACAGGCACGGAGGCAGTTGGCCACCGCTGAC
CCTCCCCCTGCATGCTGCAGACACAATCCGGAATGCTCAAGCTTCAGGTG
AAGGGTTAACACATGAGCAGTGCGTTGATAACTGGAAATCTTTTGCTGGA
GTGAAATTTGGCTGCTTATGCCTCTTAGCCTGGATAGTGATCTGACAAT
GTACCTAAAGGACAAGGCACTTGCTGCTCTCCAAAGGGAATGGGATTCAG
TTTACCCGAAAGAGTTCCTGCGTTACGACCCTCCCAAGGGAACCGGGTCA
CGGAGGCTTGTAGATGTTTTCCTTAATGATTCGAGCTTTGACCCATATGA
TGTGATAATGTATGTTGTAAGTGGAGCTTACCTCCATGACCCTGAGTTCA
ACCTGTCTTACAGCCTGAAAGAAAAGGAGATCAAGGAAACAGGTAGACTT
TTTGCTAAAATGACTTACAAAATGAGGGCATGCCAAGTGATTGCTGAAAA
TCTAATCTCAAACGGGATTGGCAAATATTTTAAGGACAATGGGATGGCCA
AGGATGAGCACGATTTGACTAAGGCACTCCACACTCTAGCTGTCTCAGGA
GTCCCCAAAGATCTCAAAGAAAGTCACAGGGGGGGGCCAGTCTTAAAAAC
CTACTCCCGAAGCCCAGTCCACACAAGTACCAGGAACGTGAGAGCAGCAA
AAGGGTTTATAGGGTTCCCTCAAGTAATTCGGCAGGACCAAGACACTGAT
CATCCGGAGAATATGGAAGCTTACGAGACAGTCAGTGCATTTATCACGAC
TGATCTCAAGAAGTACTGCCTTAATTGGAGATATGAGACCATCAGCTTGT
TTGCACAGAGGCTAAATGAGATTTACGGATTGCCCTCATTTTTCCAGTGG
CTGCATAAGAGGCTTGAGACCTCTGTCCTGTATGTAAGTGACCCTCATTG
CCCCCCCGACCTTGACGCCCATATCCCGTTATATAAAGTCCCCAATGATC
AAATCTTCATTAAGTACCCTATGGGAGGTATAGAAGGGTATTGTCAGAAG
CTGTGGACCATCAGCACCATTCCCTATCTATACCTGGCTGCTTATGAGAG
CGGAGTAAGGATTGCTTCGTTAGTGCAAGGGGACAATCAGACCATAGCCG
TAACAAAAAGGGTACCCAGCACATGGCCCTACAACCTTAAGAAACGGGAA
GCTGCTAGAGTAACTAGAGATTACTTTGTAATTCTTAGGCAAAGGCTACA
TGATATTGGCCATCACCTCAAGGCAAATGAGACAATTGTTTCATCACATT
TTTTTGTCTATTCAAAAGGAATATATTATGATGGGCTACTTGTGTCCCAA
TCACTCAAGAGCATCGCAAGATGTGTATTCTGGTCAGAGACTATAGTTGA
TGAAACAAGGGCAGCATGCAGTAATATTGCTACAACAATGGCTAAAAGCA
TCGAGAGAGGTTATGACCGTTACCTTGCATATTCCCTGAACGTCCTAAAA
GTGATACAGCAAATTCTGATCTCTCTTGGCTTCACAATCAATTCAACCAT
GACCCGGGATGTAGTCATACCCCTCCTCACAAACAACGACCTCTTAATAA
GGATGGCACTGTTGCCCGCTCCTATTGGGGGGATGAATTATCTGAATATG
AGCAGGCTGTTTGTCAGAAACATCGGTGATCCAGTAACATCATCAATTGC
```

FIGURE 32.9

```
TGATCTCAAGAGAATGATTCTCGCCTCACTAATGCCTGAAGAGACCCTCC
ATCAAGTAATGACACAACAACCGGGGGACTCTTCATTCCTAGACTGGGCT
AGCGACCCTTACTCAGCAAATCTTGTATGTGTCCAGAGCATCACTAGACT
CCTCAAGAACATAACTGCAAGGTTTGTCCTGATCCATAGTCCAAACCCAA
TGTTAAAAGGATTATTCCATGATGACAGTAAAGAAGAGGACGAGGGACTG
GCGGCATTCCTCATGGACAGGCATATTATAGTACCTAGGGCAGCTCATGA
AATCCTGGATCATAGTGTCACAGGGGCAAGAGAGTCTATTGCAGGCATGC
TGGATACCACAAAAGGCTTGATTCGAGCCAGCATGAGGAAGGGGGGGTTA
ACCTCTCGAGTGATAACCAGATTGTCCAATTATGACTATGAACAATTCAG
AGCAGGGATGGTGCTATTGACAGGAAGAAAGAGAAATGTCCTCATTGACA
AAGAGTCATGTTCAGTGCAGCTGGCGAGAGCTCTAAGAAGCCATATGTGG
GCGAGGCTAGCTCGAGGACGGCCTATTTACGGCCTTGAGGTCCCTGATGT
ACTAGAATCTATGCGAGGCCACCTTATTCGGCGTCATGAGACATGTGTCA
TCTGCGAGTGTGGATCAGTCAACTACGGATGGTTTTTTGTCCCCTCGGGT
TGCCAACTGGATGATATTGACAAGGAAACATCATCCTTGAGAGTCCCATA
TATTGGTTCTACCACTGATGAGAGAACAGACATGAAGCTTGCCTTCGTAA
GAGCCCCAAGTCGATCCTTGCGATCTGCTGTTAGAATAGCAACAGTGTAC
TCATGGGCTTACGGTGATGATGATAGCTCTTGGAACGAAGCCTGGTTGTT
GGCTAGGCAAAGGGCCAATGTGAGCCTGGAGGAGCTAAGGGTGATCACTC
CCATCTCAACTTCGACTAATTTAGCGCATAGGTTGAGGGATCGTAGCACT
CAAGTGAAATACTCAGGTACATCCCTTGTCCGAGTGGCGAGGTATACCAC
AATCTCCAACGACAATCTCTCATTTGTCATATCAGATAAGAAGGTTGATA
CTAACTTTATATACCAACAAGGAATGCTTCTAGGGTTGGGTGTTTTAGAA
ACATTGTTTCGACTCGAGAAAGATACCGGATCATCTAACACGGTATTACA
TCTTCACGTCGAAACAGATTGTTGCGTGATCCCGATGATAGATCATCCCA
GGATACCCAGCTCCCGCAAGCTAGAGCTGAGGGCAGAGCTATGTACCAAC
CCATTGATATATGATAATGCACCTTTAATTGACAGAGATGCAACAAGGCT
ATACACCCAGAGCCATAGGAGGCACCTTGTGGAATTTGTTACATGGTCCA
CACCCCAACTATATCACATTTTAGCTAAGTCCACAGCACTATCTATGATT
GACCTGGTAACAAAATTTGAGAAGGACCATATGAATGAAATTTCAGCTCT
CATAGGGGATGACGATATCAATAGTTTCATAACTGAGTTTCTGCTCATAG
AGCCAAGATTATTCACTATCTACTTGGGCCAGTGTGCGGCCATCAATTGG
GCATTTGATGTACATTATCATAGACCATCAGGGAAATATCAGATGGGTGA
GCTGTTGTCATCGTTCCTTTCTAGAATGAGCAAGGAGTGTTTAAGGTGC
TTGTCAATGCTCTAAGCCACCCAAAGATCTACAAGAAATTCTGGCATTGT
GGTATTATAGAGCCTATCCATGGTCCTTCACTTGATGCTCAAAACTTGCA
CACAACTGTGTGCAACATGGTTTACACATGCTATATGACCTACCTCGACC
TGTTGTTGAATGAAGAGTTAGAAGAGTTCACATTTCTCTTGTGTGAAAGC
GACGAGGATGTAGTACCGGACAGATTCGACAACATCCAGGCAAAACACTT
ATGTGTTCTGGCAGATTTGTACTGTCAACCAGGGACCTGCCCACCAATTC
GAGGTCTAAGACCGGTAGAGAAATGTGCAGTTCTAACCGACCATATCAAG
GCAGAGGCTATGTTATCTCCAGCAGGATCTTCGTGGAACATAAATCCAAT
TATTGTAGACCATTACTCATGCTCTCTGACTTATCTCCGGCGAGGATCGA
TCAAACAGATAAGATTGAGAGTTGATCCAGGATTCATTTTCGACGCCCTC
GCTGAGGTAAATGTCAGTCAGCCAAAGATCGGCAGCAACAACATCTCAAA
TATGAGCATCAAGGCTTTCAGACCCCACACGATGATGTTGCAAAATTGC
TCAAAGATATCAACACAAGCAAGCACAATCTTCCCATTTCAGGGGGCAAT
CTCGCCAATTATGAAATCCATGCTTTCCGCAGAATCGGGTTGAACTCATC
```

FIGURE 32.10

TGCTTGCTACAAAGCTGTTGAGATATCAACATTAATTAGGAGATGCCTTG
AGCCAGGGGAGGACGGCTTGTTCTTGGGTGAGGGATCGGGTTCTATGTTG
ATCACTTATAAAGAGATACTTAAACTAAACAAGTGCTTCTATAATAGTGG
GGTTTCCGCCAATTCTAGATCTGGTCAAAGGGAATTAGCACCCTATCCCT
CCGAAGTTGGCCTTGTCGAACACAGAATGGGAGTAGGTAATATTGTCAAA
GTGCTCTTTAACGGGAGGCCCGAAGTCACGTGGGTAGGCAGTGTAGATTG
CTTCAATTTCATAGTTAGTAATATCCCTACCTCTAGTGTGGGGTTTATCC
ATTCAGATATAGAGACCTTGCCTGACAAAGATACTATAGAGAAGCTAGAG
GAATTGGCAGCCATCTTATCGATGGCTCTGCTCCTGGGCAAAATAGGATC
AATACTGGTGATTAAGCTTATGCCTTTCAGCGGGGATTTTGTTCAGGGAT
TTATAAGTTATGTAGGGTCTCATTATAGAGAAGTGAACCTTGTATACCCT
AGATACAGCAACTTCATCTCTACTGAATCTTATTTGGTTATGACAGATCT
CAAGGCTAACCGGCTAATGAATCCTGAAAAGATTAAGCAGCAGATAATTG
AATCATCTGTGAGGACTTCACCTGGACTTATAGGTCACATCCTATCCATT
AAGCAACTAAGCTGCATACAAGCAATTGTGGGAGACGCAGTTAGTAGAGG
TGATATCAATCCTACTCTGAAAAAACTTACACCTATAGAGCAGGTGCTGA
TCAATTGCGGGTTGGCAATTAACGGACCTAAGCTGTGCAAAGAATTGATC
CACCATGATGTTGCCTCAGGGCAAGATGGATTGCTTAATTCTATACTCAT
CCTCTACAGGGAGTTGGCAAGATTCAAAGACAACCAAAGAAGTCAACAAG
GGATGTTCCACGCTTACCCCGTATTGGTAAGTAGCAGGCAACGAGAACTT
ATATCTAGGATCACCCGCAAATTCTGGGGCACATTCTTCTTTACTCCGG
GAACAAAAAGTTGATAAATAAGTTTATCCAGAATCTCAAGTCCGGCTATC
TGATACTAGACTTACACCAGAATATCTTCGTTAAGAATCTATCCAAGTCA
GAGAAACAGATTATTATGACGGGGGGTTTGAAACGTGAGTGGGTTTTTAA
GGTAACAGTCAAGGAGACCAAAGa *ATGGTATAAGTTAGTCGGATACAGTG*
*CCCTGATTAAGGACTAATTGGTTGAACTCCGGAACCCTAATCCTGCCCTA*
*GGTGGTTAGGCATTATTTGCAATATATTAAAGAAAACTTTGAAAATACGA*
*AGTTTCTATTCCCAGCTTTGTCTGGT* ggccggcatggtcccagcctcctc
gctggcgccggctggcaacattccgaggggaccgtcccctcggtaatgg
cgaatgggac GCGGCCGATCCGGCTGCTAACAAAGCCCGAAAGGAAGCTGAGTTG
GCTGCTGCCACCGCTGAGCAATAACTAGCATAACCCCTTGGGGCCTCTAAACGGG
TCTTGAGGGGTTTTTTGCTGAAAGGAGGAACTATATCCGGAT
GGCGGCCGCTCGAGCATGCATCTAGAGGGCCGCATCATGTAATTAGTT
ATGTCACGCTTACATTCACGCCCTCCCCCACATCCGCTCTAACCGAAAA
GGAAGGAGTTAGACAACCTGAAGTCTAGGTCCCTATTTATTTTTTTATAG
TTATGTTAGTATTAAGAACGTTATTTATATTTCAAATTTTTCTTTTTTTT
CTGTACAGACGCGTGTACGCATGTAACATTATACTGAAAACCTTGCTTGA
GAAGGTTTTGGGACGCTCGAAGGCTTTAATTTGCGGCC

FIGURE 33.1

Recombinant measles genome sequence (pCM603)

| | |
|---|---|
| pYES2 vector : | Capital letter |
| Measles genome sequence: | Capital letter |
| Ribozymes Sequence : | Minuscule letter |
| Leader sequence : | Bold capital letter |
| Trailer sequence : | Bold italic capital letter |
| *eGFP* sequence : | Bold minuscule letter |
| *KANMX4* sequence : | Minuscule italic letter |

```
CTGCATTAATGAATCGGCCAACGCGCGGGGAGAGGCGGTTTGCGTATTGG
GCGCTCTTCCGCTTCCTCGCTCACTGACTCGCTGCGCTCGGTCGTTCGGC
TGCGGCGAGCGGTATCAGCTCACTCAAAGGCGGTAATACGGTTATCCACA
GAATCAGGGGATAACGCAGGAAAGAACATGTGAGCAAAAGGCCAGCAAAA
GCCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGA
AACCCGACAGGACTATAAAGATACCAGGCGTTTCCCCCTGGAAGCTCCCT
CGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACC
CCCCGTTCAGCCCGACCGCTGCGCCTTATCCGGTAACTATCGTCTTGAGT
CCAACCCGGTAAGACACGACTTATCGCCACTGGCAGCAGCCACTGGTAAC
AGGATTAGCAGAGCGAGGTATGTAGGCGGTGCTACAGAGTTCTTGAAGTG
GTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGG
GGTCTGACGCTCAGTGGAACGAAAACTCACGTTAAGGGATTTTGGTCATG
AGATTATCAAAAAGGATCTTCACCTAGATCCTTTTAAATTAAAAATGAAG
TTTTAAATCAATCTAAAGTATATATGAGTAAACTTGGTCTGACAGTTACC
AATGCTTAATCAGTGAGGCACCTATCTCAGCGATCTGTCTATTTCGTTCA
TCCATAGTTGCCTGACTCCCCGTCGTGTAGATAACTACGATACGGGAGCG
CTTACCATCTGGCCCCAGTGCTGCAATGATACCGCGAGACCCACGCTCAC
CGGCTCCAGATTTATCAGCAATAAACCAGCCAGCCGGAAGGGCCGAGCGC
AGAAGTGGTCCTGCAACTTTATCCGCCTCCATTCAGTCTATTAATTGTTG
CCGGGAAGCTAGAGTAAGTAGTTCGCCAGTTAATAGTTTGCGCAACGTTG
TTGGCATTGCTACAGGCATCGTGGTGTCACTCTCGTCGTTTGGTATGGCT
TCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAAT
TCTCTTACTGTCATGCCATCCGTAAGATGCTTTTCTGTGACTGGTGAGTA
CTCAACCAAGTCATTCTGAGAATAGTGTATGCGGCGACCGAGTTGCTCTT
GCCCGGCGTCAATACGGGATAATAGTGTATCACATAGCAGAACTTTAAAA
GTGCTCATCATTGGAAAACGTTCTTCGGGGCGAAAACTCTCAAGGATCTT
ACCGCTGTTGAGATCCAGTTCGATGTAACCCACTCGTGCACCCAACTGAT
```

FIGURE 33.2

```
CTTCAGCATCTTTTACTTTCACCAGCGTTTCTGGGTGAGCAAAAACAGGA
AGGCAAAATGCCGCAAAAAGGGAATAAGGGCGACACGGAAATGTTGAAT
ACTCATACTCTTCCTTTTTCAATGGGTAATAACTGATATAATTAAATTGA
AGCTCTAATTTGTGAGTTTAGTATACATGCATTTACTTATAATACAGTTT
TTTAGTTTTGCTGGCCGCATCTTCTCAAATATGCTTCCCAGCCTGCTTTT
CTGTAACGTTCACCCTCTACCTTAGCATCCCTTCCCTTTGCAAATAGTCC
TCTTCCAACAATAATAATGTCAGATCCTGTAGAGACCACATCATCCACGG
TTCTATACTGTTGACCCAATGCGTCTCCCTTGTCATCTAAACCCACACCG
GGTGTCATAATCAACCAATCGTAACCTTCATCTCTTCCACCCATGTCTCT
TTGAGCAATAAAGCCGATAACAAAATCTTTGTCGCTCTTCGCAATGTCAA
CAGTACCCTTAGTATATTCTCCAGTAGATAGGGAGCCCTTGCATGACAAT
TCTGCTAACATCAAAAGGCCTCTAGGTTCCTTTGTTACTTCTTCTGCCGC
CTGCTTCAAACCGCTAACAATACCTGGGCCCACCACACCGTGTGCATTCG
TAATGTCTGCCCATTCTGCTATTCTGTATACACCCGCAGAGTACTGCAAT
TTGACTGTATTACCAATGTCAGCAAATTTTCTGTCTTCGAAGAGTAAAAA
ATTGTACTTGGCGGATAATGCCTTTAGCGGCTTAACTGTGCCCTCCATGG
AAAAATCAGTCAAGATATCCACATGTGTTTTTAGTAAACAAATTTTGGGA
CCTAATGCTTCAACTAACTCCAGTAATTCCTTGGTGGTACGAACATCCAA
TGAAGCACACAAGTTTGTTTGCTTTTCGTGCATGATATTAAATAGCTTGG
CAGCAACAGGACTAGGATGAGTAGCAGCACGTTCCTTATATGTAGCTTTC
GACATGATTTATCTTCGTTTCCTGCAGGTTTTTGTTCTGTGCAGTTGGGT
TAAGAATACTGGGCAATTTCATGTTTCTTCAACACTACATATGCGTATAT
ATACCAATCTAAGTCTGTGCTCCTTCCTTCGTTCTTCCTTCTGTTCGGAG
ATTACCGAATCAAAAAAATTTCAAAGAAACCGAAATCAAAAAAAAGAATA
AAAAAAAAATGATGAATTGAATTGAAAAGCTAGCTTATCGATGATAAGCT
GTCAAAGATGAGAATTAATTCCACGGACTATAGACTATACTAGATACTCC
GTCTACTGTACGATACACTTCCGCTCAGGTCCTTGTCCTTTAACGAGGCC
TTACCACTCTTTTGTTACTCTATTGATCCAGCTCAGCAAAGGCAGTGTGA
TCTAAGATTCTATCTTCGCGATGTAGTAAAACTAGCTAGACCGAGAAAGA
GACTAGAAATGCAAAAGGCACTTCTACAATGGCTGCCATCATTATTATCC
GATGTGACGCTGCAGCTTCTCAATGATATTCGAATACGCTTTGAGGAGAT
ACAGCCTAATATCCGACAAACTGTTTTACAGATTTACGATCGTACTTGTT
ACCCATCATTGAATTTTGAACATCCGAACCTGGGAGTTTTCCCTGAAACA
GATAGTATATTTGAACCTGTATAATAATATATAGTCTAGCGCTTTACGGA
AGACAATGTATGTATTTCGGTTCCTGGAGAAACTATTGCATCTATTGCAT
AGGTAATCTTGCACGTCGCATCCCCGGTTCATTTTCTGCGTTTCCATCTT
GCACTTCAATAGCATATCTTTGTTAACGAAGCATCTGTGCTTCATTTTGT
AGAACAAAAATGCAACGCGAGAGCGCTAATTTTTCAAACAAAGAATCTGA
GCTGCATTTTTACAGAACAGAAATGCAACGCGAAAGCGCTATTTTACCAA
CGAAGAATCTGTGCTTCATTTTTGTAAAACAAAAATGCAACGCGACGAGA
GCGCTAATTTTTCAAACAAAGAATCTGAGCTGCATTTTTACAGAACAGAA
ATGCAACGCGAGAGCGCTATTTTACCAACAAAGAATCTATACTTCTTTTT
TGTTCTACAAAAATGCATCCCGAGAGCGCTATTTTTCTAACAAAGCATCT
TAGATTACTTTTTTTCTCCTTTGTGCGCTCTATAATGCAGTCTCTTGATA
ACTTTTTGCACTGTAGGTCCGTTAAGGTTAGAAGAAGGCTACTTTGGTGT
CTATTTTCTCTTCCATAAAAAAGCCTGACTCCACTTCCCGCGTTTACTG
ATTACTAGCGAAGCTGCGGGTGCATTTTTTCAAGATAAAGGCATCCCCGA
TTATATTCTATACCGATGTGGATTGCGCATACTTTGTGAACAGAAAGTGA
```

FIGURE 33.3

```
TAGCGTTGATGATTCTTCATTGGTCAGAAAATTATGAACGGTTTCTTCTA
TTTTGTCTCTATATACTACGTATAGGAAATGTTTACATTTTCGTATTGTT
TTCGATTCACTCTATGAATAGTTCTTACTACAATTTTTTGTCTAAAGAG
TAATACTAGAGATAAACATAAAAATGTAGAGGTCGAGTTTAGATGCAAG
TTCAAGGAGCGAAAGGTGGATGGGTAGGTTATATAGGGATATAGCACAGA
GATATATAGCAAAGAGATACTTTTGAGCAATGTTTGTGGAAGCGGTATTC
GCAATGGGAAGCTCCACCCCGGTTGATAATCAGAAAAGCCCCAAAAACAG
GAAGATTGTATAAGCAAATATTTAAATTGTAAACGTTAATATTTTGTTAA
AATTCGCGTTAAATTTTTGTTAAATCAGCTCATTTTTTAACGAATAGCCC
GAAATCGGCAAAATCCCTTATAAATCAAAGAATAGACCGAGATAGGGTT
GAGTGTTGTTCCAGTTTCCAACAAGAGTCCACTATTAAAGAACGTGGACT
CCAACGTCAAAGGGCGAAAAAGGGTCTATCAGGGCGATGGCCCACTACGT
GAACCATCACCCTAATCAAGTTTTTTGGGGTCGAGGTGCCGTAAAGCAGT
AAATCGGAAGGGTAAACGGATGCCCCATTTAGAGCTTGACGGGGAAAGC
CGGCGAACGTGGCGAGAAAGGAAGGGAAGAAAGCGAAAGGAGCGGGGGCT
AGGGCGGTGGGAAGTGTAGGGGTCACGCTGGGCGTAACCACCACACCCGC
CGCGCTTAATGGGGCGCTACAGGGCGCGTGGGATGATCCACTAGTACGG
ATTAGAAGCCGCCGAGCGGGTGACAGCCCTCCGAAGGAAGACTCTCCTCC
GTGCGTCCTCGTCCTCACCGGTCGCGTTCCTGAAACGCAGATGTGCCTCG
CGCCGCACTGCTCCGAACAATAAAGATTCTACAATACTAGCTTTTATGGT
TATGAAGAGGAAAAATTGGCAGTAACCTGGCCCCACAAACCTTCAAATGA
ACGAATCAAATTAACAACCATAGGATGATAATGCGATTAGTTTTTTAGCC
TTATTTCTGGGGTAATTAATCAGCGAAGCGATGATTTTTGATCTATTAAC
AGATATATAAATGCAAAAACTGCATTAACCACTTTAACTAATACTTTCAA
CATTTTCGGTTTGTATTACTTCTTATTCAAATGTAATAAAAGTATCAACA
AAAAATTGTTAATATACCTCTATACTTTAACGTCAAGGAGAAAAAACCCC
GGATCGGACTACTAGCAGCTGTAATACGACTCACTATAGGGAATATAAG
CTTGGTACCGAGCTCGGATCCACTAGTAACGGCCGCCAGTGTGCTGGAAT
TCTGCAGATATCCATCACACTGGCGGCCGCTAATACGACTCACTATAGGG
ccaactttgtttggtctgatgagtccgtgaggacgaaacccggagtcccg
ggtc ACCAAACAAAGTTGGGTAAGGATAGTTCAATCAATGATCATCTTCT
AGTGCACTTAGGATTCAAGATCCTATTATCAGGGACAAGAGCAGGATTAG
GGATATCCGAGATGG CCACACTTTTAAGGAGCTTAGCATTGTTCAAAAGA
AACAAGGACAAACCACCCATTACATCAGGATCCGGTGGAGCCATCAGAGG
AATCAAACACATTATTATAGTACCAATCCCTGGAGATTCCTCAATTACCA
CTCGATCCAGACTTCTGGACCGGTTGGTGAGGTTAATTGGAAACCCGGAT
GTGAGCGGGCCCAAACTAACAGGGGCACTAATAGGTATATTATCCTTATT
TGTGGAGTCTCCAGGTCAATTGATTCAGAGGATCACCGATGACCCTGACG
TTAGCATAAGGCTGTTAGAGGTTGTCCAGAGTGACCAGTCACAATCTGGC
CTTACCTTCGCATCAAGAGGTACCAACATGGAGGATGAGGCGGACCAATA
CTTTTCACATGATGATCCAATTAGTAGTGATCAATCCAGGTTCGGATGGT
TCGGGAACAAGGAAATCTCAGATATTGAAGTGCAAGACCCTGAGGGATTC
AACATGATTCTGGGTACCATCCTAGCCCAAATTTGGGTCTTGCTCGCAAA
GGCGGTTACGGCCCCAGACACGGCAGCTGATTCGGAGCTAAGAAGGTGGA
TAAAGTACACCCAACAAGAAGGGTAGTTGGTGAATTTAGATTGGAGAGA
AAATGGTTGGATGTGGTGAGGAACAGGATTGCCGAGGACCTCTCCTTACG
CCGATTCATGGTCGCTCTAATCCTGGATATCAAGAGAACACCCGGAAACA
AACCCAGGATTGCTGAAATGATATGTGACATTGATACATATATCGTAGAG
```

FIGURE 33.4

```
GCAGGATTAGCCAGTTTTATCCTGACTATTAAGTTTGGGATAGAAACTAT
GTATCCTGCTCTTGGACTGCATGAATTTGCTGGTGAGTTATCCACACTTG
AGTCCTTGATGAACCTTTACCAGCAAATGGGGGAAACTGCACCCTACATG
GTAATCCTGGAGAACTCAATTCAGAACAAGTTCAGTGCAGGATCATACCC
TCTGCTCTGGAGCTATGCCATGGGAGTAGGAGTGGAACTTGAAAACTCCA
TGGGAGGTTTGAACTTTGGCCGATCTTACTTTGATCCAGCATATTTTAGA
TTAGGGCAAGAGATGGTAAGGAGGTCAGCTGGAAAGGTCAGTTCCACATT
GGCATCTGAACTCGGTATCACTGCCGAGGATGCAAGGCTTGTTTCAGAGA
TTGCAATGCATACTACTGAGGACAAGATCAGTAGAGCGGTTGGACCCAGA
CAAGCCCAAGTATCATTTCTACACGGTGATCAAAGTGAGAATGAGCTACC
GAGATTGGGGGGCAAGGAAGATAGGAGGGTCAAACAGAGTCGAGGAGAAG
CCAGGGAGAGCTACAGAGAAACCGGGCCCAGCAGAGCAAGTGATGCGAGA
GCTGCCCATCTTCCAACCGGCACACCCTAGACATTGACACTGCAACGGA
GTCCAGCCAAGATCCGCAGGACAGTCGAAGGTCAGCTGACGCCCTGCTTA
GGCTGCAAGCCATGGCAGGAATCTCGGAAGAACAAGGCTCAGACACGGAC
ACCCTATAGTGTACAATGACAGAAATCTTCTAGACTAGGTGCGAGAGGC
CGAGGGCCAGAACAACATCCGCCTACCATCCATCATTGTTATAAAAACT
TAGGAACCAGGTCCACACAGCCGCCAGCCCATCAACCATCCACTCCCACG
ATTGGAGCCAATGGCAGAAGAGCAGGCACGCCATGTCAAAAACGGACTGG
AATGCATCCGGGCTCTCAAGGCCGAGCCCATCGGCTCACTGGCCATCGAG
GAAGCTATGGCAGCATGGTCAGAAATATCAGACAACCCAGGACAGGAGCG
AGCCACCTGCAGGGAAGAGAAGGCAGGCAGTTCGGGTCTCAGCAAACCAT
GCCTCTCAGCAATTGGATCAACTGAAGGCGGTGCACCTCGCATCCGCGGT
CAGGGACCTGGAGAGAGCGATGACGACGCTGAAACTTTGGGAATCCCCCC
AAGAAATCTCCAGGCATCAAGCACTGGGTTACAGTGTTATTACGTTTATG
ATCACAGCGGTGAAGCGGTTAAGGGAATCCAAGATGCTGACTCTATCATG
GTTCAATCAGGCCTTGATGGTGATAGCACCCTCTCAGGAGGAGACAATGA
ATCTGAAAACAGCGATGTGGATATTGGCGAACCTGATACCGAGGGATATG
CTATCACTGACCGGGGATCTGCTCCCATCTCTATGGGGTTCAGGGCTTCT
GATGTTGAAACTGCAGAAGGAGGGGAGATCCACGAGCTCCTGAGACTCCA
ATCCAGAGGCAACAACTTTCCGAAGCTTGGGAAAACTCTCAATGTTCCTC
CGCCCCCGGACCCCGGTAGGGCCAGCACTTCCGGGACACCCATTAAAAAG
GGCACAGACGCGAGATTAGCCTCATTTGGAACGGAGATCGCGTCTTTATT
GACAGGTGGTGCAACCCAATGTGCTCGAAAGTCACCCTCGGAACCATCAG
GGCCAGGTGCACCTGCGGGGAATGTCCCGAGTGTGTGAGCAATGCCGCA
CTGATACAGGAGTGGACACCCGAATCTGGTACCACAATCTCCCCGAGATC
CCAGAATAATGAAGAAGGGGGAGACTATTATGATGATGAGCTGTTCTCTG
ATGTCCAAGATATTAAAACAGCCTTGGCCAAAATACACGAGGATAATCAG
AAGATAATCTCCAAGCTAGAATCACTGCTGTTATTGAAGGGAGAAGTTGA
GTCAATTAAGAAGCAGATCAACAGGCAAAATATCAGCATATCCACCCTGG
AAGGACACCTCTCAAGCATCATGATCGCCATTCCTGGACTTGGGAAGGAT
CCCAACGACCCCACTGCAGATGTCGAAATCAATCCCGACTTGAAACCCAT
CATAGGCAGAGATTCAGGCCGAGCACTGGCCGAAGTTCTCAAGAAACCCG
TTGCCAGCCGACAACTCCAAGGAATGACAAATGGACGGACCAGTTCCAGA
GGACAGCTGCTGAAGGAATTTCAGCTAAAGCCGATCGGGAAAAAGATGAG
CTCAGCCGTCGGGTTTGTTCCTGACACCGGCCCTGCATCACGCAGTGTAA
TCCGCTCCATTATAAAATCCAGCCGGCTAGAGGAGGATCGGAAGCGTTAC
CTGATGACTCTCCTTGATGATATCAAAGGAGCCAATGATCTTGCCAAGTT
```

FIGURE 33.5

CCACCAGATGCTGATGAAGATAATAATGAAGTAGCTACAGCTCAACTTAC
CTGCCAACCCCATGCCAGTCGACCCAACTAGCCTACCCTCCATCATTGTT
ATAAAAAACTTAGGAACCAGGTCCACACAGCCGCCAGCCCATCAACGCGT
ACG atggtgagcaagggcgaggagctgttcaccggggtggtgcccatcct
ggtcgagctggacggcgacgtaaacggccacaagttcagcgtgtccggcg
agggcgagggcgatgccacctacggcaagctgaccctgaagttcatctgc
accaccggcaagctgcccgtgccctggcccaccctcgtgaccaccctgac
ctacggcgtgcagtgcttcagccgctaccccgaccacatgaagcagcacg
acttcttcaagtccgccatgcccgaaggctacgtccaggagcgcaccatc
ttcttcaaggacgacggcaactacaagacccgcgccgaggtgaagttcga
gggcgacaccctggtgaaccgcatcgagctgaagggcatcgacttcaagg
aggacggcaacatcctggggcacaagctggagtacaactacaacagccac
aacgtctatatcatggccgacaagcagaagaacggcatcaaggtgaactt
caagatccgccacaacatcgaggacggcagcgtgcagctcgccgaccact
accagcagaacacccccatcggcgacggccccgtgctgctgcccgacaac
cactacctgagcacccagtccgccctgagcaaagaccccaacgagaagcg
cgatcacatggtcctgctggagttcgtgaccgccgcgggatcactctcg
gcatggacgagctgtacaagtag GCGCGCAGCGCTTAGACGTCTCGCGAT
CGATACTAGTACAACCTAAATCCATTATAAAAAACTTAGGAGCAAAGTGA
TTGCCTCCCAAGGTCCACAATGACAGAGACCTACGACTTCGACAAGTCGG
CATGGGACATCAAAGGGTCGATCGCTCCGATACAACCCACCACCTACAGT
GATGGCAGGCTGGTGCCCCAGGTCAGAGTCATAGATCCTGGTCTAGGCGA
CAGGAAGGATGAATGCTTTATGTACATGTTTCTGCTGGGGGTTGTTGAGG
ACAGCGATTCCCTAGGGCCTCCAATCGGGCGAGCATTTGGGTTCCTGCCC
TTAGGTGTTGGCAGATCCACAGCAAAGCCCGAAAAACTCCTCAAAGAGGC
CACTGAGCTTGACATAGTTGTTAGACGTACAGCAGGGCTCAATGAAAAAC
TGGTGTTCTACAACAACACCCCACTAACTCTCCTCACACCTTGGAGAAAG
GTCCTAACAACAGGGAGTGTCTTCAACGCAAACCAAGTGTGCAATGCGGT
TAATCTGATACCGCTCGATACCCCGCAGAGGTTCCGTGTTGTTTATATGA
GCATCACCCGTCTTTCGGATAACGGGTATTACACCGTTCCTAGAAGAATG
CTGGAATTCAGATCGGTCAATGCAGTGGCCTTCAACCTGCTGGTGACCCT
TAGGATTGACAAGGCGATAGGCCCTGGGAAGATCATCGACAATACAGAGC
AACTTCCTGAGGCAACATTTATGGTCCACATCGGGAACTTCAGGAGAAAG
AAGAGTGAAGTCTACTCTGCCGATTATTGCAAAATGAAAATCGAAAAGAT
GGGCCTGGTTTTTGCACTTGGTGGGATAGGGGCACCAGTCTTCACATTA
GAAGCACAGGCAAAATGAGCAAGACTCTCCATGCACAACTCGGGTTCAAG
AAGACCTTATGTTACCCGCTGATGGATATCAATGAAGACCTTAATCGATT
ACTCTGGAGGAGCAGATGCAAGATAGTAAGAATCCAGGCAGTTTTGCAGC
CATCAGTTCCTCAAGAATTCCGCATTTACGACGACGTGATCATAAATGAT
GACCAAGGACTATTCAAAGTTCTGTAGACCGTAGTGCCCAGCAATGCCCG
AAAACGACCCCCTCACAATGACAGCCAGAAGGCCCGGACAAAAAGCCC
CCTCCGAAAGACTCCACGGACCAAGCGAGAGGCCAGCCAGCAGCCGACGG
CAAGCGCGAACACCAGGCGGCCCCAGCACAGAACAGCCCTGACACAAGGC
CACCACCAGCCACCCCAATCTGCATCCTCCTCGTGGGACCCCCGAGGACC
AACCCCCAAGGCTGCCCCCGATCCAAACCACCAACCGCATCCCCACCACC
CCCGGGAAAGAAACCCCCAGCAATTGGAAGGCCCCTCCCCCTCTTCCTCA
ACACAAGAACTCCACAACCGAACCGCACAAGCGACCGAGGTGACCCAACC
GCAGGCATCCGACTCCCTAGACAGATCCTCTCTCCCCGGCAAACTAAACA

FIGURE 33.6

```
AAACTTAGGGGCCAAGGAACATACACACCCAACAGAACCCAGACCCCGGCC
CACGGCGCCGCGCCCCAACCCCCGACAACCAGAGGGAGCCCCCAACCAA
TCCCGCCGGCTCCCCGGTGCCCACAGGCAGGGACACCAACCCCCGAACA
GACCCAGCACCCAACCATCGACAATCCAAGACGGGGGGGCCCCCCAAAA
AAAGGCCCCAGGGGCCGACAGCCAGCACCGCGAGGAAGCCCACCCACCC
CACACACGACCACGGCAACCAAACCAGAACCCAGACCACCCTGGGCCACC
AGCTCCCAGACTCGGCCATCACCCCGCAGAAAGGAAAGGCCACAACCCGC
GCACCCCAGCCCCGATCCGGCGGGGAGCCACCCAACCCGAACCAGCACCC
AAGAGCGATCCCCGAAGGACCCCGAACCGCAAAGGACATCAGTATCCCA
CAGCCTCTCCAAGTCCCCGGTCTCCTCCTCTTCTCGAAGGGACCAAAAG
ATCAATCCACCACACCCGACGACACTCAACTCCCCACCCCTAAAGGAGAC
ACCGGGAATCCCAGAATCAAGACTCATCCAATGTCCATCATGGGTCTCAA
GGTGAACGTCTCTGCCATATTCATGGCAGTACTGTTAACTCTCCAAACAC
CCACCGGTCAAATCCATTGGGGCAATCTCTCTAAGATAGGGGTGGTAGGA
ATAGGAAGTGCAAGCTACAAAGTTATGACTCGTTCCAGCCATCAATCATT
AGTCATAAAATTAATGCCCAATATAACTCTCCTCAATAACTGCACGAGGG
TAGAGATTGCAGAATACAGGAGACTACTGAGAACAGTTTTGGAACCAATT
AGAGATGCACTTAATGCAATGACCCAGAATATAAGACCGGTTCAGAGTGT
AGCTTCAAGTAGGAGACACAAGAGATTTGCGGGAGTAGTCCTGGCAGGTG
CGGCCCTAGGCGTTGCCACAGCTGCTCAGATAACAGCCGGCATTGCACTT
CACCAGTCCATGCTGAACTCTCAAGCCATCGACAATCTGAGAGCGAGCCT
GGAAACTACTAATCAGGCAATTGAGACAATCAGACAAGCAGGGCAGGAGA
TGATATTGGCTGTTCAGGGTGTCCAAGACTACATCAATAATGAGCTGATA
CCGTCTATGAACCAACTATCTTGTGATTTAATCGGCCAGAAGCTCGGGCT
CAAATTGCTCAGATACTATACAGAAATCCTGTCATTATTTGGCCCCAGTT
TACGGGACCCCATATCTGCGGAGATATCTATCCAGGCTTTGAGCTATGCG
CTTGGAGGAGACATCAATAAGGTGTTAGAAAAGCTCGGATACAGTGGAGG
TGATTTACTGGGCATCTTAGAGAGCGGAGGAATAAAGGCCCGGATAACTC
ACGTCGACACAGAGTCCTACTTCATTGTCCTCAGTATAGCCTATCCGACG
CTGTCCGAGATTAAGGGGGTGATTGTCCACCGGCTAGAGGGGGTCTCGTA
CAACATAGGCTCTCAAGAGTGGTATACCACTGTGCCCAAGTATGTTGCAA
CCCAAGGGTACCTTATCTCGAATTTTGATGAGTCATCGTGTACTTTCATG
CCAGAGGGGACTGTGTGCAGCCAAAATGCCTTGTACCCGATGAGTCCTCT
GCTCCAAGAATGCCTCCGGGGGTACACCAAGTCCTGTGCTCGTACACTCG
TATCCGGGTCTTTTGGGAACCGGTTCATTTTATCACAAGGGAACCTAATA
GCCAATTGTGCATCAATCCTTTGCAAGTGTTACACAACAGGAACGATCAT
TAATCAAGACCCTGACAAGATCCTAACATACATTGCTGCCGATCACTGCC
CGGTAGTCGAGGTGAACGGCGTGACCATCCAAGTCGGGAGCAGGAGGTAT
CCAGACGCTGTGTACTTGCACAGAATTGACCTCGGTCCTCCCATATCATT
GGAGAGGTTGGACGTAGGGACAAATCTGGGGAATGCAATTGCTAAGTTGG
AGGATGCCAAGGAATTGTTGGAGTCATCGGACCAGATATTGAGGAGTATG
AAAGGTTTATCGAGCACTAGCATAGTCTACATCCTGATTGCAGTGTGTCT
TGGAGGGTTGATAGGGATCCCCGCTTTAATATGTTGCTGCAGGGGCGTT
GTAACAAAAAGGGAGAACAAGTTGGTATGTCAAGACCAGGCCTAAAGCCT
GATCTTACGGGAACATCAAAATCCTATGTAAGGTCGCTCTGATCCTCTAC
AACTCTTGAAACACAAATGTCCCACAAGTCTCCTCTTCGTCATCAAGCAA
CCACCGCACCCAGCATCAAGCCCACCTGAAATTATCTCCGGCTTCCCTCT
GGCCGAACAATATCGGTAGTTAATCAAAACTTAGGGTGCAAGATCATCCA
```

FIGURE 33.7

CAATGTCACCACAACGAGACCGGATAAATGCCTTCTACAAAGATAACCCC
CATCCCAAGGGAAGTAGGATAGTCATTAACAGAGAACATCTTATGATTGA
TAGACCTTATGTTTTGCTGGCTGTTCTGTTTGTCATGTTTCTGAGCTTGA
TCGGGTTGCTAGCCATTGCAGGCATTAGACTTCATCGGGCAGCCATCTAC
ACCGCAGAGATCCATAAAAGCCTCAGCACCAATCTAGATGTAACTAACTC
AATCGAGCATCAGGTCAAGGACGTGCTGACACCACTCTTCAAAATCATCG
GTGATGAAGTGGGCCTGAGGACACCTCAGAGATTCACTGACCTAGTGAAA
TTAATCTCTGACAAGATTAAATTCCTTAATCCGGATAGGGAGTACGACTT
CAGAGATCTCACTTGGTGTATCAACCCGCCAGAGAGAATCAAATTGGATT
ATGATCAATACTGTGCAGATGTGGCTGCTGAAGAGCTCATGAATGCATTG
GTGAACTCAACTCTACTGGAGACCAGAACAACCAATCAGTTCCTAGCTGT
CTCAAAGGGAAACTGCTCAGGGCCCACTACAATCAGAGGTCAATTCTCAA
ACATGTCGCTGTCCCTGTTAGACTTGTATTTAGGTCGAGGTTACAATGTG
TCATCTATAGTCACTATGACATCCCAGGGAATGTATGGGGAACTTACCT
AGTGGAAAAGCCTAATCTGAGCAGCAAAAGGTCAGAGTTGTCACAACTGA
GCATGTACCGAGTGTTTGAAGTAGGTGTTATCAGAAATCCGGGTTTGGGG
GCTCCGGTGTTCCATATGACAAACTATCTTGAGCAACCAGTCAGTAATGA
TCTCAGCAACTGTATGGTGGCTTTGGGGGAGCTCAAACTCGCAGCCCTTT
GTCACGGGGAAGATTCTATCACAATTCCCTATCAGGGATCAGGGAAAGGT
GTCAGCTTCCAGCTCGTCAAGCTAGGTGTCTGGAAATCCCCAACCGACAT
GCAATCCTGGGTCCCCTTATCAACGGATGATCCAGTGATAGACAGGCTTT
ACCTCTCATCTCACAGAGGTGTTATCGCTGACAATCAAGCAAAATGGGCT
GTCCCGACAACACGAACAGATGACAAGTTGCGAATGGAGACATGCTTCCA
ACAGGCGTGTAAGGGTAAAATCCAAGCACTCTGCGAGAATCCCGAGTGGG
CACCATTGAAGGATAACAGGATTCCTTCATACGGGGTCTTGTCTGTTGAT
CTGAGTCTGACAGTTGAGCTTAAAATCAAAATTGCTTCGGGATTCGGGCC
ATTGATCACACACGGTTCAGGGATGGACCTATACAAATCCAACCACAACA
ATGTGTATTGGCTGACTATCCCGCCAATGAAGAACCTAGCCTTAGGTGTA
ATCAACACATTGGAGTGGATACCGAGATTCAAGGTTAGTCCCTACCTCTT
CACTGTCCCAATTAAGGAAGCAGGCGAAGACTGCCATGCCCCAACATACC
TACCTGCGGAGGTGGATGGTGATGTCAAACTCAGTTCCAATCTGGTGATT
CTACCTGGTCAAGATCTCCAATATGTTTTGGCAACCTACGATACTTCCAG
GGTTGAACATGCTGTGGTTTATTACGTTTACAGCCCAAGCCGCTCATTTT
CTTACTTTTATCCTTTTAGGTTGCCTATAAAGGGGGTCCCCATCGAATTA
CAAGTGGAATGCTTCACATGGGACCAAAAACTCTGGTGCCGTCACTTCTG
TGTGCTTGCGGACTCAGAATCTGGTGGACATATCACTCACTCTGGGATGG
TGGGCATGGGAGTCAGCTGCACAGTCACCCGGGAAGATGGAACCAATCGC
AGATAGGGCTGCTAGTGAACCAATCACATGATGTCACCCAGACATCAGGC
ATACCCACTAGTCTACCCTCCATCATTGTTATAAAAACTTAGGAACCAG
GTCCACACAGCCGCCAGCCCATCAACGCGTACG *atgggtaaggaaaagac*
*tcacgtttcgaggccgcgattaaattccaacatggatgctgatttatatg*
*ggtataaatgggctcgcgataatgtcgggcaatcaggtgcgacaatctat*
*cgattgtatgggaagcccgatgcgccagagttgtttctgaaacatggcaa*
*aggtagcgttgccaatgatgttacagatgagatggtcagactaaactggc*
*tgacggaatttatgcctcttccgaccatcaagcattttatccgtactcct*
*gatgatgcatggttactcaccactgcgatccccggcaaaacagcattcca*
*ggtattagaagaatatcctgattcaggtgaaaatattgttgatgcgctgg*
*cagtgttcctgcgccggttgcattcgattcctgtttgtaattgtccttt*

FIGURE 33.8

*aacagcgatcgcgtatttcgtctcgctcaggcgcaatcacgaatgaataa*
*cggtttggttgatgcgagtgattttgatgacgagcgtaatggctggcctg*
*ttgaacaagtctggaaagaaatgcataagcttttgccattctcaccggat*
*tcagtcgtcactcatggtgatttctcacttgataaccttatttttgacga*
*ggggaaattaataggttgtattgatgttggacgagtcggaatcgcagacc*
*gataccaggatcttgccatcctatggaactgcctcggtgagttttctcct*
*tcattacagaaacggcttttttcaaaaatatggtattgataatcctgatat*
*gaataaattgcagtttcatttgatgctcgatgagttttttctaa* GCGCGCA
GCGCTTAGACGTCTCGCGATCGATGCTAGTGTGAAATAGACATCAGAATT
AAGAAAAACGTAGGGTCCAAGTGGTTCCCCGTTATGGACTCGCTATCTGT
CAACCAGATCTTATACCCTGAAGTTCACCTAGATAGCCCGATAGTTACCA
ATAAGATAGTAGCCATCCTGGAGTATGCTCGAGTCCCTCACGCTTACAGC
CTGGAGGACCCTACACTGTGTCAGAACATCAAGCACCGCCTAAAAAACGG
ATTTTCCAACCAAATGATTATAAACAATGTGGAAGTTGGGAATGTCATCA
AGTCCAAGCTTAGGAGTTATCCGGCCCACTCTCATATTCCATATCCAAAT
TGTAATCAGGATTTATTTAACATAGAAGACAAAGAGTCAACGAGGAAGAT
CCGTGAACTCCTCAAAAAGGGGAATTCGCTGTACTCCAAAGTCAGTGATA
AGGTTTTCCAATGCTTAAGGGACACTAACTCACGGCTTGGCCTAGGCTCC
GAATTGAGGGAGGACATCAAGGAGAAAGTTATTAACTTGGGAGTTTACAT
GCACAGCTCCCAGTGGTTTGAGCCCTTTCTGTTTTGGTTTACAGTCAAGA
CTGAGATGAGGTCAGTGATTAAATCACAAACCCATACTTGCCATAGGAGG
AGACACACCTGTATTCTTCACTGGTAGTTCAGTTGAGTTGCTAATCTC
TCGTGACCTTGTTGCTATAATCAGTAAAGAGTCTCAACATGTATATTACC
TGACATTTGAACTGGTTTTGATGTATTGTGATGTCATAGAGGGGAGGTTA
ATGACAGAGACCGCTATGACTATTGATGCTAGGTATACAGAGCTTCTAGG
AAGAGTCAGATACATGTGGAAACTGATAGATGGTTTCTTCCCTGCACTCG
GGAATCCAACTTATCAAATTGTAGCCATGCTGGAGCCTCTTTCACTTGCT
TACCTGCAGCTGAGGGATATAACAGTAGAACTCAGAGGTGCTTTCCTTAA
CCACTGCTTTACTGAAATACATGATGTTCTTGACCAAAACGGGTTTTCTG
ATGAAGGTACTTATCATGAGTTAACTGAAGCTCTAGATTACATTTTCATA
ACTGATGACATACATCTGACAGGGGAGATTTTCTCATTTTTCAGAAGTTT
CGGCCACCCCAGACTTGAAGCAGTAACGGCTGCTGAAAATGTTAGGAAAT
ACATGAATCAGCCTAAAGTCATTGTGTATGAGACTCTGATGAAAGGTCAT
GCCATATTTTGTGGAATCATAATCAACGGCTATCGTGACAGGCACGGAGG
CAGTTGGCCACCGCTGACCCTCCCCCTGCATGCTGCAGACACAATCCGGA
ATGCTCAAGCTTCAGGTGAAGGGTTAACACATGAGCAGTGCGTTGATAAC
TGGAAATCTTTTGCTGGAGTGAAATTTGGCTGCTTTATGCCTCTTAGCCT
GGATAGTGATCTGACAATGTACCTAAAGGACAAGGCACTTGCTGCTCTCC
AAAGGGAATGGGATTCAGTTTACCCGAAAGAGTTCCTGCGTTACGACCCT
CCCAAGGGAACCGGGTCACGGAGGCTTGTAGATGTTTTCCTTAATGATTC
GAGCTTTGACCCATATGATGTGATAATGTATGTTGTAAGTGGAGCTTACC
TCCATGACCCTGAGTTCAACCTGTCTTACAGCCTGAAAGAAAAGGAGATC
AAGGAAACAGGTAGACTTTTTGCTAAAATGACTTACAAAATGAGGGCATG
CCAAGTGATTGCTGAAAATCTAATCTCAAACGGGATTGGCAAATATTTTA
AGGACAATGGGATGGCCAAGGATGAGCACGATTTGACTAAGGCACTCCAC
ACTCTAGCTGTCTCAGGAGTCCCCAAAGATCTCAAAGAAAGTCACAGGGG
GGGGCCAGTCTTAAAAACCTACTCCCGAAGCCCAGTCCACACAAGTACCA
GGAACGTGAGAGCAGCAAAAGGGTTTATAGGGTTCCCTCAAGTAATTCGG

FIGURE 33.9

CAGGACCAAGACACTGATCATCCGGAGAATATGGAAGCTTACGAGACAGT
CAGTGCATTTATCACGACTGATCTCAAGAAGTACTGCCTTAATTGGAGAT
ATGAGACCATCAGCTTGTTTGCACAGAGGCTAAATGAGATTTACGGATTG
CCCTCATTTTTCCAGTGGCTGCATAAGAGGCTTGAGACCTCTGTCCTGTA
TGTAAGTGACCCTCATTGCCCCCCCGACCTTGACGCCCATATCCCGTTAT
ATAAAGTCCCCAATGATCAAATCTTCATTAAGTACCCTATGGGAGGTATA
GAAGGGTATTGTCAGAAGCTGTGGACCATCAGCACCATTCCCTATCTATA
CCTGGCTGCTTATGAGAGCGGAGTAAGGATTGCTTCGTTAGTGCAAGGGG
ACAATCAGACCATAGCCGTAACAAAAAGGGTACCCAGCACATGGCCCTAC
AACCTTAAGAAACGGGAAGCTGCTAGAGTAACTAGAGATTACTTTGTAAT
TCTTAGGCAAAGGCTACATGATATTGGCCATCACCTCAAGGCAAATGAGA
CAATTGTTTCATCACATTTTTTTGTCTATTCAAAAGGAATATATTATGAT
GGGCTACTTGTGTCCCAATCACTCAAGAGCATCGCAAGATGTGTATTCTG
GTCAGAGACTATAGTTGATGAAACAAGGGCAGCATGCAGTAATATTGCTA
CAACAATGGCTAAAAGCATCGAGAGAGGTTATGACCGTTACCTTGCATAT
TCCCTGAACGTCCTAAAAGTGATACAGCAAATTCTGATCTCTCTTGGCTT
CACAATCAATTCAACCATGACCCGGGATGTAGTCATACCCCTCCTCACAA
ACAACGACCTCTTAATAAGGATGGCACTGTTGCCCGCTCCTATTGGGGGG
ATGAATTATCTGAATATGAGCAGGCTGTTTGTCAGAAACATCGGTGATCC
AGTAACATCATCAATTGCTGATCTCAAGAGAATGATTCTCGCCTCACTAA
TGCCTGAAGAGACCCTCCATCAAGTAATGACACAACAACCGGGGGACTCT
TCATTCCTAGACTGGGCTAGCGACCCTTACTCAGCAAATCTTGTATGTGT
CCAGAGCATCACTAGACTCCTCAAGAACATAACTGCAAGGTTTGTCCTGA
TCCATAGTCCAAACCCAATGTTAAAAGGATTATTCCATGATGACAGTAAA
GAAGAGGACGAGGGACTGGCGGCATTCCTCATGGACAGGCATATTATAGT
ACCTAGGGCAGCTCATGAAATCCTGGATCATAGTGTCACAGGGGCAAGAG
AGTCTATTGCAGGCATGCTGGATACCACAAAAGGCTTGATTCGAGCCAGC
ATGAGGAAGGGGGGGTTAACCTCTCGAGTGATAACCAGATTGTCCAATTA
TGACTATGAACAATTCAGAGCAGGGATGGTGCTATTGACAGGAAGAAAGA
GAAATGTCCTCATTGACAAAGAGTCATGTTCAGTGCAGCTGGCGAGAGCT
CTAAGAAGCCATATGTGGGCGAGGCTAGCTCGAGGACGGCCTATTTACGG
CCTTGAGGTCCCTGATGTACTAGAATCTATGCGAGGCCACCTTATTCGGC
GTCATGAGACATGTGTCATCTGCGAGTGTGGATCAGTCAACTACGGATGG
TTTTTTGTCCCCTCGGGTTGCCAACTGGATGATATTGACAAGGAAACATC
ATCCTTGAGAGTCCCATATATTGGTTCTACCACTGATGAGAGAACAGACA
TGAAGCTTGCCTTCGTAAGAGCCCCAAGTCGATCCTTGCGATCTGCTGTT
AGAATAGCAACAGTGTACTCATGGGCTTACGGTGATGATGATAGCTCTTG
GAACGAAGCCTGGTTGTTGGCTAGGCAAAGGGCCAATGTGAGCCTGGAGG
AGCTAAGGGTGATCACTCCCATCTCAACTTCGACTAATTTAGCGCATAGG
TTGAGGGATCGTAGCACTCAAGTGAAATACTCAGGTACATCCCTTGTCCG
AGTGGCGAGGTATACCACAATCTCCAACGACAATCTCTCATTTGTCATAT
CAGATAAGAAGGTTGATACTAACTTTATATACCAACAAGGAATGCTTCTA
GGGTTGGGTGTTTTAGAAACATTGTTTCGACTCGAGAAAGATACCGGATC
ATCTAACACGGTATTACATCTTCACGTCGAAACAGATTGTTGCGTGATCC
CGATGATAGATCATCCCAGGATACCCAGCTCCCGCAAGCTAGAGCTGAGG
GCAGAGCTATGTACCAACCCATTGATATATGATAATGCACCTTTAATTGA
CAGAGATGCAACAAGGCTATACACCCAGAGCCATAGGAGGCACCTTGTGG
AATTTGTTACATGGTCCACACCCCAACTATATCACATTTTAGCTAAGTCC

FIGURE 33.10

ACAGCACTATCTATGATTGACCTGGTAACAAAATTTGAGAAGGACCATAT
GAATGAAATTTCAGCTCTCATAGGGGATGACGATATCAATAGTTTCATAA
CTGAGTTTCTGCTCATAGAGCCAAGATTATTCACTATCTACTTGGGCCAG
TGTGCGGCCATCAATTGGGCATTTGATGTACATTATCATAGACCATCAGG
GAAATATCAGATGGGTGAGCTGTTGTCATCGTTCCTTTCTAGAATGAGCA
AAGGAGTGTTTAAGGTGCTTGTCAATGCTCTAAGCCACCCAAAGATCTAC
AAGAAATTCTGGCATTGTGGTATTATAGAGCCTATCCATGGTCCTTCACT
TGATGCTCAAAACTTGCACACAACTGTGTGCAACATGGTTTACACATGCT
ATATGACCTACCTCGACCTGTTGTTGAATGAAGAGTTAGAAGAGTTCACA
TTTCTCTTGTGTGAAAGCGACGAGGATGTAGTACCGGACAGATTCGACAA
CATCCAGGCAAAACACTTATGTGTTCTGGCAGATTTGTACTGTCAACCAG
GGACCTGCCCACCAATTCGAGGTCTAAGACCGGTAGAGAAATGTGCAGTT
CTAACCGACCATATCAAGGCAGAGGCTATGTTATCTCCAGCAGGATCTTC
GTGGAACATAAATCCAATTATTGTAGACCATTACTCATGCTCTCTGACTT
ATCTCCGGCGAGGATCGATCAAACAGATAAGATTGAGAGTTGATCCAGGA
TTCATTTTCGACGCCTCGCTGAGGTAAATGTCAGTCAGCCAAAGATCGG
CAGCAACAACATCTCAAATATGAGCATCAAGGCTTTCAGACCCCCACACG
ATGATGTTGCAAAATTGCTCAAAGATATCAACACAAGCAAGCACAATCTT
CCCATTTCAGGGGGCAATCTCGCCAATTATGAAATCCATGCTTTCCGCAG
AATCGGGTTGAACTCATCTGCTTGCTACAAAGCTGTTGAGATATCAACAT
TAATTAGGAGATGCCTTGAGCCAGGGGAGGACGGCTTGTTCTTGGGTGAG
GGATCGGGTTCTATGTTGATCACTTATAAAGAGATACTTAAACTAAACAA
GTGCTTCTATAATAGTGGGGTTTCCGCCAATTCTAGATCTGGTCAAAGGG
AATTAGCACCCTATCCCTCCGAAGTTGGCCTTGTCGAACACAGAATGGGA
GTAGGTAATATTGTCAAAGTGCTCTTTAACGGGAGGCCCGAAGTCACGTG
GGTAGGCAGTGTAGATTGCTTCAATTTCATAGTTAGTAATATCCCTACCT
CTAGTGTGGGGTTTATCCATTCAGATATAGAGACCTTGCCTGACAAAGAT
ACTATAGAGAAGCTAGAGGAATTGGCAGCCATCTTATCGATGGCTCTGCT
CCTGGGCAAAATAGGATCAATACTGGTGATTAAGCTTATGCCTTTCAGCG
GGGATTTTGTTCAGGGATTTATAAGTTATGTAGGGTCTCATTATAGAGAA
GTGAACCTTGTATACCCTAGATACAGCAACTTCATCTCTACTGAATCTTA
TTTGGTTATGACAGATCTCAAGGCTAACCGGCTAATGAATCCTGAAAAGA
TTAAGCAGCAGATAATTGAATCATCTGTGAGGACTTCACCTGGACTTATA
GGTCACATCCTATCCATTAAGCAACTAAGCTGCATACAAGCAATTGTGGG
AGACGCAGTTAGTAGAGGTGATATCAATCCTACTCTGAAAAAACTTACAC
CTATAGAGCAGGTGCTGATCAATTGCGGGTTGGCAATTAACGGACCTAAG
CTGTGCAAAGAATTGATCCACCATGATGTTGCCTCAGGGCAAGATGGATT
GCTTAATTCTATACTCATCCTCTACAGGGAGTTGGCAAGATTCAAAGACA
ACCAAAGAAGTCAACAAGGGATGTTCCACGCTTACCCCGTATTGGTAAGT
AGCAGGCAACGAGAACTTATATCTAGGATCACCCGCAAATTCTGGGGGCA
CATTCTTCTTTACTCCGGGAACAAAAAGTTGATAAATAAGTTTATCCAGA
ATCTCAAGTCCGGCTATCTGATACTAGACTTACACCAGAATATCTTCGTT
AAGAATCTATCCAAGTCAGAGAAACAGATTATTATGACGGGGGTTTGAA
ACGTGAGTGGGTTTTTAAGGTAACAGTCAAGGAGACCAAAGA *ATGGTATA*
*AGTTAGTCGGATACAGTGCCCTGATTAAGGACTAATTGGTTGAACTCCGG*
*AACCCTAATCCTGCCCTAGGTGGTTAGGCATTATTTGCAATATATTAAAG*
*AAAACTTTGAAAATACGAAGTTTCTATTCCCAGCTTTGTCTGGT* ggccgg
catggtccagcctcctcgctggcgccggctgggcaacattccgagggga

FIGURE 33.11 ccgtcccctcggtaatggcgaatgggac GCGGCCGATCCGGCTGCTAACA
AAGCCCGAAAGGAAGCTGAGTTGGCTGCTGCCACCGCTGAGCAATAACTA
GCATAACCCCTTGGGGCCTCTAAACGGGTCTTGAGGGGTTTTTTGCTGAA
AGGAGGAACTATATCCGGATGGCGGCCGCTCGAGCATGCATCTAGAGGGC
CGCATCATGTAATTAGTTATGTCACGCTTACATTCACGCCCTCCCCCCAC
ATCCGCTCTAACCGAAAAGGAAGGAGTTAGACAACCTGAAGTCTAGGTCC
CTATTTATTTTTTTATAGTTATGTTAGTATTAAGAACGTTATTTATATTT
CAAATTTTTCTTTTTTTTCTGTACAGACGCGTGTACGCATGTAACATTAT
ACTGAAAACCTTGCTTGAGAAGGTTTTGGGACGCTCGAAGGCTTTAATTT
GCGGCC

REVERSE GENETICS OF NEGATIVE-STRAND RNA VIRUSES IN YEAST

CROSS REFERENCE TO RELATED APPLICATIONS

This application is a Divisional of copending application Ser. No. 12/865,567, filed on Apr. 28, 2011, which was filed as PCT International Application No. PCT/IB2009/000373 on Jan. 30, 2009, which claims the benefit under 35 USC. §119(a) to patent application Ser. No. 08/290,087,9, filed in EUROPE on Jan. 31, 2008, all of which are hereby expressly incorporated by reference into the present application.

TECHNICAL FIELD OF THE INVENTION

The present invention relates to a methodology for the generation by reverse genetics of infectious ribonucleoprotein complexes (RNPs) also designated ribonucleocapsids or ribonucleoparticles of negative-strand RNA viruses, and in particular of non-segmented negative-strand RNA viruses (Mononegavirales), in yeast, especially in budding yeast. More generally, this method provides means to implement the transcription and the replication of negative-strand virus RNA in yeast, to produce RNPs or derivatives.

Accordingly, the patent application relates to a recombinant yeast strain suitable for the expression of infectious RNPs of non-segmented negative-strand RNA viruses or RNPs encapsidating minigenomes, recombinant minigenomes or recombinant genomes, derived from the genome of non-segmented negative-strand RNA viruses (designated RNPs-like).

The invention also concerns the viral RNPs or RNPs-like obtainable from the recombinant yeast strain of the invention.

The invention also relates to the DNA constructs, especially to vectors providing expression of said viral RNPs or RNPs-like, suitable for use in the preparation of the recombinant yeast strain.

Many advantages may be seen in the preparation of RNPs or RNPs-like from yeast including the safety of the yeast as expression cells, the possibility to obtain high yield and productivity, the fact that the involved media for the yeast culture are not expensive one, the stability of the strains and the durability of the cells (yeast is able to survive over a very large if not indefinite period of time).

Vectors according to the invention encompass cloning vectors, expression vectors, especially used as complementation vectors or replacement vectors (the latter being also named genome vectors). The vectors of the invention may be designed for use as vaccine vectors or target vectors or as screening vectors.

By providing a new methodology for the preparation of infectious RNPs of non-segmented negative-strand RNA virus or RNPs-like particles, the invention further enables the preparation of new formulation of said immunogenic compositions or vaccine compositions.

The invention also provides means for the screening and the identification of antiviral compounds, or for the screening and the identification of cellular factors associated with viral replication or transcription, and for the study of virus-host interactions.

BACKGROUND INFORMATION

Negative-strand RNA viruses are associated with many diseases in humans such as influenza, rabies or measles. Other well known examples are the viral infections caused by Mumps virus, Respiratory Syncytial virus, Human Parainfluenza virus types 1-4, Ebola virus, Marburg virus, Hanta virus, Nipah virus, Vesicular Stomatitis virus, Rinderpest virus and canine Distemper virus (2). There are still many diseases associated with negative-strand RNA viruses, such as Parainfluenza virus, responsible for 30-40% of all acute respiratory infections in children and infants, for which no effective drugs or vaccines exist. Some of these viruses may re-emerge from animal species or reappear as new agents of bioterrorism. Moreover, measles virus still remains one of the leading causes of death by infectious agents worldwide. This, together with the insufficient therapy options today, has increased markedly the demand for new antiviral strategies.

Among negative-strand RNA viruses, the non-segmented negative-strand RNA viruses (Mononegavirales) are enveloped viruses that have genomes consisting of a single RNA molecule of negative sense. This order includes viruses with high medical relevance, such as the Rhabdoviridae, Paramyxoviridae, Filoviridae, and Bornaviridae families which are considered for the purpose of the invention. Although these viruses have distinct biological properties, their replicative and transcriptional system is conserved. Accordingly, the description of the invention which follows which is provided by reference to particular examples of viruses in this order, should be understood as providing disclosure of the corresponding features for other viruses of the order of Mononegavirales unless technically irrelevant for the skilled person.

The use of mammalian cells and reverse genetic tools to study negative-strand RNA virus has constituted a major advance for the comprehension of the biology of this group of pathogens and for the generation of vaccines (3). While positive-strand RNA or DNA viruses can be easily obtained in vitro after transfection of their engineered infectious cDNA or DNA in appropriate cells, the negative-strand RNA viruses cannot be rescued directly by reverse genetics from their cDNA. The genome of negative-strand RNA viruses is not able to initiate in vitro an infectious cycle because it does not code directly for proteins. Both transcription and replication require a transcriptase-polymerase enzymatic complex contained in the nucleoproteins encapsidating the viral genome (RNPs). Thus, the generation of recombinant negative-strand RNA viruses from cDNA involves reconstitution of active RNPs from individual components: RNA and proteins, to assemble nucleocapsids.

A remarkable set of work from numerous laboratories has allowed the establishment of different systems for rescuing almost all negative-strand RNA viruses from their cDNA (3). In contrast to the viruses with segmented genomes, the RNPs of non-segmented negative-strand RNA viruses (Mononegavirales) are tightly structured and contain, in addition to the nucleoprotein (N), the assembly and polymerase cofactor phosphoprotein (P) and the viral RNA polymerase large protein (L). The first infectious Mononegavirales, the rabies rhabdovirus, was recovered from cDNA in 1994 (4). The approach involved intracellular expression of rabies virus N, P, and L protein, along with a full length RNA whose correct 3' end was generated by the hepatitis delta virus (HDV) ribozyme. A transcript corresponding to the viral antigenome (positive strand) rather than to genome (negative strand) was used to avoid a severe antisense problem raised by the presence of N, P, and L sequences in full-length RNAs. In this system, the essential helper proteins were provided by a replication-competent vaccinia vector encoding the phage T7 RNA polymerase to drive T7-specific transcription of plasmids encoding the required proteins N, P and L. Similar systems allowed recovery of infectious rabies viruses, VSV, as well as the Paramyxoviridae Sendai virus, HPIV-3 and measles virus (3).

However, in previously described methods for generating negative-strand RNA viruses by reverse genetics from infectious cDNA it is often relied on transformed mammalian cell lines that would be inappropriate for GMP (good manufacturing production) production of clinical vaccine lots, according to the certification of international safety agencies. The development of an alternative reverse genetics system for Mononegavirales in yeast would therefore be extremely advantageous. Production in yeast has especially many advantages on the industrial scale.

In order to provide an alternative to the use of mammalian cells, the inventors have considered yeast strains, especially *Saccharomyces* strains.

The straightforward genetics of the budding yeast *Saccharomyces cerevisiae* and its high conservation of basic cellular processes with higher organisms make it an excellent tool for fundamental research and drug development (5). Yeast is frequently used to produce vaccines based on recombinant proteins or virus-like-particles. For example, the efficient and safe prophylactic HPV vaccine GARADASIL® is composed of recombinant HPV VLPs antigens that are produced in yeast (6). The advantages of yeast-based vaccines are the ease of manipulation and cultivation of *S. cerevisiae* and the use of the fermentation process to provide large amounts of viral particles. The budding yeast is a eukaryotic organism that can be also used as a simpler system to replicate live mammalian viruses and thus, to provide substrates to produce viral live-attenuated vaccines (7). Indeed, yeast has been used successfully as a model host to replicate a wide range of viruses. These include DNA and RNA viruses that infect plants, mammals and humans (8) (9) (10) (11). However, there is not yet such technology for negative-strand RNA viruses.

Viruses that replicate in yeast comprise two families of viruses: (i) DNA viruses including dsDNA (Human papillomavirus (11), Bovine papillomavirus (12) and ssDNA (Mung bean yellow mosaic India virus) and (ii) positive strand RNA viruses family including Brome mosaic virus (8), Carnation Italian ringspot virus (13), Tomato bushy stunt virus (9), Flock House virus (10) and Nodamura virus (14). Viruses that replicate in yeast have positive-strand RNA genomes and share a common replication process: the genomic positive-strand RNA genome serves as mRNA and as template for replication. This feature facilitates the replication and the transcription of this RNA virus family in yeast. Experimentally, the strategies used to replicate positive-strand RNA virus in budding yeast have some common traits. The viral RNA-dependent RNA polymerase and viral replication essential cofactors, if required, are expressed from yeast promoters. Next, positive-strand RNA genome is introduced into yeast cells either by spheroplast transformation or by in vivo transcription from a yeast expression vector. The integrity of the 5' and 3' ends of the RNA is respected because they harbor important replication elements. This can be achieved by using a ribozyme to generate the exact ends. The genomic RNA contains a reporter gene, which expression is dependent on viral replication system. Stable expression of all the components of the replicative system is achieved by using yeast plasmids carrying selectable markers. The expression of the reporter gene, which depends on viral RNA replication, indicates the presence of RNA virus replication (7).

Yeast technology and the so-called <<humanized yeast>> systems have a high impact in the understanding of the host/virus-related molecular process and are potential tools to discover novel medicinal compounds (7, 15). Many studies using genome-wide screening, DNA and protein micro arrays, deletion mutants libraries, expression profiling, genome wide synthetic lethal screens and gene dosage effects have allowed the identification in yeast of multiple host factors that affect positive-strand RNA/DNA replication and are involved in unexpected novel cellular pathways (16).

DISCLOSURE OF THE INVENTION

The invention discloses such an alternative system for reverse genetics of non-segmented negative-strand RNA viruses.

The invention is directed to methods and tools which enable the preparation of virus RNPs or virus RNPs-like of non-segmented negative-strand RNA viruses, and in particular enables the preparation, by reverse genetics, of RNPs-like which express heterologous polypeptides or peptides, the term "heterologous" meaning that the polynucleotide is not one of said non-segmented negative strand RNA virus used to provide the core of the RNPs-like. The prepared virus-RNPs or virus-RNPs-like can be preserved and stored in yeast strains, thus in particular avoiding the cost of cryoconservation of virus particles or virus-like particles, which are particularly relevant in the field of vaccine industry.

The invention also provides means suitable to produce in great amount, in particular out of yeast fermentors, RNPs of RNPs-like of several viruses of a great research, industrial, medical and/or vaccine interest. These RNPs or RNPs-like can be used as seeds to reproduce the viral particles or virus-like particles of the said non-segmented negative-strand RNA virus, in cell culture in conditions that would allow their use as immunogens, preferably as vaccine components. Accordingly, an object of the present invention is a new method for generating reproducibly and with high efficiency, infectious RNPs or RNPs-like from any non-segmented negative-strand RNA virus, in particular for such viruses which replicate in the cytoplasm of cells or in the nucleus of cells, as illustrated in the present application for Schwarz strain of measles virus (MV), starting from cloned cDNA of said virus RNA or derivatives thereof. Such a method is suitable to be carried out in yeast, especially budding yeast as illustrated by *Saccharomyces cerevisiae*.

The invention accordingly relates to a recombinant yeast strain, suitable for the expression of infectious non-segmented negative-strand RNA virus Ribonucleocapsids (RNPs) or infectious RNPs-like.

The recombinant yeast are obtained by transformation, i.e., by the introduction of nucleic acid in the cells. Integration of the introduced nucleic acid in the chromosomes of the yeast does not happen or is not required to carry out the invention.

In a particular embodiment of the invention, the recombinant yeast strain, suitable for the expression of infectious non-segmented negative-strand RNA virus Ribonucleocapsids (RNPs) or infectious RNPs-like, is obtained after being transformed with at least the following expression vector:

(i) At least one genome vector, comprising, as an insert under the control of regulatory expression sequences functional in yeast, a cloned DNA molecule which comprises a cDNA encoding the full-length (+) strand sequence (antigenome) of a non-segmented negative-strand RNA virus or encoding part of said antigenome, said cDNA thus comprising, in the 5' to 3' orientation, a sequence encoding the Trailer sequence of the genome said virus, one or more polynucleotide(s) which code(s) sequence(s) of interest cloned in sense orientation with respect to the cis-acting sequences of said virus, a sequence encoding the Leader sequence of the genome of said virus, and wherein said cDNA is flanked, in the cloned DNA molecule, by autocatalytic ribozyme sequences enabling the recovery of RNA after transcription and replication, having original 3' and 5' ends, of the genome of said non-segmented negative-strand virus.

In another particular embodiment of the invention, the recombinant yeast strain, suitable for the expression of infectious non-segmented negative-strand RNA virus Ribonucleocapsids (RNPs) or infectious RNPs-like, is obtained after being transformed with at least the combination of the following expression vectors:

(i) at least one genome vector, comprising, as an insert under the control of regulatory expression sequences functional in yeast, a cloned DNA molecule which comprises a cDNA encoding the full-length (+) strand sequence (antigenome) of a non-segmented negative-strand RNA virus or encoding part of said antigenome, said cDNA thus comprising, in the 5' to 3' orientation, a sequence encoding the Trailer sequence of the genome said virus, one or more polynucleotide(s) which code(s) sequence(s) of interest cloned in sense orientation with respect to the cis-acting sequences of said virus, a sequence encoding the Leader sequence of the genome of said virus, and wherein said cDNA is flanked, in the cloned DNA molecule, by autocatalytic ribozyme sequences enabling the recovery of RNA after transcription and replication, having original 3' and 5' ends, of the genome of said non-segmented negative-strand virus, (ii) one or more trans-complementation vectors comprising, under the control of regulatory expression sequences functional in yeast, nucleotide sequences which enable said vector(s) to collectively express the proteins necessary for the synthesis of the viral transcriptase complex of said non-segmented negative-strand RNA virus used in the genome vector, and enable assembly of the ribonucleocapsid (RNPs) or assembly of RNPs-like of said virus, which are functional in yeast for the replication and transcription, said vector(s) further comprising, under the control of regulatory expression sequences functional in yeast, a selectable marker.

Alternatively, the cDNA of the non-segmented negative-strand RNA virus encodes its (−) strand (genome), as a full-length sequence or part thereof. It is however noted that antigenomic sequence has been shown to be more efficiently used in the preparation of cDNA constructs for use in reverse genetics. Accordingly, the description which is provided herein with respect to the (+) strand of the viral RNA is transposable to the (−) strand.

In embodiments where the cDNA encodes either part of the antigenome of said non-segmented negative-strand RNA virus, or part of the genome of said non-segmented negative-strand RNA virus it necessarily comprises cis-active sequences necessary for replication and transcription, i.e., it comprises the Leader and Trailer sequences. Such a cDNA may further comprise additional regulatory region(s) of the gene transcription of the non-segmented negative-strand RNA virus such as a Promoter and/or a Terminator sequence of a gene of said virus. Such a cDNA may further or alternatively also comprise gene sequences or their coding sequences, intergenic regions or part thereof, derived from the non-segmented negative-strand RNA virus, which are contained in the full-length RNA of said virus.

In the cDNA used in accordance with the invention, the Leader sequence of said non-segmented negative-strand RNA virus comprises one viral promoter of said non-segmented negative-strand RNA virus.

The Trailer sequence also comprises a terminator sequence of the transcription.

The cDNA sequence used in accordance with the invention may further comprise, in a particular embodiment, coding sequences of the genes of said non-segmented negative-strand RNA virus and possibly also regulatory sequences of such genes (promoter, terminator, intergenic region). As stated above, in a particular embodiment, the cDNA does not contain the coding sequences of all the genes or does not contain the coding sequences of any of the viral genes.

In a particular embodiment of the invention, the cDNA comprises, as a substitution fragment of part or all of the coding sequences of the full-length antigenomic or genomic RNA or as an addition fragment in said full-length or in said part of the full-length viral RNA, a DNA insert encoding a polypeptide or a peptide of interest.

In order to insert such a DNA fragment encoding a polypeptide or a peptide of interest, it may be necessary or appropriate to insert an Additional Transcription Unit (ATU) in the cDNA. An ATU may comprise a transcription stop sequence, a poyadenylation sequence and a transcription start sequence as contained in an intergenic region of the non-segmented negative-strand RNA virus, such as for example in the N-P intergenic region, P-M intergenic region or H-L intergenic region when reference is for example made to the measles virus, or in corresponding intergenic regions of other Mononegavirales.

The DNA fragment encoding said polypeptide or said peptide of interest is advantageously inserted in an intergenic region of said the cDNA encoding the full-length antigenomic strand (or genomic strand) or part thereof if it contains such intergenic region.

The intergenic regions in the genome of the virus and especially the intergenic region between the Nucleoprotein and the Phosphoprotein is appropriate to insert said DNA fragment. Other intergenic regions may be considered also such as the intergenic region between the P and M gene, or between the H and L gene.

The DNA molecule comprising the cDNA can be introduced in the yeast by various methods such as electroporation, as insert in a vector including classical plasmids or recombinant plasmids carrying the genetic information required to replicate in eukaryotic yeast cells etc. . . . .

The genome vector(s) and the trans-complementation vector(s) of the invention is (are) especially plasmid(s).

In the recombinant yeast, the complementation vector(s) collectively provide expression of the proteins necessary for a non-segmented negative-strand RNA virus to express the transcriptase complex required to assemble ribonucleocapsids (as N protein associated with the RNA, i.e., N: RNA, and P and L proteins) necessary for transcription and replication of the virus, in the cytoplasm of cells and/or in their nucleus, especially in yeast.

Accordingly, the invention provides in a particular embodiment, one complementation vector encoding one unique protein of the transcriptase complex. In another embodiment, one vector encodes two or more of the proteins required for the preparation of the transcriptase complex.

Especially, the invention relates to a set of complementation vectors, where one vectors contains a sequence encoding the N protein of a non-segmented negative-strand RNA virus and a sequence encoding the P protein of the same non-segmented negative-strand RNA virus; and another complementation vector encoding the sequence of the L protein, in particular of the same non-segmented negative-strand RNA virus.

The transcriptase complex contains the Nucleoprotein (N) which associates to the viral genomic RNA, the Phosphoprotein (P) and the Polymerase (L), which harbour the catalytic activity. The transcriptase complex thus defined may alternatively comprise functional derivatives, especially functional fragments of said proteins.

If one trans-complementation vector comprises more than one, especially two nucleotide sequences coding for distinct proteins, each nucleotide sequence is under the control of a regulatory expression sequence. In particular, the coding sequences for said proteins are cloned in antisense orientation with respect to each other.

A regulatory expression sequence contains a promoter and if appropriate a terminator sequence for transcription.

The vector for complementation also comprises an origin replication (ori) of yeast, such a ori of the yeast 2 µm plasmid.

Suitable plasmids for the preparation of complementation vectors and/or the genome vectors of the invention are for example pESC or pYES yeast vectors.

Suitable yeast promoters for use in the complementation vectors and/or in the genome vectors are especially inducible promoters such as galactose-inducible promoters, such as GAL1 to GAL10 promoters.

The promoters controlling the transcription of the protein(s) of the transcriptase complex and the promoter controlling the expression of the selectable marker, present on a same vector are preferably different.

Suitable selectable markers for the construction of the complementation vector(s) are HIS, LEU, TRP, ADE or URA yeast genes encoding respectively histidine, leucine, tryptophane, adenine and uracile amino-acids necessary for the growth of yeasts in a medium which is devoid of said amino acids.

In the genome vector, the cDNA present in the cloned molecule—including when it is recombined with the DNA fragment which it may contain to encode a heterologous polypeptide or peptide of interest—should comply with the rules that govern the efficient replication of the non-segmented negative-strand virus from which it derives, if any.

In a particular embodiment, the invention provides the technology for the generation of a yeast strain (W303-NPL$_{MV}$) which expresses the viral proteins N, P and L respectively coding for the nucleoprotein, the phosphoprotein and the polymerase of the attenuated Schwarz strain of measles virus (MV). These three components are necessary and sufficient to allow the transcription and replication of non-segmented negative-strand RNA viruses in human cells. The invention demonstrates that the yeast strain W303-$NPL_{MV}$ can be used as a helper-trans-complementary cell to reconstitute de novo infectious RNPs from measles virus after transformation by synthesized cloned full-length infectious viral antigenomic/genomic cDNA.

Thus, in the case of most viruses of the genus Paramyxoviridae, in particular for measles virus (MV), said cDNA (possibly including also a cloned heterologous DNA fragment) complies with the "rule of six" meaning that the total number of the nucleotides of the sequence is an integral multiple of six.

It is specified that the rule of six applies, in principle, to the rubulaviruses, respiroviruses and morbilliviruses, although in some strains, it might apply with less stringency. Especially, the rule of six does not apply for VSV and RSV.

In a particular embodiment of the invention, the genome vector also comprises a gene for a selectable marker, especially an auxotrophy marker gene, suitable for use in yeast, under the control of an expression control sequence. Genes encoding HIS, LEU, TRP, URA in yeast as stated above are appropriate. This is especially desirable when the genome vector comprises a minigenome.

In an embodiment, the genome vector comprises a reporter gene (i.e., a coding sequence for a reporter molecule such as an antibiotic, or a gene that confers resistance to an antibiotic such as KANMX4 conferring resistance to kanamycin) in the cDNA, under the control of viral expression control sequences. Many reporter genes may be inserted in the genome vector (such as reporter gene conferring resistance to an antibiotic (e.g. KANMX4 gene) and a reporter gene suitable to visualize gene expression (e.g. the eGFP gene).

In another embodiment, the reporter gene is replaced by the sequence encoding the selectable marker.

The invention relates in particular to a recombinant strain, suitable for the expression of infectious non-segmented negative-strand RNA virus Ribonucleocapsids (RNPs) or infectious RNPs-like, wherein the yeast is transformed with the following expression vectors:

(i) a genome vector, especially a plasmid genome vector, comprising, as an insert operatively linked with expression control sequences functional in yeast, a cloned DNA molecule which comprises a cDNA encoding the (+) strand full-length sequence (antigenome) of said non-segmented negative-strand RNA virus and wherein said cDNA is flanked, in the cloned DNA molecule, by autocatalytic ribozyme sequences enabling the recovery of mRNA transcripts and of antigenomic RNAs of said non-segmented negative strand or derivatives thereof and (ii) a genome vector, preferably a plasmid genome vector, comprising, as an insert under the control of regulatory expression sequences functional in yeast, a cloned DNA molecule which comprises a cDNA encoding part of the antigenome of said non-segmented negative-strand RNA virus including in the 5' to 3' orientation, a viral Terminator sequence, a polynucleotide which codes a selectable marker cloned in sense orientation with respect to the cis-acting sequences of said virus and the Leader sequence of said virus, (iii) one or more trans-complementation vectors comprising, under the control of regulation expression sequences functional in yeast, nucleotide sequences which enable said vector(s) to collectively express the proteins necessary for the synthesis of the viral transcriptase complex of said non-segmented negative-strand RNA virus, and enable assembly of the ribonucleocapsid (RNPs) of said non-segmented negative-strand virus or assembly of RNPs-like comprising recombinant RNA derived from viral RNA of a non-segmented negative-strand RNA virus, wherein the RNPs or RNPs-like are functional for the replication and transcription, each of said vector(s) further comprises, under the control of regulatory expression sequences functional in yeast, a selectable marker and wherein in said vectors all the selectable markers are different from each other.

In a particular embodiment of the invention, the genome vector of (ii) above does not comprise the trailer sequence of the non-segmented negative-strand RNA virus.

The DNA molecule for cloning into the genome vector (especially plasmid vector) and in particular the cDNA which it contains may be obtained by any appropriate method, including by PCR elongation or by synthesis. For the cDNA, subgenomic fragments of said virus cDNA could be obtained by PCR elongation or synthesis and cloned.

In the recombinant yeast, the complementation vector(s) collectively provide expression the proteins necessary for a non-segmented negative-strand RNA virus to express the transcriptase complex required to assemble ribonucleocapsids (as NP: RNA, P and L) necessary for transcription and replication of the virus in the cytoplasm of cells. Thus the proteins necessary to express the transcriptase complex through the transcomplementation vectors encompass or consist in the N, P and L proteins. It may also be functional derivatives thereof, i.e., modified proteins with respect to the native one, to the extent that they enable the assembly of the nucleocapsids.

A functional derivative may be derived from the known native viral protein one of the following features:

- the nucleic acid encoding the functional derivative hybridizes in high stringency conditions with a nucleic acid encoding the wild-type (reference) RNA polymerase or with the N protein and the P protein of an identified non-segmented negative-strand RNA strain or virus. High stringency conditions are defined by Sambrook et al. in Molecular Cloning: a laboratory manual (1989). These conditions of high stringency encompass: use a prewashing solution for the nitrocellulose filters 5×SSC, 0.5% SDS, 1.0 mM EDTA (pH 8.0), hybridisation conditions of 50% formamide, 6×SSC at 42° C. and washing conditions at 68° C., 0.2×SSC and 0.1% SDS. Protocols are known to those having ordinary skill in the art. Moreover, the skilled artisan will recognize that the temperature and wash solution salt concentration can be adjusted as necessary according to experimental constraints;
- the nucleic acid encoding the functional variant presents at least 80%, preferably 90%, more preferably 95% or even 99% similarity with a native nucleic acid encoding the RNA polymerase, the N protein or the P protein, said similarity being calculated over the entire length of both sequences;
- the nucleic acid encoding the functional derivative differs from a native nucleic acid encoding the RNA polymerase, the N protein or the P protein by at least one nucleotide substitution, preferably 1, 2, 3, 4 or 5 substitution(s), optionally conservative substitutions (nucleotide substitution(s) not altering the amino acid sequence), by at least one nucleotide deletion or addition, preferably 1, 2, 3, 4 or 5 nucleotide(s) deletion or addition.

The functional derivative therefore may be a fragment of the native protein, whose nucleic acid sequence complies with one of the above definitions.

A fragment is defined in the present application as a part of the full-length RNA polymerase, of the N protein or of the P protein, as long as the fragment has the same activity as the entire protein from which it is derived, at least as a ribonucleoprotein complex (RNP complex) as disclosed herein. In a particular embodiment, the fragment represents at least 70%, particularly 80%, and more particularly 90% or even 95% of the full-length protein.

Accordingly, where reference is made herewith to RNA polymerase, N or P proteins or to their coding sequences, the description similarly applies to their functional derivatives as defined herein.

In order to have a functional genome vector, it is not required that the promoter contained in the DNA molecule, outside the sequence specifying the cDNA, be in the same orientation as the cis-acting sequences, especially the promoter, of the cDNA. Rather, it is necessary that the coding sequences or the Open Reading Frames (ORF) comprised in the cDNA be in a proper orientation with respect to the cis-acting sequences, especially the promoter, of the cDNA, i.e., be operatively linked to said promoter.

In a particular embodiment of the invention, the non-segmented negative-strand RNA is one selected among the group of Rhabdoviridae, Paramyxoviridae, Filoviridae, Bornaviridae and Flaviviridae.

The invention concerns in particular the use of viruses of the genus Vesiculovirus, Lyssavirus, Morbillivirus, Respirovirus, Rubulavirus, Pneunovirus, Ebola-like virus.

Among these viruses, the Measles Virus (MV) is one of the Paramyxoviridae which is much preferred to carry out the invention and has especially been used to illustrate the invention. Strains of measles virus, which are approved strains for vaccination such as the Schwarz strain, are particularly advantageous. Other viruses of interest are Rous Sarcoma Virus (RSV) or Human Parainfluenza Virus type 2 (HPIV-2), or HPIV-3.

An approved vaccine strain of a virus suitable for carrying out the invention is especially characterized by the fact that it has proven to be attenuated and stable after numerous cell passages, over a long period of time, and accordingly does not elicit detrimental secondary effects when administered to a host, for elicitation of protection against said virus. An approved vaccine strain may be one qualified as such because it complies with the following provisions: safety, efficacy, quality, reproducibility after review in laboratory.

According to a preferred embodiment, the yeast strain of the invention is a recombinant strain suitable for the expression of infectious RNPs of non-segmented negative-strand RNA virus or infectious RNPs-like, in particular when said virus is a measles virus, and the complementation and the genome vectors according to the invention are further characterized as follows:

(i) the complementation vectors are capable of expressing the nucleoprotein (N), the Phosphoprotein (P) and the Polymerase (L) or functional derivatives thereof which enable assembly of functional ribonucleoproteins (RNPs) comprising the transcriptase complex and, (ii) the genome vector comprises a cloned molecule which comprises a cDNA encoding the full-length (+) strand (antigenome) of said virus and wherein said cDNA is framed by autocatalytic ribozyme sequences.

In a particular embodiment, the genome vector thus defined further comprises a heterologous polynucleotide encoding a polypeptide or a peptide of interest, cloned in the cDNA.

In another particular embodiment of the recombinant yeast defined herein, the recombinant yeast strain is suitable for the expression of infectious RNPs or RNPs-like of non-segmented negative strand RNA virus, in particular when said virus is a measles virus and the complementation and the genome vectors of the invention are further characterized as follows:
(i) the complementation vector(s) are capable of collectively expressing the nucleoprotein (N), the Phosphoprotein (P) and the Polymerase (L) or functional derivatives thereof which enable assembly of functional ribonucleoproteins (RNPs) or RNPs-like comprising the transcriptase complex and,
(ii) the genome vector comprises, in an insert, a cloned DNA molecule which comprises a cDNA encoding a fragment of the (+)strand (antigenome) of said virus, including the cis-acting Leader and Trailer sequences, and furthermore one or more coding sequences, or ORF(s), heterologous to said virus, the expression of which is sought.

The particular embodiments which have been disclosed above or are described hereafter concerning the design of the various vectors, apply to these particular yeast strains.

In a particular embodiment, the nucleoprotein (N), phosphoprotein (P) and polymerase (L) are expressed by several plasmid expression vectors, wherein each vector comprises a cloned polynucleotide consisting of or containing viral coding sequences for one of the N, P or L proteins under the control of a promoter suitable for expression in yeast, especially an inducible promoter. In such a case, each of the vectors comprises a selectable marker operatively linked to regulatory expression sequences including a promoter and possibly a terminator; said promoter is different from the promoter controlling the expression of the viral coding sequence present on the same plasmid.

In another particular embodiment of the invention, the backbone of all the complementation vectors, especially of the plasmids, is identical and it is only the insert which is chosen to express either the N, P or L proteins, and the selectable marker which are different in each vector.

In a particular embodiment, the nucleoprotein (N), and the phosphoprotein (P) are expressed by a single expression vector, especially a single plasmid, and the polymerase (L) is expressed by another expression vector, especially a plasmid, said expression vectors comprising cloned polynucleotides consisting of viral coding sequences for the N and P proteins or for the L protein respectively, under the control of a promoter suitable for expression in yeast, especially an inducible promoter.

In a particular embodiment of the invention, the backbone of the vectors, e.g., of the plasmids, used to prepare the genome vector(s) and the trans-complementation vector(s) to carry out the transformation of the yeast cells are the same. In another embodiment of the invention, at least some of them are different independently from each other.

The inserts for cloning in the vectors may be prepared by any available methods, including by PCR elongation from a template, or by synthesis.

Promoters used for the design of the complementation vector, especially inducible promoters, may be identically used in the construction of the genome vector(s). The selectable markers are usually available as commercial DNA polynucleotides or cassettes and may be used either for the genome or for the complementation vectors.

In the genome vector(s), the inserted DNA molecule (insert) is cloned in the plasmid under the control of expression control sequences including a promoter and a transcription terminator sequence suitable for expression in yeast, in sense or in antisense orientation with respect to said promoter.

The N, P and L proteins expressed by the trans-complementation vectors may be of the same or of different viruses. They may be independently of each other of the same or of a different virus than the one providing the cDNA. The L protein expressed is advantageously of the same virus as the virus providing the RNA for the preparation of the cDNA.

A particular preferred yeast strain of the invention is one as defined in the present application, which is further characterized as follows:
(i) In one or in all the genome vectors, the cDNA in the cloned DNA molecule comprises at least one of the following polynucleotides:
(a) as Leader and/or Trailer sequences, the leader and/or trailer sequences of an MV virus, in particular of the Schwarz strain or any other vaccine strain;
(b) an additional Promoter sequence derived from the MV virus, e.g., the promoter of the nucleoprotein (N), phosphorprotein (P) or polymerase (L) of an MV virus, in particular of the Schwarz strain or any other vaccine strain; and/or
(c) an additional Terminator sequence derived from the MV virus, e.g., the terminator of the polymerase (L) or of the nucleoprotein (N), or the phosphorprotein (P) of an MV virus, in particular of the Schwarz strain or any other vaccine strain; and/or
(ii) The cDNA of the cloned molecule is framed by different or identical autocatalytic ribozymes selected among hammerhead ribozyme and hepatitis delta virus ribozyme.

The sequences of the Schwarz strain of the MV virus, for the preparation of all the vectors of the invention, may be obtained from the particular pTM-MVSchw plasmid deposited at the CNCM (Collection Nationale des Microorganismes Paris, France) under No I-2889 on Jun. 12, 2002, which contains the cDNA encoding the full-length antigenomic strand of the virus.

Sequences of a Schwarz strain of MV virus has also been disclosed in WO 98/13505.

The sequence of the cDNA from the virus, if said virus is an MV strain, may advantageously be prepared starting from particles of a commercial batch of vaccine strains such as the vaccines available for the Schwarz strain.

Primers are especially described in the examples of the present application, in order to isolate the N gene, P gene or L gene of the MV Schwarz strain, for example starting from the sequence of the insert in the pTM-MVSchw plasmid.

The leader sequence is characterized in that, in the native genome of the non-segmented negative-strand virus, it separates the 3' end of the virus genome (negative strand) from the beginning of the first viral gene which it contains, whereas the trailer sequence is characterized in that, it separates the 5' end of the genome of the virus from the end of the last viral gene, which it contains. The leader and the trailer sequences both contain promoter sequences and the trailer further contains a terminator sequence.

In non-segmented negative-strand RNA viruses, leader and trailer sequences are approximately 50-nucleotide long, and have a common sequence in each genera of viruses. Leader and trailer sequences of MV are illustrated in the examples.

MV sequences illustrated in the examples and figures may be replaced by corresponding sequences of other non-segmented negative-strand RNA viruses, and the proposed GAL or the viral promoters used in the constructs may be substituted by any other promoter functional in yeast or any other viral promoter respectively. The illustrated terminator sequence may also be substituted by any other viral terminator sequence. The gene coding for resistance to an antibiotic (such as Kanamycine) or expression reporter genes may also be replaced by a marker gene or a gene encoding a polypeptide or a peptide of interest.

The autocatalytic ribozymes in the genome vector(s) of the invention enable to achieve cleavage of the cDNA encompassed within the cloned DNA molecule with exact ends, reproducing the ends of the cDNA prior to its insertion in the DNA molecule, i.e., the terminations of the leader and trailer sequences originating from the non-segmented negative-strand RNA virus genome.

The invention relates especially to a construct described in the examples (point II) which comprises the recombinant full-length antigenomic sequence of the measles virus or a construct derived therefrom, wherein the heterologous genes KANMX4 and/or eGFP are substituted by coding sequences of interest expressing polypeptides or peptides of interest or are deleted.

One particular construct prepared on the basis of the construct provided in FIG. 8 is a full-length recombinant MV antigenome, or a plasmid containing the same, wherein one or more heterologous sequence, especially an heterologous coding sequence is inserted between the L and F genes of MV or/an between the P and N genes of MV. In such a construct the non viral promoter sequence is selected for expression in yeast.

In a preferred embodiment of the invention, the recombinant yeast strain is transformed with at least one of the plasmids pCM101, pCM103, pCM104, pCM105, pCM106, pCM112, pCM113, pCM201, pCM224, pCM225, pCM226, pCM227 deposited at the CNCM (Collection Nationale de Culture de Microorganismes, Paris, France) on 31 Jan. 2008, under numbers No. I-3896, I-3897, I-3898, I-3899, I-3900, I-3901, I-3902, I-3903, I-3904, I-3905, I-3906, I-3907 respectively.

In another particular embodiment of the invention, the recombinant yeast is transformed with a plasmid selected among pCM402, pCM476, pCM503, pCM603, deposited at the CNCM on 30 Jan. 2009 under numbers CNCM I-4117, CNCM I-4118, CNCM I-4119, CNCM I-4120 respectively.

Among yeast strains suitable for carrying out the invention, *Saccharomyces Cerevisiae* is one of the preferred strains and strain W303 is most preferred.

Other examples of suitable yeast strains for the realisation of the invention include *Pichia Pastoris*, or *Saccharomyces Pombe*, especially *Schiso Saccharomyces Pombe*.

For the purpose of the invention, the yeast strains encompass either mature cells or spheroplasts of yeasts. The yeast may be budding yeast.

The phenotype of the yeast is adapted if necessary to take into account the selectable markers present in the vectors of the invention. Accordingly, the yeast used to carry out the invention should not be capable to express the components, especially the nutrients, which are encoded by the vectors as selectable markers. In a particular embodiment, prior to recombination with the vectors of the invention, the yeasts are thus silenced for expression of markers selected among tryptophan (Trp), histidin (His), leucin (Leu), uracil (Ura) and adenine (Ade), if said vectors express these markers.

The invention thus relates to a recombinant yeast strain yCM112, yCM113 or yCM226 deposited at the CNCM on 31 Jan. 2008 under numbers NO. I-3908, I-3909, I-3910 respectively and to recombinant yeast strain yCM403 deposited at the CNCM on 30 Jan. 2009 under number I-4121.

These recombinant strains are recombinant *Saccharomyces Cerevisiae*.

It has been specified that the invention especially relates to a yeast strain wherein, in at least one of the genome vector(s), the cDNA encoding a nucleic acid derived from a genome of said non-segmented negative-strand RNA virus is devoid of all the viral genes or is devoid of all the viral coding sequences. It constitutes a minigenome. In such a minigenome, heterologous coding sequences, i.e., coding sequences which are not derived from said non-segmented negative-strand RNA virus providing the minigenome may be inserted to express polypeptide or peptide of interest, and/or a selectable marker.

According to this embodiment, the cDNA is accordingly a construct which only carries the cis-acting regions of the non-segmented negative strand RNA virus sufficient for transcription and replication of the minigenome.

When the cDNA construct cloned into the DNA molecule of the genome vector(s) contains a heterologous polynucleotide encoding a particular protein, polypeptide, or peptide, including a reporter polypeptide or a selectable marker, the DNA of the heterologous polynucleotide is inserted in said cDNA by any available means. Although the obtained nucleic acid is not necessary a cDNA on its whole length since it may comprise genomic DNA thereby forming a recombinant cDNA, the expression cDNA to designate this construct is kept for convenience in the present application to designate this chimeric nucleic acid.

According to a particular embodiment, the cDNA of the cloned molecule is a recombinant cDNA which comprises a coding sequence of a cellular protein, especially of a yeast protein, especially a protein of the yeast host strain.

In a particular embodiment of the invention, the yeast strain is such that the cDNA which it contains is a recombinant cDNA which comprises a coding sequence of an antigen or an epitope, suitable for eliciting an immune response in a host in need thereof, in particular a humoral and/or a cellular immune response.

Said coding sequence of an antigen or epitope is heterologous to said non-segmented negative-strand RNA virus. It may be selected in order to provide multi-epitopic immunogenic compositions and especially compositions for eliciting an immune reaction against the non-segmented negative-strand RNA virus providing the cDNA and, furthermore, against an additional pathogenic agent or pathogenic organism.

Examples of pathogenic organisms providing heterologous polynucleotides encoding antigens or epitopes encompass viruses especially retroviruses including in particular the lentiviruses, either human or non-human, especially HIV, in particular HIV-1 or HIV-2. Particularly, such antigens are especially from envelopes of AIDS viruses including HIV-1 or HIV-2, from capsid of HIV.

According to a particular embodiment of the invention, the heterologous nucleic acid encodes a protein from an HIV retrovirus, particularly an envelope antigen of HIV and especially a peptide derived from an envelope protein or glycoprotein of HIV-1 or HIV-2. The antigens of interest in this respect are especially gp160, gp120 and gp41 of HIV-1 or gp140, GAG or TAT of HIV-1. In a particular embodiment of the invention, the heterologous amino acid sequence is derived from a recombinant gp160, gp120 of HIV-1 or gp140, GAG or TAT of HIV-1.

In another embodiment, the V1, V2 and/or V3 loops of the gp120 (or gp160) antigen are deleted or deleted in part, or substituted or substituted in part individually or in combination in such a way that conserved epitopes are exposed on the obtained recombinant gp120 antigen. The V1, V2 and V3 loops of the gp120 (or gp160) antigen of HIV-1 have been especially disclosed in Fields virology (Fields B. N. et al. Lippincott Raven publishers 1996, p. 1953-1977).

Other polynucleotides can be derived from Yellow Fever Virus, West Nile Virus, Dengue virus (DV), Japanese encephalitis virus (JEV) or SARS-associated coronavirus. Other retroviridae, or flaviviridae or coronaviridae may also provide such polynucleotides.

As examples of heterologous polynucleotides, those encoding antigens or epitopes of the respiratory viruses different from MV such as RSV, HPIV-3, MMPN, Ebola, Influenza, Parainfluenza etc. . . . are encompassed within the definition of the invention. When such a virus provides a polynucleotide for the performance of the invention, if the virus is a non-segmented negative-strand RNA virus, in a particular embodiment, it is not used for the preparation of the DNA molecule comprising the cDNA encoding the full-length or encoding part of the RNA of the non-segmented negative-strand RNA virus.

Other heterologous polynucleotides may encode antigenic polypeptides of a human papillomavirus such as HPV18, HPV16 or antigens of Hepatitis viruses including HBV or HCV.

The polynucleotide may alternatively encode an antigen expressed on tumor cells or a tumoral antigen.

The antigens or epitopes may be from the envelopes of these viruses or from other antigenic components. The immunogenic response elicited should be cellular and/or humoral. When a cellular response is desired, it is advantageously a CD4 or a CD8 T cell response.

The recombinant yeast strain according to the invention is also useful as seeds for the preparation of immunogenic compositions or vaccines. Indeed, the recombinant yeast strain according to the invention is stable, and enables the maintenance of the vectors which it contains in usual storage conditions for yeasts. Advantageously it is also stable in the sense that it enables the expression of the viral components and their transcription and replication in culture conditions or in fermentation conditions suitable for yeasts.

Thus the recombinant yeast strains also provide seeds for the preparation of immunogenic compositions or even live vaccine whose active principle is provided as RNPs or RNPs-like. In the immunogenic composition the RNPs or the RNPs-like are formulated to enable their uptake by the target cells of the host to whom they are administered.

The invention thus also relates to a novel formulated immunogenic composition, or to a novel vaccine formulation comprising the RNPs or the RNPs-like of the invention, with a transfectant agent. Examples of transfectant agents may comprise lipofectamine or calcium phosphate or liposomes such as FUGENE® of Roche company.

When produced in the recombinant yeasts of the invention, the RNPs or the RNPs-like may be purified, or partially purified in a manner that preserve the possible adjuvant effect of some of the yeast compounds, to provide active principle of an immunogenic composition.

If appropriate, the RNPs or the RNPs-like recovered from the recombinant yeast strains are further used for the transfection of mammalian cells for the expression of viral particles or viral-like particles.

Tranfection may be carried out by using any known methods including transfectant agents. Methods such as lithium acetate-polyethylene glycol method or transfection by lipofectamine or by calcium phosphate can be used to transform the mammalian cells.

The invention is also directed to a process for the recovery of RNPs or RNPs-like expressed in the recombinant yeast cell of the invention.

Such a method comprises:
lysis of the yeast cells in an appropriate buffer solution containing protease and RNAases inhibitors;
recovering yeast extract containing RNPs or RNPs-like and filtering to remove cellular debris;
centrifugating through a sucrose cushion.

Particular conditions to recover the RNPs or the RNPs-like are described in the examples.

The invention concerns also a system for the preparation of RNPs or RNPs-like from a non-segmented negative-strand RNA virus by reverse genetics in yeast strains, wherein said system comprises:
a recombinant yeast strain according to the invention,
a culture medium for said yeast strain, which comprises an adequate culture medium for a yeast which is especially devoid of the components which are expressed by the selectable markers contained in the complementation vectors of said recombinant yeast.

In a particular embodiment of the invention, the culture medium in the system for the preparation of RNPs or RNPs-like from a non-segmented negative-strand RNA virus by reverse genetics in yeast strains comprises Raffinose in a proportion between 0.05% and 5%. Raffinose is especially added in the culture medium with the component required for induction of the promoters, if said promoters are inducible. The invention especially relates to the use of Galactose 1% and Raffinose 2% in the yeast culture media (in final volume of the culture media), when the promoters of the vectors include a Gal promoter.

For the preparation of MV RNPs or RNPs-like in *Saccharomyces Cerevisiae*, the system comprises a culture medium which is a drop out culture medium with selected nutrients omitted corresponding to the nutrients encoded by the selectable markers in the vectors. Where the yeast promoters are inducible by Galactose, the ratio of Raffinose which is provided in the culture medium is advantageously 2% Galactose and 1% Raffinose.

The invention also relates to the particular yeast culture media which are disclosed in the examples and to the yeast culture conditions described herein.

When one or several of the vectors comprise(s) a gene encoding resistance to an antibiotic, this antibiotic is further added in the culture medium in order to enable the selection of recombinant yeasts capable of growing in the presence of the antibiotic.

Many other applications of the invention are enabled by the use of the recombinant yeast including the use for the screening of factors including yeast factors interacting with transcription, replication or maintenance of infectious RNPs or RNPs-like of non-segmented negative-strand RNA virus.

To carry out such a screening, having recourse to genes contained in DNA libraries, including yeast or human libraries, the recombinant yeast strain of the invention is transformed with a vector expressing a minigenome as defined herein, said minigenome comprising a reporter gene under the control of the cis-acting sequences of the non-segmented negative-strand RNA virus and vectors expressing the transcriptase complex of said virus providing said minigenome, and is further transformed with a plasmid comprising regulatory expression control sequences functional in yeast operatively linked to the polynucleotide to be assayed for interaction.

If the expression product of said polynucleotide is assayed for interaction with replication of the RNA of the non-segmented negative-strand RNA virus the reporter gene in the minigenome is cloned in sense orientation with the leader and, if any, with the additional promoter sequences of the minigenome. The level of replication of the minigenome is measured in yeast transformed with the same.

If the expression product of said polynucleotide is assayed for interaction with transcription of the RNA of the non-segmented negative-strand RNA virus the reporter gene in the minigenome is cloned in sense orientation with the trailer sequence and, if any, with the additional terminator sequence and if any of the promoter sequences of the minigenome. The level of transcription of the minigenome is measured in yeast transformed with the same.

Another application of the recombinant yeast strain is for use for the screening of antiviral compounds interacting with infectious RNPs or RNPs-like of non-segmented negative-strand RNA virus produced in said yeast and especially antiviral molecules interacting with viral replication or with transcription of RNPs or RNPs-like in yeast.

In order to assay such an antiviral activity of a compound, as a result of interaction with viral replication, the yeast is transformed with the complementation vectors as defined in the present application and is further transformed with a vector genome which is a minigenome comprising a reporter gene (such as a gene coding for resistance to an antibiotic) under the control of the cis-acting sequences of the non-segmented negative-strand RNA virus, including the leader and trailer sequences and possibly additional viral promoter and terminator sequences. The reporter gene is encoded in sense orientation with the trailer and terminator sequences of the minigenome. The recombinant yeast is then cultured in a medium containing the antibiotic or the substrate for the reporter gene and is further contacted with the compound assayed for antiviral activity.

In order to assay an antiviral activity of a compound, as a result of interaction with viral transcription, the yeast is transformed with the complementation vectors as defined in the present application and is further transformed with a vector genome which is a minigenome comprising a reporter gene (such as a gene coding for resistance to an antibiotic) under the control of the cis-acting sequences of the non-segmented negative-strand RNA virus, including the leader and trailer sequences and possibly additional viral promoter and terminator sequences. The reporter gene is encoded in sense orientation with the leader and promoter sequences of the minigenome. The recombinant yeast is then cultured in a medium containing the antibiotic or the substrate for the reporter gene and is further contacted with the compound assayed for antiviral activity.

The invention also concerns a set of RNPs of a non-segmented negative-strand RNA virus or a set of virus RNPs-like of a non-segmented negative-strand RNA virus, which is expressed from a yeast according to the invention.

The invention also relates to a process for the preparation of infectious RNPs or RNPs-like of non-segmented negative-strand RNA virus which are expressed from yeast after:

(i) recombining a yeast strain with vectors according to the invention and, (ii) growing said recombinant yeast strain, especially in a fermentor, (iii) recovering the produced infectious virus RNPs or infectious RNPs-like.

The invention also relates to the plasmids used as vectors to carry out the invention and which are described herein. It is especially directed to the plasmids deposited at the CNCM on Jan. 31, 2008 which are described herein.

The invention also concerns the cDNA constructs of figures starting from FIG. 14. It also relates to the particular functional sequences described in these figures, such as the ribozyme sequences, the leader sequence of the MV Schwarz strain, the trailer sequence of the MV Schwarz strain, and to the insertion sites, suitable to prepare the vectors of the invention.

Other characteristics and properties of the invention in its broad definition can be derived from the examples which address the preparation of recombinant yeast strain expressing RNPs of measles virus. The figures also provide key features for the design of the vectors suitable for the preparation of the recombinant yeast strains. The features which are shown in the figures can especially be applied to corresponding features of other non-segmented negative strand RNA viruses.

LEGEND OF THE FIGURES

FIG. 1: Real time RT-PCR analysis of MV N, P and L genes expression. Real time RT-PCR was performed to quantify viral N (striped bars), P (white bars), and L (black bars) mRNA expressed in the yeast strain W303-NPL$_{MV}$. (Glu: culture with glucose, Gal: culture with galactose). In all quantitative PCR calculations, the amount of RNA was standardized using yeast 18S RNA genes. All quantification data are presented as the standardized values, mean±standard deviation of triplicates.

Figure 2A:
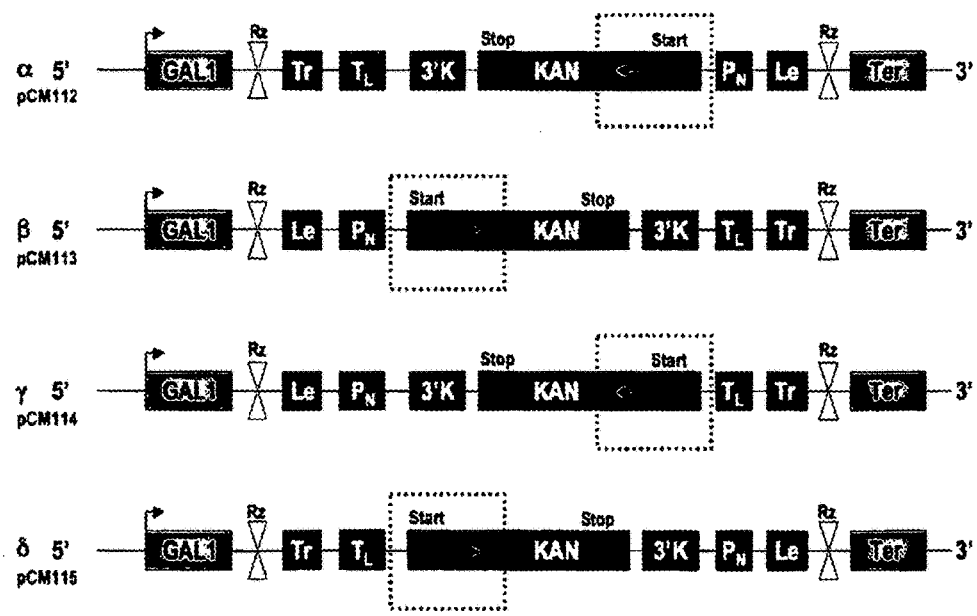

FIG. 2A: Composition of Schwarz MV minigenomes. pYES2 plasmid expression vector containing the URA3 selectable marker, 2μ replication origin and GAL1 inducible promoter were used for the different constructions. GAL1: yeast galactose inducible promoter; Rz: autocatalytic ribozymes; Tr: MV virus Trailer sequence; $T_L$: MV virus L terminator sequence; 3'K: KANMX4 gene 3' non coding sequence; KAN: KANMX4 gene coding sequence; $P_N$: MV virus N promoter sequence; Le: MV virus Leader sequence; Ter: yeast transcription terminator sequence.

Figure 2B:
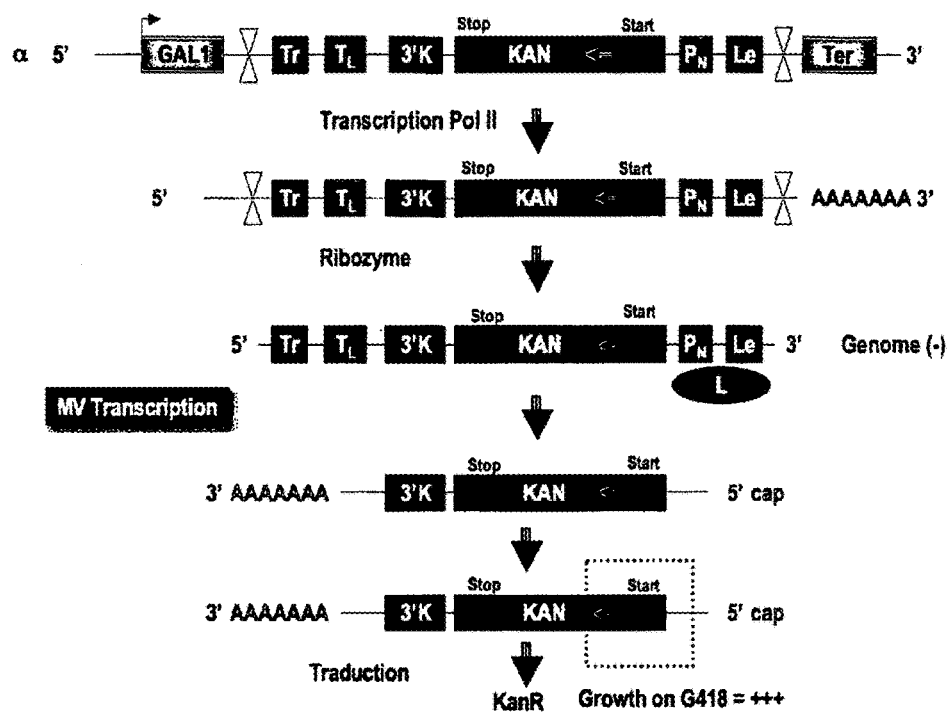

FIG. 2B: The molecular events involved in the geneticin resistance mediated by minigenome α.

Figure 2C:
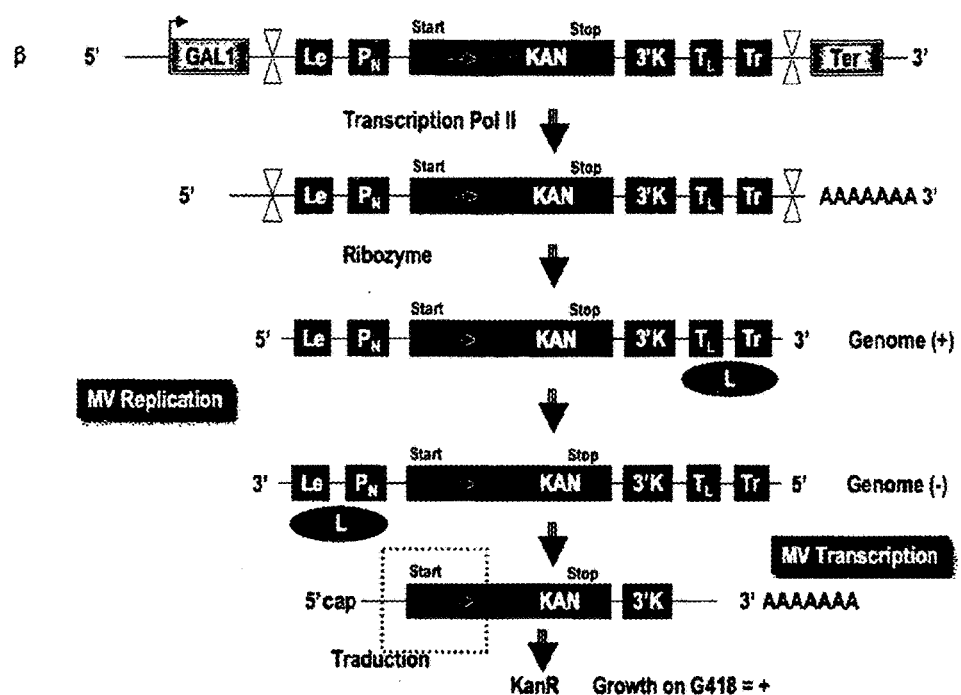

FIG. 2C: The molecular events involved in the geneticin resistance mediated by minigenome β.

Figure 3:
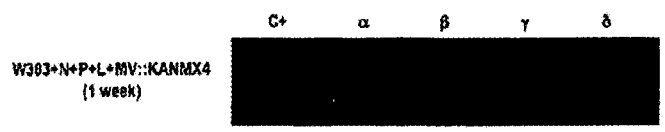

FIG. 3: Replication of MV minigenome is possible in yeast. W303-NPL$_{MV}$ yeast growth in medium containing geneticin after transformation by the four different minigenomic constructs α, β, γ, ∂ (7 days culture at 30° C., pH 5.6 and 1% raffinose et 2% galactose). Only the minigenomes α or β allow yeast to grow in selective medium. C+: positive control.

Figure 4:
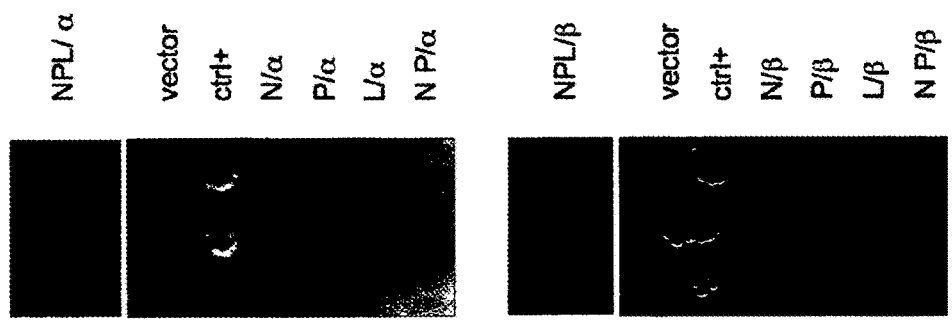

FIG. 4: Replication and transcription of MV minigenomes are strictly dependent on viral N, P and L genes. Yeast W303-NPL$_{MV}$ coexpressing different combination of MV N, P, L genes and the α or β minigenomes (7 days culture at 30° C., pH 6.5 and 1% raffinose et 2% galactose). Only the strains coexpressing simultaneously N, P, L and a or β minigenomes can grow in presence of geneticin.

Figure 5A:
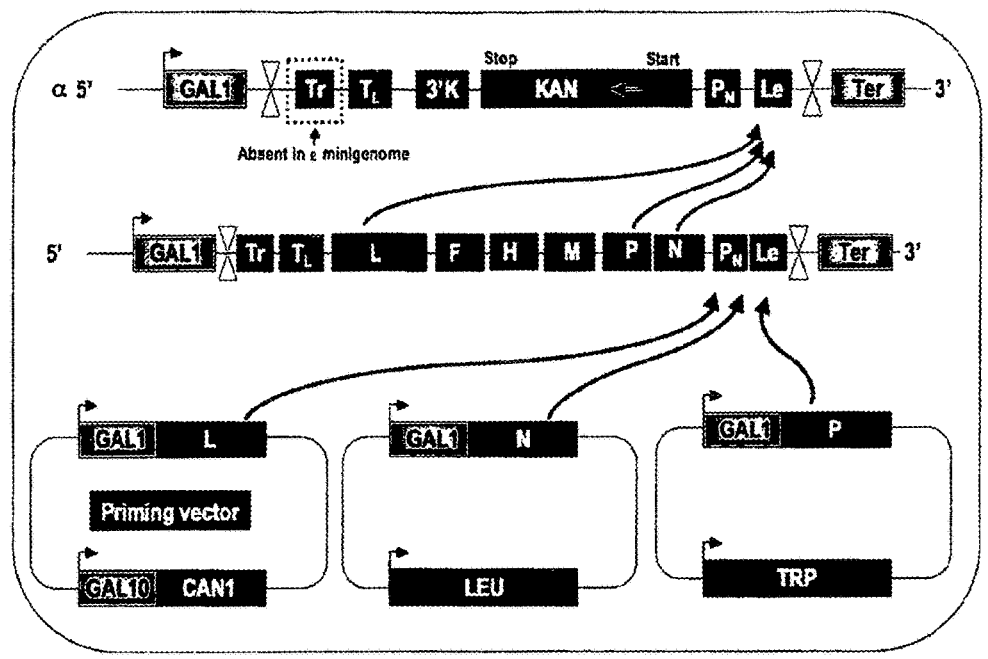
Figure 5B:
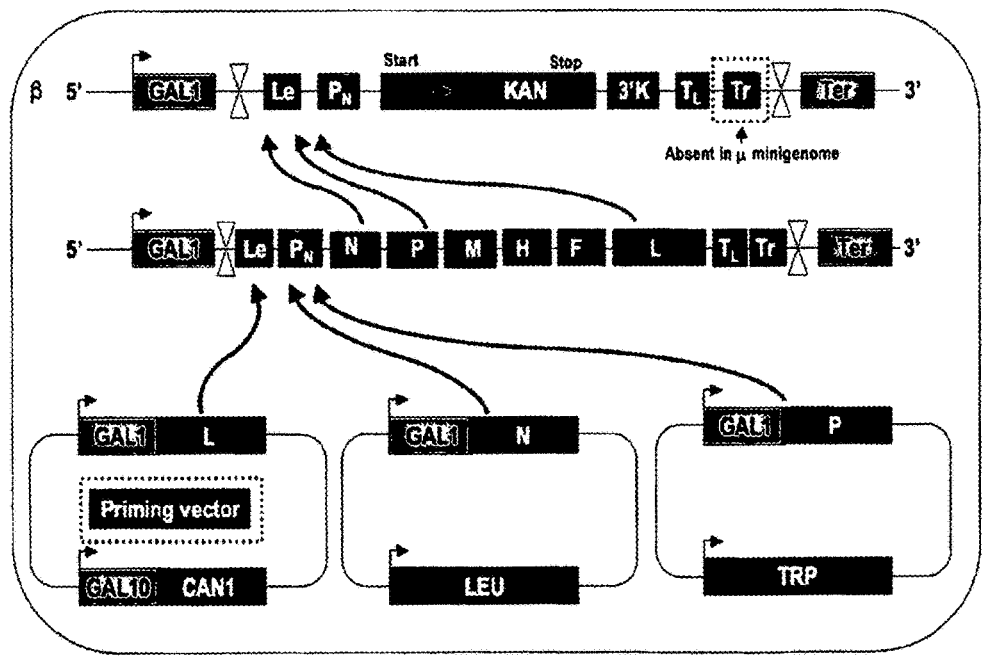

FIGS. 5A and 5B: Reconstitution of MV full-length genome RNP in S. cerevisiae. Yeast strain containing the N, P, L priming vector), the derivatives α/β minigenomes and the expression plasmid harboring full MV genome that will produce infectious viral RNPs particles. When yeast grows in presence of canavanin, the priming L vector is eliminated by counter selection. The complementation by L expressed from full-length MV genome is essential for yeast growth in presence of geneticin.

Figure 6A:
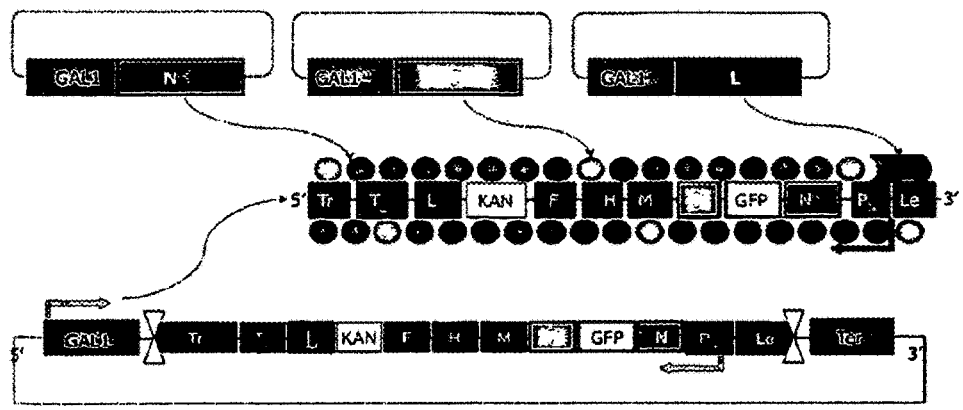
Figure 6B:
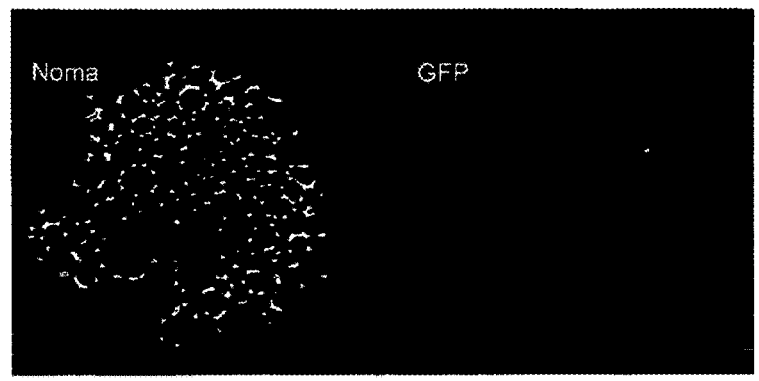

FIGS. 6A and 6B: Reconstitution of recombinant MV full-length genome RNA in Saccharomyces Cerevisiae.

A. Yeast strain containing the NPL expresser plasmid pESC-LEU-N, pESC-TRPp. pESC-HIS-L and a recombinant full-length MV genome with two additional heterologous genes eGFP and KANMX4

B. Visualisation of transformed yeast expressing eGFP from MV genome.

Figure 7:
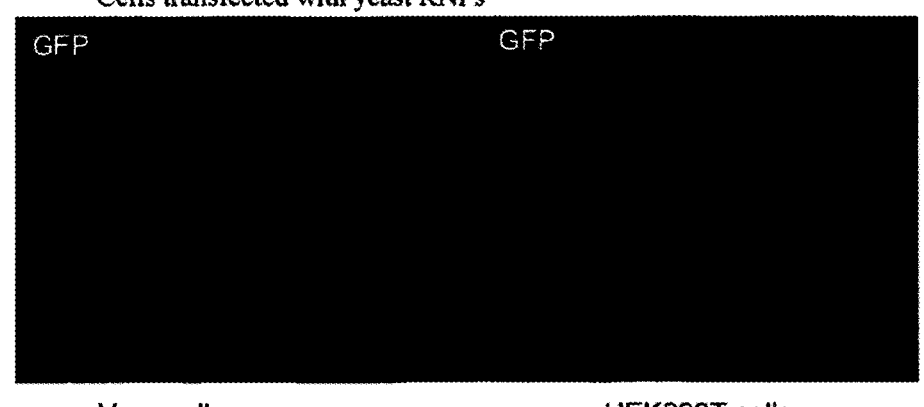

FIG. 7: Transfection of 293 T and Vero cells with RNPs obtained from yeast as described in FIG. 6 and visualization of the expression of eGFP in yeast.

Figure 8A:
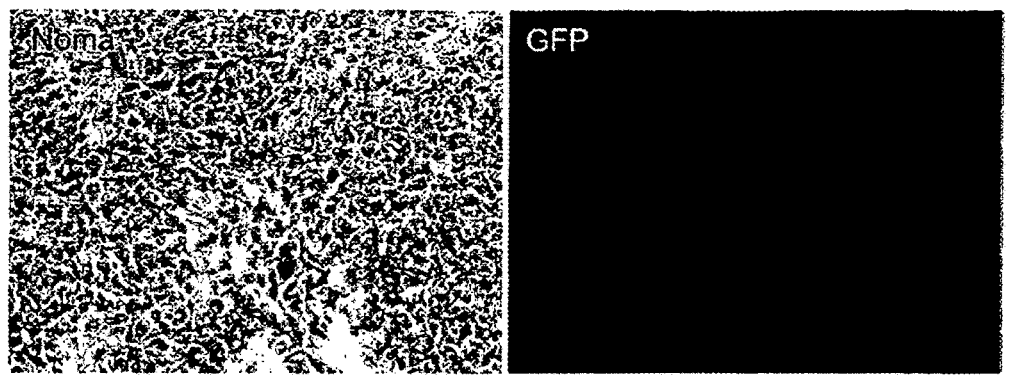
Figure 8B:
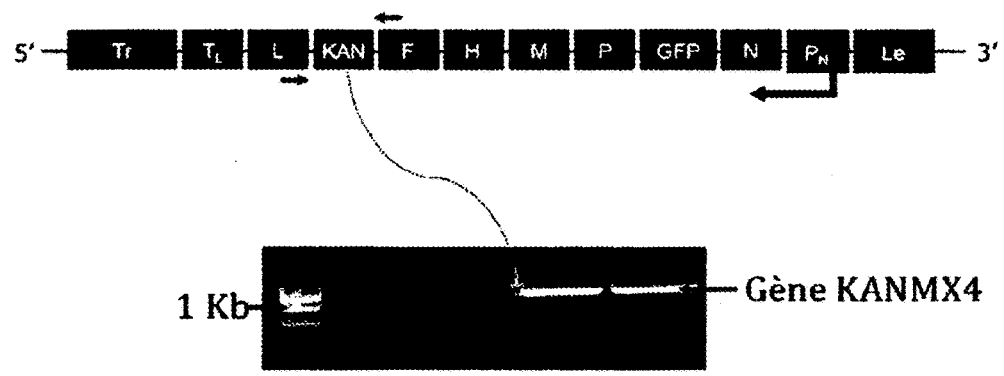

FIGS. 8A and 8B: A. Amplification of Vero cells of recombinant MV obtained from RNP transfected cells as mentioned in FIG. 7 (eGFP visualization) B. Visualization by RT PCR and sequencing of the presence of KANMX4 reporter gene in the genome of recombinant MV obtained from yeast.

Figure 9:
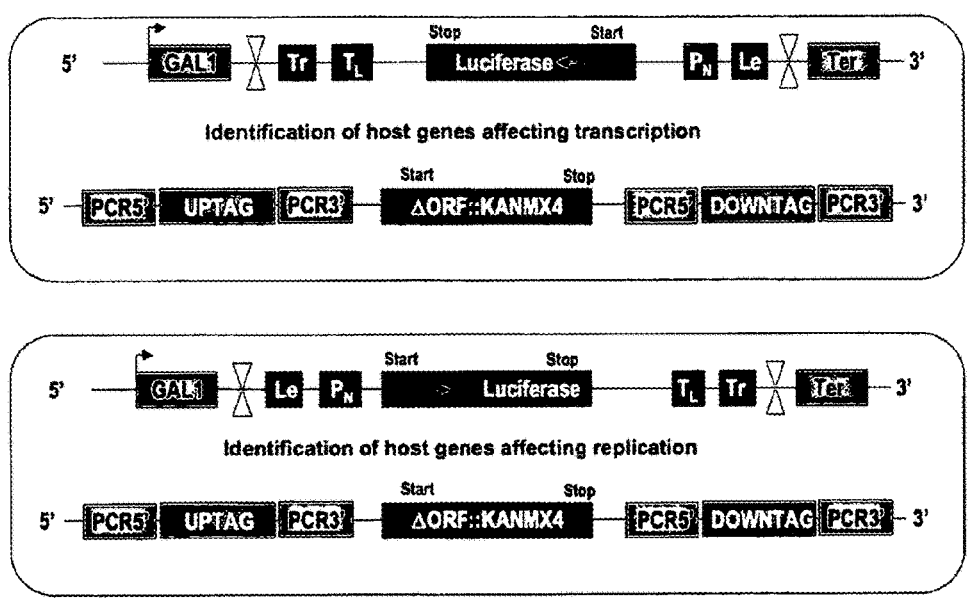

FIG. 9: Genome-wide identification of host genes affecting replication and transcription of MV virus. Yeast Knockout deletion collection (the deleted gene contain the "bar code" UPTAG and DOWNTAG unique sequences allowing the identification of the yeast strain) will be transformed by the N, P, L and the derivatives α (up)/β (down) minigenomes containing the Luciferase reporter gene and the level of transcription/replication will be measured.

Figure 10:
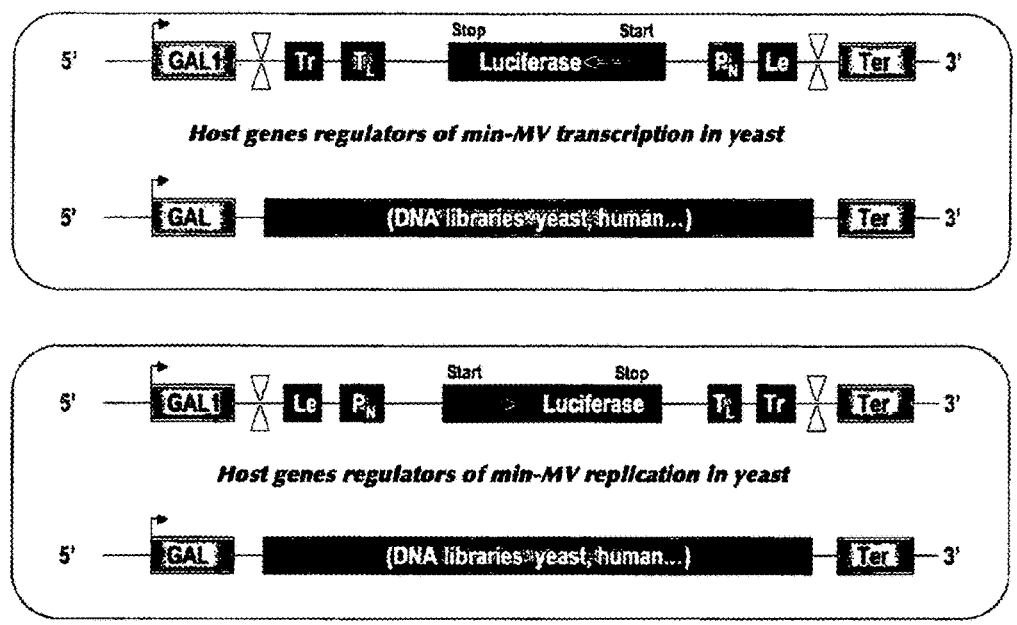

FIG. 10: Identification of host genes and peptides libraries regulators of min-MV replication/transcription in yeast. Yeast W303-NPL$_{MV}$ coexpressing viral N, P, L genes and the derivatives α minigenome will be transformed by DNA libraries coding for yeast/mammalian genes or peptides and the level of transcription/replication will be measured.

Figures 11A, 11B:
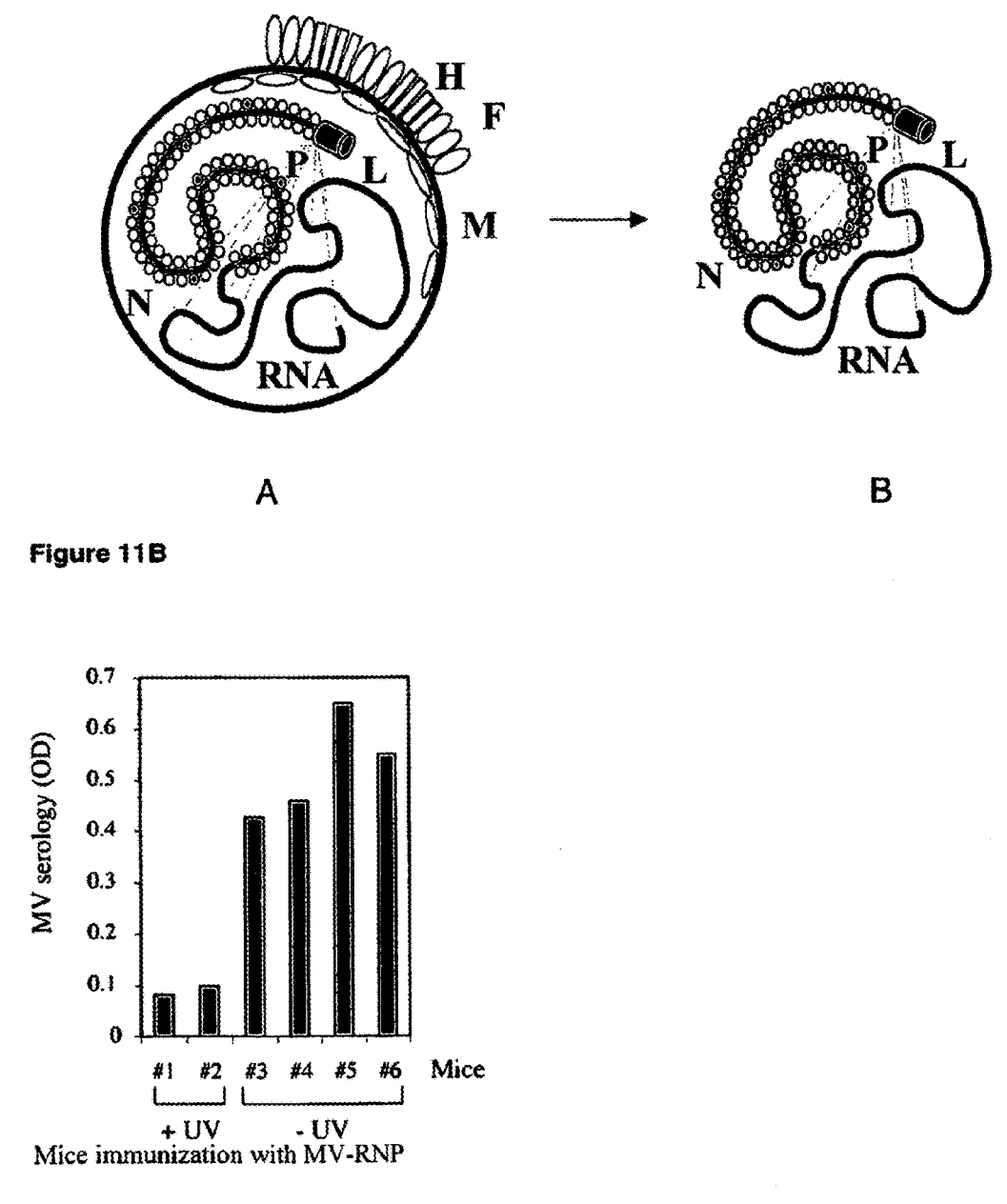

FIG. 11A: Schematic representation of MV viral particle (A) and RNP (B). N (nucleoprotein); P (phosphoprotein); M (matrix protein); F (fusion protein); H (hemagglutinin); L (large polymerase).

FIG. 11B: Mice immunization with MV-RNP

Figure 11C:
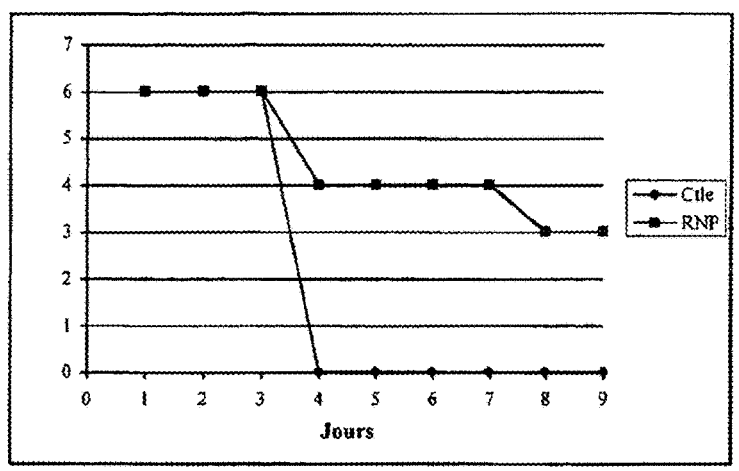

FIG. 11C: Partial protection of mice from lethal WNV challenge after immunization with RNP from recombinant MV-sEWNV expressing the envelope protein from WNV.

Figure 12A:
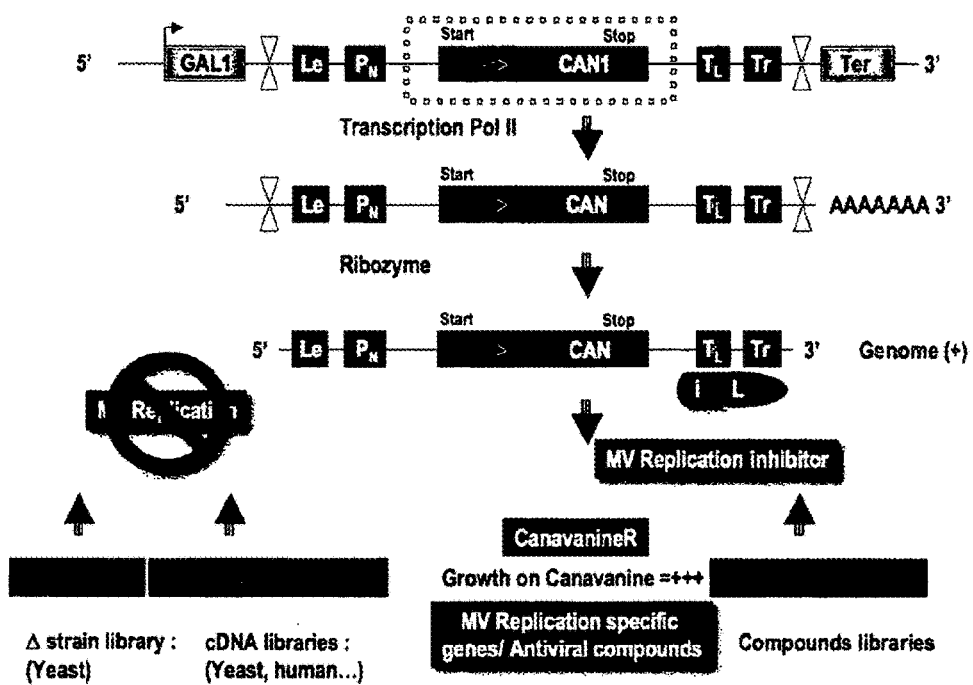

FIG. 12A: Screening and identification of antiviral compounds inhibiting viral replication in yeast. Yeast W303-NPL$_{MV}$ coexpressing MV N, P, L genes and the derivatives β minigenome containing CAN1 gene under the control of viral Trailer sequence will be exposed to chemical compound libraries and the antiviral active compounds (i) will be identified by selecting colonies growing on canavanin.

Figure 12B:
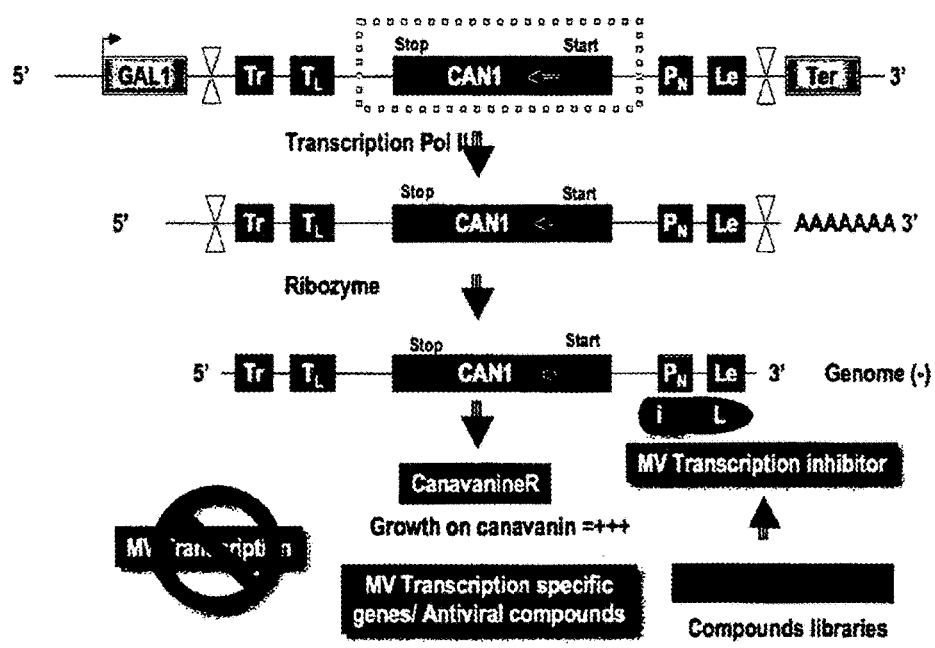

FIG. 12B: Screening and identification of antiviral compounds inhibiting viral transcription in yeast. Yeast W303-NPL$_{MV}$ coexpressing MV N, P, L genes and the derivatives α minigenome containing CAN1 gene under the control of viral Leader sequence will be exposed to chemical compound libraries and the antiviral active compounds (i) will be identified by selecting colonies growing on canavanin.

Figure 13:
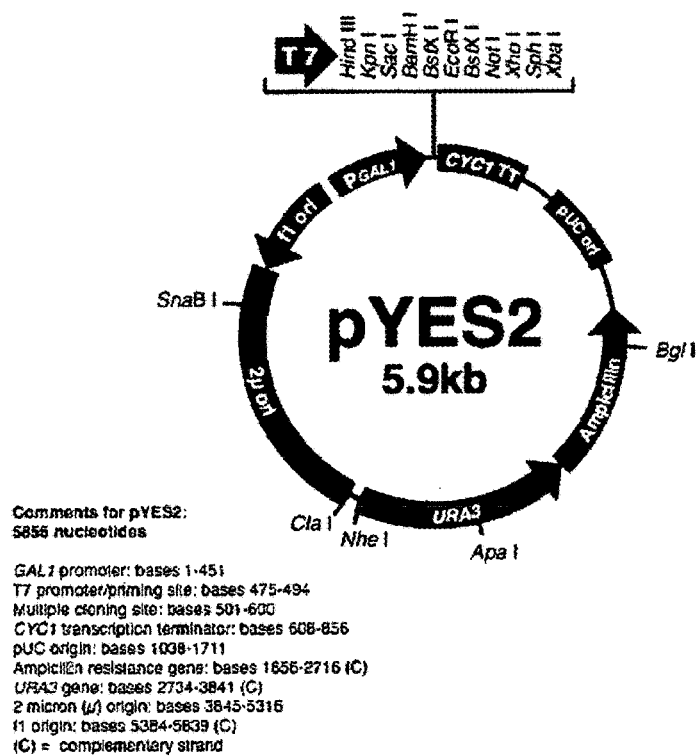
Figure 14A:
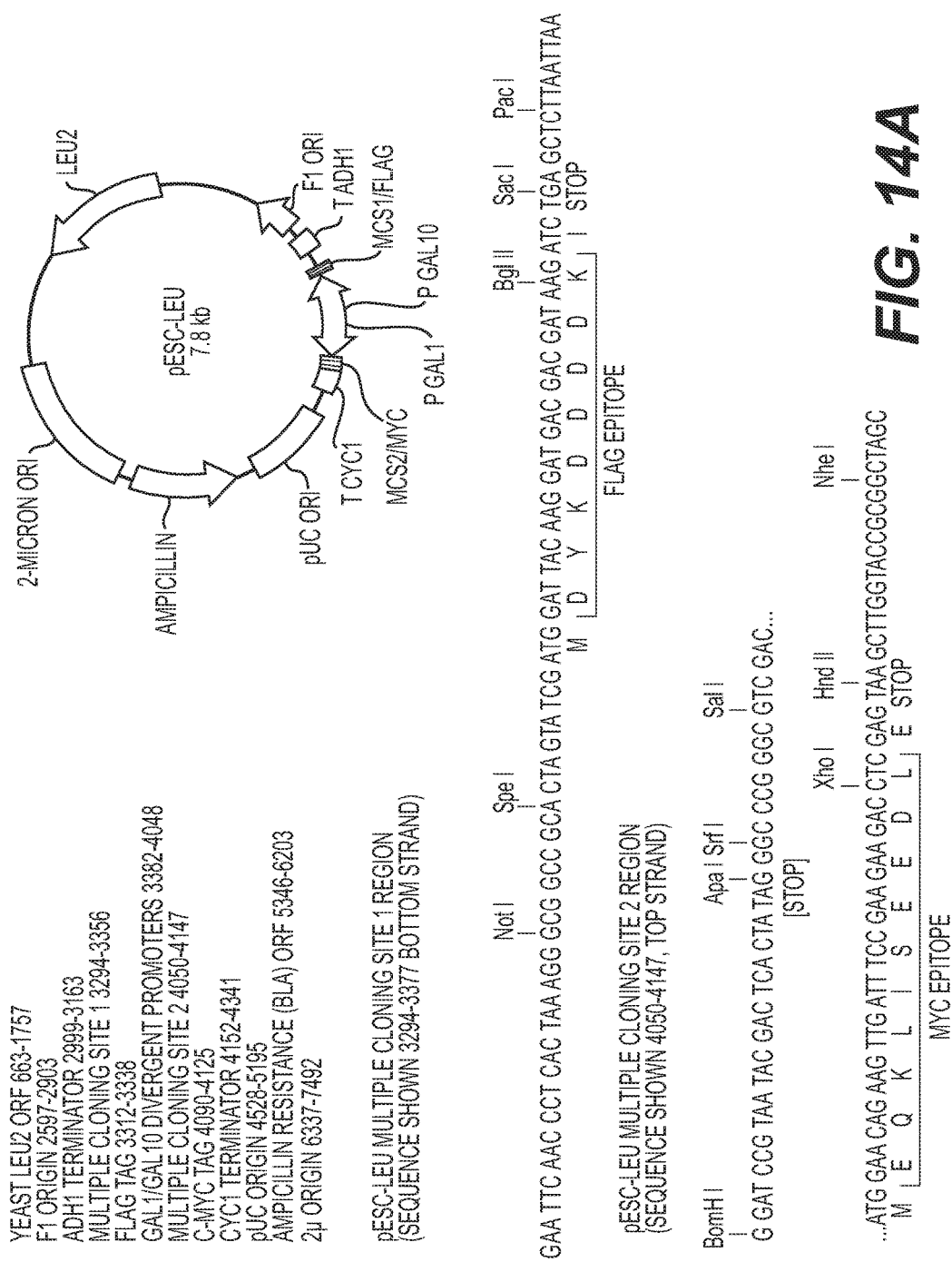
Figure 14B:
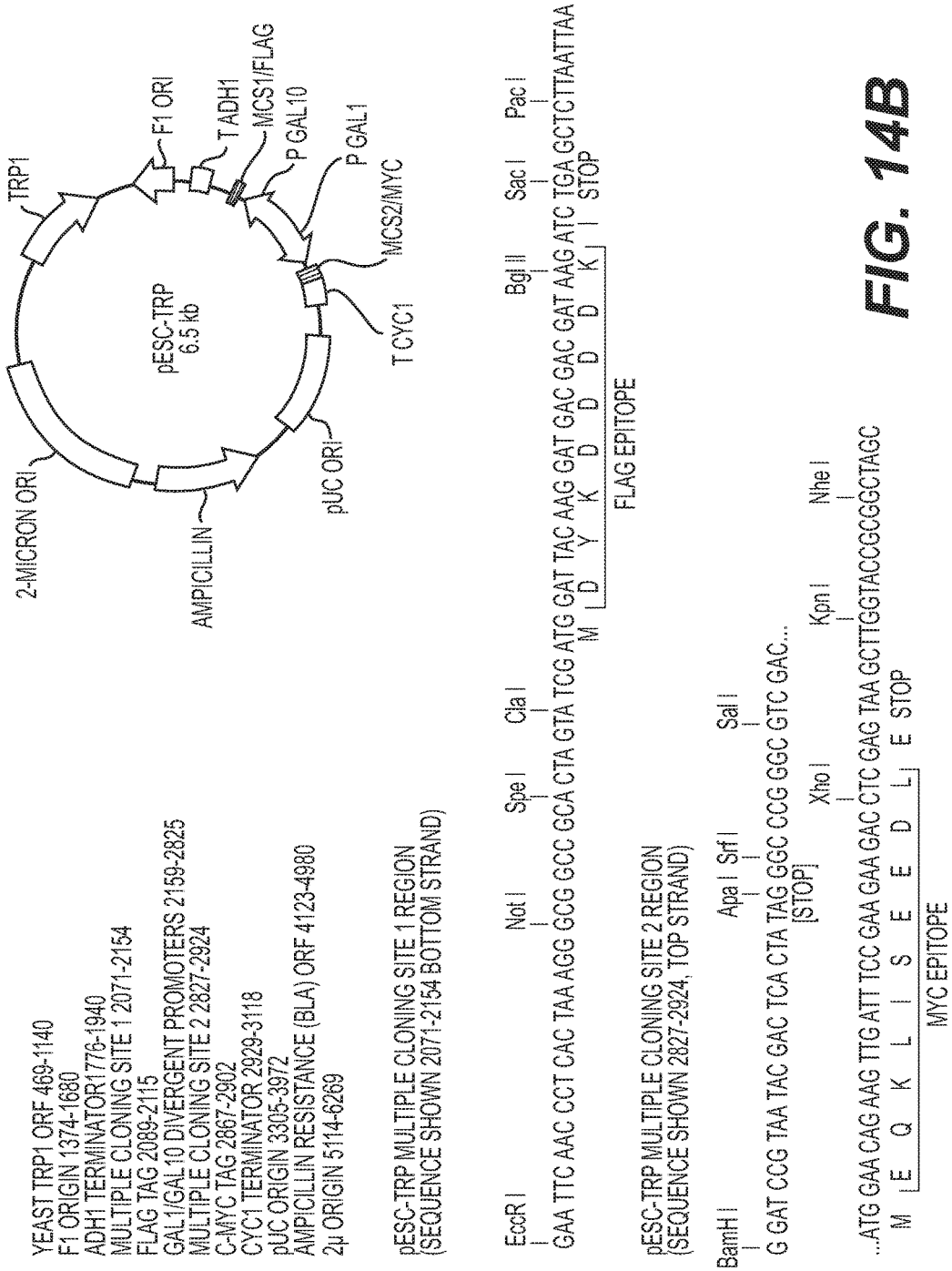
Figure 14C:
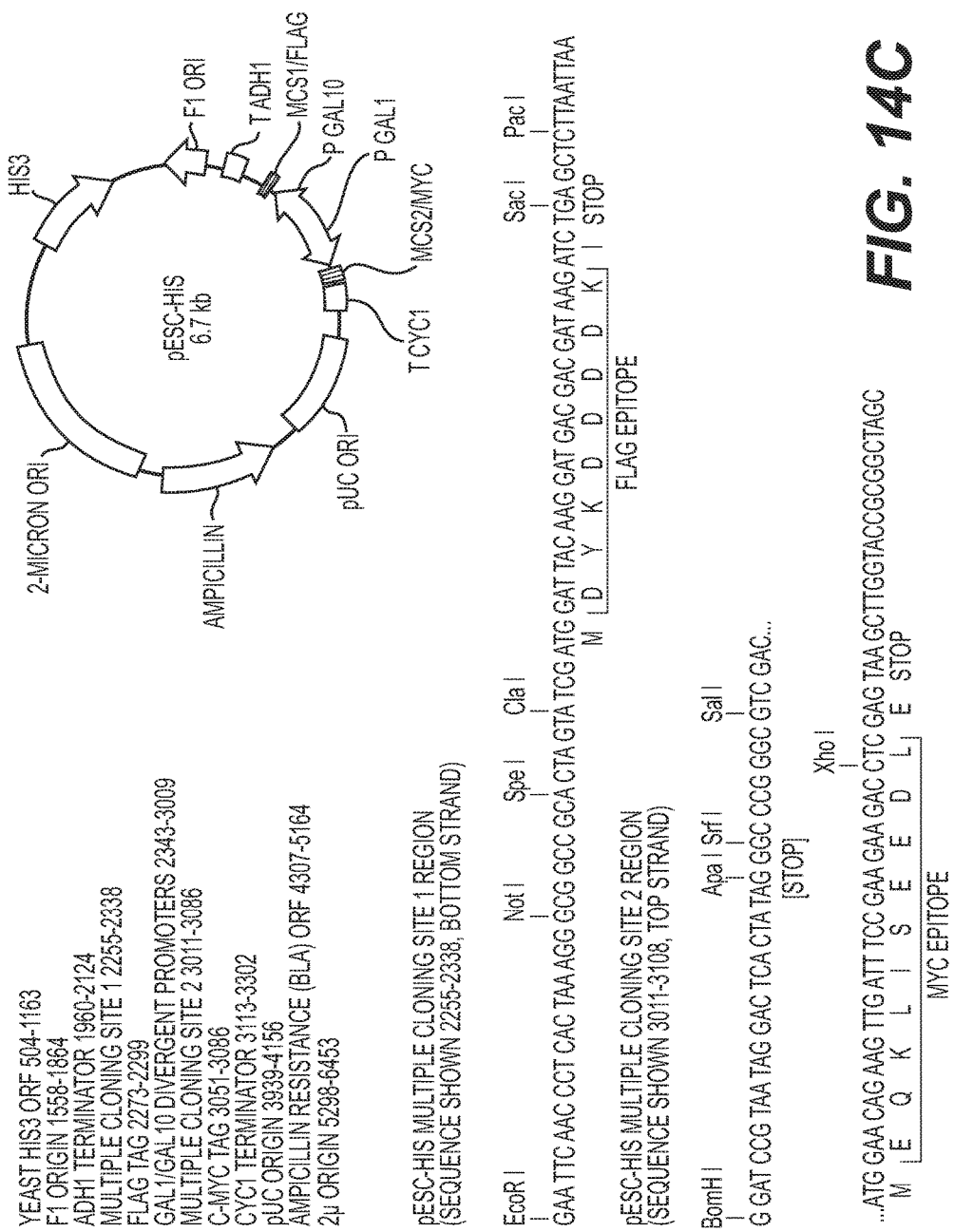
Figure 14D:
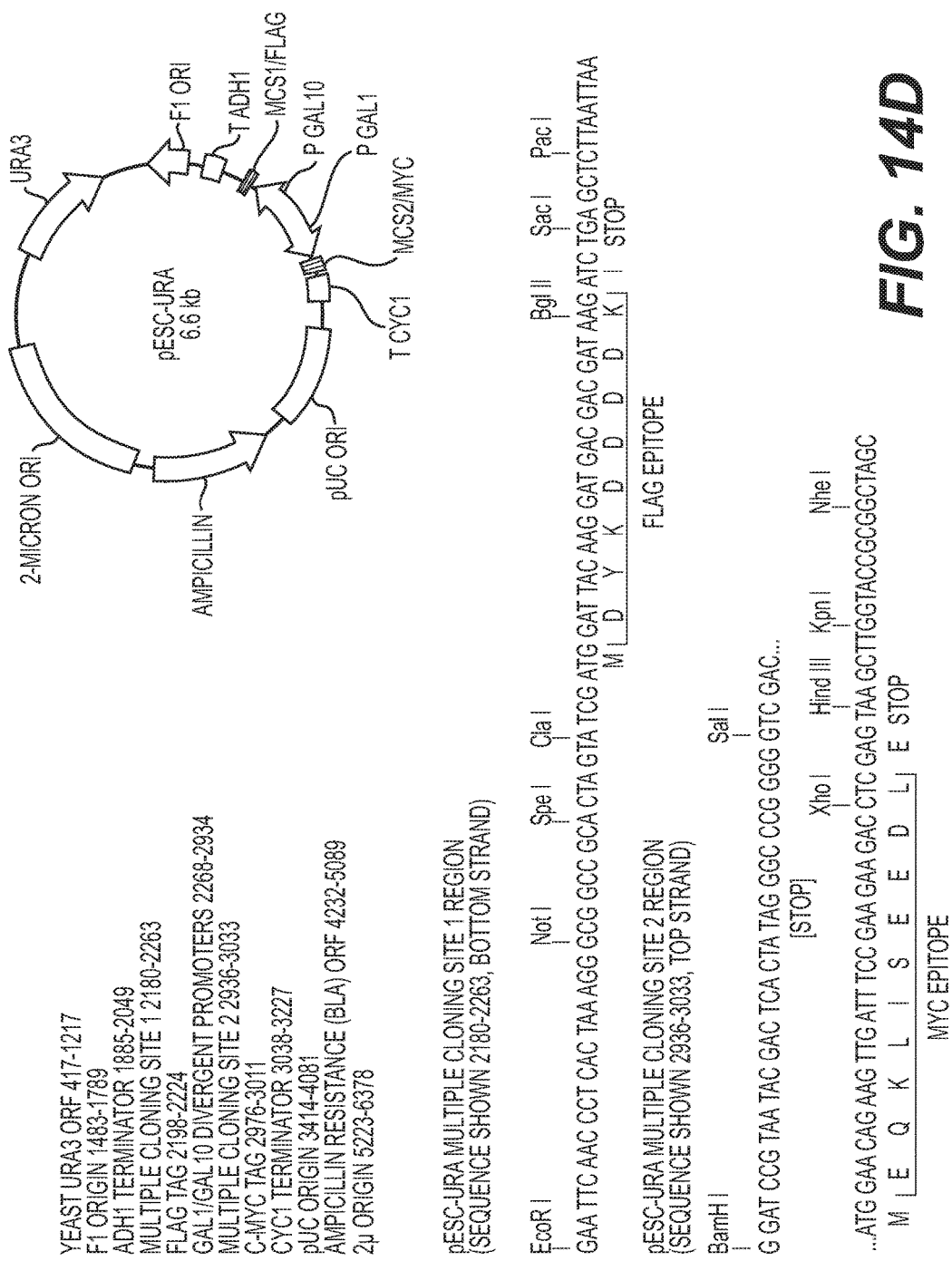

FIG. 13: pYES2: 5856 nucleotides.

FIGS. 14A, 14B, 14C, and 14D: Nucleotide sequences of plasmid constructs of minigenomes, of complementation plasmids expressing N, P and L proteins, using the Schwarz strain of the measles virus The plasmids used are pYES2 plasmids for the preparation of the minigenomes and pESC for the preparation of the complementation plasmids.

FIGS. 15.1, 15.2, 15.3, 15.4, and 15.5 show the Minigenome α sequence (PCM112).

FIGS. 16.1, 16.2, 16.3, 16.4, and 16.5 show the Minigenome β sequence (pCM113).

FIGS. 17.1, 17.2, 17.3, 17.4, and 17.5 show the Minigenome γ sequence (pCM114).

FIGS. 18.1, 18.2, 18.3, 18.4, and 18.5 show the Minigenome δ sequence (pCM115).

FIGS. 19.1, 19.2, 19.3, 19.4, 19.5, and 19.6 show the Minigenome based CAN1 sequence (pCM224).

FIGS. 20.1, 20.2, 20.3, 20.4, 20.5, 20.6, and 20.7 show the Minigenome based CAN1 sequence pCM225).

FIGS. 21.1, 21.2, 21.3, 21.4, 21.5, and 21.6 show the ADE2 plasmid containing minigenome KANMX4 based sequence (pCM226).

FIGS. 22.1, 22.2, 22.3, 22.4, 22.5, and 22.6 show the ADE2 plasmid containing minigenome KANMX4 based sequence (pCM227).

FIGS. 23.1, 23.2, 23.3, 23.4, and 23.5 show the pESC-Leu-N (pCM103) sequence.

FIGS. 24.1, 24.2, 24.3, and 24.4 show the pESC-TRP-P (pCM104) sequence.

FIGS. 25.1, 25.2, 25.3, 25.4, 25.5, and 25.6 show the pESC-LEU-NP (pCM106) sequence.

FIGS. 26.1, 26.2, 26.3, 26.4, 26.5, 26.6, and 26.7 show the pESC-HIS-L (pCM105) sequence.

FIGS. 27.1, 27.2, 27.3, 27.4, 27.5, 27.6, 27.7, 27.8, 27.9, and 27.10 show the pCM105-CAN1 (pCM201) sequence.

FIGS. 28.1, 28.2, 28.3, 28.4, 28.5, 28.6, 28.7, 28.8, 28.9, 28.10, 28.11, 28.12, 28.13, and 28.14 show the pESC-URA-MV (pCM101) sequence.

FIGS. 29.1, 29.2, and 29.3 show the Gap repair plasmid based sequence (pCM476).

FIGS. 30.1, 30.2, 30.3, 30.4, 30.5, 30.6, 30.7, 30.8, and 30.9, show the Recombinant measles genome sequence: $2^{nd}$ Gap repair plasmid (pCM402).

FIGS. 31.1, 31.2, 31.3, 31.4, 31.5, 31.6, 31.7, 31.8, 31.9, 31.10, and 31.11 show the Recombinant measles genome sequence of the resulting plasmid after the Gap repair (pCM403).

FIGS. 32.1, 32.2, 32.3, 32.4, 32.5, 32.6, 32.7, 32.8, 32.9, and 32.10 show the Recombinant measles genome sequence (pCM503).

FIGS. 33.1, 33.2, 33.3, 33.4, 33.5, 33.6, 33.7, 33.8, 33.9, 33.10, and 33.11 show the Recombinant measles genome sequence (pCM603).

EXAMPLES

To demonstrate the capacity of yeast strain W303-NPL$_{MV}$ to support the transcriptional and replicative activity of Schwarz MV RNPs, we generated various subgenomic constructions (minigenomes) derived from the Schwarz measles virus. These minigenomes contain the MV "leader-trailer" sequences necessary for viral genome transcription/replication flanking the reporter gene KANMX4 that confers to yeasts resistance to geneticin drug. Gene KANMX4 was cloned either in sense or in antisense under the control of the cis-active sequences of measles virus, cloned themselves in sense or in antisense under the control of the yeast GAL1 promoter. Autocatalytic ribozyme sequences were added at the two ends of constructions in order to prevent the expression of the minigenomes dependent on the yeast GAL1 promoter. Transformation of the yeast strain W303-NPL$_{MV}$ by the minigenomes allowed yeast to grow in presence of geneticin, the KANMX4 gene being expressed by functional MV RNPs.

This result demonstrates that the replication and the transcription of a minigenome derived from measles virus are possible in yeast. This system enabled us to determine the cloning parameters of the viral genome in a yeast expression vector, which are compatible with the production of functional RNPs. The minigenome can be replaced by a complete genome coding for the whole viral proteins.

Construction of Yeast Strain W303-NPL$_{MV}$ Expressing N, P and L Genes from Schwarz MV In order to allow replication of measles virus RNPs in yeast, we established a strain of S. cerevisiae expressing the viral proteins N, P and L coding respectively for the nucleoprotein, the phosphoprotein and the polymerase of measles virus (Schwarz vaccine strain), which are the minimal components required for measles RNP formation. We first constructed yeast expression plasmids harboring N, P, and L. The sequences corresponding to the viral N, P and L open reading frames (ORF) were cloned in the pESC series (FIG. 14) of galactose-inducible yeast expression vectors containing the LEU, TRP and HIS selectable markers, respectively, to generate pESC-LEU-N, pESC-TRP-P, pESC-HIS-L plasmids. These plasmids were used to transform the yeast strain W303 to generate the new strain W303-NPL$_{MV}$. We choose the W303 reference strain because it has been used successfully, notably to replicate papillomavirus (11). The transformed (ref. 20) yeast was cultured at 30° C. in defined drop out medium, with selected nutrients omitted (tryptophan, histidin, leucin) to provide selection for the 3 DNA plasmids together. The culture conditions were optimized to allow the expression of viral components. Optimal induction of N, P and L expression was obtained in a medium containing raffinose (see below). This nonfermentable carbon source does not interfere with galactose induction and favours cell growth.

The RNA expression of measles virus N, P and L genes under the control of the galactose inducible yeast GAL1 promoter was evaluated by real time RT-PCR in the W303-NPL$_{MV}$ strain grown in the presence of galactose. The viral N, P and L genes were highly induced (FIG. 1). Interestingly, the expression profile of N, P and L in yeast is close to their expression profile in MV infected-mammalian cells: N and P are expressed at a similar high level, while L is expressed at a much lower level. Indeed, to achieve optimal viral replication in mammalian cells, the L should be under expressed as compared to N and P(17). Thus, the observed expression profile of N, P and L in yeast appears favorable for measles minigenome replication.

Construction of Measles Virus Minigenomes

To demonstrate that measles virus N, P and L proteins are functional to assemble measles virus RNPs and to promote viral transcription and replication in yeast, we designed different minigenomic constructs harboring a reporter gene, which enabled us to analyze transcriptional and translational activities associated with viral RNPs in yeast. These minigenomes can be replaced by full-length genomes coding for all the viral proteins or by recombinant minigenome or full-length genomes. Minigenomes are viral subgenomic constructs from which all viral ORFs have been removed and replaced by a single reporter gene. Such constructs are able to form transcriptionally active RNPs when expressed together with the N, P and L viral proteins (3). The critical step consisted in designing precise Schwarz measles vaccine subgenomic constructs (minigenomes) harbouring the reporter gene KANMX4, in order to confer to yeast resistance to geneticin drug (G418), as a selectable marker. Minigenomes were designed such as after transformation of W303-NPL$_{MV}$ yeast and growth in presence of geneticin in an appropriate medium and under galactose induction, transformed yeast can grow only upon MV-dependant expression of KANMX4 gene. The minigenomes of the present invention (schematically shown in FIG. 2) contain the Schwarz MV cis-active <<leader>> (nucleotides 1-55) and <<trailer>> (nucleotides 15854-15894) sequences necessary for measles virus replication, flanking the KANMX4 reporter gene. The expression of reporter KANMX4 gene is under the control of the MV N gene promoter (contained in MV nucleotides 55-111) and MV L gene terminator (contained in MV nucleotides 15785-15854). These sequences are flanked on both sides by autocatalytic ribozyme sequences (hammerhead ribozyme in 5' and hepatitis delta virus ribozyme in 3'). The minigenomes were constructed into the galactose-inducible yeast expression vector pYES2 (FIG. 10) containing the URA3 selectable marker (FIG. 2).

Four minigenomic constructs were generated, in which the reporter KANMX4 gene was cloned in sense (α, β) or antisense (γ), according to MV genome organization. They were placed in pYES2 plasmid either in sense (β, γ) or antisense (α, δ) according to the yeast GAL1 promoter.

1. Minigenome α

Upon transformation of W303-NPL$_{MV}$ yeast by the α minigenome, the inducible GAL1-dependent transcription of KANMX4 gene, which is mediated by yeast RNA polymerase, produces non functional KANMX4 mRNA (because the KANMX4 ORF is not cloned in sens with GAL1 promoter). Yeast should thus be sensible to geneticin. However, the viral N promoter-dependant transcription of KANMX4 gene, which is mediated by viral L RNA polymerase should produce functional KANMX4 mRNA and thus induce resistance to geneticin (FIG. 2B).

2. Minigenome β

In the β minigenome construct, the KANMX4 ORF is cloned in sense with GAL1 promoter and should directly confer resistance to geneticin upon galactose induction. However, the autocatalytic ribozyme sequences added at both extremities prevent the yeast GAL1 promoter-dependant expression of minigenome by cleaving RNA molecules almost simultaneously with synthesis. Resistance to geneticin will be conferred by the β minigenome only if the viral L polymerase replicates (duplicates) the positive strand RNA minigenome (generated by yeast RNA Pol II and than cannot be translated because uncapped and unpolyadenylated) to negative strand RNA minigenome (MV genome). This negative strand MV genome will be transcribed in turn by the viral L polymerase to produce functional KANMX4 mRNA allowing yeast to grow in the presence of geneticin. The geneticin resistance occurring in the case of the β minigenome need two steps; the replication step followed by the transcription step by the viral L polymerase. While the geneticin resistance occurring in the case of the α minigenome need only the transcription step and thus the yeast cells grow faster in this case compared to the 13 minigenome associated growth on geneticin (FIG. 2C).

3. Minigenomes γ and ∂.

It cannot be excluded that some transcription of the KANMX4 gene from α or β minigenomes should arise from cryptic yeast promoters within the minigenomes sequences, or from inefficient autocatalytic ribozyme activity in yeast, or from minigenomes integration in yeast chromosomes. To exclude these eventualities we constructed the γ and δ minigenomes in which the KANMX4 ORF is cloned in antisense with the viral cis-active sequences. Thus, MV-dependant replication and transcription by the viral L polymerase will produce an antisense KANMX4 mRNA non functional to confer G418 resistance. Indeed, the γ and δ minigenomes have the same architecture than α and β minigenomes respectively regarding the KANMX4 dependent transcription by GAL1 promoter.

The FIGS. 2B and 2C explain the molecular events involved in the geneticin resistance mediated by α and β minigenomes. The following molecular mechanisms shed some light on the observed phenotypes: the yeast RNA pol II transcription of the minigenomes flanked by the ribozymes produces polyadenylated and capped mRNA followed by the nuclear export to the cytoplasm. The autocatalytic activity of ribozymes liberates the minigenome.

The viral proteins N, P and L encapsidate the minigenome to generate RNPs particles, which are functional to replicate and transcribe the KANMX4 gene. For survival in presence of G418 and a permanent expression of the KANMX4 resistance phenotype, yeast constrains MV minigenome to assemble and to replicate efficiently.

Transcription and Replication of MV Minigenomes in Yeast W303-NPL$_{MV}$

The α, β, γ or δ minigenomes constructs were coexpressed with N, P and L after galactose induction in the yeast strain W303-NPL$_{MV}$. Interestingly, only the α and β minigenomes (KANMX4 ORF cloned in sens with the viral Leader sequence and N promoter, whatever the cloning sens regarding GAL1 promoter) allowed yeast to grow in geneticin-containing selective medium. The γ or δ minigenomes were not able to confer resistance to geneticin in the same condition (FIG. 3). We thus conclude that viral N, P, L and α/β minigenomes are functional in budding yeast Saccharomyces cerevisiae. The growth in geneticin-containing selective medium of the yeast containing the α and β minigenomes constructs demonstrate that transcription and replication of negative strand RNA minigenome virus is possible in yeast.

Transcription and Replication of MV Minigenome in Yeast is Strictly Dependent on Viral Replication Factors In order to demonstrate that the activity of α and β minigenomes is strictly dependant on the association of functional measles virus RNPs containing the three viral components N, P and L proteins, we generated control W303 yeast strains containing either N, P, L alone or NP (FIG. 4) or NL or PL (data not shown). When transformed by α or β minigenomes, none of them was able to grow on selective medium. FIG. 4 shows that only the strains coexpressing simultaneously N, P, L and α or β minigenomes can grow in presence of G418. This excludes the possibility that yeast factors would be responsible of KANMX4 gene expression and demonstrates that negative strand RNA virus genomes can assemble in functional RNPs in yeast and display RNA dependent RNA polymerase activity.

I Production and Purification of MV-RNPs in Yeast

The minigenomic constructs demonstrate the proof-of-concept for negative strand RNA viruses replication in yeast. The system generated in the present invention that consists of the W303-NPL$_{MV}$ yeast strain and α- or β-type negative strand RNA virus minigenomes may be used for screening cellular factors or antiviral compounds associated with viral replication.

In another major application, the system makes it possible to generate full-length viral RNPs that could be purified from yeast and used to produce live attenuated viruses. In order to assemble functional full-length RNPs that do not contain yeast selection marker inserted inside the viral genomic sequence, yeast must harbour together with the full-length genome a minigenome expressing the resistance gene.

The yeast strain W303-NPL$_{MV}$ is mutated in the CAN1 gene (encoding arginine permease; null mutant of CAN1 gene confers resistance to the arginine analogue Canavanin). The viral polymerase L is expressed from a plasmid harboring the CAN1 gene (FIG. 5). The CAN1 yeast episomal plasmid vector replicates autonomously because of the presence of a yeast origin of replication (2 μm ori). Under conditions of non selective growth in the presence of Canavanin drug, CAN1 plasmid is highly unstable, being lost rapidly from yeast after each generation during cell division.

To produce infectious RNPs harboring full-length MV genome, the yeast W303-NPL$_{MV}$ coexpressing the N, P, L genes from MV is co-transformed by a full-length infectious cDNA corresponding to the MV antigenome and by ε minigenome (FIG. 5). The ε minigenome is an α-like minigenome lacking the MV trailer sequence, thus unable to be transcribed or replicated without complementation. The expression of viral L polymerase from CAN1 plasmid is required to prime the transcription/replication of full-length MV genome. Then, this plasmid will be lost upon yeast growth in the presence of Canavanin, thus making geneticin resistance dependent on the transcription of L polymerase from MV full-length genome (FIG. 5). The trans-complementation by L expressed from full-length MV genome after natural elimination of the L priming plasmid induced by the Canavanin drug becomes thus essential for yeast growth on geneticin. This system allows the production of viral RNPs containing a full-length genome with no selection marker inserted. The E minigenome cannot replicate in yeast or mammalian cells due to the lack of the cis-active trailer sequence (FIG. 5).

We studied the effect of Canavanin on MV minigenomes replication and observed that Canavanin does not interfere with MV minigenomes replication/transcription. We concluded that Canavanin based screening may be used. We established the optimal Canavanin concentration required for Canavanin based screening in yeast, i.e., (200 ug/ml).

We generated a plasmid expressing the viral L polymerase and the CAN1 gene. We constructed a vector containing ADE2 selectable marker from the minigenome β plasmid. The MV full-length genome was cloned into a pESC-URA3 yeast vector. After transformation, the final yeast strain will harbor five plasmids with 7 selectable markers.

Interestingly, the yeast strain W303-NPL$_{MV}$ containing the N, P, L/CAN1 or W303-MV-NP$^c$ plasmids and the α/β minigenome and a full-length MV genome was able to grow in medium containing Canavanin and G418, as compared to the same strain lacking the full-length MV genome plasmid that did not grow. Thus, despite the loss of the L plasmid due to the presence of Canavanin, the viral L polymerase was expressed from MV genome and the viral proteins N, P and L were likely encapsidated the minigenome to generate RNPs particles, which, in turn, produced functional KANMX4 mRNA, thus inducing resistance to geneticin.

After extraction from yeast, viral RNPs containing a full-length genome can be used to transfect mammalian cells in order to reproduce infectious virus with a high yield. This invention allows to produce in yeast fermentors a new formulation of measles vaccine or of any other similar live attenuated vaccine. We demonstrated that viral RNPs purified from mammalian cells are infectious and immunogenic (FIG. 11A, B).

II—Expression in Yeast of Recombinant MV Genome Containing Heterologous Genes KANMX4 and/or eGFP.

1. Generation of a Yeast Strain Capable of Stable and Long-Lasting Expression of Complete RNPs of Measles Virus.

In order to enable the replication of viral RNPs particles in the yeast, a strain of Saccharomyces Cerevisiae W303NPL MV-eGFP-KANMX4 has been prepared, which expresses N, P and L viral proteins of the measles virus, together with a full-length recombinant viral antigenome containing two additional genes: the eGFP reporter gene cloned between viral N and P genes, and the KANMX4 gene for resistance to geneticin between F and L viral genes (FIG. 26). This antigenome is cloned in reverse sense with respect to the GAL1 yeast promoter in order to prevent direct expression of the reporter genes by the RNA polymerase of the yeast. These reporter genes can only be expressed after replication and transcription of the antigenomic viral RNA through the action of the viral L polymerase using the viral promoters (Leader, Trailer and specific promoters of the viral genes). Only the first antigenomic RNA is produced by the RNA polymerase of the yeast.

The yeast strain W303 and a strain W303 MV-eGFP-KANMX4 expressing the recombinant genome and devoid of plasmids encoding N, P and L have been used as controls for this study.

2) Purification of Viral RNPs from the Cytoplasm of Yeasts

The strain WO303$^{NPL}$ MV-eGFP-KANMX4 was grown in 400 ml of SD medium for 14-18 hours until exponential phase (OD=0.6-0.8, 6-8×10$^6$ cells/ml). The yeasts have been incubated for 4-6 hours in a medium containing galactose in order to induce expression of N, P, L proteins and of recombinant antigenome. The yeasts have been yield and then transformed into spheroplasts for a part thereof and lyzed with glass microbeads for the other part. The RNPs contained in the extracts obtained by both techniques have been purified by treatment with Triton, clarification and ultracentrifugation through a 30% sucrose cushion. The material which was collected in the centrifugation pellet was taken in a Tris-EDTA buffer.

3) The RNPs Purified from the Yeast are Infectious

In order to assay its infectivity, the purified material was transfected (with lipofectamine) in Vero and 293T cells. The day after transfection for the 293T cells and 3 days after transfection for the Vero cells, fluorescent cells and fluorescent syncytia plates were apparent in the cultures (FIG. 7). These plates propagated within the following 48 hours. This experiment shows that yeast W303NPL MV-eGFP-KANMX4 has reconstituted infectious RNPs of the measles virus, which are recombinant for the eGFP reporter gene.

The Vero and 293T cells expressing the eGFP have then been grown with fresh Vero cells. FIG. 8 shows that the viruses derived from the first transfections have propagated into the culture. These viruses elicit especially the formation of typical syncytium. A Petri box was covered with syncytia (90%) in 48 hours.

After amplification of the virus on Vero cells, total RNAs of infected cells have been extracted. A PCR amplification with primers located upstream and downstream of the KANMX4 gene inserted into the measles genome has demonstrated the presence of a band corresponding to the KANMX4 insert (FIG. 8). Sequencing of the amplified band allowed to confirm its nature.

These results show that RNPs of recombinant measles obtained from yeast are infectious on cultured cells.

4) Material Et Methods

Generation of Yeast Strain W303$^{NPL}$ MV-eGFP-KANMX4

The yeast strain W303-1B (ATCC 201238) having genotype MATalpha leu2-112 trp1-1ura3-1 his3-11 his3-15 ade2-1 can1-100 has been transformed by pESC-LEU-N, pESC-TRP-P, pESC-HIS-L and with a recombinant genome containing the eGFP reporter gene, cloned between N and P genes, and containing the gene for selection with geneticin (KANMX4) cloned between the F and L genes.

To prepare the recombinant yeast strain, the following plasmids were prepared and used (the biological material was deposited on Jan. 30, 2009):

pCM476 (CNCM I-4117)

pCM476 is a plasmid comprising synthetic DNA fragment containing Ribozymes sequences and Leader Trailer sequences purchased from Genecust (Luxembourg). The fragment was synthesized in the pUC57 plasmid in SmaI restriction site. The EcoRI-SphI fragment containing the synthetic DNA fragment was then cloned into pYES2 vector containing Ampicillin marker.

The sequence of the synthetic DNA fragment is the following:

GCGGCCGCCAACTTTGTTTGGTCTGATGAGTCCGTGAGGACGAAACCCGG

AGTCCCGGGTCACCAGACAAAGCTGGGAATAGAAACTTCGTATTTTCAAA

GTTTTCTTTAATATATTGCAAATAATGCCTAACCACCTAGGGCAGGATTA

GGGTTCCGGAGTTCAACCAATTAGTCCTTAATCAGGGCACTGTATCCGAC

TAACTTATACCATTCTTTGGACTAGTGACGTCCGCGGTCGACACGTGAGA

TCTGATGGCCATCTCGGATATCCCTAATCCTGCTCTTGTCCCTGATAATA

GGATCTTGAATCCTAAGTGCACTAGAAGATGATCATTGATTGAACTATCC

TTACCCAACTTTGTTTGGTGGCCGGCATGGTCCCAGCCTCCTCGCTGGCG

CCGGCTGGGCAACATTCCGAGGGGACCGTCCCCTCGGTAATGGCGAATGG

GAC pCM402 (CNCM I-4117)

pCM402 (CNCM I-4117)

pCM402 is a plasmid comprising DNA inserts for eGFP and KANMX4 markers cloned into the Measles Schwarz genome and then cloned into pYES2 vector containing Ampicillin marker.

The KANMX4 was amplified by PCR from pFA6a-kanMX4 plasmid using the primers:

```
MscIKAN:    CACGTACGATGGGTAAGGAAAAGACTCACG

KANAatII:   TCCTTGCGCGCTTAGAAAAACTCATCGAGC
```

The pTM-MVSchw plasmid harboring BssHII/BsiWI restriction site between Measles virus F and L genes was digested with BssHII/BsiWI and the KANMX4 fragment was cloned in the same site to obtain pCM401 plasmid.

The pTM-MVSchw plasmid harboring eGFP cloned between Measles virus N and P genes and pCM401 plasmids were digested with SalI to obtain two fragments with each plasmid. The fragments containing eGFP and KANMX4 were purified and ligated to obtain pCM402 plasmid.

pCM403

The pCM403 plasmid was obtained by gap repair in yeast: pCM476 was digested with MscI/PflMI and pCM402 was digested by NotI and then the digested plasmids were cotransformed in yeast to obtain pCM403.

pCM503 (CNCM I-4119)

The pTM-MVSchw plasmid harboring eGFP cloned between Schwarz Measles virus N and P genes was digested by NotI and the Schwarz Measles genome containing the eGFP marker was cloned into pYES2 vector containing Ampicillin marker which was digested with NotI.

pCM603 (CNCM I-4120)

pCM603 contains Schwarz Measles genome containing inserts for eGFP and KNAMX4 markers cloned in pYES2 vector containing Ampicillin marker. The pCM401 plasmid was digested with NotI and the Measles virus genome containing eGFP cloned between the N and P genes and KANMX4 cloned between Measles virus genes F and L was cloned in the plasmid pYES2 digested with NotI to obtain pCM603.

Yeast Strain yCM403 (CNCM I-4121)

The yeast strain yCM403 was obtained from Yeast *S. Cerevisiae* strain W303 NPL MV-eGFP-KANMX4: the diploid of the strain W3031B (ATCC 201238) having leu2-3 leu2-112 trp1-1 ura3-1 his3-11 his3-15 ade2-1 can1-100 was co-transformed by pESC-LEU-N (such as pCM103), pESC-TRP-P (such as pCM104), pESC-HIS-L (such as pCM105). This strain contains pCM403 (Measles alpha genome harboring eGFP and KNAMX4 markers). pCM403 plasmid was obtained by gap repair in yeast: pCM476 plasmid is digested with MscI/PflMI and pCM402 plasmid was digested by Not1 and then cotransformed in yeast to obtain pCM403. Purification of RNPs from yeast: Protocol 1: Overnight culture of strain W303-MV(GFP-KAN)-NPL, strain W303-MV(GFP-KAN), strain W303 in 400 ml of SD medium in a 1 liter flask and grow 14-18 hours to a final concentration of $8\times10^6$ cells/ml (0D=0.6-0.8). The cells were washed in 20 ml of sterile water and grown in 20 ml of sterile YG (YNB+Gal+raff+AA dropout) pH6-6.5 inducing medium at 30° C. with shaking for 4-6 h. Cells were centrifuged at 22° C. 1000-1200 g for 5 minutes. The cells were washed in 20 ml of sterile water and in 20 ml of 1 M sorbitol and resuspended in 20 ml of sterile 1 M sorbitol, 10 mM EDTA then transferred to 50 ml centrifuge tubes. 100_l of 2 M DTT and 5 U Lyticase per $10^6$ cells of lyticase were added. The samples were incubated at 37° C. for 15 minutes then centrifuged at 200-300 g at 22° C. for 5 minutes. The spheroplasts were washed with 20 ml of 1 M sorbitol and with 20 ml of sterile 1 M sorbitol, 10 mM Tris pH 7.5 then centrifuged at 22° C., 200-300 g for 5 minutes. The spheroplasts were resuspended in 10 mM NaCl, 0.2% TritonX-100, 10 mM Tris pH7.5, 10 mM EDTA, a Protease Inhibitor Cocktail and RNAses inhibitors. The spheroplasts extract containing RNPs particles were centrifuged 5 mn at 1500 rpm. The extract were centrifuged through a 30% sucrose cushion in PBS, 3 h at 36 000 rpm. The RNPs were resuspended in 100 ul of Tris-EDTA and −80° C. (5 ug/ul). At the end we have 200 ug $OD_{260}$ per $10^8$ cells. By Bradford measures we obtain 0.4 ug RNP proteins/$10^6$ cells. (0.1 OD yeast=$10^6$ cells). Protocol 2: Overnight culture of strain W303-MV(GFP-KAN)-NPL, strain W303-MV(GFP-KAN), strain W303 in 400 ml of SD medium in a 1 liter fiask and grow 14-18 hours to a final concentration of $8\times10^6$ cells/ml (0D=0.8). The cells were washed in 20 ml of sterile water and grown in 20 ml of sterile YG (YNB+Gal+raff+AA dropout) pH6-6.5 inducing medium at 30° C. with shaking for 4-6 h. Cells were centrifuged 8×50 ml at 22° C. 1000-1200 g for 5 minutes in falcon tubes. The cells were washed in 20 ml of sterile water. The frozen or not yeast cell are lysed in lysis buffer containing, 10 mM NaCl, 0.2% TritonX-100, 10 mM Tris pH7.5, 10 mM EDTA, a Protease inhibitor Cocktail and RNAses inhibitors. A cold lysis buffer was added to an equal volume of glass beads and vortexed on ice. The yeast extract containing RNPs particles were centrifuged 5 mn, 1500 rpm. 10 mM Tris pH7.5, 1 mM EDTA was added then followed by centrifugation through a 30% sucrose cushion in PBS. 3 h at 36 000 rpm. Add 100 ul of Tris-EDTA and −80° C.

Transfection of Vero and 293T Cells.

Vero cells at 90% confluent in were grown in 3 ml plates of DMEM, 10% serum without antibiotic. 20 μg yRNPs were added to 375 μl DMEM w/o serum w/o antibiotic. 10 μl of Lipofectamine2000 were diluted in 375 μl DMEM w/o serum w/o antibiotic. The two solutions were mixed immediately and incubated for 20 mn at room temperature. The 750 μl mix were added to the cells in 3 ml plates. The medium were discarded after 16 h and replaced by fresh DMEM, 10% serum without antibiotic the cells were incubated for 6 days.

III Using Viral RNP as a New Formulation of Measles Vaccine,

Before the widespread use of live attenuated measles vaccine, measles was the single most lethal infectious agent. In the early 1960s, as many as 135 million cases of measles and over 6 million measles-related deaths are estimated to have occurred yearly (Clements C L, Hussey G D. Measles. In: Murray C J L, Lopez A D, Mathers C D, eds. Global Epidemiology of Infectious Diseases. Geneva: World Health Organization, 2004). The introduction of routine measles vaccination in most developing countries during the 1980s as part of the Expanded Programme on Immunization had a major effect on global measles mortality. By 1987, WHO estimated that the number of deaths from measles worldwide had been reduced to 1.9 million (Kejak K, Chan C, Hayden G, Henderson R H. Expanded Programme on Immunisation. World Health Stat Q 1988; 41: 59-63). During the 1990-1999 period, many industrialised countries introduced a second routine dose, usually at or around the time of school entry, to protect children who did not respond to the first dose (Henao-Restrepo A M, Strebel P, John Hoekstra E, Birmingham M, Bilous J. Experience in global measles control, 1990-2001. J Infect Dis 2003; 187 (suppl 1): S15-21). However, despite the availability of a safe, effective, and relatively inexpensive vaccine for over 40 years, measles remains a leading cause of childhood mortality, especially for children living in developing countries (Strebel P, Cochi S, Grabowsky M, et al. The unfinished measles immunization agenda. J Infect Dis 2003; 187 (suppl 1): S1-7). Most measles cases and deaths occur in developing countries, but outbreaks continue to occur in developed countries as well. In 2002, WHO and UNICEF began to implement a strategy for accelerated reduction in mortality due to measles by targeting 45 priority countries accounting for more than 90% of estimated global measles deaths. This program led to an important reduction in measles mortality. WHO claims that between 1999 and 2005, the mortality owing to measles was reduced by 60%, from an estimated 873 000 deaths (634 000-1 140 000) in 1999 to 345 000 deaths (247 000-458 000) in 2005 (L J Wolfson, P M Strebel, M Gacic-Dobo, E J Hoekstra, J W McFarland, B S Hersh. Has the 2005 measles mortality reduction goal been achieved A natural history modelling study. Lancet 2007; 369: 191-200).

Despite these vaccination campaigns, measles still remains the most common cause of vaccine-preventable death. The major reasons for the difficulty to control measles epidemics and outbreaks by routine vaccination are i) the failure to immunize efficiently children before the age of 9 months, mainly because of the presence of passive antibodies transmitted by the mother, and ii) problems with delivery and stability of the vaccine (live enveloped viral vaccines must be kept under 8° C.). Measles vaccine is given in developed countries between 12 and 15 months of age with seroconversion rates of 95%. In developing countries, many cases of measles occur in infants under the age of 1 year, and the vaccine is given at 9 months of age with seroconversion rates of 85% (Cutts, F T, Henao-Restrepo, A. & Olive, J M. (1999) Vaccine 17, Suppl. 3, S47-S52). In both situations, a second dose is necessary to establish sufficient herd immunity to interrupt endemic transmission (Centers for Disease Control, 2000. Morbid. Mortal. Wkly. Rep. 49, 1116-1118). A measles vaccine given before the age of 6 months despite the presence of maternal immunity and a formulation of the vaccine with a greater stability to temperature could improve measles control in many regions of the world.

To address these problems, we developed the possibility of using measles RNP as a new formulation of the vaccine. The viral glycoproteins H and F, which are targeted by neutralizing antibodies, are exposed on the surface of the viral envelope. Inside the viral particle, the RNP is composed of the negative strand RNA genome encapsidated by the nucleoprotein N and the polymerase complex P/L, involving a large number of viral proteins. FIG. 11A shows a schematic representation of MV RNP.

This viral RNPs complex contains all the information for the generation of replicating virus (full-length genome) but does not contain the surface glycoproteins. It should thus be insensitive to neutralisation by antibodies directed to the H and F glycoproteins. Using such RNPs complexes for immunisation could allow to circumvent the pre-existing neutralizing maternal immunity, at least for the first round of infection, and thus increase the uptake of the vaccine by younger infants. Moreover, the RNP formulation that does not contain the viral envelope and the surface glycoproteins should be more stable than the virus itself at higher temperatures.

Infectivity of MV RNP in Cell Culture

To first demonstrate the infectivity of MV RNPs and their capacity of initiating and spreading MV infection in cell culture, we purified MV RNPs from MV-infected cells and from a bulk vaccine batch (as a commercial product). The purification procedure consisted of cell lysis (freezing-thawing), viral membrane disruption using NP40 detergent, low-speed clarification, and centrifugation through a sucrose cushion. MV RNPs were obtained from Schwarz MV vaccine and from Vero cells infected with MV Schwarz strain. The yield was 100 μg ($OD_{260}$) per $10^7$ pfu. The infectivity of these RNPs was analyzed by transfecting Vero cells using lipofectamine. Table 1 shows that, using different conditions, MV RNPs were infectious for Vero cells after transfection, as detected by syncytia apparition in cell culture. Without lipofectamine, no infection was detected, demonstrating the absence of enveloped viral particles in the RNPs preparation. Infectivity was also tested using FUGENE reagent or calcium phosphate procedures.

TABLE 1

Transfection of Vero cells by MV RNP/lipofectamine

| RNP μl (1 μg/μl) | lipofect μl | Syncytia Vero (nb) |
|---|---|---|
| 5 | 0 | 0 |
| 10 | 0 | 0 |
| 5 | 5 | 20 |
| 5 | 10 | 1200 |
| 5 | 20 | 170 |
| 5 | 50 | 0 |
| 10 | 20 | 600 |

Immunogenicity of MV RNPs in Mice

The best condition for in vitro infection (5 μl RNP+10 μl lipofectamine) was chosen for mice immunization. $CD46^{+/-}$ $IFNAR^{-/-}$ mice (susceptible to MV infection) were inoculated intraperitoneally with a mixture of RNPs/lipofectamine. To control for passive immunization, the same preparation previously UV inactivated (MV genome is UV sensitive) was also inoculated. FIG. 8B shows that after immunization with MV RNPs-lipofectamine, mice developed an immune response against measles, as detected by ELISA (Trinity Biotech, USA) 1 month after inoculation. The mice inoculated with the UV-inactivated RNPs remained MV negative, thus showing that the antibodies detected in other mice were not due to passive immunization.

MV RNP cannot be titrated directly because the infectivity is determined after transfection. However, the dose used in this experiment was estimated at $10^3$-$10^4$ $TCID_{50}$ which corresponds to the vaccine dose of standard measles vaccine. Immunization of the same mice with standard measles vaccine, is 5-10 times more efficient (as determined by ELISA). This difference should be reduced after a better formulation of RNPs. Moreover, higher doses of RNPs should be assayed in order to determine whether the same level of immunization than with standard vaccine can be obtained.

A similar experience was performed using RNPs purified from recombinant MV-sEWNV expressing the secreted form of the envelope E protein from West Nile virus (WNV). This recombinant virus was previously shown to protect mice from a lethal WNV challenge (Despres et al. 2005, *J. of Infectious Diseases*, 191, 207-214). Mice immunized with MV-sEWNV RNPs were challenged using lethal WNV doses. FIG. 8C shows that mice immunized with recombinant RNPs were partially protected from lethal infection.

In conclusion, these experiments demonstrated that MV RNP are infectious after lipofectamine transfection, and immunogenic in mice at a reasonable dose. Indeed, this new vaccination concept depends on the possibility to provide means allowing availability of RNPs on an industrial scale.

IV Genome-Wide Identification of Host Genes Affecting Replication and Transcription of a Negative-Strand RNA Virus The engineered α/β minigenomes will be used to systematically identify host factors implicated in the replication and transcription of viral RNPs. Approximately 4500 yeast deletion strains from the Yeast Knock-out (YKO) deletion collection (more than 90% of yeast genes) can be screened (18). Each deletion strain will be transformed by the N, P, L and the derivatives α/β minigenomes in which KANMX4 gene will be replaced by a luciferase reporter gene. Luciferase expression, which is dependent on viral RNA replication and transcription, will be measured in yeast cells. This approach allows the identification of yeast genes whose absence inhibits or stimulates MV or any other negative strand RNA viruses replication/transcription. This functional genomics approach likely will reveal novel host genes required for MV or any other negative strand RNA viruses replication (FIG. 12A) and transcription processes (FIG. 12B).

The YKO deletion collection will be cotransformed in bulk by new vectors expressing N, P, L genes and the derivatives α/β minigenomes (or W303-MV-$NPL^c$ strain). To this end, we cloned the derivative 13 minigenome containing the CAN1 genes in the same plasmid expressing viral L polymerase and we generated a second plasmid expressing N and P genes from two distinct promoters. The growing yeast in the presence of Canavanin will be selected and the host genes affecting replication of the MV-minigenome will be identified. The CAN1 genes will be replaced by the Luciferase gene to obtain more quantitative results and measure the effects of each host gene in the replication of the negative-strand RNA virus.

V Genome-Wide Identification of Host Genes and Peptides Libraries Regulators of Min-MV Replication/Transcription in Yeast.

Yeast W303-$NPL_{MV}$ coexpressing MV N, P, L genes and the derivatives α and β minigenomes containing the luciferase or CAN1 genes under the control of viral transcription/replication machinery are transformed by DNA libraries coding for yeast/mammalian or peptides and the level of transcription/replication can be measured (FIG. 12A and FIG. 12B).

We generated a plasmid expressing the derivatives α and β minigenome containing the CAN1 genes and ADE2 selectable marker. The yeast strain W303-NPL$_{MV}$ coexpressing N, P, L and CAN1 genes will then be transformed by a yeast expression genomic DNA library. We performed gDNA library from yeast strain W303. Indeed, we partially digested the genomic DNA from the yeast strain W303 and cloned all the fragments (from 20 bp to 20 kb) in the expression GAL1 vector pYES2. This library is advantageous compared to the classical libraries because the DNA fragment from gDNA is not fused to any nuclear localization signal (NLS) or Tag/protein largely used in almost all genetic screens in yeast and notably yeast two hybrid screen. Thus we will be able to identify other factors required for MV replication. We cloned small fragment to identify small peptides expressed from theses short gDNA that could regulate MV replication.

We will perform cDNA library from human and screen for human cellular factors implicated in the MV replication.

VI Screening and Identification of Antiviral Compounds Inhibiting Viral Replication in Yeast.

Yeast W303-NPL$_{MV}$ coexpressing MV N, P, L genes and the derivatives α and β minigenomes containing CAN1 gene under the control of viral replication (FIG. 12A) and transcription (FIG. 12B) respectively are exposed to chemical compounds libraries and the antiviral active compounds identified by selecting colonies growing in the presence of canavanin. High-throughput screening of chemical compounds can be used to identify modulators of minigenomes replication/transcription (15).

The same strain used to identify factors required for MV replication will serve to screen and identify antiviral compounds inhibiting viral replication in yeast. Several chemical compounds libraries are under study.

Experimental Procedures

All the plasmids and yeast strains have been deposited at the CNCM on Jan. 31, 2008.

For the deposited yeast strains the culture medium is a synthetic complete drop out medium (SD): 13.4 g YNB with ammonium sulfate, 30 g Glucose, 4 g Dropout Amino Acid, 20 g Bacto-agar (Difco) and 1000 ml distilled water (final volume). Adjust the pH to 5.6 with 10 N NaOH and filter sterilize.

For the deposited plasmids, the culture medium is LB medium supplemented with ampicillin.

Construction of pESC-LEU-N Plasmid (pCM103) CNCM I-3897

The pESC series was purchased from Stratagene (#217455)

The N gene was amplified by PCR from pTM-MVSchw (19) plasmid using primers NSalI_5'CATGGTCGACAAGAGCAGGATTAGGGATAT-3' and NXhoI_SGCATCTCGAGTGGATGGTT-GATGGGCTGGC3' and was cloned in the same restriction sites of pESC-LEU (Stratagene, France) plasmid expression vector containing the LEU2 selectable marker, 2μ replication origin and GAL1 inducible promoter.

Construction of pESC-TRP-P Plasmid (pCM104) CNCM I-3898

The P gene was amplified by PCR from pTM-MVSchw plasmid using primers P2SalI_5'CATGGTCGACCAGGT CCACACAGCCGCCAG3' and P2XhoI_5'GCATCTC-GAGGGTCGACTGGCATGGGGTTG3' and was cloned in the same restriction sites of pESC-TRP (Stratagene, France) plasmid expression vector containing the TRP1 selectable marker.

Construction of pESC-HIS-L Plasmid (pCM105) CNCM I-3899

The 6.7 kb SpeI/BglI blunt ended fragment containing L coding region from pTMMVSchw plasmid was transferred to SalI/XhoI blunt ended pESC-HIS plasmid (Stratagene, France) expression vector containing the HIS3 selectable marker.

Construction of pESC-LEU-NP Plasmid (pCM106) CNCM I-3900

The 1.66 kb Xho/SalI blunt ended fragment containing P coding region from pCM104 plasmid was transferred to NotI/SacI blunt ended pCM103 plasmid.

Construction of MV Schwarz Minigenomes (pCM112—CNCM I-3901, pCM113—CNCM I-3902, and pCM114 and pCM115), The 1.1 kb DraI/EcoRV fragment containing KANMX4 coding region from pFA6a-KANM4 plasmid (1) was transferred to pTM-MVSchw, which contains a full-length infectious Schwarz MV antigenome/genome flanked by ribozymes sequences and NotI sites, digested by PflMI-MscI and blunt ended. The sequence corresponding to KANMX4 ORF was then cloned in sense (KANMX4 in frame with N promoter) and antisens (KANMX4 not in frame with N promoter) between the 5'Leader-N promoter and L terminator-Trailer sequences flanked by ribozymes sequences and NotI restriction sites.

This 1.7 kb NotI fragment containing the two minigenomes was cloned in the yeast plasmid expression vector pYES2 (Invitrogen, France) containing the URA3 selectable marker, 2μ replication origin and GAL1 inducible promoter, digested by NotI. In the one hand, the minigenome containing KANMX4 in frame with N promoter, was cloned in sens with GAL1 yeast promoter (expressing positive RNA minigenome, (3 construction or pCM113 plasmid), in the other hand, the minigenome containing KANMX4 which is not in frame with N promoter, was cloned in sense with GAL1 yeast promoter (expressing positive RNA minigenome, 6 construction or pCM115 plasmid)

The minigenome containing KANMX4 in frame with N promoter, was cloned in antisense with GAL1 promoter to obtain an intermediary plasmid containing a minigenome without ribozymes (pCM12). This construction was used to construct the a minigenome or pCM112 plasmid (expressing negative RNA minigenome). The overlapping primers below were used to obtain by PCR the a construction.

PCR from pCM 12 using the primers:

```
HHALPHA_1_5'ACCAGACAAAGCTGGGAATAGAAACTTCGTATTTTCAA

AGTTTTCTTTAATATATTGCAAATAATGCC3'
and

HDVALPHA1_5'GTCCCATTCGCCATTACCGAGGGGACGGTCCCCTCGGA

ATGTTGCCCAGCCGGCGCCAGCGAGGAGGCTGGGACCATGCCGGCCACCA

AACAAAGTTGGG3'
```

Then the PCR fragment was used to make PCR with the following primers:

```
HHALPHA1_5'GACGGATCCAACTTTGTTTGGTCTGATGAGTCCGTGAGG

ACGAAACCCGGAGTCCCGGGTCACCAGACAAAGCTGGGAATAG3'
``` and

HDVALPHA2/2_5'CGAGCTGCTCGAGTCCCATTCGCCATTACC3'

Then the PCR fragment was used to make PCR with the following primers:

HHALPHA2_5'GAAGCTTGACGGATCCAACTTTGTTTGGTCTG3'
and

HDVALPHA2/2_5'CGAGCTGCTCGAGTCCCATTCGCCATTACC3'

The PCR fragment was digested by BamHI/XhoI and cloned in the same restriction sites of the pYES2 vector to obtain pCM112 plasmid. The same strategy was used to obtain pCM114 plasmid. It is remarkable that pCM 12 plasmid confers G418 resistance in the yeast strain W303-NPL$_{MV}$ growing in medium containing G418.

Construction of MV Schwarz Minigenomes Containing ADE2 Based Minigenome (pCM226—CNCM I-3906 and pCM227—CNCM i-3907)

The ADE2 gene was amplified by PCR from yeast genomic DNA plasmid using primers ADE2NheI_5'CCATGCTAGCCGAGAATTTTGTAACAC-C and ADE2ApaI_5'GGCATGGGCCCTTGCTTCTTGT-TACTGG and was cloned in the same restriction sites of the pCM112 and pCM113 plasmids. We obtained respectively pCM322 and pCM325 plasmids.

The pCM322 and pCM325 plasmids were digested by KpnI/SacI, blunt ended and ligated to eliminate extraminigenomic SacI site to obtain pCM226 plasmid (a minigenome) and pCM227 plasmid (β minigenome) respectively.

Construction of MV Schwarz Minigenomes Containing CAN1 Based Minigenome (pCM224—CNCM I-3904 and pCM225—CNCM I-3905)

The CAN1 gene was amplified by PCR from yeast genomic DNA plasmid using primers CAN1SacI_5'GAATTCGAGCTCATGACAAATTCAAAA-G and CAN1NcoI_5'CTACTGCCATGGACTATGCTA CAACATTC, digested with SacI/NcoI and cloned in the pCM226 and the pCM227 digested with SacI/NcoI to obtain pCM224 and pCM225 respectively.

Construction of pESC-URA3-MV Plasmid (pCM101-CNCM I-3896)

The 16.2 kb NotI fragment containing full-length MV genome from pTM-MVSchw plasmid was transferred to NotI pESC-URA plasmid (Stratagene, France) expression vector containing the URA3 selectable marker.

Construction of pCM101-CAN1 Plasmid (pCM201—CNCM I-3903)

The CAN1 gene was amplified by PCR from yeast genomic DNA plasmid using primers CAN1NotI_GCTCGCGGGCCGCATGACAAATTCAAAAGA and CAN1NheI_CCATGGGCTAGCACTATGCTACAACATT-CC, digested with NotI/NheI and was cloned in pCM105 plasmid digested by NotI/SpeI.

Generation of Yeast Strain W303-NPL$_{MV}$

The strain W303-1B (=ATCC 201238) with the genotype MATalpha leu2-3 leu2-112 trp1-1 ura3-1 his3-11 his3-15 ade2-1 can1-100 was co-transformed by pESC-LEU-N (such as pCM103), pESC-TRP-P (such as pCM104), pESC-HIS-L (such as pCM105) and one of the α or β or γ or δ minigenome constructions. When the minigenome was the alpha one (pCM112), the yCM112 recombinant yeast strain was obtained. It is deposited at the CNCM on Jan. 31, 2008 under N0 I-3908. When the minigenome was the β one (pCM113), the yCM113 recombinant yeast strain was obtained. It is deposited at the CNCM on Jan. 31, 2008 under N0 I-3909.

Generation of Yeast Strain W303-MV-NPL$^c$

The strain W303-1B (=ATCC 201238) with the genotype MATalpha leu2-3 leu2-112 trp1-1 ura3-1 his3-11 his3-15 ade2-1 can1-100 was co-transformed by pESC-LEU-N (such as pCM103), pESC-TRP-P (such as pCM104), the priming plasmid pESC-HIS-L-CAN1 (such as pCM201) and one of the ADE2 (pCM226/pCM227) based minigenomes constructions. When the minigenome was the alpha one (pCM112), the yCM226 recombinant yeast strain was obtained. It is deposited at the CNCM under N0 I-3910.

Yeast Culture Conditions

The yeast strain W303 was grown in YPD medium before plasmid transformation. W303-NPL$_{MV}$ was grown at 30° C. for 24 hours in 25 ml of defined medium to an optical density at T0 of 0.5 or 5 $10^6$ cells/ml (8 h in 2% Raffinose, we do not wash away the raffinose medium before the induction for 16 h in 2% Galactose+1% Raffinose) and were pelleted. The yeasts were cultured at 30° C. in defined drop out medium, with selected nutrients omitted (tryptophan, histidin, leucin, uracil, adenin) to provide selection for DNA plasmids. The Synthetic Complete drop-out Medium Mix was enriched 2 times for YNB (Yeast Nitrogen Base with Ammonium Sulfate and without Amino Acids) (Difco, France) and 4 times for amino-acids (Sigma, France). Galactose-inducible expression of KANMX4 was obtained by using a mix of 2% of galactose (Sigma, France) and 1% of raffinose (Sigma, France). KANMX4 expression was selected by growth in medium supplemented with 100 mg/l G418 geneticin (Invitrogen, France). CAN1 based plasmid was eliminated by growth in medium supplemented with 200 mg/l L-Canavanine sulfate salt (C9758, Sigma). The pH of medium was adjusted to 5.6 or 6.5. All plasmids were introduced into yeast by the transformation method described in Gietz et al (20).

Yeast Culture Media

YPD medium (growing yeast without plasmids before transformation): 20 g yeast extract (Difco), 40 g Peptone (Difco), 30 g Glucose, 200 mg adenine hemisulphate, 20 g Bacto-agar (Difco) and 1000 ml distilled water (final volume), filter sterilize.

Synthetic complete drop-out medium (SG): 13.4 g YNB with ammonium sulfate, 10 g Galactose, 20 g Raffinose (Sigma R7630), 4 g Dropout AA, 20 g Bacto-agar (Difco) and 1000 ml distilled water (final volume). Adjust the pH to 5.6 or 6.5 with 10 N NaOH and filter sterilize.

Synthetic complete drop-out medium (SD): 13.4 g YNB with ammonium sulfate, 30 g glucose, 4 g Dropout AA, 20 g Bacto-agar (Difco) and 1000 ml distilled water (final volume). Adjust the pH to 5.6 or 6.5 with 10 N NaOH and filter sterilize.

Synthetic Complete Drop Out Mix: 2 g Arginine, 2 g Threonine, 2 g Cysteine, 2 g Isoleucine, 2 g Tyrosine, 2 g Glutamate, 2 g Lysine, 6 g Valine, 2 g Glutamine, 2 g Methionine, 2 g Alanine, 2 g Glycine, 3 g Phenylalanine, 2 g Aspartate, 2 g Proline, 2 g Serine and 2 g Asparagine.

The different metabolites used in medium complementations are 100× concentrated and filter sterilized: Adenine 2.0 mg/ml, Uracil 2.0 mg/ml, Histidine HCl 4.0 mg/ml, Leucine 6.0 mg/ml, Tryptophan 6.0 mg/ml. One ml of metabolites stock was added per plate containing 25 ml medium.

Transformation of Yeast

Yeast was inoculated into 15 ml liquid medium (2×YPD or 2×SD selection medium) and incubated overnight on a shaker at 200 rpm and 30° C. The day after, cells were diluted to an OD600=0.5 in same medium and incubated under stirring (200 rpm) at 30° C. for 3-4 hours, until OD600 reaches 1. Cells were harvested by centrifugation (3000 g for 5 min), washed two times in 25 ml and 1 ml of sterile water and centrifuged for 15 sec. to collect cell pellet. Transforming plasmid mixtures prepared according to table were added to cell pellets.

| Reagents | |
|---|---|
| PEG 3500 50% w/v | 240 μl |
| LiAc 1.0M | 36 μl |
| Boiled SS-carrier DNA | 50 μl |
| Plasmid DNA plus Water | 34 μl |
| Total | 360 μl |

PEG (Sigma P3640), LiAc (Sigma L6883), SS-carrier DNA (DNA Sodium Salt Type III from Salmon Testes, Sigma D1626).

Cells are resuspended by mixing vigorously and incubated at 42° C. for 40 min. The transformation mixture was removed by centrifugation and cells were washed with 1 ml sterile water before plating appropriate dilutions onto SD selection medium. After 3 to 4 days incubation at 30° C., the number of transformants was determined.

RNA Expression Analysis by Reverse Transcription and Real-Time PCR Assay.

The yeasts were grown at 30° C. for 24 hours in 25 ml of defined medium and were pelleted. We isolated total RNA using Trizol method (Invitrogen) followed by RNEASY® (Qiagen), a silica-membrane spin column-based RNA purification kit, and prepared cDNA using SuperScript II reverse transcriptase (Invitrogen, France) (21). Quantitative PCR analysis was done using SYBR PCR Mix (Applied Biosystems, France) and the Abiprism 7000 machine (Applied Biosystems, France). Quantification is described in Miled et al (22). In all quantitative PCR calculations, the amount of nucleic acid material was standardized using oligonucleotide primers for yeast 18S RNA genes. All quantification data are presented as the standardized values, mean±standard deviation of triplicates.

Oligonucleotides Used for qRT-PCR

| Genes | Forward | Reverse |
|---|---|---|
| Yeast Sc18S | 5'GAATAAGGGTTCGATTCCGGAG | 5'CTGCCTTCCTTGGATGTGGTAG |
| Virus MvSsN | 5'CCCTGGAGATTCCTCAATTACCA | 5'CCAATTAACCTCACCAACCGG |
| Virus MvSsP | 5'CAGACGCGAGATTAGCCTCATT | 5'GGTTGCACCACCTGTCAATAAAG |
| Virus MvSsL | 5'TGCTTATGAGAGCGGAGTAAGGA | TACGGCTATGGTCTGATTGTCCC |

Primers are purchased from Sigma-Proligo, France.

RNPs Purification from Yeast

The frozen or unfrozen yeast cells were lysed in lysis buffer containing, 10% Glycerol, 0.2% TritonX-100 150 mM NaCl, 25 mM Tris(pH7.5), 1 mM EDTA, a Protease Inhibitor Cocktail and RNAases inhibitors. A cold lysis buffer was added to an equal volume of glass beads and vortexed on ice. The yeast extract containing RNPs particles was filtered to remove cellular debris and followed by centrifugation through a 30% sucrose cushion. The resulting preparation containing purified viral RNPs may be adjuvanted with any available adjuvant.

REFERENCES

1. A. Wach, A. Brachat, R. Pohlmann, P. Philippsen (1994). New heterologous modules for classical or PCR-based gene disruptions in *Saccharomyces cerevisiae*. Yeast 10, 1793.
2. A. Pekosz, B. He, R. A. Lamb (1999). Reverse genetics of negative-strand RNA viruses: closing the circle. Proc Natl Acad Sci USA 96, 8804.
3. K. K. Conzelmann (2004). Reverse genetics of mononegavirales. Curr Top Microbiol Immunol 283, 1.
4. M. J. Schnell, T. Mebatsion, K. K. Conzelmann (1994). Infectious rabies viruses from cloned cDNA. Embo J 13, 4195.
5. B. Suter, D. Auerbach, I. Stagljar (2006). Yeast-based functional genomics and proteomics technologies: the first 15 years and beyond. Biotechniques 40, 625.
6. J. T. Bryan (2007). Developing an HPV vaccine to prevent cervical cancer and genital warts. Vaccine 25, 3001.
7. I. Alves-Rodrigues, R. P. Galao, A. Meyerhans, J. Diez (2006). *Saccharomyces cerevisiae*: a useful model host to study fundamental biology of viral replication. Virus Res 120, 49.
8. M. Janda, P. Ahlquist (1993). RNA-dependent replication, transcription, and persistence of brome mosaic virus RNA replicons in *S. cerevisiae*. Cell 72, 961.
9. T. Panavas, P. D. Nagy (2003). Yeast as a model host to study replication and recombination of defective interfering RNA of Tomato bushy stunt virus. Virology 314, 315.
10. B. D. Price, R. R. Rueckert, P. Ahlquist (1996). Complete replication of an animal virus and maintenance of expression vectors derived from it in *Saccharomyces cerevisiae*. Proc Natl Acad Sci USA 93, 9465.
11. P. C. Angeletti, K. Kim, F. J. Fernandes, P. F. Lambert (2002). Stable replication of papillomavirus genomes in *Saccharomyces cerevisiae*. J Virol 76, 3350.
12. K. N. Zhao, I. H. Frazer (2002). *Saccharomyces cerevisiae* is permissive for replication of bovine papillomavirus type 1. J Virol 76, 12265.
13. V. Pantaleo, L. Rubino, M. Russo (2003). Replication of Carnation Italian ringspot virus defective interfering RNA in *Saccharomyces cerevisiae*. J Virol 77, 2116.
14. B. D. Price, L. D. Eckerle, L. A. Ball, K. L. Johnson (2005). Nodamura virus RNA replication in *Saccharomyces cerevisiae*: heterologous gene expression allows replication-dependent colony formation. J Virol 79, 495.
15. W. H. Mager, J. Winderickx (2005). Yeast as a model for medical and medicinal research. Trends Pharmacol Sci 26, 265.

16. A. B. Parsons, R. Geyer, T. R. Hughes, C. Boone (2003). Yeast genomics and proteomics in drug discovery and target validation. Prog Cell Cycle Res 5, 159.
17. S. Plumet, W. P. Duprex, D. Gerlier (2005). Dynamics of viral RNA synthesis during measles virus infection. J Virol 79, 6900.
18. D. B. Kushner, B. D. Lindenbach, V. Z. Grdzelishvili, A. O. Noueiry, S. M. Paul, P. Ahlquist (2003). Systematic, genome-wide identification of host genes affecting replication of a positive-strand RNA virus. Proc Natl Acad Sci USA 100, 15764.
19. C. Combredet, V. Labrousse, L. Mollet, C. Lorin, F. Delebecque, B. Hurtrel, H. McClure, M. B. Feinberg, M. Brahic, F. Tangy (2003). A molecularly cloned Schwarz strain of measles virus vaccine induces strong immune responses in macaques and transgenic mice. J Virol 77, 11546.
20. R. D. Gietz, R. H. Schiestl (2007). High-efficiency yeast transformation using the LiAc/SS carrier DNA/PEG method. Nat Protoc 2, 31.
21. D. K. Fogg, C. Sibon, C. Miled, S. Jung, P. Aucouturier, D. R. Littman, A. Cumano, F. Geissmann (2006). A clonogenic bone marrow progenitor specific for macrophages and dendritic cells. Science 311, 83.
22. C. Miled, M. Pontoglio, S. Garbay, M. Yaniv, J. B. Weitzman (2005). A genomic map of p53 binding sites identifies novel p53 targets involved in an apoptotic network. Cancer Res 65, 5096.

The invention claimed is:

1. A recombinant yeast strain which expresses infectious non-segmented negative-strand RNA virus Ribonucleocapsids (RNPs) or infectious RNPs-like, wherein the yeast is transformed with the following expression vectors:
(i) a first plasmid genome vector comprising, as an insert operatively linked with expression control sequences functional in yeast, a cloned DNA molecule which comprises a cDNA encoding the (+) strand full-length sequence (antigenome) of said non-segmented negative-strand RNA virus and wherein said cDNA is flanked, in the cloned DNA molecule, by autocatalytic ribozyme sequences enabling the recovery of mRNA transcripts and of antigenomic RNAs of said non-segmented negative strand or derivatives thereof;

(ii) a second plasmid genome vector comprising, as an insert under the control of regulatory expression sequences functional in yeast, a cloned DNA molecule which comprises a cDNA encoding part of the antigenome of said non-segmented negative-strand RNA virus including in the 5' to 3' orientation, a viral Terminator sequence, a polynucleotide which codes a selectable marker cloned in sense orientation with respect to the cis-acting sequences of said virus and the Leader sequence of said virus; and (iii) one or more trans-complementation plasmid vectors comprising, under the control of regulation expression sequences functional in yeast, nucleotide sequences which enable said vector(s) to collectively express the proteins necessary for the synthesis of the viral transcriptase complex of said non-segmented negative-strand RNA virus, and enable assembly of the ribonucleocapsid (RNPs) of said non-segmented negative-strand virus or assembly of RNPs-like comprising recombinant RNA derived from viral RNA of a non-segmented negative-strand RNA virus, wherein the RNPs or RNPs-like are functional for the replication and transcription, each of said vector(s) further comprises, under the control of regulatory expression sequences functional in yeast, a selectable marker, wherein in said vectors all the selectable markers are different from each other, and wherein the vector encoding the viral L polymerase of said non-segmented negative-strand RNA virus is a priming plasmid harboring an auxotrophy marker gene.

2. The recombinant yeast strain according to claim 1, wherein the non-segmented negative-strand RNA virus is selected from the group consisting of: Rhabdoviridae, Paramyxoviridae, Filovihdae, and Bomaviridae.

3. The recombinant yeast strain according to claim 2, wherein the non-segmented negative-strand RNA virus is selected from the group consisting of: Measles virus, RSV, HPIV2, and HPIV3.

4. The recombinant yeast strain according to claim 1;

wherein the non-segmented negative-strand RNA virus is a measles virus (MV);

wherein the one or more trans-complementation plasmid vectors are capable of expressing the nucleoprotein (N), the Phosphoprotein (P) and the Polymerase (L) or derivatives thereof as functional ribonucleoproteins (RNPs) comprising the transcriptase complex; and wherein the first or second plasmid genome vector comprises a cloned molecule which comprises a cDNA encoding the full-length (+) strand antigenome of said measles virus and wherein said cDNA is framed by autocatalytic ribozyme sequences.

5. The recombinant yeast strain according to claim 1; wherein the non-segmented negative-strand RNA virus is a measles virus; and
wherein the one or more trans-complementation plasmid vectors and the first and second plasmid genome vectors are further characterized as follows:
   (a) the one or more trans-complementation plasmid vectors are capable of collectively expressing the nucleoprotein (N), the Phosphoprotein (P) and the Polymerase (L) or functional derivatives thereof which enable assembly of functional ribonucleoproteins (RNPs) or RNPs-like comprising the transcriptase complex; and
   (b) the first or second plasmid genome vectors comprises, in an insert, a cloned DNA molecule which comprises a cDNA encoding a fragment of the (+)strand (antigenome) of said virus, including the cis-acting Leader and Trailer sequences, and furthermore one or more coding sequences, or ORF(s), heterologous to said virus, the expression of which is sought.

6. The recombinant yeast strain according to claim 4, wherein the nucleoprotein (N), the phosphoprotein (P) and the polymerase (L) are expressed by several plasmid expression vectors, said expression vectors comprising cloned polynucleotides consisting of viral coding sequences for one of the N, P or L proteins, under the control of a promoter suitable for expression in yeast.

7. The recombinant yeast strain according to claim 4, wherein the nucleoprotein (N), and the phosphoprotein (P) are expressed by a single expression vector, and the polymerase (L) is expressed by another expression vector said expression vectors comprising cloned polynucleotides consisting of viral coding sequences for the N and P proteins or for the L protein respectively, under the control of a promoter suitable for expression in yeast.

8. The recombinant yeast strain according to claim 1, wherein in the first and second plasmid genome vectors the cloned molecule is cloned in a plasmid under the control of expression control sequences suitable for expression in yeast, including a promoter and a transcription terminator sequence in sense or in antisense orientation.

9. The recombinant yeast strain according to claim 1, wherein in at least one of the first and second plasmid genome vectors the cDNA in the cloned DNA molecule comprises at least one of the following polynucleotides:
   (a) a Leader and/or Trailer sequence of measles virus (MV);
   (b) an additional Promoter sequence derived from the MV, selected from the group consisting of: the promoter of the nucleoprotein (N), phosphoprotein (P) and polymerase (L) of an MV;
   (c) an additional Terminator sequence derived from the MV, selected from the group consisting of: the terminator of the polymerase (L) or of the nucleoprotein (N), and the phosphoprotein (P) of an MV; and
   (d) the cDNA of the cloned molecule is framed by different or identical autocatalytic ribozymes selected among hammerhead ribozyme and hepatitis delta virus ribozyme.

10. The recombinant yeast strain according to claim 9, wherein the measles virus is an attenuated measles virus.

11. The recombinant yeast strain according to claim 10, wherein the measles virus is a Schwarz MV.

12. The recombinant yeast strain according to claim 1, wherein at least one of said plasmid vectors is selected from pCM101, pCM103, pCM104, pCM105, pCM106, pCM112, pCM113, pCM201, pCM224, pCM225, pCM226, pCM227, pCM402, pCM476, pCM503, and pCM603 deposited at the Collection Nationale de Cultures de Microorganismes (CNCM) under No. I-3896, I-3897, I-3898, I-3899, I-3900, I-3901, I-3902, I-3903, I-3904, I-3905, I-3906, I-3907, I-4117, I-4118, I-4119, and I-4120, respectively.

13. The recombinant yeast strain according to claim 1, wherein in the second plasmid genome vector the cDNA encoding part of the antigenome of said non-segmented negative-strand RNA virus is devoid of all the viral genes or is devoid of all the viral coding sequences.

14. The recombinant yeast strain according to claim 1, wherein in at least one of the first and the second genome vectors the cDNA of the cloned molecule is a recombinant cDNA which comprises a coding sequence of a reporter gene.

15. The recombinant yeast strain according to claim 1, wherein in at least one of the first and the second genome vectors the cDNA of the cloned molecule is a recombinant cDNA which comprises a coding sequence of a cellular protein.

16. The recombinant yeast strain according to claim 1, wherein in at least one of the first and the second genome vectors the cDNA of the cloned molecule is a recombinant cDNA which comprises a coding sequence of an antigen or an epitope, suitable for eliciting an immune response in a host in need thereof.

17. The recombinant yeast strain according to claim 1, which is a strain of *Saccharomyces Cerevisiae*.

18. The recombinant yeast strain according to claim 1, which is a strain of *Pichia Pastoris* or *Saccharomyces Pombe*.

19. The recombinant yeast strain according to claim 1, which is the strain yCM112, yCM113, yCM226, or yCM403 deposited at the CNCM under No. I-3908, I-3909, I-3910, and I-4121, respectively.

20. A set of RNPs of a non-segmented negative-strand RNA virus or a set of RNPs-like of a non-segmented negative-strand RNA virus, which is expressed from a recombinant yeast strain according to claim 1.

21. The set of RNPs or RNPs-like according to claim 20, wherein the RNPs or RNPs-like are formulated with a transfectant agent.

22. An immunogenic composition comprising RNPs or RNPs-like according to claim 20.

23. A system for the preparation of RNPs or RNPs-like from a non-segmented negative-strand RNA virus by reverse genetics in yeast strains, wherein said system comprises:
   (a) the recombinant yeast strain according to claim 1; and
   (b) a culture medium for said yeast strain, which comprises an adequate culture medium for a yeast which is devoid of the components which are expressed by the selectable markers contained in complementation vectors of said recombinant yeast.

24. The recombinant yeast strain according to claim 6, wherein the promoter suitable for expression in yeast is an inducible promoter.

25. The recombinant yeast strain according to claim 7, wherein the promoter suitable for expression in yeast is an inducible promoter.

26. The recombinant yeast strain according to claim 1; wherein the one or more trans-complementation plasmid vectors each independently comprise a selectable auxotrophy marker.

27. A process for the preparation of infectious RNPs of a non-segmented negative-strand RNA virus or infectious RNPs-like, wherein said RNPs or RNPs-like are expressed from yeast after:
(a) transforming a yeast strain with vectors according to claim 1;
(b) growing said recombinant yeast strain; and
(c) recovering the produced infectious virus RNPs or infectious RNPs-like.

28. A process for preparation of RNPs or RNPs-like of a non-segmented negative-strand RNA virus characterized in that it comprises the steps of:
(a) obtaining recombinant yeasts expressing RNPs or RNPs-like according to claim 1; and
(b) recovering the RNPs or RNPs-like from said yeasts.

29. A method for preparing an immunogenic composition comprising infectious RNPs or RNPs-like, which comprises seeding a culture with the recombinant yeast strain according to claim 1, and isolating infectious RNPs or RNPs-like.

* * * * *

SEQUENCE LISTING

```
<160> NUMBER OF SEQ ID NOS: 50

<210> SEQ ID NO 1
<211> LENGTH: 30
<212> TYPE: DNA
<213> ORGANISM: Artificial
<220> FEATURE:
<223> OTHER INFORMATION: oligonucleotide

<400> SEQUENCE: 1
catggtcgac aagagcagga ttagggatat                                    30

<210> SEQ ID NO 2
<211> LENGTH: 30
<212> TYPE: DNA
<213> ORGANISM: Artificial
<220> FEATURE:
<223> OTHER INFORMATION: oligonucleotide

<400> SEQUENCE: 2
gcatctcgag tggatggttg atgggctggc                                    30

<210> SEQ ID NO 3
<211> LENGTH: 30
<212> TYPE: DNA
<213> ORGANISM: Artificial
<220> FEATURE:
<223> OTHER INFORMATION: oligonucleotide

<400> SEQUENCE: 3
catggtcgac caggtccaca cagccgccag                                    30

<210> SEQ ID NO 4
<211> LENGTH: 30
<212> TYPE: DNA
<213> ORGANISM: Artificial
<220> FEATURE:
<223> OTHER INFORMATION: oligonucleotide

<400> SEQUENCE: 4
gcatctcgag ggtcgactgg catggggttg                                    30

<210> SEQ ID NO 5
<211> LENGTH: 68
<212> TYPE: DNA
<213> ORGANISM: Artificial
<220> FEATURE:
<223> OTHER INFORMATION: oligonucleotide

<400> SEQUENCE: 5
accagacaaa gctgggaata gaaacttcgt attttcaaag ttttctttaa tatattgcaa    60
``` ataatgcc                                                              68

<210> SEQ ID NO 6
<211> LENGTH: 100
<212> TYPE: DNA
<213> ORGANISM: Artificial
<220> FEATURE:
<223> OTHER INFORMATION: oligonucleotide

<400> SEQUENCE: 6
gtcccattcg ccattaccga ggggacggtc ccctcggaat gttgcccagc cggcgccagc     60
gaggaggctg ggaccatgcc ggccaccaaa caaagttggg                          100

<210> SEQ ID NO 7
<211> LENGTH: 82
<212> TYPE: DNA
<213> ORGANISM: Artificial
<220> FEATURE:
<223> OTHER INFORMATION: oligonucleotide

<400> SEQUENCE: 7
gacggatcca actttgtttg gtctgatgag tccgtgagga cgaaacccgg agtcccgggt     60
caccagacaa agctgggaat ag                                             82

<210> SEQ ID NO 8
<211> LENGTH: 30
<212> TYPE: DNA
<213> ORGANISM: Artificial
<220> FEATURE:
<223> OTHER INFORMATION: oligonucleotide

<400> SEQUENCE: 8
cgagctgctc gagtcccatt cgccattacc                                      30

<210> SEQ ID NO 9
<211> LENGTH: 32
<212> TYPE: DNA
<213> ORGANISM: Artificial
<220> FEATURE:
<223> OTHER INFORMATION: oligonucleotide

<400> SEQUENCE: 9
gaagcttgac ggatccaact ttgtttggtc tg                                   32

<210> SEQ ID NO 10
<211> LENGTH: 30
<212> TYPE: DNA
<213> ORGANISM: Artificial
<220> FEATURE:
<223> OTHER INFORMATION: oligonucleotide

<400> SEQUENCE: 10
cgagctgctc gagtcccatt cgccattacc                                      30

<210> SEQ ID NO 11
<211> LENGTH: 28
<212> TYPE: DNA
<213> ORGANISM: Artificial
<220> FEATURE:
<223> OTHER INFORMATION: oligonucleotide

<400> SEQUENCE: 11
ccatgctagc cgagaatttt gtaacacc                                        28

-continued

```
<210> SEQ ID NO 12
<211> LENGTH: 28
<212> TYPE: DNA
<213> ORGANISM: Artificial
<220> FEATURE:
<223> OTHER INFORMATION: oligonucleotide

<400> SEQUENCE: 12
ggcatgggcc cttgcttctt gttactgg                                           28

<210> SEQ ID NO 13
<211> LENGTH: 28
<212> TYPE: DNA
<213> ORGANISM: Artificial
<220> FEATURE:
<223> OTHER INFORMATION: oligonucleotide

<400> SEQUENCE: 13
gaattcgagc tcatgacaaa ttcaaaag                                           28

<210> SEQ ID NO 14
<211> LENGTH: 29
<212> TYPE: DNA
<213> ORGANISM: Artificial
<220> FEATURE:
<223> OTHER INFORMATION: oligonucleotide

<400> SEQUENCE: 14
ctactgccat ggactatgct acaacattc                                          29

<210> SEQ ID NO 15
<211> LENGTH: 30
<212> TYPE: DNA
<213> ORGANISM: Artificial
<220> FEATURE:
<223> OTHER INFORMATION: oligonucleotide

<400> SEQUENCE: 15
gctcgcgggc cgcatgacaa attcaaaaga                                         30

<210> SEQ ID NO 16
<211> LENGTH: 30
<212> TYPE: DNA
<213> ORGANISM: Artificial
<220> FEATURE:
<223> OTHER INFORMATION: oligonucleotide

<400> SEQUENCE: 16
ccatgggcta gcactatgct acaacattcc                                         30

<210> SEQ ID NO 17
<211> LENGTH: 22
<212> TYPE: DNA
<213> ORGANISM: Artificial
<220> FEATURE:
<223> OTHER INFORMATION: oligonucleotide

<400> SEQUENCE: 17
gaataagggt tcgattccgg ag                                                 22

<210> SEQ ID NO 18
<211> LENGTH: 22
<212> TYPE: DNA
<213> ORGANISM: Artificial
<220> FEATURE:
<223> OTHER INFORMATION: oligonucleotide
```

<400> SEQUENCE: 18
ctgccttcct tggatgtggt ag					22

<210> SEQ ID NO 19
<211> LENGTH: 23
<212> TYPE: DNA
<213> ORGANISM: Artificial
<220> FEATURE:
<223> OTHER INFORMATION: oligonucleotide

<400> SEQUENCE: 19
ccctggagat tcctcaatta cca					23

<210> SEQ ID NO 20
<211> LENGTH: 21
<212> TYPE: DNA
<213> ORGANISM: Artificial
<220> FEATURE:
<223> OTHER INFORMATION: oligonucleotide

<400> SEQUENCE: 20
ccaattaacc tcaccaaccg g					21

<210> SEQ ID NO 21
<211> LENGTH: 22
<212> TYPE: DNA
<213> ORGANISM: Artificial
<220> FEATURE:
<223> OTHER INFORMATION: oligonucleotide

<400> SEQUENCE: 21
cagacgcgag attagcctca tt					22

<210> SEQ ID NO 22
<211> LENGTH: 23
<212> TYPE: DNA
<213> ORGANISM: Artificial
<220> FEATURE:
<223> OTHER INFORMATION: oligonucleotide

<400> SEQUENCE: 22
ggttgcacca cctgtcaata aag					23

<210> SEQ ID NO 23
<211> LENGTH: 23
<212> TYPE: DNA
<213> ORGANISM: Artificial
<220> FEATURE:
<223> OTHER INFORMATION: oligonucleotide

<400> SEQUENCE: 23
tgcttatgag agcggagtaa gga					23

<210> SEQ ID NO 24
<211> LENGTH: 23
<212> TYPE: DNA
<213> ORGANISM: Artificial
<220> FEATURE:
<223> OTHER INFORMATION: oligonucleotide

<400> SEQUENCE: 24
tacggctatg gtctgattgt ccc					23

<210> SEQ ID NO 25

```
<211> LENGTH: 84
<212> TYPE: DNA
<213> ORGANISM: Artificial
<220> FEATURE:
<223> OTHER INFORMATION: Plasmid - Multiple Cloning Site 1 Region
<220> FEATURE:
<221> NAME/KEY: CDS
<222> LOCATION: (40)..(69)
<223> OTHER INFORMATION:

<400> SEQUENCE: 25
gaattcaacc ctcactaaag ggcggccgca ctagtatcg atg gat tac aag gat        54
                                            Met Asp Tyr Lys Asp
                                            1               5 gac gac gat aag atc tgagctctta attaa                                  84
Asp Asp Asp Lys Ile
            10

<210> SEQ ID NO 26
<211> LENGTH: 10
<212> TYPE: PRT
<213> ORGANISM: Artificial
<220> FEATURE:
<223> OTHER INFORMATION: Plasmid - Multiple Cloning Site 1 Region

<400> SEQUENCE: 26

Met Asp Tyr Lys Asp Asp Asp Asp Lys Ile
1               5                   10

<210> SEQ ID NO 27
<211> LENGTH: 98
<212> TYPE: DNA
<213> ORGANISM: Artificial
<220> FEATURE:
<223> OTHER INFORMATION: Plasmid - Multiple Cloning Site 2 Region
<220> FEATURE:
<221> NAME/KEY: CDS
<222> LOCATION: (41)..(76)
<223> OTHER INFORMATION:

<400> SEQUENCE: 27
ggatccgtaa tacgactcac tatagggccc gggcgtcgac atg gaa cag aag ttg       55
                                            Met Glu Gln Lys Leu
                                            1               5 att tcc gaa gaa gac ctc gag taagcttggt accgcggcta gc                  98
Ile Ser Glu Glu Asp Leu Glu
            10

<210> SEQ ID NO 28
<211> LENGTH: 12
<212> TYPE: PRT
<213> ORGANISM: Artificial
<220> FEATURE:
<223> OTHER INFORMATION: Plasmid - Multiple Cloning Site 2 Region

<400> SEQUENCE: 28

Met Glu Gln Lys Leu Ile Ser Glu Glu Asp Leu Glu
1               5                   10

<210> SEQ ID NO 29
<211> LENGTH: 7525
<212> TYPE: DNA
<213> ORGANISM: Artificial
<220> FEATURE:
<223> OTHER INFORMATION: Plasmid

<400> SEQUENCE: 29
ccaactttgt ttggtctgat gagtccgtga ggacgaaacc cggagtcccg ggtcaccaga     60
```

```
caaagctggg aatagaaact tcgtattttc aaagttttct ttaatatatt gcaaataatg      120
cctaaccacc tagggcagga ttagggttcc ggagttcaac caattagtcc ttaatcaggg      180
cactgtatcc gactaactta taccatatca tcgatgaatt cgagctcgtt ttcgacactg      240
gatggcggcg ttagtatcga atcgacagca gtatagcgac cagcattcac atacgattga      300
cgcatgatat tactttctgc gcacttaact tcgcatctgg gcagatgatg tcgaggcgaa      360
aaaaaatata aatcacgcta acatttgatt aaaatagaac aactacaata taaaaaaact      420
atacaaatga caagttcttg aaaacaagaa tctttttatt gtcagtactg attagaaaaa      480
ctcatcgagc atcaaatgaa actgcaattt attcatatca ggattatcaa taccatattt      540
ttgaaaaagc cgtttctgta atgaaggaga aaactcaccg aggcagttcc ataggatggc      600
aagatcctgg tatcggtctg cgattccgac tcgtccaaca tcaatacaac ctattaattt      660
cccctcgtca aaataaggt tatcaagtga aaatcacca tgagtgacga ctgaatccgg      720
tgagaatggc aaaagcttat gcatttcttt ccagacttgt tcaacaggcc agccattacg      780
ctcgtcatca aatcactcg catcaaccaa accgttattc attcgtgatt gcgcctgagc      840
gagacgaaat acgcgatcgc tgttaaaagg acaattacaa acaggaatcg aatgcaaccg      900
gcgcaggaac actgccagcg catcaacaat attttcacct gaatcaggat attcttctaa      960
tacctggaat gctgttttgc cggggatcgc agtggtgagt aaccatgcat catcaggagt     1020
acggataaaa tgcttgatgg tcggaagagg cataaattcc gtcagccagt ttagtctgac     1080
catctcatct gtaacatcat tggcaacgct acctttgcca tgtttcagaa acaactctgg     1140
cgcatcgggc ttcccataca atcgatagat tgtcgcacct gattgcccga cattatcgcg     1200
agcccattta tacccatata aatcagcatc catgttggaa tttaatcgcg gcctcgaaac     1260
gtgagtcttt tccttaccca tggttgttta tgttcggatg tgatgtgaga actgtatcct     1320
agcaagattt tccatctcgg atatccctaa tcctgctctt gtccctgata ataggatctt     1380
gaatcctaag tgcactagaa gatgatcatt gattgaacta tccttaccca actttgtttg     1440
gtggccggca tggtcccagc ctcctcgctg gcgccggctg ggcaacattc cgaggggacc     1500
gtcccctcgg taatggcgaa tgggactcga gcatgcatct agagggccgc atcatgtaat     1560
tagttatgtc acgcttacat tcacgccctc cccccacatc cgctctaacc gaaaaggaag     1620
gagttagaca acctgaagtc taggtcccta tttattttt tatagttatg ttagtattaa     1680
gaacgttatt tatatttcaa attttttctt tttttctgta cagacgcgtg tacgcatgta     1740
acattatact gaaaaccttg cttgagaagg ttttgggacg ctcgaaggct ttaatttgcg     1800
gccctgcatt aatgaatcgg ccaacgcgcg gggagaggcg gtttgcgtat tgggcgctct     1860
tccgcttcct cgctcactga ctcgctgcgc tcggtcgttc ggctgcggcg agcggtatca     1920
gctcactcaa aggcggtaat acggttatcc acagaatcag gggataacgc aggaaagaac     1980
atgtgagcaa aaggccagca aaagcccagg aaccgtaaaa aggccgcgtt gctggcgttt     2040
ttccataggc tccgcccccc tgacgagcat cacaaaaatc gacgctcaag tcagaggtgg     2100
cgaaacccga caggactata aagataccag gcgtttcccc ctggaagctc cctcgtgcgc     2160
tctcctgttc cgaccctgcc gcttaccgga tacctgtccg cctttctccc ttcgggaagc     2220
gtggcgcttt ctcatagctc acgctgtagg tatctcagtt cggtgtaggt cgttcgctcc     2280
aagctgggct gtgtgcacga accccccgtt cagcccgacc gctgcgcctt atccggtaac     2340
tatcgtcttg agtccaaccc ggtaagacac gacttatcgc cactggcagc agccactggt     2400
```

```
aacaggatta gcagagcgag gtatgtaggc ggtgctacag agttcttgaa gtggtggcct    2460
aactacggct acactagaag gacagtattt ggtatctgcg ctctgctgaa gccagttacc    2520
ttcggaaaaa gagttggtag ctcttgatcc ggcaaacaaa ccaccgctgg tagcggtggt    2580
ttttttgttt gcaagcagca gattacgcgc agaaaaaaag gatctcaaga agatcctttg    2640
atcttttcta cggggtctga cgctcagtgg aacgaaaact cacgttaagg gattttggtc    2700
atgagattat caaaaaggat cttcacctag atccttttaa attaaaaatg aagttttaaa    2760
tcaatctaaa gtatatatga gtaaacttgg tctgacagtt accaatgctt aatcagtgag    2820
gcacctatct cagcgatctg tctatttcgt tcatccatag ttgcctgact ccccgtcgtg    2880
tagataacta cgatacggga gcgcttacca tctggcccca gtgctgcaat gataccgcga    2940
gacccacgct caccggctcc agatttatca gcaataaacc agccagccgg aagggccgag    3000
cgcagaagtg gtcctgcaac tttatccgcc tccattcagt ctattaattg ttgccgggaa    3060
gctagagtaa gtagttcgcc agttaatagt ttgcgcaacg ttgttggcat tgctacaggc    3120
atcgtggtgt cactctcgtc gtttggtatg gcttcattca gctccggttc caacgatca    3180 aggcgagtta catgatcccc catgttgtgc aaaaaagcgg ttagctcctt cggtcctccg    3240
atcgttgtca gaagtaagtt ggccgcagtg ttatcactca tggttatggc agcactgcat    3300
aattctctta ctgtcatgcc atccgtaaga tgcttttctg tgactggtga gtactcaacc    3360
aagtcattct gagaatagtg tatgcggcga ccgagttgct cttgcccggc gtcaatacgg    3420
gataatagtg tatcacatag cagaacttta aaagtgctca tcattggaaa acgttcttcg    3480
gggcgaaaac tctcaaggat cttaccgctg ttgagatcca gttcgatgta acccactcgt    3540
gcacccaact gatcttcagc atcttttact ttcaccagcg tttctgggtg agcaaaaaca    3600
ggaaggcaaa atgccgcaaa aaagggaata agggcgacac ggaaatgttg aatactcata    3660
ctcttccttt ttcaatgggt aataactgat ataattaaat tgaagctcta atttgtgagt    3720
ttagtataca tgcatttact tataatacag ttttttagtt ttgctggccg catcttctca    3780
aatatgcttc ccagcctgct tttctgtaac gttcaccctc taccttagca tcccttccct    3840
ttgcaaatag tcctcttcca acaataataa tgtcagatcc tgtagagacc acatcatcca    3900
cggttctata ctgttgaccc aatgcgtctc ccttgtcatc taaacccaca ccgggtgtca    3960
taatcaacca atcgtaacct tcatctcttc cacccatgtc tctttgagca ataaagccga    4020
taacaaaatc tttgtcgctc ttcgcaatgt caacagtacc cttagtatat ctccagtag    4080 atagggagcc cttgcatgac aattctgcta acatcaaaag gcctctaggt tcctttgtta    4140
cttcttctgc cgcctgcttc aaaccgctaa caatacctgg gcccaccaca ccgtgtgcat    4200
tcgtaatgtc tgcccattct gctattctgt atacacccgc agagtactgc aatttgactg    4260
tattaccaat gtcagcaaat tttctgtctt cgaagagtaa aaaattgtac ttggcggata    4320 atgccttag cggcttaact gtgccctcca tggaaaatc agtcaagata ccacatgtg     4380 ttttagtaa acaaattttg ggacctaatg cttcaactaa ctccagtaat tccttggtgg    4440
tacgaacatc caatgaagca cacaagtttg tttgcttttc gtgcatgata ttaaatagct    4500
tggcagcaac aggactagga tgagtagcag cacgttcctt atatgtagct ttcgacatga    4560
tttatcttcg tttcctgcag gttttttgttc tgtgcagttg ggttaagaat actgggcaat    4620
ttcatgtttc ttcaacacta catatgcgta tatataccaa tctaagtctg tgctccttcc    4680
ttcgttcttc cttctgttcg gagattaccg aatcaaaaaa atttcaaaga aaccgaaatc    4740 aaaaaaaga ataaaaaaaa aatgatgaat tgaattgaaa agctagctta tcgatgataa    4800
```

-continued

```
gctgtcaaag atgagaatta attccacgga ctatagacta tactagatac tccgtctact    4860
gtacgataca cttccgctca ggtccttgtc ctttaacgag gccttaccac tcttttgtta    4920
ctctattgat ccagctcagc aaaggcagtg tgatctaaga ttctatcttc gcgatgtagt    4980
aaaactagct agaccgagaa agagactaga atgcaaaag gcacttctac aatggctgcc     5040
atcattatta tccgatgtga cgctgcagct tctcaatgat attcgaatac gctttgagga    5100
gatacagcct aatatccgac aaactgtttt acagatttac gatcgtactt gttacccatc    5160
attgaatttt gaacatccga acctgggagt tttccctgaa acagatagta tatttgaacc    5220
tgtataataa tatatagtct agcgctttac ggaagacaat gtatgtattt cggttcctgg    5280
agaaactatt gcatctattg cataggtaat cttgcacgtc gcatccccgg ttcattttct    5340
gcgtttccat cttgcacttc aatagcatat cttttgttaac gaagcatctg tgcttcattt    5400
tgtagaacaa aaatgcaacg cgagagcgct aatttttcaa acaaagaatc tgagctgcat    5460
ttttacagaa cagaaatgca acgcgaaagc gctattttac caacgaagaa tctgtgcttc    5520
attttttgtaa aacaaaaatg caacgcgacg agagcgctaa ttttttcaaac aaagaatctg   5580
agctgcattt ttacagaaca gaaatgcaac gcgagagcgc tattttacca acaaagaatc    5640
tatacttctt ttttgttcta caaaaatgca tcccgagagc gctattttc taacaaagca     5700
tcttagatta ctttttttct cctttgtgcg ctctataatg cagtctcttg ataactttt    5760
gcactgtagg tccgttaagg ttagaagaag gctactttgg tgtctatttt ctcttccata    5820
aaaaaagcct gactccactt cccgcgttta ctgattacta gcgaagctgc gggtgcattt    5880
tttcaagata aaggcatccc cgattatatt ctataccgat gtggattgcg catactttgt    5940
gaacagaaag tgatagcgtt gatgattctt cattggtcag aaaattatga acggtttctt    6000
ctattttgtc tctatatact acgtatagga atgtttaca ttttcgtatt gttttcgatt     6060
cactctatga atagttctta ctacaatttt tttgtctaaa gagtaatact agagataaac    6120
ataaaaaatg tagaggtcga gtttagatgc aagttcaagg agcgaaaggt ggatgggtag    6180
gttatatagg gatatagcac agagatatat agcaaagaga tacttttgag caatgtttgt    6240
ggaagcggta ttcgcaatgg gaagctccac cccggttgat aatcagaaaa gccccaaaaa    6300
caggaagatt gtataagcaa atatttaaat tgtaaacgtt aatattttgt taaaattcgc    6360
gttaaatttt tgttaaatca gctcattttt taacgaatag cccgaaatcg gcaaaatccc    6420
ttataaatca aaagaataga ccgagatagg gttgagtgtt gttccagttt ccaacaagag    6480
tccactatta aagaacgtgg actccaacgt caaagggcga aaaagggtct atcagggcga    6540
tggcccacta cgtgaaccat caccctaatc aagttttttg gggtcgaggt gccgtaaagc    6600
agtaaatcgg aagggtaaac ggatgccccc atttagagct tgacggggaa agccggcgaa    6660
cgtggcgaga aggaaggga agaaagcgaa aggagcgggg gctagggcgg tgggaagtgt     6720
agggggtcacg ctgggcgtaa ccaccacacc cgccgcgctt aatggggcgc tacagggcgc    6780
gtggggatga tccactagta cggattagaa gccgccgagc gggtgacagc cctccgaagg    6840
aagactctcc tccgtgcgtc ctcgtcctca ccggtcgcgt tcctgaaacg cagatgtgcc    6900
tcgcgccgca ctgctccgaa caataaagat tctacaatac tagcttttat ggttatgaag    6960
aggaaaaatt ggcagtaacc tggccccaca aaccttcaaa tgaacgaatc aaattaacaa    7020
ccataggatg ataatgcgat tagttttta gccttatttc tggggtaatt aatcagcgaa    7080
gcgatgattt ttgatctatt aacagatata taaatgcaaa aactgcatta accactttaa    7140
```

```
ctaatactttt caacatttttc ggtttgtatt acttcttatt caaatgtaat aaaagtatca    7200
acaaaaaatt gttaatatac ctctatactt taacgtcaag gagaaaaaac cccggatcgg    7260
actactagca gctgtaatac gactcactat agggaatatt aagcttggta ccgagctcgg    7320
atccactagt aacggccgcc agtgtgctgg aattctgcag atatccatca cactggcggc    7380
cgcatccgga tatagttcct cctttcagca aaaaacccct caagacccgt ttagaggccc    7440
caaggggtta tgctagttat tgctcagcgg tggcagcagc caactcagct tcctttcggg    7500
ctttgttagc agccggatcg gccgc                                          7525

<210> SEQ ID NO 30
<211> LENGTH: 7474
<212> TYPE: DNA
<213> ORGANISM: Artificial
<220> FEATURE:
<223> OTHER INFORMATION: Plasmid

<400> SEQUENCE: 30
ccaactttgt ttggtctgat gagtccgtga ggacgaaacc cggagtcccg ggtcaccaaa      60
caaagttggg taaggatagt tcaatcaatg atcatcttct agtgcactta ggattcaaga    120
tcctattatc agggacaaga gcaggattag ggatatccga gatggaaaat cttgctagga    180
tacagttctc acatcacatc cgaacataaa caaccatggg taaggaaaag actcacgttt    240
cgaggccgcg attaaattcc aacatggatg ctgatttata tgggtataaa tgggctcgcg    300
ataatgtcgg gcaatcaggt gcgacaatct atcgattgta tgggaagccc gatgcgccag    360
agttgtttct gaaacatggc aaaggtagcg ttgccaatga tgttacagat gagatggtca    420
gactaaactg gctgacggaa tttatgcctc ttccgaccat caagcatttt atccgtactc    480
ctgatgatgc atggttactc accactgcga tccccggcaa acagcattc caggtattag      540 aagaatatcc tgattcaggt gaaaatattg ttgatgcgct ggcagtgttc ctgcgccggt    600
tgcattcgat tcctgtttgt aattgtcctt ttaacagcga tcgcgtattt cgtctcgctc    660
aggcgcaatc acgaatgaat aacggtttgg ttgatgcgag tgattttgat gacgagcgta    720
atggctggcc tgttgaacaa gtctggaaag aaatgcataa gcttttgcca ttctcaccgg    780
attcagtcgt cactcatggt gatttctcac ttgataacct tattttgac gaggggaaat      840 taataggttg tattgatgtt ggacgagtcg aatcgcaga ccgataccag gatcttgcca      900
tcctatggaa ctgcctcggt gagttttctc cttcattaca gaaacggctt tttcaaaaat    960
atggtattga taatcctgat atgaataaat tgcagtttca tttgatgctc gatgagtttt    1020
tctaatcagt actgacaata aaaagattct tgttttcaag aacttgtcat tgtatagtt    1080 tttttatatt gtagttgttc tattttaatc aaatgttagc gtgatttata ttttttttcg    1140
cctcgacatc atctgcccag atgcgaagtt aagtgcgcag aaagtaatat catgcgtcaa    1200
tcgtatgtga atgctggtcg ctatactgct gtcgattcga tactaacgcc gccatccagt    1260
gtcgaaaacg agctcgaatt catcgatgat atggtataag ttagtcggat acagtgccct    1320
gattaaggac taattggttg aactccggaa ccctaatcct gccctaggtg gttaggcatt    1380
atttgcaata tattaaagaa aactttgaaa atacgaagtt tctattccca gctttgtctg    1440
gtggccggca tggtcccagc ctcctcgctg gcgccggctg gcaacattc cgagggacc      1500 gtcccctcgg taatggcgaa tgggacgcgg ccgatccggc tgctaacaaa gcccgaaagg    1560
aagctgagtt ggctgctgcc accgctgagc aataactagc ataacccctt ggggcctcta    1620
aacgggtctt gaggggtttt ttgctgaaag gaggaactat atccggatgc ggcgctcga    1680
```

```
gcatgcatct agagggccgc atcatgtaat tagttatgtc acgcttacat tcacgccctc    1740
cccccacatc cgctctaacc gaaaaggaag gagttagaca acctgaagtc taggtcccta    1800 tttattttt tatagttatg ttagtattaa gaacgttatt tatatttcaa attttctttt    1860
tttttctgta cagacgcgtg tacgcatgta acattatact gaaaaccttg cttgagaagg    1920
ttttgggacg ctcgaaggct ttaatttgcg gccctgcatt aatgaatcgg ccaacgcgcg    1980
gggagaggcg gtttgcgtat tgggcgctct tccgcttcct cgctcactga ctcgctgcgc    2040
tcggtcgttc ggctgcggcg agcggtatca gctcactcaa aggcggtaat acggttatcc    2100
acagaatcag gggataacgc aggaaagaac atgtgagcaa aaggccagca aaagcccagg    2160
aaccgtaaaa aggccgcgtt gctggcgttt ttccataggc tccgcccccc tgacgagcat    2220
cacaaaaatc gacgctcaag tcagaggtgg cgaaacccga caggactata agataccag    2280 gcgtttcccc ctggaagctc cctcgtgcgc tctcctgttc cgaccctgcc gcttaccgga    2340
tacctgtccg cctttctccc ttcgggaagc gtggcgcttt ctcatagctc acgctgtagg    2400
tatctcagtt cggtgtaggt cgttcgctcc aagctgggct gtgtgcacga acccccgtt    2460 cagcccgacc gctgcgcctt atccggtaac tatcgtcttg agtccaaccc ggtaagacac    2520
gacttatcgc cactggcagc agccactggt aacaggatta gcagagcgag gtatgtaggc    2580
ggtgctacag agttcttgaa gtggtggcct aactacggct acactagaag gacagtattt    2640
ggtatctgcg ctctgctgaa gccagttacc ttcggaaaaa gagttggtag ctcttgatcc    2700
ggcaaacaaa ccaccgctgg tagcggtggt ttttttgttt gcaagcagca gattacgcgc    2760
agaaaaaaag gatctcaaga agatcctttg atcttttcta cggggtctga cgctcagtgg    2820
aacgaaaact cacgttaagg gattttggtc atgagattat caaaaaggat cttcacctag    2880
atccttttaa attaaaaatg aagttttaaa tcaatctaaa gtatatatga gtaaacttgg    2940
tctgacagtt accaatgctt aatcagtgag gcacctatct cagcgatctg tctatttcgt    3000
tcatccatag ttgcctgact ccccgtcgtg tagataacta cgatacggga gcgcttacca    3060
tctggcccca gtgctgcaat gataccgcga gacccacgct caccggctcc agatttatca    3120
gcaataaacc agccagccgg aagggccgag cgcagaagtg gtcctgcaac tttatccgcc    3180
tccattcagt ctattaattg ttgccgggaa gctagagtaa gtagttcgcc agttaatagt    3240
ttgcgcaacg ttgttggcat tgctacaggc atcgtggtgt cactctcgtc gtttggtatg    3300
gcttcattca gctccggttc ccaacgatca aggcgagtta catgatcccc catgttgtgc    3360
aaaaaagcgg ttagctcctt cggtcctccg atcgttgtca gaagtaagtt ggccgcagtg    3420
ttatcactca tggttatggc agcactgcat aattctctta ctgtcatgcc atccgtaaga    3480
tgcttttctg tgactggtga gtactcaacc aagtcattct gagaatagtg tatgcggcga    3540
ccgagttgct cttgcccggc gtcaatacgg gataatagtg tatcacatag cagaacttta    3600
aaagtgctca tcattggaaa acgttcttcg ggcgaaaac tctcaaggat cttaccgctg    3660
ttgagatcca gttcgatgta acccactcgt gcacccaact gatcttcagc atcttttact    3720
ttcaccagcg tttctgggtg agcaaaaaca ggaaggcaaa atgccgcaaa aaagggaata    3780
agggcgacac ggaaatgttg aatactcata ctcttccttt ttcaatgggt aataactgat    3840
ataattaaat tgaagctcta atttgtgagt ttagtataca tgcatttact tataatacag    3900 tttttttagtt ttgctggccg catcttctca aatatgcttc ccagcctgct tttctgtaac    3960
gttcaccctc taccttagca tcccttccct ttgcaaatag tcctcttcca acaataataa    4020
```

```
tgtcagatcc tgtagagacc acatcatcca cggttctata ctgttgaccc aatgcgtctc    4080
ccttgtcatc taaacccaca ccgggtgtca taatcaacca atcgtaacct tcatctcttc    4140
cacccatgtc tctttgagca ataaagccga taacaaaatc tttgtcgctc ttcgcaatgt    4200
caacagtacc cttagtatat tctccagtag atagggagcc cttgcatgac aattctgcta    4260
acatcaaaag gcctctaggt tcctttgtta cttcttctgc cgcctgcttc aaaccgctaa    4320
caatacctgg gccccaccac ccgtgtgcat tcgtaatgtc tgcccattct gctattctgt    4380
atacacccgc agagtactgc aatttgactg tattaccaat gtcagcaaat tttctgtctt    4440
cgaagagtaa aaaattgtac ttggcggata atgcctttag cggcttaact gtgccctcca    4500
tggaaaaatc agtcaagata tccacatgtg tttttagtaa acaaattttg ggacctaatg    4560
cttcaactaa ctccagtaat tccttggtgg tacgaacatc caatgaagca cacaagtttg    4620
tttgcttttc gtgcatgata ttaaatagct tggcagcaac aggactagga tgagtagcag    4680
cacgttcctt atatgtagct ttcgacatga tttatcttcg tttcctgcag gttttttgttc    4740 tgtgcagttg ggttaagaat actgggcaat ttcatgtttc ttcaacacta catatgcgta    4800
tatataccaa tctaagtctg tgctccttcc ttcgttcttc cttctgttcg gagattaccg    4860
aatcaaaaaa atttcaaaga aaccgaaatc aaaaaaaaga ataaaaaaaa aatgatgaat    4920
tgaattgaaa agctagctta tcgatgataa gctgtcaaag atgagaatta attccacgga    4980
ctatagacta tactagatac tccgtctact gtacgataca cttccgctca ggtccttgtc    5040
ctttaacgag gccttaccac tcttttgtta ctctattgat ccagctcagc aaaggcagtg    5100
tgatctaaga ttctatcttc gcgatgtagt aaaactagct agaccgagaa agagactaga    5160
aatgcaaaag gcacttctac aatggctgcc atcattatta tccgatgtga cgctgcagct    5220
tctcaatgat attcgaatac gctttgagga gatacagcct aatatccgac aaactgtttt    5280
acagatttac gatcgtactt gttacccatc attgaatttt gaacatccga acctgggagt    5340
tttccctgaa acagatagta tatttgaacc tgtataataa tatatagtct agcgctttac    5400
ggaagacaat gtatgtattt cggttcctgg agaaactatt gcatctattg cataggtaat    5460
cttgcacgtc gcatccccgg ttcattttct gcgtttccat cttgcacttc aatagcatat    5520
ctttgttaac gaagcatctg tgcttcattt tgtagaacaa aaatgcaacg cgagagcgct    5580 aattttttcaa acaaagaatc tgagctgcat ttttacagaa cagaaatgca acgcgaaagc    5640 gctatttttac caacgaagaa tctgtgcttc attttttgtaa aacaaaaatg caacgcgacg    5700
agagcgctaa ttttttcaaac aaagaatctg agctgcattt ttacagaaca gaaatgcaac    5760
gcgagagcgc tattttacca acaaagaatc tatacttctt ttttgttcta caaaaatgca    5820
tcccgagagc gctattttc taacaaagca tcttagatta cttttttttct cctttgtgcg    5880 ctctataatg cagtctcttg ataacttttt gcactgtagg tccgttaagg ttagaagaag    5940
gctactttgg tgtctatttt ctcttccata aaaaaagcct gactccactt cccgcgttta    6000
ctgattacta gcgaagctgc gggtgcattt tttcaagata aaggcatccc cgattatatt    6060
ctataccgat gtggattgcg catactttgt gaacagaaag tgatagcgtt gatgattctt    6120
cattggtcag aaaattatga acggtttctt ctatttttgtc tctatatact acgtatagga    6180
aatgtttaca ttttcgtatt gttttcgatt cactctatga atagttctta ctacaatttt    6240
tttgtctaaa gagtaatact agagataaac ataaaaaatg tagaggtcga gtttagatgc    6300
aagttcaagg agcgaaaggt ggatgggtag gttatatagg gatatagcac agagatatat    6360
agcaaagaga tacttttgag caatgtttgt ggaagcggta ttcgcaatgg gaagctccac    6420
```

```
cccggttgat aatcagaaaa gccccaaaaa caggaagatt gtataagcaa atatttaaat      6480
tgtaaacgtt aatattttgt taaaattcgc gttaaatttt tgttaaatca gctcattttt      6540
taacgaatag cccgaaatcg gcaaaatccc ttataaatca aaagaataga ccgagatagg      6600
gttgagtgtt gttccagttt ccaacaagag tccactatta agaacgtgg  actccaacgt      6660 caaagggcga aaaagggtct atcagggcga tggcccacta cgtgaaccat caccctaatc      6720
aagttttttg gggtcgaggt gccgtaaagc agtaaatcgg aagggtaaac ggatgccccc      6780
atttagagct tgacggggaa agccggcgaa cgtggcgaga aggaaggga  agaaagcgaa      6840 aggagcgggg gctagggcgg tgggaagtgt aggggtcacg ctgggcgtaa ccaccacacc      6900
cgccgcgctt aatggggcgc tacagggcgc gtggggatga tccactagta cggattagaa      6960
gccgccgagc gggtgacagc cctccgaagg aagactctcc tccgtgcgtc ctcgtcctca      7020
ccggtcgcgt tcctgaaacg cagatgtgcc tcgcgccgca ctgctccgaa caataaagat      7080
tctacaatac tagcttttat ggttatgaag aggaaaaatt ggcagtaacc tggccccaca      7140
aaccttcaaa tgaacgaatc aaattaacaa ccataggatg ataatgcgat tagttttta     7200 gccttatttc tggggtaatt aatcagcgaa gcgatgattt ttgatctatt aacagatata      7260
taaatgcaaa aactgcatta accactttaa ctaatacttt caacattttc ggtttgtatt      7320
acttcttatt caaatgtaat aaaagtatca acaaaaaatt gttaatatac ctctatactt      7380
taacgtcaag gagaaaaaac cccggatcgg actactagca gctgtaatac gactcactat      7440
agggaatatt aagcttggta ccgagctcgg atcc                                 7474
```

<210> SEQ ID NO 31
<211> LENGTH: 7525
<212> TYPE: DNA
<213> ORGANISM: Artificial
<220> FEATURE:
<223> OTHER INFORMATION: Plasmid

<400> SEQUENCE: 31

```
ccaactttgt ttggtctgat gagtccgtga ggacgaaacc cggagtcccg ggtcaccaga        60
caaagctggg aatagaaact tcgtattttc aaagttttct ttaatatatt gcaaataatg       120
cctaaccacc tagggcagga ttaggggttcc ggagttcaac caattagtcc ttaatcaggg      180
cactgtatcc gactaactta taccataaaa tcttgctagg atacagttct cacatcacat       240
ccgaacataa acaaccatgg gtaaggaaaa gactcacgtt tcgaggccgc gattaaattc       300
caacatggat gctgatttat atgggtataa atgggctcgc gataatgtcg ggcaatcagg       360
tgcgacaatc tatcgattgt atgggaagcc cgatgcgcca gagttgtttc tgaaacatgg       420
caaaggtagc gttgccaatg atgttacaga tgagatggtc agactaaact ggctgacgga       480
atttatgcct cttccgacca tcaagcattt tatccgtact cctgatgatg catggttact       540
caccactgcg atccccggca aaacagcatt ccaggtatta agaatatc   ctgattcagg       600 tgaaaatatt gttgatgcgc tggcagtgtt cctgcgccgg ttgcattcga ttcctgtttg       660
taattgtcct tttaacagcg atcgcgtatt tcgtctcgct caggcgcaat cacgaatgaa       720
taacggtttg gttgatgcga gtgattttga tgacgagcgt aatggctggc ctgttgaaca      780
agtctggaaa gaaatgcata agcttttgcc attctcaccg gattcagtcg tcactcatgg      840
tgatttctca cttgataacc ttattttga  cgaggggaaa ttaataggtt gtattgatgt       900
tggacgagtc ggaatcgcag accgatacca ggatcttgcc atcctatgga actgcctcgg       960
```

```
tgagttttct ccttcattac agaaacggct ttttcaaaaa tatggtattg ataatcctga    1020
tatgaataaa ttgcagtttc atttgatgct cgatgagttt ttctaatcag tactgacaat    1080
aaaaagattc ttgttttcaa gaacttgtca tttgtatagt ttttttatat tgtagttgtt    1140
ctattttaat caaatgttag cgtgatttat atttttttc gcctcgacat catctgccca    1200
gatgcgaagt taagtgcgca gaaagtaata tcatgcgtca atcgtatgtg aatgctggtc    1260
gctatactgc tgtcgattcg atactaacgc cgccatccag tgtcgaaaac gagctcgaat    1320
tcatcgatga tccatctcgg atatccctaa tcctgctctt gtccctgata ataggatctt    1380
gaatcctaag tgcactagaa gatgatcatt gattgaacta tccttaccca actttgtttg    1440
gtggccggca tggtcccagc ctcctcgctg gcgccggctg ggcaacattc cgagggggacc   1500 gtcccctcgg taatggcgaa tgggactcga gcatgcatct agagggccgc atcatgtaat    1560
tagttatgtc acgcttacat tcacgccctc cccccacatc cgctctaacc gaaaaggaag    1620
gagttagaca acctgaagtc taggtcccta tttattttt tatagttatg ttagtattaa    1680
gaacgttatt tatatttcaa atttttcttt ttttctgta cagacgcgtg tacgcatgta    1740
acattatact gaaaaccttg cttgagaagg ttttgggacg ctcgaaggct ttaatttgcg    1800
gccctgcatt aatgaatcgg ccaacgcgcg gggagaggcg gtttgcgtat tgggcgctct    1860
tccgcttcct cgctcactga ctcgctgcgc tcggtcgttc ggctgcggcg agcggtatca    1920
gctcactcaa aggcggtaat acggttatcc acagaatcag gggataacgc aggaaagaac    1980
atgtgagcaa aaggccagca aaagcccagg aaccgtaaaa aggccgcgtt gctggcgttt    2040
ttccataggc tccgcccccc tgacgagcat cacaaaaatc gacgctcaag tcagaggtgg    2100
cgaaacccga caggactata agataccag gcgtttcccc ctggaagctc cctcgtgcgc     2160
tctcctgttc cgaccctgcc gcttaccgga tacctgtccg cctttctccc ttcgggaagc    2220
gtggcgcttt ctcatagctc acgctgtagg tatctcagtt cggtgtaggt cgttcgctcc    2280
aagctgggct gtgtgcacga accccccgtt cagcccgacc gctgcgcctt atccggtaac    2340
tatcgtcttg agtccaaccc ggtaagacac gacttatcgc cactggcagc agccactggt    2400
aacaggatta gcagagcgag gtatgtaggc ggtgctacag agttcttgaa gtggtggcct    2460
aactacggct acactagaag gacagtattt ggtatctgcg ctctgctgaa gccagttacc    2520
ttcggaaaaa gagttggtag ctcttgatcc ggcaaacaaa ccaccgctgg tagcggtggt    2580 tttttgttt gcaagcagca gattacgcgc agaaaaaaag gatctcaaga agatcctttg    2640
atcttttcta cggggtctga cgctcagtgg aacgaaaact cacgttaagg attttggtc     2700 atgagattat caaaaaggat cttcacctag atccttttaa attaaaaatg aagttttaaa    2760
tcaatctaaa gtatatatga gtaaacttgg tctgacagtt accaatgctt aatcagtgag    2820
gcacctatct cagcgatctg tctatttcgt tcatccatag ttgcctgact ccccgtcgtg    2880
tagataacta cgatacggga gcgcttacca tctggcccca gtgctgcaat gataccgcga    2940
gacccacgct caccggctcc agatttatca gcaataaacc agccagccgg aagggccgag    3000
cgcagaagtg gtcctgcaac tttatccgcc tccattcagt ctattaattg ttgccgggaa    3060
gctagagtaa gtagttcgcc agttaatagt ttgcgcaacg ttgttggcat tgctacaggc    3120
atcgtggtgt cactctcgtc gtttggtatg gcttcattca gctccggttc ccaacgatca    3180
aggcgagtta catgatcccc catgttgtgc aaaaaagcgg ttagctcctt cggtcctccg    3240
atcgttgtca gaagtaagtt ggccgcagtg ttatcactca tggttatggc agcactgcat    3300
aattctctta ctgtcatgcc atccgtaaga tgcttttctg tgactggtga gtactcaacc    3360
```

```
aagtcattct gagaatagtg tatgcggcga ccgagttgct cttgcccggc gtcaatacgg    3420
gataatagtg tatcacatag cagaaccttta aaagtgctca tcattggaaa acgttcttcg   3480
gggcgaaaac tctcaaggat cttaccgctg ttgagatcca gttcgatgta acccactcgt    3540
gcacccaact gatcttcagc atcttttact ttcaccagcg tttctgggtg agcaaaaaca    3600
ggaaggcaaa atgccgcaaa aagggaata agggcgacac ggaaatgttg aatactcata     3660
ctcttccttt ttcaatgggt aataactgat ataattaaat tgaagctcta atttgtgagt    3720
ttagtataca tgcatttact tataatacag tttttagtt ttgctggccg catcttctca     3780
aatatgcttc ccagcctgct tttctgtaac gttcaccctc taccttagca tcccttccct    3840
ttgcaaatag tcctcttcca acaataataa tgtcagatcc tgtagagacc acatcatcca    3900
cggttctata ctgttgaccc aatgcgtctc ccttgtcatc taaacccaca ccgggtgtca    3960
taatcaacca atcgtaacct tcatctcttc cacccatgtc tctttgagca ataaagccga    4020
taacaaaatc tttgtcgctc ttcgcaatgt caacagtacc cttagtatat tctccagtag    4080
atagggagcc cttgcatgac aattctgcta acatcaaaag gcctctaggt tcctttgtta    4140
cttcttctgc cgcctgcttc aaaccgctaa caatacctgg gcccaccaca ccgtgtgcat    4200
tcgtaatgtc tgcccattct gctattctgt atacacccgc agagtactgc aatttgactg    4260
tattaccaat gtcagcaaat tttctgtctt cgaagagtaa aaaattgtac ttggcggata    4320
atgcctttag cggcttaact gtgccctcca tggaaaaatc agtcaagata tccacatgtg   4380 ttttagtaa acaaattttg ggacctaatg cttcaactaa ctccagtaat tccttggtgg     4440
tacgaacatc caatgaagca cacaagtttg tttgcttttc gtgcatgata ttaaatagct    4500
tggcagcaac aggactagga tgagtagcag cacgttcctt atatgtagct ttcgacatga    4560
tttatcttcg tttcctgcag ttttttgttc tgtgcagttg ggttaagaat actgggcaat    4620
ttcatgtttc ttcaacacta catatgcgta tataccaa tctaagtctg tgctccttcc      4680
ttcgttcttc cttctgttcg gagattaccg aatcaaaaaa atttcaaaga aaccgaaatc    4740 aaaaaaaga ataaaaaaaa aatgatgaat tgaattgaaa agctagctta tcgatgataa     4800
gctgtcaaag atgagaatta attccacgga ctatagacta tactagatac tccgtctact    4860
gtacgataca cttccgctca ggtccttgtc ctttaacgag gccttaccac tcttttgtta    4920
ctctattgat ccagctcagc aaaggcagtg tgatctaaga ttctatcttc gcgatgtagt    4980
aaaactagct agaccgagaa agagactaga aatgcaaaag gcacttctac aatggctgcc    5040
atcattatta tccgatgtga cgctgcagct tctcaatgat attcgaatac gctttgagga    5100
gatacagcct aatatccgac aaactgtttt acagatttac gatcgtactt gttacccatc    5160
attgaatttt gaacatccga acctgggagt ttttccctgaa acagatagta tatttgaacc   5220
tgtataataa tatatagtct agcgctttac ggaagacaat gtatgtattt cggttcctgg    5280
agaaactatt gcatctattg cataggtaat cttgcacgtc gcatccccgg ttcattttct    5340
gcgtttccat cttgcacttc aatagcatat cttttgttaac gaagcatctg tgcttcattt    5400
tgtagaacaa aaatgcaacg cgagagcgct aattttcaa acaaagaatc tgagctgcat     5460
ttttacagaa cagaaatgca acgcgaaagc gctattttac caacgaagaa tctgtgcttc    5520
atttttgtaa aacaaaaatg caacgcgacg agagcgctaa ttttcaaac aaagaatctg    5580 agctgcattt ttacagaaca gaaatgcaac gcgagagcgc tattttacca acaaagaatc    5640
tatacttctt ttttgttcta caaaaatgca tcccgagagc gctattttc taacaaagca    5700
```

| | |
|---|---:|
| tcttagatta cttttttct cctttgtgcg ctctataatg cagtctcttg ataacttttt | 5760 |
| gcactgtagg tccgttaagg ttagaagaag gctactttgg tgtctatttt ctcttccata | 5820 |
| aaaaaagcct gactccactt cccgcgttta ctgattacta gcgaagctgc gggtgcattt | 5880 |
| tttcaagata aaggcatccc cgattatatt ctataccgat gtggattgcg catactttgt | 5940 |
| gaacagaaag tgatagcgtt gatgattctt cattggtcag aaaattatga acggtttctt | 6000 |
| ctattttgtc tctatatact acgtatagga aatgtttaca ttttcgtatt gttttcgatt | 6060 |
| cactctatga atagttctta ctacaatttt tttgtctaaa gagtaatact agagataaac | 6120 |
| ataaaaaatg tagaggtcga gtttagatgc aagttcaagg agcgaaaggt ggatgggtag | 6180 |
| gttatatagg gatatagcac agagatatat agcaaagaga tacttttgag caatgtttgt | 6240 |
| ggaagcggta ttcgcaatgg gaagctccac cccggttgat aatcagaaaa gccccaaaaa | 6300 |
| caggaagatt gtataagcaa atatttaaat tgtaaacgtt aatattttgt taaaattcgc | 6360 |
| gttaaatttt tgttaaatca gctcattttt taacgaatag cccgaaatcg gcaaaatccc | 6420 |
| ttataaatca aaagaataga ccgagatagg gttgagtgtt gttccagttt ccaacaagag | 6480 |
| tccactatta agaacgtgg actccaacgt caaagggcga aaagggtct atcagggcga | 6540 |
| tggcccacta cgtgaaccat caccctaatc aagttttttg gggtcgaggt gccgtaaagc | 6600 |
| agtaaatcgg aagggtaaac ggatgccccc atttagagct tgacggggaa agccggcgaa | 6660 |
| cgtggcgaga aaggaaggga agaaagcgaa aggagcgggg gctagggcgg tgggaagtgt | 6720 |
| aggggtcacg ctgggcgtaa ccaccacacc cgccgcgctt aatggggcgc tacagggcgc | 6780 |
| gtggggatga tccactagta cggattagaa gccgccgagc gggtgacagc cctccgaagg | 6840 |
| aagactctcc tccgtgcgtc ctcgtcctca ccggtcgcgt tcctgaaacg cagatgtgcc | 6900 |
| tcgcgccgca ctgctccgaa caataaagat tctacaatac tagcttttat ggttatgaag | 6960 |
| aggaaaaatt ggcagtaacc tggccccaca aaccttcaaa tgaacgaatc aaattaacaa | 7020 |
| ccataggatg ataatgcgat tagttttta gccttatttc tggggtaatt aatcagcgaa | 7080 |
| gcgatgattt ttgatctatt aacagatata taaatgcaaa aactgcatta accactttaa | 7140 |
| ctaatacttt caacattttc ggtttgtatt acttcttatt caaatgtaat aaaagtatca | 7200 |
| acaaaaaatt gttaatatac ctctatactt taacgtcaag gagaaaaaac cccggatcgg | 7260 |
| actactagca gctgtaatac gactcactat agggaatatt aagcttggta ccgagctcgg | 7320 |
| atccactagt aacggccgcc agtgtgctgg aattctgcag atatccatca cactggcggc | 7380 |
| cgcatccgga tatagttcct cctttcagca aaaaacccct caagacccgt ttagaggccc | 7440 |
| caaggggtta tgctagttat tgctcagcgg tggcagcagc caactcagct tcctttcggg | 7500 |
| ctttgttagc agccggatcg gccgc | 7525 |

<210> SEQ ID NO 32
<211> LENGTH: 7474
<212> TYPE: DNA
<213> ORGANISM: Artificial
<220> FEATURE:
<223> OTHER INFORMATION: Plasmid

<400> SEQUENCE: 32

| | |
|---|---:|
| ccaactttgt ttggtctgat gagtccgtga ggacgaaacc cggagtcccg ggtcaccaaa | 60 |
| caaagttggg taaggatagt tcaatcaatg atcatcttct agtgcactta ggattcaaga | 120 |
| tcctattatc agggacaaga gcaggattag ggatatccga gatggatcat cgatgaattc | 180 |
| gagctcgttt tcgacactgg atggcggcgt tagtatcgaa tcgacagcag tatagcgacc | 240 |

| | |
|---|---|
| agcattcaca tacgattgac gcatgatatt actttctgcg cacttaactt cgcatctggg | 300 |
| cagatgatgt cgaggcgaaa aaaaatataa atcacgctaa catttgatta aaatagaaca | 360 |
| actacaatat aaaaaaacta tacaaatgac aagttcttga aaacaagaat cttttattg | 420 |
| tcagtactga ttagaaaaac tcatcgagca tcaaatgaaa ctgcaattta ttcatatcag | 480 |
| gattatcaat accatatttt tgaaaaagcc gtttctgtaa tgaaggagaa aactcaccga | 540 |
| ggcagttcca taggatggca agatcctggt atcggtctgc gattccgact cgtccaacat | 600 |
| caatacaacc tattaatttc ccctcgtcaa aaataaggtt atcaagtgag aaatcaccat | 660 |
| gagtgacgac tgaatccggt gagaatggca aaagcttatg catttctttc cagacttgtt | 720 |
| caacaggcca gccattacgc tcgtcatcaa aatcactcgc atcaaccaaa ccgttattca | 780 |
| ttcgtgattg cgcctgagcg agacgaaata cgcgatcgct gttaaaagga caattacaaa | 840 |
| caggaatcga atgcaaccgg cgcaggaaca ctgccagcgc atcaacaata ttttcacctg | 900 |
| aatcaggata ttcttctaat acctggaatg ctgttttgcc ggggatcgca gtggtgagta | 960 |
| accatgcatc atcaggagta cggataaaat gcttgatggt cggaagaggc ataaattccg | 1020 |
| tcagccagtt tagtctgacc atctcatctg taacatcatt ggcaacgcta cctttgccat | 1080 |
| gtttcagaaa caactctggc gcatcgggct tcccatacaa tcgatagatt gtcgcacctg | 1140 |
| attgcccgac attatcgcga gcccatttat acccatataa atcagcatcc atgttggaat | 1200 |
| ttaatcgcgg cctcgaaacg tgagtctttt ccttacccat ggttgtttat gttcggatgt | 1260 |
| gatgtgagaa ctgtatccta gcaagatttt atggtataag ttagtcggat acagtgccct | 1320 |
| gattaaggac taattggttg aactccggaa ccctaatcct gccctaggtg gttaggcatt | 1380 |
| atttgcaata tattaaagaa aactttgaaa atacgaagtt tctattccca gctttgtctg | 1440 |
| gtggccggca tggtcccagc ctcctcgctg gcgccggctg ggcaacattc cgagggacc | 1500 |
| gtccctcgg taatggcgaa tgggacgcgg ccgatccggc tgctaacaaa gcccgaaagg | 1560 |
| aagctgagtt ggctgctgcc accgctgagc aataactagc ataacccctt ggggcctcta | 1620 |
| aacgggtctt gagggttttt tgctgaaag gaggaactat atccggatgc ggccgctcga | 1680 |
| gcatgcatct agagggccgc atcatgtaat tagttatgtc acgcttacat tcacgccctc | 1740 |
| cccccacatc cgctctaacc gaaaaggaag gagttagaca acctgaagtc taggtcccta | 1800 |
| tttatttttt tatagttatg ttagtattaa gaacgttatt tatatttcaa attttctttt | 1860 |
| tttttctgta cagacgcgtg tacgcatgta acattatact gaaaaccttg cttgagaagg | 1920 |
| ttttgggacg ctcgaaggct ttaatttgcg gccctgcatt aatgaatcgg ccaacgcgcg | 1980 |
| gggagaggcg gtttgcgtat tgggcgctct tccgcttcct cgctcactga ctcgctgcgc | 2040 |
| tcggtcgttc ggctgcggcg agcggtatca gctcactcaa aggcggtaat acggttatcc | 2100 |
| acagaatcag gggataacgc aggaaagaac atgtgagcaa aaggccagca aaagcccagg | 2160 |
| aaccgtaaaa aggccgcgtt gctggcgttt ttccataggc tccgcccccc tgacgagcat | 2220 |
| cacaaaaatc gacgctcaag tcagaggtgg cgaaacccga caggactata agataccag | 2280 |
| gcgtttcccc ctggaagctc cctcgtgcgc tctcctgttc cgaccctgcc gcttaccgga | 2340 |
| tacctgtccg cctttctccc ttcgggaagc gtggcgcttt ctcatagctc acgctgtagg | 2400 |
| tatctcagtt cggtgtaggt cgttcgctcc aagctgggct gtgtgcacga acccccgtt | 2460 |
| cagcccgacc gctgcgcctt atccggtaac tatcgtcttg agtccaaccc ggtaagacac | 2520 |
| gacttatcgc cactggcagc agccactggt aacaggatta gcagagcgag gtatgtaggc | 2580 |

```
ggtgctacag agttcttgaa gtggtggcct aactacggct acactagaag gacagtattt    2640
ggtatctgcg ctctgctgaa gccagttacc ttcggaaaaa gagttggtag ctcttgatcc    2700
ggcaaacaaa ccaccgctgg tagcggtggt ttttttgttt gcaagcagca gattacgcgc    2760
agaaaaaaag gatctcaaga agatcctttg atcttttcta cggggtctga cgctcagtgg    2820
aacgaaaact cacgttaagg gattttggtc atgagattat caaaaaggat cttcacctag    2880
atccttttaa attaaaaatg aagttttaaa tcaatctaaa gtatatatga gtaaacttgg    2940
tctgacagtt accaatgctt aatcagtgag gcacctatct cagcgatctg tctatttcgt    3000
tcatccatag ttgcctgact ccccgtcgtg tagataacta cgatacggga gcgcttacca    3060
tctggcccca gtgctgcaat gataccgcga gacccacgct caccggctcc agatttatca    3120
gcaataaacc agccagccgg aagggccgag cgcagaagtg gtcctgcaac tttatccgcc    3180
tccattcagt ctattaattg ttgccgggaa gctagagtaa gtagttcgcc agttaatagt    3240
ttgcgcaacg ttgttggcat tgctacaggc atcgtggtgt cactctcgtc gtttggtatg    3300
gcttcattca gctccggttc ccaacgatca aggcgagtta catgatcccc catgttgtgc    3360
aaaaaagcgg ttagctcctt cggtcctccg atcgttgtca gaagtaagtt ggccgcagtg    3420
ttatcactca tggttatggc agcactgcat aattctctta ctgtcatgcc atccgtaaga    3480
tgcttttctg tgactggtga gtactcaacc aagtcattct gagaatagtg tatgcggcga    3540
ccgagttgct cttgcccggc gtcaatacgg gataatagtg tatcacatag cagaacttta    3600
aaagtgctca tcattggaaa acgttcttcg gggcgaaaac tctcaaggat cttaccgctg    3660
ttgagatcca gttcgatgta acccactcgt gcacccaact gatcttcagc atcttttact    3720
ttcaccagcg tttctgggtg agcaaaaaca ggaaggcaaa atgccgcaaa aaagggaata    3780
agggcgacac ggaaatgttg aatactcata ctcttccttt ttcaatgggt aataactgat    3840
ataattaaat tgaagctcta atttgtgagt ttagtataca tgcatttact tataatacag    3900
ttttttagtt ttgctggccg catcttctca aatatgcttc ccagcctgct tttctgtaac    3960
gttcaccctc taccttagca tccctcccct ttgcaaatag tcctcttcca acaataataa    4020
tgtcagatcc tgtagagacc acatcatcca cggttctata ctgttgaccc aatgcgtctc    4080
ccttgtcatc taaacccaca ccgggtgtca taatcaacca atcgtaacct tcatctcttc    4140
cacccatgtc tctttgagca ataaagccga taacaaaatc tttgtcgctc ttcgcaatgt    4200
caacagtacc cttagtatat tctccagtag atagggagcc cttgcatgac aattctgcta    4260
acatcaaaag gcctctaggt tcctttgtta cttcttctgc cgcctgcttc aaaccgctaa    4320
caatacctgg gcccaccaca ccgtgtgcat tcgtaatgtc tgcccattct gctattctgt    4380
atacacccgc agagtactgc aatttgactg tattaccaat gtcagcaaat tttctgtctt    4440
cgaagagtaa aaaattgtac ttggcggata atgcctttag cggcttaact gtgccctcca    4500
tggaaaaatc agtcaagata tccacatgtg ttttttagtaa acaaattttg ggacctaatg    4560
cttcaactaa ctccagtaat tccttggtgg tacgaacatc caatgaagca cacaagtttg    4620
tttgcttttc gtgcatgata ttaaatagct tggcagcaac aggactagga tgagtagcag    4680
cacgttcctt atatgtagct ttcgacatga tttatcttcg tttcctgcag gttttttgttc    4740 tgtgcagttg ggttaagaat actgggcaat ttcatgtttc ttcaacacta catatgcgta    4800
tatataccaa tctaagtctg tgctccttcc ttcgttcttc cttctgttcg gagattaccg    4860
aatcaaaaaa atttcaaaga aaccgaaatc aaaaaaaaga ataaaaaaaa aatgatgaat    4920
tgaattgaaa agctagctta tcgatgataa gctgtcaaag atgagaatta attccacgga    4980
```

```
ctatagacta tactagatac tccgtctact gtacgataca cttccgctca ggtccttgtc   5040 cttttaacgag gccttaccac tcttttgtta ctctattgat ccagctcagc aaaggcagtg   5100
tgatctaaga ttctatcttc gcgatgtagt aaaactagct agaccgagaa agagactaga   5160
aatgcaaaag gcacttctac aatggctgcc atcattatta tccgatgtga cgctgcagct   5220
tctcaatgat attcgaatac gctttgagga gatacagcct aatatccgac aaactgtttt   5280
acagatttac gatcgtactt gttacccatc attgaatttt gaacatccga acctgggagt   5340
tttccctgaa acagatagta tatttgaacc tgtataataa tatatagtct agcgctttac   5400
ggaagacaat gtatgtattt cggttcctgg agaaactatt gcatctattg cataggtaat   5460
cttgcacgtc gcatcccggg ttcattttct gcgtttccat cttgcacttc aatagcatat   5520
ctttgttaac gaagcatctg tgcttcattt tgtagaacaa aaatgcaacg cgagagcgct   5580 aattttttcaa acaaagaatc tgagctgcat ttttacagaa cagaaatgca acgcgaaagc   5640 gctatttttac caacgaagaa tctgtgcttc attttttgtaa aacaaaaatg caacgcgacg   5700
agagcgctaa ttttttcaaac aaagaatctg agctgcattt ttacagaaca gaaatgcaac   5760
gcgagagcgc tattttacca acaaagaatc tatacttctt ttttgttcta caaaaatgca   5820
tcccgagagc gctattttc taacaaagca tcttagatta ctttttttct cctttgtgcg   5880
ctctataatg cagtctcttg ataacttttt gcactgtagg tccgttaagg ttagaagaag   5940
gctactttgg tgtctatttt ctcttccata aaaaaagcct gactccactt cccgcgttta   6000
ctgattacta gcgaagctgc gggtgcattt tttcaagata aaggcatccc cgattatatt   6060
ctataccgat gtggattgcg catactttgt gaacagaaag tgatagcgtt gatgattctt   6120
cattggtcag aaaattatga acggtttctt ctattttgtc tctatatact acgtatagga   6180
aatgtttaca ttttcgtatt gttttcgatt cactctatga atagttctta ctacaatttt   6240
tttgtctaaa gagtaatact agagataaac ataaaaaatg tagaggtcga gtttagatgc   6300
aagttcaagg agcgaaaggt ggatgggtag gttatatagg gatatagcac agagatatat   6360
agcaaagaga tacttttgag caatgttgtg ggaagcggta ttcgcaatgg gaagctccac   6420
cccggttgat aatcagaaaa gccccaaaaa caggaagatt gtataagcaa atatttaaat   6480
tgtaaacgtt aatattttgt taaaattcgc gttaaatttt tgttaaatca gctcattttt   6540
taacgaatag cccgaaatcg gcaaaatccc ttataaatca aaagaataga ccgagatagg   6600
gttgagtgtt gttccagttt ccaacaagag tccactatta agaacgtgg actccaacgt   6660 caaagggcga aaagggtct atcagggcga tggcccacta cgtgaaccat caccctaatc   6720
aagttttttg gggtcgaggt gccgtaaagc agtaaatcgg aagggtaaac ggatgccccc   6780
atttagagct tgacggggaa agccggcgaa cgtggcgaga aggaaggga agaaagcgaa   6840 aggagcgggg gctagggcgg tgggaagtgt agggggtcacg ctgggcgtaa ccaccacacc   6900
cgccgcgctt aatgggcgc tacagggcgc gtggggatga tccactagta cggattagaa   6960
gccgccgagc gggtgacagc cctccgaagg aagactctcc tccgtgcgtc ctcgtcctca   7020
ccggtcgcgt tcctgaaacg cagatgtgcc tcgcgccgca ctgctccgaa caataaagat   7080
tctacaatac tagcttttat ggttatgaag aggaaaaatt ggcagtaacc tggccccaca   7140
aaccttcaaa tgaacgaatc aaattaacaa ccataggatg ataatgcgat tagttttttta   7200 gccttatttc tggggtaatt aatcagcgaa gcgatgattt ttgatctatt aacagatata   7260
taaatgcaaa aactgcatta accactttaa ctaatacttt caacatttc ggtttgtatt   7320
```

| | |
|---|---|
| acttcttatt caaatgtaat aaaagtatca acaaaaaatt gttaatatac ctctatactt | 7380 |
| taacgtcaag gagaaaaaac cccggatcgg actactagca gctgtaatac gactcactat | 7440 |
| agggaatatt aagcttggta ccgagctcgg atcc | 7474 |

<210> SEQ ID NO 33
<211> LENGTH: 9646
<212> TYPE: DNA
<213> ORGANISM: Artificial
<220> FEATURE:
<223> OTHER INFORMATION: Plasmid

<400> SEQUENCE: 33

| | |
|---|---|
| ccaactttgt ttggtctgat gagtccgtga ggacgaaacc cggagtcccg ggtcaccaga | 60 |
| caaagctggg aatagaaact tcgtattttc aaagttttct ttaatatatt gcaaataatg | 120 |
| cctaaccacc tagggcagga ttagggttcc ggagttcaac caattagtcc ttaatcaggg | 180 |
| cactgtatcc gactaactta taccatatca tcgatgaatt cgagctcatg acaaattcaa | 240 |
| aagaagacgc cgacatagag gagaagcata tgtacaatga gccggtcaca accctctttc | 300 |
| acgacgttga agcttcacaa acacaccaca gacgtgggtc aataccattg aaagatgaga | 360 |
| aaagtaaaga attgtatcca ttgcgctctt tcccgacgag agtaaatggc gaggatacgt | 420 |
| tctctatgga ggatggcata ggtgatgaag atgaaggaga agtacagaac gctgaagtga | 480 |
| agagagagct taagcaaaga catattggta tgattgccct tggtggtact attggtacag | 540 |
| gtcttttcat tggtttatcc acacctctga ccaacgccgg cccagtgggc gctcttatat | 600 |
| catatttatt tatgggttct ttggcatatt ctgtcacgca gtccttgggt gaaatggcta | 660 |
| cattcatccc tgttacatcc tctttcacag ttttctcaca agattccttt ctccagcat | 720 |
| ttggtgcggc caatgttac atgtattggt tttcttgggc aatcacttttt gccctggaac | 780 |
| ttagtgtagt tggccaagtc attcaatttt ggacgtacaa agttccactg gcggcatgga | 840 |
| ttagtatttt tgggtaatt atcacaataa tgaacttgtt ccctgtcaaa tattacggtg | 900 |
| aattcgagtt ctgggtcgct tccatcaaag ttttagccat tatcgggttt ctaatatact | 960 |
| gttttttgtat ggtttgtggt gctggggtta ccggcccagt tggattccgt tattggagaa | 1020 |
| acccaggtgc ctggggtcca ggtataatat ctaaggataa aaacgaaggg aggttcttag | 1080 |
| gttgggtttc ctcttttgatt aacgctgcct tcacatttca aggtactgaa ctagttggta | 1140 |
| tcactgctgg tgaagctgca aaccccagaa atccgttcc aagagccatc aaaaaagttg | 1200 |
| ttttccgtat cttaaccttc tacattggct ctctattatt cattggactt ttagttccat | 1260 |
| acaatgaccc taaactaaca caatctactt cctacgtttc tacttctccc tttattattg | 1320 |
| ctattgagaa ctctggtaca aaggttttgc cacatatctt caacgctgtt atcttaacaa | 1380 |
| ccattatttc tgccgcaaat tcaaatattt acgttggttc ccgtattttta tttggtctat | 1440 |
| caaagaacaa gttggctcct aaattcctgt caaggaccac caaaggtggt gttccataca | 1500 |
| ttgcagtttt cgttactgct gcatttggcg ctttggctta catggagaca tctactggtg | 1560 |
| gtgacaaagt tttcgaatgg ctattaaata tcactggtgt tgcaggcttt tttgcatggt | 1620 |
| tatttatctc aatctcgcac atcagattta tgcaagcttt gaaataccgt ggcatctctc | 1680 |
| gtgacgagtt accatttaaa gctaaattaa tgcccggctt ggcttattat gcggccacat | 1740 |
| ttatgacgat cattatcatt attcaaggtt tcacggcttt tgcaccaaaa ttcaatggtg | 1800 |
| ttagctttgc tgccgcctat atctctattt tcctgttctt agctgtttgg atcttatttc | 1860 |
| aatgcatatt cagatgcaga tttatttgga agattggaga tgtcgacatc gattccgata | 1920 |

```
gaagagacat tgaggcaatt gtatgggaag atcatgaacc aaagactttt tgggacaaat   1980
tttggaatgt tgtagcatag tccatggttg tttatgttcg gatgtgatgt gagaactgta   2040
tcctagcaag attttccatc tcggatatcc ctaatcctgc tcttgtccct gataatagga   2100
tcttgaatcc taagtgcact agaagatgat cattgattga actatcctta cccaactttg   2160
tttggtggcc ggcatggtcc cagcctcctc gctggcgccg gctgggcaac attccgaggg   2220
gaccgtcccc tcggtaatgg cgaatgggac tcgagcatgc atctagaggg ccgcatcatg   2280
taattagtta tgtcacgctt acattcacgc cctccccca catccgctct aaccgaaaag    2340
gaaggagtta gacaacctga agtctaggtc cctatttatt tttttatagt tatgttagta   2400
ttaagaacgt tatttatatt tcaaattttt ctttttttc tgtacagacg cgtgtacgca    2460
tgtaacatta tactgaaaac cttgcttgag aaggttttgg gacgctcgaa ggctttaatt   2520
tgcggccctg cattaatgaa tcggccaacg cgcggggaga ggcggtttgc gtattgggcg   2580
ctcttccgct tcctcgctca ctgactcgct gcgctcggtc gttcggctgc ggcgagcggt   2640
atcagctcac tcaaaggcgg taatacggtt atccacagaa tcaggggata acgcaggaaa   2700
gaacatgtga gcaaaaggcc agcaaaagcc caggaaccgt aaaaaggccg cgttgctggc   2760 gttttccat aggctccgcc ccctgacga gcatcacaaa atcgacgct caagtcagag       2820 gtggcgaaac ccgacaggac tataaagata ccaggcgttt ccccctggaa gctccctcgt   2880
gcgctctcct gttccgaccc tgccgcttac cggatacctg tccgcctttc tcccttcggg   2940
aagcgtggcg ctttctcata gctcacgctg taggtatctc agttcggtgt aggtcgttcg   3000
ctccaagctg ggctgtgtgc acgaaccccc cgttcagccc gaccgctgcg ccttatccgg   3060
taactatcgt cttgagtcca acccggtaag acacgactta tcgccactgg cagcagccac   3120
tggtaacagg attagcagag cgaggtatgt aggcggtgct acagagttct tgaagtggtg   3180
gcctaactac ggctacacta aaggacagt atttggtatc tgcgctctgc tgaagccagt    3240
taccttcgga aaaagagttg gtagctcttg atccggcaaa caaaccaccg ctggtagcgg   3300
tggttttttt gtttgcaagc agcagattac gcgcagaaaa aaaggatctc aagaagatcc   3360
tttgatcttt tctacggggt ctgacgctca gtggaacgaa aactcacgtt aagggatttt   3420
ggtcatgaga ttatcaaaaa ggatcttcac ctagatcctt ttaaattaaa aatgaagttt   3480
taaatcaatc taaagtatat atgagtaaac ttggtctgac agttaccaat gcttaatcag   3540
tgaggcacct atctcagcga tctgtctatt tcgttcatcc atagttgcct gactccccgt   3600
cgtgtagata actacgatac gggagcgctt accatctggc cccagtgctg caatgatacc   3660
gcgagaccca cgctcaccgg ctccagattt atcagcaata aaccagccag ccggaagggc   3720
cgagcgcaga agtggtcctg caactttatc cgcctccatt cagtctatta attgttgccg   3780
ggaagctaga gtaagtagtt cgccagttaa tagtttcgcg aacgttgttg gcattgctac   3840
aggcatcgtg gtgtcactct cgtcgtttgg tatggcttca ttcagctccg gttcccaacg   3900
atcaaggcga gttacatgat cccccatgtt gtgcaaaaaa gcggttagct ccttcggtcc   3960
tccgatcgtt gtcagaagta agttggccgc agtgttatca ctcatggtta tggcagcact   4020
gcataattct cttactgtca tgccatccgt aagatgcttt tctgtgactg gtgagtactc   4080
aaccaagtca ttctgagaat agtgtatgcg gcgaccgagt tgctcttgcc cggcgtcaat   4140 acggataat agtgtatcac atagcagaac tttaaaagtg ctcatcattg gaaaacgttc    4200
ttcggggcga aaactctcaa ggatcttacc gctgttgaga tccagttcga tgtaacccac   4260
```

```
tcgtgcaccc aactgatctt cagcatcttt tactttcacc agcgtttctg ggtgagcaaa    4320
aacaggaagg caaaatgccg caaaaaaggg aataagggcg acacggaaat gttgaatact    4380
catactcttc cttttcaat gggtaataac tgatataatt aaattgaagc tctaatttgt    4440
gagtttagta tacatgcatt tacttataat acagttttt agtttgctg ccgcatctt      4500 ctcaaatatg cttcccagcc tgcttttctg taacgttcac cctctacctt agcatccctt   4560 cccttgcaa atagtcctct tccaacaata ataatgtcag atcctgtaga gaccacatca    4620
tccacggttc tatactgttg acccaatgcg tctcccttgt catctaaacc cacaccgggt   4680
gtcataatca accaatcgta accttcatct cttccaccca tgtctctttg agcaataaag   4740
ccgataacaa aatctttgtc gctcttcgca atgtcaacag tacccttagt atattctcca   4800
gtagataggg agcccttgca tgacaattct gctaacatca aaaggcctct aggttccttt   4860
gttacttctt ctgccgcctg cttcaaaccg ctaacaatac ctgggcccttt gcttcttgtt  4920 actggatatg tatgtatgta taataagtga tcttatgtat gaaattctta aaaaaggaca   4980
cctgtaagcg ttgatttcta tgtatgaagt ccacatttga tgtaatcata acaaagccta   5040
aaaaataggt atatcatttt ataattattt gctgtacaag tatatcaata aacttatata   5100
ttacttgttt tctagataag cttcgtaacc gacagtttct aacttttgtg ctttgacaag   5160
aacttcttct tcttgcttta ataaaaactg ttccattttc gttgtataac ttgaatcata   5220
agcgccaagc agtctgacag ccaacagcgc agcgttcgta ctattattaa tagcgacggt   5280
agctactgga acacctctag gcatttgcac aattgaatgt aaagaatcta ctccatctag   5340
acaagaacct tttacgggca caccgatgac aggaagtggt gtcattgcag ccaccatacc   5400
tggcaagtga gcagccccac cagctccagc gataattgtt ttaattccac gcttgcttgc   5460
ggaaatagca tatgctgaca tcctatgtgg agttctatga gcagagacta ttgtcacttc   5520
aaatggaacg ccaaaatctt ttaaaaccgc acatgcggca gacattaccg gcaagtcaga   5580
gtctgatccc atgatgattc caaccaatgg tttgaccatt gcttccaagt ccaacttttg   5640
agcgacagag attttgattg gaatatcagt tctacctgta atgtagttca gcctttgttc   5700
acattccgcc atactggagg caataatatt tatgtgacct acttttctgt taggtctaga   5760
ctcttttcca tataagtaca ctgaggaacc tggagtcgcc aatgctcttt cgcaagtttc   5820
tagctcttta tcttttgtat gtttgtctcc aagaacattt agcataatgg cgttcgttgt   5880
aatggtggag aaagatgtga aattctttgg cattggcaaa tccaatattg atctcaaatg   5940
agcttcaaat tgagaagtga cgcaagcatc aatggtataa tgtccagagt tgtgaggcct   6000
tggggcaatt tcgttaataa gcaattcccc tgtttctaaa tagaacattt ccacaccaaa   6060
tataccacaa ccgggaaaag atttgattgc atttttctgcc aacaacttcg ccttaagttg   6120
aacggagtcc ggaactctag caggcgcata acataagtca caaatattgt ccttgtggat   6180
agtctctaca attgggtaag aaaacactaa accgttaaca gatctcacaa tcatgactgc   6240
taattcttta gtaaatggtg cccatttttc ggcgtacaaa ggacgatcct tcagtacttc   6300
caaagcttcc ggaatcattt ccttattctt tacaacgaag ttacctcttc catcgtatgc   6360
caaagtcctc gacttcaaga cgaatggaaa acccaaatct cttccaacat tcaatagtga   6420
cgtctcactg gcttgttcca caggaacact ttgggtaact gctataccat ttttgattaa   6480
atgctctttt tgaatatatt tgtcttgtat caatctgatt gtttctggag aagggtaaat   6540
ttttaatttg ggatgtttta cttgaagatt ctttagtgta ggaacatcaa catgctcaat   6600
ctcaatcgtt agcacatcac attttttcagc tagttttttcg atatcaagag gattggaaaa   6660
```

```
ggagccatta acgtggtcat tggagttgct tatttgtttg gcaggagaat tttcagcatc    6720
tagtattacc gtcttaatgt tgagcctgtt tgctgcctca acaatcatac gtcccaattg    6780
tccccctcct aatataccaa ctgttctaga atccatactt gattgttttg tccgattttc    6840 ttgttttct tgattgttat agtaggatgt acttagaaga gagatccaac gattttacgc     6900
accaatttat acatgaaatg ctccataata ttgtccattt agttcttaat aaaaggtcag    6960
caagagtcaa tcacttagta ttacccggtt cgtagccatg caacaagagt catttgtcag    7020
catagctgta ataatcaatc atgacgtaag aaatgtatca taattaaaag ttgttaaaga    7080
tgtcagtgtt atgttggtgt tacaaaattc tcggctagct tatcgatgat aagctgtcaa    7140
agatgagaat taattccacg gactatagac tatactagat actccgtcta ctgtacgata    7200
cacttccgct caggtccttg tcctttaacg aggccttacc actcttttgt tactctattg    7260
atccagctca gcaaaggcag tgtgatctaa gattctatct tcgcgatgta gtaaaactag    7320
ctagaccgag aaagagacta gaaatgcaaa aggcacttct acaatggctg ccatcattat    7380
tatccgatgt gacgctgcag cttctcaatg atattcgaat acgctttgag gagatacagc    7440
ctaatatccg acaaactgtt ttacagattt acgatcgtac ttgttaccca tcattgaatt    7500
ttgaacatcc gaacctggga gttttccctg aaacagatag tatatttgaa cctgtataat    7560
aatatatagt ctagcgcttt acggaagaca atgtatgtat ttcggttcct ggagaaacta    7620
ttgcatctat tgcataggta atcttgcacg tcgcatcccc ggttcatttt ctgcgtttcc    7680
atcttgcact tcaatagcat atcttgtta acgaagcatc tgtgcttcat tttgtagaac     7740
aaaaatgcaa cgcgagagcg ctaattttc aaacaaagaa tctgagctgc atttttacag     7800
aacagaaatg caacgcgaaa gcgctatttt accaacgaag aatctgtgct tcattttgt     7860 aaaacaaaaa tgcaacgcga cgagagcgct aatttttcaa acaaagaatc tgagctgcat    7920
ttttacagaa cagaaatgca acgcgagagc gctattttac caacaaagaa tctatacttc    7980 tttttttgttc tacaaaaatg catcccgaga gcgctatttt tctaacaaag catcttagat    8040 tactttttt ctcctttgtg cgctctataa tgcagtctct tgataacttt ttgcactgta     8100
ggtccgttaa ggttagaaga aggctacttt ggtgtctatt ttctcttcca taaaaaaagc    8160
ctgactccac ttcccgcgtt tactgattac tagcgaagct gcgggtgcat ttttcaaga    8220 taaaggcatc cccgattata ttctataccg atgtggattg cgcatacttt gtgaacagaa    8280
agtgatagcg ttgatgattc ttcattggtc agaaaattat gaacggtttc ttctattttg    8340
tctctatata ctacgtatag gaaatgttta cattttcgta ttgttttcga ttcactctat    8400
gaatagttct tactacaatt ttttttgtcta aagagtaata ctagagataa acataaaaaa    8460
tgtagaggtc gagtttagat gcaagttcaa ggagcgaaag gtggatgggt aggttatata    8520
gggatatagc acagagatat atagcaaaga gatactttg agcaatgttt gtggaagcgg     8580
tattcgcaat gggaagctcc accccggttg ataatcagaa aagcccaaa acaggaaga     8640 ttgtataagc aaatattaa attgtaaacg ttaatatttt gttaaaattc gcgttaaatt     8700
tttgttaaat cagctcattt tttaacgaat agcccgaaat cggcaaaatc ccttataaat    8760
caaaagaata daccgagata gggttgagtg ttgttccagt ttccaacaag agtccactat    8820
taaagaacgt ggactccaac gtcaaagggc gaaaaaggt ctatcagggc gatggcccac     8880
tacgtgaacc atcaccctaa tcaagttttt tggggtcgag gtgccgtaaa gcagtaaatc    8940
ggaagggtaa acggatgccc ccatttagag cttgacgggg aaagccggcg aacgtggcga    9000
```

| | |
|---|---|
| gaaaggaagg gaagaaagcg aaaggagcgg gggctagggc ggtgggaagt gtagggtca | 9060 |
| cgctgggcgt aaccaccaca cccgccgcgc ttaatgggc gctacagggc gcgtggggat | 9120 |
| gatccactag tacggattag aagccgccga gcgggtgaca gccctccgaa ggaagactct | 9180 |
| cctccgtgcg tcctcgtcct caccggtcgc gttcctgaaa cgcagatgtg cctcgcgccg | 9240 |
| cactgctccg aacaataaag attctacaat actagctttt atggttatga agaggaaaaa | 9300 |
| ttggcagtaa cctggcccca caaaccttca aatgaacgaa tcaaattaac aaccatagga | 9360 |
| tgataatgcg attagttttt tagccttatt tctggggtaa ttaatcagcg aagcgatgat | 9420 |
| ttttgatcta ttaacagata tataaatgca aaaactgcat taaccacttt aactaatact | 9480 |
| ttcaacattt tcggtttgta ttacttctta ttcaaatgta ataaaagtat caacaaaaaa | 9540 |
| ttgttaatat acctctatac tttaacgtca aggagaaaaa accccggatc ggactactag | 9600 |
| cagctgtaat acgactcact atagggaata ttaagcttgc ggatcc | 9646 |

<210> SEQ ID NO 34
<211> LENGTH: 9865
<212> TYPE: DNA
<213> ORGANISM: Artificial
<220> FEATURE:
<223> OTHER INFORMATION: Plasmid

<400> SEQUENCE: 34

| | |
|---|---|
| ccaactttgt ttggtctgat gagtccgtga ggacgaaacc cggagtcccg ggtcaccaaa | 60 |
| caaagttggg taaggatagt tcaatcaatg atcatcttct agtgcactta ggattcaaga | 120 |
| tcctattatc agggacaaga gcaggattag ggatatccga gatggaaaat cttgctagga | 180 |
| tacagttctc acatcacatc cgaacataaa caaccatgga ctatgctaca acattccaaa | 240 |
| atttgtccca aaaagtcttt ggttcatgat cttcccatac aattgcctca atgtctcttc | 300 |
| tatcggaatc gatgtcgaca ctctccaatct tccaaataaa tctgcatctg aatatgcatt | 360 |
| gaaataagat ccaaacagct aagaacagga aaatagagat ataggcggca gcaaagctaa | 420 |
| caccattgaa ttttggtgca aaagccgtga aaccttgaat aatgataatg atcgtcataa | 480 |
| atgtggccgc ataataagcc aagccgggca ttaatttagc tttaaatggt aactcgtcac | 540 |
| gagagatgcc acggtatttc aaagcttgca taaatctgat gtgcgagatt gagataaata | 600 |
| accatgcaaa aaagcctgca acaccagtga tatttaatag ccattcgaaa actttgtcac | 660 |
| caccagtaga tgtctccatg taagccaaag cgccaaatgc agcagtaacg aaaactgcaa | 720 |
| tgtatggaac accaccttg gtggtccttg acaggaattt aggagccaac ttgttctttg | 780 |
| atagaccaaa taaatacgg gaaccaacgt aaatatttga atttgcggca gaaataatgg | 840 |
| ttgttaagat aacagcgttg aagatatgtg gcaaaacctt tgtaccagag ttctcaatag | 900 |
| caataataaa gggagaagta gaaacgtagg aagtagattg tgttagttta gggtcattgt | 960 |
| atggaactaa aagtccaatg aataatagag agccaatgta gaaggttaag atacggaaaa | 1020 |
| caactttttt gatggctctt ggaacggatt ttctggggtt tgcagcttca ccagcagtga | 1080 |
| taccaactag ttcagtacct tgaaatgtga aggcagcgtt aatcaaagag gaaacccaac | 1140 |
| ctaagaacct ccccttcgttt ttatccttag atattatacc tggaccccag gcacctgggt | 1200 |
| ttctccaata acggaatcca actgggccgg taaccccagc accacaaacc atacaaaaac | 1260 |
| agtatattag aaacccgata atggctaaaa ctttgatgga agcgacccag aactcgaatt | 1320 |
| caccgtaata tttgacaggg aacaagttca ttattgtgat aattacccaa aaaatactaa | 1380 |
| tccatgccgc cagtggaact ttgtacgtcc aaaattgaat gacttggcca actacactaa | 1440 |

```
gttccagggc aaaagtgatt gcccaagaaa accaatacat gtaaccattg gccgcaccaa    1500
atgctggaga aaggaatctt tgtgagaaaa ctgtgaaaga ggatgtaaca gggatgaatg    1560
tagccatttc acccaaggac tgcgtgacag aatatgccaa agaacccata aataaatatg    1620
atataagagc gcccactggg ccggcgttgg tcagaggtgt ggataaacca atgaaaagac    1680
ctgtaccaat agtaccacca agggcaatca taccaatatg tctttgctta agctctctct    1740
tcacttcagc gttctgtact tctccttcat cttcatcacc tatgccatcc tccatagaga    1800
acgtatcctc gccatttact ctcgtcggga aagagcgcaa tggatacaat tctttacttt    1860
tctcatcttt caatggtatt gacccacgtc tgtggtgtgt tgtgaagct tcaacgtcgt     1920 gaaagagggt tgtgaccggc tcattgtaca tatgcttctc ctctatgtcg gcgtcttctt    1980
ttgaatttgt catgagctcg aattcatcga tgatatggta taagttagtc ggatacagtg    2040
ccctgattaa ggactaattg gttgaactcc ggaaccctaa tcctgcccta ggtggttagg    2100
cattatttgc aatatattaa agaaaacttt gaaaatacga agtttctatt cccagctttg    2160
tctggtggcc ggcatggtcc cagcctcctc gctggcgccg gctgggcaac attccgaggg    2220
gaccgtcccc tcggtaatgg cgaatgggac gcggccgatc cggctgctaa caaagcccga    2280
aaggaagctg agttggctgc tgccaccgct gagcaataac tagcataacc ccttggggcc    2340
tctaaacggg tcttgagggg ttttttgctg aaaggaggaa ctatatccgg atgcggccgc    2400
tcgagcatgc atctagaggg ccgcatcatg taattagtta tgtcacgctt acattcacgc    2460
cctcccccca catccgctct aaccgaaaag gaaggagtta gacaacctga agtctaggtc    2520
cctatttatt tttttatagt tatgttagta ttaagaacgt tatttatatt tcaaattttt    2580
cttttttttc tgtacagacg cgtgtacgca tgtaacatta tactgaaaac cttgcttgag    2640
aaggttttgg gacgctcgaa ggctttaatt tgcggccctg cattaatgaa tcggccaacg    2700
cgcggggaga ggcggtttgc gtattgggcg ctcttccgct tcctcgctca ctgactcgct    2760
gcgctcggtc gttcggctgc ggcgagcggt atcagctcac tcaaaggcgg taatacggtt    2820
atccacagaa tcaggggata acgcaggaaa gaacatgtga gcaaaaggcc agcaaaagcc    2880
caggaaccgt aaaaaggccg cgttgctggc gttttccat aggctccgcc ccctgacga     2940 gcatcacaaa aatcgacgct caagtcagag gtggcgaaac ccgacaggac tataaagata    3000
ccaggcgttt ccccctggaa gctccctcgt gcgctctcct gttccgaccc tgccgcttac    3060
cggatacctg tccgcctttc tcccttcggg aagcgtggcg ctttctcata gctcacgctg    3120
taggtatctc agttcggtgt aggtcgttcg ctccaagctg ggctgtgtgc acgaaccccc    3180
cgttcagccc gaccgctgcg ccttatccgg taactatcgt cttgagtcca acccggtaag    3240
acacgactta tcgccactgg cagcagccac tggtaacagg attagcagag cgaggtatgt    3300
aggcggtgct acagagttct tgaagtggtg gcctaactac ggctacacta aggacagt     3360 atttggtatc tgcgctctgc tgaagccagt taccttcgga aaaagagttg gtagctcttg    3420
atccggcaaa caaaccaccg ctggtagcgg tggttttttt gtttgcaagc agcagattac    3480
gcgcagaaaa aaaggatctc aagaagatcc tttgatcttt tctacggggt ctgacgctca    3540
gtggaacgaa aactcacgtt aagggatttt ggtcatgaga ttatcaaaaa ggatcttcac    3600
ctagatcctt ttaaattaaa aatgaagttt taaatcaatc taagtatat atgagtaaac    3660 ttggtctgac agttaccaat gcttaatcag tgaggcacct atctcagcga tctgtctatt    3720
tcgttcatcc atagttgcct gactccccgt cgtgtagata actacgatac gggagcgctt    3780
```

```
accatctggc cccagtgctg caatgatacc gcgagaccca cgctcaccgg ctccagattt      3840
atcagcaata aaccagccag ccggaagggc cgagcgcaga agtggtcctg caactttatc      3900
cgcctccatt cagtctatta attgttgccg ggaagctaga gtaagtagtt cgccagttaa      3960
tagtttgcgc aacgttgttg gcattgctac aggcatcgtg gtgtcactct cgtcgtttgg      4020
tatggcttca ttcagctccg gttcccaacg atcaaggcga gttacatgat cccccatgtt      4080
gtgcaaaaaa gcggttagct ccttcggtcc tccgatcgtt gtcagaagta agttggccgc      4140
agtgttatca ctcatggtta tggcagcact gcataattct cttactgtca tgccatccgt      4200
aagatgcttt tctgtgactg gtgagtactc aaccaagtca ttctgagaat agtgtatgcg      4260
gcgaccgagt tgctcttgcc cggcgtcaat acgggataat agtgtatcac atagcagaac      4320
tttaaaagtg ctcatcattg gaaaacgttc ttcggggcga aaactctcaa ggatcttacc      4380
gctgttgaga tccagttcga tgtaacccac tcgtgcaccc aactgatctt cagcatcttt      4440
tactttcacc agcgtttctg ggtgagcaaa aacaggaagg caaatgccg caaaaagggg      4500
aataagggcg acacggaaat gttgaatact catactcttc cttttcaat gggtaataac       4560
tgatataatt aaattgaagc tctaatttgt gagtttagta tacatgcatt tacttataat      4620
acagtttttt agttttgctg gccgcatctt ctcaaatatg cttcccagcc tgcttttctg      4680
taacgttcac cctctacctt agcatccctt cccttt gcaa atagtcctct tccaacaata     4740
ataatgtcag atcctgtaga gaccacatca tccacggttc tatactgttg acccaatgcg      4800
tctcccttgt catctaaacc cacaccgggt gtcataatca accaatcgta accttcatct      4860
cttccaccca tgtctctttg agcaataaag ccgataacaa atctttgtc gctcttcgca       4920
atgtcaacag tacccttagt atattctcca gtagataggg agcccttgca tgacaattct      4980
gctaacatca aaaggcctct aggttccttt gttacttctt ctgccgcctg cttcaaaccg      5040
ctaacaatac ctgggcccct tgcttcttgtt actggatatg tatgtatgta taataagtga    5100
tcttatgtat gaaattctta aaaaggaca cctgtaagcg ttgatttcta tgtatgaagt      5160
ccacatttga tgtaatcata acaaagccta aaaaataggt atatcatttt ataattattt     5220
gctgtacaag tatatcaata aacttatata ttacttgttt tctagataag cttcgtaacc     5280
gacagtttct aacttttgtg ctttgacaag aacttcttct tcttgcttta ataaaaactg     5340
ttccattttc gttgtataac ttgaatcata agcgccaagc agtctgacag ccaacagcgc     5400
agcgttcgta ctattattaa tagcgacggt agctactgga acacctctag gcatttgcac     5460
aattgaatgt aaagaatcta ctccatctag acaagaacct tttacgggca caccgatgac    5520
aggaagtggt gtcattgcag ccaccatacc tggcaagtga gcagcccac cagctccagc     5580
gataattgtt ttaattccac gcttgcttgc ggaaatagca tatgctgaca tcctatgtgg    5640
agttctatga gcagagacta ttgtcacttc aaatggaacg ccaaaatctt ttaaaaccgc     5700
acatgcggca gacattaccg gcaagtcaga gtctgatccc atgatgattc caaccaatgg    5760
tttgaccatt gcttccaagt ccaacttttg agcgacagag attttgattg gaatatcagt     5820
tctacctgta atgtagttca gcctttgttc acattccgcc atactggagg caataatatt    5880
tatgtgacct acttttctgt taggtctaga ctctttttcca tataagtaca ctgaggaacc   5940
tggagtcgcc aatgctcttt cgcaagtttc tagctcttta tcttttgtat gtttgtctcc   6000
aagaacattt agcataatgg cgttcgttgt aatggtggag aaagatgtga aattctttgg    6060
cattggcaaa tccaatattg atctcaaatg agcttcaaat tgagaagtga cgcaagcatc   6120
aatggtataa tgtccagagt tgtgaggcct tggggcaatt tcgttaataa gcaattcccc   6180
```

```
tgtttctaaa tagaacattt ccacaccaaa tataccacaa ccgggaaaag atttgattgc    6240
attttctgcc aacaacttcg ccttaagttg aacggagtcc ggaactctag caggcgcata    6300
acataagtca caaatattgt ccttgtggat agtctctaca attgggtaag aaaacactaa    6360
accgttaaca gatctcacaa tcatgactgc taattcttta gtaaatggtg cccatttttc    6420
ggcgtacaaa ggacgatcct tcagtacttc caaagcttcc ggaatcattt ccttattctt    6480
tacaacgaag ttacctcttc catcgtatgc caaagtcctc gacttcaaga cgaatggaaa    6540
acccaaatct cttccaacat tcaataggga cgtctcactg gcttgttcca caggaacact    6600
ttgggtaact gctataccat ttttgattaa atgctctttt tgaatatatt tgtcttgtat    6660
caatctgatt gtttctggag aagggtaaat tttaatttg ggatgtttta cttgaagatt     6720
ctttagtgta ggaacatcaa catgctcaat ctcaatcgtt agcacatcac attttcagc     6780 tagttttcg atatcaagag gattggaaaa ggagccatta acgtggtcat tggagttgct    6840
tatttgtttg gcaggagaat tttcagcatc tagtattacc gtcttaatgt tgagcctgtt    6900
tgctgcctca acaatcatac gtcccaattg tccccctcct aatataccaa ctgttctaga    6960
atccatactt gattgttttg tccgattttc ttgttttct tgattgttat agtaggatgt      7020
acttagaaga gagatccaac gattttacgc accaatttat acatgaaatg ctccataata    7080
ttgtccattt agttcttaat aaaaggtcag caagagtcaa tcacttagta ttacccggtt    7140
cgtagccatg caacaagagt catttgtcag catagctgta ataatcaatc atgacgtaag    7200
aaatgtatca taattaaaag ttgttaaaga tgtcagtgtt atgttggtgt tacaaaattc    7260
tcggctagct tatcgatgat aagctgtcaa agatgagaat taattccacg gactatagac    7320
tatactagat actccgtcta ctgtacgata cacttccgct caggtccttg tcctttaacg    7380
aggccttacc actcttttgt tactctattg atccagctca gcaaaggcag tgtgatctaa    7440
gattctatct tcgcgatgta gtaaaactag ctagaccgag aaagagacta gaaatgcaaa    7500
aggcacttct acaatggctg ccatcattat tatccgatgt gacgctgcag cttctcaatg    7560
atattcgaat acgctttgag gagatacagc ctaatatccg acaaactgtt ttacagattt     7620
acgatcgtac ttgttaccca tcattgaatt ttgaacatcc gaacctggga gttttccctg    7680
aaacagatag tatatttgaa cctgtataat aatatatagt ctagcgcttt acggaagaca    7740
atgtatgtat ttcggttcct ggagaaacta ttgcatctat tgcataggta atcttgcacg    7800
tcgcatcccc ggttcatttt ctgcgttttcc atcttgcact tcaatagcat atctttgtta    7860
acgaagcatc tgtgcttcat tttgtagaac aaaaatgcaa cgcgagagcg ctaatttttc    7920
aaacaaagaa tctgagctgc attttacag aacagaaatg caacgcgaaa gcgctatttt     7980
accaacgaag aatctgtgct tcattttgt aaaacaaaaa tgcaacgcga cgagagcgct     8040 aattttcaa acaaagaatc tgagctgcat ttttacagaa cagaaatgca acgcgagagc     8100
gctattttac caacaagaa tctatacttc ttttttgttc tacaaaaatg catcccgaga     8160
gcgctatttt tctaacaaag catcttagat tactttttt ctcctttgtg cgctctataa     8220
tgcagtctct tgataacttt ttgcactgta ggtccgttaa ggttagaaga aggctacttt    8280
ggtgtctatt ttctcttcca taaaaaagc ctgactccac ttcccgcgtt tactgattac     8340
tagcgaagct gcgggtgcat ttttcaaga taaaggcatc cccgattata ttctataccg    8400
atgtggattg cgcatacttt gtgaacgaaa agtgatagcg ttgatgattc ttcattggtc    8460
agaaaattat gaacggtttc ttctattttg tctctatata ctacgtatag gaaatgttta    8520
```

| | |
|---|---|
| cattttcgta ttgttttcga ttcactctat gaatagttct tactacaatt tttttgtcta | 8580 |
| aagagtaata ctagagataa acataaaaaa tgtagaggtc gagtttagat gcaagttcaa | 8640 |
| ggagcgaaag gtggatgggt aggttatata gggatatagc acagagatat atagcaaaga | 8700 |
| gatacttttg agcaatgttt gtggaagcgg tattcgcaat gggaagctcc accccggttg | 8760 |
| ataatcagaa aagccccaaa aacaggaaga ttgtataagc aaatatttaa attgtaaacg | 8820 |
| ttaatatttt gttaaaattc gcgttaaatt tttgttaaat cagctcattt tttaacgaat | 8880 |
| agcccgaaat cggcaaaatc ccttataaat caaaagaata gaccgagata gggttgagtg | 8940 |
| ttgttccagt ttccaacaag agtccactat taaagaacgt ggactccaac gtcaaagggc | 9000 |
| gaaaaaggt ctatcagggc gatggcccac tacgtgaacc atcaccctaa tcaagttttt | 9060 |
| tggggtcgag gtgccgtaaa gcagtaaatc ggaagggtaa acggatgccc ccatttagag | 9120 |
| cttgacgggg aaagccggcg aacgtggcga aaaggaagg gaagaaagcg aaaggagcgg | 9180 |
| gggctagggc ggtgggaagt gtaggggtca cgctgggcgt aaccaccaca cccgccgcgc | 9240 |
| ttaatggggc gctacaggc gcgtgggat gatccactag tacggattag aagccgccga | 9300 |
| gcgggtgaca gccctccgaa ggaagactct cctccgtgcg tcctcgtcct caccggtcgc | 9360 |
| gttcctgaaa cgcagatgtg cctcgcgccg cactgctccg aacaataaag attctacaat | 9420 |
| actagctttt atggttatga agaggaaaaa ttggcagtaa cctggcccca caaaccttca | 9480 |
| aatgaacgaa tcaaattaac aaccatagga tgataatgcg attagttttt tagccttatt | 9540 |
| tctggggtaa ttaatcagcg aagcgatgat ttttgatcta ttaacagata tataaatgca | 9600 |
| aaaactgcat taaccacttt aactaatact ttcaacattt tcggtttgta ttacttctta | 9660 |
| ttcaaatgta ataaaagtat caacaaaaaa ttgttaatat acctctatac tttaacgtca | 9720 |
| aggagaaaaa accccggatc ggactactag cagctgtaat acgactcact atagggaata | 9780 |
| ttaagcttgc actagtaacg gccgccagtg tgctggctgc agatatccat cacactggcg | 9840 |
| gccgctaata cgactcacta taggg | 9865 |

<210> SEQ ID NO 35
<211> LENGTH: 8922
<212> TYPE: DNA
<213> ORGANISM: Artificial
<220> FEATURE:
<223> OTHER INFORMATION: Plasmid

<400> SEQUENCE: 35

| | |
|---|---|
| ccaactttgt ttggtctgat gagtccgtga ggacgaaacc cggagtcccg ggtcaccaga | 60 |
| caaagctggg aatagaaact tcgtattttc aaagttttct ttaatatatt gcaaataatg | 120 |
| cctaaccacc tagggcagga ttagggttcc ggagttcaac caattagtcc ttaatcaggg | 180 |
| cactgtatcc gactaactta taccatatca tcgatgaatt cgagctcgtt ttcgacactg | 240 |
| gatggcggcg ttagtatcga atcgacagca gtatagcgac cagcattcac atacgattga | 300 |
| cgcatgatat tactttctgc gcacttaact tcgcatctgg gcagatgatg tcgaggcgaa | 360 |
| aaaaaatata aatcacgcta acatttgatt aaaatagaac aactacaata taaaaaaact | 420 |
| atacaaatga caagttcttg aaaacaagaa tctttttatt gtcagtactg attagaaaaa | 480 |
| ctcatcgagc atcaaatgaa actgcaattt attcatatca ggattatcaa taccatattt | 540 |
| ttgaaaaagc cgtttctgta atgaaggaga aaactcaccg aggcagttcc ataggatggc | 600 |
| aagatcctgg tatcggtctg cgattccgac tcgtccaaca tcaatacaac ctattaattt | 660 |
| cccctcgtca aaaataaggt tatcaagtga gaaatcacca tgagtgacga ctgaatccgg | 720 |

```
tgagaatggc aaaagcttat gcatttcttt ccagacttgt tcaacaggcc agccattacg      780
ctcgtcatca aaatcactcg catcaaccaa accgttattc attcgtgatt gcgcctgagc      840
gagacgaaat acgcgatcgc tgttaaaagg acaattacaa acaggaatcg aatgcaaccg      900
gcgcaggaac actgccagcg catcaacaat attttcacct gaatcaggat attcttctaa      960
tacctggaat gctgttttgc cggggatcgc agtggtgagt aaccatgcat catcaggagt     1020
acggataaaa tgcttgatgg tcggaagagg cataaattcc gtcagccagt ttagtctgac     1080
catctcatct gtaacatcat tggcaacgct acctttgcca tgtttcagaa acaactctgg     1140
cgcatcgggc ttcccataca atcgatagat tgtcgcacct gattgcccga cattatcgcg     1200
agcccattta tacccatata atcagcatc catgttggaa tttaatcgcg gcctcgaaac      1260
gtgagtcttt tccttaccca tggttgttta tgttcggatg tgatgtgaga actgtatcct     1320
agcaagattt tccatctcgg atatccctaa tcctgctctt gtccctgata taggatctt      1380 gaatcctaag tgcactagaa gatgatcatt gattgaacta tccttaccca actttgtttg     1440
gtggccggca tggtcccagc tcctcgctg gcgccggctg ggcaacattc cgagggacc      1500 gtcccctcgg taatggcgaa tgggactcga gcatgcatct agagggccgc atcatgtaat     1560
tagttatgtc acgcttacat tcacgccctc cccccacatc cgctctaacc gaaaaggaag     1620
gagttagaca acctgaagtc taggtcccta tttattttt tatagttatg ttagtattaa      1680
gaacgttatt tatatttcaa attttctttt ttttctgta cagacgcgtg tacgcatgta      1740
acattatact gaaaaccttg cttgagaagg ttttgggacg ctcgaaggct ttaatttgcg     1800
gccctgcatt aatgaatcgg ccaacgcgcg gggagaggcg gtttgcgtat gggcgctct     1860 tccgcttcct cgctcactga ctcgctgcgc tcggtcgttc ggctgcggcg agcggtatca     1920
gctcactcaa aggcggtaat acggttatcc acagaatcag gggataacgc aggaaagaac     1980
atgtgagcaa aaggccagca aaagcccagg aaccgtaaaa aggccgcgtt gctggcgttt     2040
ttccataggc tccgcccccc tgacgagcat cacaaaaatc gacgctcaag tcagaggtgg     2100
cgaaacccga caggactata aagataccag gcgtttcccc ctggaagctc cctcgtgcgc     2160
tctcctgttc cgaccctgcc gcttaccgga tacctgtccg cctttctccc ttcgggaagc     2220
gtggcgcttt ctcatagctc acgctgtagg tatctcagtt cggtgtaggt cgttcgctcc     2280
aagctgggct gtgtgcacga accccccgtt cagcccgacc gctgcgcctt atccggtaac     2340
tatcgtcttg agtccaaccc ggtaagacac gacttatcgc cactggcagc agccactggt     2400
aacaggatta gcagagcgag gtatgtaggc ggtgctacag agttcttgaa gtggtggcct     2460
aactacggct acactagaag gacagtattt ggtatctgcg ctctgctgaa gccagttacc     2520
ttcggaaaaa gagttggtag ctcttgatcc ggcaaacaaa ccaccgctgg tagcggtggt     2580
ttttttgttt gcaagcagca gattacgcgc agaaaaaaag gatctcaaga agatcctttg     2640
atcttttcta cggggtctga cgctcagtgg aacgaaaact cacgttaagg gattttggtc     2700
atgagattat caaaaaggat cttcacctag atccttttaa attaaaaatg aagttttaaa     2760
tcaatctaaa gtatatatga gtaaacttgg tctgacagtt accaatgctt aatcagtgag     2820
gcacctatct cagcgatctg tctatttcgt tcatccatag ttgcctgact ccccgtcgtg     2880
tagataacta cgatacggga gcgcttacca tctggcccca gtgctgcaat gataccgcga     2940
gacccacgct caccggctcc agatttatca gcaataaacc agccagccgg aagggccgag     3000
cgcagaagtg gtcctgcaac tttatccgcc tccattcagt ctattaattg ttgccgggaa     3060
```

```
gctagagtaa gtagttcgcc agttaatagt ttgcgcaacg ttgttggcat tgctacaggc   3120
atcgtggtgt cactctcgtc gtttggtatg gcttcattca gctccggttc ccaacgatca   3180
aggcgagtta catgatcccc catgttgtgc aaaaaagcgg ttagctcctt cggtcctccg   3240
atcgttgtca gaagtaagtt ggccgcagtg ttatcactca tggttatggc agcactgcat   3300
aattctctta ctgtcatgcc atccgtaaga tgcttttctg tgactggtga gtactcaacc   3360
aagtcattct gagaatagtg tatgcggcga ccgagttgct cttgcccggc gtcaatacgg   3420
gataatagtg tatcacatag cagaacttta aaagtgctca tcattggaaa acgttcttcg   3480
gggcgaaaac tctcaaggat cttaccgctg ttgagatcca gttcgatgta acccactcgt   3540
gcacccaact gatcttcagc atcttttact ttcaccagcg tttctgggtg agcaaaaaca   3600
ggaaggcaaa atgccgcaaa aagggaata agggcgacac ggaaatgttg aatactcata   3660
ctcttccttt ttcaatgggt aataactgat ataattaaat tgaagctcta atttgtgagt   3720
ttagtataca tgcatttact tataatacag ttttttagtt ttgctggccg catcttctca   3780
aatatgcttc ccagcctgct tttctgtaac gttcaccctc taccttagca tcccttccct   3840
ttgcaaatag tcctcttcca acaataataa tgtcagatcc tgtagagacc acatcatcca   3900
cggttctata ctgttgaccc aatgcgtctc ccttgtcatc taaacccaca ccgggtgtca   3960
taatcaacca atcgtaacct tcatctcttc cacccatgtc tctttgagca ataaagccga   4020
taacaaaatc tttgtcgctc ttcgcaatgt caacagtacc cttagtatat tctccagtag   4080
atagggagcc cttgcatgac aattctgcta acatcaaaag gcctctaggt tcctttgtta   4140
cttcttctgc cgcctgcttc aaaccgctaa caatacctgg gcccttgctt cttgttactg   4200
gatatgtatg tatgtataat aagtgatctt atgtatgaaa ttcttaaaaa aggacacctg   4260
taagcgttga tttctatgta tgaagtccac atttgatgta atcataacaa agcctaaaaa   4320
ataggtatat cattttataa ttatttgctg tacaagtata tcaataaact tatatattac   4380
ttgttttcta gataagcttc gtaaccgaca gtttctaact tttgtgcttt gacaagaact   4440
tcttcttctt gctttaataa aaactgttcc attttcgttg tataacttga atcataagcg   4500
ccaagcagtc tgacagccaa cagcgcagcg ttcgtactat tattaatagc gacggtagct   4560
actgaacacc tctaggcat ttgcacaatt gaatgtaaag aatctactcc atctagacaa   4620 gaaccttta cgggcacacc gatgacagga agtggtgtca ttgcagccac catacctggc   4680
aagtgagcag ccccaccagc tccagcgata attgttttaa ttccacgctt gcttgcggaa   4740
atagcatatg ctgacatcct atgtggagtt ctatgagcag agactattgt cacttcaaat   4800
ggaacgccaa aatcttttaa aaccgcacat gcggcagaca ttaccggcaa gtcagagtct   4860
gatcccatga tgattccaac caatggtttg accattgctt ccaagtccaa cttttgagcg   4920
acagagattt tgattggaat atcagttcta cctgtaatgt agttcagcct tgttcacat   4980 tccgccatac tggaggcaat aatatttatg tgacctactt ttctgttagg tctagactct   5040
tttccatata agtacactga ggaacctgga gtcgccaatg ctctttcgca agtttctagc   5100
tctttatctt ttgtatgttt gtctccaaga acatttagca taatggcgtt cgttgtaatg   5160
gtggagaaag atgtgaaatt ctttggcatt ggcaaatcca atattgatct caaatgagct   5220
tcaaattgag aagtgacgca agcatcaatg gtataatgtc cagagttgtg aggccttggg   5280
gcaatttcgt taataagcaa ttcccctgtt tctaaataga acattccac accaaatata   5340 ccacaaccgg gaaagatttt gattgcattt tctgccaaca acttcgcctt aagttgaacg   5400
gagtccggaa ctctagcagg cgcataacat aagtcacaaa tattgtcctt gtggatagtc   5460
```

```
tctacaattg ggtaagaaaa cactaaaccg ttaacagatc tcacaatcat gactgctaat    5520
tctttagtaa atggtgccca ttttttcggcg tacaaaggac gatccttcag tacttccaaa    5580
gcttccggaa tcatttcctt attctttaca acgaagttac ctcttccatc gtatgccaaa    5640
gtcctcgact tcaagacgaa tggaaaaccc aaatctcttc caacattcaa tagggacgtc    5700
tcactggctt gttccacagg aacactttgg gtaactgcta taccattttt gattaaatgc    5760 tcttttttgaa tatatttgtc ttgtatcaat ctgattgttt ctggagaagg gtaaattttt    5820
aatttgggat gttttacttg aagattcttt agtgtaggaa catcaacatg ctcaatctca    5880
atcgttagca catcacattt ttcagctagt ttttcgatat caagaggatt ggaaaaggag    5940
ccattaacgt ggtcattgga gttgcttatt tgtttggcag gagaattttc agcatctagt    6000
attaccgtct taatgttgag cctgtttgct gcctcaacaa tcatacgtcc caattgtccc    6060
cctcctaata taccaactgt tctagaatcc atacttgatt gttttgtccg attttcttgt    6120
ttttcttgat tgttatagta ggatgtactt agaagagaga tccaacgatt ttacgcacca    6180
atttatacat gaaatgctcc ataatattgt ccatttagtt cttaataaaa ggtcagcaag    6240
agtcaatcac ttagtattac ccggttcgta gccatgcaac aagagtcatt tgtcagcata    6300
gctgtaataa tcaatcatga cgtaagaaat gtatcataat taaaagttgt taaagatgtc    6360
agtgttatgt tggtgttaca aaattctcgg ctagcttatc gatgataagc tgtcaaagat    6420
gagaattaat tccacggact atagactata ctagatactc cgtctactgt acgatacact    6480
tccgctcagg tccttgtcct ttaacgaggc cttaccactc ttttgttact ctattgatcc    6540
agctcagcaa aggcagtgtg atctaagatt ctatcttcgc gatgtagtaa aactagctag    6600
accgagaaag agactagaaa tgcaaaaggc acttctacaa tggctgccat cattattatc    6660
cgatgtgacg ctgcagcttc tcaatgatat tcgaatacgc tttgaggaga tacagcctaa    6720
tatccgacaa actgttttac agatttacga tcgtacttgt tacccatcat tgaattttga    6780
acatccgaac ctgggagttt tccctgaaac agatagtata tttgaacctg tataataata    6840
tatagtctag cgctttacgg aagacaatgt atgtatttcg gttcctggag aaactattgc    6900
atctattgca taggtaatct tgcacgtcgc atccccggtt cattttctgc gtttccatct    6960
tgcacttcaa tagcatatct ttgttaacga agcatctgtg cttcattttg tagaacaaaa    7020
atgcaacgcg agagcgctaa tttttcaaac aaagaatctg agctgcattt ttacagaaca    7080
gaaatgcaac gcgaaagcgc tattttacca acgaagaatc tgtgcttcat ttttgtaaaa    7140
caaaaatgca acgcgacgag agcgctaatt tttcaaacaa agaatctgag ctgcattttt    7200
acagaacaga aatgcaacgc gagagcgcta ttttaccaac aaagaatcta tacttctttt    7260
ttgttctaca aaaatgcatc ccgagagcgc tattttttcta acaaagcatc ttagattact    7320
ttttttctcc tttgtgcgct ctataatgca gtctcttgat aacttttttgc actgtaggtc    7380 cgttaaggtt agaagaaggc tactttggtg tctattttct cttccataaa aaagcctga    7440 ctccacttcc cgcgtttact gattactagc gaagctgcgg gtgcatttt tcaagataaa    7500 ggcatcccg attatattct ataccgatgt ggattgcgca tactttgtga acagaaagtg    7560
atagcgttga tgattcttca ttggtcagaa aattatgaac ggtttcttct attttgtctc    7620
tatatactac gtataggaaa tgtttacatt ttcgtattgt tttcgattca ctctatgaat    7680
agttcttact acaatttttt tgtctaaaga gtaaatactag agataaacat aaaaaatgta    7740
gaggtcgagt ttagatgcaa gttcaaggag cgaaaggtgg atgggtaggt tatataggga    7800
```

```
tatagcacag agatatatag caaagagata cttttgagca atgtttgtgg aagcggtatt    7860
cgcaatggga agctccaccc cggttgataa tcagaaaagc cccaaaaaca ggaagattgt    7920
ataagcaaat atttaaattg taaacgttaa tattttgtta aaattcgcgt taaattttg    7980
ttaaatcagc tcatttttta acgaatagcc cgaaatcggc aaaatccctt ataaatcaaa    8040
agaatagacc gagatagggt tgagtgttgt tccagtttcc aacaagagtc cactattaaa    8100
gaacgtggac tccaacgtca aagggcgaaa aagggtctat cagggcgatg cccactacg    8160
tgaaccatca ccctaatcaa gttttttggg gtcgaggtgc cgtaaagcag taaatcggaa    8220
gggtaaacgg atgcccccat ttagagcttg acggggaaag ccggcgaacg tggcgagaaa    8280
ggaagggaag aaagcgaaag gagcgggggc tagggcggtg ggaagtgtag gggtcacgct    8340
gggcgtaacc accacacccg ccgcgcttaa tggggcgcta cagggcgcgt ggggatgatc    8400
cactagtacg gattagaagc cgccgagcgg gtgacagccc tccgaaggaa gactctcctc    8460
cgtgcgtcct cgtcctcacc ggtcgcgttc ctgaaacgca gatgtgcctc gcgccgcact    8520
gctccgaaca ataaagattc tacaatacta gcttttatgg ttatgaagag gaaaaattgg    8580
cagtaacctg gccccacaaa ccttcaaatg aacgaatcaa attaacaacc ataggatgat    8640
aatgcgatta gttttttagc cttatttctg gggtaattaa tcagcgaagc gatgattttt    8700
gatctattaa cagatatata aatgcaaaaa ctgcattaac cactttaact aatactttca    8760
acattttcgg tttgtattac ttcttattca aatgtaataa aagtatcaac aaaaaattgt    8820
taatataccct ctatacttta acgtcaagga gaaaaaccc cggatcggac tactagcagc    8880
tgtaatacga ctcactatag ggaatattaa gcttgcggat cc                        8922
```

<210> SEQ ID NO 36
<211> LENGTH: 9141
<212> TYPE: DNA
<213> ORGANISM: Artificial
<220> FEATURE:
<223> OTHER INFORMATION: Plasmid

<400> SEQUENCE: 36

```
ccaactttgt ttggtctgat gagtccgtga ggacgaaacc cggagtcccg ggtcaccaaa      60
caaagttggg taaggatagt tcaatcaatg atcatcttct agtgcactta ggattcaaga    120
tcctattatc agggacaaga gcaggattag ggatatccga gatggaaaat cttgctagga    180
tacagttctc acatcacatc cgaacataaa caaccatggg taaggaaaag actcacgttt    240
cgaggccgcg attaaattcc aacatggatg ctgatttata tgggtataaa tgggctcgcg    300
ataatgtcgg gcaatcaggt gcgacaatct atcgattgta tgggaagccc gatgcgccag    360
agttgtttct gaaacatggc aaaggtagcg ttgccaatga tgttacagat gagatggtca    420
gactaaactg gctgacggaa tttatgcctc ttccgaccat caagcatttt atccgtactc    480
ctgatgatgc atggttactc accactgcga tccccgcaa acagcattc caggtattag    540
aagaatatcc tgattcaggt gaaaatattg ttgatgcgct ggcagtgttc ctgcgccggt    600
tgcattcgat tcctgtttgt aattgtcctt ttaacagcga tcgcgtattt cgtctcgctc    660
aggcgcaatc acgaatgaat aacggtttgg ttgatgcgag tgattttgat gacgagcgta    720
atggctggcc tgttgaacaa gtctggaaag aaatgcataa gcttttgcca ttctcaccgg    780
attcagtcgt cactcatggt gatttctcac ttgataacct tattttgac gaggggaaat    840
taataggttg tattgatgtt ggacgagtcg gaatcgcaga ccgataccag gatcttgcca    900
tcctatggaa ctgcctcggt gagttttctc cttcattaca gaaacggctt tttcaaaaat    960
```

```
atggtattga taatcctgat atgaataaat tgcagtttca tttgatgctc gatgagtttt    1020
tctaatcagt actgacaata aaagattct tgttttcaag aacttgtcat ttgtatagtt    1080
tttttatatt gtagttgttc tattttaatc aaatgttagc gtgatttata tttttttcg    1140 cctcgacatc atctgcccag atgcgaagtt aagtgcgcag aaagtaatat catgcgtcaa    1200
tcgtatgtga atgctggtcg ctatactgct gtcgattcga tactaacgcc gccatccagt    1260
gtcgaaaacg agctcgaatt catcgatgat atggtataag ttagtcggat acagtgccct    1320
gattaaggac taattggttg aactccggaa ccctaatcct gccctaggtg gttaggcatt    1380
atttgcaata tattaaagaa actttgaaa atacgaagtt tctattccca gctttgtctg    1440
gtggccggca tggtcccagc ctcctcgctg gcgccggctg ggcaacattc gaggggacc    1500 gtcccctcgg taatggcgaa tgggacgcgg ccgatccggc tgctaacaaa gcccgaaagg    1560
aagctgagtt ggctgctgcc accgctgagc aataactagc ataaccccctt ggggcctcta    1620 aacgggtctt gagggttttt tgctgaaag gaggaactat atccggatgc ggccgctcga    1680
gcatgcatct agagggccgc atcatgtaat tagttatgtc acgcttacat tcacgccctc    1740
cccccacatc cgctctaacc gaaaaggaag gagttagaca acctgaagtc taggtcccta    1800 ttatttttt tatagttatg ttagtattaa gaacgttatt tatatttcaa attttctttt    1860
tttttctgta cagacgcgtg tacgcatgta acattatact gaaaaccttg cttgagaagg    1920
ttttgggacg ctcgaaggct ttaatttgcg gccctgcatt aatgaatcgg ccaacgcgcg    1980
gggagaggcg gtttgcgtat tgggcgctct tccgcttcct cgctcactga ctcgctgcgc    2040
tcggtcgttc ggctgcggcg agcggtatca gctcactcaa aggcggtaat acggttatcc    2100
acagaatcag gggataacgc aggaaagaac atgtgagcaa aaggccagca aaagcccagg    2160
aaccgtaaaa aggccgcgtt gctggcgttt ttccataggc tccgcccccc tgacgagcat    2220
cacaaaaatc gacgctcaag tcagaggtgg cgaaacccga caggactata agataccag    2280 gcgtttcccc ctggaagctc cctcgtgcgc tctcctgttc cgaccctgcc gcttaccgga    2340
tacctgtccg cctttctccc ttcgggaagc gtggcgcttt ctcatagctc acgctgtagg    2400
tatctcagtt cggtgtaggt cgttcgctcc aagctgggct gtgtgcacga accccccgtt    2460
cagcccgacc gctgcgcctt atccggtaac tatcgtcttg agtccaaccc ggtaagacac    2520
gacttatcgc cactggcagc agccactggt aacaggatta gcagagcgag gtatgtaggc    2580
ggtgctacag agttcttgaa gtggtggcct aactacggct acactagaag gacagtattt    2640
ggtatctgcg ctctgctgaa gccagttacc ttcggaaaaa gagttggtag ctcttgatcc    2700
ggcaaacaaa ccaccgctgg tagcggtggt ttttttgttt gcaagcagca gattacgcgc    2760
agaaaaaaag gatctcaaga agatcctttg atcttttcta cggggtctga cgctcagtgg    2820
aacgaaaact cacgttaagg gattttggtc atgagattat caaaaaggat cttcacctag    2880
atccttttaa attaaaaatg aagttttaaa tcaatctaaa gtatatatga gtaaacttgg    2940
tctgacagtt accaatgctt aatcagtgag gcacctatct cagcgatctg tctatttcgt    3000
tcatccatag ttgcctgact ccccgtcgtg tagataacta cgatacggga gcgcttacca    3060
tctggcccca gtgctgcaat gataccgcga gacccacgct caccggctcc agatttatca    3120
gcaataaacc agccagccgg aagggccgag cgcagaagtg gtcctgcaac tttatccgcc    3180
tccattcagt ctattaattg ttgccgggaa gctagagtaa gtagttcgcc agttaatagt    3240
ttgcgcaacg ttgttggcat tgctacaggc atcgtggtgt cactctcgtc gtttggtatg    3300
```

-continued

```
gcttcattca gctccggttc ccaacgatca aggcgagtta catgatcccc catgttgtgc    3360
aaaaaagcgg ttagctcctt cggtcctccg atcgttgtca gaagtaagtt ggccgcagtg    3420
ttatcactca tggttatggc agcactgcat aattctctta ctgtcatgcc atccgtaaga    3480
tgcttttctg tgactggtga gtactcaacc aagtcattct gagaatagtg tatgcggcga    3540
ccgagttgct cttgcccggc gtcaatacgg gataatagtg tatcacatag cagaacttta    3600
aaagtgctca tcattggaaa acgttcttcg gggcgaaaac tctcaaggat cttaccgctg    3660
ttgagatcca gttcgatgta acccactcgt gcacccaact gatcttcagc atcttttact    3720
ttcaccagcg tttctgggtg agcaaaaaca ggaaggcaaa atgccgcaaa aagggaata    3780
agggcgacac ggaaatgttg aatactcata ctcttccttt tcaatgggt aataactgat    3840
ataattaaat tgaagctcta atttgtgagt ttagtataca tgcatttact tataatacag    3900
tttttagtt ttgctggccg catcttctca aatatgcttc ccagcctgct tttctgtaac    3960
gttcaccctc tacccttagca tccccttccct ttgcaaatag tcctcttcca acaataataa    4020
tgtcagatcc tgtagagacc acatcatcca cggttctata ctgttgaccc aatgcgtctc    4080
ccttgtcatc taaacccaca ccgggtgtca taatcaacca atcgtaacct tcatctcttc    4140
cacccatgtc tctttgagca ataaagccga taacaaaatc tttgtcgctc ttcgcaatgt    4200
caacagtacc cttagtatat tctccagtag atagggagcc cttgcatgac aattctgcta    4260
acatcaaaag gcctctaggt tcctttgtta cttcttctgc cgcctgcttc aaaccgctaa    4320
caatacctgg gccccttgctt cttgttactg gatatgtatg tatgtataat aagtgatctt    4380
atgtatgaaa ttcttaaaaa aggacacctg taagcgttga tttctatgta tgaagtccac    4440
atttgatgta atcataacaa agcctaaaaa ataggtatat cattttataa ttatttgctg    4500
tacaagtata tcaataaact tatatattac ttgttttcta gataagcttc gtaaccgaca    4560
gtttctaact tttgtgcttt gacaagaact tcttcttctt gctttaataa aaactgttcc    4620
attttcgttg tataacttga atcataagcg ccaagcagtc tgacagccaa cagcgcagcg    4680
ttcgtactat tattaatagc gacggtagct actggaacac ctctaggcat ttgcacaatt    4740
gaatgtaaag aatctactcc atctagacaa gaacctttta cgggcacacc gatgacagga    4800
agtggtgtca ttgcagccac catacctggc aagtgagcag ccccaccagc tccagcgata    4860
attgttttaa ttccacgctt gcttgcggaa atagcatatg ctgacatcct atgtggagtt    4920
ctatgagcag agactattgt cacttcaaat ggaacgccaa aatcttttaa aaccgcacat    4980
gcggcagaca ttaccggcaa gtcagagtct gatcccatga tgattccaac caatggtttg    5040
accattgctt ccaagtccaa cttttgagcg acagagattt tgattggaat atcagttcta    5100
cctgtaatgt agttcagcct tgttcacat tccgccatac tggaggcaat aatatttatg    5160
tgacctactt ttctgttagg tctagactct tttccatata agtacactga ggaacctgga    5220
gtcgccaatg ctctttcgca agtttctagc tctttatctt ttgtatgttt gtctccaaga    5280
acatttagca taatggcgtt cgttgtaatg gtggagaaag atgtgaaatt ctttggcatt    5340
ggcaaatcca atattgatct caaatgagct tcaaattgag aagtgacgca agcatcaatg    5400
gtataatgtc cagagttgtg aggccttggg gcaatttcgt taataagcaa ttcccctgtt    5460
tctaaataga acatttccac accaaatata ccacaaccgg gaaaagattt gattgcattt    5520
tctgccaaca acttcgcctt aagttgaacg gagtccggaa ctctagcagg cgcataacat    5580
aagtcacaaa tattgtcctt gtggatagtc tctacaattg ggtaagaaaa cactaaaccg    5640
ttaacagatc tcacaatcat gactgctaat tctttagtaa atggtgccca ttttttcggcg    5700
```

```
tacaaaggac gatccttcag tacttccaaa gcttccggaa tcatttcctt attctttaca    5760
acgaagttac ctcttccatc gtatgccaaa gtcctcgact tcaagacgaa tggaaaaccc    5820
aaatctcttc caacattcaa tagggacgtc tcactggctt gttccacagg aacactttgg    5880
gtaactgcta taccattttt gattaaatgc tcttttttgaa tatatttgtc ttgtatcaat    5940
ctgattgttt ctggagaagg gtaaatttttt aatttgggat gttttacttg aagattcttt   6000
agtgtaggaa catcaacatg ctcaatctca atcgttagca catcacattt ttcagctagt    6060
ttttcgatat caagaggatt ggaaaaggag ccattaacgt ggtcattgga gttgcttatt    6120
tgtttggcag gagaattttc agcatctagt attaccgtct taatgttgag cctgtttgct    6180
gcctcaacaa tcatacgtcc caattgtccc cctcctaata taccaactgt tctagaatcc    6240
atacttgatt gttttgtccg atttttcttgt ttttcttgat tgttatagta ggatgtactt   6300
agaagagaga tccaacgatt ttacgcacca atttatacat gaaatgctcc ataatattgt    6360
ccatttagtt cttaataaaa ggtcagcaag agtcaatcac ttagtattac ccggttcgta    6420
gccatgcaac aagagtcatt tgtcagcata gctgtaataa tcaatcatga cgtaagaaat    6480
gtatcataat taaaagttgt taaagatgtc agtgttatgt tggtgttaca aaattctcgg    6540
ctagcttatc gatgataagc tgtcaaagat gagaattaat tccacggact atagactata    6600
ctagatactc cgtctactgt acgatacact tccgctcagg tccttgtcct ttaacgaggc    6660
cttaccactc ttttgttact ctattgatcc agctcagcaa aggcagtgtg atctaagatt    6720
ctatcttcgc gatgtagtaa aactagctag accgagaaag agactagaaa tgcaaaaggc    6780
acttctacaa tggctgccat cattattatc cgatgtgacg ctgcagcttc tcaatgatat    6840
tcgaatacgc tttgaggaga tacagcctaa tatccgacaa actgttttac agatttacga    6900
tcgtacttgt tacccatcat tgaattttga acatccgaac ctgggagttt tccctgaaac    6960
agatagtata tttgaacctg tataataata tatagtctag cgctttacgg aagacaatgt    7020
atgtatttcg gttcctggag aaactattgc atctattgca taggtaatct tgcacgtcgc    7080
atccccggtt cattttctgc gtttccatct tgcacttcaa tagcatatct ttgttaacga    7140
agcatctgtg cttcattttg tagaacaaaa atgcaacgcg agagcgctaa ttttttcaaac   7200
aaagaatctg agctgcattt ttacagaaca gaaatgcaac gcgaaagcgc tattttacca    7260
acgaagaatc tgtgcttcat ttttgtaaaa caaaaatgca acgcgacgag agcgctaatt    7320
tttcaaacaa gaatctgagc tgcattttt acagaacaga aatgcaacgc gagagcgcta    7380
ttttaccaac aaagaatcta tacttctttt ttgttctaca aaaatgcatc ccgagagcgc    7440
tatttttcta caaagcatc ttagattact ttttttctcc tttgtgcgct ctataatgca    7500
gtctcttgat aacttttttgc actgtaggtc cgttaaggtt agaagaaggc tactttggtg    7560
tctattttct cttccataaa aaaagcctga ctccacttcc cgcgtttact gattactagc    7620
gaagctgcgg gtgcattttt tcaagataaa ggcatcccccg attatattct ataccgatgt   7680
ggattgcgca tactttgtga acagaaagtg atagcgttga tgattcttca ttggtcagaa    7740
aattatgaac ggtttcttct attttgtctc tatatactac gtataggaaa tgtttacatt    7800
ttcgtattgt tttcgattca ctctatgaat agttcttact acaattttttt tgtctaaaga   7860
gtaatactag agataaacat aaaaaatgta gaggtcgagt ttagatgcaa gttcaaggag    7920
cgaaaggtgg atgggtaggt tatataggga tatagcacag agatatatag caaagagata    7980
cttttgagca atgtttgtgg aagcggtatt cgcaatggga agctccaccc cggttgataa    8040
```

```
tcagaaaagc cccaaaaaca ggaagattgt ataagcaaat atttaaattg taaacgttaa    8100
tattttgtta aaattcgcgt taaattttttg ttaaatcagc tcattttta acgaatagcc    8160 cgaaatcggc aaaatccctt ataaatcaaa agaatagacc gagatagggt tgagtgttgt    8220
tccagtttcc aacaagagtc cactattaaa gaacgtggac tccaacgtca aagggcgaaa    8280
aagggtctat cagggcgatg gcccactacg tgaaccatca ccctaatcaa gttttttggg    8340
gtcgaggtgc cgtaaagcag taaatcggaa gggtaaacgg atgcccccat ttagagcttg    8400
acggggaaag ccggcgaacg tggcgagaaa ggaagggaag aaagcgaaag gagcggggc    8460 tagggcggtg ggaagtgtag gggtcacgct gggcgtaacc accacacccg ccgcgcttaa    8520
tggggcgcta cagggcgcgt ggggatgatc cactagtacg gattagaagc cgccgagcgg    8580
gtgacagccc tccgaaggaa gactctcctc cgtgcgtcct cgtcctcacc ggtcgcgttc    8640
ctgaaacgca gatgtgcctc gcgccgcact gctccgaaca ataaagattc tacaatacta    8700
gcttttatgg ttatgaagag gaaaaattgg cagtaacctg gccccacaaa ccttcaaatg    8760
aacgaatcaa attaacaacc ataggatgat aatgcgatta gttttttagc cttatttctg    8820
gggtaattaa tcagcgaagc gatgattttt gatctattaa cagatatata aatgcaaaaa    8880
ctgcattaac cactttaact aatacttca acatttcgg tttgtattac ttcttattca    8940
aatgtaataa aagtatcaac aaaaaattgt taatatacct ctatacttta acgtcaagga    9000 gaaaaaccc cggatcggac tactagcagc tgtaatacga ctcactatag ggaatattaa    9060
gcttgcacta gtaacggccg ccagtgtgct ggctgcagat atccatcaca ctggcggccg    9120
ctaatacgac tcactatagg g                                              9141

<210> SEQ ID NO 37
<211> LENGTH: 9421
<212> TYPE: DNA
<213> ORGANISM: Artificial
<220> FEATURE:
<223> OTHER INFORMATION: Plasmid

<400> SEQUENCE: 37
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatcga ctacgtcgta aggccgtttc tgacagagta aaattcttga gggaactttc    240
accattatgg gaaatgcttc aagaaggtat tgacttaaac tccatcaaat ggtcaggtca    300
ttgagtgttt tttatttgtt gtattttttt tttttagag aaaatcctcc aatatcaaat    360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctaccctat gaacatattc catttttgtaa tttcgtgtcg    600 tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaacctttt aactgcatct    780 tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
```

```
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140 acagttttc tccataatct tgaagaggcc aaaagattag ctttatccaa ggaccaaata    1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg atttttagta aaccttgttc aggtctaaca   1500
ctaccggtac cccatttagg accacccaca gcacctaaca aaacggcatc agccttcttg   1560
gaggcttcca gcgcctcatc tggaagtgga acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa aacgacgatc   1740
ttcttagggg cagacattag aatggtatat ccttgaaata tatatatata tattgctgaa   1800
atgtaaaagg taagaaaagt tagaaagtaa gacgattgct aaccacctat tggaaaaaac   1860
aataggtcct taaataatat tgtcaacttc aagtattgtg atgcaagcat ttagtcatga   1920
acgcttctct attctatatg aaaagccggt tccggcgctc tcacctttcc ttttctccc    1980 aattttttcag ttgaaaaagg tatatgcgtc aggcgacctc tgaaattaac aaaaaatttc   2040
cagtcatcga atttgattct gtgcgatagc gccctgtgt gttctcgtta tgttgaggaa    2100
aaaaataatg gttgctaaga gattcgaact cttgcatctt acgatacctg agtattccca   2160
cagttaactg cggtcaagat atttcttgaa tcaggcgcct tagaccgctc ggccaaacaa   2220
ccaattactt gttgagaaat agagtataat tatcctataa atataacgtt tttgaacaca   2280
catgaacaag gaagtacagg acaattgatt ttgaagagaa tgtggatttt gatgtaattg   2340
ttgggattcc attttttaata aggcaataat attaggtatg tagatatact agaagttctc   2400
ctcgaccgtc gatatgcggt gtgaaatacc gcacagatgc gtaaggagaa aataccgcat   2460
caggaaattg taaacgttaa tattttgtta aaattcgcgt taaattttg ttaaatcagc    2520 tcattttta accaataggc cgaaatcggc aaaatccctt ataaatcaaa agaatagacc    2580
gagatagggt tgagtgttgt tccagtttgg aacaagagtc cactattaaa gaacgtggac   2640
tccaacgtca aagggcgaaa aaccgtctat cagggcgatg gcccactacg tgaaccatca   2700
ccctaatcaa gttttttggg gtcgaggtgc cgtaaagcac taaatcggaa ccctaaaggg   2760
agcccccgat ttagagcttg acggggaaag ccggcgaacg tggcgagaaa ggaagggaag   2820
aaagcgaaag gagcgggcgc tagggcgctg gcaagtgtag cggtcacgct gcgcgtaacc   2880 accacccg ccgcgcttaa tgcgccgcta caggcgcgt ccattcgcca ttcaggctgc      2940
gcaactgttg ggaagggcga tcggtgcggg cctcttcgct attacgccag ctgaattgga   3000
gcgacctcat gctatacctg agaaagcaac ctgacctaca ggaaagagtt actcaagaat   3060
aagaattttc gttttaaaac ctaagagtca ctttaaaatt tgtatacact tattttttt    3120 ataacttatt taataataaa aatcataaat cataagaaat tcgcttattt agaagtgtca   3180
acaacgtatc taccaacgat ttgacccttt tccatctttt cgtaaatttc tggcaaggta   3240
gacaagccga caaccttgat tggagacttg accaaacctc tggcgaagaa ttgttaatta   3300
```

-continued

| | |
|---|---|
| agagctcaga tcttatcgtc gtcatccttg taatccatcg atactagtgc ggccgccctt | 3360 |
| tagtgagggt tgaattcgaa ttttcaaaaa ttcttacttt tttttttggat ggacgcaaag | 3420 |
| aagtttaata atcatattac atggcattac caccatatac atatccatat acatatccat | 3480 |
| atctaatctt acttatatgt tgtggaaatg taaagagccc cattatctta gcctaaaaaa | 3540 |
| accttctctt tggaactttc agtaatacgc ttaactgctc attgctatat tgaagtacgg | 3600 |
| attagaagcc gccgagcggg tgacagccct ccgaaggaag actctcctcc gtgcgtcctc | 3660 |
| gtcttcaccg gtcgcgttcc tgaaacgcag atgtgcctcg cgccgcactg ctccgaacaa | 3720 |
| taaagattct acaatactag cttttatggt tatgaagagg aaaaattggc agtaacctgg | 3780 |
| ccccacaaac cttcaaatga acgaatcaaa ttaacaacca taggatgata atgcgattag | 3840 |
| ttttttagcc ttatttctgg ggtaattaat cagcgaagcg atgattttg atctattaac | 3900 |
| agatatataa atgcaaaaac tgcataacca ctttaactaa tactttcaac attttcggtt | 3960 |
| tgtattactt cttattcaaa tgtaataaaa gtatcaacaa aaaattgtta atatacctct | 4020 |
| atactttaac gtcaaggaga aaaaccccg gatccgtaat acgactcact atagggcccg | 4080 |
| ggcgtcgaca agagcaggat tagggatatc cgagatggcc acacttttaa ggagcttagc | 4140 |
| attgttcaaa gaaacaagg acaaccacc cattacatca ggatccggtg gagccatcag | 4200 |
| aggaatcaaa cacattatta tagtaccaat ccctggagat tcctcaatta ccactcgatc | 4260 |
| cagacttctg gaccggttgg tgaggttaat tggaaacccg gatgtgagcg ggcccaaact | 4320 |
| aacaggggca ctaataggta tattatcctt atttgtggag tctccaggtc aattgattca | 4380 |
| gaggatcacc gatgaccctg acgttagcat aaggctgtta gaggttgtcc agagtgacca | 4440 |
| gtcacaatct ggccttacct tcgcatcaag aggtaccaac atggaggatg aggcggacca | 4500 |
| atacttttca catgatgatc caattagtag tgatcaatcc aggttcggat ggttcgggaa | 4560 |
| caaggaaatc tcagatattg aagtgcaaga ccctgaggga ttcaacatga ttctgggtac | 4620 |
| catcctagcc caaatttggg tcttgctcgc aaaggcggtt acggcccag acacggcagc | 4680 |
| tgattcggag ctaagaaggt ggataaagta cacccaacaa agaagggtag ttggtgaatt | 4740 |
| tagattggag agaaaatggt tggatgtggt gaggaacagg attgccgagg acctctcctt | 4800 |
| acgccgattc atggtcgctc taatcctgga tatcaagaga cacccggaa acaaacccag | 4860 |
| gattgctgaa atgatatgtg acattgatac atatatcgta gaggcaggat tagccagttt | 4920 |
| tatcctgact attaagtttg ggatagaaac tatgtatcct gctcttggac tgcatgaatt | 4980 |
| tgctggtgag ttatccacac ttgagtcctt gatgaacctt taccagcaaa tgggggaaac | 5040 |
| tgcaccctac atggtaatcc tggagaactc aattcagaac aagttcagtg caggatcata | 5100 |
| ccctctgctc tggagctatg ccatgggagt aggagtggaa cttgaaaact ccatgggagg | 5160 |
| tttgaacttt ggccgatctt actttgatcc agcatatttt agattagggc aagagatggt | 5220 |
| aaggaggtca gctggaaagg tcagttccac attggcatct gaactcggta tcactgccga | 5280 |
| ggatgcaagg cttgtttcag agattgcaat gcatactact gaggacaaga tcagtagagc | 5340 |
| ggttggaccc agacaagccc aagtatcatt tctacacggt gatcaaagtg agaatgagct | 5400 |
| accgagattg gggggcaagg aagataggag ggtcaaacag agtcgaggag aagccaggga | 5460 |
| gagctacaga gaaaccgggc ccagcagagc aagtgatgcg agagctgccc atcttccaac | 5520 |
| cggcacaccc ctagacattg acactgcaac ggagtccagc caagatccgc aggacagtcg | 5580 |
| aaggtcagct gacgccctgc ttaggctgca agccatggca ggaatctcgg aagaacaagg | 5640 |
| ctcagacacg gacacccta tagtgtacaa tgacagaaat cttctagact aggtgcgaga | 5700 |

```
ggccgagggc cagaacaaca tccgcctacc atccatcatt gttataaaaa acttaggaac    5760
caggtccaca cagccgccag cccatcaacc atccactcga gtaagcttgg taccgcggct    5820
agctaagatc cgctctaacc gaaaaggaag gagttagaca acctgaagtc taggtcccta    5880
tttatttttt tatagttatg ttagtattaa gaacgttatt tatatttcaa attttctttt    5940
tttttctgta cagacgcgtg tacgcatgta acattatact gaaaaccttg cttgagaagg    6000
ttttgggacg ctcgaagatc cagctgcatt aatgaatcgg ccaacgcgcg gggagaggcg    6060
gtttgcgtat tgggcgctct tccgcttcct cgctcactga ctcgctgcgc tcggtcgttc    6120
ggctgcggcg agcggtatca gctcactcaa aggcggtaat acggttatcc acagaatcag    6180
gggataacgc aggaaagaac atgtgagcaa aaggccagca aaaggccagg aaccgtaaaa    6240
aggccgcgtt gctggcgttt ttccataggc tccgcccccc tgacgagcat cacaaaaatc    6300
gacgctcaag tcagaggtgg cgaaacccga caggactata aagataccag gcgtttcccc    6360
ctggaagctc cctcgtgcgc tctcctgttc cgaccctgcc gcttaccgga tacctgtccg    6420
cctttctccc ttcgggaagc gtggcgcttt ctcatagctc acgctgtagg tatctcagtt    6480
cggtgtaggt cgttcgctcc aagctgggct gtgtgcacga accccccgtt cagcccgacc    6540
gctgcgcctt atccggtaac tatcgtcttg agtccaaccc ggtaagacac gacttatcgc    6600
cactggcagc agccactggt aacaggatta gcagagcgag gtatgtaggc ggtgctacag    6660
agttcttgaa gtggtggcct aactacggct acactagaag gacagtattt ggtatctgcg    6720
ctctgctgaa gccagttacc ttcggaaaaa gagttggtag ctcttgatcc ggcaaacaaa    6780
ccaccgctgg tagcggtggt ttttttgttt gcaagcagca gattacgcgc agaaaaaaag    6840
gatctcaaga agatcctttg atcttttcta cggggtctga cgctcagtgg aacgaaaact    6900
cacgttaagg gattttggtc atgagattat caaaaaggat cttcacctag atccttttaa    6960
attaaaaatg aagttttaaa tcaatctaaa gtatatatga gtaaacttgg tctgacagtt    7020
accaatgctt aatcagtgag gcacctatct cagcgatctg tctatttcgt tcatccatag    7080
ttgcctgact ccccgtcgtg tagataacta cgatacggga gggcttacca tctggcccca    7140
gtgctgcaat gataccgcga gacccacgct caccggctcc agatttatca gcaataaacc    7200
agccagccgg aagggccgag cgcagaagtg gtcctgcaac tttatccgcc tccatccagt    7260
ctattaattg ttgccgggaa gctagagtaa gtagttcgcc agttaatagt ttgcgcaacg    7320
ttgttgccat tgctacaggc atcgtggtgt cacgctcgtc gtttggtatg gcttcattca    7380
gctccggttc ccaacgatca aggcgagtta catgatcccc catgttgtgc aaaaaagcgg    7440
ttagctcctt cggtcctccg atcgttgtca gaagtaagtt ggccgcagtg ttatcactca    7500
tggttatggc agcactgcat aattctctta ctgtcatgcc atccgtaaga tgcttttctg    7560
tgactggtga gtactcaacc aagtcattct gagaatagtg tatgcggcga ccgagttgct    7620
cttgcccggc gtcaatacgg gataataccg cgccacatag cagaacttta aaagtgctca    7680
tcattggaaa acgttcttcg ggcgaaaac tctcaaggat cttaccgctg ttgagatcca    7740
gttcgatgta acccactcgt gcacccaact gatcttcagc atcttttact ttcaccagcg    7800
tttctgggtg agcaaaaaca ggaaggcaaa atgccgcaaa aaagggaata agggcgacac    7860
ggaaatgttg aatactcata ctcttccttt ttcaatatta ttgaagcatt tatcagggtt    7920
attgtctcat gagcggatac atatttgaat gtatttagaa aaataaacaa ataggggttc    7980
cgcgcacatt tccccgaaaa gtgccacctg aacgaagcat ctgtgcttca ttttgtagaa    8040
```

```
caaaaatgca acgcgagagc gctaattttt caaacaaaga atctgagctg cattttttaca    8100 gaacagaaat gcaacgcgaa agcgctattt taccaacgaa gaatctgtgc ttcattttttg    8160 taaaacaaaa atgcaacgcg agagcgctaa tttttcaaac aaagaatctg agctgcattt    8220
ttacagaaca gaaatgcaac gcgagagcgc tattttacca acaaagaatc tatacttctt    8280
ttttgttcta caaaaatgca tcccgagagc gctatttttc taacaaagca tcttagatta    8340 cttttttttct cctttgtgcg ctctataatg cagtctcttg ataacttttt gcactgtagg    8400
tccgttaagg ttagaagaag gctactttgg tgtctatttt ctcttccata aaaaaagcct    8460
gactccactt cccgcgttta ctgattacta gcgaagctgc gggtgcattt tttcaagata    8520
aaggcatccc cgattatatt ctataccgat gtggattgcg catactttgt gaacagaaag    8580
tgatagcgtt gatgattctt cattggtcag aaaattatga acgtttctt ctattttgtc    8640 tctatatact acgtatagga aatgtttaca ttttcgtatt gttttcgatt cactctatga    8700
atagttctta ctacaatttt tttgtctaaa gagtaatact agagataaac ataaaaaatg    8760
tagaggtcga gtttagatgc aagttcaagg agcgaaaggt ggatgggtag gttatatagg    8820
gatatagcac agagatatat agcaaagaga tacttttgag caatgtttgt ggaagcggta    8880
ttcgcaatat tttagtagct cgttacagtc cggtgcgttt ttggtttttt gaaagtgcgt    8940
cttcagagcg cttttggttt tcaaaagcgc tctgaagttc ctatactttc tagagaatag    9000
gaacttcgga ataggaactt caaagcgttt ccgaaaacga gcgcttccga aaatgcaacg    9060
cgagctgcgc acatacagct cactgttcac gtcgcaccta tatctgcgtg ttgcctgtat    9120
atatatatac atgagaagaa cggcatagtg cgtgttatg cttaaatgcg tacttatatg    9180
cgtctattta tgtaggatga aaggtagtct agtacctcct gtgatattat cccattccat    9240
gcggggtatc gtatgcttcc ttcagcacta ccctttagct gttctatatg ctgccactcc    9300
tcaattggat tagtctcatc cttcaatgct atcatttcct ttgatattgg atcatactaa    9360
gaaaccatta ttatcatgac attaacctat aaaaataggc gtatcacgag gccctttcgt    9420
c                                                                    9421

<210> SEQ ID NO 38
<211> LENGTH: 8146
<212> TYPE: DNA
<213> ORGANISM: Artificial
<220> FEATURE:
<223> OTHER INFORMATION: Plasmid

<400> SEQUENCE: 38
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc     180
accataaacg acattactat atatataata taggaagcat ttaatagaac agcatcgtaa     240
tatatgtgta ctttgcagtt atgacgccag atggcagtag tggaagatat tctttattga     300
aaaatagctt gtcaccttac gtacaatctt gatccggagc ttttcttttt ttgccgatta     360
agaattaatt cggtcgaaaa aagaaaagga gaggggcaag agggagggca ttggtgacta     420
ttgagcacgt gagtatacgt gattaagcac acaaaggcag cttggagtat gtctgttatt     480
aatttcacag gtagttctgg tccattggtg aaagtttgcg gcttgcagag cacagaggcc     540
gcagaatgtg ctctagattc cgatgctgac ttgctgggta ttatatgtgt gcccaataga     600
aagagaacaa ttgacccggt tattgcaagg aaaatttcaa gtcttgtaaa agcatataaa     660
```

```
aatagttcag gcactccgaa atacttggtt ggcgtgtttc gtaatcaacc taaggaggat    720
gttttggctc tggtcaatga ttacggcatt gatatcgtcc aactgcatgg agatgagtcg    780
tggcaagaat accaagagtt cctcggtttg ccagttatta aaagactcgt atttccaaaa    840
gactgcaaca tactactcag tgcagcttca cagaaacctc attcgtttat tcccttgttt    900
gattcagaag caggtgggac aggtgaactt ttggattgga actcgatttc tgactgggtt    960
ggaaggcaag agagccccga aagcttacat tttatgttag ctggtggact gacgccagaa   1020
aatgttggtg atgcgcttag attaaatggc gttattggtg ttgatgtaag cggaggtgtg   1080
gagacaaatg gtgtaaaaga ctctaacaaa atagcaaatt tcgtcaaaaa tgctaagaaa   1140
taggttatta ctgagtagta tttatttaag tattgtttgt gcacttgcct atgcggtgtg   1200
aaataccgca cagatgcgta aggagaaaat accgcatcag gaaattgtaa acgttaatat   1260
tttgttaaaa ttcgcgttaa attttgtta aatcagctca ttttttaacc aataggccga   1320
aatcggcaaa atcccttata atcaaaaga atagaccgag ataggggttga gtgttgttcc   1380 agtttggaac aagagtccac tattaaagaa cgtggactcc aacgtcaaag ggcgaaaaac   1440
cgtctatcag ggcgatggcc cactacgtga accatcaccc taatcaagtt ttttggggtc   1500
gaggtgccgt aaagcactaa atcggaaccc taaagggagc ccccgattta gagcttgacg   1560 gggaagccg gcgaacgtgg cgagaaagga agggaagaaa gcgaaaggag cgggcgctag   1620
ggcgctggca agtgtagcgg tcacgctgcg cgtaaccacc acacccgccg cgcttaatgc   1680
gccgctacag ggcgcgtcca ttcgccattc aggctgcgca actgttggga agggcgatcg   1740
gtgcgggcct cttcgctatt acgccagctg aattggagcg acctcatgct atacctgaga   1800
aagcaacctg acctacagga aagagttact caagaataag aattttcgtt ttaaaaccta   1860
agagtcactt taaaatttgt atacacttat tttttttata acttatttaa taataaaaat   1920
cataaatcat aagaaattcg cttatttaga agtgtcaaca acgtatctac caacgatttg   1980 accctttttcc atcttttcgt aaatttctgg caaggtagac aagccgacaa ccttgattgg   2040
agacttgacc aaacctctgg cgaagaattg ttaattaaga gctcagatct tatcgtcgtc   2100
atccttgtaa tccatcgata ctagtgcggc cgccctttag tgagggttga attcgaattt   2160
tcaaaaattc ttactttttt tttggatgga cgcaaagaag tttaataatc atattacatg   2220
gcattaccac catatacata tccatataca tatccatatc taatcttact tatatgttgt   2280
ggaaatgtaa agagccccat tatcttagcc taaaaaaacc ttctctttgg aactttcagt   2340
aatacgctta actgctcatt gctatattga agtacggatt agaagccgcc gagcgggtga   2400
cagccctccg aaggaagact ctcctccgtg cgtcctcgtc ttcaccggtc gcgttcctga   2460
aacgcagatg tgcctcgcgc cgcactgctc cgaacaataa agattctaca atactagctt   2520
ttatggttat gaagaggaaa aattggcagt aacctggccc cacaaacctt caaatgaacg   2580
aatcaaatta acaaccatag gatgataatg cgattagttt tttagcctta tttctggggt   2640
aattaatcag cgaagcgatg attttgatc tattaacaga tatataaatg caaaaactgc   2700
ataaccactt taactaatac tttcaacatt ttcggtttgt attacttctt attcaaatgt   2760
aataaaagta tcaacaaaaa attgttaata tacctctata ctttaacgtc aaggagaaaa   2820
aaccccggat ccgtaatacg actcactata gggcccgggc gtcgactagg tgcgagaggc   2880
cgagggccaa gaacaacatcc gcctaccatc catcattgtt ataaaaaact taggaaccag   2940
gtccacacag ccgccagccc atcaaccatc cactcccacg attggagcca atggcagaag   3000
```

```
agcaggcacg ccatgtcaaa aacggactgg aatgcatccg ggctctcaag gccgagccca      3060
tcggctcact ggccatcgag gaagctatgg cagcatggtc agaaatatca gacaacccag      3120
gacaggagcg agccacctgc agggaagaga aggcaggcag ttcgggtctc agcaaaccat      3180
gcctctcagc aattggatca actgaaggcg gtgcacctcg catccgcggt cagggacctg      3240
gagagagcga tgacgacgct gaaactttgg gaatcccccc aagaaatctc caggcatcaa      3300
gcactgggtt acagtgttat tacgtttatg atcacagcgg tgaagcggtt aagggaatcc      3360
aagatgctga ctctatcatg gttcaatcag gccttgatgg tgatagcacc ctctcaggag      3420
gagacaatga atctgaaaac agcgatgtgg atattggcga acctgatacc gagggatatg      3480
ctatcactga ccggggatct gctcccatct ctatggggtt cagggcttct gatgttgaaa      3540
ctgcagaagg aggggagatc cacgagctcc tgagactcca atccagaggc aacaactttc      3600
cgaagcttgg gaaaactctc aatgttcctc cgcccccgga ccccggtagg ccagcactt      3660 ccgggacacc cattaaaaag ggcacagacg cgagattagc ctcatttgga acggagatcg      3720
cgtctttatt gacaggtggt gcaacccaat gtgctcgaaa gtcaccctcg gaaccatcag      3780
ggccaggtgc acctgcgggg aatgtccccg agtgtgtgag caatgccgca ctgatacagg      3840
agtggacacc cgaatctggt accacaatct ccccgagatc ccagaataat gaagaagggg      3900
gagactatta tgatgatgag ctgttctctg atgtccaaga tattaaaaca gccttggcca      3960
aaatacacga ggataatcag aagataatct ccaagctaga atcactgctg ttattgaagg      4020
gagaagttga gtcaattaag aagcagatca acaggcaaaa tatcagcata tccaccctgg      4080
aaggacacct ctcaagcatc atgatcgcca ttcctggact tgggaaggat cccaacgacc      4140
ccactgcaga tgtcgaaatc aatcccgact tgaaacccat cataggcaga gattcaggcc      4200
gagcactggc cgaagttctc aagaaacccg ttgccagccg acaactccaa ggaatgacaa      4260
atggacggac cagttccaga ggacagctgc tgaaggaatt tcagctaaag ccgatcggga      4320
aaaagatgag ctcagccgtc gggtttgttc ctgacaccgg ccctgcatca cgcagtgtaa      4380
tccgctccat tataaaatcc agccggctag aggaggatcg gaagcgttac ctgatgactc      4440
tccttgatga tatcaaagga gccaatgatc ttgccaagtt ccaccagatg ctgatgaaga      4500
taataatgaa gtagctacag ctcgagtaag cttggtaccg cggctagcta agatccgctc      4560
taaccgaaaa ggaaggagtt agacaacctg aagtctaggt ccctatttat tttttttatag      4620 ttatgttagt attaagaacg ttatttatat ttcaaatttt tctttttttt ctgtacagac      4680
gcgtgtacgc atgtaacatt atactgaaaa ccttgcttga aaggttttg gacgctcga      4740 agatccagct gcattaatga atcggccaac gcgcggggag aggcggtttg cgtattgggc      4800
gctcttccgc ttcctcgctc actgactcgc tgcgctcggt cgttcggctg cggcgagcgg      4860
tatcagctca ctcaaaggcg gtaatacggt tatccacaga atcaggggat aacgcaggaa      4920
agaacatgtg agcaaaaggc cagcaaaagg ccaggaaccg taaaaaggcc gcgttgctgg      4980 cgttttttcca taggctccgc cccctgacg agcatcacaa aaatcgacgc tcaagtcaga      5040
ggtggcgaaa cccgacagga ctataaagat accaggcgtt tcccctggaa gctccctcg      5100 tgcgctctcc tgttccgacc ctgccgctta ccggatacct gtccgccttt ctcccttcgg      5160
gaagcgtggc gctttctcat agctcacgct gtaggtatct cagttcggtg taggtcgttc      5220
gctccaagct gggctgtgtg cacgaacccc ccgttcagcc cgaccgctgc gccttatccg      5280
gtaactatcg tcttgagtcc aacccggtaa gacacgactt atcgccactg gcagcagcca      5340
ctggtaacag gattagcaga gcgaggtatg taggcggtgc tacagagttc ttgaagtggt      5400
```

```
ggcctaacta cggctacact agaaggacag tatttggtat ctgcgctctg ctgaagccag    5460
ttaccttcgg aaaaagagtt ggtagctctt gatccggcaa acaaaccacc gctggtagcg    5520 gtggttttt tgtttgcaag cagcagatta cgcgcagaaa aaaggatct caagaagatc     5580 ctttgatctt ttctacgggg tctgacgctc agtggaacga aaactcacgt taagggattt    5640
tggtcatgag attatcaaaa aggatcttca cctagatcct tttaaattaa aaatgaagtt    5700
ttaaatcaat ctaaagtata tatgagtaaa cttggtctga cagttaccaa tgcttaatca    5760
gtgaggcacc tatctcagcg atctgtctat ttcgttcatc catagttgcc tgactcccg     5820 tcgtgtagat aactacgata cgggagggct taccatctgg ccccagtgct gcaatgatac    5880
cgcgagaccc acgctcaccg gctccagatt tatcagcaat aaaccagcca gccggaaggg    5940
ccgagcgcag aagtggtcct gcaactttat ccgcctccat ccagtctatt aattgttgcc    6000
gggaagctag agtaagtagt tcgccagtta atagtttgcg caacgttgtt gccattgcta    6060
caggcatcgt ggtgtcacgc tcgtcgtttg gtatggcttc attcagctcc ggttcccaac    6120
gatcaaggcg agttacatga tccccatgt tgtgcaaaaa agcggttagc tccttcggtc     6180
ctccgatcgt tgtcagaagt aagttggccg cagtgttatc actcatggtt atggcagcac    6240
tgcataattc tcttactgtc atgccatccg taagatgctt ttctgtgact ggtgagtact    6300
caaccaagtc attctgagaa tagtgtatgc ggcgaccgag ttgctcttgc ccggcgtcaa    6360
tacgggataa taccgcgcca catagcagaa ctttaaaagt gctcatcatt ggaaaacgtt    6420
cttcggggcg aaaactctca aggatcttac cgctgttgag atccagttcg atgtaaccca    6480
ctcgtgcacc caactgatct tcagcatctt ttactttcac cagcgtttct gggtgagcaa    6540
aaacaggaag gcaaaatgcc gcaaaaaagg gaataagggc gacacggaaa tgttgaatac    6600
tcatactctt ccttttcaa tattattgaa gcatttatca gggttattgt ctcatgagcg     6660
gatacatatt tgaatgtatt tagaaaaata acaaataggg gttccgcgc acatttcccc     6720 gaaaagtgcc acctgaacga agcatctgtg cttcattttg tagaacaaaa atgcaacgcg    6780
agagcgctaa ttttttcaaac aaagaatctg agctgcattt ttacagaaca gaatgcaac    6840 gcgaaagcgc tattttacca acgaagaatc tgtgcttcat ttttgtaaaa caaaaatgca    6900
acgcgagagc gctaattttt caaacaaaga atctgagctg catttttaca gaacagaaat    6960
gcaacgcgag agcgctattt taccaacaaa gaatctatac ttcttttttg ttctacaaaa    7020
atgcatcccg agagcgctat ttttctaaca aagcatctta gattactttt tttctccttt    7080
gtgcgctcta taatgcagtc tcttgataac ttttttgcact gtaggtccgt taaggttaga    7140
agaaggctac tttggtgtct atttttctctt ccataaaaaa agcctgactc cacttcccgc    7200
gtttactgat tactagcgaa gctgcgggtg cattttttca agataaaggc atccccgatt    7260
atattctata ccgatgtgga ttgcgcatac tttgtgaaca gaaagtgata gcgttgatga    7320
ttcttcattg gtcagaaaat tatgaacggt tccttctatt ttgtctctat atactacgta    7380
taggaaatgt ttacattttc gtattgtttt cgattcactc tatgaatagt tcttactaca    7440 attttttgt ctaaagagta atactagaga taaacataaa aaatgtagag gtcgagttta    7500
gatgcaagtt caaggagcga aaggtggatg ggtaggttat atagggatat agcacagaga    7560
tatatagcaa agagatactt ttgagcaatg tttgtggaag cggtattcgc aatattttag    7620
tagctcgtta cagtccggtg cgttttggt tttttgaaag tgcgtcttca gagcgctttt     7680
ggttttcaaa agcgctctga agttcctata ctttctagag aataggaact tcggaatagg    7740
```

| | | | | |
|---|---|---|---|---|
| aacttcaaag | cgtttccgaa | aacgagcgct | tccgaaaatg caacgcgagc | tgcgcacata | 7800 |
| cagctcactg | ttcacgtcgc | acctatatct | gcgtgttgcc | tgtatatata tatacatgag | 7860 |
| aagaacggca | tagtgcgtgt | ttatgcttaa | atgcgtactt | atatgcgtct atttatgtag | 7920 |
| gatgaaaggt | agtctagtac | ctcctgtgat | attatcccat | tccatgcggg gtatcgtatg | 7980 |
| cttccttcag | cactacccctt | tagctgttct | atatgctgcc | actcctcaat tggattagtc | 8040 |
| tcatccttca | atgctatcat | ttcctttgat | attggatcat | attaagaaac cattattatc | 8100 |
| atgacattaa | cctataaaaa | taggcgtatc | acgaggccct | ttcgtc | 8146 |

<210> SEQ ID NO 39
<211> LENGTH: 11029
<212> TYPE: DNA
<213> ORGANISM: Artificial
<220> FEATURE:
<223> OTHER INFORMATION: Plasmid

<400> SEQUENCE: 39

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgggtg | 120 |
| ttggcgggtg | tcggggctgg | cttaactatg | cggcatcaga | gcagattgta ctgagagtgc | 180 |
| accatatcga | ctacgtcgta | aggccgtttc | tgacagagta | aaattcttga gggaactttc | 240 |
| accattatgg | gaaatgcttc | aagaaggtat | tgacttaaac | tccatcaaat ggtcaggtca | 300 |
| ttgagtgttt | tttatttgtt | gtattttttt | tttttagag | aaaatcctcc aatatcaaat | 360 |
| taggaatcgt | agtttcatga | ttttctgtta | cacctaactt | tttgtgtggt gccctcctcc | 420 |
| ttgtcaatat | taatgttaaa | gtgcaattct | ttttccttat | cacgttgagc cattagtatc | 480 |
| aatttgctta | cctgtattcc | tttactatcc | tcctttttct | ccttcttgat aaatgtatgt | 540 |
| agattgcgta | tatagtttcg | tctaccctat | gaacatattc | cattttgtaa tttcgtgtcg | 600 |
| tttctattat | gaatttcatt | tataaagttt | atgtacaaat | atcataaaaa aagagaatct | 660 |
| ttttaagcaa | ggattttctt | aacttcttcg | gcgacagcat | caccgacttc ggtggtactg | 720 |
| ttggaaccac | ctaaatcacc | agttctgata | cctgcatcca | aaaccttttt aactgcatct | 780 |
| tcaatggcct | taccttcttc | aggcaagttc | aatgacaatt | tcaacatcat tgcagcagac | 840 |
| aagatagtgg | cgatagggtc | aaccttattc | tttggcaaat | ctggagcaga accgtggcat | 900 |
| ggttcgtaca | aaccaaatgc | ggtgttcttg | tctggcaaag | aggccaagga cgcagatggc | 960 |
| aacaaaccca | aggaacctgg | gataacggag | gcttcatcgg | agatgatatc accaaacatg | 1020 |
| ttgctggtga | ttataatacc | atttaggtgg | gttgggttct | taactaggat catggcggca | 1080 |
| gaatcaatca | attgatgttg | aaccttcaat | gtagggaatt | cgttcttgat ggtttcctcc | 1140 |
| acagtttttc | tccataatct | tgaagaggcc | aaaagattag | ctttatccaa ggaccaaata | 1200 |
| ggcaatggtg | gctcatgttg | tagggccatg | aaagcggcca | ttcttgtgat tctttgcact | 1260 |
| tctggaacgg | tgtattgttc | actatcccaa | gcgacaccat | caccatcgtc ttcctttctc | 1320 |
| ttaccaaagt | aaatacctcc | cactaattct | ctgacaacaa | cgaagtcagt acctttagca | 1380 |
| aattgtggct | tgattggaga | taagtctaaa | agagagtcgg | atgcaaagtt acatggtctt | 1440 |
| aagttggcgt | acaattgaag | ttcttacgg | atttttagta | aaccttgttc aggtctaaca | 1500 |
| ctaccggtac | cccatttagg | accacccaca | gcacctaaca | aaacggcatc agccttcttg | 1560 |
| gaggcttcca | gcgcctcatc | tggaagtgga | acacctgtag | catcgatagc agcaccacca | 1620 |
| attaaatgat | tttcgaaatc | gaacttgaca | ttggaacgaa | catcagaaat agctttaaga | 1680 |

```
accttaatgg cttcggctgt gatttcttga ccaacgtggt cacctggcaa aacgacgatc    1740
ttcttagggg cagacattag aatggtatat ccttgaaata tatatatata tattgctgaa    1800
atgtaaaagg taagaaaagt tagaaagtaa gacgattgct aaccacctat tggaaaaaac    1860
aataggtcct taaataatat tgtcaacttc aagtattgtg atgcaagcat ttagtcatga    1920
acgcttctct attctatatg aaaagccggt tccggcgctc tcacctttcc tttttctccc    1980
aatttttcag ttgaaaaagg tatatgcgtc aggcgacctc tgaaattaac aaaaaatttc    2040
cagtcatcga atttgattct gtgcgatagc gcccctgtgt gttctcgtta tgttgaggaa    2100
aaaaataatg gttgctaaga gattcgaact cttgcatctt acgatacctg agtattccca    2160
cagttaactg cggtcaagat atttcttgaa tcaggcgcct tagaccgctc ggccaaacaa    2220
ccaattactt gttgagaaat agagtataat tatcctataa atataacgtt tttgaacaca    2280
catgaacaag gaagtacagg acaattgatt ttgaagagaa tgtggatttt gatgtaattg    2340
ttgggattcc atttttaata aggcaataat attaggtatg tagatatact agaagttctc    2400
ctcgaccgtc gatatgcggt gtgaaatacc gcacagatgc gtaaggagaa ataccgcat    2460 caggaaattg taaacgttaa tattttgtta aaattcgcgt taaattttg ttaaatcagc    2520 tcatttttta accaataggc cgaaatcggc aaaatccctt ataaatcaaa agaatagacc    2580
gagatagggt tgagtgttgt tccagtttgg aacaagagtc cactattaaa gaacgtggac    2640
tccaacgtca aagggcgaaa aaccgtctat cagggcgatg gcccactacg tgaaccatca    2700
ccctaatcaa gttttttggg gtcgaggtgc cgtaaagcac taaatcggaa ccctaaaggg    2760
agcccccgat ttagagcttg acggggaaag ccggcgaacg tggcgagaaa ggaagggaag    2820
aaagcgaaag gagcgggcgc tagggcgctg gcaagtgtag cggtcacgct gcgcgtaacc    2880
accacacccg ccgcgcttaa tgcgccgcta cagggcgcgt ccattcgcca ttcaggctgc    2940
gcaactgttg ggaagggcga tcggtgcggg cctcttcgct attacgccag ctgaattgga    3000
gcgacctcat gctatacctg agaaagcaac ctgacctaca ggaaagagtt actcaagaat    3060
aagaattttc gttttaaaac ctaagagtca ctttaaaatt tgtatacact tattttttt    3120 ataacttatt taataataaa aatcataaat cataagaaat tcgcttattt agaagtgtca    3180
acaacgtatc taccaacgat ttgacccttt tccatctttt cgtaaatttc tggcaaggta    3240
gacaagccga caaccttgat tggagacttg accaaacctc tggcgaagaa ttgttaatta    3300
agagctgctg tagctacttc attattatct tcatcagcat ctggtggaac ttggcaagat    3360
cattggctcc tttgatatca tcaaggagag tcatcaggta acgcttccga tcctcctcta    3420
gccggctgga ttttataatg gagcggatta cactgcgtga tgcagggccg gtgtcaggaa    3480
caaacccgac ggctgagctc atctttttcc cgatcggctt tagctgaaat tccttcagca    3540
gctgtcctct ggaactggtc cgtccatttg tcattccttg gagttgtcgg ctggcaacgg    3600
gtttcttgag aacttcggcc agtgctcggc ctgaatctct gcctatgatg ggtttcaagt    3660
cgggattgat ttcgacatct gcagtggggt cgttgggatc cttcccaagt ccaggaatgg    3720
cgatcatgat gcttgagagg tgtccttcca gggtggatat gctgatattt tgcctgttga    3780
tctgcttctt aattgactca acttctccct tcaataacag cagtgattct agcttggaga    3840
ttatcttctg attatcctcg tgtattttgg ccaaggctgt tttaatatct tggacatcag    3900
agaacagctc atcatcataa tagtctcccc cttcttcatt attctgggat ctcggggaga    3960
ttgtggtacc agattcgggt gtccactcct gtatcagtgc ggcattgctc acacactcgg    4020
```

```
ggacattccc cgcaggtgca cctggccctg atggttccga gggtgacttt cgagcacatt    4080
gggttgcacc acctgtcaat aaagacgcga tctccgttcc aaatgaggct aatctcgcgt    4140
ctgtgccctt tttaatgggt gtcccggaag tgctggccct accggggtcc ggggcggag    4200 gaacattgag agttttccca agcttcggaa agttgttgcc tctggattgg agtctcagga    4260
gctcgtggat ctcccctcct tctgcagttt caacatcaga agccctgaac cccatagaga    4320
tgggagcaga tccccggtca gtgatagcat atccctcggt atcaggttcg ccaatatcca    4380
catcgctgtt ttcagattca ttgtctcctc ctgagagggt gctatcacca tcaaggcctg    4440
attgaaccat gatagagtca gcatcttgga ttcccttaac cgcttcaccg ctgtgatcat    4500
aaacgtaata acactgtaac ccagtgcttg atgcctggag atttcttggg gggattccca    4560
aagtttcagc gtcgtcatcg ctctctccag gtccctgacc gcggatgcga ggtgcaccgc    4620
cttcagttga tccaattgct gagaggcatg gtttgctgag acccgaactg cctgccttct    4680
cttccctgca ggtggctcgc tcctgtcctg ggttgtctga tatttctgac catgctgcca    4740
tagcttcctc gatggccagt gagccgatgg gctcggcctt gagagcccgg atgcattcca    4800
gtccgttttt gacatggcgt gcctgctctt ctgccattgg ctccaatcgt gggagtggat    4860
ggttgatggg ctggcggctg tgtggacctg gttcctaagt tttttataac aatgatggat    4920
ggtaggcgga tgttgttctg gccctcggcc tctcgcacct aggccctttta gtgagggttg    4980 aattcgaatt ttcaaaaatt cttactttt ttttggatgg acgcaaagaa gtttaataat    5040
catattacat ggcattacca ccatatacat atccatatac atatccatat ctaatcttac    5100
ttatatgttg tggaaatgta aagagcccca ttatcttagc ctaaaaaaac cttctctttg    5160
gaactttcag taatacgctt aactgctcat tgctatattg aagtacggat tagaagccgc    5220
cgagcgggtg acagccctcc gaaggaagac tctcctccgt gcgtcctcgt cttcaccggt    5280
cgcgttcctg aaacgcagat gtgcctcgcg ccgcactgct ccgaacaata aagattctac    5340
aatactagct tttatggtta tgaagaggaa aaattggcag taacctggcc ccacaaacct    5400
tcaaatgaac gaatcaaatt aacaaccata ggatgataat gcgattagtt ttttagcctt    5460
atttctgggg taattaatca gcgaagcgat gattttgat ctattaacag atatataaat    5520
gcaaaaactg cataaccact ttaactaata ctttcaacat tttcggtttg tattacttct    5580
tattcaaatg taataaaagt atcaacaaaa aattgttaat atacctctat actttaacgt    5640
caaggagaaa aaaccccgga tccgtaatac gactcactat agggcccggg cgtcgacaag    5700
agcaggatta gggatatccg agatggccac acttttaagg agcttagcat tgttcaaaag    5760
aaacaaggac aaaccaccca ttacatcagg atccggtgga gccatcagag gaatcaaaca    5820
cattattata gtaccaatcc ctggagattc ctcaattacc actcgatcca gacttctgga    5880
ccggttggtg aggttaattg gaaacccgga tgtgagcggg cccaaactaa caggggcact    5940
aataggtata ttatccttat ttgtggagtc tccaggtcaa ttgattcaga ggatcaccga    6000
tgaccctgac gttagcataa ggctgttaga ggttgtccag agtgaccagt cacaatctgg    6060
ccttaccttc gcatcaagag gtaccaacat ggaggatgag gcggaccaat acttttcaca    6120
tgatgatcca attagtagtg atcaatccag gttcggatgg ttcgggaaca aggaaatctc    6180
agatattgaa gtgcaagacc ctgagggatt caacatgatt ctgggtacca tcctagccca    6240
aatttgggtc ttgctcgcaa aggcggttac ggcccagac acggcagctg attcggagct    6300
aagaaggtgg ataaagtaca cccaacaaag aagggtagtt ggtgaattta gattggagag    6360
aaaatggttg gatgtggtga ggaacaggat tgccgaggac ctctccttac gccgattcat    6420
```

```
ggtcgctcta atcctggata tcaagagaac acccggaaac aaacccagga ttgctgaaat      6480
gatatgtgac attgatacat atatcgtaga ggcaggatta gccagtttta tcctgactat      6540
taagtttggg atagaaacta tgtatcctgc tcttggactg catgaatttg ctggtgagtt      6600
atccacactt gagtccttga tgaaccttta ccagcaaatg ggggaaactg caccctacat      6660
ggtaatcctg gagaactcaa ttcagaacaa gttcagtgca ggatcatacc ctctgctctg      6720
gagctatgcc atgggagtag gagtggaact tgaaaactcc atgggaggtt tgaactttgg      6780
ccgatcttac tttgatccag catattttag attagggcaa gagatggtaa ggaggtcagc      6840
tggaaaggtc agttccacat tggcatctga actcggtatc actgccgagg atgcaaggct      6900
tgtttcagag attgcaatgc atactactga ggacaagatc agtagagcgg ttggacccag      6960
acaagcccaa gtatcatttc tacacggtga tcaaagtgag aatgagctac cgagattggg      7020
gggcaaggaa gataggaggg tcaaacagag tcgaggagaa gccagggaga gctacagaga      7080
aaccgggccc agcagagcaa gtgatgcgag agctgcccat cttccaaccg gcacacccct      7140
agacattgac actgcaacgg agtccagcca agatccgcag gacagtcgaa ggtcagctga      7200
cgccctgctt aggctgcaag ccatggcagg aatctcggaa gaacaaggct cagacacgga      7260 caccectata gtgtacaatg acagaaatct tctagactag gtgcgagagg ccgagggcca      7320
gaacaacatc cgcctaccat ccatcattgt tataaaaaac ttaggaacca ggtccacaca      7380
gccgccagcc catcaaccat ccactcgagt aagcttggta ccgcggctag ctaagatccg      7440
ctctaaccga aaaggaagga gttagacaac ctgaagtcta ggtccctatt tattttttta      7500
tagttatgtt agtattaaga acgttattta tatttcaaat ttttcttttt tttctgtaca      7560
gacgcgtgta cgcatgtaac attatactga aaaccttgct tgagaaggtt ttgggacgct      7620
cgaagatcca gctgcattaa tgaatcggcc aacgcgcggg gagaggcggt ttgcgtattg      7680
ggcgctcttc cgcttcctcg ctcactgact cgctgcgctc ggtcgttcgg ctgcggcgag      7740
cggtatcagc tcactcaaag gcggtaatac ggttatccac agaatcaggg gataacgcag      7800
gaaagaacat gtgagcaaaa ggccagcaaa aggccaggaa ccgtaaaaag gccgcgttgc      7860
tggcgttttt ccataggctc cgcccccctg acgagcatca caaaaatcga cgctcaagtc      7920
agaggtggcg aaacccgaca ggactataaa gataccaggc gtttccccct ggaagctccc      7980
tcgtgcgctc tcctgttccg accctgccgc ttaccggata cctgtccgcc tttctccctt      8040
cgggaagcgt ggcgctttct catagctcac gctgtaggta tctcagttcg gtgtaggtcg      8100
ttcgctccaa gctgggctgt gtgcacgaac cccccgttca gcccgaccgc tgcgccttat      8160
ccggtaacta tcgtcttgag tccaacccgg taagacacga cttatcgcca ctggcagcag      8220
ccactggtaa caggattagc agagcgaggt atgtaggcgg tgctacagag ttcttgaagt      8280
ggtggcctaa ctacggctac actagaagga cagtatttgg tatctgcgct ctgctgaagc      8340
cagttacctt cggaaaaaga gttggtagct cttgatccgg caaacaaacc accgctggta      8400
gcggtggttt ttttgtttgc aagcagcaga ttacgcgcag aaaaaaagga tctcaagaag      8460
atcctttgat cttttctacg ggtctgacgc tcagtggaa cgaaaactca cgttaaggga      8520
ttttggtcat gagattatca aaaaggatct tcacctagat ccttttaaat taaaaatgaa      8580
gttttaaatc aatctaaagt atatatgagt aaacttggtc tgacagttac caatgcttaa      8640
tcagtgaggc acctatctca gcgatctgtc tatttcgttc atccatagtt gcctgactcc      8700
ccgtcgtgta gataactacg atacgggagg gcttaccatc tggccccagt gctgcaatga      8760
```

```
taccgcgaga cccacgctca ccggctccag atttatcagc aataaaccag ccagccggaa    8820
gggccgagcg cagaagtggt cctgcaactt tatccgcctc catccagtct attaattgtt    8880
gccgggaagc tagagtaagt agttcgccag ttaatagttt gcgcaacgtt gttgccattg    8940
ctacaggcat cgtggtgtca cgctcgtcgt ttggtatggc ttcattcagc tccggttccc    9000
aacgatcaag gcgagttaca tgatccccca tgttgtgcaa aaagcggtt agctccttcg     9060 gtcctccgat cgttgtcaga agtaagttgg ccgcagtgtt atcactcatg gttatggcag    9120
cactgcataa ttctcttact gtcatgccat ccgtaagatg cttttctgtg actggtgagt    9180
actcaaccaa gtcattctga gaatagtgta tgcggcgacc gagttgctct tgcccggcgt    9240
caatacggga taataccgcg ccacatagca gaactttaaa agtgctcatc attggaaaac    9300
gttcttcggg gcgaaaactc tcaaggatct taccgctgtt gagatccagt tcgatgtaac    9360
ccactcgtgc acccaactga tcttcagcat cttttacttt caccagcgtt tctgggtgag    9420
caaaaacagg aaggcaaaat gccgcaaaaa agggaataag ggcgacacgg aaatgttgaa    9480
tactcatact cttcctttt caatattatt gaagcattta tcagggttat tgtctcatga    9540
gcggatacat atttgaatgt atttagaaaa ataaacaaat aggggttccg cgcacatttc    9600
cccgaaaagt gccacctgaa cgaagcatct gtgcttcatt tgtagaaca aaaatgcaac    9660 gcgagagcgc taattttca aacaaagaat ctgagctgca tttttacaga acagaaatgc    9720
aacgcgaaag cgctatttta ccaacgaaga tctgtgcttt catttttgta aaacaaaaat    9780
gcaacgcgag agcgctaatt tttcaaacaa agaatctgag ctgcattttt acagaacaga    9840
aatgcaacgc gagagcgcta ttttaccaac aaagaatcta tacttctttt ttgttctaca    9900
aaaatgcatc ccgagagcgc tatttttcta caaagcatc ttagattact ttttttctcc     9960
tttgtgcgct ctataatgca gtctcttgat aacttttgc actgtaggtc cgttaaggtt    10020
agaagaaggc tactttggtg tctattttct cttccataaa aaagcctga ctccacttcc    10080 cgcgttact gattactagc gaagctgcgg gtgcatttt tcaagataaa ggcatccccg     10140
attatattct ataccgatgt ggattgcgca ctttgtga acagaaagtg atagcgttga    10200
tgattcttca ttggtcagaa aattatgaac ggtttcttct attttgtctc tatatactac     10260
gtataggaaa tgtttacatt ttcgtattgt tttcgattca ctctatgaat agttcttact    10320
acaatttttt tgtctaaaga gtaatactag agataaacat aaaaaatgta gaggtcgagt    10380
ttagatgcaa gttcaaggag cgaaaggtgg atgggtaggt tatataggga tatagcacag    10440
agatatatag caaagagata cttttgagca atgtttgtgg aagcggtatt cgcaatattt    10500
tagtagctcg ttacagtccg gtgcgttttt ggttttttga aagtgcgtct tcagagcgct    10560
tttggttttc aaaagcgctc tgaagttcct atactttcta gagaatagga acttcggaat    10620
aggaacttca aagcgtttcc gaaaacgagc gcttccgaaa atgcaacgcg agctgcgcac    10680
atacagctca ctgttcacgt cgcacctata tctgcgtgtt gcctgtatat atatatacat    10740
gagaagaacg gcatagtgcg tgtttatgct taaatgcgta cttatatgcg tctatttatg    10800
taggatgaaa ggtagtctag tacctcctgt gatattatcc cattccatgc ggggtatcgt    10860
atgcttcctt cagcactacc ctttagctgt tctatatgct gccactcctc aattggatta    10920
gtctcatcct tcaatgctat catttccttt gatattggat catactaaga aaccattatt    10980
atcatgacat aacctataa aaataggcgt atcacgaggc cctttcgtc                11029
```

<210> SEQ ID NO 40
<211> LENGTH: 13404

```
<212> TYPE: DNA
<213> ORGANISM: Artificial
<220> FEATURE:
<223> OTHER INFORMATION: Plasmid

<400> SEQUENCE: 40
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accataaatt cccgttttaa gagcttggtg agcgctagga gtcactgcca ggtatcgttt   240
gaacacggca ttagtcaggg aagtcataac acagtccttt cccgcaattt tcttttcta    300 ttactcttgg cctcctctag tacactctat attttttat gcctcggtaa tgattttcat    360 tttttttt cccctagcgg atgactcttt tttttctta gcgattggca ttatcacata     420
atgaattata cattatataa agtaatgtga tttcttcgaa gaatatacta aaaatgagc   480 aggcaagata aacgaaggca aagatgacag agcagaaagc cctagtaaag cgtattacaa   540
atgaaaccaa gattcagatt gcgatctctt taaagggtgg tcccctagcg atagagcact   600
cgatcttccc agaaaaagag gcagaagcag tagcagaaca ggccacacaa tcgcaagtga   660
ttaacgtcca cacaggtata gggtttctgg accatatgat acatgctctg gccaagcatt   720
ccggctggtc gctaatcgtt gagtgcattg gtgacttaca catagacgac catcacacca   780
ctgaagactg cgggattgct ctcggtcaag cttttaaaga ggccctaggg gccgtgcgtg   840
gagtaaaaag gtttggatca ggatttgcgc ctttggatga ggcactttcc agagcggtgg   900
tagatctttc gaacaggccg tacgcagttg tcgaacttgg tttgcaaagg gagaaagtag   960
gagatctctc ttgcgagatg atcccgcatt ttcttgaaag ctttgcagag gctagcagaa  1020
ttaccctcca cgttgattgt ctgcgaggca agaatgatca tcaccgtagt gagagtgcgt  1080
tcaaggctct tgcggttgcc ataagagaag ccacctcgcc caatggtacc aacgatgttc  1140
cctccaccaa aggtgttctt atgtagtgac accgattatt aaagctgca gcatacgata   1200 tatatacatg tgtatatatg tatacctatg aatgtcagta agtatgtata cgaacagtat  1260
gatactgaag atgacaaggt aatgcatcat tctatacgtg tcattctgaa cgaggcgcgc  1320
tttccttttt tcttttttgct ttttcttttt ttttctcttg aactcgacgg atctatgcgg  1380
tgtgaaatac cgcacagatg cgtaaggaga aaataccgca tcaggaaatt gtaaacgtta  1440
atattttgtt aaaattcgcg ttaaattttt gttaaatcag ctcatttttt aaccaatagg   1500
ccgaaatcgg caaaatccct tataaatcaa agaatagac cgagataggg ttgagtgttg   1560
ttccagtttg gaacaagagt ccactattaa agaacgtgga ctccaacgtc aaagggcgaa  1620
aaaccgtcta tcagggcgat ggcccactac gtgaaccatc accctaatca agttttttgg  1680
ggtcgaggtg ccgtaaagca ctaaatcgga accctaaagg gagcccccga tttagagctt  1740
gacggggaaa gccggcgaac gtggcgagaa aggaagggaa gaaagcgaaa ggagcgggcg  1800
ctagggcgct ggcaagtgta gcggtcacgc tgcgcgtaac caccacaccc gccgcgctta  1860
atgcgccgct acagggcgcg tccattcgcc attcaggctg cgcaactgtt gggaagggcg  1920
atcggtgcgg gcctcttcgc tattacgcca gctgaattgg agcgacctca tgctatacct  1980
gagaaagcaa cctgacctac aggaaagagt tactcaagaa taagaatttt cgttttaaaa  2040
cctaagagtc actttaaaat ttgtatacac ttatttttt tataacttat ttaataataa   2100
aaatcataaa tcataagaaa ttcgcttatt tagaagtgtc aacaacgtat ctaccaacga  2160
```

```
tttgaccctt ttccatcttt tcgtaaattt ctggcaaggt agacaagccg acaaccttga   2220
ttggagactt gaccaaacct ctggcgaaga attgttaatt aagagctcag atcttatcgt   2280
cgtcatcctt gtaatccatc gatactagtg cggccgccct ttagtgaggg ttgaattcga   2340
attttcaaaa attcttactt ttttttttgga tggacgcaaa gaagtttaat aatcatatta   2400
catggcatta ccaccatata catatccata tacatatcca tatctaatct tacttatatg   2460
ttgtggaaat gtaaagagcc ccattatctt agcctaaaaa aaccttctct ttggaactt    2520 cagtaatacg cttaactgct cattgctata ttgaagtacg gattagaagc cgccgagcgg   2580
gtgacagccc tccgaaggaa gactctcctc cgtgcgtcct cgtcttcacc ggtcgcgttc   2640
ctgaaacgca gatgtgcctc gcgccgcact gctccgaaca ataaagattt tacaatacta   2700
gcttttatgg ttatgaagag gaaaaattgg cagtaacctg gccccacaaa ccttcaaatg   2760
aacgaatcaa attaacaacc ataggatgat aatgcgatta gttttttagc cttatttctg   2820
gggtaattaa tcagcgaagc gatgattttt gatctattaa cagatatata aatgcaaaaa   2880
atgcataacc actttaacta atactttcaa cattttcggt ttgtattact ttttattcaa   2940
atgtaataaa agtatcaaca aaaaattgtt aatatacctc tatactttaa cgtcaaggag   3000
aaaaaacccc ggatccgtaa tacgactcac tatagggccc gggcgtgtga atagacatc   3060 agaattaaga aaacgtagg gtccaagtgg ttccccgtta tggactcgct atctgtcaac   3120
cagatcttat accctgaagt tcacctagat agcccgatag ttaccaataa gatagtagcc   3180
atcctggagt atgctcgagt ccctcacgct tacagcctgg aggaccctac actgtgtcag   3240
aacatcaagc accgcctaaa aaacggattt tccaaccaaa tgattataaa caatgtggaa   3300
gttgggaatg tcatcaagtc caagcttagg agttatccgg cccactctca tattccatat   3360
ccaaattgta atcaggattt atttaacata gaagacaaag agtcaacgag gaagatccgt   3420
gaactcctca aaaggggaa ttcgctgtac tccaaagtca gtgataaggt tttccaatgc   3480
ttaagggaca ctaactcacg gcttggccta ggctccgaat tgagggagga catcaaggag   3540
aaagttatta acttgggagt ttacatgcac agctcccagt ggtttgagcc ctttctgttt   3600
tggtttacag tcaagactga gatgaggtca gtgattaaat cacaaaccca tacttgccat   3660
aggaggagac acacacctgt attcttcact ggtagttcag ttgagttgct aatctctcgt   3720
gaccttgttg ctataatcag taaagagtct caacatgtat attacctgac atttgaactg   3780
gttttgatgt attgtgatgt catagagggg aggttaatga cagagaccgc tatgactatt   3840
gatgctaggt atacagagct tctaggaaga gtcagataca tgtggaaact gatagatggt   3900
ttcttccctg cactcgggaa tccaacttat caaattgtag ccatgctgga gcctctttca   3960
cttgcttacc tgcagctgag ggatataaca gtagaactca gaggtgcttt ccttaaccac   4020
tgctttactg aaatacatga tgttcttgac caaaacgggt tttctgatga aggtacttat   4080
catgagttaa ctgaagctct agattacatt tcataactg atgacataca tctgacaggg   4140
gagattttct cattttcag aagtttcggc cacccagac ttgaagcagt aacggctgct   4200
gaaaatgtta ggaaatacat gaatcagcct aaagtcattg tgtatgagac tctgatgaaa   4260
ggtcatgcca tattgtgg aatcataatc aacggctatc gtgacaggca cggaggcagt   4320
tggccaccgc tgaccctccc cctgcatgct gcagacacaa tccggaatgc tcaagcttca   4380
ggtgaagggt taacacatga gcagtgcgtt gataactgga aatcttttgc tggagtgaaa   4440
tttggctgct ttatgcctct tagcctggat agtgatctga caatgtacct aaaggacaag   4500
gcacttgctg ctctccaaag ggaatgggat tcagtttacc cgaaagagtt cctgcgttac   4560
```

```
gaccctccca agggaaccgg gtcacggagg cttgtagatg ttttccttaa tgattcgagc   4620
tttgacccat atgatgtgat aatgtatgtt gtaagtggag cttacctcca tgaccctgag   4680
ttcaacctgt cttacagcct gaaagaaaag gagatcaagg aaacaggtag acttttgct    4740 aaaatgactt acaaaatgag ggcatgccaa gtgattgctg aaaatctaat ctcaaacggg   4800
attggcaaat attttaagga caatgggatg ccaaggatg agcacgattt gactaaggca    4860
ctccacactc tagctgtctc aggagtcccc aaagatctca agaaagtca caggggggg    4920 ccagtcttaa aaacctactc ccgaagccca gtccacacaa gtaccaggaa cgtgagagca   4980
gcaaaagggt ttatagggtt ccctcaagta attcggcagg accaagacac tgatcatccg   5040
gagaatatgg aagcttacga gacagtcagt gcatttatca cgactgatct caagaagtac   5100
tgccttaatt ggagatatga gaccatcagc ttgtttgcac agaggctaaa tgagatttac   5160
ggattgccct catttttcca gtggctgcat aagaggcttg agacctctgt cctgtatgta   5220
agtgaccctc attgcccccc cgaccttgac gcccatatcc cgttatataa agtccccaat   5280
gatcaaatct tcattaagta ccctatggga ggtatagaag ggtattgtca gaagctgtgg   5340
accatcagca ccattcccta tctataccctg gctgcttatg agagcggagt aaggattgct   5400
tcgttagtgc aaggggacaa tcagaccata gccgtaacaa aaagggtacc cagcacatgg   5460
ccctacaacc ttaagaaacg ggaagctgct agagtaacta gagattactt tgtaattctt   5520
aggcaaaggc tacatgatat tggccatcac ctcaaggcaa atgagacaat tgtttcatca   5580 cattttttg tctattcaaa aggaatatat tatgatgggc tacttgtgtc ccaatcactc   5640
aagagcatcg caagatgtgt attctggtca gagactatag ttgatgaaac aagggcagca   5700
tgcagtaata ttgctacaac aatggctaaa agcatcgaga gaggttatga ccgttacctt   5760
gcatattccc tgaacgtcct aaaagtgata cagcaaattc tgatctctct tggcttcaca   5820
atcaattcaa ccatgacccg ggatgtagtc ataccccctcc tcacaaacaa cgacctctta   5880
ataaggatgg cactgttgcc cgctcctatt gggggatga attatctgaa tatgagcagg   5940
ctgtttgtca gaaacatcgg tgatccagta acatcatcaa ttgctgatct caagagaatg   6000
attctcgcct cactaatgcc tgaagagacc ctccatcaag taatgacaca acaaccgggg   6060
gactcttcat tcctagactg ggctagcgac ccttactcag caaatcttgt atgtgtccag   6120
agcatcacta gactcctcaa gaacataact gcaaggtttg tcctgatcca tagtccaaac   6180
ccaatgttaa aaggattatt ccatgatgac agtaaagaag aggacgaggg actggcggca   6240
ttcctcatgg acaggcatat tatagtacct agggcagctc atgaaatcct ggatcatagt   6300
gtcacagggg caagagagtc tattgcaggc atgctggata ccacaaaagg cttgattcga   6360
gccagcatga ggaaggggg gttaacctct cgagtgataa ccagattgtc caattatgac   6420
tatgaacaat tcagagcagg gatggtgcta ttgacaggaa gaaagagaaa tgtcctcatt   6480
gacaaagagt catgttcagt gcagctggcg agagctctaa gaagccatat gtgggcgagg   6540
ctagctcgag gacggcctat ttacggcctt gaggtccctg atgtactaga atctatgcga   6600
ggccacctta ttcggcgtca tgagacatgt gtcatctgcg agtgtggatc agtcaactac   6660
ggatggtttt ttgtcccctc gggttgccaa ctggatgata ttgacaagga acatcatcc    6720 ttgagagtcc catatattgg ttctaccact gatgagagaa cagacatgaa gcttgccttc   6780
gtaagagccc caagtcgatc cttgcgatct gctgttagaa tagcaacagt gtactcatgg   6840
gcttacggtg atgatgatag ctcttggaac gaagcctggt tgttggctag gcaaagggcc   6900
```

```
aatgtgagcc tggaggagct aagggtgatc actcccatct caacttcgac taatttagcg    6960
cataggttga gggatcgtag cactcaagtg aaatactcag gtacatccct tgtccgagtg    7020
gcgaggtata ccacaatctc caacgacaat ctctcatttg tcatatcaga taagaaggtt    7080
gatactaact ttatatacca acaaggaatg cttctagggt tgggtgtttt agaaacattg    7140
tttcgactcg agaaagatac cggatcatct aacacggtat tacatcttca cgtcgaaaca    7200
gattgttgcg tgatcccgat gatagatcat cccaggatac ccagctcccg caagctagag    7260
ctgagggcag agctatgtac caacccattg atatatgata atgcaccttt aattgacaga    7320
gatgcaacaa ggctatacac ccagagccat aggaggcacc ttgtggaatt tgttacatgg    7380
tccacacccc aactatatca cattttagct aagtccacag cactatctat gattgacctg    7440
gtaacaaaat ttgagaagga ccatatgaat gaaatttcag ctctcatagg ggatgacgat    7500
atcaatagtt tcataactga gtttctgctc atagagccaa gattattcac tatctacttg    7560
ggccagtgtg cggccatcaa ttgggcattt gatgtacatt atcatagacc atcagggaaa    7620
tatcagatgg gtgagctgtt gtcatcgttc ctttctagaa tgagcaaagg agtgtttaag    7680
gtgcttgtca atgctctaag ccacccaaag atctacaaga aattctggca ttgtggtatt    7740
atagagccta tccatggtcc ttcacttgat gctcaaaact tgcacacaac tgtgtgcaac    7800
atggtttaca catgctatat gacctacctc gacctgttgt tgaatgaaga gttagaagag    7860
ttcacatttc tcttgtgtga aagcgacgag gatgtagtac cggacagatt cgacaacatc    7920
caggcaaaac acttatgtgt tctggcagat ttgtactgtc aacccagggac ctgcccacca    7980 attcgaggtc taagaccggt agagaaatgt gcagttctaa ccgaccatat caaggcgagg    8040
gctatgttat ctccagcagg atcttcgtgg aacataaatc caattattgt agaccattac    8100
tcatgctctc tgacttatct ccggcgagga tcgatcaaac agataagatt gagagttgat    8160
ccaggattca tttttcgacgc cctcgctgag gtaaatgtca gtcagccaaa gatcggcagc    8220
aacaacatct caaatatgag catcaaggct ttcagacccc cacacgatga tgttgcaaaa    8280
ttgctcaaag atatcaacac aagcaagcac aatcttccca tttcaggggg caatctcgcc    8340
aattatgaaa tccatgcttt ccgcagaatc gggttgaact catctgcttg ctacaaagct    8400
gttgagatat caacattaat taggagatgc cttgagccag gggaggacgg cttgttcttg    8460
ggtgagggat cgggttctat gttgatcact tataaagaga tacttaaaact aaacaagtgc    8520 ttctataata gtggggtttc cgccaattct agatctggtc aaagggaatt agcaccctat    8580
ccctccgaag ttggccttgt cgaacacaga atgggagtag gtaatattgt caaagtgctc    8640
tttaacggga ggcccgaagt cacgtgggta ggcagtgtag attgcttcaa tttcatagtt    8700
agtaatatcc ctacctctag tgtggggttt atccattcag atatagagac cttgcctgac    8760
aaagatacta tagagaagct agaggaattg gcagccatct tatcgatggc tctgctcctg    8820
ggcaaaatag gatcaatact ggtgattaag cttatgcctt tcagcgggga ttttgttcag    8880
ggatttataa gttatgtagg gtctcattat agagaagtga accttgtata ccctagatac    8940
agcaacttca tctctactga atcttatttg gttatgacag atctcaaggc taaccggcta    9000
atgaatcctg aaaagattaa gcagcagata attgaatcat ctgtgaggac ttcacctgga    9060
cttataggtc acatcctatc cattaagcaa ctaagctgca tacaagcaat tgtgggagac    9120
gcagttagta gaggtgatat caatcctact ctgaaaaaac ttacacctat agagcaggtg    9180
ctgatcaatt gcgggttggc aattaacgga cctaagctgt gcaaagaatt gatccaccat    9240
gatgttgcct cagggcaaga tggattgctt aattctatac tcatcctcta cagggagttg    9300
```

```
gcaagattca aagacaacca aagaagtcaa caagggatgt tccacgctta ccccgtattg   9360
gtaagtagca ggcaacgaga acttatatct aggatcaccc gcaaattctg ggggcacatt   9420
cttctttact ccgggaacaa aaagttgata ataagtttta tccagaatct caagtccggc   9480
tatctgatac tagacttaca ccagaatatc ttcgttaaga atctatccaa gtcagagaaa   9540
cagattatta tgacgggggg tttgaaacgt gagtgggttt ttaaggtaac agtcaaggag   9600
accaaagaat ggtataagtt agtcggatac agtgccctga ttaaggacta attggttgaa   9660
ctccggaacc ctaatcctgc cctaggtggt taggcattat ttgcaatata ttaaagaaaa   9720 cttttgaaaat acgaagtttc tattcccagc tttgtctggt ggccggcatg gtcccagcct   9780
tcgagtaagc ttggtaccgc ggctagctaa gatccgctct aaccgaaaag gaaggagtta   9840
gacaacctga agtctaggtc cctatttatt tttttatagt tatgttagta ttaagaacgt   9900
tatttatatt tcaaattttt ctttttttc tgtacagacg cgtgtacgca tgtaacatta   9960
tactgaaaac cttgcttgag aaggttttgg gacgctcgaa gatccagctg cattaatgaa  10020
tcggccaacg cgcggggaga ggcggtttgc gtattgggcg ctcttccgct tcctcgctca  10080
ctgactcgct gcgctcggtc gttcggctgc ggcgagcggt atcagctcac tcaaaggcgg  10140
taatacggtt atccacagaa tcaggggata acgcaggaaa gaacatgtga gcaaaaggcc  10200
agcaaaaggc caggaaccgt aaaaaggccg cgttgctggc gttttttccat aggctccgcc  10260 cccctgacga gcatcacaaa aatcgacgct caagtcagag gtggcgaaac ccgacaggac  10320
tataaagata ccaggcgttt ccccctggaa gctccctcgt gcgctctcct gttccgaccc  10380
tgccgcttac cggatacctg tccgcctttc tcccttcggg aagcgtggcg ctttctcata  10440
gctcacgctg taggtatctc agttcggtgt aggtcgttcg ctccaagctg ggctgtgtgc  10500
acgaaccccc cgttcagccc gaccgctgcg ccttatccgg taactatcgt cttgagtcca  10560
acccggtaag acacgactta tcgccactgg cagcagccac tggtaacagg attagcagag  10620
cgaggtatgt aggcggtgct acagagttct tgaagtggtg gcctaactac ggctacacta  10680
gaaggacagt atttggtatc tgcgctctgc tgaagccagt taccttcgga aaaagagttg  10740
gtagctcttg atccggcaaa caaaccaccg ctggtagcgg tggttttttt gtttgcaagc  10800
agcagattac gcgcagaaaa aaaggatctc aagaagatcc tttgatcttt tctacggggt  10860
ctgacgctca gtggaacgaa aactcacgtt aagggatttt ggtcatgaga ttatcaaaaa  10920
ggatcttcac ctagatcctt ttaaattaaa aatgaagttt taaatcaatc taaagtatat  10980
atgagtaaac ttggtctgac agttaccaat gcttaatcag tgaggcacct atctcagcga  11040
tctgtctatt tcgttcatcc atagttgcct gactccccgt cgtgtagata actacgatac  11100
gggagggctt accatctggc cccagtgctg caatgatacc gcgagaccca cgctcaccgg  11160
ctccagattt atcagcaata aaccagccag ccggaagggc cgagcgcaga agtggtcctg  11220
caactttatc cgcctccatc cagtctatta attgttgccg ggaagctaga gtaagtagtt  11280
cgccagttaa tagtttgcgc aacgttgttg ccattgctac aggcatcgtg gtgtcacgct  11340
cgtcgtttgg tatggcttca ttcagctccg gttcccaacg atcaaggcga gttacatgat  11400
cccccatgtt gtgcaaaaaa gcggttagct ccttcggtcc tccgatcgtt gtcagaagta  11460
agttggccgc agtgttatca ctcatggtta tggcagcact gcataattct cttactgtca  11520
tgccatccgt aagatgcttt tctgtgactg gtgagtactc aaccaagtca ttctgagaat  11580
agtgtatgcg gcgaccgagt tgctcttgcc cggcgtcaat acgggataat accgcgccac  11640
```

```
atagcagaac tttaaaagtg ctcatcattg gaaaacgttc ttcggggcga aaactctcaa    11700
ggatcttacc gctgttgaga tccagttcga tgtaacccac tcgtgcaccc aactgatctt    11760
cagcatcttt tactttcacc agcgtttctg ggtgagcaaa aacaggaagg caaaatgccg    11820 caaaaaggg aataagggcg acacggaaat gttgaatact catactcttc ctttttcaat    11880
attattgaag catttatcag ggttattgtc tcatgagcgg atacatattt gaatgtattt    11940
agaaaaataa acaaataggg gttccgcgca catttccccg aaaagtgcca cctgaacgaa    12000
gcatctgtgc ttcattttgt agaacaaaaa tgcaacgcga gagcgctaat ttttcaaaca    12060
aagaatctga gctgcatttt tacagaacag aaatgcaacg cgaaagcgct attttaccaa    12120
cgaagaatct gtgcttcatt tttgtaaaac aaaaatgcaa cgcgagagcg ctaattttc    12180 aaacaaagaa tctgagctgc atttttacag aacagaaatg caacgcgaga gcgctatttt    12240
accaacaaag aatctatact tctttttttgt tctacaaaaa tgcatcccga gagcgctatt    12300
tttctaacaa agcatcttag attactttt ttctcctttg tgcgctctat aatgcagtct    12360
cttgataact ttttgcactg taggtccgtt aaggttagaa gaaggctact ttggtgtcta    12420
ttttctcttc cataaaaaaa gcctgactcc acttcccgcg tttactgatt actagcgaag    12480
ctgcgggtgc attttttcaa gataaaggca tccccgatta tattctatac cgatgtggat    12540
tgcgcatact ttgtgaacag aaagtgatag cgttgatgat tcttcattgg tcagaaaatt    12600
atgaacggtt tcttctattt tgtctctata tactacgtat aggaaatgtt acatttcg    12660 tattgttttc gattcactct atgaatagtt cttactacaa tttttttgtc taaagagtaa    12720
tactagagat aaacataaaa aatgtagagg tcgagtttag atgcaagttc aaggagcgaa    12780
aggtggatgg gtaggttata tagggatata gcacagagat atatagcaaa gagatacttt    12840
tgagcaatgt ttgtggaagc ggtattcgca atatttagt agctcgttac agtccggtgc    12900
gtttttggtt ttttgaaagt gcgtcttcag agcgcttttg gttttcaaaa gcgctctgaa    12960
gttcctatac tttctagaga ataggaactt cggaatagga acttcaaagc gtttccgaaa    13020
acgagcgctt ccgaaaatgc aacgcgagct gcgcacatac agctcactgt tcacgtcgca    13080
cctatatctg cgtgttgcct gtatatat atacatgaga gaacggcat agtgcgtgtt    13140 tatgcttaaa tgcgtactta tatgcgtcta tttatgtagg atgaaaggta gtctagtacc    13200
tcctgtgata ttatcccatt ccatgcgggg tatcgtatgc ttccttcagc actaccttt    13260 agctgttcta tatgctgcca ctcctcaatt ggattagtct catccttcaa tgctatcatt    13320
tcctttgata ttggatcatc taagaaacca ttattatcat gacattaacc tataaaaata    13380
ggcgtatcac gaggcccttt cgtc                                          13404
```

<210> SEQ ID NO 41
<211> LENGTH: 15185
<212> TYPE: DNA
<213> ORGANISM: Artificial
<220> FEATURE:
<223> OTHER INFORMATION: Plasmid

<400> SEQUENCE: 41

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc     180
accataaatt cccgtttttaa gagcttggtg agcgctagga gtcactgcca ggtatcgttt     240
gaacacggca ttagtcaggg aagtcataac acagtccttt cccgcaattt tctttttcta     300
```

```
ttactcttgg cctcctctag tacactctat attttttat gcctcggtaa tgattttcat      360
tttttttttt cccctagcgg atgactcttt tttttttctta gcgattggca ttatcacata     420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tcccctagcg atagagcact     600
cgatcttccc agaaaagag gcagaagcag tagcagaaca ggccacacaa tcgcaagtga      660
ttaacgtcca cacaggtata gggtttctgg accatatgat acatgctctg ccaagcatt      720
ccggctggtc gctaatcgtt gagtgcattg gtgacttaca catagacgac catcacacca     780
ctgaagactg cgggattgct ctcggtcaag cttttaaaga ggccctaggg gccgtgcgtg     840
gagtaaaaag gtttggatca ggatttgcgc ctttggatga ggcactttcc agagcggtgg     900
tagatctttc gaacaggccg tacgcagttg tcgaacttgg tttgcaaagg gagaaagtag     960
gagatctctc ttgcgagatg atcccgcatt ttcttgaaag ctttgcagag gctagcagaa    1020
ttaccctcca cgttgattgt ctgcgaggca agaatgatca tcaccgtagt gagagtgcgt    1080
tcaaggctct tgcggttgcc ataagagaag ccacctcgcc caatggtacc aacgatgttc    1140
cctccaccaa aggtgttctt atgtagtgac accgattatt taaagctgca gcatacgata    1200
tatatacatg tgtatatatg tatacctatg aatgtcagta agtatgtata cgaacagtat    1260
gatactgaag atgacaaggt aatgcatcat tctatacgtg tcattctgaa cgaggcgcgc    1320
tttccttttt tctttttgct ttttcttttt ttttctcttg aactcgacgg atctatgcgg    1380
tgtgaaatac cgcacagatg cgtaaggaga aaataccgca tcaggaaatt gtaaacgtta    1440
atattttgtt aaaattcgcg ttaaattttt gttaaatcag ctcattttt aaccaatagg     1500
ccgaaatcgg caaaatccct tataaatcaa agaatagac cgagatagg ttgagtgttg      1560
ttccagtttg gaacaagagt ccactattaa agaacgtgga ctccaacgtc aaagggcgaa    1620
aaaccgtcta tcagggcgat ggcccactac gtgaaccatc accctaatca agttttttgg    1680
ggtcgaggtg ccgtaaagca ctaaatcgga accctaaagg gagcccccga tttagagctt    1740
gacggggaaa gccggcgaac gtggcgagaa aggaagggaa gaaagcgaaa ggagcgggcg    1800
ctagggcgct ggcaagtgta gcggtcacgc tgcgcgtaac caccacaccc gccgcgctta    1860
atgcgccgct acagggcgcg tccattcgcc attcaggctg cgcaactgtt gggaagggcg    1920
atcggtgcgg gcctcttcgc tattacgcca gctgaattgg agcgacctca tgctatacct    1980
gagaaagcaa cctgacctac aggaaagagt tactcaagaa taagaatttt cgttttaaaa    2040
cctaagagtc actttaaaat ttgtatacac ttatttttt tataacttat ttaataataa    2100
aaatcataaa tcataagaaa ttcgcttatt tagaagtgtc aacaacgtat ctaccaacga    2160
tttgacccct ttccatcttt tcgtaaattt ctggcaaggt agacaagccg acaaccttga    2220
ttggagactt gaccaaacct ctggcgaaga attgttaatt aagagctcag atcttatcgt    2280
cgtcatcctt gtaatccatc gatactagca ctatgctaca acattccaaa atttgtccca    2340
aaaagtcttt ggttcatgat cttcccatac aattgcctca atgtctcttc tatcggaatc    2400
gatgtcgaca tctccaatct tccaaataaa tctgcatctg aatatgcatt gaaataagat    2460
ccaaacagct aagaacagga aaatagagat ataggcggca gcaaagctaa caccattgaa    2520
ttttggtgca aaagccgtga aaccttgaat aatgataatg atcgtcataa atgtggccgc    2580
ataataagcc aagccgggca ttaatttagc tttaaatggt aactcgtcac gagagatgcc    2640
```

| | |
|---|---|
| acggtatttc aaagcttgca taaatctgat gtgcgagatt gagataaata accatgcaaa | 2700 |
| aaagcctgca acaccagtga tatttaatag ccattcgaaa actttgtcac caccagtaga | 2760 |
| tgtctccatg taagccaaag cgccaaatgc agcagtaacg aaaactgcaa tgtatggaac | 2820 |
| accacctttg gtggtccttg acaggaattt aggagccaac ttgttctttg atagaccaaa | 2880 |
| taaaatacgg gaaccaacgt aaatatttga atttgcggca gaaataatgg ttgttaagat | 2940 |
| aacagcgttg aagatatgtg gcaaaacctt tgtaccagag ttctcaatag caataataaa | 3000 |
| gggagaagta gaaacgtagg aagtagattg tgttagttta gggtcattgt atggaactaa | 3060 |
| aagtccaatg aataatagag agccaatgta gaaggttaag atacggaaaa caacttttt | 3120 |
| gatggctctt ggaacggatt tctgggggtt tgcagcttca ccagcagtga taccaactag | 3180 |
| ttcagtacct tgaaatgtga aggcagcgtt aatcaaagag gaaacccaac ctaagaacct | 3240 |
| cccttcgttt ttatccttag atattatacc tggaccccag gcacctgggt ttctccaata | 3300 |
| acggaatcca actgggccgg taaccccagc accacaaacc atacaaaaac agtatattag | 3360 |
| aaacccgata atggctaaaa cttttgatgga agcgacccag aactcgaatt caccgtaata | 3420 |
| tttgacaggg aacaagttca ttattgtgat aattacccaa aaaatactaa tccatgccgc | 3480 |
| cagtggaact ttgtacgtcc aaaattgaat gacttggcca actacactaa gttccagggc | 3540 |
| aaaagtgatt gcccaagaaa accaatacat gtaaccattg gccgcaccaa atgctggaga | 3600 |
| aaggaatctt tgtgagaaaa ctgtgaaaga ggatgtaaca gggatgaatg tagccatttc | 3660 |
| acccaaggac tgcgtgacag aatatgccaa agaacccata aataaatatg atataagagc | 3720 |
| gcccactggg ccggcgttgg tcagaggtgt ggataaacca atgaaaagac ctgtaccaat | 3780 |
| agtaccacca agggcaatca taccaatatg tctttgctta agctctctct tcacttcagc | 3840 |
| gttctgtact tctccttcat cttcatcacc tatgccatcc tccatagaga acgtatcctc | 3900 |
| gccatttact ctcgtcggga aagagcgcaa tggatacaat tctttacttt tctcatcttt | 3960 |
| caatggtatt gacccacgtc tgtggtgtgt ttgtgaagct tcaacgtcgt gaaagagggt | 4020 |
| tgtgaccggc tcattgtaca tatgcttctc ctctatgtcg gcgtcttctt ttgaatttgt | 4080 |
| catgcggccg ccctttagtg agggttgaat tcgaattttc aaaaattctt acttttttt | 4140 |
| tggatggacg caaagaagtt taataatcat attacatggc attaccacca tatacatatc | 4200 |
| catatacata tccatatcta atcttactta tatgttgtgg aaatgtaaag agccccatta | 4260 |
| tcttagccta aaaaaacctt ctctttggaa cttttcagtaa tacgcttaac tgctcattgc | 4320 |
| tatattgaag tacggattag aagccgccga gcgggtgaca gccctccgaa ggaagactct | 4380 |
| cctccgtgcg tcctcgtctt caccggtcgc gttcctgaaa cgcagatgtg cctcgcgccg | 4440 |
| cactgctccg aacaataaag attttacaat actagctttt atggttatga agaggaaaaa | 4500 |
| ttggcagtaa cctggcccca caaaccttca aatgaacgaa tcaaattaac aaccatagga | 4560 |
| tgataatgcg attagttttt tagccttatt tctggggtaa ttaatcagcg aagcgatgat | 4620 |
| ttttgatcta ttaacagata tataaatgca aaaaatgcat aaccacttta actaatactt | 4680 |
| tcaacatttt cggtttgtat tacttttat tcaaatgtaa taaaagtatc aacaaaaaat | 4740 |
| tgttaatata cctctatact ttaacgtcaa ggagaaaaaa ccccggatcc gtaatacgac | 4800 |
| tcactatagg gcccgggcgt gtgaaataga catcagaatt aagaaaaacg tagggtccaa | 4860 |
| gtggttcccc gttatggact cgctatctgt caaccagatc ttatacctg aagttcacct | 4920 |
| agatagcccg atagttacca ataagatagt agccatcctg gagtatgctc gagtccctca | 4980 |
| cgcttacagc ctggaggacc ctacactgtg tcagaacatc aagcaccgcc taaaaaacgg | 5040 |

```
attttccaac caaatgatta taaacaatgt ggaagttggg aatgtcatca agtccaagct   5100
taggagttat ccggcccact ctcatattcc atatccaaat tgtaatcagg atttatttaa   5160
catagaagac aaagagtcaa cgaggaagat ccgtgaactc ctcaaaaagg ggaattcgct   5220
gtactccaaa gtcagtgata aggttttcca atgcttaagg gacactaact cacggcttgg   5280
cctaggctcc gaattgaggg aggacatcaa ggagaaagtt attaacttgg gagtttacat   5340
gcacagctcc cagtggtttg agccctttct gttttggttt acagtcaaga ctgagatgag   5400
gtcagtgatt aaatcacaaa cccatacttg ccataggagg agacacacac ctgtattctt   5460
cactggtagt tcagttgagt tgctaatctc tcgtgacctt gttgctataa tcagtaaaga   5520
gtctcaacat gtatattacc tgacatttga actggttttg atgtattgtg atgtcataga   5580
ggggaggtta atgacagaga ccgctatgac tattgatgct aggtatacag agcttctagg   5640
aagagtcaga tacatgtgga aactgataga tggtttcttc cctgcactcg ggaatccaac   5700
ttatcaaatt gtagccatgc tggagcctct ttcacttgct tacctgcagc tgagggatat   5760
aacagtagaa ctcagaggtg ctttccttaa ccactgcttt actgaaatac atgatgttct   5820
tgaccaaaac gggttttctg atgaaggtac ttatcatgag ttaactgaag ctctagatta   5880
cattttcata actgatgaca tacatctgac aggggagatt ttctcatttt tcagaagttt   5940
cggccacccc agacttgaag cagtaacggc tgctgaaaat gttaggaaat acatgaatca   6000
gcctaaagtc attgtgtatg agactctgat gaaaggtcat gccatatttt gtggaatcat   6060
aatcaacggc tatcgtgaca ggcacggagg cagttggcca ccgctgaccc tcccctgca   6120 tgctgcagac acaatccgga atgctcaagc ttcaggtgaa gggttaacac atgagcagtg   6180
cgttgataac tggaaatctt ttgctggagt gaaatttggc tgctttatgc ctcttagcct   6240
ggatagtgat ctgacaatgt acctaaagga caaggcactt gctgctctcc aaagggaatg   6300
ggattcagtt tacccgaaag agttcctgcg ttacgaccct cccaagggaa ccgggtcacg   6360
gaggcttgta gatgttttcc ttaatgattc gagctttgac ccatatgatg tgataatgta   6420
tgttgtaagt ggagcttacc tccatgaccc tgagttcaac ctgtcttaca gcctgaaaga   6480
aaaggagatc aaggaaacag gtagactttt tgctaaaatg acttacaaaa tgagggcatg   6540
ccaagtgatt gctgaaaatc taatctcaaa cgggattggc aaatatttta aggacaatgg   6600
gatggccaag gatgagcacg atttgactaa ggcactccac actctagctg tctcaggagt   6660
ccccaaagat ctcaaagaaa gtcacagggg ggggccagtc ttaaaaacct actcccgaag   6720
cccagtccac acaagtacca ggaacgtgag agcagcaaaa gggtttatag ggttccctca   6780
agtaattcgg caggaccaag acactgatca tccggagaat atggaagctt acgagacagt   6840
cagtgcattt atcacgactg atctcaagaa gtactgcctt aattggagat atgagaccat   6900
cagcttgttt gcacagaggc taaatgagat ttacggattg ccctcatttt tccagtggct   6960
gcataagagg cttgagacct ctgtcctgta tgtaagtgac cctcattgcc ccccgacct   7020 tgacgcccat atcccgttat ataaagtccc caatgatcaa atcttcatta agtaccctat   7080
gggaggtata gaagggtatt gtcagaagct gtggaccatc agcaccattc cctatctata   7140
cctggctgct tatgagagcg gagtaaggat tgcttcgtta gtgcaagggg acaatcagac   7200
catagccgta acaaaaaggg tacccagcac atggccctac aaccttaaga aacgggaagc   7260
tgctagagta actagagatt actttgtaat tcttaggcaa aggctacatg atattggcca   7320
tcacctcaag gcaaatgaga caattgtttc atcacatttt tttgtctatt caaaaggaat   7380
```

```
atattatgat gggctacttg tgtcccaatc actcaagagc atcgcaagat gtgtattctg    7440
gtcagagact atagttgatg aaacaagggc agcatgcagt aatattgcta caacaatggc    7500
taaaagcatc gagagaggtt atgaccgtta ccttgcatat tccctgaacg tcctaaaagt    7560
gatacagcaa attctgatct ctcttggctt cacaatcaat tcaaccatga cccgggatgt    7620
agtcataccc ctcctcacaa acaacgacct cttaataagg atggcactgt tgcccgctcc    7680
tattgggggg atgaattatc tgaatatgag caggctgttt gtcagaaaca tcggtgatcc    7740
agtaacatca tcaattgctg atctcaagag aatgattctc gcctcactaa tgcctgaaga    7800
gaccctccat caagtaatga cacaacaacc gggggactct tcattcctag actgggctag    7860
cgacccttac tcagcaaatc ttgtatgtgt ccagagcatc actagactcc tcaagaacat    7920
aactgcaagg tttgtcctga tccatagtcc aaacccaatg ttaaaaggat tattccatga    7980
tgacagtaaa gaagaggacg agggactggc ggcattcctc atggacaggc atattatagt    8040
acctagggca gctcatgaaa tcctggatca tagtgtcaca ggggcaagag agtctattgc    8100
aggcatgctg gataccacaa aaggcttgat tcgagccagc atgaggaagg ggggttaac     8160
ctctcgagtg ataaccagat tgtccaatta tgactatgaa caattcagag cagggatggt    8220
gctattgaca ggaagaaaga gaaatgtcct cattgacaaa gagtcatgtt cagtgcagct    8280
ggcgagagct ctaagaagcc atatgtgggc gaggctagct cgaggacggc ctatttacgg    8340
ccttgaggtc cctgatgtac tagaatctat gcgaggccac cttattcggc gtcatgagac    8400
atgtgtcatc tgcgagtgtg atcagtcaa ctacggatgg ttttttgtcc cctcgggttg     8460
ccaactggat gatattgaca aggaaacatc atccttgaga gtcccatata ttggttctac    8520
cactgatgag agaacagaca tgaagcttgc cttcgtaaga gccccaagtc gatccttgcg    8580
atctgctgtt agaatagcaa cagtgtactc atgggcttac ggtgatgatg atagctcttg    8640
gaacgaagcc tggttgttgg ctaggcaaag ggccaatgtg agcctggagg agctaagggt    8700
gatcactccc atctcaactt cgactaattt agcgcatagg ttgagggatc gtagcactca    8760
agtgaaatac tcaggtacat cccttgtccg agtggcgagg tataccacaa tctccaacga    8820
caatctctca tttgtcatat cagataagaa ggttgatact aactttatat accaacaagg    8880
aatgcttcta gggttgggtg ttttagaaac attgtttcga ctcgagaaag ataccggatc    8940
atctaacacg gtattacatc ttcacgtcga aacagattgt tgcgtgatcc cgatgataga    9000
tcatcccagg ataccagct cccgcaagct agagctgagg gcagagctat gtaccaaccc     9060
attgatatat gataatgcac ctttaattga cagagatgca acaaggctat acacccagag    9120
ccataggagg caccttgtgg aatttgttac atggtccaca ccccaactat atcacatttt    9180
agctaagtcc acagcactat ctatgattga cctggtaaca aaatttgaga aggaccatat    9240
gaatgaaatt tcagctctca tagggatga cgatatcaat agtttcataa ctgagtttct     9300
gctcatagag ccaagattat tcactatcta cttgggccag tgtgcggcca tcaattgggc    9360
atttgatgta cattatcata gaccatcagg gaaatatcag atgggtgagc tgttgtcatc    9420
gttcctttct agaatgagca aaggagtgtt taaggtgctt gtcaatgctc taagccaccc    9480
aaagatctac aagaaattct ggcattgtgg tattatagag cctatccatg gtccttcact    9540
tgatgctcaa aacttgcaca caactgtgtg caacatggtt tacacatgct atatgaccta    9600
cctcgacctg ttgttgaatg aagagttaga agagttcaca tttctcttgt gtgaaagcga    9660
cgaggatgta gtaccggaca gattcgacaa catccaggca aaaacttat gtgttctggc     9720
agatttgtac tgtcaaccag ggacctgccc accaattcga ggtctaagac cggtagagaa    9780
```

```
atgtgcagtt ctaaccgacc atatcaaggc agaggctatg ttatctccag caggatcttc   9840
gtggaacata aatccaatta ttgtagacca ttactcatgc tctctgactt atctccggcg   9900
aggatcgatc aaacagataa gattgagagt tgatccagga ttcattttcg acgccctcgc   9960
tgaggtaaat gtcagtcagc caaagatcgg cagcaacaac atctcaaata tgagcatcaa  10020
ggctttcaga cccccacacg atgatgttgc aaaattgctc aaagatatca acacaagcaa  10080
gcacaatctt cccatttcag ggggcaatct cgccaattat gaaatccatg ctttccgcag  10140
aatcgggttg aactcatctg cttgctacaa agctgttgag atatcaacat taattaggag  10200
atgccttgag ccaggggagg acggcttgtt cttgggtgag ggatcgggtt ctatgttgat  10260
cacttataaa gagatactta aactaaacaa gtgcttctat aatagtgggg tttccgccaa  10320
ttctagatct ggtcaaaggg aattagcacc ctatccctcc gaagttggcc ttgtcgaaca  10380
cagaatggga gtaggtaata ttgtcaaagt gctctttaac gggaggcccg aagtcacgtg  10440
ggtaggcagt gtagattgct tcaatttcat agttagtaat atccctacct ctagtgtggg  10500
gtttatccat tcagatatag agaccttgcc tgacaaagat actatagaga gctagagga   10560 attggcagcc atcttatcga tggctctgct cctgggcaaa ataggatcaa tactggtgat  10620
taagcttatg cctttcagcg gggattttgt tcagggattt ataagttatg tagggtctca  10680
ttatagagaa gtgaaccttg tataccctag atacagcaac ttcatctcta ctgaatctta  10740
tttggttatg acagatctca aggctaaccg gctaatgaat cctgaaaaga ttaagcagca  10800
gataattgaa tcatctgtga ggacttcacc tggacttata ggtcacatcc tatccattaa  10860
gcaactaagc tgcatacaag caattgtggg agacgcagtt agtagaggtg atatcaatcc  10920
tactctgaaa aaacttacac ctatagcaca ggtgctgatc aattgcgggt tggcaattaa  10980
cggacctaag ctgtgcaaag aattgatcca ccatgatgtt gcctcagggc aagatggatt  11040
gcttaattct atactcatcc tctcagggga gttggcaaga ttcaaagaca accaaagaag  11100
tcaacaaggg atgttccacg cttaccccgt attggtaagt agcaggcaac gagaacttat  11160
atctaggatc acccgcaaat tctgggggca cattcttctt tactccggga acaaaaagtt  11220
gataaataag tttatccaga atctcaagtc cggctatctg atactagact tacaccagaa  11280
tatcttcgtt aagaatctat ccaagtcaga gaaacagatt attatgacgg ggggtttgaa  11340
acgtgagtgg gttttaagg taacagtcaa ggagaccaaa gaatggtata agttagtcgg  11400
atacagtgcc ctgattaagg actaattggt tgaactccgg aaccctaatc ctgccctagg  11460
tggttaggca ttatttgcaa tatattaaag aaaactttga aaatacgaag tttctattcc  11520
cagctttgtc tggtggccgg catggtccca gcctcctcgc tggcggtaag cttggtaccg  11580
cggctagcta agatccgctc taaccgaaaa ggaaggagtt agacaacctg aagtctaggt  11640
ccctatttat tttttttatag ttatgttagt attaagaacg ttatttatat ttcaaatttt  11700 tcttttttt ctgtacagac gcgtgtacg atgtaacatt atactgaaaa ccttgcttga  11760
gaaggttttg ggacgctcga agatccagct gcattaatga atcggccaac gcgcggggag  11820
aggcggtttg cgtattgggc gctcttccgc ttcctcgctc actgactcgc tgcgctcggt  11880
cgttcggctg cggcgagcgg tatcagctca ctcaaaggcg gtaatacggt tatccacaga  11940
atcaggggat aacgcaggaa agaacatgtg agcaaaaggc cagcaaaagg ccaggaaccg  12000
taaaaaggcc gcgttgctgg cgttttccca taggctccgc ccccctgacg agcatcacaa  12060
aaatcgacgc tcaagtcaga ggtggcgaaa cccgacagga ctataaagat accaggcgtt  12120
```

```
tcccctgga agctccctcg tgcgctctcc tgttccgacc ctgccgctta ccggatacct  12180
gtccgccttt ctcccttcgg gaagcgtggc gctttctcat agctcacgct gtaggtatct  12240
cagttcggtg taggtcgttc gctccaagct gggctgtgtg cacgaacccc ccgttcagcc  12300
cgaccgctgc gccttatccg gtaactatcg tcttgagtcc aacccggtaa gacacgactt  12360
atcgccactg gcagcagcca ctggtaacag gattagcaga gcgaggtatg taggcggtgc  12420
tacagagttc ttgaagtggt ggcctaacta cggctacact agaaggacag tatttggtat  12480
ctgcgctctg ctgaagccag ttaccttcgg aaaaagagtt ggtagctctt gatccggcaa  12540
acaaaccacc gctggtagcg gtggtttttt tgtttgcaag cagcagatta cgcgcagaaa  12600
aaaaggatct caagaagatc ctttgatctt ttctacgggg tctgacgctc agtggaacga  12660
aaactcacgt taagggattt tggtcatgag attatcaaaa aggatcttca cctagatcct  12720
tttaaattaa aaatgaagtt ttaaatcaat ctaaagtata tatgagtaaa cttggtctga  12780
cagttaccaa tgcttaatca gtgaggcacc tatctcagcg atctgtctat ttcgttcatc  12840
catagttgcc tgactccccg tcgtgtagat aactacgata cgggagggct taccatctgg  12900
ccccagtgct gcaatgatac cgcgagaccc acgctcaccg gctccagatt tatcagcaat  12960
aaaccagcca gccggaaggg ccgagcgcag aagtggtcct gcaactttat ccgcctccat  13020
ccagtctatt aattgttgcc gggaagctag agtaagtagt tcgccagtta atagtttgcg  13080
caacgttgtt gccattgcta caggcatcgt ggtgtcacgc tcgtcgtttg gtatggcttc  13140
attcagctcc ggttcccaac gatcaaggcg agttacatga tcccccatgt tgtgcaaaaa  13200
agcggttagc tccttcggtc ctccgatcgt tgtcagaagt aagttggccg cagtgttatc  13260
actcatggtt atggcagcac tgcataattc tcttactgtc atgccatccg taagatgctt  13320
ttctgtgact ggtgagtact caaccaagtc attctgagaa tagtgtatgc ggcgaccgag  13380
ttgctcttgc ccggcgtcaa tacgggataa taccgcgcca catagcagaa ctttaaaagt  13440
gctcatcatt ggaaaacgtt cttcggggcg aaaactctca aggatcttac cgctgttgag  13500
atccagttcg atgtaaccca ctcgtgcacc caactgatct tcagcatctt ttactttcac  13560
cagcgtttct gggtgagcaa aaacaggaag gcaaaatgcc gcaaaaaagg gaataagggc  13620
gacacggaaa tgttgaatac tcatactctt cctttttcaa tattattgaa gcatttatca  13680
gggttattgt ctcatgagcg gatacatatt tgaatgtatt tagaaaaata aacaaatagg  13740
ggttccgcgc acatttcccc gaaaagtgcc acctgaacga agcatctgtg cttcattttg  13800
tagaacaaaa atgcaacgcg agagcgctaa ttttttcaaac aaagaatctg agctgcattt  13860
ttacagaaca gaaatgcaac gcgaaagcgc tattttacca acgaagaatc tgtgcttcat  13920
ttttgtaaaa caaaaatgca acgcgagagc gctaattttt caaacaaaga atctgagctg  13980 cattttttaca gaacagaaat gcaacgcgag agcgctattt taccaacaaa gaatctatac  14040
ttcttttttg ttctacaaaa atgcatcccg agagcgctat ttttctaaca aagcatctta  14100
gattactttt tttctccttt gtgcgctcta taatgcagtc tcttgataac ttttttgcact  14160 gtaggtccgt taaggttaga agaaggctac tttggtgtct attttctctt ccataaaaaa  14220
agcctgactc cacttcccgc gtttactgat tactagcgaa gctgcgggtg cattttttca  14280
agataaaggc atccccgatt atattctata ccgatgtgga ttgcgcatac tttgtgaaca  14340
gaaagtgata gcgttgatga ttcttcattg gtcagaaaat tatgaacggt ttcttctatt  14400
ttgtctctat atactacgta taggaaatgt ttacattttc gtattgtttt cgattcactc  14460
tatgaatagt tcttactaca attttttgt ctaaagagta atactagaga taaacataaa  14520
```

```
aaatgtagag gtcgagttta gatgcaagtt caaggagcga aaggtggatg ggtaggttat     14580
atagggatat agcacagaga tatatagcaa agagatactt ttgagcaatg tttgtggaag     14640
cggtattcgc aatattttag tagctcgtta cagtccggtg cgttttggt tttttgaaag      14700 tgcgtcttca gagcgctttt ggttttcaaa agcgctctga agttcctata ctttctagag     14760
aataggaact tcggaatagg aacttcaaag cgtttccgaa aacgagcgct tccgaaaatg     14820
caacgcgagc tgcgcacata cagctcactg ttcacgtcgc acctatatct gcgtgttgcc     14880
tgtatatata tatacatgag aagaacggca tagtgcgtgt ttatgcttaa atgcgtactt     14940
atatgcgtct atttatgtag gatgaaaggt agtctagtac ctcctgtgat attatcccat     15000
tccatgcggg gtatcgtatg cttccttcag cactacccct tagctgttct atatgctgcc     15060
actcctcaat tggattagtc tcatccttca atgctatcat ttcctttgat attggatcat     15120
ctaagaaacc attattatca tgacattaac ctataaaaat aggcgtatca cgaggccctt     15180
tcgtc                                                                 15185

<210> SEQ ID NO 42
<211> LENGTH: 22833
<212> TYPE: DNA
<213> ORGANISM: Artificial
<220> FEATURE:
<223> OTHER INFORMATION: Plasmid

<400> SEQUENCE: 42
ccaactttgt ttggtctgat gagtccgtga ggacgaaacc cggagtcccg ggtcaccaaa        60
caaagttggg taaggatagt tcaatcaatg atcatcttct agtgcactta ggattcaaga       120
tcctattatc agggacaaga gcaggattag ggatatccga gatggccaca cttttaagga       180
gcttagcatt gttcaaaaga aacaaggaca aaccacccat tacatcagga tccggtggag       240
ccatcagagg aatcaaacac attattatag taccaatccc tggagattcc tcaattacca       300
ctcgatccag acttctggac cggttggtga ggttaattgg aaacccggat gtgagcgggc       360
ccaaactaac aggggcacta ataggtatat tatccttatt tgtggagtct ccaggtcaat       420
tgattcagag gatcaccgat gaccctgacg ttagcataag gctgttagag gttgtccaga       480
gtgaccagtc acaatctggc cttaccttcg catcaagagg taccaacatg gaggatgagg       540
cggaccaata cttttcacat gatgatccaa ttagtagtga tcaatccagg ttcggatggt       600
tcgggaacaa ggaaatctca gatattgaag tgcaagaccc tgagggattc aacatgattc       660
tgggtaccat cctagcccaa atttgggtct tgctcgcaaa ggcggttacg gccccagaca       720
cggcagctga ttcggagcta agaaggtgga taaagtacac ccaacaaaga agggtagttg       780
gtgaatttag attggagaga aaatggttgg atgtggtgag gaacaggatt gccgaggacc       840
tctccttacg ccgattcatg gtcgctctaa tcctggatat caagagaaca cccggaaaca       900
aacccaggat tgctgaaatg atatgtgaca ttgatacata tatcgtagag gcaggattag       960
ccagttttat cctgactatt aagtttggga tagaaactat gtatcctgct cttggactgc      1020
atgaatttgc tggtgagtta tccacacttg agtccttgat gaacctttac cagcaaatgg      1080
gggaaactgc accctacatg gtaatcctgg agaactcaat tcagaacaag ttcagtgcag      1140
gatcataccc tctgctctgg agctatgcca tgggagtagg agtggaactt gaaaactcca      1200
tgggaggttt gaactttggc cgatcttact ttgatccagc atattttaga ttagggcaag      1260
agatggtaag gaggtcagct ggaaaggtca gttccacatt ggcatctgaa ctcggtatca      1320
```

```
ctgccgagga tgcaaggctt gtttcagaga ttgcaatgca tactactgag gacaagatca   1380
gtagagcggt tggacccaga caagcccaag tatcatttct acacggtgat caaagtgaga   1440
atgagctacc gagattgggg ggcaaggaag ataggagggt caaacagagt cgaggagaag   1500
ccagggagag ctacagagaa accgggccca gcagagcaag tgatgcgaga gctgcccatc   1560
ttccaaccgg cacaccccta gacattgaca ctgcaacgga gtccagccaa gatccgcagg   1620
acagtcgaag gtcagctgac gccctgctta ggctgcaagc catggcagga atctcggaag   1680
aacaaggctc agacacggac accctatag tgtacaatga cagaaatctt ctagactagg    1740
tgcgagaggc cgagggccag aacaacatcc gcctaccatc catcattgtt ataaaaaact   1800
taggaaccag gtccacacag ccgccagccc atcaaccatc cactcccacg attggagcca   1860
atggcagaag agcaggcacg ccatgtcaaa aacggactgg aatgcatccg ggctctcaag   1920
gccgagccca tcggctcact ggccatcgag gaagctatgg cagcatggtc agaaatatca   1980
gacaacccag gacaggagcg agccacctgc agggaagaga aggcaggcag ttcgggtctc   2040
agcaaaccat gcctctcagc aattggatca actgaaggcg gtgcacctcg catccgcggt   2100
cagggacctg gagagagcga tgacgacgct gaaactttgg gaatcccccc aagaaatctc   2160
caggcatcaa gcactgggtt acagtgttat tacgtttatg atcacagcgg tgaagcggtt   2220
aagggaatcc aagatgctga ctctatcatg gttcaatcag gccttgatgg tgatagcacc   2280
ctctcaggag gagacaatga atctgaaaac agcgatgtgg atattggcga acctgatacc   2340
gagggatatg ctatcactga ccggggatct gctcccatct ctatggggtt cagggcttct   2400
gatgttgaaa ctgcagaagg aggggagatc cacgagctcc tgagactcca atccagaggc   2460
aacaactttc gaagcttgg gaaaactctc aatgttcctc cgcccccgga ccccggtagg    2520
gccagcactt ccgggacacc cattaaaaag ggcacagacg cgagattagc ctcatttgga   2580
acggagatcg cgtctttatt gacaggtggt gcaacccaat gtgctcgaaa gtcaccctcg   2640
gaaccatcag ggccaggtgc acctgcgggg aatgtccccg agtgtgtgag caatgccgca   2700
ctgatacagg agtggacacc cgaatctggt accacaatct ccccgagatc ccagaataat   2760
gaagaagggg gagactatta tgatgatgag ctgttctctg atgtccaaga tattaaaaca   2820
gccttggcca aaatacacga ggataatcag aagataatct ccaagctaga atcactgctg   2880
ttattgaagg gagaagttga gtcaattaag aagcagatca acaggcaaaa tatcagcata   2940
tccaccctgg aaggacacct ctcaagcatc atgatcgcca ttcctggact tgggaaggat   3000
cccaacgacc ccactgcaga tgtcgaaatc aatcccgact tgaaacccat cataggcaga   3060
gattcaggcc gagcactggc cgaagttctc aagaaacccg ttgccagccg acaactccaa   3120
ggaatgacaa atggacggac cagttccaga ggacagctgc tgaaggaatt tcagctaaag   3180
ccgatcggga aaaagatgag ctcagccgtc gggtttgttc ctgacaccgg ccctgcatca   3240
cgcagtgtaa tccgctccat tataaaatcc agccggctag aggaggatcg gaagcgttac   3300
ctgatgactc tccttgatga tatcaaagga gccaatgatc ttgccaagtt ccaccagatg   3360
ctgatgaaga taataatgaa gtagctacag ctcaacttac ctgccaaccc catgccagtc   3420
gacccaacta gtacaaccta aatccattat aaaaaactta ggagcaaagt gattgcctcc   3480
caaggtccac aatgacagag acctacgact tcgacaagtc ggcatgggac atcaaagggt   3540
cgatcgctcc gatacaaccc accacctaca gtgatggcag gctggtgccc caggtcagag   3600
tcatagatcc tggtctaggc gacaggaagg atgaatgctt tatgtacatg tttctgctgg   3660
gggttgttga ggacagcgat tccctagggc ctccaatcgg gcgagcattt gggttcctgc   3720
```

```
ccttaggtgt tggcagatcc acagcaaagc ccgaaaaact cctcaaagag gccactgagc    3780
ttgacatagt tgttagacgt acagcagggc tcaatgaaaa actggtgttc tacaacaaca    3840
ccccactaac tctcctcaca ccttggagaa aggtcctaac aacagggagt gtcttcaacg    3900
caaaccaagt gtgcaatgcg gttaatctga taccgctcga tacccgcag aggttccgtg     3960 ttgtttatat gagcatcacc cgtctttcgg ataacgggta ttacaccgtt cctagaagaa    4020
tgctggaatt cagatcggtc aatgcagtgg ccttcaacct gctggtgacc cttaggattg    4080
acaaggcgat aggccctggg aagatcatcg acaatacaga gcaacttcct gaggcaacat    4140
ttatggtcca catcgggaac ttcaggagaa agaagagtga agtctactct gccgattatt    4200
gcaaaatgaa aatcgaaaag atgggcctgg tttttgcact tggtgggata gggggcacca    4260
gtcttcacat tagaagcaca ggcaaaatga gcaagactct ccatgcacaa ctcgggttca    4320
agaagacctt atgttacccg ctgatggata tcaatgaaga ccttaatcga ttactctgga    4380
ggagcagatg caagatagta agaatccagg cagttttgca gccatcagtt cctcaagaat    4440
tccgcattta cgacgacgtg atcataaatg atgaccaagg actattcaaa gttctgtaga    4500
ccgtagtgcc cagcaatgcc cgaaaacgac cccctcaca atgacagcca gaaggcccgg     4560
acaaaaaagc cccctccgaa agactccacg gaccaagcga gaggccagcc agcagccgac    4620
ggcaagcgcg aacaccaggc ggccccagca cagaacagcc ctgacacaag gccaccacca    4680
gccaccccaa tctgcatcct cctcgtggga ccccgagga ccaaccccca aggctgcccc     4740
cgatccaaac caccaccgc atccccacca ccccgggaa agaaacccc agcaattgga       4800 aggcccctcc ccctcttcct caacacaaga actccacaac cgaaccgcac aagcgaccga    4860
ggtgacccaa ccgcaggcat ccgactccct agacagatcc tctctcccg gcaaactaaa     4920 caaaacttag ggccaaggaa catacacacc caacagaacc cagaccccgg cccacggcgc    4980
ccgcgcccca accccgaca accagaggga gccccaacc aatcccgccg gctccccgg       5040 tgcccacagg cagggacacc aaccccgaa cagacccagc acccaaccat cgacaatcca    5100
agacgggggg gccccccaa aaaaaggccc ccaggggccg acagccagca ccgcgaggaa    5160
gcccacccac cccacacacg accacggcaa ccaaaccaga acccagacca ccctgggcca    5220
ccagctccca gactcggcca tcaccccgca gaaaggaaag gccacaaccc gcgcacccca    5280
gccccgatcc ggcggggagc cacccaaccc gaaccagcac ccaagagcga tccccgaagg    5340 accccccgaac cgcaaaggac atcagtatcc cacagcctct ccaagtcccc cggtctcctc    5400
ctcttctcga agggaccaaa agatcaatcc accacacccg acgacactca actccccacc    5460
cctaaaggag acaccgggaa tcccagaatc aagactcatc caatgtccat catgggtctc    5520
aaggtgaacg tctctgccat attcatggca gtactgttaa ctctccaaac acccaccggt    5580
caaatccatt ggggcaatct ctctaagata ggggtggtag aataggaag tgcaagctac     5640 aaagttatga ctcgttccag ccatcaatca ttagtcataa aattaatgcc caatataact    5700
ctcctcaata actgcacgag ggtagagatt gcagaataca ggagactact gagaacagtt    5760
ttggaaccaa ttagagatgc acttaatgca atgacccaga atataagacc ggttcagagt    5820
gtagcttcaa gtaggagaca caagagattt gcgggagtag tcctggcagg tgcggcccta    5880
ggcgttgcca cagctgctca gataacagcc ggcattgcac ttcaccagtc catgctgaac    5940
tctcaagcca tcgacaatct gagagcgagc ctggaaacta ctaatcaggc aattgagaca    6000
atcagacaag cagggcagga gatgatattg gctgttcagg gtgtccaaga ctacatcaat    6060
```

```
aatgagctga taccgtctat gaaccaacta tcttgtgatt taatcggcca gaagctcggg      6120
ctcaaattgc tcagatacta tacagaaatc ctgtcattat ttggcccag tttacgggac       6180 cccatatctg cggagatatc tatccaggct ttgagctatg cgcttggagg agacatcaat     6240
aaggtgttag aaaagctcgg atacagtgga ggtgatttac tgggcatctt agagagcgga     6300
ggaataaagg cccggataac tcacgtcgac acagagtcct acttcattgt cctcagtata    6360
gcctatccga cgctgtccga gattaagggg gtgattgtcc accggctaga gggggtctcg    6420
tacaacatag gctctcaaga gtggtatacc actgtgccca agtatgttgc aacccaaggg    6480
taccttatct cgaattttga tgagtcatcg tgtactttca tgccagaggg gactgtgtgc    6540
agccaaaatg ccttgtaccc gatgagtcct ctgctccaag aatgcctccg ggggtacacc    6600
aagtcctgtg ctcgtacact cgtatccggg tcttttggga accggttcat tttatcacaa    6660
gggaacctaa tagccaattg tgcatcaatc ctttgcaagt gttacacaac aggaacgatc    6720
attaatcaag ccctgacaa gatcctaaca tacattgctg ccgatcactg cccggtagtc     6780
gaggtgaacg gcgtgaccat ccaagtcggg agcaggagg atccagacgc tgtgtacttg     6840
cacagaattg acctcggtcc tcccatatca ttggagaggt tggacgtagg gacaaatctg    6900
gggaatgcaa ttgctaagtt ggaggatgcc aaggaattgt tggagtcatc ggaccagata    6960
ttgaggagta tgaaaggttt atcgagcact agcatagtct acatcctgat tgcagtgtgt    7020
cttggagggt tgatagggat ccccgcttta atatgttgct gcagggggcg ttgtaacaaa    7080
aagggagaac aagttggtat gtcaagacca ggcctaaagc ctgatcttac gggaacatca    7140
aaatcctatg taaggtcgct ctgatcctct acaactcttg aaacacaaat gtcccacaag    7200
tctcctcttc gtcatcaagc aaccaccgca cccagcatca agcccacctg aaattatctc    7260
cggcttccct ctggccgaac aatatcggta gttaatcaaa acttagggtg caagatcatc    7320
cacaatgtca ccacaacgag accggataaa tgccttctac aaagataacc cccatcccaa    7380
gggaagtagg atagtcatta acagagaaca tcttatgatt gatagacctt atgttttgct    7440
ggctgttctg tttgtcatgt ttctgagctt gatcgggttg ctagccattg caggcattag    7500
acttcatcgg gcagccatct acaccgcaga gatccataaa agcctcagca ccaatctaga    7560
tgtaactaac tcaatcgagc atcaggtcaa ggacgtgctg acaccactct tcaaaatcat    7620
cggtgatgaa gtgggcctga ggacacctca gagattcact gacctagtga aattaatctc    7680
tgacaagatt aaattcctta atccggatag ggagtacgac ttcagagatc tcacttggtg    7740
tatcaacccg ccagagagaa tcaaattgga ttatgatcaa tactgtgcag atgtggctgc    7800
tgaagagctc atgaatgcat ggtgaactc aactctactg gagaccagaa caaccaatca    7860
gttcctagct gtctcaaagg gaaactgctc agggcccact acaatcagag gtcaattctc    7920
aaacatgtcg ctgtccctgt tagacttgta tttaggtcga ggttacaatg tgtcatctat    7980
agtcactatg acatcccagg gaatgtatgg gggaacttac ctagtggaaa agcctaatct    8040
gagcagcaaa aggtcagagt tgtcacaact gagcatgtac cgagtgtttg aagtaggtgt    8100
tatcagaaat ccgggttgg gggctccggt gttccatatg acaaactatc ttgagcaacc    8160
agtcagtaat gatctcagca actgtatggt ggctttgggg gagctcaaac tcgcagccct    8220
ttgtcacggg gaagattcta tcacaattcc ctatcaggga tcagggaaag tgtcagctt    8280 ccagctcgtc aagctaggtg tctggaaatc cccaaccgac atgcaatcct gggtcccctt    8340
atcaacggat gatccagtga tagacaggct ttacctctca tctcacagag gtgttatcgc    8400
tgacaatcaa gcaaaatggg ctgtcccgac aacacgaaca gatgacaagt tgcgaatgga    8460
```

```
gacatgcttc caacaggcgt gtaagggtaa aatccaagca ctctgcgaga atcccgagtg   8520
ggcaccattg aaggataaca ggattccttc atacggggtc ttgtctgttg atctgagtct   8580
gacagttgag cttaaaatca aaattgcttc gggattcggg ccattgatca cacacggttc   8640
agggatggac ctatacaaat ccaaccacaa caatgtgtat tggctgacta tcccgccaat   8700
gaagaaccta gccttaggtg taatcaacac attggagtgg ataccgagat tcaaggttag   8760
tccctacctc ttcactgtcc caattaagga agcaggcgaa gactgccatg ccccaacata   8820
cctacctgcg gaggtggatg gtgatgtcaa actcagttcc aatctggtga ttctacctgg   8880
tcaagatctc caatatgttt tggcaaccta cgatacttcc agggttgaac atgctgtggt   8940
ttattacgtt tacagcccaa gccgctcatt ttcttacttt tatcctttta ggttgcctat   9000
aaagggggtc cccatcgaat tacaagtgga atgcttcaca tgggaccaaa aactctggtg   9060
ccgtcacttc tgtgtgcttg cggactcaga atctggtgga catatcactc actctgggat   9120
ggtgggcatg ggagtcagct gcacagtcac ccgggaagat ggaaccaatc gcagataggg   9180
ctgctagtga accaatcaca tgatgtcacc cagacatcag gcatacccac tagtgtgaaa   9240
tagacatcag aattaagaaa aacgtagggt ccaagtggtt ccccgttatg gactcgctat   9300
ctgtcaacca gatcttatac cctgaagttc acctagatag cccgatagtt accaataaga   9360
tagtagccat cctggagtat gctcgagtcc ctcacgctta cagcctggag gaccctacac   9420
tgtgtcagaa catcaagcac cgcctaaaaa acggatttc caaccaaatg attataaaca   9480
atgtggaagt tgggaatgtc atcaagtcca agcttaggag ttatccggcc cactctcata   9540
ttccatatcc aaattgtaat caggatttat ttaacataga agacaaagag tcaacgagga   9600
agatccgtga actcctcaaa aagggggaatt cgctgtactc caaagtcagt gataaggttt   9660
tccaatgctt aagggacact aactcacggc ttggcctagg ctccgaattg agggaggaca   9720
tcaaggagaa agttattaac ttgggagttt acatgcacag ctcccagtgg tttgagccct   9780
ttctgttttg gtttacagtc aagactgaga tgaggtcagt gattaaatca caaacccata   9840
cttgccatag gaggagacac acacctgtat tcttcactgg tagttcagtt gagttgctaa   9900
tctctcgtga ccttgttgct ataatcagta aagagtctca acatgtatat tacctgacat   9960
ttgaactggt tttgatgtat tgtgatgtca tagaggggag gttaatgaca gagaccgcta  10020
tgactattga tgctaggtat acagagcttc taggaagagt cagatacatg tggaaactga  10080
tagatggttt cttccctgca ctcgggaatc caacttatca aattgtagcc atgctggagc  10140
ctcttttcact tgcttacctg cagctgaggg atataacagt agaactcaga ggtgctttcc  10200
ttaaccactg ctttactgaa atacatgatg ttcttgacca aaacgggttt tctgatgaag  10260
gtacttatca tgagttaact gaagctctag attacatttt cataactgat gacatacatc  10320
tgacaggga gattttctca ttttcagaa gtttcggcca ccccagactt gaagcagtaa  10380
cggctgctga aaatgttagg aaatacatga atcagcctaa agtcattgtg tatgagactc  10440
tgatgaaagg tcatgccata ttttgtggaa tcataatcaa cggctatcgt gacaggcacg  10500
gaggcagttg gccaccgctg accctccccc tgcatgctgc agacacaatc cggaatgctc  10560
aagcttcagg tgaagggtta acacatgagc agtgcgttga taactggaaa tcttttgctg  10620
gagtgaaatt tggctgcttt atgcctctta gcctggatag tgatctgaca atgtacctaa  10680
aggacaaggc acttgctgct ctccaaaggg aatgggatte agtttacccg aaagagttcc  10740
tgcgttacga ccctcccaag ggaaccgggt cacggaggct tgtagatgtt ttccttaatg  10800
```

```
attcgagctt tgacccatat gatgtgataa tgtatgttgt aagtggagct tacctccatg   10860
accctgagtt caacctgtct tacagcctga agaaaaagga gatcaaggaa acaggtagac   10920
tttttgctaa aatgacttac aaaatgaggg catgccaagt gattgctgaa aatctaatct   10980
caaacgggat tggcaaatat tttaaggaca atgggatggc caaggatgag cacgatttga   11040
ctaaggcact ccacactcta gctgtctcag gagtccccaa agatctcaaa gaaagtcaca   11100 gggggggggcc agtcttaaaa acctactccc gaagcccagt ccacacaagt accaggaacg   11160
tgagagcagc aaaagggttt atagggttcc ctcaagtaat tcggcaggac caagacactg   11220
atcatccgga gaatatggaa gcttacgaga cagtcagtgc atttatcacg actgatctca   11280
agaagtactg ccttaattgg agatatgaga ccatcagctt gtttgcacag aggctaaatg   11340
agatttacgg attgccctca ttttccagt ggctgcataa gaggcttgag acctctgtcc   11400
tgtatgtaag tgaccctcat tgcccccccg accttgacgc ccatatcccg ttatataaag   11460
tccccaatga tcaaatcttc attaagtacc ctatgggagg tatagaaggg tattgtcaga   11520
agctgtggac catcagcacc attccctatc tatacctggc tgcttatgag agcggagtaa   11580
ggattgcttc gttagtgcaa ggggacaatc agaccatagc cgtaacaaaa agggtaccca   11640
gcacatggcc ctacaacctt aagaaacggg aagctgctag agtaactaga gattactttg   11700
taattcttag gcaaaggcta catgatattg gccatcacct caaggcaaat gagacaattg   11760
tttcatcaca ttttttttgtc tattcaaaag gaatatatta tgatgggcta cttgtgtccc   11820
aatcactcaa gagcatcgca agatgtgtat tctggtcaga gactatagtt gatgaaacaa   11880
gggcagcatg cagtaatatt gctacaacaa tggctaaaag catcgagaga ggttatgacc   11940
gttaccttgc atattccctg aacgtcctaa aagtgataca gcaaattctg atctctcttg   12000
gcttcacaat caattcaacc atgacccggg atgtagtcat acccctcctc acaaacaacg   12060
acctcttaat aaggatggca ctgttgcccg ctcctattgg ggggatgaat tatctgaata   12120
tgagcaggct gtttgtcaga aacatcggtg atccagtaac atcatcaatt gctgatctca   12180
agagaatgat tctcgcctca ctaatgcctg aagagaccct ccatcaagta atgacacaac   12240
aaccggggga ctcttcattc ctagactggg ctagcgaccc ttactcagca aatcttgtat   12300
gtgtccagag catcactaga ctcctcaaga acataactgc aaggtttgtc ctgatccata   12360
gtccaaaccc aatgttaaaa ggattattcc atgatgacag taaagaagag gacgagggac   12420
tggcggcatt cctcatggac aggcatatta tagtacctag ggcagctcat gaaatcctgg   12480
atcatagtgt cacaggggca agagagtcta ttgcaggcat gctggatacc acaaaaggct   12540
tgattcgagc cagcatgagg aagggggggt taacctctcg agtgataacc agattgtcca   12600
attatgacta tgaacaattc agagcaggga tggtgctatt gacaggaaga aagagaaatg   12660
tcctcattga caaagagtca tgttcagtgc agctggcgag agctctaaga agccatatgt   12720
gggcgaggct agctcgagga cggcctattt acggccttga ggtccctgat gtactagaat   12780
ctatgcgagg ccaccttatt cggcgtcatg agacatgtgt catctgcgag tgtggatcag   12840
tcaactacgg atggttttttt gtcccctcgg gttgccaact ggatgatatt gacaaggaaa   12900
catcatcctt gagagtccca tatattggtt ctaccactga tgagaaaca gacatgaagc   12960 ttgccttcgt aagagcccca agtcgatcct tgcgatctgc tgttagaata gcaacagtgt   13020
actcatgggc ttacggtgat gatgatagct cttggaacga agcctggttg ttggctaggc   13080
aaagggccaa tgtgagcctg gaggagctaa gggtgatcac tcccatctca acttcgacta   13140
atttagcgca taggttgagg gatcgtagca ctcaagtgaa atactcaggt acatcccttg   13200
```

-continued

```
tccgagtggc gaggtatacc acaatctcca cgacaatct ctcatttgtc atatcagata    13260
agaaggttga tactaacttt atataccaac aaggaatgct tctagggttg ggtgttttag    13320
aaacattgtt tcgactcgag aaagataccg gatcatctaa cacggtatta catcttcacg    13380
tcgaaacaga ttgttgcgtg atcccgatga tagatcatcc caggataccc agctcccgca    13440
agctagagct gagggcagag ctatgtacca acccattgat atatgataat gcacctttaa    13500
ttgacagaga tgcaacaagg ctatacaccc agagccatag gaggcaccct gtggaatttg    13560
ttacatggtc cacaccccaa ctatatcaca ttttagctaa gtccacagca ctatctatga    13620
ttgacctggt aacaaaattt gagaaggacc atatgaatga aatttcagct ctcatagggg    13680
atgacgatat caatagtttc ataactgagt ttctgctcat agagccaaga ttattcacta    13740
tctacttggg ccagtgtgcg gccatcaatt gggcatttga tgtacattat catagaccat    13800
cagggaaata tcagatgggt gagctgttgt catcgttcct ttctagaatg agcaaaggag    13860
tgtttaaggt gcttgtcaat gctctaagcc acccaaagat ctacaagaaa ttctggcatt    13920
gtggtattat agagcctatc catggtcctt cacttgatgc tcaaaacttg cacacaactg    13980
tgtgcaacat ggtttacaca tgctatatga cctacctcga cctgttgttg aatgaagagt    14040
tagaagagtt cacatttctc ttgtgtgaaa gcgacgagga tgtagtaccg gacagattcg    14100
acaacatcca ggcaaaacac ttatgtgttc tggcagattt gtactgtcaa ccagggacct    14160
gcccaccaat tcgaggtcta agaccggtag agaaatgtgc agttctaacc gaccatatca    14220
aggcagaggc tatgttatct ccagcaggat cttcgtggaa cataaatcca attattgtag    14280
accattactc atgctctctg acttatctcc ggcgaggatc gatcaaacag ataagattga    14340
gagttgatcc aggattcatt ttcgacgccc tcgctgaggt aaatgtcagt cagccaaaga    14400
tcggcagcaa caacatctca aatatgagca tcaaggcttt cagaccccca cacgatgatg    14460
ttgcaaaatt gctcaaagat atcaacacaa gcaagcacaa tcttcccatt tcaggggggca    14520
atctcgccaa ttatgaaatc catgctttcc gcagaatcgg gttgaactca tctgcttgct    14580
acaaagctgt tgagatatca acattaatta ggagatgcct tgagccaggg gaggacggct    14640
tgttcttggg tgagggatcg ggttctatgt tgatcactta taaagagata cttaaactaa    14700
acaagtgctt ctataatagt ggggtttccg ccaattctag atctggtcaa agggaattag    14760
caccctatcc ctccgaagtt ggccttgtcg aacacagaat gggagtaggt aatattgtca    14820
aagtgctctt taacgggagg cccgaagtca cgtgggtagg cagtgtagat tgcttcaatt    14880
tcatagttag taatatccct acctctagtg tggggtttat ccattcagat atagagacct    14940
tgcctgacaa agatactata gagaagctag aggaattggc agccatctta tcgatggctc    15000
tgctcctggg caaaatagga tcaatactgg tgattaagct tatgccttc agcggggatt    15060
ttgttcaggg atttataagt tatgtagggt ctcattatag agaagtgaac cttgtatacc    15120
ctagatacag caacttcatc tctactgaat cttatttggt tatgacagat ctcaaggcta    15180
accggctaat gaatcctgaa aagattaagc agcagataat tgaatcatct gtgaggactt    15240
cacctggact tataggtcac atcctatcca ttaagcaact aagctgcata caagcaattg    15300
tgggagacgc agttagtaga ggtgatatca atccctactct gaaaaaactt acacctatag    15360
agcaggtgct gatcaattgc gggttggcaa ttaacggacc taagctgtgc aaagaattga    15420
tccaccatga tgttgcctca gggcaagatg gattgcttaa ttctatactc atcctctaca    15480
gggagttggc aagattcaaa gacaaccaaa gaagtcaaca agggatgttc cacgcttacc    15540
```

```
ccgtattggt aagtagcagg caacgagaac ttatatctag gatcacccgc aaattctggg    15600
ggcacattct tctttactcc gggaacaaaa agttgataaa taagtttatc cagaatctca    15660
agtccggcta tctgatacta gacttacacc agaatatctt cgttaagaat ctatccaagt    15720
cagagaaaca gattattatg acgggggggtt tgaaacgtga gtgggttttt aaggtaacag    15780
tcaaggagac caaagaatgg tataagttag tcggatacag tgccctgatt aaggactaat    15840
tggttgaact ccggaaccct aatcctgccc taggtggtta ggcattattt gcaatatatt    15900
aaagaaaact ttgaaaatac gaagtttcta ttcccagctt tgtctggtgg ccggcatggt    15960
cccagcctcc tcgctggcgc cggctgggca acattccgag gggaccgtcc cctcggtaat    16020
ggcgaatggg acgcggccga tccggctgct aacaaagccc gaaaggaagc tgagttggct    16080
gctgccaccg ctgagcaata actagcataa ccccttgggg cctctaaacg ggtcttgagg    16140
ggttttttgc tgaaaggagg aactatatcc ggatgcggcc gcactagtat cgatggatta    16200
caaggatgac gacgataaga tctgagctct taattaacaa ttcttcgcca gaggtttggt    16260
caagtctcca atcaaggttg tcggcttgtc taccttgcca gaaatttacg aaaagatgga    16320
aaagggtcaa atcgttggta gatacgttgt tgacacttct aaataagcga atttcttatg    16380
atttatgatt tttattatta aataagttat aaaaaaaata agtgtataca aattttaaag    16440
tgactcttag gttttaaaac gaaaattctt attcttgagt aactctttcc tgtaggtcag    16500
gttgctttct caggtatagc atgaggtcgc tccaattcag ctggcgtaat agcgaagagg    16560
cccgcaccga tcgcccttcc caacagttgc gcagcctgaa tggcgaatgg acgcgccctg    16620
tagcggcgca ttaagcgcgg cgggtgtggt ggttacgcgc agcgtgaccg ctacacttgc    16680
cagcgcccta gcgcccgctc ctttcgcttt cttcccttcc tttctcgcca cgttcgccgg    16740
ctttccccgt caagctctaa atcggggggct ccctttaggg ttccgattta gtgctttacg    16800
gcacctcgac cccaaaaaac ttgattaggg tgatggttca cgtagtgggc catcgccctg    16860
atagacggtt tttcgccctt tgacgttgga gtccacgttc tttaatagtg gactcttgtt    16920
ccaaactgga acaacactca accctatctc ggtctattct tttgatttat aagggatttt    16980
gccgatttcg gcctattggt taaaaaatga gctgatttaa caaaaattta acgcgaattt    17040
taacaaaata ttaacgttta caatttcctg atgcggtatt ttctccttac gcatctgtgc    17100
ggtatttcac accgcatagg gtaataactg atataattaa attgaagctc taatttgtga    17160
gtttagtata catgcattta cttataatac agttttttag ttttgctggc cgcatcttct    17220
caaatatgct tcccagcctg cttttctgta acgttcaccc tctacctag catcccttcc    17280 ctttgcaaat agtcctcttc caacaataat aatgtcagat cctgtagaga ccacatcatc    17340
cacggttcta tactgttgac ccaatgcgtc tcccttgtca tctaaaccca caccgggtgt    17400
cataatcaac caatcgtaac cttcatctct tccacccatg tctctttgag caataaagcc    17460
gataacaaaa tctttgtcgc tcttcgcaat gtcaacagta cccttagtat attctccagt    17520
agatagggag cccttgcatg acaattctgc taacatcaaa aggcctctag gttcctttgt    17580
tacttcttct gccgcctgct tcaaaccgct aacaatacct gggcccacca caccgtgtgc    17640
attcgtaatg tctgcccatt ctgctattct gtatacaccc gcagagtact gcaatttgac    17700
tgtattacca atgtcagcaa attttctgtc ttcgaagagt aaaaaattgt acttggcgga    17760
taatgccttt agcggcttaa ctgtgccctc catggaaaaa tcagtcaaga tatccacatg    17820
tgtttttagt aaacaaattt tgggacctaa tgcttcaact aactccagta attccttggt    17880
ggtacgaaca tccaatgaag cacacaagtt tgtttgcttt tcgtgcatga tattaaatag    17940
```

```
cttggcagca acaggactag gatgagtagc agcacgttcc ttatatgtag ctttcgacat   18000
gatttatctt cgtttcctgc aggtttttgt tctgtgcagt tgggttaaga atactgggca   18060
atttcatgtt tcttcaacac tacatatgcg tatatatacc aatctaagtc tgtgctcctt   18120
ccttcgttct tccttctgtt cggagattac cgaatcaaaa aaatttcaaa gaaaccgaaa   18180
tcaaaaaaaa gaataaaaaa aaaatgatga attgaattga aaagctgtgg tatggtgcac   18240
tctcagtaca atctgctctg atgccgcata gttaagccag ccccgacacc cgccaacacc   18300
cgctgacgcg ccctgacggg cttgtctgct cccggcatcc gcttacagac aagctgtgac   18360
cgtctccggg agctgcatgt gtcagaggtt ttcaccgtca tcaccgaaac gcgcgagacg   18420
aaagggcctc gtgatacgcc tatttttata ggttaatgtc atgataataa tggtttctta   18480
gtatgatcca atatcaaagg aaatgatagc attgaaggat gagactaatc caattgagga   18540
gtggcagcat atagaacagc taaagggtag tgctgaagga agcatacgat accccgcatg   18600
gaatgggata atatcacagg aggtactaga ctacctttca tcctacataa atagacgcat   18660
ataagtacgc atttaagcat aaacacgcac tatgccgttc ttctcatgta tatatatata   18720
caggcaacac gcagatatag gtgcgacgtg aacagtgagc tgtatgtgcg cagctcgcgt   18780
tgcattttcg gaagcgctcg ttttcggaaa cgctttgaag ttcctattcc gaagttccta   18840
ttctctagaa agtataggaa cttcagagcg cttttgaaaa ccaaaagcgc tctgaagacg   18900
cactttcaaa aaccaaaaa cgcaccggac tgtaacgagc tactaaaata ttgcgaatac   18960
cgcttccaca aacattgctc aaaagtatct ctttgctata tatctctgtg ctatatccct   19020
atataaccta cccatccacc tttcgctcct tgaacttgca tctaaactcg acctctacat   19080
tttttatgtt tatctctagt attactcttt agacaaaaaa attgtagtaa gaactattca   19140
tagagtgaat cgaaaacaat acgaaaatgt aaacatttcc tatacgtagt atatagagac   19200
aaaatagaag aaaccgttca taattttctg accaatgaag aatcatcaac gctatcactt   19260
tctgttcaca agtatgcgc aatccacatc ggtatagaat ataatcgggg atgcctttat   19320
cttgaaaaaa tgcacccgca gcttcgctag taatcagtaa acgcgggaag tggagtcagg   19380
ctttttttat ggaagagaaa atagacacca aagtagcctt cttctaacct taacggacct   19440
acagtgcaaa aagttatcaa gagactgcat tatagagcgc acaaaggaga aaaaaagtaa   19500
tctaagatgc tttgttagaa aaatagcgct ctcgggatgc attttgtag aacaaaaaag   19560
aagtatagat tctttgttgg taaaatagcg ctctcgcgtt gcatttctgt tctgtaaaaa   19620
tgcagctcag attctttgtt tgaaaaatta gcgctctcgc gttgcatttt tgttttacaa   19680
aaatgaagca cagattcttc gttggtaaaa tagcgctttc gcgttgcatt tctgttctgt   19740
aaaaatgcag ctcagattct ttgtttgaaa aattagcgct ctcgcgttgc atttttgttc   19800
tacaaaatga agcacagatg cttcgttcag gtggcacttt tcggggaaat gtgcgcggaa   19860
cccctatttg tttatttttc taaatacatt caaatatgta tccgctcatg agacaataac   19920
cctgataaat gcttcaataa tattgaaaaa ggaagagtat gagtattcaa catttccgtg   19980
tcgcccttat tcccttttt gcggcatttt gccttcctgt ttttgctcac ccagaaacgc   20040
tggtgaaagt aaaagatgct gaagatcagt tgggtgcacg agtgggttac atcgaactgg   20100
atctcaacag cggtaagatc cttgagagtt ttcgccccga agaacgtttt ccaatgatga   20160
gcacttttaa agttctgcta tgtggcgcgg tattatcccg tattgacgcc gggcaagagc   20220
aactcggtcg ccgcatacac tattctcaga atgacttggt tgagtactca ccagtcacag   20280
```

```
aaaagcatct tacggatggc atgacagtaa gagaattatg cagtgctgcc ataaccatga   20340
gtgataacac tgcggccaac ttacttctga caacgatcgg aggaccgaag gagctaaccg   20400
cttttttgca caacatgggg gatcatgtaa ctcgccttga tcgttgggaa ccggagctga   20460
atgaagccat accaaacgac gagcgtgaca ccacgatgcc tgtagcaatg caacaacgt    20520 tgcgcaaact attaactggc gaactactta ctctagcttc ccggcaacaa ttaatagact   20580
ggatggaggc ggataaagtt gcaggaccac ttctgcgctc ggcccttccg gctggctggt   20640
ttattgctga taaatctgga gccggtgagc gtgggtctcg cggtatcatt gcagcactgg   20700
ggccagatgg taagccctcc cgtatcgtag ttatctacac gacggggagt caggcaacta   20760
tggatgaacg aaatagacag atcgctgaga taggtgcctc actgattaag cattggtaac   20820
tgtcagacca agtttactca tatatacttt agattgattt aaaacttcat ttttaattta   20880
aaaggatcta ggtgaagatc ctttttgata atctcatgac caaaatccct taacgtgagt   20940
tttcgttcca ctgagcgtca gaccccgtag aaaagatcaa aggatcttct tgagatcctt   21000
tttttctgcg cgtaatctgc tgcttgcaaa caaaaaaacc accgctacca gcggtggttt   21060
gtttgccgga tcaagagcta ccaactcttt ttccgaaggt aactggcttc agcagagcgc   21120
agataccaaa tactgtcctt ctagtgtagc cgtagttagg ccaccacttc aagaactctg   21180
tagcaccgcc tacatacctc gctctgctaa tcctgttacc agtggctgct gccagtggcg   21240
ataagtcgtg tcttaccggg ttggactcaa gacgatagtt accggataag cgcagcggt    21300 cgggctgaac ggggggttcg tgcacacagc ccagcttgga gcgaacgacc tacaccgaac   21360
tgagatacct acagcgtgag ctatgagaaa gcgccacgct tcccgaaggg agaaaggcgg   21420
acaggtatcc ggtaagcggc agggtcggaa caggagagcg cacgagggag cttccagggg   21480
gaaacgcctg gtatctttat agtcctgtcg ggtttcgcca cctctgactt gagcgtcgat   21540
ttttgtgatg ctcgtcaggg gggcggagcc tatggaaaaa cgccagcaac gcggcctttt   21600
tacggttcct ggccttttgc tggccttttg ctcacatgtt ctttcctgcg ttatcccctg   21660
attctgtgga taaccgtatt accgcctttg agtgagctga taccgctcgc cgcagccgaa   21720
cgaccgagcg cagcgagtca gtgagcgagg aagcggaaga gcgcccaata cgcaaaccgc   21780
ctctccccgc gcgttggccg attcattaat gcagctggat cttcgagcgt cccaaaacct   21840
tctcaagcaa ggttttcagt ataatgttac atgcgtacac gcgtctgtac agaaaaaaaa   21900
gaaaaatttg aaatataaat aacgttctta atactaacat aactataaaa aaataaatag   21960
ggacctagac ttcaggttgt ctaactcctt ccttttcggt tagagcggat cttagctagc   22020
cgcggtacca agcttactcg aggtcttctt cggaaatcaa cttctgttcc atgtcgacgc   22080
ccgggcccta tagtgagtcg tattacggat ccggggtttt ttctccttga cgttaaagta   22140
tagaggtata ttaacaattt tttgttgata cttttattac atttgaataa gaagtaatac   22200
aaaccgaaaa tgttgaaagt attagttaaa gtggttatgc agttttttgca tttatatatc   22260 tgttaataga tcaaaaatca tcgcttcgct gattaattac cccagaaata aggctaaaaa   22320
actaatcgca ttatcatcct atggttgtta atttgattcg ttcatttgaa ggtttgtggg   22380
gccaggttac tgccaatttt tcctcttcat aaccataaaa gctagtattg tagaatcttt   22440
attgttcgga gcagtgcggc gcgaggcaca tctgcgtttc aggaacgcga ccggtgaaga   22500
cgaggacgca cggaggagag tcttccttcg ggggctgtc acccgctcgg cggcttctaa    22560
tccgtacttc aatatagcaa tgagcagtta agcgtattac tgaaagttcc aaagagaagg   22620
tttttttagg ctaagataat ggggctcttt acatttccac aacatataag taagattaga   22680
```

-continued

| | |
|---|---|
| tatggatatg tatatggata tgtatatggt ggtaatgcca tgtaatatga ttattaaact | 22740 |
| tctttgcgtc catccaaaaa aaaagtaaga atttttgaaa attcgaattc aaccctcact | 22800 |
| aaagggcggc cgctaatacg actcactata ggg | 22833 |

<210> SEQ ID NO 43
<211> LENGTH: 6339
<212> TYPE: DNA
<213> ORGANISM: Artificial
<220> FEATURE:
<223> OTHER INFORMATION: Plasmid

<400> SEQUENCE: 43

| | |
|---|---|
| gtacggatta gaagccgccg agcgggtgac agccctccga aggaagactc tcctccgtgc | 60 |
| gtcctcgtcc tcaccggtcg cgttcctgaa acgcagatgt gcctcgcgcc gcactgctcc | 120 |
| gaacaataaa gattctacaa tactagcttt tatggttatg aagaggaaaa attggcagta | 180 |
| acctggcccc acaaaccttc aaatgaacga atcaaattaa caaccatagg atgataatgc | 240 |
| gattagtttt ttagccttat ttctggggta attaatcagc gaagcgatga ttttttgatct | 300 |
| attaacagat atataaatgc aaaaactgca ttaaccactt taactaatac tttcaacatt | 360 |
| ttcggtttgt attacttctt attcaaatgt aataaaagta tcaacaaaaa attgttaata | 420 |
| tacctctata ctttaacgtc aaggagaaaa acccccggat cggactacta gcagctgtaa | 480 |
| tacgactcac tatagggaat attaagcttg gtaccgagct cggatccact agtaacggcc | 540 |
| gccagtgtgc tggaattcga gctcggtacc tcgcgaatgc atctagatat cggatcccgc | 600 |
| ggccgccaac tttgtttggt ctgatgagtc cgtgaggacg aaacccggag tcccgggtca | 660 |
| ccagacaaag ctgggaatag aaacttcgta ttttcaaagt tttctttaat atattgcaaa | 720 |
| taatgcctaa ccacctaggg caggattagg gttccggagt tcaaccaatt agtccttaat | 780 |
| cagggcactg tatccgacta acttatacca ttctttggac tagtgacgtc cgcggtcgac | 840 |
| acgtgagatc tgatggccat ctcggatatc cctaatcctg ctcttgtccc tgataatagg | 900 |
| atcttgaatc ctaagtgcac tagaagatga tcattgattg aactatcctt acccaacttt | 960 |
| gtttggtgcc ggcatggtcc cagcctcctc gctggcgccg gctgggcaac attccgaggg | 1020 |
| gaccgtcccc tcggtaatgg cgaatgggac gggcccgtcg actgcagagg cctgcatgca | 1080 |
| tctagagggc cgcatcatgt aattagttat gtcacgctta cattcacgcc ctcccccac | 1140 |
| atccgctcta accgaaaagg aaggagttag acaacctgaa gtctaggtcc ctatttattt | 1200 |
| ttttatagtt atgttagtat taagaacgtt atttatattt caattttttc ttttttttct | 1260 |
| gtacagacgc gtgtacgcat gtaacattat actgaaaacc ttgcttgaga aggttttggg | 1320 |
| acgctcgaag gctttaattt gcggccctgc attaatgaat cggccaacgc gcggggagag | 1380 |
| gcggtttgcg tattgggcgc tcttccgctt cctcgctcac tgactcgctg cgctcggtcg | 1440 |
| ttcggctgcg gcgagcggta tcagctcact caaaggcggt aatacggtta tccacagaat | 1500 |
| cagggggataa cgcaggaaag aacatgtgag caaaaggcca gcaaagccc aggaaccgta | 1560 |
| aaaaggccgc gttgctggcg ttttttccata ggctccgccc ccctgacgag catcacaaaa | 1620 |
| atcgacgctc aagtcagagg tggcgaaacc cgacaggact ataaagatac caggcgtttc | 1680 |
| cccctggaag ctccctcgtg cgctctcctg ttccgaccct gccgcttacc ggatacctgt | 1740 |
| ccgcctttct cccttcggga agcgtggcgc tttctcatag ctcacgctgt aggtatctca | 1800 |
| gttcggtgta ggtcgttcgc tccaagctgg gctgtgtgca cgaaccccc gttcagcccg | 1860 |

```
accgctgcgc cttatccggt aactatcgtc ttgagtccaa cccggtaaga cacgacttat    1920
cgccactggc agcagccact ggtaacagga ttagcagagc gaggtatgta ggcggtgcta    1980
cagagttctt gaagtggtgg cctaactacg gctacactag aaggacagta tttggtatct    2040
gcgctctgct gaagccagtt accttcggaa aaagagttgg tagctcttga tccggcaaac    2100
aaaccaccgc tggtagcggt ggtttttttg tttgcaagca gcagattacg cgcagaaaaa    2160
aaggatctca agaagatcct ttgatctttt ctacggggtc tgacgctcag tggaacgaaa    2220
actcacgtta agggattttg gtcatgagat tatcaaaaag gatcttcacc tagatccttt    2280
taaattaaaa atgaagtttt aaatcaatct aaagtatata tgagtaaact tggtctgaca    2340
gttaccaatg cttaatcagt gaggcaccta tctcagcgat ctgtctattt cgttcatcca    2400
tagttgcctg actccccgtc gtgtagataa ctacgatacg ggagcgctta ccatctggcc    2460
ccagtgctgc aatgataccg cgagacccac gctcaccggc tccagattta tcagcaataa    2520
accagccagc cggaagggcc gagcgcagaa gtggtcctgc aactttatcc gcctccattc    2580
agtctattaa ttgttgccgg gaagctagag taagtagttc gccagttaat agtttgcgca    2640
acgttgttgg cattgctaca ggcatcgtgg tgtcactctc gtcgtttggt atggcttcat    2700
tcagctccgg ttcccaacga tcaaggcgag ttacatgatc ccccatgttg tgcaaaaagc    2760
ggttagctcc ttcggtcctc cgatcgttgt cagaagtaag ttggccgcag tgttatcact    2820
catggttatg gcagcactgc ataattctct tactgtcatg ccatccgtaa gatgcttttc    2880
tgtgactggt gagtactcaa ccaagtcatt ctgagaatag tgtatgcggc gaccgagttg    2940
ctcttgcccg gcgtcaatac gggataatag tgtatcacat agcagaactt taaaagtgct    3000
catcattgga aaacgttctt cggggcgaaa actctcaagg atcttaccgc tgttgagatc    3060
cagttcgatg taacccactc gtgcacccaa ctgatcttca gcatctttta ctttcaccag    3120
cgtttctggg tgagcaaaaa caggaaggca aaatgccgca aaaaagggaa taagggcgac    3180
acggaaatgt tgaatactca tactcttcct ttttcaatgg gtaataactg atataattaa    3240
attgaagctc taatttgtga gtttagtata catgcattta cttataatac agttttttag    3300
ttttgctggc cgcatcttct caaatatgct tcccagcctg cttttctgta acgttcaccc    3360
tctaccttag catcccttcc cttttgcaaat agtcctcttc aacaataat aatgtcagat    3420 cctgtagaga ccacatcatc cacggttcta tactgttgac ccaatgcgtc tcccttgtca    3480
tctaaaccca caccgggtgt cataatcaac caatcgtaac cttcatctct tccacccatg    3540
tctctttgag caataaagcc gataacaaaa tctttgtcgc tcttcgcaat gtcaacagta    3600
cccttagtat attctccagt agatagggag cccttgcatg acaattctgc taacatcaaa    3660
aggcctctag gttcctttgt tacttcttct gccgcctgct tcaaaccgct aacaatacct    3720
gggcccacca caccgtgtgc attcgtaatg tctgcccatt ctgctattct gtatacaccc    3780
gcagagtact gcaatttgac tgtattacca atgtcagcaa atttttctgtc ttcgaagagt    3840 aaaaaattgt acttggcgga taatgccttt agcggcttaa ctgtgccctc catgaaaaa    3900 tcagtcaaga tatccacatg tgtttttagt aaacaaattt tgggacctaa tgcttcaact    3960
aactccagta attccttggt ggtacgaaca tccaatgaag cacacaagtt tgtttgcttt    4020
tcgtgcatga tattaaatag cttggcagca acaggactag gatgagtagc agcacgttcc    4080
ttatatgtag ctttcgacat gatttatctt cgtttcctgc aggtttttgt tctgtgcagt    4140
tgggttaaga atactgggca atttcatgtt tcttcaacac tacatatgcg tatatatacc    4200
aatctaagtc tgtgctcctt ccttcgttct tccttctgtt cggagattac cgaatcaaaa    4260
```

```
aaatttcaaa gaaaccgaaa tcaaaaaaaa gaataaaaaa aaatgatgaa attgaattga    4320
aaagctagct tatcgatgat aagctgtcaa agatgagaat taattccacg gactatagac    4380
tatactagat actccgtcta ctgtacgata cacttccgct caggtccttg tcctttaacg    4440
aggccttacc actcttttgt tactctattg atccagctca gcaaaggcag tgtgatctaa    4500
gattctatct tcgcgatgta gtaaaactag ctagaccgag aaagagacta gaaatgcaaa    4560
aggcacttct acaatggctg ccatcattat tatccgatgt gacgctgcag cttctcaatg    4620
atattcgaat acgctttgag gagatacagc ctaatatccg acaaactgtt ttacagattt    4680
acgatcgtac ttgttaccca tcattgaatt ttgaacatcc gaacctggga gttttccctg    4740
aaacagatag tatatttgaa cctgtataat aatatatagt ctagcgcttt acggaagaca    4800
atgtatgtat ttcggttcct ggagaaacta ttgcatctat tgcataggta atcttgcacg    4860
tcgcatcccc ggttcatttt ctgcgtttcc atcttgcact tcaatagcat atctttgtta    4920
acgaagcatc tgtgcttcat tttgtagaac aaaaatgcaa cgcgagagcg ctaattttc    4980 aaacaaagaa tctgagctgc atttttacag aacagaaatg caacgcgaaa gcgctatttt    5040
accaacgaag aatctgtgct tcatttttgt aaaacaaaaa tgcaacgcga cgagagcgct    5100 aattttcaa acaaagaatc tgagctgcat tttacagaa cagaaatgca acgcgagagc     5160
gctattttac caacaagaa tctatacttc ttttttgttc tacaaaaatg catcccgaga    5220
gcgctatttt tctaacaaag catcttagat tactttttt ctcctttgtg cgctctataa    5280
tgcagtctct tgataacttt ttgcactgta ggtccgttaa ggttagaaga aggctactt    5340 ggtgtctatt ttctcttcca taaaaaaagc ctgactccac ttcccgcgtt tactgattac    5400
tagcgaagct gcgggtgcat ttttcaaga taaaggcatc cccgattata ttctataccg    5460
atgtggattg cgcatacttt gtgaacagaa agtgatagcg ttgatgattc ttcattggtc    5520
agaaaattat gaacggtttc ttctatttg tctctatata ctacgtatag gaatgttta    5580 cattttcgta ttgttttcga ttcactctat gaatagttct tactacaatt tttttgtcta    5640
aagagtaata ctagagataa acataaaaaa tgtagaggtc gagtttagat gcaagttcaa    5700
ggagcgaaag gtggatgggt aggttatata gggatatagc acagagatat atagcaaaga    5760 gatactttg agcaatgttt gtggaagcgg tattcgcaat gggaagctcc accccgttg     5820 ataatcagaa aagccccaaa acaggaaga ttgtataagc aaatatttaa attgtaaacg    5880
ttaatatttt gttaaaattc gcgttaaatt tttgttaaat cagctcattt tttaacgaat    5940
agcccgaaat cggcaaaatc ccttataaat caaaagaata gaccgagata gggttgagtg    6000
ttgttccagt ttccaacaag agtccactat taaagaacgt ggactccaac gtcaagggc    6060 gaaaagggc ctatcagggc gatggcccac tacgtgaacc atcaccctaa tcaagttttt    6120
tggggtcgag gtgccgtaaa gcagtaaatc ggaagggtaa acggatgccc ccatttagag    6180 cttgacggg aaagccggcg aacgtggcga aaggaagg gaagaaagcg aaaggagcgg     6240
gggctagggc ggtgggaagt gtaggggtca cgctggcgt aaccaccaca cccgccgcgc    6300 ttaatgggc gctacagggc gcgtggggat gatccacta                            6339
```

<210> SEQ ID NO 44
<211> LENGTH: 20712
<212> TYPE: DNA
<213> ORGANISM: Artificial
<220> FEATURE:
<223> OTHER INFORMATION: Plasmid

<400> SEQUENCE: 44

```
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag ggacaagagc aggattaggg     180
atatccgaga tggccacact tttaaggagc ttagcattgt tcaaaagaaa caaggacaaa     240
ccacccatta catcaggatc cggtggagcc atcagaggaa tcaaacacat tattatagta     300
ccaatccctg gagattcctc aattaccact cgatccagac ttctggaccg gttggtgagg     360
ttaattggaa acccggatgt gagcgggccc aaactaacag gggcactaat aggtatatta     420
tccttatttg tggagtctcc aggtcaattg attcagagga tcaccgatga ccctgacgtt     480
agcataaggc tgttagaggt tgtccagagt gaccagtcac aatctggcct taccttcgca     540
tcaagaggta ccaacatgga ggatgaggcg gaccaatact tttcacatga tgatccaatt     600
agtagtgatc aatccaggtt cggatggttc gggaacaagg aaatctcaga tattgaagtg     660
caagaccctg agggattcaa catgattctg ggtaccatcc tagcccaaat ttgggtcttg     720
ctcgcaaagg cggttacggc cccagacacg gcagctgatt cggagctaag aaggtggata     780
aagtacaccc aacaaagaag ggtagttggt gaatttagat tggagagaaa atggttggat     840
gtggtgagga acaggattgc cgaggacctc tccttacgcc gattcatggt cgctctaatc     900
ctggatatca agagaacacc cggaaacaaa cccaggattg ctgaaatgat atgtgacatt     960
gatacatata tcgtagaggc aggattagcc agttttatcc tgactattaa gtttgggata    1020
gaaactatgt atcctgctct tggactgcat gaatttgctg gtgagttatc cacacttgag    1080
tccttgatga acctttacca gcaaatgggg gaaactgcac cctacatggt aatcctggag    1140
aactcaattc agaacaagtt cagtgcagga tcataccctc tgctctggag ctatgccatg    1200
ggagtaggag tggaacttga aaactccatg ggaggtttga actttggccg atcttacttt    1260
gatccagcat attttagatt agggcaagag atggtaagga ggtcagctgg aaaggtcagt    1320
tccacattgg catctgaact cggtatcact gccgaggatg caaggcttgt tcagagatt     1380
gcaatgcata ctactgagga caagatcagt agagcggttg acccagaca agcccaagta     1440
tcatttctac acggtgatca aagtgagaat gagctaccga gattgggggg caaggaagat    1500
aggagggtca acagagtcg aggagaagcc agggagagct acagagaaac cgggcccagc     1560
agagcaagtg atgcgagagc tgcccatctt ccaaccggca caccctaga cattgacact    1620
gcaacggagt ccagccaaga tccgcaggac agtcgaaggt cagctgacgc cctgcttagg    1680
ctgcaagcca tggcaggaat ctcggaagaa caaggctcag acacggacac ccctatagtg    1740
tacaatgaca gaaatcttct agactaggtg cgagaggccg agggccagaa caacatccgc    1800
ctaccatcca tcattgttat aaaaaactta ggaaccaggt ccacacagcc gccagcccat    1860
caaccatcca ctcccacgat ggagccaat ggcagaagag caggcacgcc atgtcaaaaa     1920
cggactggaa tgcatccggg ctctcaaggc cgagcccatc ggctcactgg ccatcgagga    1980
agctatggca gcatggtcag aaatatcaga caacccagga caggagcgag ccacctgcag    2040
ggaagagaag gcaggcagtt cgggtctcag caaaccatgc ctctcagcaa ttggatcaac    2100
tgaaggcggt gcacctcgca tccgcggtca gggacctgga gagagcgatg acgacgctga    2160
aactttggga atcccccaa gaaatctcca ggcatcaagc actgggttac agtgttatta    2220
cgtttatgat cacagcggtg aagcggttaa gggaatccaa gatgctgact ctatcatggt    2280
tcaatcaggc cttgatggtg atagcaccct ctcaggagga gacaatgaat ctgaaaacag    2340
```

```
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agagaagggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg gaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata taatgaagt agctacagct   3420 caacttacct gccaaccca tgccagtcga cccaactagc ctaccctcca tcattgttat   3480
aaaaaactta ggaaccaggt ccacacagcc gccagcccat caacgcgtac gatggtgagc   3540
aagggcgagg agctgttcac cggggtggtg cccatcctgg tcgagctgga cggcgacgta   3600
aacggccaca gttcagcgt gtccggcgag ggcgagggcg atgccaccta cggcaagctg   3660
accctgaagt tcatctgcac caccggcaag ctgcccgtgc cctggcccac cctcgtgacc   3720
accctgacct acggcgtgca gtgcttcagc cgctacccccg accacatgaa gcagcacgac   3780
ttcttcaagt ccgccatgcc cgaaggctac gtccaggagc gcaccatctt cttcaaggac   3840
gacggcaact acaagacccg cgccgaggtg aagttcgagg gcgacaccct ggtgaaccgc   3900
atcgagctga agggcatcga cttcaaggag gacggcaaca tcctggggca aagctggag   3960 tacaactaca acagccacaa cgtctatatc atggccgaca agcagaagaa cggcatcaag   4020
gtgaacttca agatccgcca caacatcgag gacggcagcg tgcagctcgc cgaccactac   4080
cagcagaaca cccccatcgg cgacggcccc gtgctgctgc ccgacaacca ctacctgagc   4140
acccagtccg ccctgagcaa agaccccaac gagaagcgcg atcacatggt cctgctggag   4200
ttcgtgaccg ccgccgggat cactctcggc atggacgagc tgtacaagta ggcgcgcagc   4260
gcttagacgt ctcgcgatcg atactagtac aacctaaatc cattataaaa aacttaggag   4320
caaagtgatt gcctcccaag gtccacaatg acagagacct acgacttcga caagtcggca   4380
tgggacatca aagggtcgat cgctccgata caacccacca cctacagtga tgcaggctg   4440 gtgccccagg tcagagtcat agatcctggt ctaggcgaca ggaaggatga atgctttatg   4500
tacatgtttc tgctgggggt tgttgaggac agcgattccc tagggcctcc aatcgggcga   4560
gcatttgggt tcctgcccctt aggtgttggc agatccacag caaagcccga aaactcctc   4620 aaagaggcca ctgagcttga catagttgtt agacgtacag cagggctcaa tgaaaaactg   4680
```

```
gtgttctaca acaacacccc actaactctc ctcacacctt ggagaaaggt cctaacaaca   4740
gggagtgtct tcaacgcaaa ccaagtgtgc aatgcggtta atctgatacc gctcgatacc   4800
ccgcagaggt tccgtgttgt ttatatgagc atcacccgtc tttcggataa cgggtattac   4860
accgttccta gaagaatgct ggaattcaga tcggtcaatg cagtggcctt caacctgctg   4920
gtgaccctta ggattgacaa ggcgataggc cctgggaaga tcatcgacaa tacagagcaa   4980
cttcctgagg caacatttat ggtccacatc gggaacttca ggagaaagaa gagtgaagtc   5040
tactctgccg attattgcaa aatgaaaatc gaaagatgg gcctggtttt tgcacttggt     5100
gggatagggg gcaccagtct tcacattaga agcacaggca aaatgagcaa gactctccat   5160
gcacaactcg ggttcaagaa gaccttatgt tacccgctga tggatatcaa tgaagacctt   5220
aatcgattac tctggaggag cagatgcaag atagtaagaa tccaggcagt tttgcagcca   5280
tcagttcctc aagaattccg catttacgac gacgtgatca taaatgatga ccaaggacta   5340
ttcaaagttc tgtagaccgt agtgcccagc aatgcccgaa acgaccccc ctcacaatga   5400
cagccagaag gcccggacaa aaagcccccc tccgaaagac tccacggacc aagcgagagg   5460
ccagccagca gccgacggca agcgcgaaca ccaggcggcc ccagcacaga acagccctga   5520
cacaaggcca ccaccagcca ccccaatctg catcctcctc gtgggacccc cgaggaccaa   5580
cccccaaggc tgcccccgat ccaaaccacc aaccgcatcc ccaccacccc cgggaaagaa   5640
accccccagca attggaaggc ccctcccccct cttcctcaac acaagaactc cacaaccgaa   5700
ccgcacaagc gaccgaggtg acccaaccgc aggcatccga ctccctagac agatcctctc   5760
tccccggcaa actaaacaaa acttagggcc aaggaacata cacacccaac agaacccaga   5820
ccccggccca cggcgccgcg ccccaacccc ccgacaacca gagggagccc ccaaccaatc   5880
ccgccggctc ccccggtgcc cacaggcagg gacaccaacc cccgaacaga cccagcaccc   5940
aaccatcgac aatccaagac ggggggcccc cccaaaaaaa aggcccccag gggccgacag   6000
ccagcaccgc gaggaagccc acccaccccca cacgacca cggcaaccaa accagaaccc     6060
agaccaccct gggccaccag ctcccagact cggccatcac cccgcagaaa ggaaaggcca   6120
caacccgcgc accccagccc cgatccggcg gggagccacc caacccgaac cagcacccaa   6180
gagcgatccc cgaaggaccc ccgaaccgca aaggacatca gtatcccaca gcctctccaa   6240
gtcccccggt ctcctcctct tctcgaaggg accaaaagat caatccacca cacccgacga   6300
cactcaactc cccaccccta aaggagacac cgggaatccc agaatcaaga ctcatccaat   6360
gtccatcatg ggtctcaagg tgaacgtctc tgccatattc atggcagtac tgttaactct   6420
ccaaacaccc accggtcaaa tccattgggg caatctctct aagatagggg tggtaggaat   6480
aggaagtgca agctacaaag ttatgactcg ttccagccat caatcattag tcataaaatt   6540
aatgcccaat ataactctcc tcaataactg cacgagggta gagattgcag aatacaggag   6600
actactgaga acagttttgg aaccaattag agatgcactt aatgcaatga cccagaaatat   6660
aagaccggtt cagagtgtag cttcaagtag gagacacaag agatttgcgg gagtagtcct   6720
ggcaggtgcg gccctaggcg ttgccacagc tgctcagata acagccggca ttgcacttca   6780
ccagtccatg ctgaactctc aagccatcga caatctgaga gcgagcctgg aaactactaa   6840
tcaggcaatt gagacaatca gacaagcagg gcaggagatg atattggctg ttcagggtgt   6900
ccaagactac atcaataatg agctgatacc gtctatgaac caactatctt gtgatttaat   6960
cggcagaag ctcgggctca aattgctcag atactataca gaaatcctgt cattatttgg   7020
ccccagttta cgggacccca tatctgcgga gatatctatc caggctttga gctatgcgct   7080
```

```
tggaggagac atcaataagg tgttagaaaa gctcggatac agtggaggtg atttactggg    7140
catcttagag agcggaggaa taaaggcccg gataactcac gtcgacacag agtcctactt    7200
cattgtcctc agtatagcct atccgacgct gtccgagatt aaggggggtga ttgtccaccg   7260 gctagagggg gtctcgtaca acataggctc tcaagagtgg tataccactg tgcccaagta   7320
tgttgcaacc caagggtacc ttatctcgaa ttttgatgag tcatcgtgta ctttcatgcc   7380 agagggact gtgtgcagcc aaaatgcctt gtacccgatg agtcctctgc tccaagaatg    7440
cctccggggg tacaccaagt cctgtgctcg tacactcgta tccgggtctt tgggaaccg    7500 gttcatttta tcacaaggga acctaatagc caattgtgca tcaatccttt gcaagtgtta   7560
cacaacagga acgatcatta atcaagaccc tgacaagatc ctaacataca ttgctgccga   7620
tcactgcccg gtagtcgagg tgaacggcgt gaccatccaa gtcgggagca ggaggtatcc   7680
agacgctgtg tacttgcaca gaattgacct cggtcctccc atatcattgg agaggttgga   7740
cgtagggaca aatctgggga atgcaattgc taagttggag gatgccaagg aattgttgga   7800
gtcatcggac cagatattga ggagtatgaa aggtttatcg agcactagca tagtctacat   7860
cctgattgca gtgtgtcttg gagggttgat agggatcccc gctttaatat gttgctgcag   7920
ggggcgttgt aacaaaaagg gagaacaagt tggtatgtca agaccaggcc taaagcctga   7980
tcttacggga acatcaaaat cctatgtaag gtcgctctga tcctctacaa ctcttgaaac   8040
acaaatgtcc cacaagtctc ctcttcgtca tcaagcaacc accgcaccca gcatcaagcc   8100
cacctgaaat tatctccggc ttccctctgg ccgaacaata tcggtagtta atcaaaactt   8160
agggtgcaag atcatccaca atgtcaccac aacgagaccg gataaatgcc ttctacaaag   8220
ataaccccca tcccaaggga agtaggatag tcattaacag agaacatctt atgattgata   8280
gaccttatgt tttgctggct gttctgtttg tcatgtttct gagcttgatc gggttgctag   8340
ccattgcagg cattagactt catcgggcag ccatctacac cgcagagatc cataaaagcc   8400
tcagcaccaa tctagatgta actaactcaa tcgagcatca ggtcaaggac gtgctgacac   8460
cactcttcaa aatcatcggt gatgaagtgg gcctgaggac acctcagaga ttcactgacc   8520
tagtgaaatt aatctctgac aagattaaat tccttaatcc ggatagggag tacgacttca   8580
gagatctcac ttggtgtatc aacccgccag agagaatcaa attggattat gatcaatact   8640
gtgcagatgt ggctgctgaa gagctcatga atgcattggt gaactcaact ctactggaga   8700
ccagaacaac caatcagttc ctagctgtct caaagggaaa ctgctcaggg cccactacaa   8760
tcagaggtca attctcaaac atgtcgctgt ccctgttaga cttgtattta ggtcgaggtt   8820
acaatgtgtc atctatagtc actatgacat cccagggaat gtatggggga acttacctag   8880
tggaaaagcc taatctgagc agcaaaaggt cagagttgtc acaactgagc atgtaccgag   8940
tgtttgaagt aggtgttatc agaaatccgg gtttgggggc tccggtgttc catatgacaa   9000
actatcttga gcaaccagtc agtaatgatc tcagcaactg tatggtggct tggggggagc   9060
tcaaactcgc agccctttgt cacggggaag attctatcac aattccctat cagggatcag   9120
ggaaaggtgt cagcttccag ctcgtcaagc taggtgtctg gaaatcccca accgacatgc   9180
aatcctgggt ccccttatca acggatgatc cagtgataga caggctttac ctctcatctc   9240
acagaggtgt tatcgctgac aatcaagcaa atgggctgtg cccgacaaca cgaacagatg   9300
acaagttgcg aatggagaca tgcttccaac aggcgtgtaa gggtaaaatc caagcactct   9360
gcgagaatcc cgagtgggca ccattgaagg ataacaggat tccttcatac ggggtcttgt   9420
```

```
ctgttgatct gagtctgaca gttgagctta aaatcaaaat tgcttcggga ttcgggccat    9480
tgatcacaca cggttcaggg atggacctat acaaatccaa ccacaacaat gtgtattggc    9540
tgactatccc gccaatgaag aacctagcct taggtgtaat caacacattg gagtggatac    9600
cgagattcaa ggttagtccc tacctcttca ctgtcccaat taaggaagca ggcgaagact    9660
gccatgcccc aacatacctc cctgcggagg tggatggtga tgtcaaactc agttccaatc    9720
tggtgattct acctggtcaa gatctccaat atgttttggc aacctacgat acttccaggg    9780
ttgaacatgc tgtggtttat tacgtttaca gcccaagccg ctcattttct tacttttatc    9840
cttttaggtt gcctataaag ggggtcccca tcgaattaca agtggaatgc ttcacatggg    9900
accaaaaact ctggtgccgt cacttctgtg tgcttgcgga ctcagaatct ggtggacata    9960
tcactcactc tgggatggtg ggcatgggag tcagctgcac agtcacccgg aagatggaa    10020 ccaatcgcag atagggctgc tagtgaacca atcacatgat gtcacccaga catcaggcat    10080
acccactagt ctaccctcca tcattgttat aaaaaactta ggaaccaggt ccacacagcc    10140
gccagcccat caacgcgtac gatgggtaag gaaaagactc acgtttcgag gccgcgatta    10200
aattccaaca tggatgctga tttatatggg tataaatggg ctcgcgataa tgtcgggcaa    10260
tcaggtgcga caatctatcg attgtatggg aagcccgatg cgccagagtt gtttctgaaa    10320
catggcaaag gtagcgttgc caatgatgtt acagatgaga tggtcagact aaactggctg    10380
acggaattta tgcctcttcc gaccatcaag cattttatcc gtactcctga tgatgcatgg    10440
ttactcacca ctgcgatccc cggcaaaaca gcattccagg tattagaaga atatcctgat    10500
tcaggtgaaa atattgttga tgcgctggca gtgttcctgc gccggttgca ttcgattcct    10560
gtttgtaatt gtccttttaa cagcgatcgc gtatttcgtc tcgctcaggc gcaatcacga    10620
atgaataacg gtttggttga tgcgagtgat tttgatgacg agcgtaatgg ctggcctgtt    10680
gaacaagtct ggaaagaaat gcataagctt ttgccattct caccggattc agtcgtcact    10740
catggtgatt tctcacttga taaccttatt tttgacgagg ggaaattaat aggttgtatt    10800
gatgttggac gagtcggaat cgcagaccga taccaggatc ttgccatcct atggaactgc    10860
ctcggtgagt tttctccttc attacagaaa cggcttttc aaaaatatgg tattgataat    10920
cctgatatga ataaattgca gtttcatttg atgctcgatg agttttctta acgcgcagcg    10980
cttagacgtc tcgcgatcga tgctagtgtg aaatagacat cagaattaag aaaaacgtag    11040
ggtccaagtg gttccccgtt atggactcgc tatctgtcaa ccagatctta taccctgaag    11100
ttcacctaga tagcccgata gttaccaata agatagtagc catcctggag tatgctcgag    11160
tccctcacgc ttacagcctg gaggaccta cactgtgtca gaacatcaag caccgcctaa    11220
aaaacggatt ttccaaccaa atgattataa acaatgtgga agttgggaat gtcatcaagt    11280
ccaagcttag gagttatccg gcccactctc atattccata tccaaattgt aatcaggatt    11340
tatttaacat agaagacaaa gagtcaacga ggaagatccg tgaactcctc aaaaagggga    11400
attcgctgta ctccaaagtc agtgataagg ttttccaatg cttaagggac actaactcac    11460
ggcttggcct aggctccgaa ttgagggagg acatcaagga gaaagttatt aacttgggag    11520
tttacatgca cagctcccag tggtttgagc cctttctgtt ttggtttaca gtcaagactc    11580
agatgaggtc agtgattaaa tcacaaaccc atacttgcca taggaggaga cacacacctg    11640
tattcttcac tggtagttca gttgagttgc taatctctcg tgaccttgtt gctataatca    11700
gtaaagagtc tcaacatgta tattacctga catttgaact ggtttgatg tattgtgatg    11760 tcatagaggg gaggttaatg acagagaccg ctatgactat tgatgctagg tatacagagc    11820
```

```
ttctaggaag agtcagatac atgtggaaac tgatagatgg tttcttccct gcactcggga    11880
atccaactta tcaaattgta gccatgctgg agcctctttc acttgcttac ctgcagctga    11940
gggatataac agtagaactc agaggtgctt tccttaacca ctgctttact gaaatacatg    12000
atgttcttga ccaaaacggg ttttctgatg aaggtactta tcatgagtta actgaagctc    12060
tagattacat tttcataact gatgacatac atctgacagg ggagattttc tcattttca    12120 gaagtttcgg ccaccccaga cttgaagcag taacggctgc tgaaaatgtt aggaaataca    12180
tgaatcagcc taaagtcatt gtgtatgaga ctctgatgaa aggtcatgcc atattttgtg    12240
gaatcataat caacggctat cgtgacaggc acggaggcag ttggccaccg ctgaccctcc    12300
ccctgcatgc tgcagacaca atccggaatg ctcaagcttc aggtgaaggg ttaacacatg    12360
agcagtgcgt tgataactgg aaatcttttg ctggagtgaa atttggctgc tttatgcctc    12420
ttagcctgga tagtgatctg acaatgtacc taaaggacaa ggcacttgct gctctccaaa    12480
gggaatggga ttcagtttac ccgaaagagt tcctgcgtta cgaccctccc aagggaaccg    12540
ggtcacggag gcttgtagat gttttcctta atgattcgag cttgacccca tatgatgtga    12600
taatgtatgt tgtaagtgga gcttacctcc atgaccctga gttcaacctg tcttacagcc    12660
tgaaagaaaa ggagatcaag gaaacaggta gacttttgc taaaatgact acaaaatga    12720 gggcatgcca agtgattgct gaaaatctaa tctcaaacgg gattggcaaa tattttaagg    12780
acaatgggat ggccaaggat gagcacgatt tgactaaggc actccacact ctagctgtct    12840
caggagtccc caaagatctc aaagaaagtc acaggggggg gccagtctta aaaacctact    12900
cccgaagccc agtccacaca agtaccagga acgtgagagc agcaaaaggg tttataggggt    12960 tccctcaagt aattcggcag gaccaagaca ctgatcatcc ggagaatatg gaagcttacg    13020
agacagtcag tgcatttatc acgactgatc tcaagaagta ctgccttaat tggagatatg    13080
agaccatcag cttgttttgca cagaggctaa atgagattta cggattgccc tcattttcc    13140 agtggctgca taagaggctt gagacctctg tcctgtatgt aagtgaccct cattgccccc    13200
ccgaccttga cgcccatatc ccgttatata aagtccccaa tgatcaaatc ttcattaagt    13260
accctatggg aggtatagaa gggtattgtc agaagctgtg gaccatcagc accattccct    13320
atctatacct ggctgcttat gagagcggag taaggattgc ttcgttagtg caaggggaca    13380
atcagaccat agccgtaaca aaaagggtac ccagcacatg gccctacaac cttaagaaac    13440
gggaagctgc tagagtaact agagattact ttgtaattct taggcaaagg ctacatgata    13500
ttggccatca cctcaaggca aatgagacaa ttgtttcatc acattttttt gtctattcaa    13560
aaggaatata ttatgatggg ctacttgtgt cccaatcact caagagcatc gcaagatgtg    13620
tattctggtc agagactata gttgatgaaa caagggcagc atgcagtaat attgctacaa    13680
caatggctaa aagcatcgag agaggttatg accgttacct tgcatattcc ctgaacgtcc    13740
taaaagtgat acagcaaatt ctgatctctc ttggcttcac aatcaattca accatgaccc    13800
gggatgtagt catacccctc ctcacaaaca acgacctctt aataaggatg gcactgttgc    13860
ccgctcctat tggggggatg aattatctga atatgagcag gctgtttgtc agaaacatcg    13920
gtgatccagt aacatcatca attgctgatc tcaagagaat gattctcgcc tcactaatgc    13980
ctgaagagac cctccatcaa gtaatgacac aacaaccggg ggactcttca ttcctagact    14040 gggcctagcga cccttactca gcaaatcttg tatgtgtcca gagcatcact agactcctca    14100
agaacataac tgcaaggttt gtcctgatcc atagtccaaa cccaatgtta aaaggattat    14160
```

```
tccatgatga cagtaaagaa gaggacgagg gactggcggc attcctcatg acaggcata     14220 ttatagtacc tagggcagct catgaaatcc tggatcatag tgtcacaggg gcaagagagt    14280
ctattgcagg catgctggat accacaaaag gcttgattcg agccagcatg aggaagggg     14340 ggttaacctc tcgagtgata accagattgt ccaattatga ctatgaacaa ttcagagcag    14400
ggatggtgct attgacagga agaaagagaa atgtcctcat tgacaaagag tcatgttcag    14460
tgcagctggc gagagctcta agaagccata tgtgggcgag gctagctcga ggacggccta    14520
tttacggcct tgaggtccct gatgtactag aatctatgcg aggccacctt attcggcgtc    14580
atgagacatg tgtcatctgc gagtgtggat cagtcaacta cggatggttt tttgtcccct    14640
cgggttgcca actggatgat attgacaagg aaacatcatc cttgagagtc ccatatattg    14700
gttctaccac tgatgagaga acagacatga agcttgcctt cgtaagagcc ccaagtcgat    14760
ccttgcgatc tgctgttaga atagcaacag tgtactcatg ggcttacggt gatgatgata    14820
gctcttggaa cgaagcctgg ttgttggcta ggcaaagggc caatgtgagc ctggaggagc    14880
taagggtgat cactcccatc tcaacttcga ctaatttagc gcataggttg agggatcgta    14940
gcactcaagt gaaatactca ggtacatccc ttgtccgagt ggcgaggtat accacaatct    15000
ccaacgacaa tctctcattt gtcatatcag ataagaaggt tgatactaac tttatatacc    15060
aacaaggaat gcttctaggg ttgggtgttt tagaaacatt gtttcgactc gagaaagata    15120
ccggatcatc taacacggta ttacatcttc acgtcgaaac agattgttgc gtgatcccga    15180
tgatagatca tcccaggata cccagctccc gcaagctaga gctgagggca gagctatgta    15240
ccaacccatt gatatatgat aatgcaccct taattgacag agatgcaaca aggctataca    15300
cccagagcca taggaggcac cttgtggaat ttgttacatg gtccacaccc caactatatc    15360
acattttagc taagtccaca gcactatcta tgattgacct ggtaacaaaa tttgagaagg    15420
accatatgaa tgaaatttca gctctcatag gggatgacga tatcaatagt ttcataactg    15480
agtttctgct catagagcca agattattca ctatctactt gggccagtgt gcggccatca    15540
attgggcatt tgatgtacat tatcatagac catcaggaa atatcagatg ggtgagctgt    15600
tgtcatcgtt cctttctaga atgagcaaag gagtgtttaa ggtgcttgtc aatgctctaa    15660
gccacccaaa gatctacaag aaattctggc attgtggtat tatagagcct atccatggtc    15720
cttcacttga tgctcaaaac ttgcacacaa ctgtgtgcaa catggtttac acatgctata    15780
tgacctacct cgacctgttg ttgaatgaag agttagaaga gttcacattt ctcttgtgtg    15840
aaagcgacga ggatgtagta ccggacagat tcgacaacat ccaggcaaaa cacttatgtg    15900
ttctggcaga tttgtactgt caaccaggga cctgcccacc aattcgaggt ctaagaccgg    15960
tagagaaatg tgcagttcta accgaccata tcaaggcaga ggctatgtta tctccagcag    16020
gatcttcgtg gaacataaat ccaattattg tagaccatta ctcatgctct ctgacttatc    16080
tccggcgagg atcgatcaaa cagataagat tgagagttga tccaggattc atttttcgacg    16140 ccctcgctga ggtaaatgtc agtcagccaa agatcggcag caacaacatc tcaaatatga    16200
gcatcaaggc tttcagaccc ccacacgatg atgttgcaaa attgctcaaa gatatcaaca    16260
caagcaagca caatcttccc atttcagggg gcaatctcgc caattatgaa atccatgctt    16320
tccgcagaat cgggttgaac tcatctgctt gctacaaagc tgttgagata tcaacattaa    16380
ttaggagatg ccttgagcca ggggaggacg gcttgttctt gggtgaggga tcgggttcta    16440
tgttgatcac ttataaagag atacttaaac taaacaagtg cttctataat agtgggtttt    16500
ccgccaattc tagatctggt caagggaat tagcacccta tccctccgaa gttggccttg     16560
```

```
tcgaacacag aatgggagta ggtaatattg tcaaagtgct ctttaacggg aggcccgaag   16620
tcacgtgggt aggcagtgta gattgcttca atttcatagt tagtaatatc cctacctcta   16680
gtgtggggtt tatccattca gatatagaga ccttgcctga caaagatact atagagaagc   16740
tagaggaatt ggcagccatc ttatcgatgg ctctgctcct gggcaaaata ggatcaatac   16800
tggtgattaa gcttatgcct ttcagcgggg attttgttca gggatttata agttatgtag   16860
ggtctcatta tagagaagtg aaccttgtat accctagata cagcaacttc atctctactg   16920
aatcttattt ggttatgaca gatctcaagg ctaaccggct aatgaatcct gaaaagatta   16980
agcagcagat aattgaatca tctgtgagga cttcacctgg acttataggt cacatcctat   17040
ccattaagca actaagctgc atacaagcaa ttgtgggaga cgcagttagt agaggtgata   17100
tcaatcctac tctgaaaaaa cttacaccta tagagcaggt gctgatcaat tgcgggttgg   17160
caattaacgg acctaagctg tgcaaagaat tgatccacca tgatgttgcc tcagggcaag   17220
atggattgct taattctata ctcatcctct acagggagtt ggcaagattc aaagacaacc   17280
aaagaagtca acaagggatg ttccacgctt accccgtatt ggtaagtagc aggcaacgag   17340
aacttatatc taggatcacc cgcaaattct gggggcacat tcttctttac tccgggaaca   17400
aaaagttgat aaataagttt atccagaatc tcaagtccgg ctatctgata ctagacttac   17460
accagaatat cttcgttaag aatctatcca agtcagagaa acagattatt atgacggggg   17520
gtttgaaacg tgagtgggtt tttaaggtaa cagtcaagga gaccaaagaa tggtataagt   17580
tagtcggata cagtgccctg attaaggact aattggttga actccggaac cctaatcctg   17640
ccctaggtgg ttaggcatta tttgcaatat attaaagaaa actttgaaaa tacgaagttt   17700
ctattcccag ctttgtctgg tggccggcat ggtcccagcc tcctcgctgg cgccggctgg   17760
gcaacattcc gaggggaccg tccccctcggt aatggcgaat gggacgcggc cgatccggct   17820
gctaacaaag cccgaaagga agctgagttg gctgctgcca ccgctgagca ataactagca   17880 taacccccttg gggcctctaa acgggtcttg aggggttttt tgctgaaagg aggaactata   17940
tccggatgcg gccgcgggcc ctatggtacc cagcttttgt tccctttagt gagggttaat   18000
tccgagcttg gcgtaatcat ggtcatagct gtttcctgtg tgaaattgtt atccgctcac   18060
aattccacac aacataggag ccggaagcat aaagtgtaaa gcctggggtg cctaatgagt   18120
gaggtaactc acattaattg cgttgcgctc actgcccgct ttccagtcgg gaaacctgtc   18180
gtgccagctg cattaatgaa tcggccaacg cgcggggaga ggcggtttgc gtattgggcg   18240
ctcttccgct tcctcgctca ctgactcgct gcgctcggtc gttcggctgc ggcgagcggt   18300
atcagctcac tcaaaggcgg taatacggtt atccacagaa tcaggggata acgcaggaaa   18360
gaacatgtga gcaaaaggcc agcaaaaggc caggaaccgt aaaaaggccg cgttgctggc   18420
gtttttccat aggctccgcc ccctgacga gcatcacaaa aatcgacgct caagtcagag   18480
gtggcgaaac ccgacaggac tataaagata ccaggcgttc ccccctggaa gctccctcgt   18540
gcgctctcct gttccgaccc tgccgcttac cggatacctg tccgcctttc tcccttcggg   18600
aagcgtggcg ctttctcaat gctcacgctg taggtatctc agttcggtgt aggtcgttcg   18660
ctccaagctg ggctgtgtgc acgaaccccc cgttcagccc gaccgctgcg ccttatccgg   18720
taactatcgt cttgagtcca acccggtaag acacgactta tcgccactgg cagcagccac   18780
tggtaacagg attagcagag cgaggtatgt aggcggtgct acagagttct tgaagtggtg   18840
gcctaactac ggctacacta aaggacagt atttggtatc tgcgctctgc tgaagccagt   18900
```

```
taccttcgga aaaagagttg gtagctcttg atccggcaaa caaaccaccg ctggtagcgg   18960
tggttttttt gtttgcaagc agcagattac gcgcagaaaa aaaggatctc aagaagatcc   19020
tttgatcttt tctacggggt ctgacgctca gtggaacgaa actcacgtt aagggatttt    19080
ggtcatgaga ttatcaaaaa ggatcttcac ctagatcctt ttaaattaaa aatgaagttt   19140
taaatcaatc taaagtatat atgagtaaac ttggtctgac agttaccaat gcttaatcag   19200
tgaggcacct atctcagcga tctgtctatt tcgttcatcc atagttgcct gactgcccgt   19260
cgtgtagata actacgatac gggagggctt accatctggc cccagtgctg caatgatacc   19320
gcgagaccca cgctcaccgg ctccagattt atcagcaata aaccagccag ccggaagggc   19380
cgagcgcaga agtggtcctg caactttatc cgcctccatc cagtctatta attgttgccg   19440
ggaagctaga gtaagtagtt cgccagttaa tagtttgcgc aacgttgttg ccattgctac   19500
aggcatcgtg gtgtcacgct cgtcgtttgg tatggcttca ttcagctccg gttcccaacg   19560
atcaaggcga gttacatgat cccccatgtt gtgaaaaaaa gcggttagct ccttcggtcc   19620
tccgatcgtt gtcagaagta agttggccgc agtgttatca ctcatgctta tggcagcact   19680
gcataattct cttactgtca tgccatccgt aagatgcttt tctgtgactg gtgagtactc   19740
aaccaagtca ttctgagaat agtgtatgcg gcgaccgagt tgctcttgcc cggcgtcaat   19800
acgggataat accgcgccac atagcagaac tttaaaagtg ctcatcattg gaaaacgttc   19860
ttcggggcga aaactctcaa ggatcttacc gctgttgaga tccagttcga tgtaacccac   19920
tcgtgcaccc aactgatctt cagcatcttt tactttcacc agcgtttctg ggtgagcaaa   19980
aacaggaagg caaaatgccg caaaaaaggg aataagggcg acacggaaat gttgaatact   20040
catactcttc ctttttcaat attattgaag catttatcag ggttattgtc tcatgagcgg   20100
atacatattt gaatgtattt agaaaaataa acaataggg gttccgcgca catttccccg    20160
aaaagtgcca cctgaaattg taaacgttaa tattttgtta aaattcgcgt taaattttttg   20220
ttaaatcagc tcatttttta accaataggc cgaaatcggc aaaatccctt ataaatcaaa   20280
agaatagacc gagatagggt tgagtgttgt tccagtttgg aacaagagtc cactattaaa   20340
gaacgtggac tccaacgtca aagggcgaaa aaccgtctat cagggcgatg gcccactacg   20400
tgaaccatca ccctaatcaa gttttttggg gtcgaggtgc cgtaaagcac taaatcggaa   20460
ccctaaaggg agcccccgat ttagagcttg acggggaaag ccggcgaacg tggcgagaaa   20520
ggaagggaag aaagcgaaag gagcgggcgc tagggcgctg gcaagtgtag cggtcacgct   20580
gcgcgtaacc accacacccg ccgcgcttaa tgcgccgcta cagggcgcgt cccattcgcc   20640
attcaggctg cgcaactgtt gggaagggcg atcggtgcgg gcctcttcgc tattacgcca   20700
gccaccgcgg tg                                                       20712
```

<210> SEQ ID NO 45
<211> LENGTH: 23672
<212> TYPE: DNA
<213> ORGANISM: Artificial
<220> FEATURE:
<223> OTHER INFORMATION: Plasmid

<400> SEQUENCE: 45

```
tagtggatca tcccacgcg ccctgtagcg ccccattaag cgcggcgggt gtggtggtta     60
cgcccagcgt gacccctaca cttcccaccg ccctagcccc cgctcctttc gctttcttcc   120
cttcctttct cgccacgttc gccggctttc cccgtcaagc tctaaatggg ggcatccgtt   180
tacccttccg atttactgct ttacggcacc tcgaccccaa aaaacttgat tagggtgatg   240
```

```
gttcacgtag tgggccatcg ccctgataga cccttttcg cccttgacg ttggagtcca    300
cgttctttaa tagtggactc ttgttggaaa ctggaacaac actcaaccct atctcggtct   360
attcttttga tttataaggg attttgccga tttcgggcta ttcgttaaaa aatgagctga   420
tttaacaaaa atttaacgcg aattttaaca aatattaac gttacaatt taaatatttg    480
cttatacaat cttcctgttt tggggctttt tctgattatc aaccggggtg gagcttcca    540
ttgcgaatac cgcttccaca aacattgctc aaaagtatct ctttgctata tatctctgtg   600
ctatatccct ataaaccta cccatccacc tttcgctcct tgaacttgca tctaaactcg    660
acctctacat tttttatgtt tatctctagt attactcttt agacaaaaaa attgtagtaa   720
gaactattca tagagtgaat cgaaaacaat acgaaaatgt aaacatttcc tatacgtagt   780
atatagagac aaaatagaag aaaccgttca taattttctg accatgaag aatcatcaac    840
gctatcactt tctgttcaca aagtatgcgc aatccacatc ggtatagaat ataatcgggg   900
atgcctttat cttgaaaaaa tgcacccgca gcttcgctag taatcagtaa acgcgggaag   960
tggagtcagg cttttttat ggaagagaaa atagacacca aagtagcctt cttctaacct    1020
taacggacct acagtgcaaa aagttatcaa gagactgcat tatagagcgc acaaaggaga   1080
aaaaagtaa tctaagatgc tttgttagaa aaatagcgct ctcgggatgc attttgtag    1140
aacaaaaag aagtatagat tcttgttgg taaaatagcg ctctcgcgtt gcatttctgt    1200
tctgtaaaaa tgcagctcag attctttgtt tgaaaaatta gcgctctcgt cgcgttgcat   1260
ttttgtttta caaaaatgaa gcacagattc ttcgttggta aaatagcgct ttcgcgttgc    1320
atttctgttc tgtaaaatg cagctcagat tctttgtttg aaaaattagc gctctcgcgt     1380
tgcattttg ttctacaaaa tgaagcacag atgcttcgtt aacaaagata tgctattgaa    1440
gtgcaagatg gaaacgcaga aaatgaaccg gggatgcgac gtgcaagatt acctatgcaa    1500
tagatgcaat agtttctcca ggaaccgaaa tacatacatt gtcttccgta aagcgctaga   1560
ctatatatta ttatacaggt tcaaatatac tatctgtttc agggaaaact cccaggttcg    1620
gatgttcaaa attcaatgat gggtaacaag tacgatcgta aatctgtaaa acagtttgtc    1680
ggatattagg ctgtatctcc tcaaagcgta ttcgaatatc attgagaagc tgcagcgtca    1740
catcggataa taatgatggc agccattgta gaagtgcctt ttgcatttct agtctctttc    1800
tcggtctagc tagttttact acatcgcgaa gatagaatct tagatcacac tgcctttgct    1860
gagctggatc aatagagtaa caaaagagtg gtaaggcctc gttaaaggac aaggacctga    1920
gcggaagtgt atcgtacagt agacggagta tctagtatag tctatagtcc gtggaattaa    1980
ttctcatctt tgacagctta tcatcgataa gctagctttt caattcaatt catcattttt    2040
tttttattct tttttttgat ttcggtttct ttgaaatttt tttgattcgg taatctccga    2100
acagaaggaa gaacgaagga aggagcacag acttagattg gtatatatac gcatatgtag    2160
tgttgaagaa acatgaaatt gcccagtatt cttaacccaa ctgcacagaa caaaaacctg    2220
caggaaacga agataaatca tgtcgaaagc tacatataag gaacgtgctg ctactcatcc    2280
tagtcctgtt gctgccaagc tatttaatat catgcacgaa aagcaaacaa acttgtgtgc    2340
ttcattggat gttcgtacca ccaaggaatt actggagtta gttgaagcat taggtcccaa    2400
aattgttta ctaaaaacac atgtggatat cttgactgat ttttccatgg agggcacagt    2460
taagccgcta aaggcattat ccgccaagta caatttttta ctcttcgaag acagaaaatt    2520
tgctgacatt ggtaatacag tcaaattgca gtactctgcg ggtgtataca gaatagcaga    2580
```

```
atgggcagac attacgaatg cacacggtgt ggtgggccca ggtattgtta gcggtttgaa    2640
gcaggcggca gaagaagtaa caaaggaacc tagaggcctt ttgatgttag cagaattgtc    2700
atgcaagggc tccctatcta ctggagaata tactaagggt actgttgaca ttgcgaagag    2760
cgacaaagat tttgttatcg gctttattgc tcaaagagac atgggtggaa gagatgaagg    2820
ttacgattgg ttgattatga cacccggtgt gggtttagat gacaagggag acgcattggg    2880
tcaacagtat agaaccgtgg atgatgtggt ctctacagga tctgacatta ttattgttgg    2940
aagaggacta tttgcaaagg aagggatgc taaggtagag ggtgaacgtt acagaaaagc    3000
aggctgggaa gcatatttga gaagatgcgg ccagcaaaac taaaaaactg tattataagt    3060
aaatgcatgt atactaaact cacaaattag agcttcaatt taattatatc agttattacc    3120
cattgaaaaa ggaagagtat gagtattcaa catttccgtg tcgcccttat tccctttttt    3180
gcggcatttt gccttcctgt ttttgctcac ccagaaacgc tggtgaaagt aaaagatgct    3240
gaagatcagt tgggtgcacg agtgggttac atcgaactgg atctcaacag cggtaagatc    3300
cttgagagtt ttcgccccga gaacgttttt ccaatgatga gcacttttaa agttctgcta    3360
tgtgatacac tattatcccg tattgacgcc gggcaagagc aactcggtcg ccgcatacac    3420
tattctcaga atgacttggt tgagtactca ccagtcacag aaaagcatct tacgatggc    3480
atgacagtaa gagaattatg cagtgctgcc ataaccatga gtgataacac tgcggccaac    3540
ttacttctga caacgatcgg aggaccgaag gagctaaccg cttttttgca acatgggg    3600
gatcatgtaa ctcgccttga tcgttgggaa ccggagctga atgaagccat accaaacgac    3660
gagagtgaca ccacgatgcc tgtagcaatg ccaacaacgt tgcgcaaact attaactggc    3720
gaactactta ctctagcttc ccggcaacaa ttaatagact gaatggaggc ggataaagtt    3780
gcaggaccac ttctgcgctc ggcccttccg gctggctggt ttattgctga taatctgga    3840
gccggtgagc gtgggtctcg cggtatcatt gcagcactgg ggccagatgg taagcgctcc    3900
cgtatcgtag ttatctacac gacggggagt caggcaacta tggatgaacg aaatagacag    3960
atcgctgaga taggtgcctc actgattaag cattggtaac tgtcagacca gtttactca    4020
tatatacttt agattgattt aaaacttcat ttttaattta aaaggatcta ggtgaagatc    4080
cttttttgata atctcatgac caaaatccct taacgtgagt tttcgttcca ctgagcgtca    4140
gaccccgtag aaaagatcaa aggatcttct tgagatcctt tttttctgcg cgtaatctgc    4200
tgcttgcaaa caaaaaaacc accgctacca gcggtggttt gtttgccgga tcaagagcta    4260
ccaactcttt ttccgaaggt aactggcttc agcagagcgc agataccaaa tactgtcctt    4320
ctagtgtagc cgtagttagg ccaccacttc aagaactctg tagcaccgcc tacatacctc    4380
gctctgctaa tcctgttacc agtggctgct gccagtggcg ataagtcgtg tcttaccggg    4440
ttggactcaa gacgatagtt accggataag gcgcagcggt cgggctgaac ggggggttcg    4500
tgcacacagc ccagcttgga gcgaacgacc tacaccgaac tgagatacct acagcgtgag    4560
ctatgagaaa gcgccacgct tcccgaaggg agaaaggcgg acaggtatcc ggtaagcggc    4620
agggtcggaa caggagagcg cacgagggag cttccagggg gaaacgcctg gtatctttat    4680
agtcctgtcg ggtttcgcca cctctgactt gagcgtcgat ttttgtgatg ctcgtcaggg    4740
gggcggagcc tatggaaaaa cgccagcaac gcggcctttt tacggttcct ggcttttgc    4800
tggccttttg ctcacatgtt ctttcctgcg ttatcccctg attctgtgga taaccgtatt    4860
accgcctttg agtgagctga taccgctcgc cgcagccgaa cgaccgagcg cagcgagtca    4920
gtgagcgagg aagcggaaga gcgcccaata cgcaaaccgc ctctccccgc gcgttggccg    4980
```

```
attcattaat gcagggccgc aaattaaagc cttcgagcgt cccaaaacct tctcaagcaa     5040
ggttttcagt ataatgttac atgcgtacac gcgtctgtac agaaaaaaaa gaaaaatttg     5100
aaatataaat aacgttctta atactaacat aactataaaa aataaaatag ggacctagac     5160
ttcaggttgt ctaactcctt ccttttcggt tagagcggat gtgggggag ggcgtgaatg      5220 taagcgtgac ataactaatt acatgatgcg gccctctaga tgcatgcagg cctctgcagt     5280
cgacgggccc gtcccattcg ccattaccga ggggacggtc ccctcggaat gttgcccagc     5340
cggcgccagc gaggaggctg ggaccatgcc ggccaccaaa caagttggg taaggatagt      5400 tcaatcaatg atcatcttct agtgcactta ggattcaaga tcctattatc agggacaaga     5460
gcaggattag ggatatccga gatggccaca cttttaagga gcttagcatt gttcaaaaga     5520
aacaaggaca aacccaccat tacatcagga tccggtggag ccatcagagg aatcaaacac     5580
attattatag taccaatccc tggagattcc tcaattacca ctcgatccag acttctggac     5640
cggttggtga ggttaattgg aaacccggat gtgagcgggc ccaaactaac aggggcacta     5700
ataggtatat tatccttatt tgtggagtct ccaggtcaat tgattcagag gatcaccgat     5760
gaccctgacg ttagcataag gctgttagag gttgtccaga gtgaccagtc acaatctggc     5820
cttaccttcg catcaagagg taccaacatg gaggatgagg cggaccaata ctttttcacat    5880 gatgatccaa ttagtagtga tcaatccagg ttcggatggt tcgggaacaa ggaaatctca     5940
gatattgaag tgcaagaccc tgagggattc aacatgattc tgggtaccat cctagcccaa     6000
atttgggtct tgctcgcaaa ggcggttacg gccccagaca cggcagctga ttcggagcta     6060
agaaggtgga taaagtacac ccaacaaaga agggtagttg gtgaatttag attggagaga     6120
aaatggttgg atgtggtgag gaacaggatt gccgaggacc tctccttacg ccgattcatg     6180
gtcgctctaa tcctggatat caagagaaca cccggaaaca aacccaggat tgctgaaatg     6240
atatgtgaca ttgatacata tatcgtagag gcaggattag ccagttttat cctgactatt     6300
aagtttggga tagaaactat gtatcctgct cttggactgc atgaatttgc tggtgagtta     6360
tccacacttg agtccttgat gaacctttac cagcaaatgg gggaaactgc accctacatg     6420
gtaatcctgg agaactcaat tcagaacaag ttcagtgcag gatcataccc tctgctctgg     6480
agctatgcca tgggagtagg agtggaactt gaaaactcca tgggaggttt gaactttggc     6540
cgatcttact ttgatccagc atattttaga ttagggcaag agatggtaag gaggtcagct     6600
ggaaaggtca gttccacatt ggcatctgaa ctcggtatca ctgccgagga tgcaaggctt     6660
gtttcagaga ttgcaatgca tactactgag gacaagatca gtagagcggt tggacccaga     6720
caagcccaag tatcatttct acacggtgat caaagtgaga atgagctacc gagattgggg     6780
ggcaaggaag ataggagggt caaacagagt cgaggagaag ccaggagag ctacagagaa      6840 accgggccca gcagagcaag tgatgcgaga gctgcccatc ttccaaccgg cacaccccta     6900
gacattgaca ctgcaacgga gtccagccaa gatccgcagg acagtcgaag gtcagctgac     6960
gccctgctta ggctgcaagc catggcagga atctcggaag aacaaggctc agacacggac     7020 accectatag tgtacaatga cagaaatctt ctagactagg tgcgagaggc cgagggccag     7080
aacaacatcc gcctaccatc catcattgtt ataaaaaact taggaaccag gtccacacag     7140
ccgccagccc atcaaccatc cactcccacg attggagcca atggcagaag agcaggcacg     7200
ccatgtcaaa aacggactgg aatgcatccg ggctctcaag gccgagccca tcggctcact     7260
ggccatcgag gaagctatgg cagcatggtc agaaatatca gacaacccag gacaggagcg     7320
```

```
agccacctgc agggaagaga aggcaggcag ttcgggtctc agcaaaccat gcctctcagc    7380
aattggatca actgaaggcg gtgcacctcg catccgcggt cagggacctg agagagcga     7440
tgacgacgct gaaactttgg gaatccccca agaaatctc caggcatcaa gcactgggtt    7500
acagtgttat tacgtttatg atcacagcgg tgaagcggtt aagggaatcc aagatgctga    7560
ctctatcatg gttcaatcag gccttgatgg tgatagcacc ctctcaggag gagacaatga    7620
atctgaaaac agcgatgtgg atattggcga acctgatacc gagggatatg ctatcactga    7680
ccggggatct gctcccatct ctatggggtt cagggcttct gatgttgaaa ctgcagaagg    7740
aggggagatc cacgagctcc tgagactcca atccagaggc aacaactttc cgaagcttgg    7800
gaaaactctc aatgttcctc cgcccccgga ccccggtagg gccagcactt ccgggacacc    7860
cattaaaaag ggcacagacg cgagattagc ctcatttgga acggagatcg cgtctttatt    7920
gacaggtggt gcaacccaat gtgctcgaaa gtcaccctcg gaaccatcag gccaggtgc     7980
acctgcgggg aatgtccccg agtgtgtgag caatgccgca ctgatacagg agtggacacc    8040
cgaatctggt accacaatct ccccgagatc ccagaataat gaagaagggg gagactatta    8100
tgatgatgag ctgttctctg atgtccaaga tattaaaaca gccttggcca aaatacacga    8160
ggataatcag aagataatct ccaagctaga atcactgctg ttattgaagg gagaagttga    8220
gtcaattaag aagcagatca acaggcaaaa tatcagcata tccaccctgg aaggacacct    8280
ctcaagcatc atgatcgcca ttcctggact tgggaaggat cccaacgacc ccactgcaga    8340
tgtcgaaatc aatcccgact gaaacccat cataggcaga gattcaggcc gagcactggc    8400
cgaagttctc aagaaacccg ttgccagccg acaactccaa ggaatgacaa atggacggac    8460
cagttccaga ggacagctgc tgaaggaatt tcagctaaag ccgatcggga aaagatgag    8520
ctcagccgtc gggtttgttc ctgacaccgg ccctgcatca cgcagtgtaa tccgctccat    8580
tataaatcc agccggctag aggaggatcg gaagcgttac ctgatgactc tccttgatga    8640
tatcaaagga gccaatgatc ttgccaagtt ccaccagatg ctgatgaaga taataatgaa    8700
gtagctacag ctcaacttac ctgccaaccc catgccagtc gacccaacta gcctaccctc    8760
catcattgtt ataaaaaact taggaaccag gtccacacag ccgccagccc atcaacgcgt    8820
acgatggtga gcaagggcga ggagctgttc accggggtgg tgcccatcct ggtcgagctg    8880
gacggcgacg taaacggcca caagttcagc gtgtccggcg agggcgaggg cgatgccacc    8940
tacggcaagc tgaccctgaa gttcatctgc accaccggca agctgcccgt gccctggccc    9000
accctcgtga ccaccctgac ctacggcgtg cagtgcttca gccgctaccc cgaccacatg    9060
aagcagcacg acttcttcaa gtccgccatg cccgaaggct acgtccagga gcgcaccatc    9120
ttcttcaagg acgacggcaa ctacaagacc cgcgccgagg tgaagttcga gggcgacacc    9180
ctggtgaacc gcatcgagct gaagggcatc gacttcaagg aggacggcaa catcctgggg    9240
cacaagctgg agtacaacta caacagccac aacgtctata tcatggccga caagcagaag    9300
aacggcatca aggtgaactt caagatccgc cacaacatcg aggacggcag cgtgcagctc    9360
gccgaccact accagcagaa cacccccatc ggcgacggcc ccgtgctgct gcccgacaac    9420
cactacctga gcacccagtc cgccctgagc aaagaccca acgagaagcg cgatcacatg    9480
gtcctgctgg agttcgtgac cgccgccggg atcactctcg gcatggacga gctgtacaag    9540
taggcgcgca gcgcttagac gtctcgcgat cgatactagt acaacctaaa tccattataa    9600
aaaacttagg agcaaagtga ttgcctccca aggtccacaa tgcagagac ctacgacttc     9660
gacaagtcgg catgggacat caaagggtcg atcgctccga tacaacccac cacctacagt    9720
```

```
gatggcaggc tggtgcccca ggtcagagtc atagatcctg gtctaggcga caggaaggat   9780
gaatgcttta tgtacatgtt tctgctgggg gttgttgagg acagcgattc cctagggcct   9840
ccaatcgggc gagcatttgg gttcctgccc ttaggtgttg gcagatccac agcaaagccc   9900
gaaaaactcc tcaaagaggc cactgagctt gacatagttg ttagacgtac agcagggctc   9960
aatgaaaaac tggtgttcta caacaacacc ccactaactc tcctcacacc ttggagaaag  10020
gtcctaacaa cagggagtgt cttcaacgca aaccaagtgt gcaatgcggt taatctgata  10080
ccgctcgata ccccgcagag gttccgtgtt gtttatatga gcatcacccg tctttcggat  10140
aacgggtatt acaccgttcc tagaagaatg ctggaattca gatcggtcaa tgcagtggcc  10200
ttcaacctgc tggtgaccct taggattgac aaggcgatag ccctgggaa gatcatcgac   10260 aatacagagc aacttcctga ggcaacattt atggtccaca tcgggaactt caggagaaag  10320
aagagtgaag tctactctgc cgattattgc aaaatgaaaa tcgaaaagat gggcctggtt  10380
tttgcacttg gtgggatagg gggcaccagt cttcacatta gaagcacagg caaaatgagc  10440
aagactctcc atgcacaact cgggttcaag aagaccttat gttacccgct gatggatatc  10500
aatgaagacc ttaatcgatt actctggagg agcagatgca agatagtaag aatccaggca  10560
gttttgcagc catcagttcc tcaagaattc cgcatttacg acgacgtgat cataaatgat  10620
gaccaaggac tattcaaagt tctgtagacc gtagtgccca gcaatgcccg aaaacgaccc  10680
ccctcacaat gacagccaga aggcccggac aaaaaagccc cctccgaaag actccacgga  10740
ccaagcgaga ggccagccag cagccgacgg caagcgcgaa caccaggcgg ccccagcaca  10800
gaacagccct gacacaaggc caccaccagc cacccccaatc tgcatcctcc tcgtgggacc  10860
cccgaggacc aaccccccaag gctgccccccg atccaaacca ccaaccgcat ccccaccacc  10920
cccgggaaag aaacccccag caattggaag gcccctcccc ctcttcctca acacaagaac  10980
tccacaaccg aaccgcacaa gcgaccgagg tgacccaacc gcaggcatcc gactccctag  11040
acagatcctc tctccccggc aaactaaaca aaacttaggg ccaaggaaca tacacaccca  11100
acagaaccca gaccccggcc cacggcgccg cgccccccaac ccccgacaac cagagggagc  11160
ccccaaccaa tcccgccggc tcccccggtg cccacaggca gggacaccaa cccccgaaca  11220
gacccagcac ccaaccatcg acaatccaag acggggggc cccccaaaa aaaggccccc   11280 aggggccgac agccagcacc gcgaggaagc ccacccaccc cacacacgac cacggcaacc  11340
aaaccagaac ccagaccacc ctgggccacc agctcccaga ctcggccatc accccgcaga  11400
aaggaaaggc cacaacccgc gcaccccagc cccgatccgg cggggagcca cccaaccccga  11460 accagcaccc aagagcgatc cccgaaggac ccccgaaccg caaaggacat cagtatccca  11520
cagcctctcc aagtcccccg gtctcctcct cttctcgaag ggaccaaaag atcaatccac  11580
cacacccgac gacactcaac tccccacccc taaaggagac accgggaatc ccagaatcaa  11640
gactcatcca atgtccatca tgggtctcaa ggtgaacgtc tctgccatat tcatggcagt  11700
actgttaact ctccaaacac ccaccggtca aatccattgg ggcaatctct ctaagatagg  11760
ggtggtagga ataggaagtg caagctacaa agttatgact cgttccagcc atcaatcatt  11820
agtcataaaa ttaatgccca atataactct cctcaataac tgcacgaggg tagagattgc  11880
agaatacagg agactactga gaacagtttt ggaaccaatt agagatgcac ttaatgcaat  11940
gacccagaat ataagaccgg ttcagagtgt agcttcaagt aggagacaca agagatttgc  12000
gggagtagtc ctggcaggtg cggccctagg cgttgccaca gctgctcaga taacagccgg  12060
```

```
cattgcactt caccagtcca tgctgaactc tcaagccatc gacaatctga gagcgagcct    12120
ggaaactact aatcaggcaa ttgagacaat cagacaagca gggcaggaga tgatattggc    12180
tgttcagggt gtccaagact acatcaataa tgagctgata ccgtctatga accaactatc    12240
ttgtgattta atcggccaga agctcgggct caaattgctc agatactata cagaaatcct    12300
gtcattattt ggccccagtt tacgggaccc catatctgcg gagatatcta tccaggcttt    12360
gagctatgcg cttggaggag acatcaataa ggtgttagaa aagctcggat acagtggagg    12420
tgatttactg ggcatcttag agagcggagg aataaaggcc cggataactc acgtcgacac    12480
agagtcctac ttcattgtcc tcagtatagc ctatccgacg ctgtccgaga ttaaggtggt    12540
gattgtccac cggctagagg gggtctcgta caacataggc tctcaagagt ggtataccac    12600
tgtgcccaag tatgttgcaa cccaagggta ccttatctcg aattttgatg agtcatcgtg    12660
tactttcatg ccagagggga ctgtgtgcag ccaaaatgcc ttgtacccga tgagtcctct    12720
gctccaagaa tgcctccggg ggtacaccaa gtcctgtgct cgtacactcg tatccgggtc    12780 tttgggaac cggttcattt tatcacaagg gaacctaata gccaattgtg catcaatcct    12840
ttgcaagtgt tacacaacag gaacgatcat taatcaagac cctgacaaga tcctaacata    12900
cattgctgcc gatcactgcc cggtagtcga ggtgaacggc gtgaccatcc aagtcggag    12960 caggaggtat ccagacgctg tgtacttgca cagaattgac ctcggtcctc ccatatcatt    13020
ggagaggttg gacgtaggga caaatctggg gaatgcaatt gctaagttgg aggatgccaa    13080
ggaattgttg gagtcatcgg accagatatt gaggagtatg aaaggtttat cgagcactag    13140
catagtctac atcctgattg cagtgtgtct tggagggttg atagggatcc ccgctttaat    13200
atgttgctgc agggggcgtt gtaacaaaaa gggagaacaa gttggtatgt caagaccagg    13260
cctaaagcct gatcttacgg gaacatcaaa atcctatgta aggtcgctct gatcctctac    13320
aactcttgaa acacaaatgt cccacaagtc tcctcttcgt catcaagcaa ccaccgcacc    13380
cagcatcaag cccacctgaa attatctccg gcttccctct ggccgaacaa tatcggtagt    13440
taatcaaaac ttagggtgca agatcatcca caatgtcacc acaacgagac cggataaatg    13500
ccttctacaa agataacccc catcccaagg gaagtaggat agtcattaac agagaacatc    13560
ttatgattga tagaccttat gttttgctgg ctgttctgtt tgtcatgttt ctgagcttga    13620
tcgggttgct agccattgca ggcattagac ttcatcgggc agccatctac accgcagaga    13680
tccataaaag cctcagcacc aatctagatg taactaactc aatcgagcat caggtcaagg    13740
acgtgctgac accactcttc aaaatcatcg gtgatgaagt gggcctgagg acacctcaga    13800
gattcactga cctagtgaaa ttaatctctg acaagattaa attccttaat ccggataggg    13860
agtacgactt cagagatctc acttggtgta tcaacccgcc agagagaatc aaattggatt    13920
atgatcaata ctgtgcagat gtggctgctg aagagctcat gaatgcattg gtgaactcaa    13980
ctctactgga gaccagaaca accaatcagt tcctagctgt ctcaaaggga aactgctcag    14040
ggcccactac aatcagaggt caattctcaa acatgtcgct gtccctgtta gacttgtatt    14100
taggtcgagg ttacaatgtg tcatctatag tcactatgac atcccaggga atgtatgggg    14160
gaacttacct agtggaaaag cctaatctga gcagcaaaag gtcagagttg tcacaactga    14220
gcatgtaccg agtgtttgaa gtaggtgtta tcagaaatcc gggtttgggg ctccggtgt    14280 tccatatgac aaactatctt gagcaaccag tcagtaatga tctcagcaac tgtatggtgg    14340
cttttgggga gctcaaactc gcagcccttt gtcacgggga agattctatc acaattccct    14400
atcagggatc agggaaaggt gtcagcttcc agctcgtcaa gctaggtgtc tggaaatccc    14460
```

```
caaccgacat gcaatcctgg gtccccttat caacggatga tccagtgata gacaggcttt    14520
acctctcatc tcacagaggt gttatcgctg acaatcaagc aaaatgggct gtcccgacaa    14580
cacgaacaga tgacaagttg cgaatggaga catgcttcca acaggcgtgt aagggtaaaa    14640
tccaagcact ctgcgagaat cccgagtggg caccattgaa ggataacagg attccttcat    14700
acggggtctt gtctgttgat ctgagtctga cagttgagct taaaatcaaa attgcttcgg    14760
gattcgggcc attgatcaca cacggttcag ggatggacct atacaaatcc aaccacaaca    14820
atgtgtattg gctgactatc cgccaatgaa agaacctagc cttaggtgta atcaacacat    14880
tggagtggat accgagattc aaggttagtc cctacctctt cactgtccca attaaggaag    14940
caggcgaaga ctgccatgcc ccaacatacc tacctgcgga ggtggatggt gatgtcaaac    15000
tcagttccaa tctggtgatt ctacctggtc aagatctcca atatgttttg gcaacctacg    15060
atacttccag ggttgaacat gctgtggttt attacgttta cagcccaagc cgctcatttt    15120
cttactttta tccttttagg ttgcctataa agggggtccc catcgaatta caagtggaat    15180
gcttcacatg ggaccaaaaa ctctggtgcc gtcacttctg tgtgcttgcg gactcagaat    15240
ctggtggaca tatcactcac tctgggatgg tgggcatggg agtcagctgc acagtcaccc    15300
gggaagatgg aaccaatcgc agatagggct gctagtgaac caatcacatg atgtcaccca    15360
gacatcaggc atacccacta gtctaccctc catcattgtt ataaaaaact taggaaccag    15420
gtccacacag ccgccagccc atcaacgcgt acgatgggta aggaaaagac tcacgtttcg    15480
aggccgcgat taaattccaa catggatgct gatttatatg ggtataaatg ggctcgcgat    15540
aatgtcgggc aatcaggtgc gacaatctat cgattgtatg ggaagcccga tgcgccagag    15600
ttgtttctga acatggcaa aggtagcgtt gccaatgatg ttacagatga gatggtcaga    15660
ctaaactggc tgacggaatt tatgcctctt ccgaccatca agcatttat ccgtactcct    15720 gatgatgcat ggttactcac cactgcgatc cccggcaaaa cagcattcca ggtattagaa    15780
gaatatcctg attcaggtga aaatattgtt gatgcgctgg cagtgttcct gcgccggttg    15840
cattcgattc ctgttttgtaa ttgtcctttt aacagcgatc gcgtatttcg tctcgctcag    15900
gcgcaatcac gaatgaataa cggtttggtt gatgcgagtg attttgatga cgagcgtaat    15960
ggctggcctg ttgaacaagt ctggaaagaa atgcataagc ttttgccatt ctcaccggat    16020
tcagtcgtca ctcatggtga tttctcactt gataacctta ttttgacga ggggaaatta    16080 ataggttgta ttgatgttgg acgagtcgga atcgcagacc gataccagga tcttgccatc    16140
ctatggaact gcctcggtga gttttctcct tcattacaga aacggctttt tcaaaaatat    16200
ggtattgata atcctgatat gaataaattg cagtttcatt tgatgctcga tgagttttc    16260 taagcgcgca gcgcttagac gtctcgcgat cgatgctagt gtgaaataga catcagaatt    16320
aagaaaaacg tagggtccaa gtggttcccc gttatggact cgctatctgt caaccagatc    16380
ttataccctg aagttcacct agatagcccg atagttacca ataagatagt agccatcctg    16440
gagtatgctc gagtccctca cgcttacagc ctggaggacc ctacactgtg tcagaacatc    16500
aagcaccgcc taaaaacgg attttccaac caaatgatta taaacaatgt ggaagttggg    16560
aatgtcatca agtccaagct taggagttat ccggcccact ctcatattcc atatccaaat    16620
tgtaatcagg atttatttaa catgaagac aaagagtcaa cgaggaagat ccgtgaactc    16680
ctcaaaaagg ggaattcgct gtactccaaa gtcagtgata aggttttcca atgcttaagg    16740
gacactaact cacggcttgg cctaggctcc gaattgaggg aggacatcaa ggagaaagtt    16800
```

```
attaacttgg gagtttacat gcacagctcc cagtggtttg agccctttct gttttggttt    16860
acagtcaaga ctgagatgag gtcagtgatt aaatcacaaa cccatacttg ccataggagg    16920
agacacacac ctgtattctt cactggtagt tcagttgagt tgctaatctc tcgtgacctt    16980
gttgctataa tcagtaaaga gtctcaacat gtatattacc tgacatttga actggttttg    17040
atgtattgtg atgtcataga ggggaggtta atgacagaga ccgctatgac tattgatgct    17100
aggtatacag agcttctagg aagagtcaga tacatgtgga aactgataga tggtttcttc    17160
cctgcactcg ggaatccaac ttatcaaatt gtagccatgc tggagcctct ttcacttgct    17220
tacctgcagc tgagggatat aacagtagaa ctcagaggtg ctttccttaa ccactgcttt    17280
actgaaatac atgatgttct tgaccaaaac gggttttctg atgaaggtac ttatcatgag    17340
ttaactgaag ctctagatta cattttcata actgatgaca tacatctgac aggggagatt    17400
ttctcatttt tcagaagttt cggccacccc agacttgaag cagtaacggc tgctgaaaat    17460
gttaggaaat acatgaatca gcctaaagtc attgtgtatg agactctgat gaaaggtcat    17520
gccatatttt gtggaatcat aatcaacggc tatcgtgaca ggcacggagg cagttggcca    17580
ccgctgaccc tcccctgca tgctgcagac acaatccgga atgctcaagc ttcaggtgaa    17640
gggttaacac atgagcagtg cgttgataac tggaaatctt ttgctggagt gaaatttggc    17700
tgctttatgc ctcttagcct ggatagtgat ctgacaatgt acctaaagga caaggcactt    17760
gctgctctcc aaagggaatg ggattcagtt tacccgaaag agttcctgcg ttacgaccct    17820
cccaagggaa ccgggtcacg gaggcttgta gatgttttcc ttaatgattc gagctttgac    17880
ccatatgatg tgataatgta tgttgtaagt ggagcttacc tccatgaccc tgagttcaac    17940
ctgtcttaca gcctgaaaga aaggagatc aaggaaacag gtagacttt tgctaaaatg    18000 acttacaaaa tgagggcatg ccaagtgatt gctgaaaatc taatctcaaa cgggattggc    18060
aaatatttta aggacaatgg gatggccaag gatgagcacg atttgactaa ggcactccac    18120
actctagctg tctcaggagt ccccaaagat ctcaaagaaa gtcacagggg ggggccagtc    18180 ttaaaaaccct actcccgaag cccagtccac acaagtacca ggaacgtgag agcagcaaaa    18240
gggtttatag ggttccctca agtaattcgg caggaccaag acactgatca tccggagaat    18300
atggaagctt acgagacagt cagtgcattt atcacgactg atctcaagaa gtactgcctt    18360
aattggagat atgagaccat cagcttgttt gcacagaggc taaatgagat ttacggattg    18420
ccctcatttt tccagtggct gcataagagg cttgagacct ctgtcctgta tgtaagtgac    18480
cctcattgcc cccccgacct tgacgcccat atcccgttat ataaagtccc caatgatcaa    18540
atcttcatta agtaccctat gggaggtata gaagggtatt gtcagaagct gtggaccatc    18600
agcaccattc cctatctata cctggctgct tatgagagcg gagtaaggat tgcttcgtta    18660
gtgcaagggg acaatcagac catagccgta acaaaaaggg tacccagcac atggccctac    18720
aaccttaaga aacgggaagc tgctagagta actagagatt actttgtaat tcttaggcaa    18780
aggctacatg atattggcca tcacctcaag gcaaatgaga caattgtttc atcacatttt    18840
tttgtctatt caaaaggaat atattatgat gggctacttg tgtcccaatc actcaagagc    18900
atcgcaagat gtgtattctg gtcagagact atagttgatg aaacaagggc agcatgcagt    18960
aatattgcta caacaatggc taaaagcatc gagagaggtt atgaccgtta ccttgcatat    19020
tccctgaacg tcctaaaagt gatacagcaa attctgatct ctcttggctt cacaatcaat    19080
tcaaccatga cccgggatgt agtcataccc ctcctcacaa acaacgacct cttaataagg    19140
atggcactgt tgcccgctcc tattgggggg atgaattatc tgaatatgag caggctgttt    19200
```

```
gtcagaaaca tcggtgatcc agtaacatca tcaattgctg atctcaagag aatgattctc   19260
gcctcactaa tgcctgaaga gaccctccat caagtaatga cacaacaacc gggggactct   19320
tcattcctag actgggctag cgacccttac tcagcaaatc ttgtatgtgt ccagagcatc   19380
actagactcc tcaagaacat aactgcaagg tttgtcctga tccatagtcc aaacccaatg   19440
ttaaaaggat tattccatga tgacagtaaa gaagaggacg agggactggc ggcattcctc   19500
atggacaggc atattatagt acctagggca gctcatgaaa tcctggatca tagtgtcaca   19560
ggggcaagag agtctattgc aggcatgctg gataccacaa aaggcttgat tcgagccagc   19620
atgaggaagg gggggttaac ctctcgagtg ataaccagat tgtccaatta tgactatgaa   19680
caattcagag cagggatggt gctattgaca ggaagaaaga gaaatgtcct cattgacaaa   19740
gagtcatgtt cagtgcagct ggcgagagct ctaagaagcc atatgtgggc gaggctagct   19800
cgaggacggc ctatttacgg ccttgaggtc cctgatgtac tagaatctat gcgaggccac   19860
cttattcggc gtcatgagac atgtgtcatc tgcgagtgtg atcagtcaa ctacggatgg   19920
ttttttgtcc cctcgggttg ccaactggat gatattgaca aggaaacatc atccttgaga   19980
gtcccatata ttggttctac cactgatgag agaacagaca tgaagcttgc cttcgtaaga   20040
gccccaagtc gatccttgcg atctgctgtt agaatagcaa cagtgtactc atgggcttac   20100
ggtgatgatg atagctcttg gaacgaagcc tggttgttgg ctaggcaaag ggccaatgtg   20160
agcctggagg agctaagggt gatcactccc atctcaactt cgactaattt agcgcatagg   20220
ttgagggatc gtagcactca agtgaaatac tcaggtacat cccttgtccg agtggcgagg   20280
tataccacaa tctccaacga caatctctca tttgtcatat cagataagaa ggttgatact   20340
aactttatat accaacaagg aatgcttcta gggttgggtg ttttagaaac attgtttcga   20400
ctcgagaaag ataccggatc atctaacacg gtattacatc ttcacgtcga aacagattgt   20460
tgcgtgatcc cgatgataga tcatcccagg ataccagct cccgcaagct agagctgagg   20520
gcagagctat gtaccaaccc attgatatat gataatgcac ctttaattga cagagatgca   20580
acaaggctat acacccagag ccataggagg caccttgtgg aatttgttac atggtccaca   20640
ccccaactat atcacatttt agctaagtcc acagcactat ctatgattga cctggtaaca   20700
aaatttgaga aggaccatat gaatgaaatt tcagctctca tagggatga cgatatcaat   20760
agtttcataa ctgagtttct gctcatagag ccaagattat tcactatcta cttgggccag   20820
tgtgcggcca tcaattgggc atttgatgta cattatcata gaccatcagg gaaatatcag   20880
atgggtgagc tgttgtcatc gttcctttct agaatgagca aaggagtgtt taaggtgctt   20940
gtcaatgctc taagccaccc aaagatctac aagaaattct ggcattgtgg tattatagag   21000
cctatccatg gtccttcact tgatgctcaa aacttgcaca caactgtgtg caacatggtt   21060
tacacatgct atatgaccta cctcgacctg ttgttgaatg aagagttaga agagttcaca   21120
tttctcttgt gtgaaagcga cgaggatgta gtaccggaca gattcgacaa catccaggca   21180
aaacactat gtgttctggc agatttgtac tgtcaaccag ggacctgccc accaattcga   21240
ggtctaagac cggtagagaa atgtgcagtt ctaaccgacc atatcaaggc agaggctatg   21300
ttatctccag caggatcttc gtggaacata aatccaatta ttgtagacca ttactcatgc   21360
tctctgactt atctccggcg aggatcgatc aaacagataa gattgagagt tgatccagga   21420
ttcatttcg acgccctcgc tgaggtaaat gtcagtcagc caaagatcgg cagcaacaac   21480
atctcaaata tgagcatcaa ggctttcaga ccccccacacg atgatgttgc aaaattgctc   21540
```

```
aaagatatca acacaagcaa gcacaatctt cccatttcag ggggcaatct cgccaattat    21600
gaaatccatg ctttccgcag aatcggttg aactcatctg cttgctacaa agctgttgag    21660
atatcaacat taattaggag atgccttgag ccaggggagg acggcttgtt cttgggtgag    21720
ggatcgggtt ctatgttgat cacttataaa gagatactta aactaaacaa gtgcttctat    21780
aatagtgggg tttccgccaa ttctagatct ggtcaaaggg aattagcacc ctatccctcc    21840
gaagttggcc ttgtcgaaca cagaatggga gtaggtaata ttgtcaaagt gctctttaac    21900
gggaggcccg aagtcacgtg ggtaggcagt gtagattgct tcaatttcat agttagtaat    21960
atccctacct ctagtgtggg gtttatccat tcagatatag agaccttgcc tgacaaagat    22020
actatagaga agctagagga attggcagcc atcttatcga tggctctgct cctgggcaaa    22080
ataggatcaa tactggtgat taagcttatg cctttcagcg gggattttgt tcagggattt    22140
ataagttatg tagggtctca ttatagagaa gtgaaccttg tatacctag atacagcaac    22200
ttcatctcta ctgaatctta tttggttatg acagatctca aggctaaccg gctaatgaat    22260
cctgaaaaga ttaagcagca gataattgaa tcatctgtga ggacttcacc tggacttata    22320
ggtcacatcc tatccattaa gcaactaagc tgcatacaag caattgtggg agacgcagtt    22380
agtagaggtg atatcaatcc tactctgaaa aaacttacac ctatagagca ggtgctgatc    22440
aattgcgggt tggcaattaa cggacctaag ctgtgcaaag aattgatcca ccatgatgtt    22500
gcctcagggc aagatggatt gcttaattct atactcatcc tctacaggga gttggcaaga    22560
ttcaaagaca accaaagaag tcaacaaggg atgttccacg cttaccccgt attggtaagt    22620
agcaggcaac gagaacttat atctaggatc acccgcaaat tctgggggca cattcttctt    22680
tactccggga acaaaaagtt gataaataag tttatccaga atctcaagtc cggctatctg    22740
atactagact tacaccagaa tatcttcgtt aagaatctat ccaagtcaga gaaacagatt    22800
attatgacgg ggggtttgaa acgtgagtgg gtttttaagg taacagtcaa ggagaccaaa    22860
gaatggtata agttagtcgg atacagtgcc ctgattaagg actaattggt tgaactccgg    22920
aaccctaatc ctgccctagg tggttaggca ttatttgcaa tatattaaag aaaactttga    22980
aaatacgaag tttctattcc cagctttgtc tggtgacccg ggactccggg tttcgtcctc    23040
acggactcat cagaccaaac aaagttgggg ccgcgggatc cgatatctag atgcattcgc    23100
gaggtaccga gctcgaattc cagcacactg gcggccgtta ctagtggatc cgagctcggt    23160
accaagctta atattcccta tagtgagtcg tattacagct gctagtagtc cgatccgggg    23220
ttttttctcc ttgacgttaa agtatagagg tatattaaca attttttgtt gatacttta    23280
ttacatttga ataagaagta atacaaaccg aaaatgttga agtattagt taaagtggtt    23340
aatgcagttt ttgcatttat atatctgtta atagatcaaa aatcatcgct tcgctgatta    23400
attacccag aaataaggct aaaaaactaa tcgcattatc atcctatggt tgttaatttg    23460
attcgttcat ttgaaggttt gtggggccag gttactgcca atttttcctc ttcataacca    23520
taaaagctag tattgtagaa tctttattgt tcggagcagt gcggcgcgag gcacatctgc    23580
gtttcaggaa cgcgaccggt gaggacgagg acgcacggag gagagtcttc cttcggaggg    23640
ctgtcacccg ctcggcggct tctaatccgt ac                                 23672
```

<210> SEQ ID NO 46
<211> LENGTH: 22888
<212> TYPE: DNA
<213> ORGANISM: Artificial
<220> FEATURE:
<223> OTHER INFORMATION: Plasmid

<400> SEQUENCE: 46

```
ctgcattaat gaatcggcca acgcgcgggg agaggcggtt tgcgtattgg gcgctcttcc      60
gcttcctcgc tcactgactc gctgcgctcg gtcgttcggc tgcggcgagc ggtatcagct     120
cactcaaagg cggtaatacg gttatccaca gaatcagggg ataacgcagg aaagaacatg     180
tgagcaaaag gccagcaaaa gcccaggaac cgtaaaaagg ccgcgttgct ggcgttttc     240
cataggctcc gcccccctga cgagcatcac aaaaatcgac gctcaagtca gaggtggcga     300
aacccgacag gactataaag ataccaggcg tttccccctg gaagctccct cgtgcgctct     360
cctgttccga ccctgccgct taccggatac ctgtccgcct ttctcccttc gggaagcgtg     420
gcgctttctc atagctcacg ctgtaggtat ctcagttcgg tgtaggtcgt tcgctccaag     480
ctgggctgtg tgcacgaacc ccccgttcag cccgaccgct gcgccttatc cggtaactat     540
cgtcttgagt ccaacccggt aagacacgac ttatcgccac tggcagcagc cactggtaac     600
aggattagca gagcgaggta tgtaggcggt gctacagagt tcttgaagtg gtggcctaac     660
tacggctaca ctagaaggac agtatttggt atctgcgctc tgctgaagcc agttaccttc     720
ggaaaaagag ttggtagctc ttgatccggc aaacaaacca ccgctggtag cggtggtttt     780
tttgtttgca agcagcagat tacgcgcaga aaaaaggat ctcaagaaga tcctttgatc     840
ttttctacgg ggtctgacgc tcagtggaac gaaaactcac gttaagggat tttggtcatg     900
agattatcaa aaaggatctt cacctagatc cttttaaatt aaaaatgaag ttttaaatca     960
atctaaagta tatatgagta aacttggtct gacagttacc aatgcttaat cagtgaggca    1020
cctatctcag cgatctgtct atttcgttca tccatagttg cctgactccc cgtcgtgtag    1080
ataactacga tacgggagcg cttaccatct ggccccagtg ctgcaatgat accgcgagac    1140
ccacgctcac cggctccaga tttatcagca ataaccagc cagccggaag ggccgagcgc    1200
agaagtggtc ctgcaacttt atccgcctcc attcagtcta ttaattgttg ccgggaagct    1260
agagtaagta gttcgccagt taatagtttg cgcaacgttg ttggcattgc tacaggcatc    1320
gtggtgtcac tctcgtcgtt tggtatggct tcattcagct ccggttccca acgatcaagg    1380
cgagttacat gatcccccat gttgtgcaaa aaagcggtta gctccttcgg tcctccgatc    1440
gttgtcagaa gtaagttggc cgcagtgtta tcactcatgg ttatggcagc actgcataat    1500
tctcttactg tcatgccatc cgtaagatgc ttttctgtga ctggtgagta ctcaaccaag    1560
tcattctgag aatagtgtat gcggcgaccg agttgctctt gcccggcgtc aatacgggat    1620
aatagtgtat cacatagcag aactttaaaa gtgctcatca ttggaaaacg ttcttcgggg    1680
cgaaaactct caaggatctt accgctgttg agatccagtt cgatgtaacc cactcgtgca    1740
cccaactgat cttcagcatc ttttactttc accagcgttt ctgggtgagc aaaaacagga    1800
aggcaaaatg ccgcaaaaaa gggaataagg gcgacacgga aatgttgaat actcatactc    1860
ttcctttttc aatgggtaat aactgatata attaaattga agctctaatt tgtgagttta    1920
gtatacatgc atttacttat aatacagttt tttagttttg ctggccgcat cttctcaaat    1980
atgcttccca gcctgctttt ctgtaacgtt caccctctac cttagcatcc cttcccttg    2040
caaatagtcc tcttccaaca ataataatgt cagatcctgt agagaccaca tcatccacgg    2100
ttctatactg ttgacccaat gcgtctccct tgtcatctaa acccacaccg ggtgtcataa    2160
tcaaccaatc gtaaccttca tctcttccac ccatgtctct ttgagcaata aagccgataa    2220
caaaatcttt gtcgctcttc gcaatgtcaa cagtacccct agtatattct ccagtagata    2280
```

```
gggagcccttt gcatgacaat tctgctaaca tcaaaaggcc tctaggttcc tttgttactt     2340
cttctgccgc ctgcttcaaa ccgctaacaa tacctgggcc caccacaccg tgtgcattcg     2400
taatgtctgc ccattctgct attctgtata cacccgcaga gtactgcaat ttgactgtat     2460
taccaatgtc agcaaatttt ctgtcttcga agagtaaaaa attgtacttg gcggataatg     2520
cctttagcgg cttaactgtg ccctccatgg aaaaatcagt caagatatcc acatgtgttt     2580
ttagtaaaca aattttggga cctaatgctt caactaactc cagtaattcc ttggtggtac     2640
gaacatccaa tgaagcacac aagtttgttt gcttttcgtg catgatatta aatagcttgg     2700
cagcaacagg actaggatga gtagcagcac gttccttata tgtagctttc gacatgattt     2760
atcttcgttt cctgcaggtt tttgttctgt gcagttgggt taagaatact gggcaatttc     2820
atgtttcttc aacactacat atgcgtatat ataccaatct aagtctgtgc tccttccttc     2880
gttcttcctt ctgttcggag attaccgaat caaaaaaatt tcaaagaaac cgaaatcaaa     2940
aaaaagaata aaaaaaaat gatgaattga attgaaaagc tagcttatcg atgataagct     3000
gtcaaagatg agaattaatt ccacggacta tagactatac tagatactcc gtctactgta     3060
cgatacactt ccgctcaggt ccttgtcctt taacgaggcc ttaccactct tttgttactc     3120
tattgatcca gctcagcaaa ggcagtgtga tctaagattc tatcttcgcg atgtagtaaa     3180
actagctaga ccgagaaaga gactagaaat gcaaaggca cttctacaat ggctgccatc     3240
attattatcc gatgtgacgc tgcagcttct caatgatatt cgaatacgct ttgaggagat     3300
acagcctaat atccgacaaa ctgttttaca gatttacgat cgtacttgtt acccatcatt     3360
gaattttgaa catccgaacc tgggagtttt ccctgaaaca gatagtatat ttgaacctgt     3420
ataataatat atagtctagc gctttacgga agacaatgta tgtatttcgg ttcctggaga     3480
aactattgca tctattgcat aggtaatctt gcacgtcgca tccccggttc attttctgcg     3540
tttccatctt gcacttcaat agcatatctt tgttaacgaa gcatctgtgc ttcattttgt     3600
agaacaaaaa tgcaacgcga gagcgctaat ttttcaaaca aagaatctga gctgcatttt     3660
tacagaacag aaatgcaacg cgaaagcgct attttaccaa cgaagaatct gtgcttcatt     3720
tttgtaaaac aaaaatgcaa cgcgacgaga gcgctaattt ttcaaacaaa gaatctgagc     3780
tgcatttta cagaacagaa atgcaacgcg agagcgctat tttaccaaca agaatctat     3840
acttcttttt tgttctacaa aaatgcatcc cgagagcgct attttctaa caaagcatct     3900
tagattactt ttttctcct tgtgcgctc tataatgcag tctcttgata actttttgca     3960
ctgtaggtcc gttaaggtta gaagaaggct actttggtgt ctattttctc ttccataaaa     4020
aaagcctgac tccacttccc gcgttactg attactagcg aagctgcggg tgcattttt     4080
caagataaag gcatcccga ttatattcta taccgatgtg gattgcgcat actttgtgaa     4140
cagaaagtga tagcgttgat gattcttcat tggtcagaaa attatgaacg gtttcttcta     4200
ttttgtctct atatactacg tataggaaat gtttacattt tcgtattgtt ttcgattcac     4260
tctatgaata gttcttacta caattttttt gtctaaagag taatactaga gataaacata     4320
aaaaatgtag aggtcgagtt tagatgcaag ttcaaggagc gaaaggtgga tgggtaggtt     4380
atatagggat atagcacaga gatatatagc aaagagatac ttttgagcaa tgtttgtgga     4440
agcggtattc gcaatgggaa gctccacccc ggttgataat cagaaaagcc ccaaaaacag     4500
gaagattgta taagcaaata tttaaattgt aaacgttaat attttgttaa aattcgcgtt     4560
aaatttttgt taaatcagct catttttaa cgaatagccc gaaatcggca aaatccctta     4620
taaatcaaaa gaatagaccg agatagggtt gagtgttgtt ccagtttcca acaagagtcc     4680
```

```
actattaaag aacgtggact ccaacgtcaa agggcgaaaa aggtctatc agggcgatgg      4740
cccactacgt gaaccatcac cctaatcaag ttttttgggg tcgaggtgcc gtaaagcagt    4800
aaatcggaag ggtaaacgga tgcccccatt tagagcttga cggggaaagc ggcgaacgt     4860
ggcgagaaaa gaagggaaga aagcgaaagg agcgggggct agggcggtgg gaagtgtagg    4920
ggtcacgctg ggcgtaacca ccacacccgc cgcgcttaat ggggcgctac agggcgcgtg    4980
gggatgatcc actagtacgg attagaagcc gccgagcggg tgacagccct ccgaaggaag    5040
actctcctcc gtgcgtcctc gtcctcaccg gtcgcgttcc tgaaacgcag atgtgcctcg    5100
cgccgcactg ctccgaacaa taaagattct acaatactag cttttatggt tatgaagagg    5160
aaaaattggc agtaacctgg ccccacaaac cttcaaatga acgaatcaaa ttaacaacca    5220
taggatgata atgcgattag ttttttagcc ttatttctgg ggtaattaat cagcgaagcg    5280
atgattttg atctattaac agatatataa atgcaaaaac tgcattaacc actttaacta     5340
atactttcaa cattttcggt ttgtattact tcttattcaa atgtaataaa agtatcaaca    5400
aaaaattgtt aatataccct tatactttaa cgtcaaggag aaaaaacccc ggatcggact    5460
actagcagct gtaatacgac tcactatagg gaatattaag cttggtaccg agctcggatc    5520
cactagtaac ggccgccagt gtgctggaat tctgcagata ccatcacac tggcggccgc     5580
taatacgact cactataggg ccaactttgt ttggtctgat gagtccgtga ggacgaaacc    5640
cggagtcccg ggtcaccaaa caaagttggg taaggatagt tcaatcaatg atcatcttct    5700
agtgcactta ggattcaaga tcctattatc agggacaaga gcaggattag ggatatccga    5760
gatggccaca cttttaagga gcttagcatt gttcaaaaga acaaggaca aaccacccat     5820
tacatcagga tccggtggag ccatcagagg aatcaaacac attattatag taccaatccc    5880
tggagattcc tcaattacca ctcgatccag acttctggac cggttggtga ggttaattgg    5940
aaacccggat gtgagcgggc ccaaactaac aggggcacta ataggtatat tatccttatt    6000
tgtggagtct ccaggtcaat tgattcagag gatcaccgat gaccctgacg ttagcataag    6060
gctgttagag gttgtccaga gtgaccagtc acaatctggc cttaccttcg catcaagagg    6120
taccaacatg gaggatgagg cggaccaata cttttcacat gatgatccaa ttagtagtga    6180
tcaatccagg ttcggatggt tcgggaacaa ggaaatctca gatattgaag tgcaagaccc    6240
tgagggattc aacatgattc tgggtaccat cctagcccaa atttgggtct tgctcgcaaa    6300
ggcggttacg gccccagaca cggcagctga ttcggagcta agaaggtgga taaagtacac    6360
ccaacaaaga agggtagttg gtgaatttag attggagaga aaatggttgg atgtggtgag    6420
gaacaggatt gccgaggacc tctccttacg ccgattcatg gtcgctctaa tcctggatat    6480
caagagaaca cccggaaaca aacccaggat tgctgaaatg atatgtgaca ttgatacata    6540
tatcgtagag gcaggattag ccagttttat cctgactatt aagtttggga tagaaactat    6600
gtatcctgct cttggactgc atgaatttgc tggtgagtta ccacacttg agtccttgat     6660
gaacctttac cagcaaatgg gggaaactgc accctacatg gtaatcctgg agaactcaat    6720
tcagaacaag ttcagtgcag gatcataccc tctgctctgg agctatgcca tgggagtagg    6780
agtggaactt gaaaactcca tgggaggttt gaactttggc cgatcttact tgatccagc     6840
atattttaga ttagggcaag agatggtaag gaggtcagct ggaaaggtca gttccacatt    6900
ggcatctgaa ctcggtatca ctgccgagga tgcaaggctt gtttcagaga ttgcaatgca    6960
tactactgag gacaagatca gtagagcggt tggacccaga caagcccaag tatcatttct    7020
```

```
acacggtgat caaagtgaga atgagctacc gagattgggg ggcaaggaag ataggagggt    7080
caaacagagt cgaggagaag ccagggagag ctacagagaa accgggccca gcagagcaag    7140
tgatgcgaga gctgcccatc ttccaaccgg cacacccta gacattgaca ctgcaacgga     7200
gtccagccaa gatccgcagg acagtcgaag gtcagctgac gccctgctta ggctgcaagc    7260
catggcagga atctcggaag aacaaggctc agacacggac accectatag tgtacaatga    7320
cagaaatctt ctagactagg tgcgagaggc cgagggccag aacaacatcc gcctaccatc    7380
catcattgtt ataaaaaact taggaaccag gtccacacag ccgccagccc atcaaccatc    7440
cactcccacg attggagcca atggcagaag agcaggcacg ccatgtcaaa aacggactgg    7500
aatgcatccg ggctctcaag gccgagccca tcggctcact ggccatcgag aagctatgg    7560
cagcatggtc agaaatatca gacaacccag gacaggagcg agccacctgc agggaagaga    7620
aggcaggcag ttcgggtctc agcaaaccat gcctctcagc aattggatca actgaaggcg    7680
gtgcacctcg catccgcggt cagggacctg gagagagcga tgacgacgct gaaactttgg    7740
gaatccccc aagaaatctc caggcatcaa gcactgggtt acagtgttat tacgtttatg     7800
atcacagcgg tgaagcggtt aagggaatcc aagatgctga ctctatcatg gttcaatcag    7860
gccttgatgg tgatagcacc ctctcaggag gagacaatga atctgaaaac agcgatgtgg    7920
atattggcga acctgatacc gagggatatg ctatcactga ccggggatct gctcccatct    7980
ctatggggtt cagggcttct gatgttgaaa ctgcagaagg aggggagatc cacgagctcc    8040
tgagactcca atccagaggc aacaactttc gaagcttgg gaaaactctc aatgttcctc      8100
cgcccccgga ccccggtagg gccagcactt ccgggacacc cattaaaaag ggcacagacg    8160
cgagattagc ctcatttgga acggagatcg cgtctttatt gacaggtggt gcaacccaat    8220
gtgctcgaaa gtcaccctcg gaaccatcag ggccaggtgc acctgcgggg aatgtccccg    8280
agtgtgtgag caatgccgca ctgatacagg agtggacacc cgaatctggt accacaatct    8340
ccccgagatc ccagaataat gaagaagggg gagactatta tgatgatgag ctgttctctg    8400
atgtccaaga tattaaaaca gccttggcca aaatacacga ggataatcag aagataatct    8460
ccaagctaga atcactgctg ttattgaagg gagaagttga gtcaattaag aagcagatca    8520
acaggcaaaa tatcagcata tccaccctgg aaggacacct ctcaagcatc atgatcgcca    8580
ttcctggact tgggaaggat cccaacgacc ccactgcaga tgtcgaaatc aatcccgact    8640
tgaaacccat cataggcaga gattcaggcc gagcactggc cgaagttctc aagaaacccg    8700
ttgccagccg acaactccaa ggaatgacaa atggacggac cagttccaga ggacagctgc    8760
tgaaggaatt tcagctaaag ccgatcggga aaaagatgag ctcagccgtc gggtttgttc    8820
ctgacaccgg ccctgcatca cgcagtgtaa tccgctccat tataaaatcc agccggctag    8880
aggaggatcg gaagcgttac ctgatgactc tccttgatga tatcaaagga gccaatgatc    8940
ttgccaagtt ccaccagatg ctgatgaaga taataatgaa gtagctacag ctcaacttac    9000
ctgccaaccc catgccagtc gacccaacta gtacaaccta atccattat aaaaaactta     9060
ggagcaaagt gattgcctcc caaggtccac aatgacagag acctacgact tcgacaagtc    9120
ggcatgggac atcaaaggt cgatcgctcc gatacaaccc accacctaca gtgatggcag     9180
gctggtgccc caggtcagag tcatagatcc tggtctaggc gacaggaagg atgaatgctt    9240
tatgtacatg tttctgctgg gggttgttga ggacagcgat tccctagggc ctccaatcgg    9300
gcgagcattt gggttcctgc ccttaggtgt tggcagatcc acagcaaagc ccgaaaaact    9360
cctcaaagag gccactgagc ttgacatagt tgttagacgt acagcagggc tcaatgaaaa    9420
```

```
actggtgttc tacaacaaca ccccactaac tctcctcaca ccttggagaa aggtcctaac   9480
aacagggagt gtcttcaacg caaaccaagt gtgcaatgcg gttaatctga taccgctcga   9540
taccccgcag aggttccgtg ttgtttatat gagcatcacc cgtctttcgg ataacgggta   9600
ttacaccgtt cctagaagaa tgctggaatt cagatcggtc aatgcagtgg ccttcaacct   9660
gctggtgacc cttaggattg acaaggcgat aggccctggg aagatcatcg acaatacaga   9720
gcaacttcct gaggcaacat ttatggtcca catcgggaac ttcaggagaa agaagagtga   9780
agtctactct gccgattatt gcaaaatgaa aatcgaaaag atgggcctgg tttttgcact  9840
tggtgggata gggggcacca gtcttcacat tagaagcaca ggcaaaatga gcaagactct  9900
ccatgcacaa ctcgggttca agaagacctt atgttacccg ctgatggata tcaatgaaga  9960
ccttaatcga ttactctgga gggcagatgc aagatagta agaatccagg cagttttgca 10020
gccatcagtt cctcaagaat tccgcattta cgacgacgtg atcataaatg atgaccaagg 10080
actattcaaa gttctgtaga ccgtagtgcc cagcaatgcc cgaaaacgac cccctcaca  10140 atgacagcca gaaggcccgg acaaaaagc cccctccgaa agactccacg gaccaagcga 10200
gaggccagcc agcagccgac ggcaagcgcg aacaccaggc ggcccagca cagaacagcc  10260 ctgacacaag gccaccacca gccaccccaa tctgcatcct cctcgtggga cccccgagga 10320
ccaaccccca aggctgcccc cgatccaaac caccaaccgc atccccacca ccccgggaa  10380 agaaaccccc agcaattgga aggcccctcc ccctcttcct caacacaaga actccacaac 10440
cgaaccgcac aagcgaccga ggtgacccaa ccgcaggcat ccgactccct agacagatcc  10500
tctctccccg gcaaactaaa caaaacttag gccaaggaa catacacacc caacagaacc  10560
cagaccccgg cccacggcgc cgcgccccca accccgaca accagaggga gccccaacc  10620 aatcccgccg gctcccccgg tgcccacagg cagggacacc aaccccgaa cagacccagc   10680 acccaaccat cgacaatcca agacggggggg gcccccccaa aaaaaggccc caggggccg 10740 acagccagca ccgcgaggaa gcccacccac cccacacacg accacggcaa ccaaaccaga 10800
acccagacca ccctgggcca ccagctccca gactcggcca tcaccccgca gaaaggaaag 10860
gccacaaccc gcgcacccca gccccgatcc ggcggggagc cacccaaccc gaaccagcac 10920
ccaagagcga tccccgaagg acccccgaac cgcaaaggac atcagtatcc cacagcctct 10980
ccaagtcccc cggtctcctc ctcttctcga agggaccaaa agatcaatcc accacacccg 11040
acgacactca actcccccacc cctaaaggag acaccgggaa tcccagaatc aagactcatc 11100
caatgtccat catgggtctc aaggtgaacg tctctgccat attcatggca gtactgttaa 11160
ctctccaaac acccaccggt caaatccatt ggggcaatct ctctaagata ggggtggtag 11220
gaataggaag tgcaagctac aaagttatga ctcgttccag ccatcaatca ttagtcataa 11280
aattaatgcc caatataact ctcctcaata actgcacgag ggtagagatt gcagaataca 11340
ggagactact gagaacagtt ttggaaccaa ttagagatgc acttaatgca atgacccaga 11400
atataagacc ggttcagagt gtagcttcaa gtaggagaca caagagattt gcgggagtag 11460
tcctggcagg tgcggcccta ggcgttgcca cagctgctca gataacagcc ggcattgcac 11520
ttcaccagtc catgctgaac tctcaagcca tcgacaatct gagagcgagc ctggaaacta 11580
ctaatcaggc aattgagaca atcagacaag cagggcagga gatgatattg gctgttcagg 11640
gtgtccaaga ctcatcaat aatgagctga taccgtctat gaaccaacta tcttgtgatt  11700
taatcggcca gaagctcggg ctcaaattgc tcagatacta tacagaaatc ctgtcattat 11760
```

```
ttggccccag tttacgggac cccatatctg cggagatatc tatccaggct ttgagctatg   11820
cgcttggagg agacatcaat aaggtgttag aaaagctcgg atacagtgga ggtgatttac   11880
tgggcatctt agagagcgga ggaataaagg cccggataac tcacgtcgac acagagtcct   11940
acttcattgt cctcagtata gcctatccga cgctgtccga gattaagggg gtgattgtcc   12000
accggctaga gggggtctcg tacaacatag gctctcaaga gtggtatacc actgtgccca   12060
agtatgttgc aacccaaggg taccttatct cgaattttga tgagtcatcg tgtactttca   12120
tgccagaggg gactgtgtgc agccaaaatg ccttgtaccc gatgagtcct ctgctccaag   12180
aatgcctccg ggggtacacc aagtcctgtg ctcgtacact cgtatccggg tcttttggga   12240
accggttcat tttatcacaa gggaacctaa tagccaattg tgcatcaatc ctttgcaagt   12300
gttacacaac aggaacgatc attaatcaag accctgacaa gatcctaaca tacattgctg   12360
ccgatcactg cccggtagtc gaggtgaacg gcgtgaccat ccaagtcggg agcaggaggt   12420
atccagacgc tgtgtacttg cacagaattg acctcggtcc tcccatatca ttggagaggt   12480
tggacgtagg gacaaatctg gggaatgcaa ttgctaagtt ggaggatgcc aaggaattgt   12540
tggagtcatc ggaccagata ttgaggagta tgaaaggttt atcgagcact agcatagtct   12600
acatcctgat tgcagtgtgt cttggagggt tgatagggat ccccgcttta atatgttgct   12660
gcaggggggcg ttgtaacaaa aagggagaac aagttggtat gtcaagacca ggcctaaagc   12720
ctgatcttac gggaacatca aaatcctatg taaggtcgct ctgatcctct acaactcttg   12780
aaacacaaat gtcccacaag tctcctcttc gtcatcaagc aaccaccgca cccagcatca   12840
agcccacctg aaattatctc cggcttccct ctggccgaac aatatcggta gttaatcaaa   12900
acttagggtg caagatcatc cacaatgtca ccacaacgag accggataaa tgccttctac   12960
aaagataacc cccatcccaa gggaagtagg atagtcatta acagagaaca tcttatgatt   13020
gatagacctt atgttttgct ggctgttctg tttgtcatgt ttctgagctt gatcgggttg   13080
ctagccattg caggcattag acttcatcgg gcagccatct acaccgcaga gatccataaa   13140
agcctcagca ccaatctaga tgtaactaac tcaatcgagc atcaggtcaa ggacgtgctg   13200
acaccactct tcaaaatcat cggtgatgaa gtgggcctga ggacacctca gagattcact   13260
gacctagtga aattaatctc tgacaagatt aaattcctta atccggatag ggagtacgac   13320
ttcagagatc tcacttggtg tatcaacccg ccagagagaa tcaaattgga ttatgatcaa   13380
tactgtgcag atgtggctgc tgaagagctc atgaatgcat tggtgaactc aactctactg   13440
gagaccagaa caaccaatca gttcctagct gtctcaaagg gaaactgctc agggcccact   13500
acaatcagag gtcaattctc aaacatgtcg ctgtccctgt tagacttgta tttaggtcga   13560
ggttacaatg tgtcatctat agtcactatg acatcccagg gaatgtatgg gggaacttac   13620
ctagtggaaa agcctaatct gagcagcaaa aggtcagagt tgtcacaact gagcatgtac   13680
cgagtgtttg aagtaggtgt tatcagaaat ccgggtttgg gggctccggt gttccatatg   13740
acaaactatc ttgagcaacc agtcagtaat gatctcagca actgtatggt ggctttgggg   13800
gagctcaaac tcgcagccct ttgtcacggg gaagattcta tcacaattcc ctatcaggga   13860
tcagggaaag gtgtcagctt ccagctcgtc aagctaggtg tctggaaatc ccaaccgac    13920
atgcaatcct gggtcccctt atcaacggat gatccagtga tagacaggct ttacctctca   13980
tctcacagag gtgttatcgc tgacaatcaa gcaaaatggg ctgtcccgac aacacgaaca   14040
gatgacaagt tgcgaatgga gacatgcttc caacaggcgt gtaagggtaa aatccaagca   14100
ctctgcgaga atcccgagtg ggcaccattg aaggataaca ggattccttc atacgggggtc   14160
```

```
ttgtctgttg atctgagtct gacagttgag cttaaaatca aaattgcttc gggattcggg   14220
ccattgatca cacacggttc agggatggac ctatacaaat ccaaccacaa caatgtgtat   14280
tggctgacta tcccgccaat gaagaaccta gccttaggtg taatcaacac attggagtgg   14340
ataccgagat tcaaggttag tccctacctc ttcactgtcc caattaagga agcaggcgaa   14400
gactgccatg ccccaacata cctacctgcg gaggtggatg gtgatgtcaa actcagttcc   14460
aatctggtga ttctacctgg tcaagatctc caatatgttt tggcaaccta cgatacttcc   14520
agggttgaac atgctgtggt ttattacgtt tacagcccaa gccgctcatt ttcttacttt   14580
tatcctttta ggttgcctat aaaggggggtc cccatcgaat acaagtggaa atgcttcaca   14640
tgggaccaaa aactctggtg ccgtcacttc tgtgtgcttg cggactcaga atctggtgga   14700
catatcactc actctgggat ggtgggcatg ggagtcagct gcacagtcac ccggaagat   14760
ggaaccaatc gcagataggg ctgctagtga accaatcaca tgatgtcacc cagacatcag   14820
gcatacccac tagtctaccc tccatcattg ttataaaaaa cttaggaacc aggtccacac   14880
agccgccagc ccatcaacgc gtacgatgag taaaggagaa gaactttca ctggagttgt   14940
cccaattctt gttgaattag atggtgatgt taatgggcac aaattttctg tcagtggaga   15000
gggtgaaggt gatgcaacat acggaaaact taccctaaa tttatttgca ctactggaaaa   15060
actacctgtt ccatggccaa cacttgtcac tactttcacc tatggtgttc aatgcttttc   15120
aagataccca gatcatatga acggcatga cttttcaag agtgccatgc cgaaggtta   15180
tgtacaggaa agaactatat ttttcaaaga tgacgggaac tacaagacac gtgctgaagt   15240
caagtttgaa ggtgataccc ttgttaatag aatcgagtta aaaggtattg attttaaaga   15300
agatggaaac attcttggac acaaattgga atacaactat aactcacaca atgtatacat   15360
catggcagac aaacaaaaga atggaatcaa agttaacttc aaaattagac acaacattga   15420
agatggaagc gttcaactag cagaccatta tcaacaaaat actccaattg gcgatggccc   15480
tgtccttta ccagacaacc attacctgtc cacacaatct gcccttcga agatcccaa   15540
cgaaaagaga gaccacatgg tccttcttga gtttgtaaca gctgctggga ttacacatgg   15600
catggatgaa ctatacaaat agtgagcgcg cagcgcttag acgtctcgcg atcgatgcta   15660
gtgtgaaata gacatcagaa ttaagaaaaa cgtagggtcc aagtggttcc ccgttatgga   15720
ctcgctatct gtcaaccaga tcttatacc tgaagttcac ctagatagcc cgatagttac   15780
caataagata gtagccatcc tggagtatgc tcgagtccct cacgcttaca gcctggagga   15840
ccctacactg tgtcagaaca tcaagcaccg cctaaaaac ggattttcca accaaatgat   15900
tataaacaat gtggaagttg ggaatgtcat caagtccaag cttaggagtt atccggccca   15960
ctctcatatt ccatatccaa attgtaatca ggatttattt aacatagaag acaaagagtc   16020
aacgaggaag atccgtgaac tcctcaaaaa ggggaattcg ctgtactcca agtcagtga   16080
taaggttttc caatgcttaa gggacactaa ctcacggctt ggcctaggct ccgaattgag   16140
ggaggacatc aaggagaaag ttattaactt gggagtttac atgcacagct cccagtggtt   16200
tgagcccttt ctgttttggt ttacagtcaa gactgagatg aggtcagtga ttaaatcaca   16260
aacccatact tgccataga ggagacacac acctgtattc ttcactggta gttcagttga   16320
gttgctaatc tctcgtgacc ttgttgctat aatcagtaaa gagtctcaac atgtatatta   16380
cctgacattt gaactggttt tgatgtattg tgatgtcata gagggaggt taatgacaga   16440
gaccgctatg actattgatg ctaggtatac agagcttcta ggaagagtca gatacatgtg   16500
```

```
gaaactgata gatggtttct tccctgcact cgggaatcca acttatcaaa ttgtagccat    16560
gctggagcct ctttcacttg cttacctgca gctgagggat ataacagtag aactcagagg    16620
tgctttcctt aaccactgct ttactgaaat acatgatgtt cttgaccaaa acgggttttc    16680
tgatgaaggt acttatcatg agttaactga agctctagat tacattttca taactgatga    16740
catacatctg acaggggaga ttttctcatt tttcagaagt ttcggccacc ccagacttga    16800
agcagtaacg gctgctgaaa atgttaggaa atacatgaat cagcctaaag tcattgtgta    16860
tgagactctg atgaaaggtc atgccatatt ttgtggaatc ataatcaacg gctatcgtga    16920
caggcacgga ggcagttggc caccgctgac cctcccctg catgctgcag acacaatccg     16980
gaatgctcaa gcttcaggtg aagggttaac acatgagcag tgcgttgata actggaaatc    17040
ttttgctgga gtgaaatttg gctgctttat gcctcttagc ctggatagtg atctgacaat    17100
gtacctaaag gacaaggcac ttgctgctct ccaaagggaa tgggattcag tttacccgaa    17160
agagttcctg cgttacgacc ctcccaaggg aaccgggtca cggaggcttg tagatgtttt    17220
ccttaatgat tcgagctttg acccatatga tgtgataatg tatgttgtaa gtggagctta    17280
cctccatgac cctgagttca acctgtctta cagcctgaaa gaaaaggaga tcaaggaaac    17340
aggtagactt tttgctaaaa tgacttacaa aatgagggca tgccaagtga ttgctgaaaa    17400
tctaatctca aacgggattg gcaaatattt taaggacaat gggatggcca aggatgagca    17460
cgatttgact aaggcactcc acactctagc tgtctcagga gtccccaaag atctcaaaga    17520
aagtcacagg gggggccag tcttaaaaac ctactcccga agcccagtcc acacaagtac     17580
caggaacgtg agagcagcaa aagggtttat agggttccct caagtaattc ggcaggacca    17640
agacactgat catccggaga atatggaagc ttacgagaca gtcagtgcat ttatcacgac    17700
tgatctcaag aagtactgcc ttaattggag atatgagacc atcagcttgt ttgcacagag    17760
gctaaatgag atttacggat tgccctcatt tttccagtgg ctgcataaga ggcttgagac    17820
ctctgtcctg tatgtaagtg accctcattg ccccccccgac cttgacgccc atatcccgtt    17880
atataaagtc cccaatgatc aaatcttcat taagtaccct atgggaggta tagaagggta    17940
ttgtcagaag ctgtggacca tcagcaccat tccctatcta tacctggctg cttatgagag    18000
cggagtaagg attgcttcgt tagtgcaagg ggacaatcag accatagccg taacaaaaag    18060
ggtacccagc acatggccct acaaccttaa gaaacgggaa gctgctagag taactagaga    18120
ttactttgta attcttaggc aaaggctaca tgatattggc catcacctca aggcaaatga    18180
gacaattgtt tcatcacatt ttttgtcta ttcaaaagga atatattatg atgggctact     18240
tgtgtcccaa tcactcaaga gcatcgcaag atgtgtattc tggtcagaga ctatagttga    18300
tgaaacaagg gcagcatgca gtaatattgc tacaacaatg gctaaaagca tcgagagagg    18360
ttatgaccgt taccttgcat attccctgaa cgtcctaaaa gtgatacagc aaattctgat    18420
ctctcttggc ttcacaatca attcaaccat gaccccgggat gtagtcatac ccctcctcac    18480
aaacaacgac ctcttaataa ggatggcact gttgcccgct cctattgggg ggatgaatta    18540
tctgaatatg agcaggctgt ttgtcagaaa catcggtgat ccagtaacat catcaattgc    18600
tgatctcaag agaatgattc tcgcctcact aatgcctgaa gagaccctcc atcaagtaat    18660
gacacaacaa ccgggggact cttcattcct agactgggct agcgaccctt actcagcaaa    18720
tcttgtatgt gtccagagca tcactagact cctcaagaac ataactgcaa ggtttgtcct    18780
gatccatagt ccaaacccaa tgttaaaagg attattccat gatgacagta agaagagga     18840 cgagggactg gcggcattcc tcatggacag gcatattata gtacctaggg cagctcatga    18900
```

```
aatcctggat catagtgtca caggggcaag agagtctatt gcaggcatgc tggataccac   18960
aaaaggcttg attcgagcca gcatgaggaa ggggggggtta acctctcgag tgataaccag   19020
attgtccaat tatgactatg aacaattcag agcagggatg gtgctattga caggaagaaa   19080
gagaaatgtc ctcattgaca aagagtcatg ttcagtgcag ctggcgagag ctctaagaag   19140
ccatatgtgg gcgaggctag ctcgaggacg gcctatttac ggccttgagg tccctgatgt   19200
actagaatct atgcgaggcc acttattcg gcgtcatgag acatgtgtca tctgcgagtg   19260
tggatcagtc aactacggat ggttttttgt cccctcgggt tgccaactgg atgatattga   19320
caaggaaaca tcatccttga gagtcccata tattggttct accactgatg agagaacaga   19380
catgaagctt gccttcgtaa gagccccaag tcgatccttg cgatctgctg ttagaatagc   19440
aacagtgtac tcatgggctt acggtgatga tgatagctct tggaacgaag cctggttgtt   19500
ggctaggcaa agggccaatg tgagcctgga ggagctaagg gtgatcactc ccatctcaac   19560
ttcgactaat ttagcgcata ggttgaggga tcgtagcact caagtgaaat actcaggtac   19620
atcccttgtc cgagtggcga ggtataccac aatctccaac gacaatctct catttgtcat   19680
atcagataag aaggttgata ctaactttat ataccaacaa ggaatgcttc tagggttggg   19740
tgttttagaa acattgtttc gactcgagaa agataccgga tcatctaaca cggtattaca   19800
tcttcacgtc gaaacagatt gttgcgtgat cccgatgata gatcatccca ggatacccag   19860
ctcccgcaag ctagagctga gggcagagct atgtaccaac ccattgatat atgataatgc   19920
acctttaatt gacagagatg caacaaggct atacacccag agccatagga ggcaccttgt   19980
ggaatttgtt acatggtcca cacccccaact atatcacatt ttagctaagt ccacagcact   20040
atctatgatt gacctggtaa caaaatttga gaggaccat atgaatgaaa tttcagctct   20100 catagggat gacgatatca atagtttcat aactgagttt ctgctcatag agccaagatt   20160
attcactatc tacttgggcc agtgtgcggc catcaattgg gcatttgatg tacattatca   20220
tagaccatca gggaaatatc agatgggtga gctgttgtca tcgttccttt ctagaatgag   20280
caaaggagtg tttaaggtgc ttgtcaatgc tctaagccac ccaaagatct acaagaaatt   20340
ctggcattgt ggtattatag agcctatcca tggtccttca cttgatgctc aaaacttgca   20400
cacaactgtg tgcaacatgg tttacacatg ctatatgacc tacctcgacc tgttgttgaa   20460
tgaagagtta gaagagttca catttctctt gtgtgaaagc gacgaggatg tagtaccgga   20520
cagattcgac aacatccagg caaaacactt atgtgttctg gcagatttgt actgtcaacc   20580 agggaccgc ccaccaattc gaggtctaag accggtagaa aaatgtgcag ttctaaccga   20640
ccatatcaag gcagaggcta tgttatctcc agcaggatct tcgtggaaca taaatccaat   20700
tattgtagac cattactcat gctctctgac ttatctccgg cgaggatcga tcaaacagat   20760
aagattgaga gttgatccag gattcatttt cgacgccctc gctgaggtaa atgtcagtca   20820
gccaaagatc ggcagcaaca acatctcaaa tatgagcatc aaggctttca gaccccaca   20880 cgatgatgtt gcaaaattgc tcaaagatat caacacaagc aagcacaatc ttcccatttc   20940
agggggcaat ctcgccaatt atgaaatcca tgctttccgc agaatcgggt tgaactcatc   21000
tgcttgctac aaagctgttg agatatcaac attaattagg gatgccttg agccagggga   21060 ggacggcttg ttcttgggtg agggatcggg ttctatgttg atcacttata aagagatact   21120
taaactaaac aagtgcttct ataatagtgg ggtttccgcc aattctagat ctggtcaaag   21180
ggaattagca ccctatccct ccgaagttgg ccttgtcgaa cacagaatgg gagtaggtaa   21240
```

```
tattgtcaaa gtgctcttta acgggaggcc cgaagtcacg tgggtaggca gtgtagattg    21300
cttcaatttc atagttagta atatccctac ctctagtgtg gggtttatcc attcagatat    21360
agagaccttg cctgacaaag atactataga gaagctagag gaattggcag ccatcttatc    21420
gatggctctg ctcctgggca aaataggatc aatactggtg attaagctta tgcctttcag    21480
cggggatttt gttcagggat ttataagtta tgtagggtct cattatagag aagtgaacct    21540
tgtataccct agatacagca acttcatctc tactgaatct tatttggtta tgacagatct    21600
caaggctaac cggctaatga atcctgaaaa gattaagcag cagataattg aatcatctgt    21660
gaggacttca cctggactta taggtcacat cctatccatt aagcaactaa gctgcataca    21720
agcaattgtg ggagacgcag ttagtagagg tgatatcaat cctactctga aaaacttac     21780 acctatagag caggtgctga tcaattgcgg gttggcaatt aacggaccta agctgtgcaa    21840
agaattgatc caccatgatg ttgcctcagg gcaagatgga ttgcttaatt ctatactcat    21900
cctctacagg gagttggcaa gattcaaaga caaccaaaga agtcaacaag ggatgttcca    21960
cgcttacccc gtattggtaa gtagcaggca acgagaactt atatctagga tcacccgcaa    22020
attctggggg cacattcttc tttactccgg gaacaaaaag ttgataaaata agttatatcca   22080 gaatctcaag tccggctatc tgatactaga cttacaccag aatatcttcg ttaagaatct    22140
atccaagtca gagaaacaga ttattatgac ggggggtttg aaacgtgagt gggtttttaa    22200
ggtaacagtc aaggagacca aagaatggta taagttagtc ggatacagtg ccctgattaa    22260
ggactaattg gttgaactcc ggaaccctaa tcctgcccta ggtggttagg cattatttgc    22320
aatatattaa agaaaacttt gaaaatacga agtttctatt cccagctttg tctggtggcc    22380
ggcatggtcc cagcctcctc gctggcgccg gctgggcaac attccgaggg accgtcccc    22440 tcggtaatgg cgaatgggac gcggccgatc cggctgctaa caaagcccga aaggaagctg    22500
agttggctgc tgccaccgct gagcaataac tagcataacc ccttggggcc tctaaacggg    22560
tcttgagggg ttttttgctg aaaggaggaa ctatatccgg atggcggccg ctcgagcatg    22620
catctagagg gccgcatcat gtaattagtt atgtcacgct tacattcacg ccctcccccc    22680
acatccgctc taaccgaaaa ggaaggagtt agacaacctg aagtctaggt ccctatttat    22740
ttttttatag ttatgttagt attaagaacg ttatttatat ttcaaatttt tctttttttt    22800
ctgtacagac gcgtgtacgc atgtaacatt atactgaaaa ccttgcttga aaggttttg    22860 ggacgctcga aggctttaat ttgcggcc                                       22888
```

<210> SEQ ID NO 47
<211> LENGTH: 23805
<212> TYPE: DNA
<213> ORGANISM: Artificial
<220> FEATURE:
<223> OTHER INFORMATION: Plasmid

<400> SEQUENCE: 47

```
ctgcattaat gaatcggcca acgcgcgggg agaggcggtt tgcgtattgg gcgctcttcc      60
gcttcctcgc tcactgactc gctgcgctcg gtcgttcggc tgcggcgagc ggtatcagct     120
cactcaaagg cggtaatacg gttatccaca gaatcagggg ataacgcagg aaagaacatg    180
tgagcaaaag gccagcaaaa gcccaggaac cgtaaaaagg ccgcgttgct ggcgtttttc    240
cataggctcc gccccctga cgagcatcac aaaaatcgac gctcaagtca gaggtggcga    300
aacccgacag gactataaag ataccaggcg tttccccctg gaagctccct cgtgcgctct    360
cctgttccga ccctgccgct taccggatac ctgtccgcct ttctcccttc gggaagcgtg    420
```

```
gcgctttctc atagctcacg ctgtaggtat ctcagttcgg tgtaggtcgt tcgctccaag    480
ctgggctgtg tgcacgaacc ccccgttcag cccgaccgct gcgccttatc cggtaactat    540
cgtcttgagt ccaacccggt aagacacgac ttatcgccac tggcagcagc cactggtaac    600
aggattagca gagcgaggta tgtaggcggt gctacagagt tcttgaagtg gtggcctaac    660
tacggctaca ctagaaggac agtatttggt atctgcgctc tgctgaagcc agttaccttc    720
ggaaaaagag ttggtagctc ttgatccggc aaacaaacca ccgctggtag cggtggtttt    780
tttgtttgca agcagcagat tacgcgcaga aaaaaggat ctcaagaaga tcctttgatc    840
ttttctacgg ggtctgacgc tcagtggaac gaaaactcac gttaagggat tttggtcatg    900
agattatcaa aaaggatctt cacctagatc cttttaaatt aaaaatgaag ttttaaatca    960
atctaaagta tatatgagta aacttggtct gacagttacc aatgcttaat cagtgaggca   1020
cctatctcag cgatctgtct atttcgttca tccatagttg cctgactccc cgtcgtgtag   1080
ataactacga tacgggagcg cttaccatct ggccccagtg ctgcaatgat accgcgagac   1140
ccacgctcac cggctccaga tttatcagca ataaaccagc cagccggaag ggccgagcgc   1200
agaagtggtc ctgcaacttt atccgcctcc attcagtcta ttaattgttg ccgggaagct   1260
agagtaagta gttcgccagt taatagtttg cgcaacgttg ttggcattgc tacaggcatc   1320
gtggtgtcac tctcgtcgtt tggtatggct tcattcagct ccggttccca acgatcaagg   1380
cgagttacat gatcccccat gttgtgcaaa aaagcggtta gctccttcgg tcctccgatc   1440
gttgtcagaa gtaagttggc cgcagtgtta tcactcatgg ttatggcagc actgcataat   1500
tctcttactg tcatgccatc cgtaagatgc ttttctgtga ctggtgagta ctcaaccaag   1560
tcattctgag aatagtgtat gcggcgaccg agttgctctt gcccggcgtc aatacgggat   1620
aatagtgtat cacatagcag aactttaaaa gtgctcatca ttggaaaacg ttcttcgggg   1680
cgaaaactct caaggatctt accgctgttg agatccagtt cgatgtaacc cactcgtgca   1740
cccaactgat cttcagcatc ttttactttc accagcgttt ctgggtgagc aaaaacagga   1800
aggcaaaatg ccgcaaaaaa gggaataagg gcgacacgga aatgttgaat actcatactc   1860
ttccttttc aatgggtaat aactgatata attaaattga agctctaatt tgtgagttta   1920
gtatacatgc atttacttat aatacagttt tttagttttg ctggccgcat cttctcaaat   1980
atgcttccca gcctgctttt ctgtaacgtt caccctctac cttagcatcc cttccctttg   2040
caaatagtcc tcttccaaca ataataatgt cagatcctgt agagaccaca tcatccacgg   2100
ttctatactg ttgacccaat gcgtctccct tgtcatctaa acccacaccg ggtgtcataa   2160
tcaaccaatc gtaaccttca tctcttccac ccatgtctct tgagcaata aagccgataa   2220
caaaatcttt gtcgctcttc gcaatgtcaa cagtacccct agtatattct ccagtagata   2280
gggagcccct tgcatgacaat tctgctaaca tcaaaaggcc tctaggttcc tttgttactt   2340
cttctgccgc ctgcttcaaa ccgctaacaa tacctgggcc caccacaccg tgtgcattcg   2400
taatgtctgc ccattctgct attctgtata cacccgcaga gtactgcaat ttgactgtat   2460
taccaatgtc agcaaatttt ctgtcttcga agagtaaaaa attgtacttg gcggataatg   2520
cctttagcgg cttaactgtg ccctccatgg aaaaatcagt caagatatcc acatgtgttt   2580
ttagtaaaca aattttggga cctaatgctt caactaactc cagtaattcc ttggtggtac   2640
gaacatccaa tgaagcacac aagtttgttt gcttttcgtg catgatatta aatagcttgg   2700
cagcaacagg actaggatga gtagcagcac gttccttata tgtagctttc gacatgattt   2760
```

```
atcttcgttt cctgcaggtt tttgttctgt gcagttgggt taagaatact gggcaatttc    2820
atgtttcttc aacactacat atgcgtatat ataccaatct aagtctgtgc tccttccttc    2880
gttcttcctt ctgttcggag attaccgaat caaaaaaatt tcaaagaaac cgaaatcaaa    2940
aaaaagaata aaaaaaaaat gatgaattga attgaaaagc tagcttatcg atgataagct    3000
gtcaaagatg agaattaatt ccacggacta tagactatac tagatactcc gtctactgta    3060
cgatacactt ccgctcaggt ccttgtcctt taacgaggcc ttaccactct tttgttactc    3120
tattgatcca gctcagcaaa ggcagtgtga tctaagattc tatcttcgcg atgtagtaaa    3180
actagctaga ccgagaaaga gactagaaat gcaaaaggca cttctacaat ggctgccatc    3240
attattatcc gatgtgacgc tgcagcttct caatgatatt cgaatacgct ttgaggagat    3300
acagcctaat atccgacaaa ctgttttaca gatttacgat cgtacttgtt acccatcatt    3360
gaattttgaa catccgaacc tgggagtttt ccctgaaaca gatagtatat ttgaacctgt    3420
ataataatat atagtctagc gctttacgga agacaatgta tgtatttcgg ttcctggaga    3480
aactattgca tctattgcat aggtaatctt gcacgtcgca tccccggttc attttctgcg    3540
tttccatctt gcacttcaat agcatatctt tgttaacgaa gcatctgtgc ttcattttgt    3600
agaacaaaaa tgcaacgcga gagcgctaat ttttcaaaca aagaatctga gctgcatttt    3660
tacagaacag aaatgcaacg cgaaagcgct attttaccaa cgaagaatct gtgcttcatt    3720
tttgtaaaac aaaaatgcaa cgcgacgaga gcgctaattt ttcaaacaaa gaatctgagc    3780
tgcattttta cagaacagaa atgcaacgcg agagcgctat tttaccaaca aagaatctat    3840
acttcttttt tgttctacaa aaatgcatcc cgagagcgct attttctaa caaagcatct    3900 tagattactt tttttctcct ttgtgcgctc tataatgcag tctcttgata acttttttgca    3960 ctgtaggtcc gttaaggtta gaagaaggct actttggtgt ctattttctc ttccataaaa    4020
aaagcctgac tccacttccc gcgtttactg attactagcg aagctgcggg tgcattttt    4080 caagataaag gcatccccga ttatattcta taccgatgtg gattgcgcat actttgtgaa    4140
cagaaagtga tagcgttgat gattcttcat tggtcagaaa attatgaacg gtttcttcta    4200
ttttgtctct atatactacg tataggaaat gtttacattt tcgtattgtt ttcgattcac    4260
tctatgaata gttcttacta caattttttt gtctaaagag taatactaga gataaacata    4320
aaaaatgtag aggtcgagtt tagatgcaag ttcaaggagc gaaaggtgga tgggtaggtt    4380 ataagggat atagcacaga gatatatagc aaagagatac ttttgagcaa tgtttgtgga    4440
agcggtattc gcaatgggaa gctccacccc ggttgataat cagaaaagcc ccaaaaacag    4500
gaagattgta taagcaaata tttaaattgt aaacgttaat attttgttaa aattcgcgtt    4560
aaatttttgt taaatcagct cattttttaa cgaatagccc gaaatcggca aaatccctta    4620
taaatcaaaa gaatagaccg agatagggtt gagtgttgtt ccagtttcca acaagagtcc    4680
actattaaag aacgtggact ccaacgtcaa agggcgaaaa aggtctatc agggcgatgg    4740 cccactacgt gaaccatcac cctaatcaag ttttttgggg tcgaggtgcc gtaaagcagt    4800
aaatcggaag ggtaaacgga tgcccccatt tagagcttga cggggaaagc cggcgaacgt    4860
ggcgagaaag gaagggaaga aagcgaaagg agcgggggct agggcggtgg gaagtgtagg    4920
ggtcacgctg ggcgtaacca ccacacccgc cgcgcttaat ggggcgctac agggcgcgtg    4980
gggatgatcc actagtacgg attagaagcc gccgagcggg tgacagccct ccgaaggaag    5040
actctcctcc gtgcgtcctc gtcctcaccg gtcgcgttcc tgaaacgcag atgtgcctcg    5100
cgccgcactg ctccgaacaa taaagattct acaatactag cttttatggt tatgaagagg    5160
```

```
aaaaattggc agtaacctgg ccccacaaac cttcaaatga acgaatcaaa ttaacaacca    5220
taggatgata atgcgattag ttttttagcc ttatttctgg ggtaattaat cagcgaagcg    5280
atgattttg atctattaac agatatataa atgcaaaaac tgcattaacc actttaacta    5340
atactttcaa cattttcggt ttgtattact tcttattcaa atgtaataaa agtatcaaca    5400
aaaaattgtt aatatacctc tatactttaa cgtcaaggag aaaaaacccc ggatcggact    5460
actagcagct gtaatacgac tcactatagg gaatattaag cttggtaccg agctcggatc    5520
cactagtaac ggccgccagt gtgctggaat tctgcagata tccatcacac tggcggccgc    5580
taatacgact cactataggg ccaactttgt ttggtctgat gagtccgtga ggacgaaacc    5640
cggagtcccg ggtcaccaaa caaagttggg taaggatagt tcaatcaatg atcatcttct    5700
agtgcactta ggattcaaga tcctattatc agggacaaga gcaggattag ggatatccga    5760
gatggccaca cttttaagga gcttagcatt gttcaaaaga aacaaggaca aaccacccat    5820
tacatcagga tccggtggag ccatcagagg aatcaaacac attattatag taccaatccc    5880
tggagattcc tcaattacca ctcgatccag acttctggac cggttggtga ggttaattgg    5940
aaacccggat gtgagcgggc ccaaactaac aggggcacta ataggtatat tatccttatt    6000
tgtggagtct ccaggtcaat tgattcagag gatcaccgat gaccctgacg ttagcataag    6060
gctgttagag gttgtccaga gtgaccagtc acaatctggc cttaccttcg catcaagagg    6120
taccaacatg gaggatgagg cggaccaata cttttcacat gatgatccaa ttagtagtga    6180
tcaatccagg ttcggatggt tcgggaacaa ggaaatctca gatattgaag tgcaagaccc    6240
tgagggattc aacatgattc tgggtaccat cctagcccaa atttgggtct tgctcgcaaa    6300
ggcggttacg gccccagaca cggcagctga ttcggagcta agaaggtgga taaagtacac    6360
ccaacaaaga agggtagttg gtgaatttag attggagaga aaatggttgg atgtggtgag    6420
gaacaggatt gccgaggacc tctccttacg ccgattcatg gtcgctctaa tcctggatat    6480
caagagaaca cccggaaaca aacccaggat tgctgaaatg atatgtgaca ttgatacata    6540
tatcgtagag gcaggattag ccagttttat cctgactatt aagtttggga tagaaactat    6600
gtatcctgct cttggactgc atgaatttgc tggtgagtta tccacacttg agtccttgat    6660
gaacctttac cagcaaatgg gggaaactgc accctacatg gtaatcctgg agaactcaat    6720
tcagaacaag ttcagtgcag atcataccc tctgctctgg agctatgcca tgggagtagg    6780
agtggaactt gaaaactcca tgggaggttt gaactttggc cgatcttact ttgatccagc    6840
atattttaga ttagggcaag agatggtaag gaggtcagct ggaaaggtca gttccacatt    6900
ggcatctgaa ctcggtatca ctgccgagga tgcaaggctt gtttcagaga ttgcaatgca    6960
tactactgag gacaagatca gtagagcggt tggacccaga caagcccaag tatcatttct    7020
acacggtgat caaagtgaga atgagctacc gagattgggg ggcaaggaag ataggagggt    7080
caaacagagt cgaggagaag ccagggagag ctacagagaa accgggccca gcagagcaag    7140
tgatgcgaga gctgcccatc ttccaaccgg cacacccta gacattgaca ctgcaacgga    7200
gtccagccaa gatccgcagg acagtcgaag gtcagctgac gccctgctta ggctgcaagc    7260
catggcagga atctcggaag aacaaggctc agacacggac accctatag tgtacaatga    7320
cagaaatctt ctagactagg tgcgagaggc cgagggccag aacaacatcc gcctaccatc    7380
catcattgtt ataaaaaact taggaaccag gtccacacag ccgccagccc atcaaccatc    7440
cactcccacg attggagcca atggcagaag agcaggcacg ccatgtcaaa aacggactgg    7500
```

```
aatgcatccg ggctctcaag gccgagccca tcggctcact ggccatcgag gaagctatgg    7560
cagcatggtc agaaatatca gacaacccag gacaggagcg agccacctgc agggaagaga    7620
aggcaggcag ttcgggtctc agcaaaccat gcctctcagc aattggatca actgaaggcg    7680
gtgcacctcg catccgcggt cagggacctg gagagagcga tgacgacgct gaaactttgg    7740
gaatccccca agaaatctc caggcatcaa gcactgggtt acagtgttat tacgtttatg    7800
atcacagcgg tgaagcggtt aagggaatcc aagatgctga ctctatcatg gttcaatcag    7860
gccttgatgg tgatagcacc ctctcaggag gagacaatga atctgaaaac agcgatgtgg    7920
atattggcga acctgatacc gagggatatg ctatcactga ccggggatct gctcccatct    7980
ctatggggtt cagggcttct gatgttgaaa ctgcagaagg aggggagatc cacgagctcc    8040
tgagactcca atccagaggc aacaactttc gaagcttgg gaaaactctc aatgttcctc    8100
cgcccccgga ccccggtagg gccagcactt ccgggacacc cattaaaaag ggcacagacg    8160
cgagattagc ctcatttgga acggagatcg cgtctttatt gacaggtggt gcaacccaat    8220
gtgctcgaaa gtcaccctcg gaaccatcag ggccaggtgc acctgcgggg aatgtccccg    8280
agtgtgtgag caatgccgca ctgatacagg agtggacacc cgaatctggt accacaatct    8340
ccccgagatc ccagaataat gaagaagggg gagactatta tgatgatgag ctgttctctg    8400
atgtccaaga tattaaaaca gccttggcca aaatacacga ggataatcag aagataatct    8460
ccaagctaga atcactgctg ttattgaagg gagaagttga gtcaattaag aagcagatca    8520
acaggcaaaa tatcagcata tccaccctgg aaggacacct ctcaagcatc atgatcgcca    8580
ttcctggact tgggaaggat cccaacgacc ccactgcaga tgtcgaaatc aatcccgact    8640
tgaaacccat cataggcaga gattcaggcc gagcactggc cgaagttctc aagaaacccg    8700
ttgccagccg acaactccaa ggaatgacaa atggacggac cagttccaga ggacagctgc    8760
tgaaggaatt tcagctaaag ccgatcggga aaaagatgag ctcagccgtc gggtttgttc    8820
ctgacaccgg ccctgcatca cgcagtgtaa tccgctccat tataaaatcc agccggctag    8880
aggaggatcg gaagcgttac ctgatgactc tccttgatga tatcaaagga gccaatgatc    8940
ttgccaagtt ccaccagatg ctgatgaaga taataatgaa gtagctacag ctcaacttac    9000
ctgccaaccc catgccagtc gacccaacta gcctaccctc catcattgtt ataaaaaact    9060
taggaaccag gtccacacag ccgccagccc atcaacgcgt acgtggtgag caagggcgag    9120
gagctgttca ccggggtggt gcccatcctg gtcgagctgg acggcgacgt aaacggccac    9180
aagttcagcg tgtccggcga gggcgagggc gatgccacct acggcaagct gacccctgaag    9240 ttcatctgca ccaccggcaa gctgcccgtg ccctggccca ccctcgtgac caccctgacc    9300
tacggcgtgc agtgcttcag ccgctacccc gaccacatga gcagcacga cttcttcaag    9360 tccgccatgc ccgaaggcta cgtccaggag cgcaccatct tcttcaagga cgacggcaac    9420
tacaagaccc gcgccgaggt gaagttcgag ggcgacaccc tggtgaaccg catcgagctg    9480
aagggcatcg acttcaagga ggacggcaac atcctggggc acaagctgga gtacaactac    9540
aacagccaca acgtctatat catggccgac aagcagaaga acggcatcaa ggtgaacttc    9600
aagatccgcc acaacatcga ggacggcagc gtgcagctcg ccgaccacta ccagcagaac    9660
acccccatcg gcgacggccc cgtgctgctg cccgacaacc actacctgag cacccagtcc    9720
gccctgagca agacccccaa cgagaagcgc gatcacatgg tcctgctgga gttcgtgacc    9780
gccgccggga tcactctcgg catggacgag ctgtacaagt aggcgcgcag cgcttagacg    9840
tctcgcgatc gatactagta caacctaaat ccattataaa aaacttagga gcaaagtgat    9900
```

```
tgcctcccaa ggtccacaat gacagagacc tacgacttcg acaagtcggc atgggacatc    9960
aaagggtcga tcgctccgat acaacccacc acctacagtg atggcaggct ggtgcccag    10020
gtcagagtca tagatcctgg tctaggcgac aggaaggatg aatgctttat gtacatgttt   10080
ctgctggggg ttgttgagga cagcgattcc ctagggcctc caatcgggcg agcatttggg   10140
ttcctgccct taggtgttgg cagatccaca gcaaagcccg aaaaactcct caaagaggcc   10200
actgagcttg acatagttgt tagacgtaca gcagggctca atgaaaaact ggtgttctac   10260
aacaacaccc cactaactct cctcacacct tggagaaagg tcctaacaac agggagtgtc   10320
ttcaacgcaa accaagtgtg caatgcggtt aatctgatac cgctcgatac cccgcagagg   10380
ttccgtgttg tttatatgag catcacccgt ctttcggata acgggtatta caccgttcct   10440
agaagaatgc tggaattcag atcggtcaat gcagtggcct tcaacctgct ggtgacccTT   10500
aggattgaca aggcgatagg ccctgggaag atcatcgaca atacagagca acttcctgag   10560
gcaacattta tggtccacat cgggaacttc aggagaaaga agagtgaagt ctactctgcc   10620
gattattgca aaatgaaaat cgaaaagatg ggcctggttt ttgcacttgg tgggataggg   10680
ggcaccagtc ttcacattag aagcacaggc aaaatgagca agactctcca tgcacaactc   10740
gggttcaaga agaccttatg ttacccgctg atggatatca atgaagacct taatcgatta   10800
ctctggagga gcagatgcaa gatagtaaga atccaggcag ttttgcagcc atcagttcct   10860
caagaattcc gcatttacga cgacgtgatc ataaatgatg accaaggact attcaaagtt   10920
ctgtagaccg tagtgcccag caatgcccga aaacgacccc cctcacaatg acagccagaa   10980
ggcccggaca aaaagccccc tccgaaaga ctccacggac caagcgagag gccagccagc   11040
agccgacggc aagcgcgaac accaggcggc cccagcacag aacagccctg acacaaggcc   11100
accaccagcc accccaatct gcatcctcct cgtgggaccc ccgaggacca accccaagg    11160
ctgccccga tccaaaccac caaccgcatc cccaccaccc ccgggaaaga aaccccagc    11220
aattggaagg cccctccccc tcttcctcaa cacaagaact ccacaaccga accgcacaag   11280
cgaccgaggt gacccaaccg caggcatccg actccctaga cagatcctct ctccccggca   11340
aactaaacaa aacttagggc caaggaacat acacacccaa cagaacccag accccggccc   11400
acggcgccgc gccccaacc cccgacaacc agagggagcc cccaaccaat cccgccggct   11460
cccccggtgc ccacaggcag ggacaccaac ccccgaacag acccagcacc caaccatcga   11520
caatccaaga cggggggcc ccccaaaaa aaggccccca ggggccgaca gccagcaccg   11580
cgaggaagcc cacccacccc acacacgacc acggcaacca aaccgaaacc cagaccaccc   11640
tgggccacca gctcccagac tcggccatca ccccgcagaa aggaaaggcc acaacccgcg   11700
caccccagcc ccgatccggc ggggagccac ccaacccgaa ccagcaccca agagcgatcc   11760
ccgaaggacc cccgaaccgc aaaggacatc agtatcccac agcctctcca gtcccccgg   11820
tctcctcctc ttctcgaagg gaccaaaaga tcaatccacc acaccgacg acactcaact   11880
ccccacccct aaaggagaca ccgggaatcc cagaatcaag actcatccaa tgtccatcat   11940
gggtctcaag gtgaacgtct ctgccatatt catggcagta ctgttaactc tccaaacacc   12000
caccggtcaa atccattggg gcaatctctc taagataggg tgtaggaa taggaagtgc   12060
aagctacaaa gttatgactc gttccagcca tcaatcatta gtcataaaat taatgcccaa   12120
tataactctc ctcaataact gcacgagggt agagattgca gaatacagga gactactgag   12180
aacagttttg gaaccaatta gagatgcact taatgcaatg acccagaata taagaccggt   12240
```

```
tcagagtgta gcttcaagta ggagacacaa gagatttgcg ggagtagtcc tggcaggtgc    12300
ggccctaggc gttgccacag ctgctcagat aacagccggc attgcacttc accagtccat    12360
gctgaactct caagccatcg acaatctgag agcgagcctg gaaactacta atcaggcaat    12420
tgagacaatc agacaagcag gcaggagat gatattggct gttcagggtg tccaagacta     12480
catcaataat gagctgatac cgtctatgaa ccaactatct tgtgatttaa tcggccagaa    12540
gctcgggctc aaattgctca gatactatac agaaatcctg tcattatttg gccccagttt    12600
acgggacccc atatctgcgg agatatctat ccaggctttg agctatgcgc ttggaggaga    12660
catcaataag gtgttagaaa agctcggata cagtggaggt gatttactgg gcatcttaga    12720
gagcggagga ataaaggccc ggataactca cgtcgacaca gagtcctact tcattgtcct    12780
cagtatagcc tatccgacgc tgtccgagat taagggggtg attgtccacc ggctagaggg    12840
ggtctcgtac aacataggct ctcaagagtg gtataccact gtgcccaagt atgttgcaac    12900
ccaagggtac cttatctcga atttttgatga gtcatcgtgt actttcatgc cagaggggac    12960
tgtgtgcagc caaaatgcct tgtacccgat gagtcctctg ctccaagaat gcctccgggg    13020
gtacaccaag tcctgtgctc gtacactcgt atccgggtct tttgggaacc ggttcatttt    13080
atcacaaggg aacctaatag ccaattgtgc atcaatcctt tgcaagtgtt acacaacagg    13140
aacgatcatt aatcaagacc ctgacaagat cctaacatac attgctgccg atcactgccc    13200
ggtagtcgag gtgaacggcg tgaccatcca agtcggagc aggaggtatc cagacgctgt     13260
gtacttgcac agaattgacc tcggtcctcc catatcattg gagaggttgg acgtagggac    13320 aaaatctgggg aatgcaattg ctaagttgga ggatgccaag gaattgttgg agtcatcgga   13380
ccagatattg aggagtatga aggtttatc gagcactagc atagtctaca tcctgattgc     13440
agtgtgtctt ggagggttga tagggatccc cgctttaata tgttgctgca ggggcgttg    13500 taacaaaaag ggagaacaag ttggtatgtc aagaccaggc ctaaagcctg atcttacggg    13560
aacatcaaaa tcctatgtaa ggtcgctctg atcctctaca actcttgaaa cacaaatgtc    13620
ccacaagtct cctcttcgtc atcaagcaac caccgcaccc agcatcaagc ccacctgaaa    13680
ttatctccgg cttccctctg ccgaacaat atcggtagtt aatcaaaact tagggtgcaa     13740
gatcatccac aatgtcacca caacgagacc ggataaatgc cttctacaaa gataaccccc    13800
atcccaaggg aagtaggata gtcattaaca gagaacatct tatgattgat agaccttatg    13860
ttttgctggc tgttctgttt gtcatgtttc tgagcttgat cgggttgcta gccattgcag    13920
gcattagact tcatcgggca gccatctaca ccgcagagat ccataaaagc ctcagcacca    13980
atctagatgt aactaactca atcgagcatc aggtcaagga cgtgctgaca ccactcttca    14040
aaatcatcgg tgatgaagtg ggcctgagga cacctcagag attcactgac ctagtgaaat    14100
taatctctga caagattaaa ttccttaatc cggatagga gtacgacttc agagatctca    14160
cttggtgtat caacccgcca gagagaatca aattggatta tgatcaatac tgtgcagatg    14220
tggctgctga agagctcatg aatgcattgg tgaactcaac tctactggag accagaacaa    14280
ccaatcagtt cctagctgtc tcaaagggaa actgctcagg gcccactaca atcagaggtc    14340
aattctcaaa catgtcgctg tccctgttag acttgtattt aggtcgaggt tacaatgtgt    14400
catctatagt cactatgaca tcccagggaa tgtatggggg aacttaccta gtggaaaagc    14460
ctaatctgag cagcaaaagg tcagagttgt cacaactgag catgtaccga gtgttttgaag   14520 taggtgttat cagaaatccg ggtttggggg ctccggtgtt ccatatgaca aactatcttg    14580
agcaaccagt cagtaatgat ctcagcaact gtatggtggc tttggggag ctcaaactcg      14640
```

```
cagccctttg tcacggggaa gattctatca caattcccta tcaggatca gggaaaggtg    14700 tcagcttcca gctcgtcaag ctaggtgtct ggaaatcccc aaccgacatg caatcctggg    14760
tccccttatc aacggatgat ccagtgatag acaggcttta cctctcatct cacagaggtg    14820
ttatcgctga caatcaagca aaatgggctg tcccgacaac acgaacagat acaagttgc    14880 gaatggagac atgcttccaa caggcgtgta agggtaaaat ccaagcactc tgcgagaatc    14940
ccgagtgggc accattgaag gataacagga ttccttcata cggggtcttg tctgttgatc    15000
tgagtctgac agttgagctt aaaatcaaaa ttgcttcggg attcgggcca ttgatcacac    15060
acggttcagg gatggaccta tacaaatcca accacaacaa tgtgtattgg ctgactatcc    15120
cgccaatgaa gaacctagcc ttaggtgtaa tcaacacatt ggagtggata ccgagattca    15180
aggttagtcc ctacctcttc actgtcccaa ttaaggaagc aggcgaagac tgccatgccc    15240
caacatacct acctgcggag gtggatggtg atgtcaaact cagttccaat ctggtgattc    15300
tacctggtca agatctccaa tatgttttgg caacctacga tacttccagg gttgaacatg    15360
ctgtggttta ttacgtttac agcccaagcc gctcattttc ttacttttat ccttttaggt    15420
tgcctataaa gggggtcccc atcgaattac aagtggaatg cttcacatgg gaccaaaaac    15480
tctggtgccg tcacttctgt gtgcttgcgg actcagaatc tggtggacat atcactcact    15540
ctgggatggt gggcatggga gtcagctgca cagtcacccg ggaagatgga accaatcgca    15600
gatagggctg ctagtgaacc aatcacatga tgtcacccag acatcaggca tacccactag    15660
tctaccctcc atcattgtta taaaaaactt aggaaccagg tccacacagc cgccagccca    15720
tcaacgcgta cgatgggtaa ggaaaagact cacgtttcga ggccgcgatt aaattccaac    15780
atggatgctg atttatatgg gtataaatgg gctcgcgata atgtcgggca atcaggtgcg    15840
acaatctatc gattgtatgg gaagcccgat gcgccagagt tgtttctgaa acatggcaaa    15900
ggtagcgttg ccaatgatgt tacagatgag atggtcagac taaactggct gacggaattt    15960
atgcctcttc cgaccatcaa gcattttatc cgtactcctg atgatgcatg gttactcacc    16020
actgcgatcc ccggcaaaac agcattccag gtattagaag aatatcctga ttcaggtgaa    16080
aatattgttg atgcgctggc agtgttcctg cgccggttgc attcgattcc tgtttgtaat    16140 tgtccttta acagcgatcg cgtatttcgt ctcgctcagg cgcaatcacg aatgaataac    16200
ggtttggttg atgcgagtga ttttgatgac gagcgtaatg gctggcctgt tgaacaagtc    16260
tggaaagaaa tgcataagct tttgccattc tcaccggatt cagtcgtcac tcatggtgat    16320
ttctcacttg ataaccttat ttttgacgag gggaaattaa taggttgtat tgatgttgga    16380
cgagtcggaa tcgcagaccg ataccaggat cttgccatcc tatggaactg cctcggtgag    16440
ttttctcctt cattacagaa acggcttttt caaaaatatg gtattgataa tcctgatatg    16500
aataaattgc agtttcattt gatgctcgat gagtttttct aagcgcgcag cgcttagacg    16560
tctcgcgatc gatgctagtg tgaaatagac atcagaatta agaaaaacgt agggtccaag    16620
tggttccccg ttatggactc gctatctgtc aaccagatct tatacccctga agttcaccta    16680 gatagcccga tagttaccaa taagatagta gccatcctgg agtatgctcg agtccctcac    16740
gcttacagcc tggaggaccc tacactgtgt cagaacatca agcaccgcct aaaaaacgga    16800
ttttccaacc aaatgattat aaacaatgtg gaagttggga atgtcatcaa gtccaagctt    16860
aggagttatc cggcccactc tcatattcca tatccaaatt gtaatcagga ttttatttaac    16920 atagaagaca aagagtcaac gaggaagatc cgtgaactcc tcaaaaaggg gaattcgctg    16980
```

```
tactccaaag tcagtgataa ggttttccaa tgcttaaggg acactaactc acggcttggc   17040
ctaggctccg aattgaggga ggacatcaag gagaaagtta ttaacttggg agtttacatg   17100
cacagctccc agtggtttga gccctttctg ttttggttta cagtcaagac tgagatgagg   17160
tcagtgatta aatcacaaac ccatacttgc cataggagga gacacacacc tgtattcttc   17220
actggtagtt cagttgagtt gctaatctct cgtgaccttg ttgctataat cagtaaagag   17280
tctcaacatg tatattacct gacatttgaa ctggttttga tgtattgtga tgtcatagag   17340
gggaggttaa tgacagagac cgctatgact attgatgcta ggtatacaga gcttctagga   17400
agagtcagat acatgtggaa actgatagat ggtttcttcc ctgcactcgg gaatccaact   17460
tatcaaattg tagccatgct ggagcctctt tcacttgctt acctgcagct gagggatata   17520
acagtagaac tcagaggtgc tttccttaac cactgcttta ctgaaataca tgatgttctt   17580
gaccaaaacg ggttttctga tgaaggtact tatcatgagt taactgaagc tctagattac   17640
attttcataa ctgatgacat acatctgaca ggggagattt tctcattttt cagaagtttc   17700
ggccacccca gacttgaagc agtaacggct gctgaaaatg ttaggaaata catgaatcag   17760
cctaaagtca ttgtgtatga gactctgatg aaaggtcatg ccatattttg tggaatcata   17820
atcaacggct atcgtgacag gcacggaggc agttggccac cgctgaccct ccccctgcat   17880
gctgcagaca caatccggaa tgctcaagct tcaggtgaag ggttaacaca tgagcagtgc   17940
gttgataact ggaaatcttt tgctggagtg aaatttggct gctttatgcc tcttagcctg   18000
gatagtgatc tgacaatgta cctaaaggac aaggcacttg ctgctctcca aagggaatgg   18060
gattcagttt acccgaaaga gttcctgcgt tacgaccctc ccaagggaac cgggtcacgg   18120
aggcttgtag atgttttcct taatgattcg agctttgacc catatgatgt gataatgtat   18180
gttgtaagtg gagcttacct ccatgaccct gagttcaacc tgtcttacag cctgaaagaa   18240
aaggagatca aggaaacagg tagactttttt gctaaaatga cttacaaaat gagggcatgc   18300
caagtgattg ctgaaaatct aatctcaaac gggattggca atatttttaa ggacaatggg   18360
atggccaagg atgagcacga tttgactaag gcactccaca ctctagctgt ctcaggagtc   18420
cccaaagatc tcaaagaaag tcacaggggg gggccagtct taaaaaccta ctcccgaagc   18480
ccagtccaca caagtaccag gaacgtgaga gcagcaaaag ggtttatagg gttccctcaa   18540
gtaattcggc aggaccaaga cactgatcat ccggagaata tggaagctta cgagacagtc   18600
agtgcattta tcacgactga tctcaagaag tactgcctta attggagata tgagaccatc   18660
agcttgtttg cacagaggct aaatgagatt tacggattgc cctcatttttt ccagtggctg   18720 cataagaggc ttgagacctc tgtcctgtat gtaagtgacc ctcattgccc ccccgacctt   18780
gacgcccata tcccgttata taagtcccc aatgatcaaa tcttcattaa gtaccctatg   18840
ggaggtatag aagggtattg tcagaagctg tggaccatca gcaccattcc ctatctatac   18900
ctggctgctt atgagagcgg agtaaggatt gcttcgttag tgcaagggga caatcagacc   18960
atagccgtaa caaaaagggt acccagcaca tggccctaca accttaagaa acgggaagct   19020
gctagagtaa ctagagatta ctttgtaatt cttaggcaaa ggctacatga tattggccat   19080
cacctcaagg caaatgagac aattgtttca tcacattttt ttgtctattc aaaaggaata   19140
tattatgatg ggctacttgt gtcccaatca ctcaagagca tcgcaagatg tgtattctgg   19200
tcagagacta tagttgatga acaagggca gcatgcagta atattgctac aacaatggct   19260
aaaagcatcg agagaggtta tgaccgttac cttgcatatt ccctgaacgt cctaaaagtg   19320
atacagcaaa ttctgatctc tcttggcttc acaatcaatt caaccatgac ccgggatgta   19380
```

```
gtcatacccc tcctcacaaa caacgacctc ttaataagga tggcactgtt gcccgctcct   19440
attggggga tgaattatct gaatatgagc aggctgtttg tcagaaacat cggtgatcca    19500
gtaacatcat caattgctga tctcaagaga atgattctcg cctcactaat gcctgaagag   19560
accctccatc aagtaatgac acaacaaccg ggggactctt cattcctaga ctgggctagc   19620
gacccttact cagcaaatct tgtatgtgtc cagagcatca ctagactcct caagaacata   19680
actgcaaggt ttgtcctgat ccatagtcca aacccaatgt taaaaggatt attccatgat   19740
gacagtaaag aagaggacga gggactggcg gcattcctca tggacaggca tattatagta   19800
cctagggcag ctcatgaaat cctggatcat agtgtcacag gggcaagaga gtctattgca   19860
ggcatgctgg ataccacaaa aggcttgatt cgagccagca tgaggaaggg ggggttaacc   19920
tctcgagtga taaccagatt gtccaattat gactatgaac aattcagagc agggatggtg   19980
ctattgacag gaagaaagag aaatgtcctc attgacaaag agtcatgttc agtgcagctg   20040
gcgagagctc taagaagcca tatgtgggcg aggctagctc gaggacggcc tatttacggc   20100
cttgaggtcc ctgatgtact agaatctatg cgaggccacc ttattcggcg tcatgagaca   20160
tgtgtcatct gcgagtgtgg atcagtcaac tacggatggt ttttgtccc ctcgggttgc    20220
caactggatg atattgacaa ggaaacatca tccttgagag tcccatatat tggttctacc   20280
actgatgaga aacagacat gaagcttgcc ttcgtaagag ccccaagtcg atccttgcga    20340
tctgctgtta aatagcaac agtgtactca tgggcttacg gtgatgatga tagctcttgg    20400
aacgaagcct ggttgttggc taggcaaagg gccaatgtga gcctggagga gctaagggtg   20460
atcactccca tctcaacttc gactaattta gcgcataggt tgagggatcg tagcactcaa   20520
gtgaaatact caggtacatc ccttgtccga gtggcgaggt ataccacaat ctccaacgac   20580
aatctctcat ttgtcatatc agataagaag gttgatacta actttatata ccaacaagga   20640
atgcttctag ggttgggtgt tttagaaaca ttgtttcgac tcgagaaaga taccggatca   20700
tctaacacgg tattacatct tcacgtcgaa acagattgtt gcgtgatccc gatgatagat   20760
catcccagga tacccagctc ccgcaagcta gagctgaggg cagagctatg taccaaccca   20820
ttgatatatg ataatgcacc tttaattgac agagatgcaa caaggctata cacccagagc   20880
cataggaggc accttgtgga atttgttaca tggtccacac cccaactata tcacatttta   20940
gctaagtcca cagcactatc tatgattgac ctggtaacaa aatttgagaa ggaccatatg   21000
aatgaaattt cagctctcat aggggatgac gatatcaata gtttcataac tgagtttctg   21060
ctcatagagc caagattatt cactatctac ttgggccagt gtgcggccat caattgggca   21120
tttgatgtac attatcatag accatcaggg aaatatcaga tgggtgagct gttgtcatcg   21180
ttcctttcta gaatgagcaa aggagtgttt aaggtgcttg tcaatgctct aagccaccca   21240
aagatctaca agaaattctg gcattgtggt attatagagc ctatccatgg tccttcactt   21300
gatgctcaaa acttgcacac aactgtgtgc aacatggttt acacatgcta tatgacctac   21360
ctcgacctgt tgttgaatga agagttagaa gagttcacat ttctcttgtg tgaaagcgac   21420
gaggatgtag taccggacag attcgacaac atccaggcaa aacacttatg tgttctggca   21480
gatttgtact gtcaaccagg gacctgccca ccaattcgag gtctaagacc ggtagagaaa   21540
tgtgcagttc taaccgacca tatcaaggca gaggctatgt tatctccagc aggatcttcg   21600
tggaacataa atccaattat tgtagaccat tactcatgct ctctgactta tctccggcga   21660
ggatcgatca aacagataag attgagagtt gatccaggat tcattttcga cgccctcgct   21720
```

```
gaggtaaatg tcagtcagcc aaagatcggc agcaacaaca tctcaaatat gagcatcaag   21780
gctttcagac ccccacacga tgatgttgca aaattgctca agatatcaa cacaagcaag    21840 cacaatcttc ccatttcagg gggcaatctc gccaattatg aaatccatgc tttccgcaga   21900
atcgggttga actcatctgc ttgctacaaa gctgttgaga tatcaacatt aattaggaga   21960
tgccttgagc caggggagga cggcttgttc ttgggtgagg gatcgggttc tatgttgatc   22020
acttataaag agatacttaa actaaacaag tgcttctata atagtggggt ttccgccaat   22080
tctagatctg gtcaaaggga attagcaccc tatccctccg aagttggcct tgtcgaacac   22140
agaatgggag taggtaatat tgtcaaagtg ctctttaacg ggaggcccga agtcacgtgg   22200
gtaggcagtg tagattgctt caatttcata gttagtaata tccctacctc tagtgtgggg   22260
tttatccatt cagatataga gaccttgcct gacaaagata ctatagagaa gctagaggaa   22320
ttggcagcca tcttatcgat ggctctgctc ctgggcaaaa taggatcaat actggtgatt   22380
aagcttatgc ctttcagcgg ggattttgtt cagggattta taagttatgt agggtctcat   22440
tatagagaag tgaaccttgt atacctaga tacagcaact tcatctctac tgaatcttat    22500
ttggttatga cagatctcaa ggctaaccgg ctaatgaatc ctgaaaagat taagcagcag   22560
ataattgaat catctgtgag gacttcacct ggacttatag gtcacatcct atccattaag   22620
caactaagct gcatacaagc aattgtggga gacgcagtta gtagaggtga tatcaatcct   22680
actctgaaaa aacttacacc tatagagcag gtgctgatca attgcgggtt ggcaattaac   22740
ggacctaagc tgtgcaaaga attgatccac catgatgttg cctcagggca agatggattg   22800
cttaattcta tactcatcct ctacaggggag ttggcaagat tcaaagacaa ccaaagaagt   22860
caacaaggga tgttccacgc ttaccccgta ttggtaagta gcaggcaacg agaacttata   22920
tctaggatca cccgcaaatt ctgggggcac attcttcttt actccgggaa caaaaagttg   22980
ataaataagt ttatccagaa tctcaagtcc ggctatctga tactagactt acaccagaat   23040
atcttcgtta agaatctatc caagtcgagg aaacagatta ttatgacggg gggtttgaaa   23100
cgtgagtggg ttttttaaggt aacagtcaag gagaccaaag aatggtataa gttagtcgga   23160
tacagtgccc tgattaagga ctaattggtt gaactccgga accctaatcc tgccctaggt   23220
ggttaggcat tatttgcaat atattaaaga aaactttgaa aatacgaagt ttctattccc   23280
agctttgtct ggtggccggc atggtcccag cctcctcgct ggcgccggct gggcaacatt   23340
ccgaggggac cgtcccctcg gtaatggcga atgggacgcg gccgatccgg ctgctaacaa   23400
agcccgaaag gaagctgagt tggctgctgc caccgctgag caataactag cataacccct   23460
tggggcctct aaacgggtct tgagggggtt tttgctgaaa ggaggaacta tatccggatg   23520
gcggccgctc gagcatgcat ctagagggcc gcatcatgta attagttatg tcacgcttac   23580
attcacgccc tccccccaca tccgctctaa ccgaaaagga aggagttaga caacctgaag   23640
tctaggtccc tatttatttt tttatagtta tgttagtatt aagaacgtta tttatatttc   23700
aaattttcct tttttttctg tacagacgcg tgtacgcatg taacattata ctgaaaacct   23760
tgcttgagaa ggttttggga cgctcgaagg ctttaatttg cggcc                   23805
```

<210> SEQ ID NO 48
<211> LENGTH: 453
<212> TYPE: DNA
<213> ORGANISM: Artificial
<220> FEATURE:
<223> OTHER INFORMATION: Plasmid

<400> SEQUENCE: 48

```
gcggccgcca actttgtttg gtctgatgag tccgtgagga cgaaacccgg agtcccgggt     60
caccagacaa agctgggaat agaaacttcg tattttcaaa gttttcttta atatattgca    120
aataatgcct aaccacctag ggcaggatta gggttccgga gttcaaccaa ttagtcctta    180
atcagggcac tgtatccgac taacttatac cattctttgg actagtgacg tccgcggtcg    240
acacgtgaga tctgatggcc atctcggata tccctaatcc tgctcttgtc cctgataata    300
ggatcttgaa tcctaagtgc actagaagat gatcattgat tgaactatcc ttacccaact    360
ttgtttggtg gccggcatgg tcccagcctc ctcgctggcg ccggctgggc aacattccga    420
ggggaccgtc ccctcggtaa tggcgaatgg gac                                 453

<210> SEQ ID NO 49
<211> LENGTH: 30
<212> TYPE: DNA
<213> ORGANISM: Artificial
<220> FEATURE:
<223> OTHER INFORMATION: Primer

<400> SEQUENCE: 49
cacgtacgat gggtaaggaa aagactcacg                                      30

<210> SEQ ID NO 50
<211> LENGTH: 30
<212> TYPE: DNA
<213> ORGANISM: Artificial
<220> FEATURE:
<223> OTHER INFORMATION: Primer

<400> SEQUENCE: 50
tccttgcgcg cttagaaaaa ctcatcgagc                                      30
```